(12) United States Patent
Pasqualato et al.

(10) Patent No.: US 12,403,144 B2
(45) Date of Patent: Sep. 2, 2025

(54) HECT E3 LIGASE INHIBITORS AND USES THEREOF

(71) Applicants: IFOM FONDAZIONE ISTITUTO FIRC DI ONCOLOGIA MOLECOLARE, Milan (IT); IEO—ISTITUTO EUROPEO DI ONCOLOGIA S.R.L., Milan (IT)

(72) Inventors: Sebastiano Pasqualato, Milan (IT); Maurizio Pasi, Torre d'Isola (IT); Raffaella Amici, Codogno (IT); Mario Varasi, Milan (IT); Ciro Mercurio, Legnano (IT); Luca Sartori, Milan (IT); Simona Polo, Milan (IT); Elena Maspero, Milan (IT); Giovanni Faga', Milan (IT)

(73) Assignees: IFOM —FONDAZIONE ISTITUTO FIRC DI ONCOLOGIA MOLECOLARE, Milan (IT); IEO—ISTITUTO EUROPEO DI ONCOLOGIA S.R.L., Milan (IT)

( * ) Notice: Subject to any disclaimer, the term of this patent is extended or adjusted under 35 U.S.C. 154(b) by 820 days.

(21) Appl. No.: 17/616,070

(22) PCT Filed: Jun. 3, 2020

(86) PCT No.: PCT/EP2020/065372
§ 371 (c)(1),
(2) Date: Dec. 2, 2021

(87) PCT Pub. No.: WO2020/245213
PCT Pub. Date: Dec. 10, 2020

(65) Prior Publication Data
US 2022/0339163 A1 Oct. 27, 2022

(30) Foreign Application Priority Data
Jun. 3, 2019 (EP) .................................. 19177953

(51) Int. Cl.
| | |
|---|---|
| *A61K 31/5517* | (2006.01) |
| *A61K 31/55* | (2006.01) |
| *A61K 31/5513* | (2006.01) |
| *A61K 31/553* | (2006.01) |
| *A61P 35/00* | (2006.01) |
| *C07D 223/28* | (2006.01) |
| *C07D 243/38* | (2006.01) |
| *C07D 267/20* | (2006.01) |
| *C07D 487/04* | (2006.01) |
| *C07D 495/04* | (2006.01) |

(52) U.S. Cl.
CPC .......... *A61K 31/5517* (2013.01); *A61K 31/55* (2013.01); *A61K 31/5513* (2013.01); *A61K 31/553* (2013.01); *A61P 35/00* (2018.01); *C07D 223/28* (2013.01); *C07D 243/38* (2013.01); *C07D 267/20* (2013.01); *C07D 487/04* (2013.01); *C07D 495/04* (2013.01)

(58) Field of Classification Search
CPC ................ A61K 31/5517; A61K 31/55; A61K 31/5513; A61P 35/00
See application file for complete search history.

(56) References Cited

U.S. PATENT DOCUMENTS

2016/0016893 A1  1/2016  Statsyuk et al.

FOREIGN PATENT DOCUMENTS

WO  2018/064589 A1  4/2018

OTHER PUBLICATIONS

ISA/EP, "PCT International Search Report and Written Opinion", issued in connection with PCT International Application No. PCT/EP2020/065372, which was mailed Jul. 27, 2020 (8 pages).

*Primary Examiner* — Adam C Milligan
*Assistant Examiner* — Ernesto Valle, Jr.
(74) *Attorney, Agent, or Firm* — Lucas & Mercanti, LLP

(57) ABSTRACT

The present invention relates to tricyclic derivatives of formula (I), which are useful as inhibitors of HECT-domain-containing E3 ligases, in particular NEDD4. The present invention also refers to pharmaceutical compositions comprising compounds of formula (I), to their medical use and to their process of preparation.

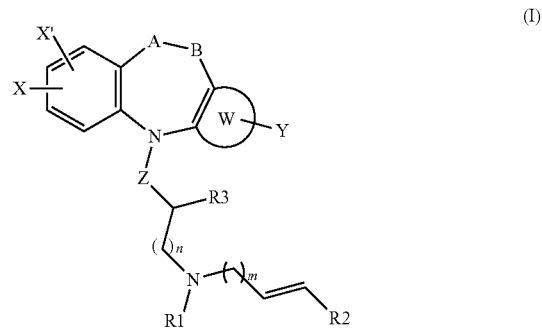

19 Claims, 3 Drawing Sheets

HECT E3 LIGASE INHIBITORS AND USES THEREOF

CROSS-REFERENCE TO RELATED APPLICATIONS

Figure 1:
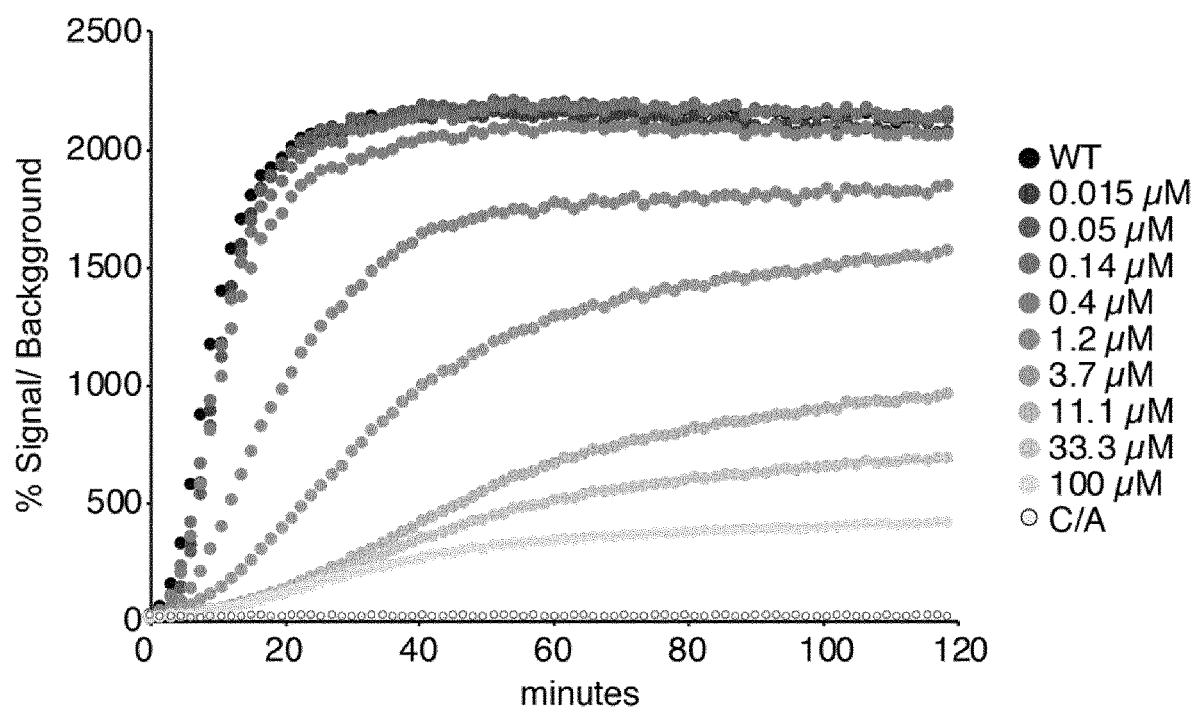

This application is a 371 of PCT/EP2020/065372, filed Jun. 3, 2020, which claims the benefit of European Patent Application No. 19177953.7, filed Jun. 3, 2019.

FIELD OF THE INVENTION

The present invention relates to tricyclic derivatives, pharmaceutical compositions containing them, their use in therapy and process of preparation.

BACKGROUND OF THE INVENTION

During the past two decades evidence has accumulated, supporting a paramount role of ubiquitin (Ub) in regulation of various biological and pathological phenomena. It is therefore not surprising that ubiquitin system deregulation contributes to a wide range of human diseases, including development of many types of tumors (D. Popovic et al. Nat. Med. 20, 1242-53 (2014)). Indeed, oncogenes or tumor suppressors involved in several common malignancies, for example breast (BRCA1), colon (APC), renal carcinoma (VHL) and cervical cancer (E6AP) code for ubiquitin ligase components. The therapeutic potential of targeting ubiquitin system has been recognized by FDA approval of the proteasome inhibitor Velcade (Bortezomib) for treatment of multiple myeloma. Better than the proteasome, E3 ligases appear to be promising targets for drug discovery as they represent the last step of the enzymatic cascade, capable of conferring a high degree of specificity and selectivity towards target substrates in cells (D. Senft et al. Nature Reviews Cancer 18, 69-88 (2018)). The C2-WW-HECT E3s, also named NEDD4 family, are strong candidates for such role. These proteins belong to HECT type of E3 ligases characterized by a C-terminal Homologous to E6AP C Terminus (HECT) domain that catalyzes covalent attachment of ubiquitin to substrate proteins and by N-terminal extensions of variable length and domain architecture that determines the substrate spectrum specificity. The human family of NEDD4 HECT comprises nine members: NEDD4, NEDD4L, ITCH, SMURF1, SMURF2, WWP1, WWP2, HECW1 and HECW2 (M. Scheffner et al. Biochim. Biophys. Acta. 1843, 61-74 (2014)). Despite having different biological functions, they all share similar domain architecture (D. Rotin and S. Kumar. Nature Rev. Mol. Cell Biol. 10, 398-409 (2009)) with an N-terminal extension that comprises a C2 domain (calcium-dependent lipid binding domain) and 3 to 4 WW domains, critical for substrate specificity as they recognize PPxY, LPxY or proline-rich motifs in substrates, adaptors and regulatory proteins (R. J. Ingham et al. Mol Cell Biol. 25, 7092-7106 (2005)).

Their enzymatic activity is tightly controlled through an auto-inhibitory interaction of C2 with HECT domain (S. Mari et al. Structure. 22, 1639-49 (2014); S. Wiesner et al. Cell. 130, 651-62 (2007)). This inhibitory close conformation in NEDD4 can be released upon tyrosine (Tyr) phosphorylation occurring at C2 and at HECT domain (A. Persaud et al. Sci Signal. 2014 7(346):ra95(2014)). From the biological point of view, these enzymes are involved in endo-lysosomal trafficking of membrane receptors through ubiquitination of cargos, adaptors or key signaling components (M. Scheffnerand S. Kumar. Biochim. Biophys. Acta 1843, 61-74 (2014); S. Polo. BMC Biol. 10, 25 (2012)). Since their discovery in 1993 (J. Scheffner et al. Cell. 75, 495-505 (1993)), it has become clear that their deregulation plays an eminent role in several human diseases including viral infection, hypertension, cardiovascular diseases, inflammation, autoimmunity and, last but not least cancer (D. Senft et al. Nature Reviews Cancer 18, 69-88 (2018)).

NEDD4, the founding member of HECT E3 ligase NEDD4 family, has been initially identified as a gene downregulated in mouse neuronal precursor cells during brain development (S. Kumar et al. Biochem. Biophys. Res. Commun., 185, 1155-1161 (1992)). Subsequently, the involvement of NEDD4 in the regulation of fluid and electrolyte homeostasis (O. Staub et al. EMBO J., 16, 6325-6336 (1997)), in embryonic development and cell growth (X. R. Cao et al. Sci Signal. 2008 1(38):ra5 (2008)) has been reported. NEDD4 also regulates T cell function, converting naïve T cells into active T cells (B. Yang et al. Nat. Immunol., 9, 1356-1363 (2008)) and neurite growth and arborization in neurons (H. Kawabe et al. Neuron, 65, 358-372 (2010); J. Drinjakovic et al. Neuron, 65, 341-357 (2010)). Furthermore, NEDD4 is required for the proper formation and functioning of the neuromuscular junctions (Y. Liu et al. Dev. Biol., 330 153-166 (2009)), the vascular development (F. Fouladkou et al. J. Biol. Chem. 285 6770-6780 (2010)). NEDD4 appears also to facilitate budding of various viruses by ubiquitinating viral matrix proteins via PPxY motifs (R. Harthy et al. Proc. Natl. Acad. Sci. U.S.A, 97 (2000), pp. 13871-13876; J. Martin-Serrano et al J. Cell Biol. 168:89-101 (2005)); E. R. Weiss et al PLOS Pathol. 6 PLoS Pathog. 6:e1001107, doi: 10.1371/journal.ppat.1001107 (2010)). The requirement of NEDD4 involvement for the infection of human immunodeficiency virus (HIV) (Sette, P., et al. *Journal of virology* 84, 8181-8192 (2010)), Ebola virus (R. Harthy et al. Proc. Natl. Acad. Sci. U.S.A, 97 (2000), pp. 13871-13876), and influenza virus (A Chesarino et al. *PLoS Pathog* 11, e1005095(2015), as well as for the promotion of Japanese encephalitis virus (JEV) replication (Xu Q. et al Sci Rep. March 28; 7:45375(2017) indicates its important role in the pathogenesis of viral diseases and the possibility to consider the inhibition of NEDD4 as a therapeutic target approach for viral infection. In addition, an important role of NEDD4 regulating the autophagy has been recently demonstrated (A. Sun et al. Autophagy. 13(3), 522-537 (2017)). Several potential NEDD4 substrates, including tumor suppressor such as PTEN and LATS1 have been identified (N. A. Boase and S. Kumar. Gene, 2, 113-122 (2015)).

Regarding the link of NEDD4 with cancer, high expression of NEDD4 has been reported in several cancer types including: gastric carcinoma (Kim S S et al. APMIS. 116 (9):779-84 (2008)), colorectal and breast cancer (P W Eide et al. Cell Signal. 25(1):12-8 (2013); S. W. Hong et al. Cell Death Differ. 21, 146-160 (2014); S. Jung et al. Int. J. Oncol., 43 1587-1595(2013)), non-small cell lung cancer (N. Amodio et al. Am. J. Pathol. 177, 2622-2634(2010)), hepatocellular carcinoma (Z J. Huang et al. Oncol. Lett. 14(3):2649-2656(2017)), pancreatic adenocarcinoma (M. Weng et al. Oncotarget. 8(12):20288-20296 (2017)), and most aggressive endometrial cancer tumors (Y. Zhang et al. Gynecol Oncol. 139(1):127-33 (2015)). A critical role of NEDD4 in cancer cell growth and/or invasion has been observed in hepatocellular carcinoma (H. Zheng et al. Cell Cycle. February 26:1-29,(2018)), bladder cancer (W. Wen et al. Cell Cycle. (16):1509-1514(2017)), glioma (H. Zhang et al. PLoS One. 8(12):e82789 (2013)), lung and pancreatic cancer (G. Shao et al. Mol Cancer. 17(1):24 (2018); M.

Weng et al. Oncotarget. 8(12):20288-20296 (2017)). Importantly, down regulation of NEDD4 in cells of several of above indicated cancers strongly affects cell growth and migration in vitro and in vivo. Starting from data describing NEDD4 as a proto-oncogene for its role in negatively regulating tumor suppressor PTEN via ubiquitination (X. Wang et al. Cell. 128, 129-139 (2007)), it became evident that cellular context strongly impacts NEDD4's substrate preference and activity level (F. Fouladkou et al. Proc. Natl. Acad. Sci. 105, 8585-8590 (2008); T. Zeng et al. Cell Rep. 7, 871-882 (2014); S.-W. Hong et al. Cell Death Differ. 21, 146-160 (2014)). One of the most relevant observations links Ras activation to NEDD4 overexpression and subsequent PTEN degradation in human colorectal cancer (T. Zeng et al. Cell Rep. 7, 871-882 (2014)). Notably, NEDD4 has been found highly expressed in Non-Small Cell Lung Cancer (N. Amodio et al. Am. J. Pathol. 177, 2622-2634 (2010)) where K-Ras mutation affects amongst 15-25% of NSCLC patients.

In addition, it is relevant to remember the positive regulatory role of NEDD4 on IGF and insulin signaling cell growth pathways (X. R. Cao et al. Sci Signal. 2008 1(38):ra5 (2008); T. Fukushima et al. Nature Communications 6, 6780 (2015)) both of them promoting the growth of human cancer.

Lastly, a critical role of NEDD4 in regulating histone H3 acetylation and tumorigenesis has also been recently reported (X. Zhang et al. Nat. Commun. 8:14799 (2017)).

Covalent inhibitors of NEDD4 with a suboptimal potency and absence of data on cancer cells have been identified (S J. Kathman et al. J. Am Chem Soc. 137(39):12442-5 (2015)). In addition, some indole-3-carbinol (I3C) analogues, active in the high micromolar range, have been identified as NEDD4 inhibitor (J G. Quirit et al. Biochem Pharmacol. 127:13-27(2017)).

In this context, there is still the need to identify NEDD4 inhibitors, which would represent an interesting approach for cancer therapy and for other conditions associated with the activity of NEDD4, such as infectious diseases.

DESCRIPTION OF THE INVENTION

The inventors have surprisingly found tricyclic derivatives endowed with inhibitory activity towards HECT-domain-containing E3 ligases, in particular towards NEDD4 ligases, more in particular toward NEDD4, useful in the prevention and/or therapy of conditions associated with the activity of such ligases, in particular conditions wherein a HECT-domain-containing E3 ligase is deregulated, such as cancer and infectious diseases. Preferably and advantageously, the tricyclic derivatives are selective for NEDD4 over other ligases of the same family. Also preferably and advantageously, the tricyclic derivatives can inhibit cancer cell growth and are thus useful as antiproliferative medicaments.

It is therefore an object of the present invention a compound of general formula (I):

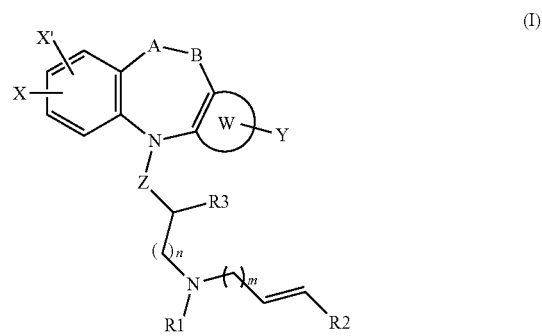

wherein:
Z is $CH_2$ or CO;
R1 is hydrogen or $C_1$-$C_6$ alkyl;
R2 is COOR4, CO—R5, CN or CONR6R7;
R3 is H or OH;
n is an integer from 1 to 3;
m is 1 or 2;
W is aryl or heteroaryl;
A-B is $CH_2$—$CH_2$, O—$CH_2$, $CH_2$—O, NR8-CO or CO—NR8;
X, X', Y are each independently selected from the group consisting of: hydrogen, $C_1$-$C_6$ alkyl, OH, $NH_2$, $C_1$-$C_6$-alkoxy, $C_1$-$C_6$-alkylamino, $C_1$-$C_6$-dialkylamino, CONR6R7, halogen, $CF_3$, $NO_2$ and CN, said $C_1$-$C_6$ alkyl or $C_1$-$C_6$ alkoxy being optionally substituted with a substituent selected from the group consisting of: R9, OH, $NH_2$, $C_1$-$C_6$-alkoxy, ($C_1$-$C_6$-alkoxy)$C_1$-$C_6$-alkoxy, $C_2$-$C_6$-alkynyloxy, $C_2$-$C_6$-alkynyl, $C_1$-$C_6$-alkylamino, $C_1$-$C_6$-dialkylamino, aryl and heteroaryl;
R4 is hydrogen or $C_1$-$C_6$ alkyl, said $C_1$-$C_6$ alkyl being optionally substituted with a substituent selected from the group consisting of: R9, $C_2$-$C_6$-alkynyl, $C_1$-$C_6$-alkoxy, $C_2$-$C_6$-alkynyloxy and ($C_1$-$C_6$-alkoxy)$C_1$-$C_6$-alkoxy;
R5 is $C_{3-6}$ cycloalkyl, $C_1$-$C_6$ alkyl, aryl, heteroaryl,

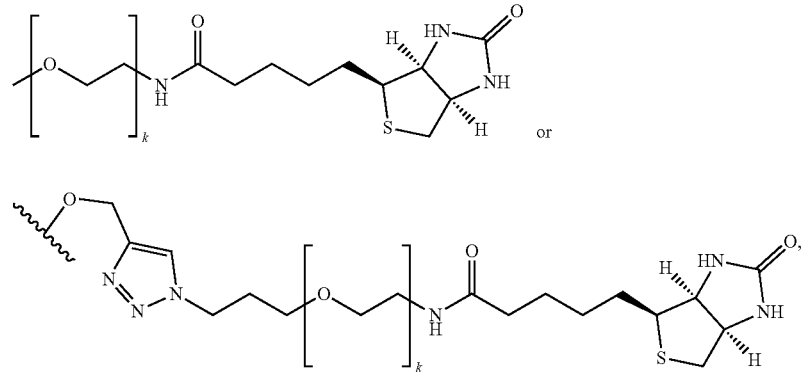

said $C_1$-$C_6$ alkyl being optionally substituted by aryl or heteroaryl;

R6, R7 are each independently selected from the group consisting of: hydrogen, aryl, $C_1$-$C_6$ alkyl, $C_1$-$C_6$-alkoxy, O-aryl and O-heterocycloalkyl, said $C_1$-$C_6$ alkyl, $C_1$-$C_6$-alkoxy, O-aryl or O-heterocycloalkyl being optionally substituted with a substituent selected from the group consisting of: OH, $NH_2$, $C_1$-$C_6$-alkoxy, $C_1$-$C_6$-alkylamino, $C_1$-$C_6$-dialkylamino, aryl, heteroaryl and $C_2$-$C_6$-alkynyl;

R8 is hydrogen or $C_1$-$C_6$ alkyl, said $C_1$-$C_6$ alkyl being optionally substituted with a substituent selected from the group consisting of: OH, $NH_2$, $C_1$-$C_6$-alkoxy, $C_1$-$C_6$-alkylamino, $C_1$-$C_6$-dialkylamino, aryl, heteroaryl, $(C_1$-$C_6$-alkoxy)$C_1$-$C_6$-alkoxy, [$(C_1$-$C_6$-alkoxy)$C_1$-$C_6$-alkoxy]$C_1$-$C_6$-alkoxy and $C_2$-$C_6$-alkynyloxy;

R9 is

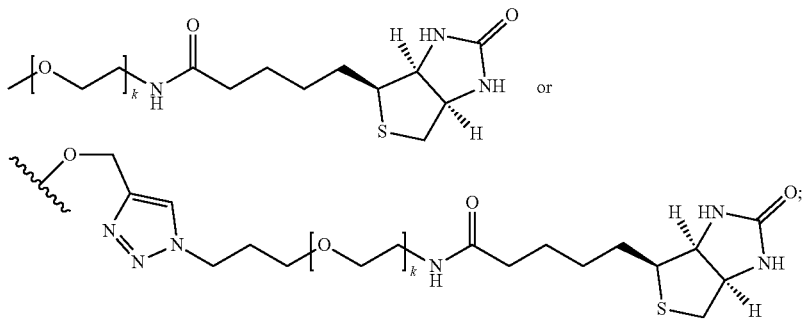

k is an integer from 1 to 10;

or a stereoisomer, solvate, tautomer or pharmaceutically acceptable salt thereof.

All the following preferred embodiments may be combined amongst themselves in any possible way that would give rise to a chemically-stable compound.

Preferably, when R6 is O—$C_1$-$C_6$ alkyl, R7 is $C_1$-$C_6$ alkyl.

In a preferred aspect,

X, X', Y are each independently hydrogen, $C_1$-$C_6$ alkyl, OH, $NH_2$, $C_1$-$C_6$-alkoxy, $C_1$-$C_6$-alkylamino, $C_1$-$C_6$-dialkylamino, CONR6R7, halogen, $CF_3$, $NO_2$ or CN;

R4 is hydrogen or $C_1$-$C_6$ alkyl;

R5 is $C_{3-6}$ cycloalkyl, $C_1$-$C_6$ alkyl, aryl or heteroaryl, said $C_1$-$C_6$ alkyl being optionally substituted by aryl or heteroaryl;

R6, R7 are each independently hydrogen, aryl, $C_1$-$C_6$ alkyl or O—$C_1$-$C_6$ alkyl, said $C_1$-$C_6$ alkyl or O—$C_1$-$C_6$ alkyl being optionally substituted with a substituent selected from the group consisting of: OH, $NH_2$, $C_1$-$C_6$-alkoxy, $C_1$-$C_6$-alkylamino, $C_1$-$C_6$-dialkylamino, aryl and heteroaryl, with the proviso that when R6 is O—$C_1$-$C_6$ alkyl, R7 is $C_1$-$C_6$ alkyl; and R8 is hydrogen or $C_1$-$C_6$ alkyl, said $C_1$-$C_6$ alkyl being optionally substituted with a substituent selected from the group consisting of: OH, $NH_2$, $C_1$-$C_6$-alkoxy, $C_1$-$C_6$-alkylamino, $C_1$-$C_6$-dialkylamino, aryl and heteroaryl.

Preferably, when R3 is OH, n is 1.

Preferably, Z is $CH_2$. Preferably, R1 is hydrogen or $C_1$-$C_3$ alkyl (in particular Me, Et or iPr). Preferably, R3 is H. Preferably, A-B is $CH_2$—$CH_2$, O—$CH_2$ or CO—NR8, more preferably A-B is $CH_2$—$CH_2$, O—$CH_2$, CO—NH, CO—NMe, CO—$NCH_2CH_2$Ph, CO—$NCH_2$Ph, CO—$NCH_2CH_2$OH, CO—$NCH_2CH_2CH_2$OH, CO—$NCH_2CH_2OCH_2C\equiv CH$. Preferably, X, X', Y are each independently selected from the group consisting of: hydrogen, chlorine, bromine, trifluoromethyl, $NO_2$, OH, methyl, methoxyl, $CH_2OH$, $CH_2OCH_3$, $OCH_2CH_2OCH_3$, $CH_2OCH_2CH_2OCH_3$, $OCH_2$Ph, $OCH_2C\equiv CH$ and $OCH_2CH_2OCH_2C\equiv CH$. Preferably, R4 is hydrogen or $C_1$-$C_3$ alkyl (in particular methyl, ethyl), $CH_2CH_2OCH_2C\equiv CH$ or $CH_2CH_2OCH_3$. Preferably, R5 is $C_1$-$C_3$ alkyl (in particular methyl or ethyl), aryl (in particular phenyl) or $C_1$-$C_3$ alkyl substituted by aryl (in particular $CH_2CH_2$phenyl). Preferably, R6 and R7 are each independently selected from the group consisting of: H, $C_1$-$C_3$ alkyl (in particular methyl or ethyl), aryl (in particular phenyl), $C_1$-$C_3$ alkyl substituted by aryl (in particular $CH_2CH_2$phenyl), $C_1$-$C_3$ alkoxy (in particular methoxy, isopropoxy, $OCH_2C\equiv CH$, $OCH_2$Ph), aryloxy (in particular phenoxy). Preferably, R8 is hydrogen, $C_1$-$C_3$ alkyl (in particular methyl) optionally substituted by aryl (in particular phenyl) or OH. Preferably, any one or more of said aryl is phenyl. Preferably, any one or more of said optionally substituted groups (in particular $C_1$-$C_6$ alkyl and $C_1$-$C_6$ alkoxy) is unsubstituted or substituted at the terminal atom. In a preferred embodiment, the present invention provides a compound of formula (I) or a stereoisomer, solvate, tautomer or pharmaceutically acceptable salt thereof as defined above, wherein:

R1 is hydrogen or $C_1$-$C_3$ alkyl;

X, X', Y are each independently hydrogen, OH, halogen, $CF_3$ or $NO_2$;

R4 is hydrogen or $C_1$-$C_3$ alkyl;

R5 is cyclopropyl, phenyl or $C_1$-$C_3$ alkyl optionally substituted by aryl or heteroaryl;

R6, R7 are each independently hydrogen, phenyl, $C_1$-$C_3$ alkyl or O—$C_1$-$C_3$ alkyl; and R8 is hydrogen or $C_1$-$C_3$ alkyl optionally substituted with OH, $NH_2$ or aryl.

In a preferred embodiment, the present invention provides a compound of formula (I) or a stereoisomer, solvate, tautomer or pharmaceutically acceptable salt thereof as defined above, wherein:
R1 is hydrogen or $C_1$-$C_3$ alkyl;
R2 is COOR4 or CONR6R7;
A-B is $CH_2$—$CH_2$ or CO—NR8;
X, X', Y are each independently halogen, hydrogen, OH, $CF_3$ or $NO_2$;
R4 is hydrogen or $C_1$-$C_3$ alkyl;
R6, R7 are each independently hydrogen, phenyl, $C_1$-$C_3$ alkyl or O—$C_1$-$C_3$ alkyl; and
R8 is hydrogen or $C_1$-$C_3$ alkyl optionally substituted with OH, $NH_2$ or aryl.

In a preferred embodiment, the present invention provides a compound of formula (I) or a stereoisomer, solvate, tautomer or pharmaceutically acceptable salt thereof as defined above, wherein:
R2 is COOR4;
R3 is H;
m is 1; and
R4 is $C_1$-$C_6$ alkyl.

In a preferred embodiment, the present invention provides a compound of formula (I) or a stereoisomer, solvate, tautomer or pharmaceutically acceptable salt thereof as defined above, wherein:
Z is $CH_2$;
R2 is COOR4;
R3 is OH;
n is 1;
m is 1; and
R4 is $C_1$-$C_6$ alkyl.

In a preferred embodiment, the present invention provides a compound of formula (I) or a stereoisomer, solvate, tautomer or pharmaceutically acceptable salt thereof as defined above, wherein:
R2 is COOR4;
m is 2; and
R4 is $C_1$-$C_6$ alkyl.

Preferably, W is selected from the group consisting of: benzene, pyrazole, pyrimidine, pyridine, pyrrole, thiophene and oxazole.

Preferably, the compound according to the present invention is selected from the group consisting of:
Methyl (E)-4-[3-(3-chloro-10,11-dihydro-5H-dibenzo[b,f]azepin-5-yl)propyl-methyl-amino]but-2-enoate;
Ethyl (E)-4-[3-(7-chlorodibenzo[b,e][1,4]oxazepin-5(11H)-yl)propylamino]but-2-enoate;
Ethyl (E)-4-{3-[7-(trifluoromethyl)dibenzo[b,e][1,4]oxazepin-5(11H)-yl]propylamino}but-2-enoate;
Ethyl (E)-4-[3-(3-chloro-10,11-dihydro-5H-dibenzo[b,f]azepin-5-yl)propylamino]but-2-enoate;
Ethyl (E)-5-[3-(3-chloro-10,11-dihydro-5H-dibenzo[b,f]azepin-5-yl)propylamino]pent-2-enoate;
(E)-4-[3-(3-Chloro-10,11-dihydro-5H-dibenzo[b,f]azepin-5-yl)propyl-methyl-amino]-N-methoxy-N-methyl-but-2-enamide;
(E)-5-[3-(3-chloro-10,11-dihydro-5H-dibenzo[b,f]azepin-5-yl)propyl-methyl-amino]pent-3-en-2-one;
(E)-4-[3-(3-chloro-10,11-dihydro-5H-dibenzo[b,f]azepin-5-yl)propyl-methyl-amino]-1-phenyl-but-2-en-1-one;
(E)-4-[4-(3-Chloro-10,11-dihydro-5H-dibenzo[b,f]azepin-5-yl)butyl-methyl-amino]-N-methoxy-N-methyl-but-2-enamide;
(E)-5-[4-(3-chloro-10,11-dihydro-5H-dibenzo[b,f]azepin-5-yl)butyl-methyl-amino]pent-3-en-2-one;
Ethyl (E)-4-[3-(10,11-dihydro-5H-dibenzo[b,f]azepin-5-yl)propylamino]but-2-enoate;
Ethyl (E)-4-[4-(3-chloro-10,11-dihydro-5H-dibenzo[b,f]azepin-5-yl)butylamino]but-2-enoate;
Ethyl (E)-4-[5-(3-chloro-10,11-dihydro-5H-dibenzo[b,f]azepin-5-yl)pentylamino]but-2-enoate;
Ethyl (E)-4-[3-(3-nitro-10,11-dihydro-5H-dibenzo[b,f]azepin-5-yl)propylamino]but-2-enoate;
Ethyl (E)-4-[3-(3-bromo-10,11-dihydro-5H-dibenzo[b,f]azepin-5-yl)propylamino]but-2-enoate;
(E)-4-[3-(3-chloro-10,11-dihydro-5H-dibenzo[b,f]azepin-5-yl)propylamino]but-2-enoic acid;
(E)-4-[4-(3-chloro-10,11-dihydro-5H-dibenzo[b,f]azepin-5-yl)butylamino]but-2-enoic acid;
(E)-4-{[3-(3-chloro-10,11-dihydro-5H-dibenzo[b,f]azepin-5-yl)propyl]amino}but-2-enamide;
(E)-4-{[3-(3-chloro-10,11-dihydro-5H-dibenzo[b,f]azepin-5-yl)propyl]amino}-N-methyl-but-2-enamide;
(E)-4-{[3-(3-chloro-10,11-dihydro-5H-dibenzo[b,f]azepin-5-yl)propyl]amino}-N,N-dimethyl-but-2-enamide;
(E)-4-{[3-(3-chloro-10,11-dihydro-5H-dibenzo[b,f]azepin-5-yl)propyl]amino}-N-phenyl-but-2-enamide;
(E)-4-{[3-(3-chloro-10,11-dihydro-5H-dibenzo[b,f]azepin-5-yl)propyl]amino}but-2-enenitrile;
Ethyl (E)-4-{[3-(3-chloro-11-oxo-10,11-dihydro-5H-dibenzo[b,e][1,4]diazepin-5-yl)propyl]amino}but-2-enoate;
Ethyl (E)-4-{[4-(3-chloro-11-oxo-10,11-dihydro-5H-dibenzo[b,e][1,4]diazepin-5-yl)butyl]amino}but-2-enoate;
Ethyl (E)-4-{[3-(11-oxo-3-(trifluoromethyl)-10,11-dihydro-5H-dibenzo[b,e][1,4]diazepin-5-yl)propyl]amino}but-2-enoate;
Ethyl (E)-4-{[3-(7-chloro-11-oxo-10,11-dihydro-5H-dibenzo[b,e][1,4]diazepin-5-yl)propyl]amino}but-2-enoate;
Ethyl (E)-4-{[3-(3-chloro-10-methyl-11-oxo-10,11-dihydro-5H-dibenzo[b,e][1,4]diazepin-5-yl)propyl]amino}but-2-enoate;
Ethyl (E)-4-{[3-(7-chloro-10-methyl-11-oxo-10,11-dihydro-5H-dibenzo[b,e][1,4]diazepin-5-yl)propyl]amino}but-2-enoate;
Ethyl (E)-4-{[4-(7-chloro-10-methyl-11-oxo-10,11-dihydro-5H-dibenzo[b,e][1,4]diazepin-5-yl)butyl]amino}but-2-enoate;
Ethyl (E)-4-{[3-(8-chloro-1-methyl-4,5-dihydropyrazolo[3,4-b][1]-benzazepin-10(1H)-yl)propyl]amino}but-2-enoate;
Ethyl (E)-4-{[3-(8-chloro-2-methyl-4,5-dihydropyrazolo[3,4-b][1]-benzazepin-10(2H)-yl)propyl]amino}but-2-enoate;
Ethyl (E)-4-{[3-(9-chloro-5,6-dihydro-11H-pyrimido[4,5-b][1]-benzazepin-11-yl)propyl]amino}but-2-enoate;
Ethyl (E)-4-{[3-(3-chloro-10,11-dihydro-5H-dibenzo[b,f]azepin-5-yl)-3-oxo-propyl]amino}but-2-enoate;
Ethyl (E)-4-{[2-hydroxy-3-(3-chloro-10,11-dihydro-5H-dibenzo[b,f]azepin-5-yl)]propylamino} but-2-enoate;
Ethyl (E)-4-{3-[3-chlorodibenzo[b,e][1,4]oxazepin-5(11H)-yl]propylamino}but-2-enoate;
Ethyl (E)-4-{4-[3-chlorodibenzo[b,e][1,4]oxazepin-5(11H)-yl]butylamino}but-2-enoate;
Ethyl (E)-4-{4-[7-chlorodibenzo[b,e][1,4]oxazepin-5(11H)-yl]butylamino}but-2-enoate;
Ethyl (E)-4-{[4-(3-chloro-10,11-dihydro-5H-dibenzo[b,f]azepin-5-yl)-4-oxo-butyl]amino}but-2-enoate;
Ethyl (E)-4-[4-(7-Chloro-2-hydroxy-10,11-dihydro-dibenzo[b,f]azepin-5-yl)-butylamino]-but-2-enoate;

Ethyl (E)-4-[4-(3-Chloro-2-hydroxy-10,11-dihydro-dibenzo [b,f]azepin-5-yl)-butylamino]-but-2-enoate;
Ethyl (E)-4-{[4-(7-chloro-11-oxo-10,11-dihydro-5H-dibenzo[b,e][1,4]diazepin-5-yl)butyl]amino}but-2-enoate;
Ethyl (E)-4-{[4-(3-chloro-10-methyl-11-oxo-10,11-dihydro-5H-dibenzo[b,e][1,4]diazepin-5-yl)butyl] amino}but-2-enoate;
Ethyl (E)-4-{[4-(8-chloro-1-methyl-4,5-dihydropyrazolo-[3,4-b][1]-benzazepin-10(1H)-yl)butyl]amino}but-2-enoate;
Ethyl (E)-4-{[4-(7-chloro-10-(2-phenylethyl)-11-oxo-10, 11-dihydro-5H-dibenzo[b,e][1,4]diazepin-5-yl)butyl] amino}but-2-enoate;
Ethyl (E)-4-{[4-(10-benzyl-7-chloro-11-oxo-10,11-dihydro-5H-dibenzo[b,e][1,4]diazepin-5-yl)butyl]amino}but-2-enoate;
Ethyl (E)-4-({4-[3-chloro-10-(2-hydroxyethyl)-11-oxo-10, 11-dihydro-5H-dibenzo[b,e][1,4]diazepin-5-yl] butyl}amino)but-2-enoate;
Ethyl (E)-4-({3-[3-chloro-10-(2-hydroxyethyl)-11-oxo-10, 11-dihydro-5H-dibenzo[b,e][1,4]diazepin-5-yl] propyl}amino)but-2-enoate;
Ethyl (E)-4-({4-[3-chloro-10-(3-hydroxypropyl)-11-oxo-10, 11-dihydro-5H-dibenzo[b,e][1,4]diazepin-5-yl] butyl}amino)but-2-enoate;
Ethyl (E)-4-({3-[3-chloro-10-(3-hydroxypropyl)-11-oxo-10, 11-dihydro-5H-dibenzo[b,e][1,4]diazepin-5-yl] propyl}amino)but-2-enoate;
Ethyl (E)-4-({4-[7-chloro-10-(2-hydroxyethyl)-11-oxo-10, 11-dihydro-5H-dibenzo[b,e][1,4]diazepin-5-yl] butyl}amino)but-2-enoate;
Ethyl (E)-4-({4-[7-chloro-10-(3-hydroxypropyl)-11-oxo-10, 11-dihydro-5H-dibenzo[b,e][1,4]diazepin-5-yl] butyl}amino)but-2-enoate;
Ethyl (E)-4-({3-[7-chloro-10-(3-hydroxypropyl)-11-oxo-10, 11-dihydro-5H-dibenzo[b,e][1,4]diazepin-5-yl] propyl}amino)but-2-enoate;
(E)-6-[4-(3-chloro-10,11-dihydro-5H-dibenzo[b,f]azepin-5-yl)butyl-methyl-amino]-1-phenyl-hex-4-en-3-one;
(E)-6-[4-(3-chloro-10,11-dihydro-5H-dibenzo[b,f]azepin-5-yl)butyl-methyl-amino]hex-4-en-3-one;
Ethyl (E)-4-({3-[7-chloro-10-(2-hydroxyethyl)-11-oxo-10, 11-dihydro-5H-dibenzo[b,e][1,4]diazepin-5-yl] propyl}amino)but-2-enoate;
Ethyl (E)-4-((4-(10-benzyl-3-chloro-11-oxo-10,11-dihydro-5H-dibenzo[b,e][1,4]diazepin-5-yl)butyl)amino)but-2-enoate;
Methyl (E)-4-{[4-(3-chloro-10-methyl-11-oxo-10,11-dihydro-5H-dibenzo[b,e][1,4]diazepin-5-yl)butyl](methyl) amino}but-2-enoate;
(E)-4-{[4-(3-chloro-10-methyl-11-oxo-10,11-dihydro-5H-dibenzo[b,e][1,4]diazepin-5-yl)butyl](methyl)amino}-N-methoxy-N-methyl-but-2-enamide;
3-Chloro-10-methyl-5-(4-{methyl[(E)-4-oxopent-2-en-1-yl]amino}butyl)-5,10-dihydro-11H-dibenzo[b,e][1,4]diazepin-11-one;
Methyl (E)-4-{[4-(10-benzyl-3-chloro-11-oxo-10,11-dihydro-5H-dibenzo[b,e][1,4]diazepin-5-yl)butyl](methyl) amino}but-2-enoate;
(E)-4-{[4-(10-Benzyl-3-chloro-11-oxo-10,11-dihydro-5H-dibenzo[b,e][1,4]diazepin-5-yl)butyl](methyl)amino}-N-methoxy-N-methyl-but-2-enamide;
10-Benzyl-3-chloro-5-(4-{methyl[(E)-4-oxo-pent-2-en-1-yl]amino}butyl)-5,10-dihydro-11H-dibenzo[b,e][1,4]diazepin-11-one;
(E)-4-{[4-(10-benzyl-3-chloro-11-oxo-10,11-dihydro-5H-dibenzo[b,e][1,4]diazepin-5-yl)butyl](methyl)amino}but-2-enenitrile;
Methyl (E)-4-[4-(3-chloro-10,11-dihydro-5H-dibenzo[b,f]azepin-5-yl)butylamino]but-2-enoate;
Ethyl (E)-4-{[4-(3-chloro-10,11-dihydro-5H-dibenzo[b,f]azepin-5-yl)butyl]-methyl-amino}but-2-enoate;
Ethyl (E)-4-{[4-(3-chloro-10,11-dihydro-dibenzo[b,f]azepin-5-yl)butyl]-ethyl-amino}but-2-enoate;
Ethyl (E)-4-{[4-(3-chloro-10,11-dihydro-dibenzo[b,f]azepin-5-yl)butyl]-isopropyl-amino}but-2-enoate;
(E)-4-{[4-(3-chloro-10,11-dihydro-5H-dibenzo[b,f]azepin-5-yl)butyl]amino}-N-methyl-but-2-enamide;
Ethyl (E)-4-[4-(7-Chloro-2-methoxy-10,11-dihydro-dibenzo[b,f]azepin-5-yl)-butylamino]-but-2-enoate;
Methyl (E)-4-[4-(3-chlorodibenzo[b,e][1,4]oxazepin-5 (11H)-yl)butyl-methyl-amino]-but-2-enoate;
(E)-4-[4-(3-Chlorodibenzo[b,e][1,4]oxazepin-5(11H)-yl) butyl-methyl-amino]-N-methoxy-N-methyl-but-2-enamide;
(E)-5-[4-(3-Chlorodibenzo[b,e][1,4]oxazepin-5(11H)-yl) butyl-methyl-amino]pent-3-en-2-one;
(E)-4-[4-(3-chloro-10,11-dihydro-5H-dibenzo[b,f]azepin-5-yl)butylamino]but-2-enenitrile;
(E)-4-[4-(3-Chloro-10,11-dihydro-5H-dibenzo[b,f]azepin-5-yl)butyl-methyl-amino]-but-2-enamide;
(E)-4-[4-(3-Chloro-10,11-dihydro-5H-dibenzo[b,f]azepin-5-yl)butyl-methyl-amino]but-2-enenitrile;
Ethyl (E)-4-[4-(7-Chloro-2-hydroxymethyl-10,11-dihydro-dibenzo[b,f]azepin-5-yl)-butylamino]-but-2-enoate;
Ethyl (E)-4-[4-(7-chloro-2-methoxymethyl-10,11-dihydro-dibenzo[b,f]azepin-5-yl)-butylamino]-but-2-enoate;
Ethyl (E)-4-[4-(7-chloro-2-methoxyethoxymethyl-10,11-dihydro-dibenzo[b,f]azepin-5-yl)-butylamino]-but-2-enoate;
(E)-4-[4-(3-Chloro-10,11-dihydro-5H-dibenzo[b,f]azepin-5-yl)butyl-methyl-amino]-N-methyl-N-prop-2-ynoxy-but-2-enamide;
(E)-4-[4-(3-Chloro-10,11-dihydro-5H-dibenzo[b,f]azepin-5-yl)butylamino]-N-methoxy-but-2-enamide;
(E)-4-[4-(3-chloro-10,11-dihydro-5H-dibenzo[b,f]azepin-5-yl)butylamino]-N-benzyloxy-but-2-enamide;
(E)-4-[4-(3-chloro-10,11-dihydro-5H-dibenzo[b,f]azepin-5-yl)butylamino]-N-ethoxy-but-2-enamide;
(E)-4-[4-(3-chloro-10,11-dihydro-5H-dibenzo[b,f]azepin-5-yl)butylamino]-N-isopropoxy-but-2-enamide;
(E)-4-[4-(3-chloro-10,11-dihydro-5H-dibenzo[b,f]azepin-5-yl)butylamino]-N-phenoxy-but-2-enamide;
(E)-4-[4-(3-Chloro-10,11-dihydro-5H-dibenzo[b,f]azepin-5-yl)butylamino]-N-(4-piperidyloxy)-but-2-enamide;
(E)-4-[4-(3-Chloro-10,11-dihydro-5H-dibenzo[b,f]azepin-5-yl)butylamino]-N-(2-phenylethyloxy)-but-2-enamide;
(E)-4-[4-(3-Chloro-10,11-dihydro-5H-dibenzo[b,f]azepin-5-yl)butyl-methyl-amino]-N-methoxy-but-2-enamide;
Ethyl (E)-4-{[4-(3-chloro-10-[2-(2-methoxyethoxy)ethyl]-11-oxo-10,11-dihydro-5H-dibenzo[b,e][1,4]diazepin-5-yl)butyl]amino}but-2-enoate;
Ethyl (E)-4-{[4-(3-chloro-10-[2-[2-(2-methoxyethoxy) ethoxy]ethyl]-11-oxo-10,11-dihydro-5H-dibenzo[b,e][1, 4]diazepin-5-yl)butyl]amino}but-2-enoate;
Ethyl (E)-4-{[4-(3-chloro-10-[2-(prop-2-yn-1-yloxy)ethyl]-11-oxo-10,11-dihydro-5H-dibenzo[b,e][1,4]diazepin-5-yl)butyl]amino}but-2-enoate;
Methyl (E)-4-{4-[7-chloro-2-(2-prop-2-ynoxyethoxy)-10, 11-dihydro-5H-dibenzo[b,f]azepin-5-yl]-butyl-methyl-amino}-but-2-enoate;

(E)-4-{4-[7-chloro-2-(2-prop-2-ynoxyethoxy)-10,11-dihydro-5H-dibenzo[b,f]azepin-5-yl]butyl-methyl-amino}but-2-enenitrile;
Prop-2-yn-1-yl (E)-4-[4-(3-chloro-10,11-dihydro-5H-dibenzo[b,f]azepin-5-yl)butylamino]but-2-enoate;
2-Prop-2-ynyloxy-ethyl (E)-4-[4-(3-chloro-10,11-dihydro-5H-dibenzo[b,f]azepin-5-yl)butylamino] but-2-enoate;
2-(2-Methoxy-ethoxy)-ethyl (E)-4-[4-(3-chloro-10,11-dihydro-dibenzo[b,f]azepin-5-yl)-butylamino]but-2-enoate:
2-[2-(2-{2-[5-((3aS,4S,6aR)-2-Oxo-hexahydro-thieno[3,4-d]imidazol-4-yl)-pentanoylamino]-ethoxy}-ethoxy)-ethoxy]-ethyl (E)-4-{[4-(3-chloro-10,11-dihydro-dibenzo[b,f]azepin-5-yl)-butyl]-methyl-amino}but-2-enoate;
2-(2-{2-[2-(2-{2-[5-((3aS,4S,6aR)-2-Oxo-hexahydro-thieno[3,4-d]imidazol-4-yl)-pentanoylamino]-ethoxy}-ethoxy)-ethoxy]-ethoxy}-ethoxy)-ethyl (E)-4-{[4-(3-chloro-10,11-dihydro-dibenzo[b,f]azepin-5-yl)-butyl]-methyl-amino}but-2-enoate;
2-(2-{2-[2-(2-{2-[2-(2-{2-[5-((3aS,4S,6aR)-2-Oxo-hexahydro-thieno[3,4-d]imidazol-4-yl)-pentanoylamino]-ethoxy)-ethoxy]-ethoxy}-ethoxy)-ethoxy]-ethoxy}-ethoxy)-ethyl (E)-4-{[4-(3-chloro-10,11-dihydro-dibenzo[b,f]azepin-5-yl)-butyl]-methyl-amino} but-2-enoate;
Ethyl (E)-4-{4-[7-Chloro-2-(2-methoxy-ethoxy)-10,11-dihydro-5H-dibenzo[b,f]azepin-5-yl]-butylamino}-but-2-enoate;
Ethyl (E)-4-(4-{7-chloro-2-[2-(2-methoxy-ethoxy)-ethoxy]-10,11-dihydro-5H-dibenzo[b,f]azepin-5-yl}-butylamino)-but-2-enoate;
5-((3aS,4S,6aR)-2-Oxo-hexahydro-thieno[3,4-d]imidazol-4-yl)-(2-{2-[2-(2-{4-[2-(7-chloro-5-{4-[((E)-3-cyano-allyl)-methyl-amino]-butyl}-10,11-dihydro-5H-dibenzo[b,f]azepin-2-yloxy)-ethoxymethyl]-[1,2,3] triazol-1-yl}-ethoxy)-ethoxy]-ethoxy}-ethyl)pentanamide;
Ethyl (E)-4-[4-(7-Chloro-2-prop-2-ynyloxy-10,11-dihydro-dibenzo[b,f]azepin-5-yl)-butylamino]-but-2-enoate;
Ethyl (E)-4-[4-(2-benzyloxy-7-chloro-10,11-dihydro-dibenzo[b,f]azepin-5-yl)-butylamino]-but-2-enoate; and
2-methoxy-ethyl (E)-4-[4-(3-chloro-10,11-dihydro-dibenzo[b,f]azepin-5-yl)-butylamino]-but-2-enoate;
or a stereoisomer, a solvate, a tautomer or a pharmaceutically acceptable salt thereof.

Preferably, said pharmaceutically acceptable salt is a hydrochloride salt, a fumarate salt or a maleate salt.

Preferably, said compound or stereoisomer, solvate, tautomer or pharmaceutically acceptable salt thereof is an inhibitor of an E3 ligase comprising a HECT domain. More preferably, said compound or stereoisomer, solvate, tautomer or pharmaceutically acceptable salt thereof is an inhibitor of an E3 ligase belonging to the NEDD4 family. Still preferably, said compound or stereoisomer, solvate, tautomer or pharmaceutically acceptable salt thereof is an inhibitor of NEDD4, ITCH, SMURF1, SMURF2, WWP1, WWP2, HECW1 and/or HECW2, more preferably of NEDD4.

It is also an object of the present invention the compound or stereoisomer, solvate, tautomer or pharmaceutically acceptable salt thereof as defined above for use as a medicament.

Preferably, said medicament is an inhibitor of at least one E3 ligase comprising a HECT domain as herein defined, preferably, said medicament is a NEDD4 inhibitor.

In particular, it is an object of the present invention the compound or stereoisomer, solvate, tautomer or pharmaceutically acceptable salt thereof as defined above for use in the prevention and/or treatment of a condition wherein an E3 ligase comprising a HECT domain is deregulated, preferably said E3 ligase comprising a HECT domain is an E3 ligase belonging to the NEDD4 family, more preferably said E3 ligase is NEDD4, ITCH, SMURF1, SMURF2, WWP1, WWP2, HECW1 and/or HECW2, still preferably it is NEDD4.

Preferably, said compound or stereoisomer, solvate, tautomer or pharmaceutically acceptable salt thereof as defined above is for use in the prevention and/or treatment of a pathology selected from the group consisting of: cancer, an infectious disease, hypertension, a cardiovascular disease, a neurological disorder, a neurodegenerative disease, inflammation, an autoimmune disorder and an autism spectrum disorder.

Preferably, said cancer is selected from the group consisting of: leukemia, lymphoma, gastric carcinoma, breast cancer, medulloblastoma, prostate cancer, colon cancer, non-small cell lung cancer, hepatocellular carcinoma, pancreas cancer, glioblastoma, glioma, colorectal cancer, pancreatic adenocarcinoma, endometrial cancer, bladder cancer, lung cancer, a myelodysplastic syndrome, multiple myeloma, mammary tumor, pulmonary tumor, pleural mesothelioma, adenocarcinoma, small-cell lung cancer, skin tumor, Kaposi's sarcoma, osteosarcoma, fibrosarcoma, rhabdomyosarcoma, neuroblastoma, cerebral tumor, head and neck cancer, testicular tumor, ovarian tumor, cervical carcinoma, thyroid carcinoma, gastric tumor, gastrointestinal adenocarcinoma, pancreatic carcinoma, renal tumor, teratocarcinoma and embryonic carcinoma, said leukemia being preferably acute and chronic myeloid leukaemia, acute and chronic lymphoblastic leukaemia or adult T-cell leukemia, said lymphoma being preferably Hodgkin's lymphoma, non-Hodgkin's lymphoma, cutaneous and peripheral T-cell lymphoma or large B-cell lymphoma, said prostate cancer being preferably advanced prostate cancer, said colon cancer being preferably colon adenocarcinoma or colon adenoma, said glioblastoma being preferably a giant cell glioblastoma or a gliosarcoma, said skin tumor being preferably a melanoma, a basal cell carcinoma (basalioma), a squamous cell carcinoma, or a keratocanthoma said thyroid carcinoma being preferably thyroid follicular cancer, said pancreatic carcinoma being preferably exocrine pancreatic carcinoma. More preferably, said cancer is selected from the group consisting of: leukemia, lymphoma, gastric carcinoma, breast cancer, medulloblastoma, prostate cancer, colon cancer, non-small cell lung cancer, hepatocellular carcinoma, pancreas cancer, melanoma and glioblastoma. Preferably, said cancer is primary or metastatic.

Preferably, said infectious disease is caused or determined by a virus. Preferably, said virus is selected from the group consisting of: a Japanese encephalitis virus, an influenza virus, a filovirus, a retrovirus and an arenavirus. Preferably, said filovirus is an Ebola virus or a Marburg virus. Preferably, said retrovirus is a human immunodeficiency virus (HIV) or a murine leukemia virus (MLV). Preferably, said arenavirus is a Lassa virus or a Junin virus. Then, the compounds of the present invention are for use in the prevention and/or treatment of a Japanese encephalitis virus, an influenza virus, a filovirus, a retrovirus and an arenavirus, said filovirus being preferably an Ebola virus or a Marburg virus, said retrovirus being preferably a human immunodeficiency virus (HIV) or a murine leukemia virus (MLV), said arenavirus being preferably a Lassa virus or a Junin virus.

In the context of the invention, neurological disorders include Angelman syndrome (AS). Preferably, neurodegenerative diseases include familial amyotrophic sclerosis (FALS) and amyotrphic lateral sclerosis as well as any motor dysfunction, degeneration of neurons in the lumbar spinal cord and muscle atrophy.

Preferably, said compound or stereoisomer, solvate, tautomer or pharmaceutically acceptable salt thereof as defined above is for use as an inhibitor of an E3 ligase comprising a HECT domain in the treatment of any one or more of the above defined conditions and/or pathologies, said E3 ligase comprising a HECT domain being as herein defined and including in particular NEDD4.

In another embodiment, the present invention provides a method of preventing and/or treating the above-indicated conditions and pathologies, wherein the method comprises the step of administering an effective amount of the compound of general formula (I) or the stereoisomer, solvate, tautomer or pharmaceutically acceptable salt thereof as defined above to a subject in need thereof.

In a further embodiment, the present invention provides the use of the compound of general formula (I) or the stereoisomer, solvate, tautomer or pharmaceutically acceptable salt thereof as defined above for the manufacture of a medicament for preventing and/or treating the above-indicated conditions and pathologies.

The invention also provides the compound or stereoisomer, solvate, tautomer or pharmaceutically acceptable salt thereof as defined above for use in combination with radiotherapy and/or at least one additional therapeutic agent. Preferably, said at least one additional therapeutic agent is a chemotherapeutic agent or an antiretroviral drug. More preferably, said additional therapeutic agent is selected from the group consisting of: histone deacetylase inhibitor, retinoid receptor modulator, anti-proliferative/antineoplastic agent, cytostatic agent, agent which inhibits cancer cell invasion, inhibitor of growth factor function, anti-angiogenic agent, cell cycle inhibitor, proteasome inhibitor, HSP90 inhibitor, COX-2 inhibitor, non selective NSAID, anti-CD20 antibody, anti-interleukin 6 antibody, immunomodulator agent, epigenetic drug, IDH-1/2 inhibitor, PARP inhibitor, DNA damage response inhibitor, WEE1 inhibitor, standard chemotherapy combination, Nucleoside/Nucleotide Reverse Transcriptase Inhibitor, non Nucleoside/Nucleotide Reverse Transcriptase Inhibitor, protease inhibitor, fusion inhibitor, CCR5 antagonist, integrase inhibitor, monoclonoal antibody and combinations thereof.

It is also an object of the present invention a combination of the compound or stereoisomer, solvate, tautomer or pharmaceutically acceptable salt thereof as defined above and at least one additional therapeutic agent, said at least one additional therapeutic agent being preferably as defined above.

It is another object of the present invention a pharmaceutical composition comprising the compound or stereoisomer, solvate, tautomer or pharmaceutically acceptable salt thereof as defined above and a pharmaceutically acceptable excipient and/or diluent.

Preferably, the pharmaceutical composition further comprises at least one additional therapeutic agent, said at least one additional therapeutic agent being preferably as defined above.

Preferably, the pharmaceutical composition is intended for the medical uses defined above for the compounds of the invention. In particular, the pharmaceutical composition is for use in the prevention and/or treatment of a condition wherein an E3 ligase comprising a HECT domain is deregulated, preferably said E3 ligase comprising a HECT domain is an E3 ligase belonging to the NEDD4 family, more preferably said E3 ligase is NEDD4, ITCH, SMURF1, SMURF2, WWP1, WWP2, HECW1 and/or HECW2, still preferably it is NEDD4. The pharmaceutical composition may alternatively or additionally be for use in the prevention and/or treatment of a pathology selected from the group consisting of: cancer (in particular cancer as defined above), an infectious disease (in particular an infectious disease as defined above), hypertension, a cardiovascular disease, a neurological disorder, a neurodegenerative disease, inflammation, an autoimmune disorder and an autism spectrum disorder.

It is a further object of the present invention a process for the preparation of a compound of formula (I) as defined above, comprising at least one of the following steps:

reacting a compound of formula A1

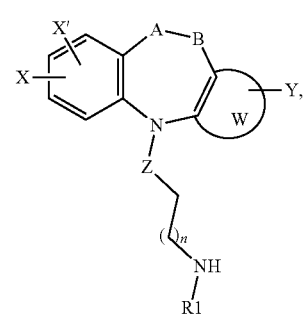

A1 wherein A-B, X, X' Y, W, Z, R1 and n are as defined above, with an aldehyde of formula CHOCH=CHCOOR4, wherein R4 is $C_1$-$C_6$ alkyl optionally substituted as defined above, in the presence of a reducing agent to obtain a compound of formula (I) as defined above, wherein R2 is COOR4, R3 is H, R4 is $C_1$-$C_6$ alkyl optionally substituted as defined above and m is 1;

reacting a compound of formula A1

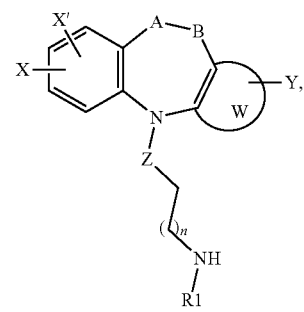

A1 wherein A-B, X, X', Y, W, Z, R1 and n are as defined above, with an allylic compound of formula LG-$CH_2$CH=CHCOOR4, wherein R4 is $C_1$-$C_6$ alkyl optionally substituted as defined above and LG is a leaving group, optionally in the presence of a base to obtain a compound of formula (I) as defined above, wherein R2 is COOR4, R3 is H, R4 is $C_1$-$C_6$ alkyl optionally substituted as defined above and m is 1;

reacting a compound of formula A1d

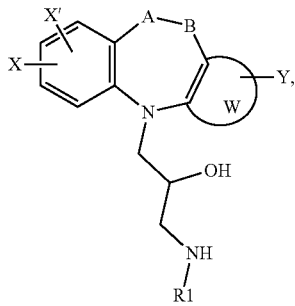

A1d wherein A-B, X, X', Y, W and R1 are as defined above, with an aldehyde of formula CHOCH=CHCOOR4, wherein R4 is $C_1$-$C_6$ alkyl optionally substituted as defined above, in the presence of a reducing agent to obtain a compound of formula (I) as defined above, wherein Z is $CH_2$, R2 is COOR4, R3 is OH, R4 is $C_1$-$C_6$ alkyl optionally substituted as defined above, m is 1 and n is 1;

reacting a compound of formula A1d

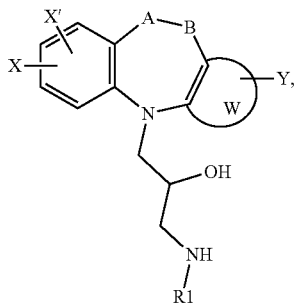

A1d wherein A-B, X, X', Y, W and R1 are as defined above, with an allylic compound of formula LG-$CH_2$CH=CHCOOR4, wherein R4 is $C_1$-$C_6$ alkyl optionally substituted as defined above and LG is a leaving group, optionally in the presence of a base to obtain a compound of formula (I) as defined above, wherein Z is $CH_2$, R2 is COOR4, R3 is OH, R4 is $C_1$-$C_6$ alkyl optionally substituted as defined above, m is 1 and n is 1;

reacting a compound of formula A10

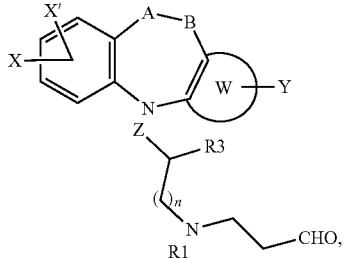

A10 wherein A-B, X, X', Y, W, Z, R1, R3 and n are as defined above, with a phosphorane of formula $Ph_3P$=CHCOOR4, wherein R4 is $C_1$-$C_6$ alkyl optionally substituted as defined above to obtain a compound of formula (I) as defined above wherein R2 is COOR4, R4 is $C_1$-$C_6$ alkyl optionally substituted as defined above and m is 2.

Preferably, the compound A1 wherein Z is $CH_2$ and R1 is H, labelled as compound A1a, is prepared by a process according to scheme B1:

Scheme B1

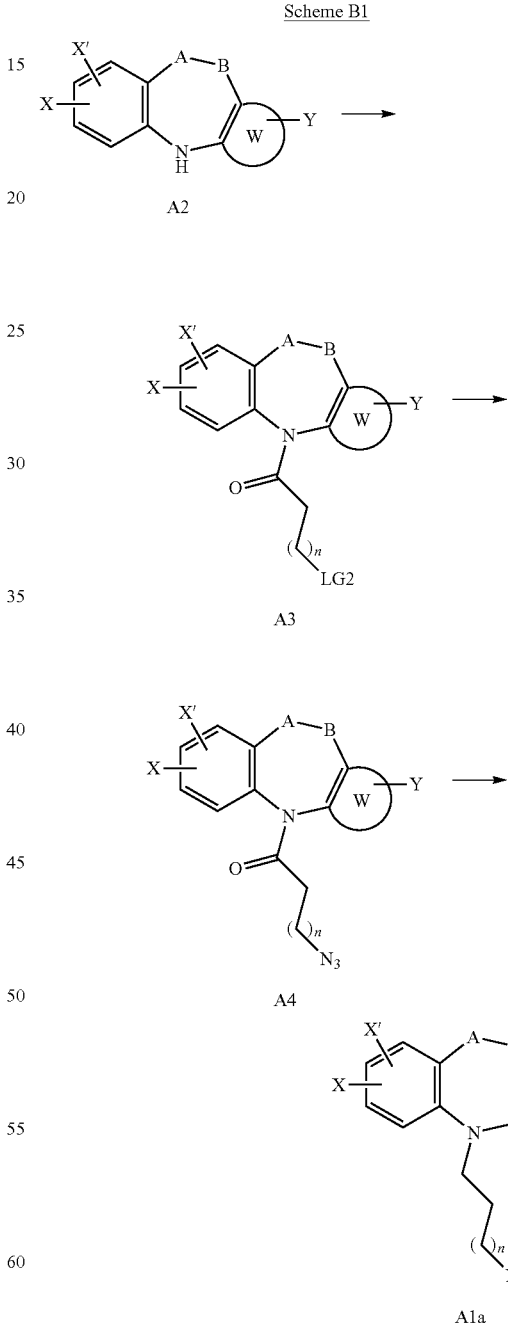

Preferably, the compound A1 wherein Z is $CH_2$, labelled as compound A1b, is prepared by a process according to scheme B2:

Scheme B2
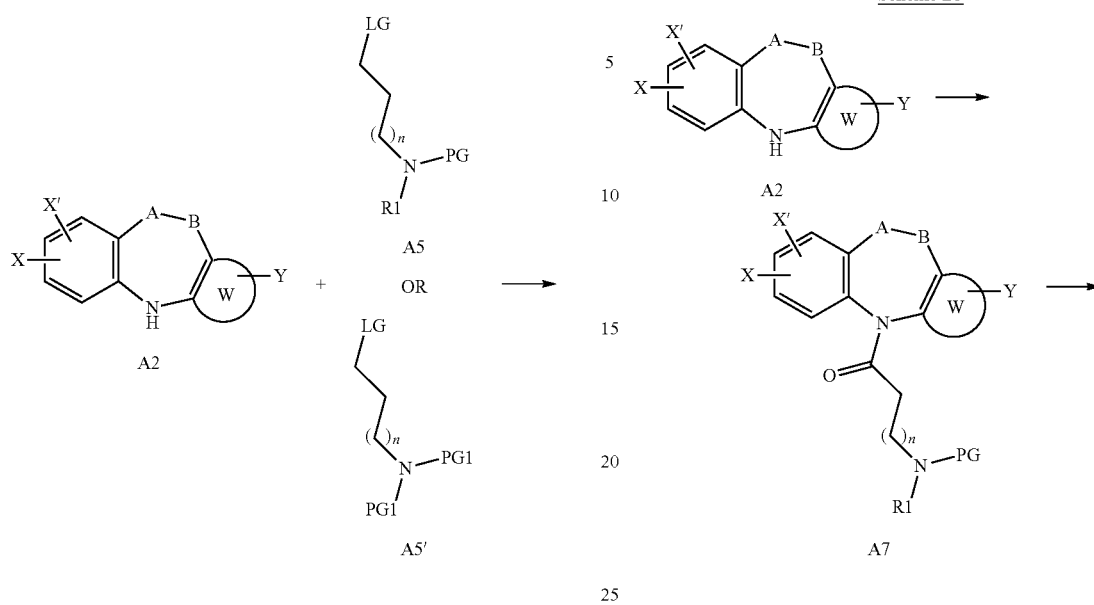
A2
A5
OR
A5'
A6
OR
A6'
A1b
Preferably, the compound of formula A1 wherein Z is CO, labelled as compound A1c, is prepared by a process according to scheme B3:
Scheme B3
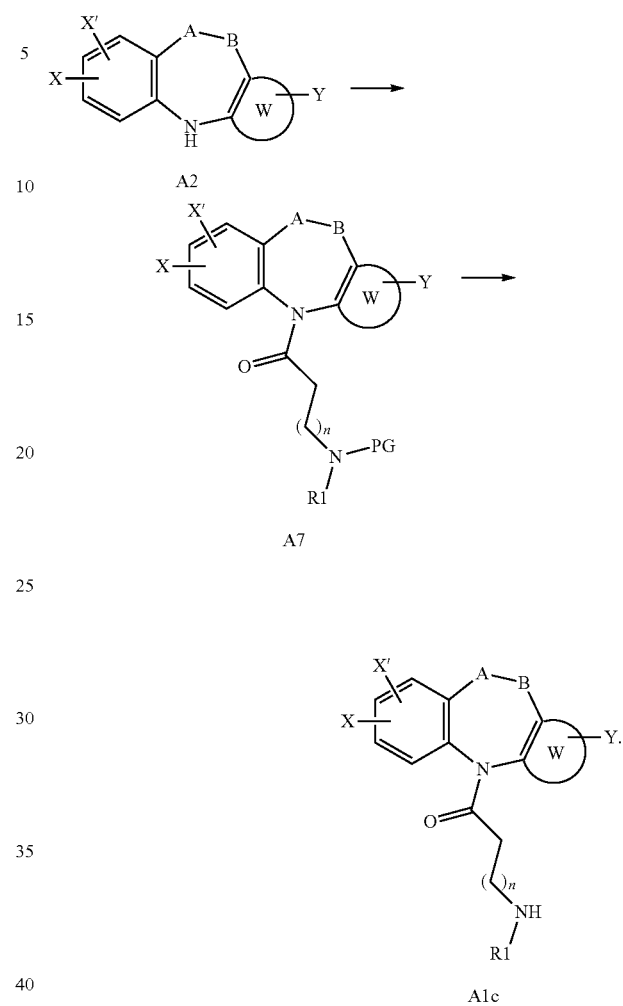
A2
A7
A1c
Preferably, the compound of formula A1d is prepared by a process according to scheme B4:
Scheme B4
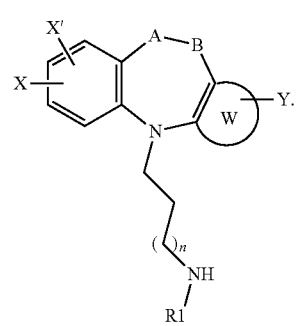
A2
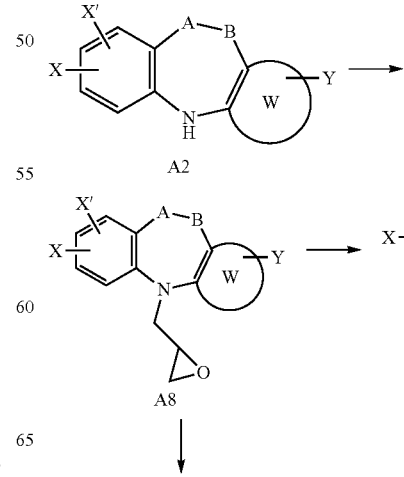
A8
A1d -continued

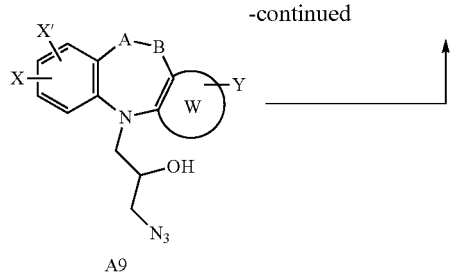

A9

Preferably, the compound of formula A10 is prepared by a process according to scheme B5:

Scheme B5

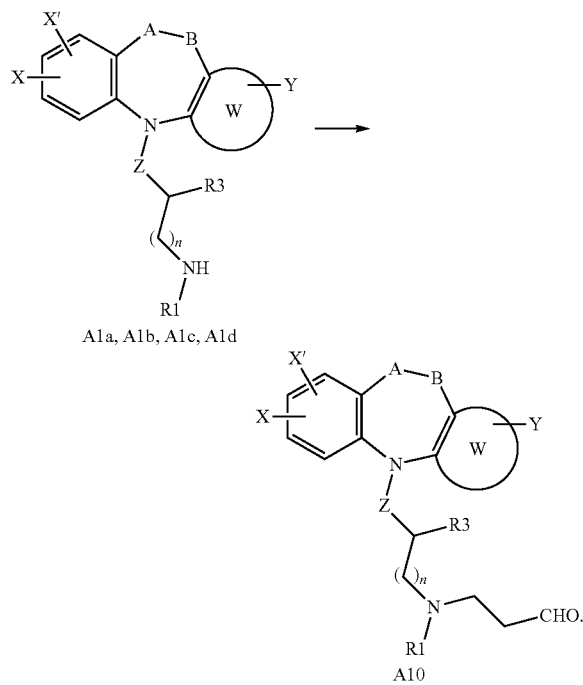

A1a, A1b, A1c, A1d

A10

Preferably, the process as defined above further comprises at least one of the following steps:
hydrolysis of a compound of general formula (I) as defined above, wherein R2 is COOR4 and R4 is $C_1$-$C_6$ alkyl optionally substituted as defined above to obtain a compound of general formula (I) as defined above, wherein R2 is COOR4 and R4 is H;
treating a compound of general formula (I) as defined above, wherein R2 is COOR4 and R4 is $C_1$-$C_6$ alkyl, with N,O-dimethylhydroxylamine in the presence of a suitable Grignard reagent to obtain a Weinreb amide and reacting said Weinreb amide with a reagent of formula R5-MgBr, R5-MgCl or R5-Li, wherein R5 is as defined above, to obtain a compound of general formula (I) as defined above, wherein R2 is COR5 and R5 is as defined above;
treating a compound of general formula (I) as defined above, wherein R2 is COOR4 and R4 is H, with an amine of formula R6R7NH, wherein R6 and R7 are as defined above, in the presence of a coupling agent to obtain a compound of general formula (I) as defined above, wherein R2 is CONR6R7 and R6 and R7 are as defined above;
treating a compound of general formula (I) as defined above, wherein R2 is COOR4 and R4 is $C_1$-$C_6$ alkyl optionally substituted as defined above, with an amine of formula R6R7NH, wherein R6 and R7 are as defined above, in the presence of a base to obtain a compound of general formula (I) as defined above, wherein R2 is CONR6R7 and R6 and R7 are as defined above;
treating a compound of general formula (I) as defined above, wherein R2 is CONR6R7 and R6 and R7 are H, with a dehydrating agent to obtain a compound of general formula (I) as defined above, wherein R2 is CN.

Preferably, in any one or more of the above steps, $C_1$-$C_6$ alkyl in position R4 is unsubstituted.

Said Weinreb amide is a further object of the present invention.

The present invention also provides the compound or stereoisomer, solvate, tautomer or pharmaceutically acceptable salt thereof as defined above for use in a method of inhibiting an E3 ligase comprising a HECT domain, preferably said E3 ligase comprising a HECT domain is an E3 ligase belonging to the NEDD4 family, more preferably said E3 ligase comprising a HECT domain is NEDD4, ITCH, SMURF1, SMURF2, WWP1, WWP2, HECW1 and/or HECW2, still preferably it is NEDD4.

The present invention further provides an in vitro method of inhibiting an E3 ligase comprising a HECT domain by using the compound or stereoisomer, solvate, tautomer or pharmaceutically acceptable salt thereof as defined above, preferably said E3 ligase comprising a HECTC domain is an E3 ligase belonging to the NEDD4 family, more preferably said E3 ligase comprising a HECT domain is NEDD4, ITCH, SMURF1, SMURF2, WWP1, WWP2, HECW1 and/or HECW2, still preferably it is NEDD4.

In the instant invention, "aryl" represents a mono or bicyclic aromatic ring system of 5 to 10 atoms, examples of such an aryl are phenyl, indenyl, indanyl, naphthyl and tetrahydronaphthalenyl. A very preferred aryl is phenyl. Preferably, any one or more of the above-mentioned aryl(s) is phenyl.

"Heteroaryl" represents a mono or bicyclic heteroaromatic ring system of 5 to 10 members, which contains at least one heteroatom selected from nitrogen, oxygen or sulphur and one to nine carbon atoms. Examples of said heteroaryls include, but are not limited to: pyrrolyl, furyl, thienyl, pyrazolyl, imidazolyl, oxazolyl, thiazolyl, 1,2,3-oxadiazolyl, 1,3,4-thiadiazolyl, tetrazolyl, pyridyl, pyridazinyl, pyrimidinyl, pyrazinyl, indolyl, isoindolyl, benzo[b]furanyl, benzo[b]thienyl, benzopyranyl, indazolyl, benzimidazolyl, purinyl, quinolyl, isoquinolyl, quinazolinyl, and quinoxalinyl. Preferred heteroaryls are pyrazolyl and pyrimidinyl.

The term "halogen" refers to fluoro, chloro, bromo, or iodo. Preferably, halogen is chloro.

The term "$C_1$-$C_6$ alkyl" refers to a straight or branched hydrocarbon chain radical, consisting solely of carbon and hydrogen atoms, having from one to six carbon atoms. Suitable examples of $C_1$-$C_6$ alkyl include methyl, ethyl, n-propyl, isopropyl, butyl, tert-butyl, pentyl, and hexyl. Preferably, $C_1$-$C_6$ alkyl is methyl or ethyl. Also preferably, $C_1$-$C_6$ alkyl is a $C_1$-$C_3$ alkyl, i.e. a straight or branched hydrocarbon chain radical, consisting solely of carbon and hydrogen atoms, having from one to three carbon atoms.

The term "$C_{3-6}$ cycloalkyl" refers to a saturated monocyclic hydrocarbon ring system having three to six carbon atoms. Suitable examples of $C_{3-6}$-cycloalkyl groups include cyclopropyl, cyclobutyl, cyclopentyl, and cyclohexyl. Preferably, $C_{3-6}$-cycloalkyl is cyclopropyl.

The term "$C_1$-$C_6$ alkoxy" refers to a straight or branched O—$C_1$-$C_6$ alkyl, where alkyl is as defined herein. The "$C_1$-$C_6$ alkoxy" group is preferably a linear or branched $C_1$-$C_4$ alkoxy group, more preferably a $C_1$-$C_2$ alkoxy group.

Terms including the term "alkyl" such as alkylamino or dialkylamino will be understood by those skilled in the art to comprise an alkyl group as defined above linked to other functional group, where the alkylamino, dialkylamino or other alkyl-functionality group is linked to the compound through the last group listed. Suitable, but not limiting examples of alkylamino or dialkylamino groups include methylamino, ethylamino, isopropylamino and dimethylamino. The term "heterocycloalkyl" means a non-aromatic monocyclic or polycyclic ring comprising carbon and hydrogen atoms and at least one heteroatom, preferably, 1 to 4 heteroatoms and/or preferably selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 2 to 6 carbon atoms and from 1 to 3 heteroatoms, referred to herein as "$C_2$-$C_6$ heterocycloalkyl".

The term "($C_1$-$C_6$-alkoxy)$C_1$-$C_6$-alkoxy" refers to a straight or branched O—$C_1$-$C_6$ alkyl bound to another straight or branched O—$C_1$-$C_6$ alkyl, where alkyl is as defined herein. The "($C_1$-$C_6$ alkoxy)$C_1$-$C_6$ alkoxy" group is preferably a linear or branched ($C_1$-$C_4$ alkoxy)$C_1$-$C_4$ alkoxy group, more preferably a ($C_1$-$C_2$ alkoxy)$C_1$-$C_2$ alkoxy group. Examples of ($C_1$-$C_6$-alkoxy)$C_1$-$C_6$-alkoxy groups include methoxyethoxy, ethoxyethoxy, methoxypropoxy, ethoxypropoxy. The term "[($C_1$-$C_6$-alkoxy)$C_1$-$C_6$-alkoxy]$C_1$-$C_6$-alkoxy" refers to a straight or branched ($C_1$-$C_6$-alkoxy)$C_1$-$C_6$-alkoxy bound to another straight or branched O—$C_1$-$C_6$ alkyl, where alkyl is as defined herein. The "[($C_1$-$C_6$-alkoxy)$C_1$-$C_6$-alkoxy]$C_1$-$C_6$-alkoxy" group is preferably a linear or branched [($C_1$-$C_4$ alkoxy)$C_1$-$C_4$ alkoxy]$C_1$-$C_4$ alkoxy group, more preferably a [($C_1$-$C_2$ alkoxy)$C_1$-$C_2$ alkoxy]$C_1$-$C_2$ alkoxy group. Examples of [($C_1$-$C_6$-alkoxy)$C_1$-$C_6$-alkoxy]$C_1$-$C_6$-alkoxy groups include methoxyethoxyethoxy, ethoxyethoxyethoxy, methoxyethoxypropoxy, ethoxyethoxypropoxy.

The term "$C_2$-$C_6$-alkynyl" refers to a straight or branched hydrocarbon chain radical, consisting solely of carbon and hydrogen atoms, having from two to six carbon atoms bound by at least one C—C triple bond. Suitable examples of $C_2$-$C_6$ alkynyl include ethynyl, propynyl, butynyl, pentynyl, and hexynyl.

The terms "$C_2$-$C_6$-alkynyloxy" or "$C_2$-$C_6$-alkynoxy" refer to straight or branched O—$C_2$-$C_6$ alkynyl where alkynyl is as defined herein. Suitable examples of $C_2$-$C_6$ alkynyloxy include ethynyloxy, propynyloxy, butynyloxy, pentynyloxy, and hexynyloxy.

It is to be understood that substituted groups may bear one or more substituents at any one or more positions.

Pharmaceutically acceptable salts comprise conventional non-toxic salts obtained by salification of a compound of formula (I) with inorganic acids (e.g. hydrochloric, hydrobromic, sulphuric, or phosphoric acids), or with organic acids (e.g. acetic, propionic, succinic, benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). Preferred pharmaceutically acceptable salts are hydrochloride, fumarate and maleate. For reviews on suitable pharmaceutical salts see Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc, New York 1996, Volume 13, page 453-497. Other salts, which are not pharmaceutically acceptable, for example the trifluoroacetate salt, may be useful in the preparation of compounds of this invention and these form a further aspect of the invention. The invention includes within its scope all possible stoichiometric and non-stoichiometric forms of the salts of the compounds of formula (I). Salification of the compounds of formula (I), and preparation of compounds of formula (I), free of their salts, may be carried out by known conventional methods.

In addition, the compounds of formula (I) may exist in unsolvated as well as in solvated forms with pharmaceutically acceptable solvents such as water, EtOH and the like.

Compounds of formula (I) may contain one or more asymmetric carbon atoms. The individual stereoisomers (enantiomers and diastereomers) as well as mixtures of these are included within the scope of the present invention.

Likewise, it is understood that compounds of the invention may exist in tautomeric forms other than that shown in the formula and all of these are also included within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the invention, for example, those in which a radioactive isotope such as 3H or $^{14}$C is incorporated, are useful in drug and/or substrate tissue distribution studies. Tritiated $^3$H, and carbon-14 $^{14}$C, isotopes are particularly preferred for their ease of preparation and detectability. Further, substitution with isotopes such as deuterium $^2$H, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the examples hereafter using appropriate isotopic variations of suitable reagents.

Compounds of general formula (Ia) as shown in Scheme A wherein A-B, X, X', Y, W, Z, R1 and n are as defined above, and R4 is $C_1$-$C_6$ alkyl can be prepared by standard chemical methods, e.g. according to Scheme A Scheme A

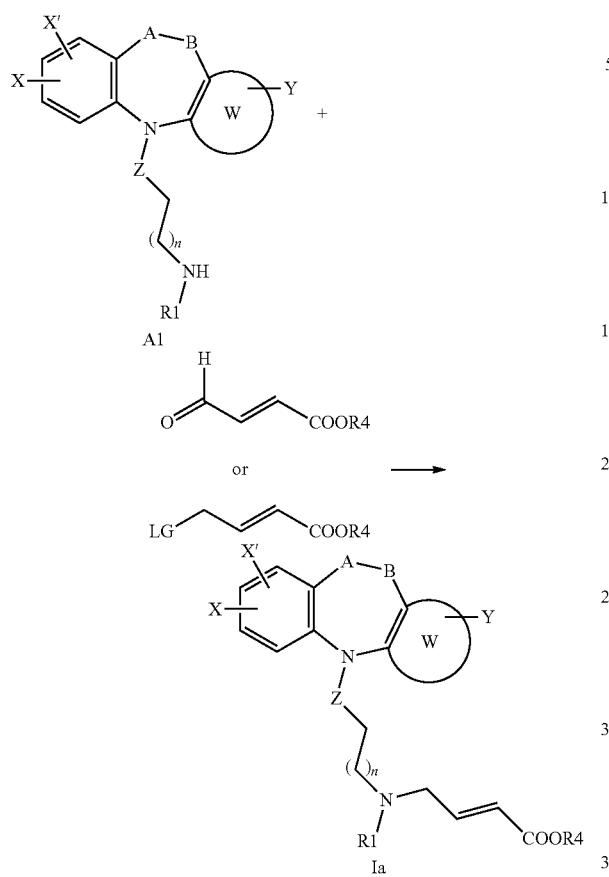

by reacting a compound of formula A1 as shown in Scheme A wherein A-B, X, X', Y, W, Z, R1 and n are as defined above, with the suitable aldehyde CHOCH=CHCOOR4 in the presence of a reducing agent, such as sodium borohydride, sodium cyanoborohydride, sodium triacetoxyborohydride, in a suitable solvent, e.g. methanol, dichloromethane (DCM), 1,2-dichloroethane, usually in the presence of acetic acid or trifluoroacetic acid (TFA), at a temperature ranging from 0° C. to the boiling temperature of the solvent; or with the suitable allylic compound LG-CH$_2$CH=CHCOOR4 wherein LG is a leaving group, such as Cl or Br, in the presence of a base such as potassium carbonate, sodium carbonate, cesium carbonate, in a suitable solvent, e.g. DCM, acetonitrile, tetrahydrofuran (THF), 1,4-dioxane, at a temperature ranging from 0° C. to the boiling temperature of the solvent.

Compounds of formula A1a as shown in Scheme B1 wherein A-B, X, X', Y, W and n are as defined above, can be prepared by known methods, e.g. according to Scheme B1

Scheme B1

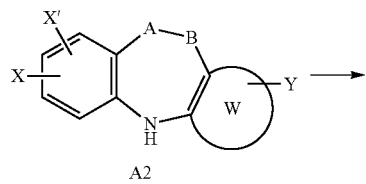

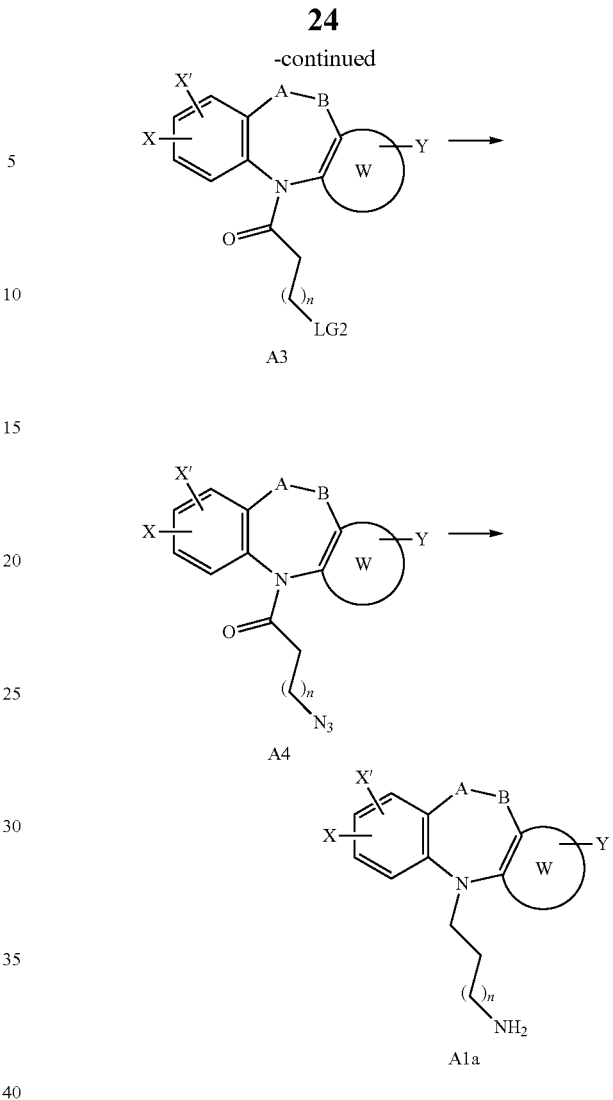

Compounds of formula A2 are known compounds or can be prepared by known methods. Compounds of formula A3 can be obtained by reacting a compound of formula A2 with a compound of formula LG1-COCH$_2$(CH$_2$)$_n$-LG2, wherein n is as defined above and LG1 and LG2 are suitable leaving groups (for LG1, e.g. Cl or Br, for LG2, e.g. Cl, Br, I, OSO$_2$Me, OSO$_2$(p-tolyl)), in a suitable solvent, such as THF, DCM, acetonitrile, toluene, at a temperature ranging from 0° C. to the boiling temperature of the solvent. Compounds of formula A4 can be obtained by reacting a compound of formula A3 for instance with sodium azide (NaN$_3$), in a solvent such as dimethylformamide (DMF), dimethylacetamide (DMA), toluene, acetonitrile, THF, in the presence of potassium iodide (KI), tetrabutylammonium iodide or a crown ether when needed, at a temperature ranging from 0° C. to the boiling temperature of the solvent. A compound of formula A1a can be obtained by treating a compound of formula A4 with a suitable reducing agent, e.g. borane, lithium aluminium hydride, triphenylphosphine/water in a solvent such as THF and at a temperature ranging from room temperature to the boiling temperature of the solvent.

Compounds of formula A1b as shown in Scheme B2 wherein A-B, X, X', Y, W, R1 and n are as defined above, can be prepared by known methods, e.g. according to Scheme B2

Scheme B2

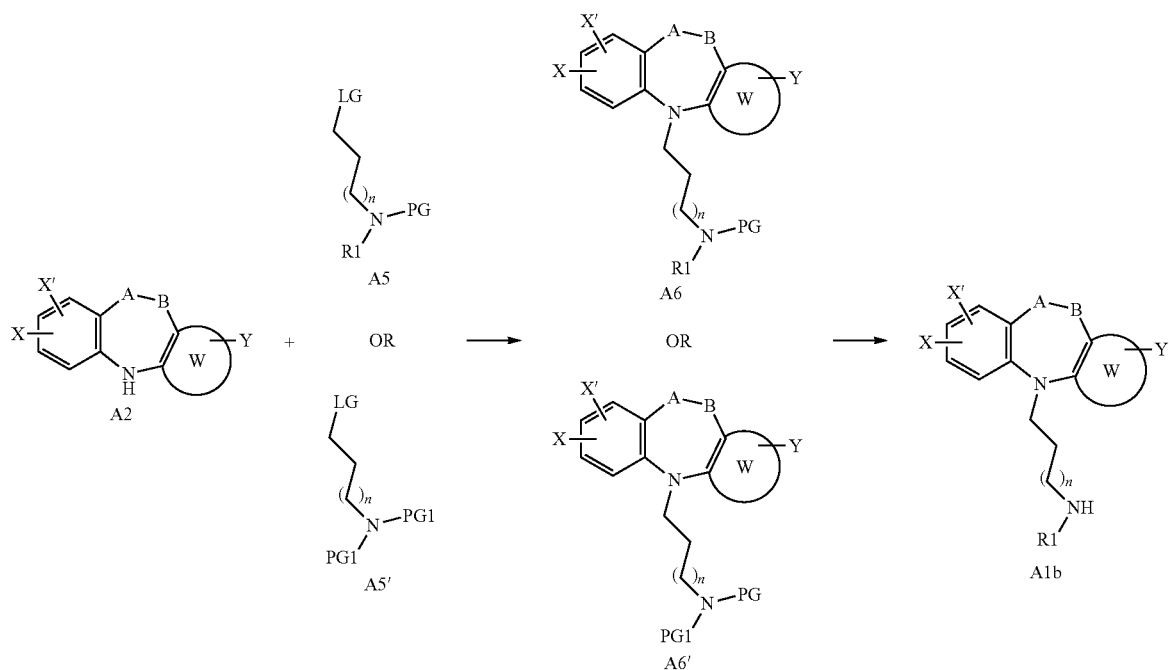

wherein LG is a suitable leaving group, e.g. Cl, Br, OSO₂Me or OSO₂(p-tolyl) and PG and PG1 are suitable protective groups chosen among those known in the art; examples of a suitable protective group for PG may include a carbamate, e.g. BOC, and examples for PG1 may include a carbamate, such as BOC, or the two PG1 taken together form a phthalimido group.

A compound of formula A6 or A6' can be obtained according to known methods, e.g. by reacting a compound of formula A2 with a compound of formula A5 or A5', in the presence of a base, for instance sodium hydride (NaH), n-butyllithium (n-BuLi), lithium or sodium bis(trimethylsilyl)amide, sodium amide, in the presence of KI, tetrabutylammonium iodide or a crown ether when needed, in a suitable solvent, e.g. DCM, THF, DMF, acetonitrile, toluene, at a temperature ranging from −78° C. to the boiling temperature of the solvent. A compound of formula A1b can be obtained from a compound of formula A6 or A6' by removing the protective group(s), e.g. in the case PG or PG1 is BOC, the deprotection of the amine can be achieved by treatment of the BOC protected amine with trifluoroacetic acid or hydrochloric acid (HCl) in solvents such as DCM, THF, diethyl ether, 1,4-dioxane or a methanol/1,4-dioxane mixture at a temperature ranging from 0° C. to room temperature; in the case the two PG1 taken together form a phthalimido group, hydrolysis of the protective group can be achieved by using hydrazine, in a solvent such as ethanol, preferably at the boiling temperature of the solvent.

Alternatively, compounds of formula A1c as shown in Scheme B3 wherein A-B, X, X', Y, W, R1 and n are as defined above can be prepared by known methods, e.g. according to Scheme B3

Scheme B3

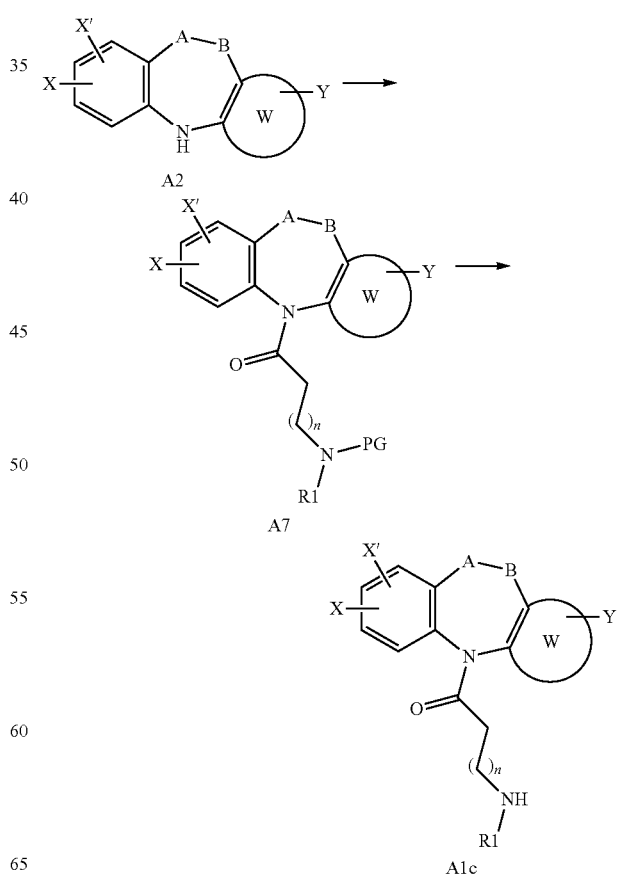

Compounds of formula A7, where PG is a suitable protective group chosen among those known in the art (e.g. a carbamate such as Fmoc) can be obtained by known methods, for instance by reaction of a compound of formula A2 with a suitable acyl chloride of formula ClCOCH$_2$(CH$_2$)$_n$NR1(PG) in a solvent such as toluene, DCM, THF, at a temperature ranging from room temperature to the boiling temperature of the solvent. Compounds of formula A1c can be obtained by removing the amino protective group, e.g. in the case PG is Fmoc, deprotection of the amine can be achieved by using for instance piperidine in DMF at room temperature.

Compounds of general formula (Ib) as shown in Scheme A1, wherein A-B, X, X', Y, W and R1 are as defined above and R4 is C$_1$-C$_6$ alkyl, can be prepared by standard chemical methods, e.g. according to Scheme A1

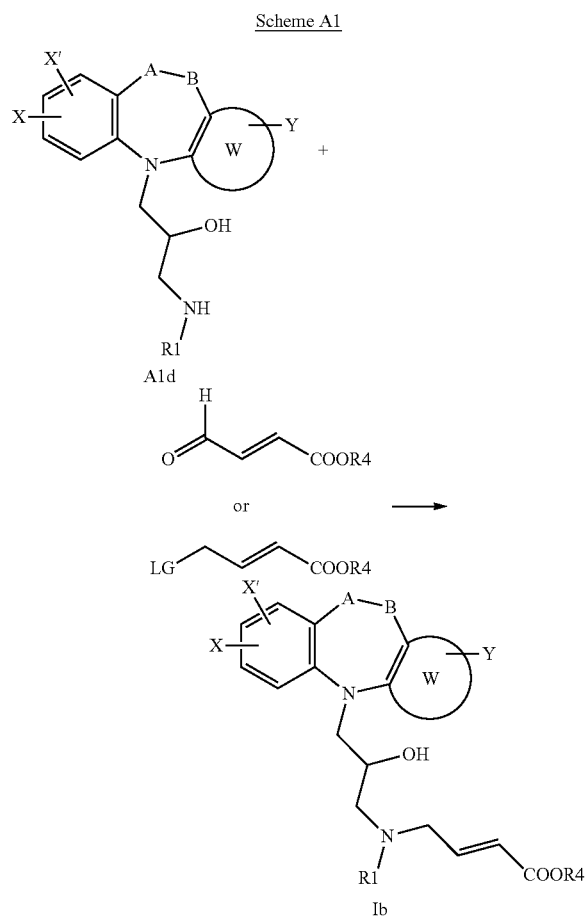

by reacting a compound of formula A1d as shown in Scheme A1 wherein A-B, X, X', Y, W and R1 are as defined above, with the suitable aldehyde CHOCH=CHCOOR4 in the presence of a reducing agent, such as sodium borohydride, sodium cyanoborohydride, sodium triacetoxyborohydride, in a suitable solvent (e.g. methanol, DCM, 1,2-dichloroethane), usually in the presence of acetic acid or TFA, at a temperature ranging from 0° C. to the boiling temperature of the solvent; or with the suitable allylic compound LG-CH$_2$CH=CHCOOR4 wherein LG is a leaving group, such as Cl or Br, in the presence of a base such as potassium carbonate, sodium carbonate, cesium carbonate, in a suitable solvent, e.g. acetonitrile, THF, 1,4-dioxane, a ta temperature ranging from 0° C. to the boiling temperature of the solvent.

Compounds of formula A1d as shown in Scheme B4, wherein A-B, X, X', Y, W and R1 are as defined above can be prepared by known methods, e.g. according to Scheme B4

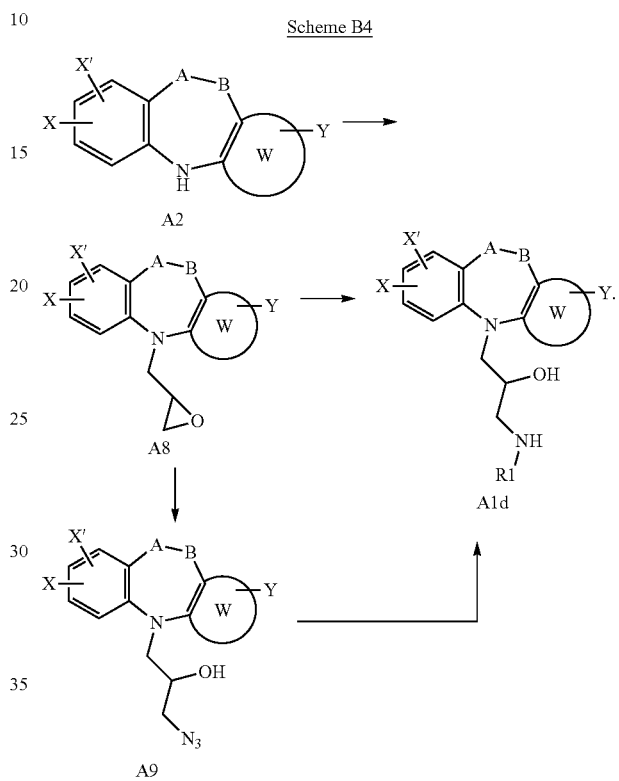

Compounds of formula A8 can be obtained by known methods, for instance by reaction of a compound of formula A2 with epichlorohydrin or epibromohydrin, in the presence of a base such as NaH, n-BuLi, lithium or sodium bis (trimethylsilyl)amide, sodium amide, in the presence of KI, tetrabutylammonium iodide or a crown ether when needed, in a suitable solvent, e.g. DCM, THF, DMF, acetonitrile, toluene, at a temperature ranging from −78° C. to the boiling temperature of the solvent. When R1 is H, a compound of formula A1d can be obtained for instance by first reacting a compound of formula A8 with NaN$_3$, in a solvent such as DMF, DMA, toluene, acetonitrile, THF, or an ethanol/water mixture in the presence of KI, tetrabutylammonium iodide, ammonium chloride or a crown ether when needed, at a temperature ranging from 0° C. to the boiling temperature of the solvent; and then reacting a compound of formula A9 with a suitable reducing agent, e.g. borane, lithium aluminium hydride, triphenylphosphine/water in a solvent such as THF, at a temperature ranging from 0° C. to the boiling temperature of the solvent. When R1 is C$_1$-C$_6$ alkyl a compound of formula A1d can be obtained for instance by reacting a compound of formula A8 with a suitable amine, in a solvent such as THF, iso-propanol, tert-butanol, at a temperature ranging from room temperature to the boiling temperature of the solvent.

Compounds of general formula (I), wherein A-B, X, X', Y, W, Z, R1, R3, m and n are as defined above and R2 is COOH may be prepared from a compound of formula (I) wherein A-B, X, X', Y, W, Z, R1, R3, m and n are as defined above and R2 is COOR4, wherein R4 is $C_1$-$C_6$ alkyl according to standard chemical methods, e.g. by treatment of the ester with lithium hydroxide, sodium hydroxide or potassium hydroxide in a suitable solvent, for example in ethanol/water, THF, THF/water, methanol/water, or in a 1,4-dioxane/ethanol/water mixture. The hydrolysis may be carried out at a temperature ranging from 0° C. to the boiling point of the solvent.

Compounds of general formula (I), wherein A-B, X, X', Y, W, Z, R1, R3, m and n are as defined above and R2 is COR5, wherein R5 is as defined above, may be prepared for instance from a compound of formula (I) wherein A-B, X, X', Y, W, Z, R1, R3, m and n are as defined above and R2 is COOR4, wherein R4 is as defined above, according to standard chemical methods, e.g. when R4 is $C_1$-$C_6$ alkyl, first by treating the ester with N,O-dimethylhydroxylamine, in the presence of a suitable Grignard reagent, such as i-propylmagnesium chloride, i-propylmagnesium bromide, n-propylmagnesium bromide, ethylmagnesium chloride, t-butylmagnesium chloride, in a solvent such as THF, diethyl ether, at a temperature ranging from −78° C. to 0° C. and then reacting the resulting Weinreb amide with the suitable R5-MgCl, R5-MgBr or R5-Li, in a solvent such as THF, diethyl ether, at a temperature ranging from −78° C. to room temperature.

Compounds of general formula (I), wherein A-B, X, X', Y, W, Z, R1, R3, m and n are as defined above and R2 is CONR6R7, wherein R6 and R7 are as defined above, may be prepared from a compound of formula (I) wherein A-B, X, X', Y, W, Z, R1, R3, m and n are as defined above and R2 is COOH, according to standard chemical methods, e.g. by treatment of the acid with the suitable amine R6R7NH, in the presence of suitable coupling agents, for instance 1-[Bis (dimethylamino)methylene]-1H-1,2,3-triazolo[4,5-b]pyridinium 3-oxid hexafluorophosphate (HATU), benzotriazol-1-yl-oxytripyrrolidinophosphonium hexafluorophosphate (PyBOP), benzotriazol-1-yloxy-tris(dimethylamino)phosphonium hexafluorophosphate (BOP) or 1-(3-dimethylaminopropyl)-3-ethylcarbodiimide (EDC), in the presence of a suitable base (e.g. triethylamine or di-isopropylethylamine) in a suitable solvent (e.g. THF, DCM or DMF). Generally, an activator of the condensation reaction, such as 1-hydroxybenzotriazole (HOBt) or 1-hydroxy-7-aza-benzotriazole (HOAt), can be added to the reaction mixture. The reaction can be carried out for instance at room temperature. Compounds of general formula (I), wherein A-B, X, X', Y, W, Z, R1, R3, m and n are as defined above and R2 is CONR6R7, wherein R6 and R7 are as defined above, may otherwise be prepared from a compound of formula (I) wherein A-B, X, X', Y, W, Z, R1, R3, m and n are as defined above and R2 is COOR4 wherein R4 is $C_1$-$C_6$ alkyl, according to standard chemical methods, e.g by treating the ester with the suitable R6R7NH, in the presence of a suitable base, such as lithium bis(trimethylsilyl)amide, i-propylmagnesium chloride, in a solvent such as THF, diethyl ether, at a temperature ranging from −78° C. to 0° C.

Compounds of general formula (I), wherein A-B, X, X', Y, W, Z, R1, R3, m and n are as defined above and R2 is CN, may be prepared from a compound of formula (I) wherein A-B, X, X', Y, W, Z, R1, R3, m and n are as defined above and R2 is $CONH_2$ according to standard chemical methods, e.g. by treatment of the amide with a suitable dehydrating agent, e.g. diethylchlorophosphate/1,8-diazabiciclo[5.4.0]undec-7-ene (DBU), trichlorophosphate, dicyclohexylcarbodiimide, in solvents such as DCM, DMF, a DCM/DMF mixture, at a suitable temperature, ranging from 0° C. to the boiling temperature of the solvent.

Compounds of general formula (Ic), wherein A-B, X, X' Y, W, Z, R1, R3 and n are as defined above, R2 is COOR4 and R4 is $C_1$-$C_6$ alkyl, can be prepared, according to standard chemical methods, e.g. according to Scheme A2

Scheme A2

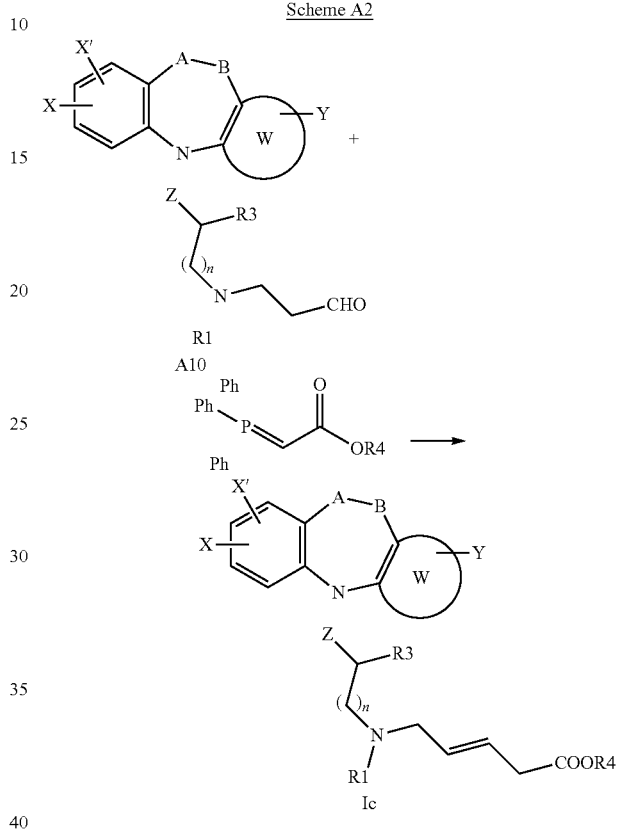

by reacting a compound of formula A10, wherein A-B, X, X', Y, W, Z, R1, R3 and n are as defined above with the suitable phosphorane of formula $Ph_3P=CHCOOR4$, wherein R4 is as defined above, in a solvent such as DCM, toluene, THF, ethanol, at a temperature ranging from 0° C. to the boiling temperature of the solvent.

Compounds of formula A10 can be obtained by known methods, e.g. according to Scheme B5

Scheme B5

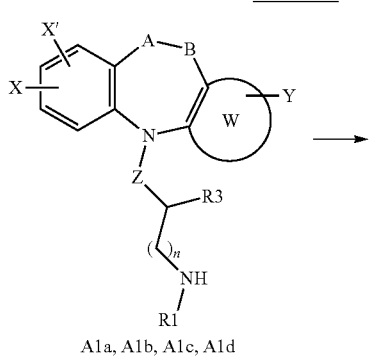

A1a, A1b, A1c, A1d

-continued

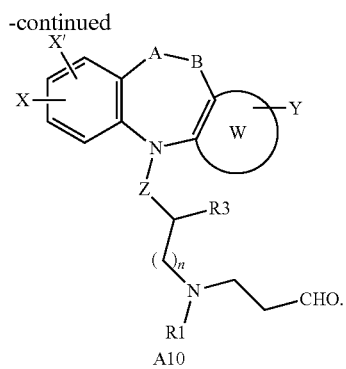

A10 by reacting a compound of formula A1a-A1d, with 2-(2-bromoethyl)-1,3-dioxolane, in the presence of a base such as triethylamine, cesium carbonate, potassium carbonate, NaH, in a suitable solvent, e.g. acetonitrile, DCM, THF, DMF, toluene, at a temperature ranging from 0° C. to the boiling temperature of the solvent and then hydrolysing the aldehyde protective group, for instance with oxalic acid in water/THF at the boiling temperature. Compounds of formula A1a-A1d are described above in Schemes B1-4.

In the case it is necessary to protect a chemical group of a compound of the present invention and/or an intermediate thereof, before carrying out one of the aforedescribed reactions, said chemical group may be protected and deprotected according to known methods. A thorough discussion for suitable protecting groups and the means for protection/deprotection steps can be found for example in Greene and Wuts (Greene, T. W.; Wuts, P. G. M. "Protective Groups in Organic Synthesis", John Wiley & Sons Inc., 1991) or in Kocienski (Kocienski, P. J. "Protecting Groups", George Thieme Verlag, 1994).

It will be understood by those skilled in the art that certain compounds of formula (I) can be converted into other compounds of formula (I) according to standard chemical methods.

The compounds of the present invention are capable of inhibiting E3 ligases comprising a HECT domain. "Inhibiting E3 ligases comprising a HECT domain" means for example that compounds of the invention can inhibit the activity or function of an E3 ligase comprising a HECT domain. Then, the present invention relates to compounds for use as inhibitors of E3 ligases comprising a HECT domain, i.e. for use in inhibiting at least one function of at least on E3 ligase comprising a HECT domain. The present invention also relates to a method of inhibiting E3 ligases comprising a HECT domain, i.e. a method of inhibiting at least one function of at least one E3 ligase comprising a HECT domain comprising the step of contacting said at least one E3 ligase comprising a HECT domain with a compound as described herein.

In the context of the present invention, E3 ligases, or E3 ubiquitin-protein ligases, are a family of proteins that mediate the substrate specifity of the ubiquitin-conjugation system. In particular, E3 ligases in the context of the present invention comprise a HECT domain (then also referred to as HECT E3 ligase) and/or belong to the NEDD4 family.

As used herein, "HECT domain" refers to a C-terminal Homologous to E6AP C Terminus (HECT) domain. HECT E3s range in size from approximately 80 kDa to more than 500 kDa and are characterized by the HECT domain, a C-terminal region of approximately 350 amino acids in length with significant similarity to the C terminus of E6AP (Homologous to E6AP C Terminus) (Scheffner et al., Biochimica et Biophysica Acta (BBA)—Molecular Cell Research, Vol. 1843, Issue 1, 2014, pages 61-74). The HECT-domain E3 ligases catalyze two distinct reactions: a transthioesterification reaction, in which ubiquitin is transferred from the E2 active site cysteine to a cysteine in the HECT domain, and a subsequent attack on the HECT-Ub thioester by a substrate lysine. These reactions, and thus inhibition of the activity or function of an E3 ligase comprising a HECT domain, can be measured by a ubiquitination assay, for instance employing TR-FRET, Western blot, etc. and/or as described in the Examples below. In particular, inhibition of activity or function of an E3 ligase comprising a HECT domain can be measured by the $IC_{50}$ (concentration of inhibitor which reduces the activity of the ligase to half-maximal level) and/or by the percentage of inhibition, calculated for example as described in the assays hereinbelow. Preferably, compounds of the invention exhibit a percentage of inhibition for an E3 ligase comprising a HECT domain equal to or higher than approximately 10%, 20%, 30%, 40%, 50%, 60%, 80%, 90% or 95%.

As used herein, "E3 ligase(s) comprising a HECT domain" and "E3 ligase(s) belonging to the NEDD4 family" and grammatical variants thereof comprise at least: NEDD4, NEDD4L, ITCH, SMURF1, SMURF2, WWP1, WWP2, HECW1 and HECW2, preferably NEDD4.

Preferably, NEDD4 is characterized by the sequence disclosed in the NCBI database with with Gene ID: 4734, updated on 13 Feb. 2019.

Preferably, NEDD4L is characterized by the sequence disclosed in the NCBI database with with Gene ID: 23327.

Preferably, ITCH is characterized by the sequence disclosed in the NCBI database with with Gene ID: 83737.

Preferably, SMURF1 is characterized by the sequence disclosed in the NCBI database with with Gene ID: 36999.

Preferably, SMURF2 is characterized by the sequence disclosed in the NCBI database with with Gene ID: 64750.

Preferably, WWP1 is characterized by the sequence disclosed in the NCBI database with with Gene ID: 11059.

Preferably, WWP2 is characterized by the sequence disclosed in the NCBI database with with Gene ID: 11060.

Preferably, HECW1 is characterized by the sequence disclosed in the NCBI database with with Gene ID: 23072.

Preferably, HECW2 is characterized by the sequence disclosed in the NCBI database with with Gene ID: 57520.

It is to be understood that each one of the above-indicated Gene IDs encompasses all possible coded protein sequences, i.e. isoforms, whether existing in nature or obtained by computational data.

Preferably, the compounds of the invention selectively inhibit NEDD4, i.e. they are selective for NEDD4 over other HECT-E3 ligases. In particular, by "selective", it is meant that the compounds of the invention exhibit a percentage of inhibition for NEDD4 higher than for other HECT-E3 ligases or an IC50 for NEDD4 lower than for other HECT-E3 ligases.

Therefore, the compounds of the invention may be useful in the prevention and/or treatment of any condition that may be ameliorated by the inhibition of an E3 ligase comprising a HECT domain, in particular an E3 ligase belonging to the NEDD4 family, more in particular NEDD4, ITCH, SMURF1, SMURF2, WWP1, WWP2, HECW1 or HECW2. Preferably, the compounds of the invention may be useful in the prevention and/or treatment of any condition that may be ameliorated by the inhibition of NEDD4.

Such conditions include any condition wherein an E3 ligase comprising a HECT domain, in particular an E3 ligase belonging to the NEDD4 family, more in particular NEDD4, ITCH, SMURF1, SMURF2, WWP1, WWP2, HECW1 or HECW2, is deregulated.

Conditions wherein an E3 ligase comprising a HECT domain is deregulated include any condition wherein an E3 ligase comprising a HECT domain is overexpressed (which can be seen for example by Immunoistochemistry (IHC) analysis), amplified (which can be seen for example by Fluorescent in situ ibridization (FISH) analysis) or hyperactivated (which can be seen for example by specific point mutation). Such conditions also include those indicated in M. Scheffner, S. Kumar, *Biochimica et Biophysica Acta*, 1843 (2014), 61-74, herein incorporated by reference.

The compounds of formula (I) or stereoisomers, solvates, tautomers or pharmaceutically acceptable salts thereof can also be used in combination with additional agents, in particular with any agent useful in the treatment of the above defined conditions either by separate administrations, or by including the two active principles in the same pharmaceutical formulation. For example, the compounds of the invention may be used in combination with anti-tumor (i.e. chemotherapeutic) agents, differentiating agents and/or anti-retroviral drugs.

Non-exhaustive examples of suitable additional agents include:

a) histone deacetylase inhibitors (for example, but not limited to SAHA, PXD101, JNJ-26481585, SB939, ITF-2357, LBH589, PCI-24781, valproic acid, butyric acid, MS-275, Tacedinaline (CI994), Chidamide (CS055), MGCD0103 and FK-228);

b) retinoid receptor modulators such as 13-cis-retinoic acid, 9-cis-retinoic acid, bexarotene, alitretinoin, or tretinoin; vitamin D;

c) antiproliferative/antineoplastic agents and combinations thereof, as used in medical oncology, such as alkylating agents (for example platin derivatives like cis-platin, carboplatin, oxaliplatin, lobaplatin, satraplatin, nedaplatin, heptaplatin; nitrogen mustard such as chlorambucil, melphalan, chlormethine, cyclophosphamide, ifosfamide, trofosfamide, uramustine, bendamustine, estramustine; busulphan, temozolomide or nitrosoureas); antimetabolites (for example antifolates such as aminopterin, methotrexate, pemetrexed, raltitrexed); purines such as cladribine, clofarabine, fludarabine, mercaptopurine, pentostatin, thioguanine; pyrimidines like capecitabine, cytarabine, fluorouracil, floxuridine, gemcitabine; azacitidine, decitabine; cytosine arabinoside or hydroxyurea; antitumour antibiotics (for example anthracyclines like aclarubicin, amrubicin, daunomycin, doxorubicin, epirubicin, idarabicin, valrubicin, zorubicine; mitoxantrone; or antibiotics from *Streptomyces* like actinomycin, bleomycin, mitomycin, or plicamycin); antimitotic agents (for example vinca alkaloids like vincristine, vinblastine, vindesine or vinorelbine; taxoids like docetaxel, paclitaxel or tesetaxel; epothilones like ixabepilone) and topoisomerase inhibitors (for example epipodophyllotoxins like etoposide and teniposide; amsacrine, camptothecin, irinotecan, rubitecan, and topotecan);

d) cytostatic agents such as antioestrogens (for example but not limited to tamoxifen, toremifene, raloxifene, droloxifene and idoxifene), oestrogen receptor down regulators (for example but not limited to fulvestrant), antiandrogens (for example but not limited to bicalutamide, flutamide, nilutamide, liarozole or cyproterone acetate), LHRH antagonists or LHRH agonists (for example but not limited to goserelin, leuprorelin or buserelin), progestogens (for example but not limited to megestrol acetate), aromatase inhibitors (for example but not limited to anastrozole, letrozole, vorazole and exemestane) and inhibitors of 5-alpha-reductase such as finasteride;

e) agents which inhibit cancer cell invasion (for example metalloproteinase inhibitors and inhibitors of urokinase plasminogen activator receptor function);

f) inhibitors of growth factor function, for example growth factor antibodies, growth factor receptor antibodies (for example the anti-erbb2 antibody trastuzumab as well as ado-trastuzumab emtasine and pertuzumab, the anti-erbb1 antibody cetuximab and panitumumab, the anti IGF1R antibody figitumumab), farnesyl transferase inhibitors, MEK inhibitor (for example trametinib), tyrosine kinase inhibitors and serine/threonine kinase inhibitors, for example enzastaurin, dasatinib, erlotinib, gefitinib, imatinib, lapatinib, ponatinib, nilotinib, sorafenib, sunitinib, afatinib, axinitinib, bosutinib, caboratinib, ceritinib, crizotinib, dafrafenib, ibrutinib, idelalisib, lenvatinib, pazopanib, regorafenib, ruxolinitinib, vandetanib, vefuramenib, midostaurin, everolimus, sirolimus or temsirolimus;

g) antiangiogenic agents such as those which inhibit the effects of vascular endothelial growth factor, for example the anti-vascular endothelial cell growth factor antibody bevacizumab, ramucirumab, lenalidomide or thalidomide;

h) cell cycle inhibitors including for example CDK inhibitors (for example but not limited to flavopiridol, roscovitine, palbociclib and milciclib) and other inhibitors of cell cycle checkpoints; inhibitors of aurora kinase and other kinases involved in mitosis and cytokinesis regulation;

i) proteasome inhibitors (for example but not limited to lactacystin, bortezomib, epoxomicin, Carfilzomib Ixazomib);

j) HSP90 inhibitors (for example but not limited to AT-13387, KOS-953, KOS-1022, CNF-1010, CNF-2024, SNX 5422, STA-9090, NVP-HSP990, NVP-AUY922, PU-H17 and XL-888);

k) Selective COX-2 inhibitors (for example but not limited to celecoxib), or non selective NSAIDs (for example but not limited to diclofenac, flurbiprofen, ibuprofen, ketoprofen, or naproxen);

l) anti CD20 antibodies (for example but not limited to ibritumomab tiuxetan, obinutuzumab, ofatumumab, rituximab and tositumomab), and antibodies targeting soluble and membrane-bound interleukin 6 as siltuximab;

m) immunomodulators agents as anti PD1 antibody (for example nivolumab and pembrolizumab), anti PD-L1 antibody (for example Atezolizumab, Avelumab, Durvalumab) anti CD30 antibodies such as brentuximab vedotin, anti CLTA-4 antibodies (for example ipilimumab);

n) epigenetic drugs such as other histone demethylase inhibitors (for example but not limited to KDM1A and EZH2 inhibitors), and bromodomain inhibitors (for example but not limited to GSK525762, OTX015, CPI-0610, TEN-010 and BAY1238097);

o) IDH-1/2 inhibitors such as AG-120, AG-221 and AG-881;

p) PARP inhibitors (for example but not limited to Olaparib, Rucaparib, Niraparib, Veliparib, Talazorapib);

q) DNA damage response inhibitors (for example ATM, ATR, CHK1, CHK2, DNAPK and WEE1 inhibitors (for example but not limited to AZD0156, VX970, AZD6738, MK8776 (SCH 900776), LY2603618, CCT245737, GDC-0575, LY2606368, MSC2490484A, VX-984, AZD1775 (Adavosertib), KU-55933, AZ20, VE-822, and CGK 733);

r) standard chemotherapy combinations such as, but not restricted to, CMF (cyclophosphamide, methotrexate and 5-fluorouracil), CAF (cyclophosphamide, doxorubicin and 5-fluorouracil), AC (doxorubicin and cyclophosphamide), FEC (5-fluorouracil, epirubicin, and cyclophosphamide), ACT or ATC (doxorubicin, cyclophosphamide, and paclitaxel), or CMFP (cyclophosphamide, methotrexate, 5-fluorouracil and prednisone);

s) Nucleoside/Nucleotide Reverse Transcriptase Inhibitors such as but not limited to Abacavir, Didanosine, Emcitribanine, Lamivudine and Zidovudine;

t) non-Nucleoside/Nucleotide Reverse Transcriptase Inhibitors such as but not limited to Delavirdine, Doravirine, Evafirenz, Etravirine;

u) protease inhibitors such as but not limited to Azatanavir, Darunavir, Ritonavir;

v) fusion inhibitors such as Enfuvirtide;

w) CCR5 antagonist such as but not limited to Maraviroc;

x) integrase inhibitors such as but not limited to Dolutegravir, Raltegravir;

y) monoclonal antibodies such as but not limited to Ibalizumab-uiyk, Cobicistat.

In addition or in alternative to the above-indicated therapeutic agents, a compound of general formula (I), or a stereoisomer, solvate, tautomer or pharmaceutically acceptable salt thereof, can be used in combination with radiation therapy.

The invention also provides pharmaceutical compositions comprising one or more compounds of formula (I), or one or more stereoisomers, solvates, tautomers or pharmaceutically acceptable salts thereof and one or more pharmaceutically acceptable excipients and/or diluents. The pharmaceutical compositions can be chosen on the basis of the treatment requirements. Such compositions are prepared by blending and are suitably adapted to oral or parenteral administration, and as such can be in the form of tablets, capsules, oral preparations, powders, granules, pills, injectable or infusible liquid solutions, suspensions, emulsions, suppositories, ointments, creams, lotions, gels, pastes, transdermal delivery devices.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules. Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Typical transdermal formulations comprise conventional aqueous and non-aqueous vectors, such as creams, oils, lotions or pastes or can be in the form of membranes or medicated patches.

A reference for the formulations is the book by Remington ("Remington: The Science and Practice of Pharmacy", Lippincott Williams & Wilkins, 2000).

The compounds of the invention may be presented in a liposome or other micro particulate or other nanoparticle designed to target the compound. Acceptable liposomes can be neutral, negatively, or positively charged, the charge being a function of the charge of the liposome components and pH of the liposome solution. Liposomes can be normally prepared using a mixture of phospholipids and cholesterol. Suitable phospholipids include phosphatidylcholine, phosphatidylethanolamine, phosphatidic acid, phosphotidylglycerol, phosphatidylinositol. Polyethylene glycol can be added to improve the blood circulation time of liposomes. Acceptable nanoparticles include albumin nanoparticles and gold nanoparticles.

The compounds of the present invention may be employed alone as a sole therapy or in combination with other therapeutic agents for the treatment of the above-mentioned conditions. The combination can be administered as separate compositions (simultaneous, sequential) of the individual components of the treatment or as a single dosage form containing both agents. When the compounds of this invention are in combination with other active ingredients, the active ingredients may be separately formulated into single-ingredient preparations of one of the above-described forms and then provided as combined preparations, which are given at the same time or different times, or may be formulated together into a two- or more-ingredient preparation.

Compounds of general formula (I) or stereoisomers, solvates, tautomers or pharmaceutically acceptable salts thereof may be administered to a patient in a total daily dose of, for example, from 0.001 to 1000 mg/kg body weight daily. Dosage unit compositions may contain such amounts or submultiples thereof to make up the daily dose. The determination of optimum dosages for a particular patient is well known to one skilled in the art.

As is common practice, the compositions are normally accompanied by written or printed instructions for use in the treatment in question.

The following non limiting examples and biological data are presented and reference to the following figures is made in order to further illustrate the invention.

FIG. 1: TR-FRET kinetic assay performed with compound 12. Bacterially expressed and purified proteins (E1, E2 and untagged HECT of NEDD4 WT, labelled in FIG. 1 as WT) or NEDD4 catalytically inactive mutant (C/A) were incubated with a mixture of labeled and unlabeled ubiquitin in an optimized ratio. Compound 12 dissolved in DMSO in the concentrations indicated in the figure was added. Reactions were initiated with the addition of ATP. As labeled ubiquitin molecules become incorporated into chains they come into close proximity, resulting in energy transfer and increased signal to background detection. The activity of the enzyme is continuously and real time detected and it is expressed as % of signal/background during the time.

Figure 2:
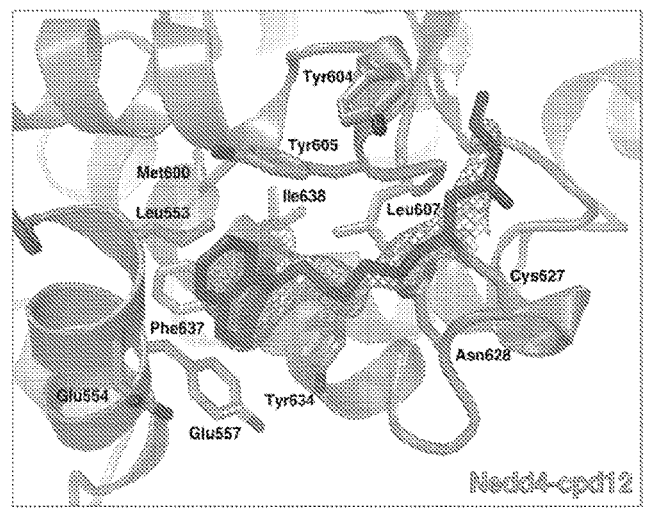
Figure 2:
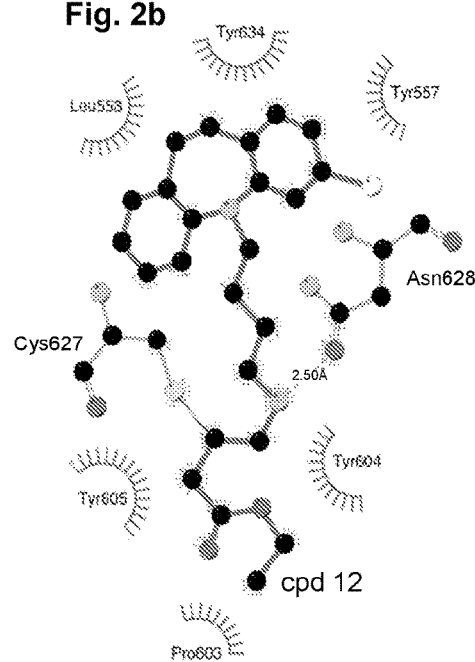

FIG. 2: Structure of NEDD4 HECT in complex with compound 12. a. Compound 12 (dark grey sticks representation) binding to the HECT of NEDD4 (light grey), with a Fo-Fc map, calculated omitting the ligand, contoured at 2.5α level (represented as a grey mesh). b. Details of ligand binding: compound 12 and covalently or hydrogen-bonded NEDD4 residues are in ball-and-stick representation, hydrogen bond is shown as dotted line; spoked arcs represent protein residues making nonbonded contacts with the ligand.

Figure 3:
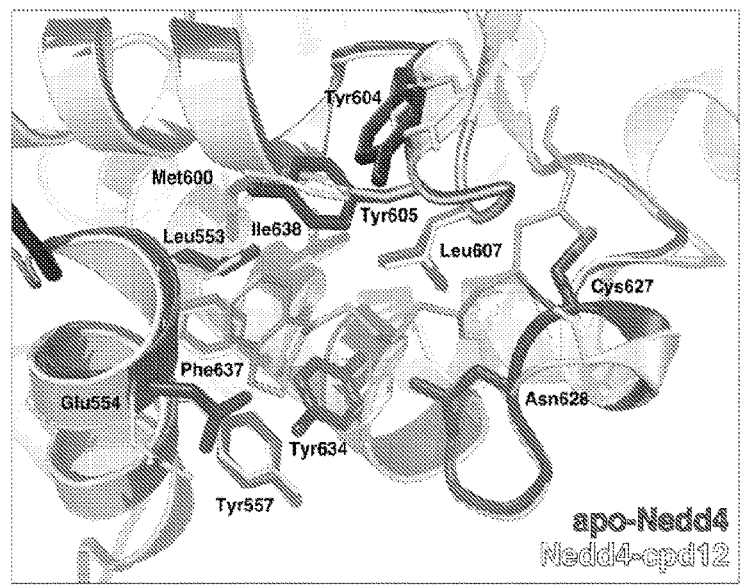

FIG. 3: Structure of apo NEDD4 HECT superimposed with the one of the complex HECT-compound 12. Changes in the HECT structure upon compound 12 binding. Apo-HECT (pdb entry 2xbf, version 1.2, 13 Jul. 2011) depicted as dark grey ribbon; complex depicted as light grey ribbon. Side chains of residues Glu554 and Tyr634, and to a less extent those of Tyr604 and Tyr605, as well as main and side chain of residue Cys627 (covalently bound to the inhibitor) are rearranged upon inhibitor binding.

Figure 4:
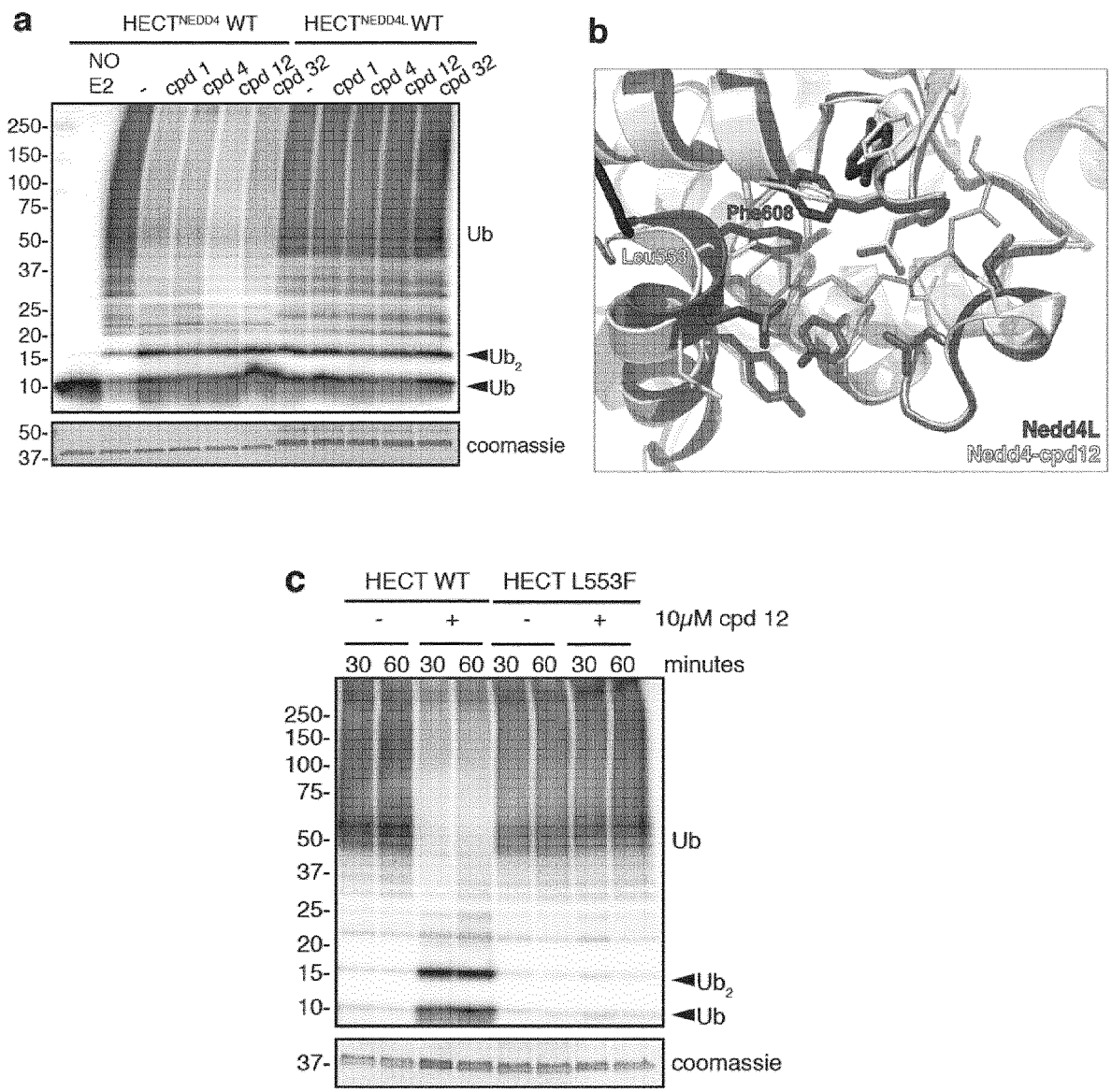

FIG. 4: NEDD4 inhibitors are highly selective. a. In vitro ubiquitination assay performed with HECT NEDD4 WT and HECT NEDD4L WT in presence of the indicated compounds at 10 µM concentration. The symbol "–" indicates the DMSO-treated sample. Reactions were stopped after 1 hour with Laemmli buffer. Coomassie staining shows comparable loading of HECT proteins. b. HECT of NEDD4 bound to compound 12 is shown in light grey, superposed with the structure of HECT of NEDD4L (pdb entry 2oni, version 1.2, 13 Jul. 2011, shown in dark grey). c. In vitro ubiquitination assay using the HECT of NEDD4 WT (HECT WT) and L553F (HECT L553F) was performed in presence of compound 12 at 10 µM concentration. The symbol "–" indicates the DMSO-treated sample. Immunoblot was performed with the anti-ubiquitin antibody (upper panel). Coomassie staining (lower panel) shows comparable loading of HECT proteins.

1. CHEMICAL SYNTHESIS

Unless otherwise indicated, commercially available reagents and solvents (HPLC grade) were used without further purification.

Specifically, the following abbreviations may have been used in the descriptions of the experimental methods:

| | |
|---|---|
| NMR (Nuclear Magnetic Resonance) | $^1$H (proton) |
| MHz (Megahertz) | Hz (Hertz) |
| HPLC (High Performance Liquid Chromatography) | LC-MS (Liquid Chromatography Mass Spectrum) |
| s (seconds) | min (minutes) |
| h (hours) | mg (milligrams) |
| g (grams) | µl (microlitres) |
| ml (millilitres) | mmol (millimoles) |
| nm (nanometers) | µM (micromolar) |
| M (molarity) | r.t. (room temperature) |
| (BOC)$_2$O (di-tert-butyl dicarbonate) | iPr$_2$O (diisopropyl ether) |
| ACN (acetonitrile) | i-PrMgCl (isopropylmagnesium chloride) |
| AcOH (acetic acid) | K$_2$CO$_3$ (potassium carbonate) |
| AcONa (sodium acetate) | LiOH (lithium hydroxide) |
| BH$_3$-THF (borane-tetrahydrofuran) | MeMgCl (methylmagnesium chloride) |
| BOC or boc (tert-butyloxycarbonyl) | MeOH (methanol) |
| CS$_2$CO$_3$ (cesium carbonate) | Na$_2$SO$_4$ (sodium sulphate) |
| D$_2$O (deuterium oxide) | NaBH(OAc)s (sodium triacetoxyborohydride) |
| DBU (1,8-diazabiciclo[5.4.0]undec-7-ene) | NaBH$_4$ (sodium borohydride) |
| DCE (dichloroethane) | NaCl (sodium chloride) |
| DCM (dichloromethane) | NaH (sodium hydride) |
| DIPEA (N,N-diisopropylethylamine) | NaHCOs (sodium bicarbonate) |
| DMF (dimethylformamide) | NaNs (sodium azide) |
| DMSO (dimethyl sulfoxide) | NaOH (sodium hydroxide) |
| DMSO-d$_6$ (deuterated dimethyl sulfoxide) | NH$_4$Cl (ammonium chloride) |
| EDC 1-(3-dimethylaminopropyl)-3-ethylcarbodiimide hydrochloride | NH$_4$OH (ammonium hydroxide) |
| Et$_2$O (diethyl ether) | PhMgBr (phenylmagnesium bromide) |
| EtOAc (ethyl acetate) | TBTU (O-benzotriazole-1-yl-N,N,N',N'-tetramethyluronium tetrafluoroborate) |
| EtOH (ethanol) | TEA (thethylamine) |
| HCl (hydrochloric acid) | TFA (2,2,2-trifluoroacetic acid) |
| HOBt (1-hydroxybenzotriazole) | TFAA ((2,2,2-trifluoroacetyl) 2,2,2-trifluoroacetate) |
| IPA (propan-2-ol) | THF (tetrahydrofuran) |
| n-BuLi (n-butyllithium) | TPP (triphenylphosphine) |

Except where indicated otherwise, all temperatures are expressed in ° C. (degrees centigrade).

The $^1$H-NMR spectra were acquired with a Varian 500 MHz instrument. The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet), bm (broad multiplet).

The LC-MS analyses were carried out on a Waters Acquity UPLC or Waters Acquity UPLC H-Class linked to with a SQD Single quadrupole (Waters) using an Acquity UPLC BEH 018 (50×2.1 mm, 1.7 μm) or Acquity UPLC HSS T3 (50×2.1 mm, 1.8 μm) column. Phase A was composed by either Milli-Q water/CH$_3$CN 95/5+0.07% formic acid or Milli-Q water+0.07% formic acid; Phase B by CH$_3$CN+0.05% formic acid; flow rate: 0.6 mL/min; UV detection (DIODE array) from 210 to 400 nm; ESI+ detection in the 100-2000 m/z range. The structure of all intermediates and final products was confirmed by NMR and LC-MS analysis. The yields were calculated assuming that products were 100% pure if not stated otherwise.

Intermediate 1: 3-(3-Chloro-10,11-dihydro-5H-dibenzo[b,f]azepin-5-yl)-N-methyl-propan-1-amine

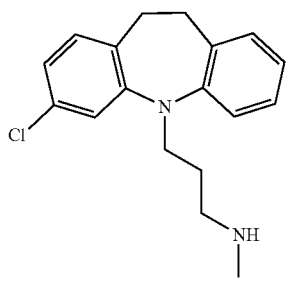 [SMILES: CNCCCN1c2ccccc2CCc2ccc(Cl)cc21]

Step 1: tert-Butyl 3-(3-chloro-10,11-dihydro-5H-dibenzo[b,f]azepin-5-yl)-propyl-(methyl)-carbamate 2.0 g (8.53 mmol) of 3-chloro-10,11-dihydro-5H-dibenzo[b,f]azepine (FLROCHEM, Cat. No. 211409) were dissolved in dry THF (60 ml). The solution was cooled to 0° C. and treated with 12.5 ml of lithium bis(trimethylsilyl)amide (1 M in THF, 12.46 mmol). The mixture was warmed to r.t., stirred for 45 min, then treated with 2.85 g (10.67 mmol) of 3-[tert-butoxycarbonyl(methyl)amino]propyl methanesulfonate (prepared according to literature procedure, J. Med. Chem. 2018, 61, 2753-2775) in THF (20 ml). The mixture was heated to 75° C. for 5 h. The reaction mixture was cooled with ice, quenched with a solution of saturated aqueous NH$_4$Cl (200 ml) and extracted using EtOAc (300 ml). The organic phase was washed with brine, dried (Na$_2$SO$_4$) and the solvent evaporated. The crude product was purified by flash chromatography (eluent: hexane/EtOAc 90:10) to afford 3-(3-chloro-10,11-dihydro-5H-dibenzo[b,f]azepin-5-yl)-propyl-(methyl)-carbamate as a colorless oil (1.873 g, 55%). $^1$H NMR (CDCl$_3$) δ (ppm): 7.19-6.94 (m, 6H), 6.90-6.84 (m, 1H), 3.71 (t, J=6.8 Hz, 2H), 3.30-3.20 (m, 2H), 3.19-3.07 (m, 4H), 2.75 (s, 3H), 1.82-1.71 (m, 2H), 1.44 (s, 9H); MS (ESI): m/z: 401 [M+H]$^+$.

Step 2: 3-(3-Chloro-10,11-dihydro-5H-dibenzo[b,f]azepin-5-yl)-N-methyl-propan-1-amine A solution of 0.399 g (0.995 mmol) of 3-(3-chloro-10,11-dihydro-5H-dibenzo[b,f]azepin-5-yl)-propyl-(methyl)-carbamate in dry DCM (6 ml) was cooled to 0° C. and treated with TFA (1.52 ml). The mixture was warmed to r.t. and stirred overnight. The reaction was concentrated in vacuo. The residue was taken up with Et2O (100 ml) and water (50 ml), the aqueous phase was basified with NaHCO$_3$(pH 7-8, ice-cooling) and then the organic phase was separated, washed with brine, dried (Na2SO4) and evaporated to afford 3-(3-chloro-10,11-dihydro-5H-dibenzo[b,f]azepin-5-yl)-N-methyl-propan-1-amine as a yellow oil (0.287 g, 96%). $^1$H NMR (CDCl$_3$) δ (ppm): 7.20-6.93 (m, 6H), 6.87 (dd, J=2.2, 8.1 Hz, 1H), 3.77 (t, J=6.8 Hz, 2H), 3.20-3.05 (m, 4H), 2.63 (t, J=7.1 Hz, 2H), 2.39 (s, 3H), 1.83-1.71 (m, 2H); MS (ESI): m/z: 301 [M+H]$^+$.

Intermediate 2: 4-(3-Chloro-10,11-dihydro-5H-dibenzo[b,f]azepin-5-yl)-N-methyl-butan-1-amine

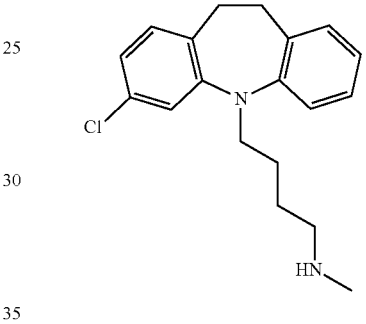

Step 1: tert-Butyl [4-(3-chloro-10,11-dihydro-5H-dibenzo[b,f]azepin-5-yl)butyl]methycarbamate 0.242 g (1 mmol) of 3-chloro-10,11-dihydro-5H-dibenzo[b,f]azepine (FLROCHEM, Cat. No. 211409) were dissolved in dry DMF (5 ml). The solution was cooled to 0° C. and treated with 0.08 g of NaH (60% oil suspension, 2 mmol). The mixture was warmed to r.t., stirred for 1 h, then cooled to 0° C. and treated with 0.422 g (1.5 mmol) of 4-[tert-butoxycarbonyl(methyl)amino]butyl methanesulfonate (prepared according to literature procedure, J. Med. Chem. 2013, 56, 5819-5828) in dry DMF (2.5 ml). The mixture was heated to 55° C. overnight. The reaction mixture was cooled, quenched with a solution of saturated aqueous NaCl and extracted with EtOAc. The organic phase was washed with brine, dried (Na$_2$SO$_4$) and the solvent evaporated. The crude product was purified by flash chromatography (eluent: hexane/EtOAc 95:5) to afford tert-butyl [4-(3-chloro-10,11-dihydro-5H-dibenzo[b,f]azepin-5-yl)butyl]methylcarbamate as a pale yellow oil (0.374 g, 86%). $^1$H NMR (CDCl$_3$) δ (ppm): 7.18-7.10 (m, 2H), 7.09-7.06 (m, 1H), 7.05-7.02 (m, 1H), 7.01-6.94 (m, 2H), 6.87 (dd, J=1.5, 7.8 Hz, 1H), 3.77-3.67 (m, 2H), 3.19-3.06 (m, 6H), 2.76 (s, 3H), 1.60-1.54 (m, 4H), 1.39 (bs, 9H); MS (ESI): m/z: 415 [M+H]$^+$.

Step 2: 4-(3-Chloro-10,11-dihydro-5H-dibenzo[b,f]azepin-5-yl)-N-methyl-butan-1-amine 0.245 g (98%) of 4-(3-chloro-10,11-dihydro-5H-dibenzo[b,f]azepin-5-yl)-N-methyl-butan-1-amine were prepared according to the procedure described for Intermediate 1, Step 2, starting from 0.327 g (0.788 mmol) of tert-butyl [4-(3-chloro-10,11-dihydro-5H-dibenzo[b,f]azepin-5-yl) butyl]methylcarbamate and 1.21 ml (15.76 mmol) of TFA. $^1$H NMR (CDCl$_3$) δ (ppm): 7.18-7.10 (m, 2H), 7.05-7.02 (m, 1H), 7.01-6.95 (m, 3H), 6.88 (dd, J=2.0, 7.8 Hz, 1H), 3.70 (t, J=6.6 Hz, 2H), 3.16-3.06 (m, 4H), 2.81-2.76 (m, 2H), 2.52 (s, 3H), 1.77-1.68 (m, 2H), 1.65-1.56 (m, 2H); MS (ESI): m/z: 315 [M+H]$^+$.

Intermediate 3: 3-(3-Chloro-10,11-dihydro-5H-dibenzo[b,f]azepin-5-yl)propan-1-amine

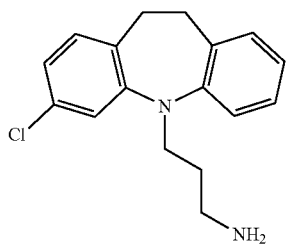 [SMILES: NCCCN1c2ccccc2CCc2ccc(Cl)cc21]

Step 1: 3-Chloro-1-(3-chloro-10,11-dihydro-5H-dibenzo[b,f]azepin-5-yl)-propan-1-one 1.496 ml (15.36 mmol) of 3-chloropropanoyl chloride in toluene (3 ml) were added dropwise to a solution of 3 g (12.80 mmol) of 3-chloro-10,11-dihydro-5H-dibenzo[b,f] azepine (FLROCHEM, Cat. No. 211409) in toluene (30 ml). The mixture was heated to 100° C. for 4 h. The solvent was removed under vacuo. The crude was purified by flash chromatography (eluent: hexane/EtOAc from 80:20 to 70:30) to afford 3-chloro-1-(3-chloro-10,11-dihydro-5H-dibenzo[b,f]azepin-5-yl)-propan-1-one as an off-white solid (3.56 g, 87%). $^1$H NMR (CDCl$_3$), mixture of conformers, δ (ppm): 7.42-7.04 (m, 7H), 3.93-3.75 (m, 2H), 3.47-3.27 (m, 2H), 2.93-2.76 (m, 3H), 2.63-2.48 (m, 1H); MS (ESI): m/z: 320 [M+H]$^+$.

Step 2: 3-Azido-1-(3-chloro-10,11-dihydro-5H-dibenzo[b,f]azepin-5-yl)-propan-1-one A solution of 3.5 g (10.93 mmol) of 3-chloro-1-(3-chloro-10,11-dihydro-5H-dibenzo[b,f]azepin-5-yl)-propan-1-one in DMF (35 ml) was cooled to 0° C. and treated with 2.15 g (32.79 mmol) of NaN3 and 0.036 g (0.22 mmol) of KI. The mixture was warmed to r.t., stirred for 5 days and then it was partitioned between saturated aqueous NaCl (150 ml) and DCM (120 ml). The aqueous layer was extracted with DCM (120 ml). The combined organic layers were washed with saturated aqueous NaCl (2×75 ml), dried (Na2SO4) and concentrated in vacuo. The residue was taken up with toluene and evaporated. The crude was purified by flash chromatography (eluent: DCM/EtOAc from 100:1 to 95:5) to afford 3-azido-1-(3-chloro-10,11-dihydro-5H-dibenzo[b, f]azepin-5-yl)-propan-1-one as an off-white solid (1.37 g, 38%). $^1$H NMR (CDCl3), mixture of conformers, δ (ppm): 7.43-7.05 (m, 7H), 3.74-3.53 (m, 2H), 3.47-3.23 (m, 2H), 2.91-2.76 (m, 2H), 2.70-2.55 (m, 1H), 2.37-2.22 (m, 1H); MS (ESI): m/z: 327 [M+H]$^+$.

Step 3: 3-(3-Chloro-10,11-dihydro-5H-dibenzo[b,f]azepin-5-yl)-propan-1-amine

A solution of 1.37 g (4.19 mmol) of 3-azido-1-(3-chloro-10,11-dihydro-5H-dibenzo[b,f]azepin-5-yl)-propan-1-one in THF (6 ml) was cooled to 0° C., treated with 16.8 ml of BH3-THF (1 M in THF, 16.77 mmol). The flask was sealed, heated to 70° C. for 5 h, and then cooled to 0° C. The solution was slowly treated, dropwise with a solution of aqueous 1 M HCl (34 ml), stirred for additional 0.5 h, and then heated to 70° C. for 1 h. The mixture was cooled to 0° C., treated with aqueous 4 M NaOH until pH>8, and then extracted with EtOAc (2×100 ml). The combined extracts were washed with saturated aqueous NaCl (50 ml), dried (Na2SO4), and concentrated. The crude was purified by flash chromatography (eluent: DCM/MeOH/NH4OH 90:10: 1) to afford 3-(3-chloro-10,11-dihydro-5H-dibenzo[b,f]azepin-5-yl)-propan-1-amine as a yellow oil (1.02 g, 85%). $^1$H NMR (CDCl3) δ (ppm): 7.20-7.04 (m, 4H), 7.03-6.94 (m, 2H), 6.87 (dd, J=2.0, 8.3 Hz, 1H), 3.78 (t, J=6.8 Hz, 2H), 3.19-3.06 (m, 4H), 2.74 (t, J=6.8 Hz, 2H), 1.77-1.67 (m, 2H); MS (ESI): m/z: 287 [M+H]$^+$.

Intermediate 4: 7-Chloro-5,11-dihydro-dibenzo[b,e][1,4]oxazepine

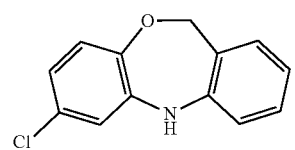 [SMILES: Clc1ccc2c(c1)Nc1ccccc1CO2]

Step 1: 1-[(2-Bromophenyl)methoxy]-4-chloro-2-nitro-benzene 35 ml of acetonitrile were added to a flask containing 4.54 g (18.2 mmol) of 2-bromobenzyl bromide, 3 g (17.3 mmol) of 4-chloro-2-nitro-phenol and 5.97 g (43.2 mmol) of K$_2$CO$_3$. The solution was heated to 70° C. for 2 h. The reaction was quenched with water (200 ml) and extracted with EtOAc (2×150 ml). The combined organics were washed with brine (2×75 ml), dried (Na$_2$SO$_4$) and the solvent removed under vacuo. The resulting solid was triturated with hexane to afford 1-[(2-bromophenyl) methoxy]-4-chloro-2-nitro-benzene as a beige solid (5.15 g, 87%). $^1$H NMR (CDCl$_3$) δ (ppm): 7.92 (d, J=2.4 Hz, 1H), 7.66 (d, J=7.8 Hz, 1H), 7.63-7.58 (m, 1H), 7.52 (dd, J=2.4, 8.8 Hz, 1H), 7.40 (dt, J=1.0, 7.6 Hz, 1H), 7.24 (dt, J=1.5, 7.6 Hz, 1H), 7.12 (d, J=8.8 Hz, 1H), 5.28 (s, 2H).

Step 2: 2-[(2-Bromophenyl)methoxy]-5-chloro-aniline 2.5 g (7.30 mmol) of 1-[(2-bromophenyl)methoxy]-4-chloro-2-nitro-benzene in IPA (100 ml) were heated to 60° C. To this solution was added 1.12 ml of 12 N HCl followed by 6.11 g (109.5 mmol) of Fe. The reaction was allowed to stir for 20 h 30 min at 60° C. and then filtered hot through a pad of celite. The cloudy solution was evaporated under vacuo and the crude was purified by flash chromatography (eluent: hexane/EtOAc 80:20) to afford 2-[(2-bromophenyl) methoxy]-5-chloro-aniline as a brown oil that solidified on-standing (1.99 g, 87%). $^1$H NMR (CDCl$_3$) δ (ppm): 7.61 (dd, J=1.2, 8.1 Hz, 1H), 7.52-7.48 (m, 1H), 7.34 (dt, J=1.0, 7.6 Hz, 1H), 7.24-7.18 (m, 1H), 6.78 (d, J=2.0 Hz, 1H), 6.77-6.73 (m, 1H), 6.72-6.66 (m, 1H), 5.15 (s, 2H), 4.43 (bs, 2H); MS (ESI): m/z: 313 [M+H]$^+$.

Step 3: N-[2-[(2-Bromophenyl)methoxy]-5-chlorophenyl]formamide

A mixture of 1.79 g (5.73 mmol) of 2-[(2-bromophenyl)methoxy]-5-chloro-aniline, 0.78 g (11.45 mmol) of sodium formate and 8.7 ml of formic acid was stirred and heated under reflux for 3 h. The mixture was cooled somewhat, and poured into 60 ml ca. of ice-water. The solid which separated was filtered, washed with water twice, and dried in vacuo to afford N-[2-[(2-bromophenyl)methoxy]-5-chloro-phenyl]formamide as a beige solid (1.82 g, 93%). ¹H NMR (CDCl₃), mixture of rotamers, δ (ppm): 8.76, 8.51-8.43 (d, J=11.2 Hz, m, 2H), 7.84, 7.73 (2 bs, 1H), 7.68-7.61 (m, 1H), 7.45-7.33 (m, 2H), 7.31-7.22 (m, 1H), 7.13-7.01 (m, 1H), 6.95-6.85 (m, 1H), 5.21-5.14 (m, 2H); MS (ESI): m/z: 340 [M+H]⁺.

Step 4: 7-Chloro-5,11-dihydro-dibenzo[b,e][1,4]oxazepine

A vial was charged with 1.81 g (5.32 mmol) of N-[2-[(2-bromophenyl)methoxy]-5-chloro-phenyl]formamide, 0.205 g (3.19 mmol) of copper powder and 1.47 g (10.64 mmol) of K₂CO₃ then it was purged with nitrogen. DMF (17 ml) was added by syringe, the reaction vessel was capped and heated at 155-160° C. for 5 h 45 min. The reaction mixture was allowed to cool to r.t. and water (200 ml ca.) was added. The mixture was extracted with EtOAc (2×150 ml), and the combined extracts were washed with brine, dried (Na₂SO₄), and the solvent was removed under vacuo. The residue was taken up with toluene and evaporated. The crude was purified by flash chromatography (eluent: hexane/EtOAc from 95:5 to 90:10) to afford 7-chloro-5,11-dihydro-dibenzo[b,e][1,4]oxazepine as a yellow solid (0.786 g, 64%). ¹H NMR (DMSO-d₆) δ (ppm): 8.75 (s, 1H), 7.21-7.16 (m, 1H), 7.13-7.09 (m, 1H), 7.04 (d, J=2.9 Hz, 1H), 6.94 (d, J=7.8 Hz, 1H), 6.86 (d, J=8.8 Hz, 1H), 6.74 (dt, J=1.0, 7.3 Hz, 1H), 6.62 (dd, J=2.4, 8.3 Hz, 1H), 4.94 (s, 2H); MS (ESI): m/z: 232 [M+H]⁺.

Intermediate 5: 7-(Trifluoromethyl)-5,11-dihydrodibenzo[b,e][1,4]oxazepine

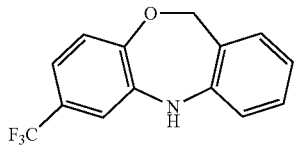 [SMILES: FC(F)(F)c1ccc2c(c1)Nc1ccccc1CO2]

Step 1: 2-Bromobenzyl 2-nitro-4-(trifluoromethyl)phenyl ether 5.3 g (97%) of 2-bromobenzyl 2-nitro-4-(trifluoromethyl)phenyl ether were prepared according to the procedure described for Step 1, starting from 3 g (14.5 mmol) of 2-nitro-4-(trifluoromethyl)phenol and 3.8 g (15.2 mmol) of 1-bromo-2-(bromomethyl)benzene. ¹H NMR (CDCl₃) δ (ppm): 8.20 (d, J=2.4 Hz, 1H), 7.81 (dd, J=2.0, 8.8 Hz, 1H), 7.69-7.58 (m, 2H), 7.45-7.37 (m, 1H), 7.30-7.19 (m, 2H), 5.36 (s, 2H).

Step 2: 2-[(2-Bromobenzyl)oxy]-5-(trifluoromethyl)aniline 2.3 g (87%) of 2-[(2-bromobenzyl)oxy]-5-(trifluoromethyl)aniline were prepared according to the procedure described for Intermediate 4, Step 2, starting from 2.5 g (6.65 mmol) of 2-bromobenzyl 2-nitro-4-(trifluoromethyl)phenyl ether. ¹H NMR (CDCl₃) δ (ppm): 7.63 (dd, J=1.0, 8.3 Hz, 1H), 7.52-7.45 (m, 1H), 7.36 (dt, J=1.0, 7.6 Hz, 1H), 7.29-7.20 (m, 1H), 7.01-6.94 (m, 2H), 6.87 (d, J=7.8 Hz, 1H), 5.22 (s, 2H), 4.51-3.53 (bs, 2H); MS (ESI): m/z: 347 [M+H]⁺.

Step 3: N-{2-[(2-Bromobenzyl)oxy]-5-(trifluoromethyl)phenyl}formamide 2.16 g (97%) of N-{2-[(2-bromobenzyl)oxy]-5-(trifluoromethyl)phenyl}formamide were prepared according to the procedure described for Intermediate 4, Step 3, starting from 2 g (5.78 mmol) of 2-[(2-bromobenzyl)oxy]-5-(trifluoromethyl)aniline. ¹H NMR (CDCl₃) δ (ppm): 8.76 (d, J=2.0 Hz, 1H), 8.50 (d, J=1.5 Hz, 1H), 7.90 (bs, 1H), 7.71-7.62 (m, 1H), 7.47-7.23 (m, 4H), 7.05-7.00 (m, 1H), 5.25 (s, 2H); MS (ESI): m/z: 375 [M+H]⁺.

Step 4: 7-(Trifluoromethyl)-5,11-dihydrodibenzo[b,e][1,4]oxazepine 1.474 g (66%) of 7-(trifluoromethyl)-5,11-dihydrodibenzo[b,e][1,4]oxazepine were prepared according to the procedure described for Intermediate 4, Step 4, starting from 2.08 g (5.56 mmol) of N-{2-[(2-bromobenzyl)oxy]-5-(trifluoromethyl)phenyl}formamide. ¹H NMR (DMSO-d₆) δ (ppm): 8.90 (s, 1H), 7.35 (d, J=2.0 Hz, 1H), 7.24-7.12 (m, 2H), 7.06-6.88 (m, 3H), 6.80-6.73 (m, 1H), 5.01 (s, 2H); MS (ESI): m/z: 266 [M+H]⁺.

Intermediate 6: 3-(7-chlorodibenzo[b,e][1,4]oxazepin-5(11H)-yl)propan-1-amine

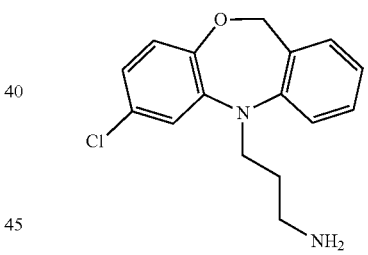

Step 1: 3-Chloro-1-(7-chlorodibenzo[b,e][1,4]oxazepin-5(11H)-yl)propan-1-one 0.623 g (90%) of 3-chloro-1-(7-chlorodibenzo[b,e][1,4]oxazepin-5(11H)-yl)propan-1-one were prepared according to the procedure described for Intermediate 3, Step 1, starting from 0.50 g (2.16 mmol) of 7-chloro-5,11-dihydro-dibenzo[b,e][1,4]oxazepine (Intermediate 4) and 0.42 ml (4.32 mmol) of 3-chloropropanoyl chloride. ¹H NMR (CDCl₃), mixture of rotamers, δ (ppm): 7.59-7.01 (m, 6H), 6.94-6.71 (m, 1H), 5.67 (d, J=12.2 Hz, 1H), 4.86 (d, J=12.2 Hz, 1H), 4.02-3.72 (bm, 2H), 3.11-2.35 (bm, 2H); MS (ESI): m/z: 322 [M+H]⁺.

Step 2: 3-Azido-1-(7-chlorodibenzo[b,e][1,4]oxazepin-5(11H)-yl)propan-1-one 0.173 g (27%) of 3-azido-1-(7-chlorodibenzo[b,e][1,4]oxazepin-5(11H)-yl)propan-1-one were prepared according to the procedure described for Intermediate 3, Step 2, starting from 0.62 g (1.92 mmol) of 3-chloro-1-(7-chlorodibenzo[b,e][1,4]oxazepin-5(11H)-yl)propan-1-one. ¹H NMR (CDCl₃), mixture of rotamers, δ (ppm): 7.58-7.02 (m, 6H), 6.91-6.69 (m, 1H), 5.63 (bs, 1H), 4.87 (d, J=12.7 Hz, 1H), 3.82-3.49 (bm, 2H), 2.88-2.15 (bm, 2H); MS (ESI): m/z: 329 [M+H]⁺.

Step 3: 3-(7-Chlorodibenzo[b,e][1,4]oxazepin-5(11H)-yl)propan-1-amine 0.119 g (79%) of 3-(7-chlorodibenzo[b,e][1,4]oxazepin-5(11H)-yl)propan-1-amine were prepared according to the procedure described for Intermediate 3, Step 3, starting from 0.171 g (0.52 mmol) of 3-azido-1-(7-chlorodibenzo[b,e][1,4]oxazepin-5(11H)-yl)propan-1-one. ¹H NMR (CDCl₃, D₂O) δ (ppm): 7.38-7.28 (m, 2H), 7.15-7.05 (m, 2H), 6.97 (d, J=2.4 Hz, 1H), 6.77-6.73 (m, 1H), 6.72-6.68 (m, 1H), 5.27 (s, 2H), 3.78 (t, J=6.8 Hz, 2H), 2.74 (t, J=6.8 Hz, 2H), 1.79 (quint, J=6.8 Hz, 2H); MS (ESI): m/z: 289 [M+H]⁺.

Intermediate 7: 3-[7-(Trifluoromethyl)dibenzo[b,e][1,4]oxazepin-5(11H)-yl]propan-1-amine

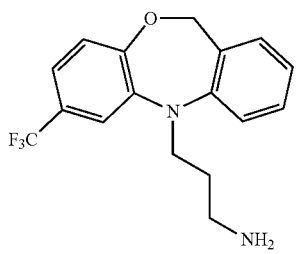 [SMILES: NCCCN1c2ccccc2COc2ccc(C(F)(F)F)cc21]

Step 1: di-tert-Butyl [3-(7-(trifluoromethyl)-dibenzo[b,e][1,4]oxazepin-5(11H)-yl)propyl]imidodicarbonate 0.079 g of NaH (60% oil suspension, 1.98 mmol) were added portionwise to a solution of 0.350 g (1.32 mmol) of 7-(trifluoromethyl)-5,11-dihydrodibenzo[b,e][1,4]oxazepine (Intermediate 5) in dry DMF (6 ml) cooled to 0° C. and the mixture was then stirred at r.t. for 1 h; a solution of 0.670 g (1.98 mmol) of di-tert-butyl (3-bromopropyl) imidodicarbonate (prepared according to literature procedure, *Org. & Biomol. Chem.* 2006, 4, 3228-3234) in dry DMF (4 ml) was added dropwise at 0° C. and the mixture was then stirred at r.t. for 2 h 30 min. The mixture was quenched with brine, then extracted with EtOAc (3×40 ml) and washed with brine (60 ml). The organic layer was dried (Na₂SO₄) and concentrated under vacuo. The crude was purified by flash chromatography (eluent: hexane/EtOAc from 99:1 to 90:10) to afford di-tert-butyl [3-(7-(trifluoromethyl)-dibenzo[b,e][1,4]oxazepin-5(11H)-yl)propyl]imidodicarbonate as a colorless oil (0.414 g, 60%). ¹H NMR (DMSO-d₆), δ (ppm): 7.46-7.43 (m, 1H), 7.42-7.35 (m, 1H), 7.26-7.20 (m, 2H), 7.14-7.07 (m, 2H), 6.85 (d, J=8.8 Hz, 2H 1H), 5.40 (s, 2H), 3.74 (t, J=6.4 Hz, 2H), 3.53 (t, J=6.8 Hz, 2H), 1.82-1.72 (m, 2H), 1.31 (s, 18H); MS (ESI): m/z: 523 [M+H]⁺.

Step 2: 3-[7-(Trifluoromethyl)dibenzo[b,e][1,4]oxazepin-5(11H)-yl]propan-1-amine 1.21 ml (15.8 mmol) of TFA were added to a solution of 0.413 (0.79 mmol) of di-tert-butyl [3-(7-(trifluoromethyl)-dibenzo[b,e][1,4]oxazepin-5(11H)-yl)propyl]imidodicarbonate in dry DCM (7.5 ml). The mixture was stirred at r.t. for 1 h. It was then diluted with DCM (30 ml), washed once with saturated aqueous NaHCO₃ (50 ml), and then with brine (50 ml). The organic layer was dried (Na₂SO₄) and evaporated to give 3-[7-(trifluoromethyl)dibenzo[b,e][1,4]oxazepin-5(11H)-yl]propan-1-amine (0.250 g, 98%) as a yellow oil. ¹H NMR (DMSO-d₆), δ (ppm): 7.48-7.34 (m, 2H), 7.32-7.22 (m, 2H), 7.14-7.06 (m, 2H), 6.85 (d, J=8.8 Hz, 2H 1H), 5.34 (s, 2H), 3.79 (t, J=6.8 Hz, 2H), 2.54 (t, J=6.6 Hz, 2H), 1.63-1.52 (m, 2H); MS (ESI): m/z: 323 [M+H]⁺.

Intermediate 8: 3-(10,11-Dihydro-5H-dibenzo[b,f]azepin-5-yl)propan-1-amine

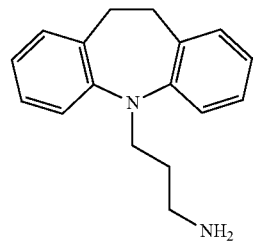 [SMILES: NCCCN1c2ccccc2CCc2ccccc21]

Step 1: 3-Chloro-1-(10,11-dihydro-5H-dibenzo[b,f]azepin-5-yl)propan-1-one 1.42 g (99%) of 3-chloro-1-(10,11-dihydro-5H-dibenzo[b,f]azepin-5-yl)propan-1-one were prepared according to the procedure described for Intermediate 3, Step 1, starting from 1.01 g (5 mmol) of 10,11-dihydro-5H-dibenzo[b,f]azepine (ABCR, Cat. No. AB 125966) and 0.53 ml (5.25 mmol) of 3-chloropropanoyl chloride. ¹H NMR (CDCl₃), mixture of rotamers, δ (ppm): 7.42-7.12 (m, 8H), 3.91-3.76 (m, 2H), 3.51-3.32 (m, 2H), 2.94-2.79 (m, 3H), 2.61-2.49 (m, 1H); MS (ESI): m/z: 285 [M+H]⁺.

Step 2: 3-Azido-1-(10,11-dihydro-5H-dibenzo[b,f]azepin-5-yl)propan-1-one 0.727 g (50%) of 3-azido-1-(10,11-dihydro-5H-dibenzo[b,f]azepin-5-yl)propan-1-one were prepared according to the procedure described for Intermediate 3, Step 2, starting from 1.42 g (4.97 mmol) of 3-chloro-1-(10,11-dihydro-5H-dibenzo[b,f]azepin-5-yl)propan-1-one. ¹H NMR (CDCl₃), mixture of rotamers, δ (ppm): 7.39-7.34 (m, 1H), 7.32-7.14 (m, 7H), 3.70-3.56 (m, 2H), 3.49-3.29 (m, 2H), 2.93-2.77 (m, 2H), 2.70-2.55 (m, 1H), 2.39-2.22 (m, 1H); MS (ESI): m/z: 293 [M+H]⁺.

Step 3: 3-(10,11-Dihydro-5H-dibenzo[b,f]azepin-5-yl)propan-1-amine 0.507 g (92%) of 3-(10,11-dihydro-5H-dibenzo[b,f]azepin-5-yl)propan-1-amine were prepared according to the procedure described for Intermediate 3, Step 3, starting from 0.638 g (2.18 mmol) of 3-azido-1-(10,11-dihydro-5H-dibenzo[b,f]azepin-5-yl)propan-1-one. ¹H NMR (CDCl₃) δ (ppm): 7.18-7.06 (m, 6H), 6.95-6.89 (m, 2H), 3.81 (t, J=6.6 Hz, 2H), 3.17 (s, 4H), 2.75 (t, J=6.8 Hz, 2H), 1.80-1.57 (m, 4H); MS (ESI): m/z: 253 [M+H]⁺.

Intermediate 9: 4-(3-Chloro-10,11-dihydro-5H-dibenzo[b,f]azepin-5-yl)butan-1-amine

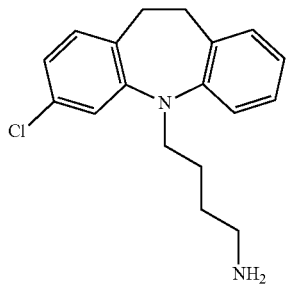 [SMILES: NCCCCN1c2ccccc2CCc2ccc(Cl)cc21]

Step 1: 2-[4-(3-Chloro-10,11-dihydro-5H-dibenzo[b,f]azepin-5-yl)butyl]-1H-isoindole-1,3(2H)-dione A solution of 0.484 g (2 mmol) of 3-chloro-10,11-dihydro-5H-dibenzo[b,f]azepine (FLROCHEM, Cat. No. 211409) in dry DMF (3 ml) was cooled to 0° C., treated with 0.160 g of NaH (60% oil suspension, 4 mmol), and stirred for 1 h at 0° C. A solution of N-(4-bromobutyl)phthalimide (0.864 g, 3 mmol) in DMF (1 ml) was added dropwise and the mixture was heated to 55° C. and stirred for 4 h. The mixture was quenched with brine (5 ml), diluted with water (20 ml) and extracted with EtOAc (3×30 ml). The combined extracts were dried ($Na_2SO_4$), concentrated in vacuo and the residue was purified by flash chromatography (eluent: hexane/EtOAc 90:10) to provide 2-[4-(3-chloro-10,11-dihydro-5H-dibenzo[b,f]azepin-5-yl)butyl]-1H-isoindole-1,3(2H)-dione as a pale yellow solid (0.5 g, 58%). $^1$H NMR (CDCl$_3$), δ (ppm): 7.84-7.77 (m, 2H), 7.74-7.67 (m, 2H), 7.12-7.07 (m, 1H), 7.06-7.02 (m, 2H), 7.00-6.98 (m, 1H), 6.95-6.91 (m, 1H), 6.90-6.85 (m, 1H), 6.80-6.75 (m, 1H), 3.73 (t, J=6.6 Hz, 2H), 3.63 (t, J=7.1 Hz, 2H), 3.17-3.04 (m, 4H), 1.78-1.68 (m, 2H), 1.66-1.60 (m, 2H); MS (ESI): m/z: 431 [M+H]$^+$.

Step 2: 4-(3-Chloro-10,11-dihydro-5H-dibenzo[b,f]azepin-5-yl)butan-1-amine

A solution of 0.5 g of 2-[4-(3-chloro-10,11-dihydro-5H-dibenzo[b,f]azepin-5-yl)butyl]-1H-isoindole-1,3(2H)-dione (1.16 mmol) in EtOH (4 mL) was treated with 0.17 ml of hydrazine hydrate (3.48 mmol) and heated to 80° C. for 1 h. The mixture was cooled to r.t., filtered to remove the white solid that had formed, and then concentrated. The residue was purified by flash chromatography (eluent: DCM/MeOH/NH$_4$OH 95:5:0.5) to afford 4-(3-chloro-10,11-dihydro-5H-dibenzo[b,f]azepin-5-yl)butan-1-amine as a yellow oil (0.34 g, 97%). $^1$H NMR (CDCl$_3$, D$_2$O) δ (ppm): 7.18-7.10 (m, 2H), 7.09-7.06 (m, 1H), 7.05-7.02 (m, 1H), 7.01-6.94 (m, 2H), 6.87 (dd, J=2.0, 8.3 Hz, 1H), 3.71 (t, J=6.8 Hz, 2H), 3.18-3.07 (m, 4H), 2.63 (t, J=7.1 Hz, 2H), 1.66-1.55 (m, 2H), 1.52-1.40 (m, 2H); MS (ESI): m/z: 301 [M+H]$^+$.

Intermediate 10: 5-(3-Chloro-10,11-dihydro-5H-dibenzo[b,f]azepin-5-yl)pentan-1-amine

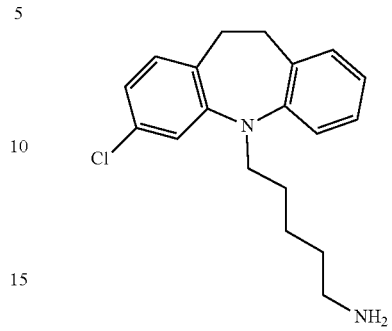

Step 1: 2-[5-(3-Chloro-10,11-dihydro-5H-dibenzo[b,f]azepin-5-yl)pentyl]-1H-isoindole-1,3(2H)-dione 0.7 g (79%) of 2-[5-(3-chloro-10,11-dihydro-5H-dibenzo[b,f]azepin-5-yl)pentyl]-1H-isoindole-1,3(2H)-dione were prepared according to the procedure described for Intermediate 9, Step 1, starting from 0.469 g (2 mmol) of 3-chloro-10,11-dihydro-5H-dibenzo[b,f]azepine (FLROCHEM, Cat. No. 211409) and 0.907 g (3 mmol) of N-(5-bromopentyl)phthalimide. $^1$H NMR (CDCl$_3$), δ (ppm): 7.88-7.81 (m, 2H), 7.75-7.69 (m, 2H), 7.17-7.11 (m, 1H), 7.11-7.04 (m, 2H), 7.03-7.00 (m, 1H), 6.99-6.92 (m, 2H), 6.85 (dd, J=2.0, 8.3 Hz, 1H), 3.71-3.61 (m, 4H), 3.14-3.04 (m, 4H), 1.69-1.58 (m, 4H), 1.42-1.32 (m, 2H); MS (ESI): m/z: 445 [M+H]$^+$.

Step 2: 5-(3-Chloro-10,11-dihydro-5H-dibenzo[b,f]azepin-5-yl)pentan-1-amine 0.36 g (73%) of 5-(3-chloro-10,11-dihydro-5H-dibenzo[b,f]azepin-5-yl)pentan-1-amine were prepared according to the procedure described for Intermediate 9, Step 2, starting from 0.696 g (1.56 mmol) of 2-[5-(3-chloro-10,11-dihydro-5H-dibenzo[b,f]azepin-5-yl)pentyl]-1H-isoindole-1,3(2H)-dione. $^1$H NMR (CDCl$_3$), δ (ppm): 7.19-7.10 (m, 2H), 7.09-7.05 (m, 1H), 7.05-7.02 (m, 1H), 7.01-6.94 (m, 2H), 6.87 (dd, J=2.0, 8.3 Hz, 1H), 3.70 (t, J=6.8 Hz, 2H), 3.20-3.07 (m, 4H), 2.65 (t, J=6.6 Hz, 2H), 1.63-1.54 (m, 2H), 1.46-1.31 (m, 4H); MS (ESI): m/z: 315 [M+H]$^+$.

Intermediate 11: 3-Nitro-10,11-dihydro-5H-dibenzo[b,f]azepine

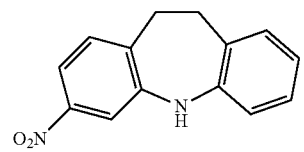 [SMILES: O=[N+]([O-])c1ccc2c(c1)Nc1ccccc1CC2]

0.644 g (2.28 mmol) of 1-(3-nitro-10,11-5H-dibenzo[b,f]azepin-5yl)ethanone (prepared according to the procedure described in WO 2016/064682) were dissolved in a solution of 11 ml of 12 N HCl and 11 ml of AcOH and stirred at reflux overnight. The reaction was cooled to r.t., basified with saturated aqueous Na$_2$CO$_3$ and extracted with EtOAc. The organic phase was concentrated under vacuo and the crude was purified by flash chromatography (eluent: hexane/EtOAc 96:4) to provide 3-nitro-10,11-dihydro-5H-dibenzo[b,f]azepine as a yellow solid (0.294 g, 54%). $^1$H NMR (DMSO-d$_6$), δ (ppm): 8.88 (s, 1H), 7.95-7.83 (m, 1H), 7.46 (dd, J=2.0, 8.3 Hz, 1H), 7.30-7.22 (m, 1H), 7.12-7.03 (m, 2H), 7.01-6.96 (m, 1H), 6.78-6.73 (m, 1H), 3.10-3.03 (m, 2H), 3.01-2.95 (m, 2H); MS (ESI): m/z: 241 [M+H]$^+$.

Intermediate 12: 3-(3-Nitro-10,11-dihydro-5H-dibenzo[b,f]azepin-5-yl)propan-1-amine

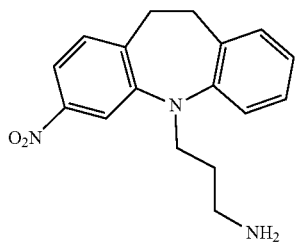 [SMILES: NCCCN1c2ccccc2CCc2ccc([N+](=O)[O-])cc21]

Step 1: 3-Chloro-1-(3-nitro-10,11-dihydro-5H-dibenzo[b,f]azepin-5-yl)propan-1-one 0.49 g (92%) of 3-chloro-1-(3-nitro-10,11-dihydro-5H-dibenzo[b,f]azepin-5-yl)propan-1-one were prepared according to the procedure described for Intermediate 3, Step 1, starting from 0.386 g (1.61 mmol) of 3-nitro-10,11-dihydro-5H-dibenzo[b,f]azepine (Intermediate 11) and 0.17 ml (1.69 mmol) of 3-chloropropanoyl chloride. $^1$H NMR (CDCl$_3$), mixture of rotamers, δ (ppm): 8.37-7.97 (m, 2H), 7.54-7.14 (m, 5H), 3.96-3.71 (m, 2H), 3.60-3.37 (m, 2H), 3.04-2.79 (m, 3H), 2.67-2.51 (m, 1H); MS (ESI): m/z: 331 [M+H]$^+$.

Step 2: 3-Azido-1-(3-nitro-10,11-dihydro-5H-dibenzo[b,f]azepin-5-yl)propan-1-one 0.217 g (44%) of 3-azido-1-(3-nitro-10,11-dihydro-5H-dibenzo[b,f]azepin-5-yl)propan-1-one were prepared according to the procedure described for Intermediate 3, Step 2, starting from 0.489 g (1.48 mmol) of 3-chloro-1-(3-nitro-10,11-dihydro-5H-dibenzo[b,f]azepin-5-yl)propan-1-one. $^1$H NMR (CDCl$_3$), mixture of rotamers, δ (ppm): 8.33-7.96 (m, 2H), 7.57-7.12 (m, 5H), 3.83-3.35 (m, 4H), 3.06-2.81 (m, 2H), 2.70-2.54 (m, 1H), 2.39-2.21 (m, 1H); MS (ESI): m/z: 338 [M+H]$^+$.

Step 3: 3-(3-Nitro-10,11-dihydro-5H-dibenzo[b,f]azepin-5-yl)propan-1-amine 0.168 g (89%) of 3-(3-nitro-10,11-dihydro-5H-dibenzo[b,f]azepin-5-yl)propan-1-amine were prepared according to the procedure described for Intermediate 3, Step 3, starting from 0.215 g (0.64 mmol) of 3-azido-1-(3-nitro-10,11-dihydro-5H-dibenzo[b,f]azepin-5-yl)propan-1-one. $^1$H NMR (CDCl$_3$, D$_2$O) δ (ppm): 7.95-7.92 (m, 1H), 7.73 (dd, J=2.2, 8.6 Hz, 1H), 7.23-7.12 (m, 4H), 7.06-7.01 (m, 1H), 3.88 (t, J=6.8 Hz, 2H), 3.26-3.14 (m, 4H), 2.74 (t, J=7.1 Hz, 2H), 1.79-1.69 (m, 2H); MS (ESI): m/z: 298 [M+H]$^+$.

Intermediate 13: 3-(3-Bromo-10,11-dihydro-5H-dibenzo[b,f]azepin-5-yl)propan-1-amine

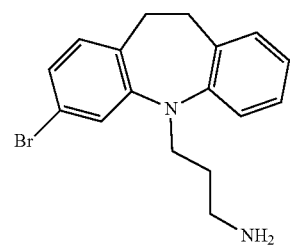 [SMILES: NCCCN1c2ccccc2CCc2ccc(Br)cc21]

Step 1: 3-Chloro-1-(3-bromo-10,11-dihydro-5H-dibenzo[b,f]azepin-5-yl)propan-1-one 0.443 g (93%) of 3-chloro-1-(3-bromo-10,11-dihydro-5H-dibenzo[b,f]azepin-5-yl)propan-1-one were prepared according to the procedure described for Intermediate 3, Step 1, starting from 0.360 g (1.31 mmol) of 3-bromo-10,11-dihydro-5H-dibenzo[b,f]azepine (prepared according to literature procedure, J. Prakt. Chem. 1997, 339, 587-589) and 0.14 ml (1.38 mmol) of 3-chloropropanoyl chloride. $^1$H NMR (CDCl$_3$), mixture of rotamers, δ (ppm): 7.60-6.94 (m, 7H), 3.95-3.71 (m, 2H), 3.48-3.22 (m, 2H), 2.96-2.75 (m, 3H), 2.64-2.44 (m, 1H); MS (ESI): m/z: 364 [M+H]$^+$.

Step 2: 3-Azido-1-(3-bromo-10,11-dihydro-5H-dibenzo[b,f]azepin-5-yl)propan-1-one 0.124 g (28%) of 3-azido-1-(3-bromo-10,11-dihydro-5H-dibenzo[b,f]azepin-5-yl)propan-1-one were prepared according to the procedure described for Intermediate 3, Step 2, starting from 0.435 g (1.19 mmol) of 3-chloro-1-(3-bromo-10,11-dihydro-5H-dibenzo[b,f]azepin-5-yl)propan-1-one. $^1$H NMR (CDCl$_3$), mixture of rotamers, δ (ppm): 7.61-6.98 (m, 7H), 3.75-3.53 (m, 2H), 3.45-3.22 (m, 2H), 2.92-2.74 (m, 2H), 2.68-2.55 (m, 1H), 2.39-2.21 (m, 1H); MS (ESI): m/z: 371 [M+H]$^+$.

Step 3: 3-(3-Bromo-10,11-dihydro-5H-dibenzo[b,f]azepin-5-yl)propan-1-amine 0.095 g (87%) of 3-(3-bromo-10,11-dihydro-5H-dibenzo[b,f]azepin-5-yl)propan-1-amine were prepared according to the procedure described for Intermediate 3, Step 3, starting from 0.122 g (0.33 mmol) of 3-azido-1-(3-bromo-10,11-dihydro-5H-dibenzo[b,f]azepin-5-yl)propan-1-one. $^1$H NMR (CDCl$_3$, D$_2$O) δ (ppm): 7.23-7.07 (m, 4H), 7.04-6.92 (m, 3H), 3.78 (t, J=6.6 Hz, 2H), 3.19-3.05 (m, 4H), 2.71 (t, J=6.8 Hz, 2H), 1.77-1.65 (m, 2H); MS (ESI): m/z: 331 [M+H]$^+$.

Intermediate 14: 5-(3-Aminopropyl)-3-chloro-5,10-dihydro-11H-dibenzo[b,e][1,4]diazepin-11-one

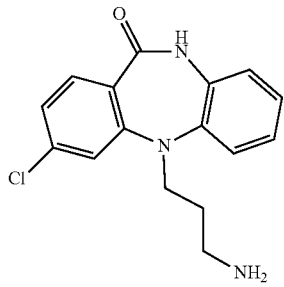 [SMILES: NCCCN1c2ccccc2NC(=O)c2ccc(Cl)cc21]

Step 1: 3-Chloro-10-(4-methoxybenzyl)-5,10-dihydro-11H-dibenzo[b,e][1,4]diazepin-11-one A solution of 0.196 g (0.8 mmol) of 3-chloro-5,10-dihydro-11H-dibenzo[b,e][1,4]diazepin-11-one (prepared according to literature procedure, Synthesis 1985, 1, 550-552) in dry DMF (15 ml) was cooled to 0° C. and treated with NaH (60% oil suspension, 0.037 g, 0.92 mmol).

The mixture was warmed to r.t. and stirred for 1 h, then cooled at 0° C. and 0.12 ml of p-methoxybenzyl chloride (0.84 mmol) were added dropwise. The reaction mixture was warmed to r.t. and stirred for 5 h, then it was quenched with brine (20 ml), diluted with water (50 ml) and extracted with EtOAc (3×50 mL). The combined extracts were washed with brine, dried ($Na_2SO_4$) and concentrated in vacuo. The residue was purified by flash chromatography (eluent: hexane/EtOAc 87:13) to provide 3-chloro-10-(4-methoxybenzyl)-5,10-dihydro-11H-dibenzo[b,e][1,4]diazepin-11-one as a pale yellow solid (0.116 g, 40%). $^1$H NMR (CDCl$_3$), δ (ppm): 7.91-7.76 (m, 1H), 7.30-7.23 (m, 2H), 7.23-7.18 (m, 1H), 7.05-6.98 (m, 3H), 6.91-6.86 (m, 1H), 6.86-6.84 (m, 1H), 6.84-6.78 (m, 2H), 5.51 (bs, 1H), 5.22 (s, 2H), 3.76 (s, 3H); MS (ESI): m/z: 365 [M+H]$^+$.

Step 2: di-tert-Butyl {3-[3-chloro-10-(4-methoxybenzyl)-11-oxo-10,11-dihydro-5H-dibenzo[b,e][1,4]diazepin-5-yl]propyl}imidodicarbonate A solution of 0.168 g (0.46 mmol) of 3-chloro-10-(4-methoxybenzyl)-5,10-dihydro-11H-dibenzo[b,e][1,4]diazepin-11-one in dry DMF (2.5 ml) was cooled to 0° C. and treated with 0.028 g of NaH (60% oil suspension, 0.69 mmol). The reaction mixture was warmed to r.t., stirred for 1 h, then cooled to 0° C. and treated with 0.243 g (0.69 mmol) of di-tert-butyl (3-bromopropyl)imidodicarbonate (prepared according to literature procedure, Org. & Biomol. Chem. 2006, 4, 3228-3234) in dry DMF (1.2 ml). The combined solution was warmed to r.t. and stirred for 2 h. The mixture was quenched with brine (5 ml), diluted with water (20 ml) and extracted with EtOAc (3×20 mL). The combined extracts were washed with brine, dried ($Na_2SO_4$) and concentrated in vacuo. The residue was purified by flash chromatography (eluent: hexane/EtOAc 85:15) to provide di-tert-butyl {3-[3-chloro-10-(4-methoxybenzyl)-11-oxo-10,11-dihydro-5H-dibenzo[b,e][1,4]diazepin-5-yl]propyl}imidodicarbonate as a white solid (0.218 g, 76%). $^1$H NMR (CDCl$_3$), δ (ppm): 7.76-7.64 (m, 1H), 7.26-7.20 (m, 3H), 7.13-7.08 (m, 1H), 7.07-7.02 (m, 1H), 7.00-6.97 (m, 1H), 6.82-6.77 (m, 2H), AB System: ν$_A$=5.5, ν$_B$=4.96, $J_{AB}$=15.2 Hz, 3.76 (s, 3H), 3.71-3.57 (m, 2H), 3.54 (t, J=6.8 Hz, 2H), 1.93-1.73 (m, 2H), 1.47 (s, 18H); MS (ESI): m/z: 566 [M−56+H]$^+$.

Step 3: 5-(3-Aminopropyl)-3-chloro-5,10-dihydro-11H-dibenzo[b,e][1,4]diazepin-11-one 1.21 ml of TFA were added to a solution of 0.215 g (0.35 mmol) of di-tert-butyl {3-[3-chloro-10-(4-methoxybenzyl)-11-oxo-10,11-dihydro-5H-dibenzo[b,e][1,4]diazepin-5-yl]propyl}imidodicarbonate in dry DCM (1.2 ml) at 0° C. followed by trifluoromethanesulfonic acid (0.104 ml, 1.05 mmol), added dropwise. The mixture was warmed to r.t. and stirred overnight. The reaction mixture was cooled to 0° C. and 0.035 ml (0.35 mmol) of trifluoromethanesulfonic acid was added and the mixture was warmed to r.t. and stirred for additional 6 h. The mixture was cautiously partitioned between chilled saturated aqueous NaHCO$_3$ and DCM. The aqueous phase was extracted with DCM and the combined organic extracts were dried ($Na_2SO_4$) and concentrated. The crude was purified by flash chromatography (eluent: DCM/MeOH/NH$_4$OH 90:10:1) to afford 5-(3-aminopropyl)-3-chloro-5,10-dihydro-11H-dibenzo[b,e][1,4]diazepin-11-one as on off-white solid (0.090 g, 86%). $^1$H NMR (DMSO-d$_6$) δ (ppm): 10.34 (bs, 1H), 7.65-7.52 (m, 1H), 7.29-7.25 (m, 1H), 7.22-7.18 (m, 1H), 7.16-7.08 (m, 2H), 7.07-7.02 (m, 2H), 3.83-3.70 (m, 2H), 2.56 (t, J=6.6 Hz, 2H), 1.59-1.43 (m, 2H); MS (ESI): m/z: 302 [M+H]$^+$.

Intermediate 15: 5-(4-Aminobutyl)-3-chloro-5,10-dihydro-11H-dibenzo[b,e][1,4]diazepin-11-one

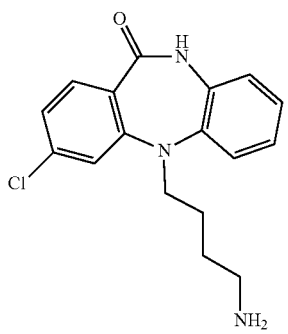 [SMILES: NCCCCN1c2ccccc2NC(=O)c2ccc(Cl)cc21]

Step 1: di-tert-Butyl (4-bromobutyl)imidodicarbonate 1.54 g of di-tert-butyl (4-bromobutyl)imidodicarbonate were prepared according to literature procedure (Org. & Biomol. Chem. 2006, 4, 3228-3234) starting from 1.13 g (5 mmol) of di-tert-butyl iminodicarboxylate (Sigma-Aldrich, Cat. No. 375276) and 2.71 ml (22.5 mmol) of 1,4-dibromobutane. $^1$H NMR (CDCl$_3$), δ (ppm): 3.61 (t, J=7.3 Hz, 2H), 3.43 (t, J=6.6 Hz, 2H), 1.94-1.82 (m, 2H), 1.79-1.68 (m, 2H), 1.52 (s, 18H).

Step 2: di-tert-Butyl {4-[3-chloro-10-(4-methoxybenzyl)-11-oxo-10,11-dihydro-5H-dibenzo[b,e][1,4]diazepin-5-yl]butyl}imidodicarbonate 0.165 g (83%) of di-tert-butyl {4-[3-chloro-10-(4-methoxybenzyl)-11-oxo-10,11-dihydro-5H-dibenzo[b,e][1,4]diazepin-5-yl]butyl}imidodicarbonate were prepared according to the procedure described for Intermediate 14, Step 2, starting from 0.114 g (0.31 mmol) of 3-chloro-10-(4-methoxybenzyl)-5,10-dihydro-11H-dibenzo[b,e][1,4]diazepin-11-one (Intermediate 14, Step 1) and 0.172 g (0.47 mmol) of di-tert-butyl (4-bromobutyl)imidodicarbonate. $^1$H NMR (CDCl$_3$), δ (ppm): 7.77-7.62 (m, 1H), 7.25-7.19 (m, 3H), 7.13-7.01 (m, 4H), 6.99-6.96 (m, 1H), 6.83-6.77 (m, 2H), AB System: $v_A$=5.44, $v_B$=4.99, $J_{AB}$=15.1 Hz, 3.77 (s, 3H), 3.69-3.48 (m, 4H), 1.68-1.44 (m, 22H); MS (ESI): m/z: 580 [M−56+H]$^+$.

Step 3: 5-(4-Aminobutyl)-3-chloro-5,10-dihydro-11H-dibenzo[b,e][1,4]diazepin-11-one 0.062 g (76%) of 5-(4-aminobutyl)-3-chloro-5,10-dihydro-11H-dibenzo[b,e][1,4]diazepin-11-one were prepared according to the procedure described for Intermediate 14, Step 3, starting from 0.164 g (0.26 mmol) of di-tert-butyl {4-[3-chloro-10-(4-methoxybenzyl)-11-oxo-10,11-dihydro-5H-dibenzo[b,e][1,4]diazepin-5-yl]butyl}imidodicarbonate. $^1$H NMR (DMSO-d$_6$) δ (ppm): 10.21 (bs, 1H), 7.62-7.55 (m, 1H), 7.27-7.24 (m, 1H), 7.21-7.17 (m, 1H), 7.15-7.08 (m, 2H), 7.07-7.01 (m, 2H), 3.71 (t, J=7.1 Hz, 2H), 2.47 (t, J=6.8 Hz, 2H), 1.63-1.30 (m, 6H); MS (ESI): m/z: 316 [M+H]$^+$.

Intermediate 16: 3-(Trifluoromethyl)-5,10-dihydro-11H-dibenzo[b,e][1,4]diazepin-11-one

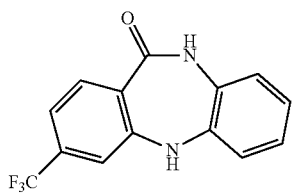 [SMILES: O=C1Nc2ccccc2Nc2cc(C(F)(F)F)ccc21]

A well stirred suspension of 2.364 g (10 mmol) of 2-chloro-4-(trifluoromethyl)benzoic acid, 1.087 g (10 mmol) of o-phenylenediamine and 0.642 g (10 mmol) of copper powder in chlorobenzene (30 ml) was heated for 8 h in a flask equipped with a Dean-Stark apparatus. The hot mixture was rapidly filtered and the filtrate was concentrated under vacuo. The residue was purified by flash chromatography (eluent: hexane/EtOAc 80:20) to provide 3-trifluormethyl-5,10-dihydro-11H-dibenzo[b,e][1,4]diazepin-11-one as a yellow/ochre solid (0.677 g, 24%). $^1$H NMR (DMSO-d$_6$), δ (ppm): 10.08 (s, 1H), 8.21 (s, 1H), 7.86 (d, J=8.1 Hz, 1H), 7.37 (d, J=1.2 Hz, 1H), 7.19 (dd, J=1.2, 8.1 Hz, 1H), 7.02-6.88 (m, 4H); MS (ESI): m/z: 279 [M+H]$^+$.

Intermediate 17: 5-(3-Aminopropyl)-3-(trifluoromethyl)-5,10-dihydro-11H-dibenzo[b,e][1,4]diazepin-11-one

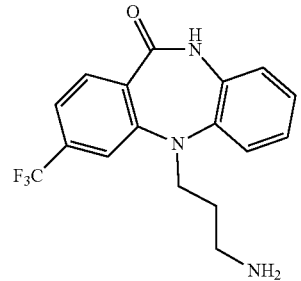 [SMILES: NCCCN1c2ccccc2NC(=O)c2ccc(C(F)(F)F)cc21]

Step 1: 10-(4-Methoxybenzyl)-3-trifluromethyl-5,10-dihydro-11H-dibenzo[b,e][1,4]diazepin-11-one 0.35 g (71%) of 10-(4-methoxybenzyl)-3-trifluromethyl-5,10-dihydro-11H-dibenzo[b,e][1,4]diazepin-11-one were prepared according to the procedure described for Intermediate 14, Step 1, starting from 0.342 g (1.23 mmol) of 3-trifluormethyl-5,10-dihydro-11H-dibenzo[b,e][1,4]diazepin-11-one (Intermediate 16) and 0.179 ml (1.29 mmol) of p-methoxybenzyl chloride. $^1$H NMR (DMSO-d$_6$), δ (ppm): 8.20 (s, 1H), 7.89-7.74 (m, 1H), 7.48-7.43 (m, 1H), 7.40-7.35 (m, 1H), 7.32-7.28 (m, 1H), 7.22-7.15 (m, 2H), 7.13-7.08 (m, 1H), 7.08-6.99 (m, 2H), 6.85-6.79 (m, 2H), 5.19 (s, 2H), 3.68 (s, 3H); MS (ESI): m/z: 399 [M+H]$^+$.

Step 2: di-tert-Butyl {3-[10-(4-methoxybenzyl)-11-oxo-3-(trifluromethyl)-10,11-dihydro-5H-dibenzo[b,e][1,4]diazepin-5-yl]propyl}imidodicarbonate 0.236 g (64%) of di-tert-butyl {3-[10-(4-methoxybenzyl)-11-oxo-3-(trifluoromethyl)-10,11-dihydro-5H-dibenzo[b,e][1,4]diazepin-5-yl]propyl}imidodicarbonate were prepared according to the procedure described for Intermediate 14, Step 2, starting from 0.223 g (0.56 mmol) of 10-(4-methoxybenzyl)-3-trifluoromethyl-5,10-dihydro-11H-dibenzo[b,e][1,4]diazepin-11-one and 0.296 g (0.84 mmol) of di-tert-butyl (3-bromopropyl)imidodicarbonate. $^1$H NMR (CDCl$_3$), δ (ppm): 7.92-7.82 (m, 1H), 7.33-7.30 (m, 1H), 7.29-7.26 (m, 1H), 7.25-7.20 (m, 3H), 7.15-7.05 (m, 3H), 6.82-6.78 (m, 2H), AB System: $v_A$=5.52, $v_B$=4.97, $J_{AB}$=14.9 Hz, 3.77 (s, 3H), 3.71-3.65 (m, 2H), 3.54 (t, J=7.1 Hz, 2H), 1.94-1.71 (m, 2H), 1.46 (s, 18H); MS (ESI): m/z: 600 [M−56+H]$^+$.

Step 3: 5-(3-Aminopropyl)-3-(trifluoromethyl)-5,10-dihydro-11H-dibenzo[b,e][1,4]diazepin-11-one 0.107 g (90%) of 5-(3-aminopropyl)-3-(trifluoromethyl)-5,10-dihydro-11H-dibenzo[b,e][1,4]diazepin-11-one were prepared according to the procedure described for Intermediate 14, Step 3, starting from 0.233 g (0.35 mmol) of di-tert-butyl {3-[10-(4-methoxybenzyl)-11-oxo-3-(trifluromethyl)-10,11-dihydro-5H-dibenzo[b,e][1,4]diazepin-5-yl]propyl}imidodicarbonate. $^1$H NMR (CDCl$_3$) δ (ppm): 8.11-7.80 (m, 2H), 7.37-7.30 (m, 2H), 7.21-7.15 (m, 2H), 7.12-7.06 (m, 1H), 7.04-6.97 (m, 1H), 3.97-3.78 (m, 2H), 2.81 (t, J=6.8 Hz, 2H), 1.81-1.75 (m, 2H); MS (ESI): m/z: 336 [M+H]$^+$.

Intermediate 18: 7-Chloro-5,10-dihydro-11H-dibenzo[b,e][1,4]diazepin-11-one

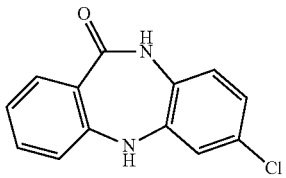 [SMILES: O=C1Nc2ccc(Cl)cc2Nc2ccccc21]

Step 1: 2[(5-Chloro-2-nitrophenyl)amino]benzoic acid 8.562 g (26 mmol) of Cs$_2$CO$_3$ were added to a solution of 2.451 g (17.5 mmol) of 2-aminobenzoic acid and 3.728 g (21 mmol) of 4-chloro-2-fluoro-1-nitrobenzene in dry DMF (22 ml) and the resulting mixture was stirred at 140° C. for 4 h. After cooling to r.t., the mixture was diluted with water, acidified with 2 N HCl and extracted with EtOAc. The combined organic layers were dried (Na$_2$SO$_4$), filtered and concentrated. The residue was slurried in EtOAc and filtered to afford an orange solid. The filtrate was concentrated and purified by flash chromatography (eluent: DCM/MeOH from 100:0 to 95:5) to provide an orange powder. Both solids were combined to give 2[(5-chloro-2-nitrophenyl)amino]benzoic acid as an orange powder (2.130 g, 41%). $^1$H NMR (DMSO-d$_6$), δ (ppm): 13.49 (bs, 1H), 11.13 (s, 1H), 8.19-8.15 (m, 1H), 8.01-7.97 (m, 1H), 7.62-7.58 (m, 2H), 7.57-7.54 (m, 1H), 7.20-7.14 (m, 1H), 7.08 (dd, J=2.2, 9.0 Hz, 1H); MS (ESI): m/z: 293 [M+H]$^+$.

Step 2: 2-[(2-Amino-5-chlorophenyl)amino]benzoic acid 7.607 g (35.82 mmol) of Na$_2$S$_2$O$_4$ (82%) were added to a solution of 2.097 g (7.16 mmol) of 2[(5-chloro-2-nitrophenyl)amino]benzoic acid in 16.94 ml of 2 M K$_2$CO$_3$ (33.89 mmol) and EtOH (16 ml) and the reaction was stirred at r.t. for 20 min. EtOH was removed at reduced pressure and the resulting aqueous mixture was acidified with 2 N HCl until pH 2 and poured into EtOAc. The separated organic layer, was washed with water, brine, dried (Na$_2$SO$_4$), filtered and evaporated to give 2-[(2-Amino-5-chlorophenyl)amino]benzoic acid as a yellow solid (1.695 g, 90%). $^1$H NMR (DMSO-d$_6$), δ (ppm): 12.93 (bs, 1H), 9.03 (s, 1H), 7.92-7.81 (m, 1H), 7.39-7.30 (m, 1H), 7.10-7.04 (m, 1H), 6.97 (dd, J=2.4, 8.3 Hz, 1H), 6.83-6.76 (m, 1H), 6.74-6.69 (m, 1H), 6.67-6.63 (m, 1H), 5.07 (bs, 2H); MS (ESI): m/z: 263 [M+H]$^+$.

Step 3: 7-Chloro-5,10-dihydro-11H-dibenzo[b,e][1,4]diazepin-11-one 1.69 g (6.46 mmol) of 2-[(2-amino-5-chlorophenyl)amino]benzoic, 4.276 g (12.92 mmol) of TBTU, 4.5 ml (25.84 mmol) of DIPEA were dissolved in dry DMF (21 ml). The mixture was stirred at r.t. for about 22 h. The reaction was poured into water, extracted with EtOAc and the combined organic phases were washed with brine, dried (Na$_2$SO$_4$), filtered and concentrated. The residue was purified by flash chromatography (eluent: hexane/EtOAc 80:20) to afford 7-chloro-5,10-dihydro-11H-dibenzo[b,e][1,4]diazepin-11-one as a yellow solid (1.083 g, 80%). $^1$H NMR (DMSO-d$_6$) δ (ppm): 9.94 (s, 1H), 7.98 (s, 1H), 7.73-7.59 (m, 1H), 7.39-7.33 (m, 1H), 7.08-7.02 (m, 1H), 6.98-6.87 (m, 4H); MS (ESI): m/z: 245 [M+H]$^+$.

Intermediate 19: 5-(3-Aminopropyl)-7-chloro-5,10-dihydro-11H-dibenzo[b,e][1,4]diazepin-11-one

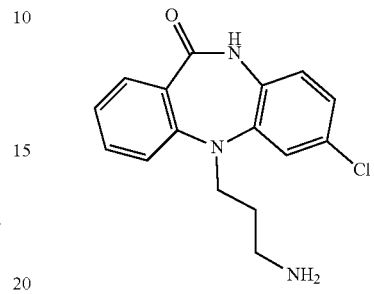

Step 1: 7-Chloro-10-(4-methoxybenzyl)-5,10-dihydro-11H-dibenzo[b,e][1,4]diazepin-11-one 0.400 g (74%) of 7-chloro-10-(4-methoxybenzyl)-5,10-dihydro-11H-dibenzo[b,e][1,4]diazepin-11-one were prepared according to the procedure described for Intermediate 14, Step 1, starting from 0.300 g (1.23 mmol) of 7-chloro-5,10-dihydro-11H-dibenzo[b,e][1,4]diazepin-11-one (Intermediate 18) and 0.178 ml (1.29 mmol) of p-methoxybenzyl chloride. $^1$H NMR (CDCl$_3$), δ (ppm): 7.90 (dd, J=2.0, 7.8 Hz, 1H), 7.36-7.31 (m, 1H), 7.26-7.22 (m, 2H), 7.14-7.10 (m, 1H), 7.10-7.06 (m, 1H), 6.95 (dd, J=2.2, 8.6 Hz, 1H), 6.91-6.88 (m, 1H), 6.85-6.79 (m, 3H), 5.31 (s, 1H), 5.20 (s, 2H), 3.78 (s, 3H); MS (ESI): m/z: 365 [M+H]$^+$.

Step 2: di-tert-Butyl {3-[7-chloro-10-(4-methoxybenzyl)-11-oxo-10,11-dihydro-5H-dibenzo[b,e][1,4]diazepin-5-yl]propyl}imidodicarbonate 0.173 g (49%) of di-tert-butyl {3-[7-chloro-10-(4-methoxybenzyl)-11-oxo-10,11-dihydro-5H-dibenzo[b,e][1,4]diazepin-5-yl]propyl}imidodicarbonate were prepared according to the procedure described for Intermediate 14, Step 2, starting from 0.250 g (0.57 mmol) of 7-chloro-10-(4-methoxybenzyl)-5,10-dihydro-11H-dibenzo[b,e][1,4]diazepin-11-one and 0.302 g (0.86 mmol) of di-tert-butyl (3-bromopropyl)imidodicarbonate. $^1$H NMR (CDCl$_3$), δ (ppm): 7.82-7.70 (m, 1H), 7.41-7.34 (m, 1H), 7.24-7.20 (m, 2H), 7.16-7.13 (m, 1H), 7.12-7.07 (m, 1H), 7.03-6.96 (m, 3H), 6.83-6.79 (m, 2H), AB System: ν$_A$=5.47, ν$_B$=4.96, J$_{AB}$=15.1 Hz, 3.77 (s, 3H), 3.76-3.70 (m, 1H), 3.56-3.48 (m, 3H), 1.93-1.76 (m, 2H), 1.46 (s, 18H); MS (ESI): m/z: 644 [M+Na]$^+$.

Step 3: 5-(3-Aminopropyl)-7-chloro-5,10-dihydro-11H-dibenzo[b,e][1,4]diazepin-11-one 0.073 g (88%) of 5-(3-aminopropyl)-7-chloro-5,10-dihydro-11H-dibenzo[b,e][1,4]diazepin-11-one were prepared according to the procedure described for Intermediate 14, Step 3, starting from 0.171 g (0.275 mmol) of di-tert-butyl {3-[7-chloro-10-(4-methoxybenzyl)-11-oxo-10,11-dihydro-5H-dibenzo[b,e][1,4]diazepin-5-yl]propyl}imidodicarbonate. $^1$H NMR (CDCl$_3$) δ (ppm): 7.82 (dd, J=1.5, 7.8 Hz, 1H), 7.78-7.69 (m, 1H), 7.51-7.44 (m, 1H), 7.16-7.09 (m, 3H), 7.02 (dd, J=2.2, 8.6 Hz, 1H), 6.92-6.86 (m, 1H), 3.91-3.73 (m, 2H), 2.80 (t, J=6.8 Hz, 2H), 1.81-1.71 (m, 2H); MS (ESI): m/z: 302 [M+H]$^+$.

Intermediate 20: 5-(3-Aminopropyl)-3-choro-10-methyl-5,10-dihydro-11H-dibenzo[b,e][1,4]diazepin-11-one

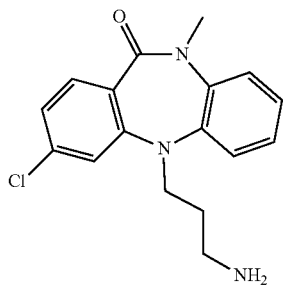 [SMILES: CN1C(=O)c2ccc(Cl)cc2N(CCCN)c2ccccc21]

Step 1:3-Chloro-10-methyl-5,10-dihydro-11H-dibenzo[b,e][1,4]diazepin-11-one 0.092 g (73%) of 3-chloro-10-methyl-5,10-dihydro-11H-dibenzo[b,e][1,4]diazepin-11-one were prepared according to the procedure described for Intermediate 14, Step 1, starting from 0.126 g (0.49 mmol) of 3-chloro-5,10-dihydro-11H-dibenzo[b,e][1,4]diazepin-11-one (prepared according to literature, *Synthesis* 1985, 1, 550-552) and 0.032 ml (0.51 mmol) of iodomethane. $^1$H NMR (DMSO-d$_6$), δ (ppm): 8.10 (s, 1H), 7.70-7.60 (m, 1H), 7.32-7.27 (m, 1H), 7.16-7.14 (m, 1H), 7.13-7.08 (m, 3H), 7.00 (dd, J=2.0, 8.3 Hz, 1H), 3.36 (s, 3H); MS (ESI): m/z: 259 [M+H]$^+$.

Step 2: di-tert-Butyl [3-[3-chloro-10-methyl-11-oxo-10,11-dihydro-5H-dibenzo[b,e][1,4]diazepin-5-yl]propyl]imidodicarbonate 0.137 g (75%) of di-tert-butyl [3-(3-chloro-10-methyl-11-oxo-10,11-dihydro-5H-dibenzo[b,e][1,4]diazepin-5-yl)propyl]imidodicarbonate were prepared according to the procedure described for Intermediate 14, Step 2, starting from 0.090 g (0.35 mmol) of 3-chloro-10-methyl-5,10-dihydro-11H-dibenzo[b,e][1,4]diazepin-11-one and 0.178 g (0.53 mmol) of di-tert-butyl (3-bromopropyl)imidodicarbonate. $^1$H NMR (DMSO-d$_6$), δ (ppm): 7.59-7.54 (m, 1H), 7.40-7.34 (m, 1H), 7.26-7.21 (m, 2H), 7.21-7.15 (m, 2H), 7.14 (dd, J=2.0, 8.3 Hz, 1H), 3.80-3.65 (m, 2H), 3.59-3.39 (m, 5H), 1.80-1.66 (m, 2H), 1.33 (s, 18H); MS (ESI): m/z: 460 [M−56+H]$^+$.

Step 3: 5-(3-Aminopropyl)-3-chloro-10-methyl-5,10-dihydro-11H-dibenzo[b,e][1,4]diazepin-11-one 0.46 ml (6 mmol) of TFA were added to a solution of 0.154 g (0.3 mmol) of di-tert-butyl [3-(3-chloro-10-methyl-11-oxo-10,11-dihydro-5H-dibenzo[b,e][1,4]diazepin-5-yl)propyl]imidodicarbonate in dry DCM (3 ml) at 0° C. The mixture was warmed to r.t. and stirred for 45 min. The mixture was cautiously partitioned between chilled saturated aqueous NaHCO$_3$ and DCM. The aqueous phase was extracted with DCM and the combined organic extracts were dried (Na$_2$SO$_4$) and concentrated. The crude was purified by flash chromatography (eluent: DCM/MeOH/NH$_4$OH 95:5:

0.5) to afford 5-(3-aminopropyl)-3-chloro-10-methyl-5,10-dihydro-11H-dibenzo[b,e][1,4]diazepin-11-one as a pale yellow solid (0.083 g, 88%). $^1$H NMR (DMSO-d$_6$) δ (ppm): 7.59-7.53 (m, 1H), 7.36 (dd, J=1.5, 7.3 Hz, 1H), 7.29-7.23 (m, 2H), 7.22-7.14 (m, 2H), 7.12 (dd, J=1.5, 8.3 Hz, 1H), 3.75 (t, J=6.8 Hz, 2H), 3.42 (s, 3H), 2.55 (t, J=6.6 Hz, 2H), 1.59-1.52 (m, 2H), 1.46 (bs, 2H); MS (ESI): m/z: 316 [M+H]$^+$.

Intermediate 21: 5-(3-Aminopropyl)-7-choro-10-methyl-5,10-dihydro-11H-dibenzo[b,e][1,4]diazepin-11-one

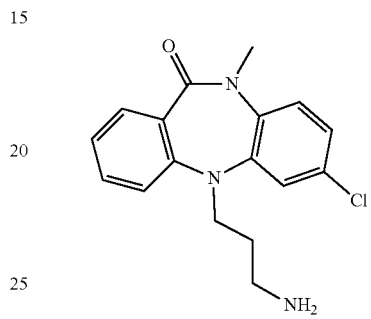

Step 1: 7-Chloro-10-methyl-5,10-dihydro-11H-dibenzo[b,e][1,4]diazepin-11-one 0.250 g (78%) of 7-chloro-10-methyl-5,10-dihydro-11H-dibenzo[b,e][1,4]diazepin-11-one were prepared according to the procedure described for Intermediate 14, Step 1, starting from 0.301 g (1.23 mmol) of 7-chloro-5,10-dihydro-11H-dibenzo[b,e][1,4]diazepin-11-one (Intermediate 18) and 0.081 ml (1.29 mmol) of iodomethane. $^1$H NMR (DMSO-d$_6$), δ (ppm): 8.03 (s, 1H), 7.69-7.58 (m, 1H), 7.39-7.33 (m, 1H), 7.32-7.27 (m, 1H), 7.20-7.16 (m, 1H), 7.13 (dd, J=2.4, 8.3 Hz, 1H), 7.07-7.02 (m, 1H), 7.01-6.95 (m, 1H), 3.35 (s, 3H); MS (ESI): m/z: 259 [M+H]$^+$.

Step 2: di-tert-Butyl [3-(7-chloro-10-methyl-11-oxo-10,11-dihydro-5H-dibenzo[b,e][1,4]diazepin-5-yl]propyl]imidodicarbonate 0.210 g (63%) of di-tert-butyl [3-(7-chloro-10-methyl-11-oxo-10,11-dihydro-5H-dibenzo[b,e][1,4]diazepin-5-yl)propyl]imidodicarbonate were prepared according to the procedure described for Intermediate 14, Step 2, starting from 0.168 g (0.65 mmol) of 7-chloro-10-methyl-5,10-dihydro-11H-dibenzo[b,e][1,4]diazepin-11-one and 0.343 g (0.97 mmol) of di-tert-butyl (3-bromopropyl)imidodicarbonate. $^1$H NMR (CDCl$_3$), δ (ppm): 7.82-7.68 (m, 1H), 7.42-7.35 (m, 1H), 7.14-7.05 (m, 4H), 7.03-6.99 (m, 1H), 3.77-3.58 (m, 4H), 3.56 (s, 3H), 1.97-1.86 (m, 2H), 1.45 (s, 18H); MS (ESI): m/z: 460 [M−56+H]$^+$.

Step 3: 5-(3-Aminopropyl)-7-chloro-10-methyl-5,10-dihydro-11H-dibenzo[b,e][1,4]diazepin-11-one 0.114 g (90%) of 5-(3-aminopropyl)-3-chloro-10-methyl-5,10-dihydro-11H-dibenzo[b,e][1,4]diazepin-11-one were prepared according to the procedure described for Intermediate 20, Step 3, starting from 0.207 g (0.4 mmol) of di-tert-butyl [3-(7-chloro-10-methyl-11-oxo-10,11-dihydro-5H-dibenzo[b,e][1,4]diazepin-5-yl)propyl]imidodicarbonate and 0.62 ml (8 mmol) of TFA. ¹H NMR (DMSO-d₆) δ (ppm): 7.56 (dd, J=1.7, 7.6 Hz, 1H), 7.49-7.41 (m, 1H), 7.39-7.35 (m, 1H), 7.33-7.31 (m, 1H), 7.22-7.17 (m, 2H), 7.11-7.06 (m, 1H), 3.82-3.65 (m, 2H), 3.41 (s, 3H), 2.56 (t, J=6.8 Hz, 2H), 1.62-1.51 (m, 2H); MS (ESI): m/z: 316 [M+H]⁺.

Intermediate 22: 5-(4-Aminobutyl)-7-choro-10-methyl-5,10-dihydro-11H-dibenzo[b,e][1,4]diazepin-11-one

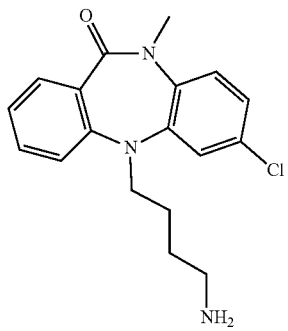 [SMILES: CN1C(=O)c2ccccc2N(CCCCN)c2cc(Cl)ccc21]

Step 1: di-tert-Butyl [4-(7-chloro-10-methyl-11-oxo-10,11-dihydro-5H-dibenzo[b,e][1,4]diazepin-5-yl)butyl]imidodicarbonate 0.128 g (64%) of di-tert-butyl [4-(7-chloro-10-methyl-11-oxo-10,11-dihydro-5H-dibenzo[b,e][1,4]diazepin-5-yl)butyl]imidodicarbonate were prepared according to the procedure described for Intermediate 14, Step 2, starting from 0.098 g (0.379 mmol) of 7-chloro-10-methyl-5,10-dihydro-11H-dibenzo[b,e][1,4]diazepin-11-one (Intermediate 21, Step 1) and 0.208 g (0.568 mmol) of di-tert-butyl (4-bromobutyl)imidodicarbonate. ¹H NMR (CDCl₃), δ (ppm): 7.79-7.75 (m, 1H), 7.43-7.37 (m, 1H), 7.15-7.07 (m, 4H), 7.05-7.01 (m, 1H), 3.69 (bs, 2H), 3.61-3.49 (m, 5H), 1.73-1.61 (m, 4H), 1.49 (s, 18H); MS (ESI): m/z: 474 [M−56+H]⁺.

Step 3: 5-(4-Aminobutyl)-7-chloro-10-methyl-5,10-dihydro-11H-dibenzo[b,e][1,4]diazepin-11-one 0.085 g (92%) of 5-(4-aminobutyl)-3-chloro-10-methyl-5,10-dihydro-11H-dibenzo[b,e][1,4]diazepin-11-one were prepared according to the procedure described for Intermediate 20, Step 3, starting from 0.207 g (0.4 mmol) of di-tert-butyl [4-(7-chloro-10-methyl-11-oxo-10,11-dihydro-5H-dibenzo[b,e][1,4]diazepin-5-yl)butyl]imidodicarbonate and 0.62 ml (8 mmol) of TFA. ¹H NMR (DMSO-d₆) δ (ppm): 7.61-7.55 (m, 1H), 7.51-7.45 (m, 1H), 7.43-7.38 (m, 1H), 7.36-7.32 (m, 1H), 7.26-7.17 (m, 2H), 7.15-7.08 (m, 1H), 3.77-3.68 (m, 2H), 3.44 (s, 3H), 2.50 (t, J=6.8 Hz, 2H), 1.58-1.50 (m, 2H), 1.45-1.36 (m, 2H); MS (ESI): m/z: 330 [M+H]⁺.

Intermediate 23 and 24: 8-Chloro-1-methyl-1,4,5,10-tetrahydropyrazolo[3,4-b][1]benzazepine (23) and 8-Chloro-2-methyl-1,4,5,10-tetrahydropyrazolo[3,4-b][1]benzazepine (24)

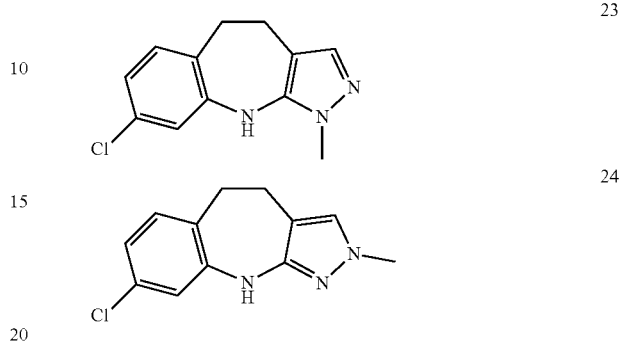

A mixture of 0.673 g (2.78 mmol) of 2,8-dichloro-4,5-dihydro-1H-1-benzazepine-3-carbaldehyde (prepared according to literature procedure, Chem. Pharm. Bull., 1972, 20 (6), 1325-1327), 0.224 ml (4.17 mmol) of methylhydrazine and 0.622 g (7.5 mmol) of AcONa in EtOH (17 ml) was heated to reflux for 1.5 h. EtOH was removed under reduced pressure and the crude was partitioned between water and EtOAc. Aqueous phase was extracted with EtOAc and the combined organic phases were dried (Na₂SO₄), filtered and concentrated under vacuo. The crude was purified by flash chromatography (eluent: hexane/acetone from 87:13 to 80:20) to afford 8-chloro-1-methyl-1,4,5,10-tetrahydropyrazolo[3,4-b][1]benzazepine as an off-white solid (Intermediate 23, 0.132 g, 45%) and 8-chloro-2-methyl-1,4,5,10-tetrahydropyrazolo[3,4-b][1]benzazepine as an off-white solid (Intermediate 24, 0.110 g, 37%). Intermediate 23: ¹H NMR (DMSO-d₆), δ (ppm): 8.16 (s, 1H), 7.28-7.25 (m, 1H), 7.12-7.07 (m, 1H), 6.99 (s, 1H), 6.83 (dd, J=2.2, 8.1 Hz, 1H), 3.69 (s, 3H), 2.90-2.79 (m, 2H), 2.73-2.62 (m, 2H); MS (ESI): m/z: 234 [M+H]⁺. Intermediate 24: ¹H NMR (DMSO-d₆), δ (ppm): 8.63 (s, 1H), 7.24 (s, 1H), 7.05-7.00 (m, 2H), 6.72-6.65 (m, 1H), 3.61 (s, 3H), 2.84-2.76 (m, 2H), 2.70-2.62 (m, 2H); MS (ESI): m/z: 234 [M+H]⁺.

Intermediate 25: 3-(8-Chloro-1-methyl-4,5-dihydropyrazolo[3,4-b][1]benzazepin-10(1H)-yl)propan-1-amine

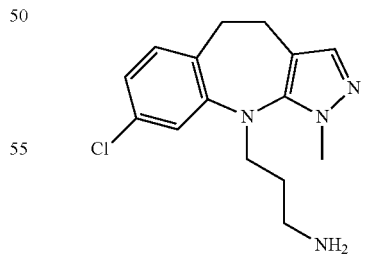

Step 1: 2-[3-(8-Chloro-1-methyl-4,5-dihydropyrazolo-[3,4-b][1]-benzazepin-10(1H)-yl)propyl]-1H-isoindole-1,3(2H)-dione 0.062 g (purity 78%) of 2-[3-(8-chloro-1-methyl-4,5-dihydropyrazolo[3,4-b][1]benzazepin-10(1H)-yl)propyl]-

1H-isoindole-1,3(2H)-dione were prepared according to the procedure described for Intermediate 9, Step 1, starting from 0.065 g (0.28 mmol) of 8-chloro-1-methyl-1,4,5,10-tetrahydropyrazolo[3,4-b][1]benzazepine (Intermediate 23) and 0.114 g (0.42 mmol) of N-(3-bromopropyl)phthalimide. $^1$H NMR (CDCl$_3$), δ (ppm): 7.90-7.81 (m, 2H), 7.78-7.68 (m, 2H), 7.24-7.21 (m, 1H), 7.17 (s, 1H), 7.15-7.12 (m, 2H), 3.78 (s, 3H), 3.72 (t, J=7.1 Hz, 2H), 3.48-3.40 (m, 2H), 2.97 (bs, 2H), 2.71 (bs, 2H), 2.05-1.93 (m, 2H); MS (ESI): m/z: 421 [M+H]$^+$.

Step 2: 3-(8-Chloro-1-methyl-4,5-dihydropyrazolo[3,4-b][1]benzazepin-10(1H)-yl)propan-1-amine 0.027 g (85%) of 3-(8-chloro-1-methyl-4,5-dihydropyrazolo[3,4-b][1]benzazepin-10(1H)-yl)propan-1-amine was prepared according to the procedure described for Intermediate 9, Step 2, starting from 0.06 g (0.111 mmol) of 2-[3-(8-chloro-1-methyl-4,5-dihydropyrazolo[3,4-b][1]benzazepin-10(1H)-yl)propyl]-1H-isoindole-1,3(2H)-dione. $^1$H NMR (CDCl$_3$), δ (ppm): 7.23-7.10 (m, 4H), 3.82 (s, 3H), 3.48-3.40 (m, 2H), 2.98 (bs, 2H), 2.77-2.67 (m, 4H), 1.80-1.69 (m, 2H); MS (ESI): m/z: 291 [M+H]$^+$.

Intermediate 26: 3-(8-Chloro-2-methyl-4,5-dihydropyrazolo[3,4-b][1]benzazepin-10(2H)-yl)propan-1-amine

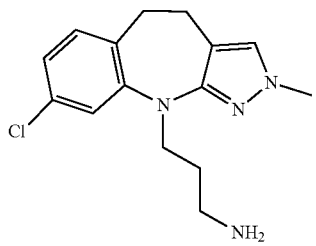 [SMILES: Cn1cc2c(n1)N(CCCN)c1cc(Cl)ccc1CC2]

Step 1: 2-[3-(8-Chloro-2-methyl-4,5-dihydropyrazolo-[3,4-b][1]-benzazepin-10(2H)-yl)propyl]-1H-isoindole-1,3(2H)-dione 0.050 g (purity 84%) of 2-[3-(8-chloro-2-methyl-4,5-dihydropyrazolo[3,4-b][1]benzazepin-10(1H)-yl)propyl]-1H-isoindole-1,3(2H)-dione were prepared according to the procedure described for Intermediate 9, Step 1, starting from 0.083 g (0.35 mmol) of 8-chloro-2-methyl-1,4,5,10-tetrahydropyrazolo[3,4-b][1]benzazepine (Intermediate 24) and 0.165 g (0.60 mmol) of N-(3-bromopropyl)phthalimide. $^1$H NMR (CDCl$_3$), δ (ppm): 7.84-7.78 (m, 2H), 7.72-7.66 (m, 2H), 7.08-7.03 (m, 2H), 6.95-6.91 (m, 2H), 3.97 (t, J=6.6 Hz, 2H), 3.75 (t, J=7.1 Hz, 2H), 3.64 (s, 3H), 3.05-3.00 (m, 2H), 2.77-2.72 (m, 2H), 2.16-2.07 (m, 2H); MS (ESI): m/z: 421 [M+H]$^+$.

Step 2: 3-(8-Chloro-2-methyl-4,5-dihydropyrazolo[3,4-b][1]benzazepin-10(2H)-yl)propan-1-amine 0.024 g (87%) of 3-(8-chloro-2-methyl-4,5-dihydro-pyrazolo[3,4-b][1]benzazepin-10(2H)-yl)propan-1-amine were prepared according to the procedure described for Intermediate 9, Step 2, starting from 0.047 g (0.094 mmol) of 2-[3-(8-chloro-2-methyl-4,5-dihydropyrazolo[3,4-b][1]benzazepin-10(2H)-yl)propyl]-1H-isoindole-1,3(2H)-dione. $^1$H NMR (DMSO-d$_6$), δ (ppm): 7.26 (s, 1H), 7.19-7.12 (m, 2H), 7.00-6.94 (m, 1H), 3.94-3.82 (m, 2H), 3.62 (s, 3H), 3.16 (t, J=6.3 Hz, 1H), 2.91-2.81 (m, 2H), 2.69-2.62 (m, 2H), 2.52 (t, J=6.8 Hz, 1H), 1.92-1.84 (m, 1H), 1.68-1.60 (m, 1H); MS (ESI): m/z: 291 [M+H]$^+$.

Intermediate 27: 3-(9-Chloro-5,6-dihydro-11H-pyrimido[4,5-b][1]benzazepin-11-yl)propan-1-amine

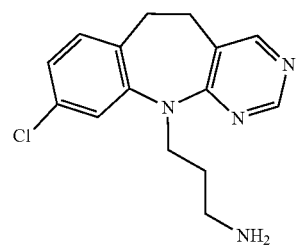 [SMILES: NCCCN1c2cc(Cl)ccc2CCc2cncnc21]

Step 1: 2-[3-(9-Chloro-5,6-dihydro-11H-pyrimido[4,5-b][1]benzazepin-11-yl)propyl]-1H-isoindole-1,3(2H)-dione 0.127 g (26%) of 2-[3-(9-Chloro-5,6-dihydro-11H-pyrimido[4,5-b][1]benzazepin-11-yl)propyl]-1H-isoindole-1,3(2H)-dione were prepared according to the procedure described for Intermediate 9, Step 1, starting from 0.267 g (1.15 mmol) of 9-chloro-6,11-dihydro-5H-pyrimido[4,5-b][1]benzazepine (prepared according to literature procedure *Bull. Chem. Soc. Jap.*, 1973, 46, 2835-2839) and 0.473 g (1.73 mmol) of N-(3-bromopropylyl)phthalimide. $^1$H NMR (CDCl$_3$), δ (ppm): 8.48 (s, 1H), 8.12 (s, 1H), 7.85-7.79 (m, 2H), 7.74-7.68 (m, 2H), 7.21 (s, 1H), 7.12-7.08 (m, 2H), 4.26 (t, J=6.8 Hz, 2H), 3.72 (t, J=7.1 Hz, 2H), 3.20-3.11 (m, 2H), 3.01-2.96 (m, 2H), 2.14-2.04 (m, 2H); MS (ESI): m/z: 419 [M+H]$^+$.

Step 2: 3-(9-Chloro-5,6-dihydro-11H-pyrimido[4,5-b][1]benzazepin-11-yl)propan-1-amine 0.060 g (79%) of 3-(9-chloro-5,6-dihydro-11H-pyrimido[4,5-b][1]benzazepin-11-yl)propan-1-amine were prepared according to the procedure described for Intermediate 9, Step 2, starting from 0.126 g (0.26 mmol) of 2-[3-(9-chloro-5,6-dihydro-11H-pyrimido[4,5-b][1]benzazepin-11-yl)propyl]-1H-isoindole-1,3(2H)-dione. $^1$H NMR (CDCl$_3$, D$_2$O), δ (ppm): 8.62 (s, 1H), 8.12 (s, 1H), 7.26-7.22 (m, 1H), 7.12-7.06 (m, 2H), 4.24 (t, J=6.8 Hz, 2H), 3.08-3.00 (m, 2H), 3.00-2.91 (m, 2H), 2.71 (t, J=7.1 Hz, 2H), 1.86-1.74 (m, 2H); MS (ESI): m/z: 289 [M+H]$^+$.

Intermediate 28: 3-Amino-1-(3-chloro-10,11-dihydro-5H-dibenzo[b,f]azepin-5-yl)propan-1-one

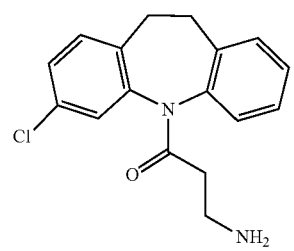 [SMILES: NCCC(=O)N1c2ccccc2CCc2ccc(Cl)cc21]

Step 1: 9H-fluoren-9-ylmethyl [3-(3-chloro-10,11-dihydro-5H-dibenzo[b,f]azepin-5-yl)-3-oxo-propyl] carbamate 0.221 ml (3 mmol) of SOCl₂ was added to a solution of 0.629 g (2 mmol) of Fmoc-β-Ala-OH (Sigma-Aldrich, Cat. No. 47587) in dry DCM (7 ml), followed by 3 drops of dry DMF. The mixture was stirred at 60° C. for 2 h, then cooled and concentrated to provide 9H-fluoren-9-ylmethyl (3-chloro-3-oxopropyl)carbamate as an off-white solid which was used without any further purification and treated with a solution of 0.446 g (1.94 mmol) of 3-chloro-10,11-dihydro-5H-dibenzo[b,f]azepine (FLROCHEM, Cat. No. 211409) in dry toluene (5 ml). The reaction mixture was heated to 100° C. for 2 h, then cooled to r.t. and concentrated in vacuo to remove the solvent. The crude was purified by flash chromatography (eluent: hexane/EtOAc 65:35) to provide (9H-fluoren-9-yl)methyl[3-(3-chloro-10,11-dihydro-5H-dibenzo[b,f]azepin-5-yl)-3-oxopropyl]carbamate as a foamy white solid (0.776 g, 74%). ¹H NMR (CDCl₃), δ (ppm): 7.82-7.72 (m, 2H), 7.63-7.55 (m, 2H), 7.46-7.05 (m, 11H), 5.62 (bs, 1H), 4.35 (d, J=7.3 Hz, 2H), 4.21 (t, J=7.3 Hz, 1H), 3.57-3.43 (m, 2H), 3.35-3.19 (m, 2H), 2.90-2.72 (m, 2H), 2.69-2.56 (m, 1H), 2.34-2.17 (m, 1H); MS (ESI): m/z: 523 [M+H]⁺.

Step 2: 3-Amino-1-(3-chloro-10,11-dihydro-5H-dibenzo[b,f]azepin-5-yl)propan-1-one A solution of 0.247 g (0.472 mmol) of (9H-fluoren-9-yl)methyl[3-(3-chloro-10,11-dihydro-5H-dibenzo[b,f]azepin-5-yl)-3-oxopropyl]carbamate in dry DMF (1.1 ml) was treated with 0.141 ml (1.471 mmol) of piperidine and the reaction mixture was stirred at r.t. for 30 min. The mixture was diluted with brine and extracted with EtOAc, the organic phases were dried (Na₂SO₄), filtered and concentrated. The crude was purified by flash chromatography (eluent: DCM/MeOH/NH₄OH (93:7:0.7) to afford 3-amino-1-(3-chloro-10,11-dihydro-5H-dibenzo[b,f]azepin-5-yl)propan-1-one (0.105 g, 74%) as a foamy white solid. ¹H NMR (CDCl₃), δ (ppm): 7.47-7.00 (m, 7H), 3.48-3.22 (m, 2H), 3.11-2.91 (m, 2H), 2.89-2.75 (m, 2H), 2.64-2.49 (m, 1H), 2.31-2.12 (m, 1H), 1.80 (bs, 2H); MS (ESI): m/z: 301 [M+H]⁺.

Intermediate 29: 3-Chloro-5,11-dihydrodibenzo[b,e][1,4]oxazepine

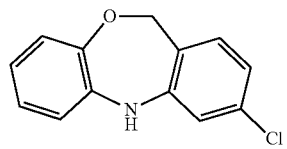 [SMILES: Clc1ccc2c(c1)Nc1ccccc1OC2]

Step 1: 2-Bromo-4-chlorobenzyl-2-nitrophenyl ether 1.47 g (88%) of 2-bromo-4-chlorobenzyl-2-nitrophenyl ether were prepared according to the procedure described for Intermediate 4, Step 1, starting from 0.69 g (4.86 mmol) of 2-nitrophenol and 1.5 g (5.1 mmol) of 2-bromo-1-(bromomethyl)-4-chloro-benzene. ¹H NMR (CDCl₃) δ (ppm): 7.93 (dd, J=1.5, 7.8 Hz, 1H), 7.67 (d, J=8.3 Hz, 1H), 7.62 (d, J=2.0 Hz, 1H), 7.60-7.55 (m, 1H), 7.39 (dd, J=2.0, 8.3 Hz, 1H), 7.17-7.14 (m, 1H), 7.13-7.08 (m, 1H), 5.24 (s, 2H).

Step 2: 2-[(2-Bromo-4-chlorobenzyl)oxy]aniline 1.13 g (84%) of 2-[(2-bromo-4-chlorobenzyl)oxy]aniline were prepared according to the procedure described for Intermediate 4, Step 2, starting from 1.47 g (4.3 mmol) of 2-bromo-4-chlorobenzyl-2-nitrophenyl ether. ¹H NMR (CDCl₃) δ (ppm): 7.62 (d, J=2.4 Hz, 1H), 7.47 (d, J=8.3 Hz, 1H), 7.32 (dd, J=2.0, 8.3 Hz, 1H), 6.89-6.76 (m, 3H), 6.76-6.71 (m, 1H), 5.14 (s, 2H), 4.06 (bs, 2H); MS (ESI): m/z: 313 [M+H]⁺.

Step 3: N-{2-[(2-Bromo-4-chlorobenzyl)oxy]phenyl}formamide 1.12 g (91%) of N-{2-[(2-bromo-4-chlorobenzyl)oxy]phenyl}formamide were prepared according to the procedure described for Intermediate 4, Step 3, starting from 1.13 g (3.62 mmol) of 2-[(2-bromo-4-chlorobenzyl)oxy]aniline. ¹H NMR (CDCl₃), mixture of rotamers, δ (ppm): 8.77 e 8.47 (2d, J=11.2, 1.5 Hz, 1H), 8.41 e 7.26 (2dd, J=1.5, 7.8 Hz, 1H), 7.80 e 7.71 (2bs., 1H), 7.67 e 7.65 (2d, J=2.0 Hz, 1H), 7.42-7.33 (m, 2H), 7.18-6.89 (m, 3H), 5.17 e 5.15 (2s, 2H); MS (ESI): m/z: 341 [M+H]⁺.

Step 4: 3-Chloro-5,11-dihydrodibenzo[b,e][1,4]oxazepine 0.49 g (64%) of 3-chloro-5,11-dihydrodibenzo[b,e][1,4]oxazepine were prepared according to the procedure described for Intermediate 4, Step 4, starting from 1.12 g (3.28 mmol) of N-{2-[(2-bromo-4-chlorobenzyl)oxy]phenyl}formamide. ¹H NMR (DMSO-d₆) δ (ppm): 8.79 (s, 1H), 7.10 (d, J=8.3 Hz, 1H), 7.00 (d, J=2.0 Hz, 1H), 6.98-6.95 (m, 1H), 6.93-6.86 (m, 2H), 6.70 (dd, J=2.0, 8.3 Hz, 1H), 6.69-6.65 (m, 1H), 4.92 (s, 2H); MS (ESI): m/z: 232 [M+H]⁺.

Intermediate 30: 3-(3-Chlorodibenzo[b,e][1,4]oxazepin-5(11H)-yl)propan-1-amine

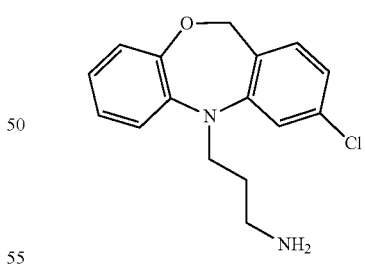

Step 1: di-tert-Butyl [3-(3-chlorodibenzo[b,e][1,4]oxazepin-5(11H)-yl)propyl]imidodicarbonate 0.21 g (44%) of di-tert-butyl [3-(3-chlorodibenzo[b,e][1,4]oxazepin-5(11H)-yl)propyl]imidodicarbonate were prepared according to the procedure described for Intermediate 3, Step 1, starting from 0.23 g (0.99 mmol) of 3-chloro-5,11-dihydro-dibenzo[b,e][1,4]oxazepine (Intermediate 4) and 0.50 g (1.49 mmol) of di-tert-butyl (3-bromopropyl)imidodicarbonate (prepared according to literature procedure,

*Org. & Biomol. Chem.* 2006, 4, 3228-3234). ¹H NMR (DMSO-d₆), δ (ppm): 7.44-7.38 (m, 1H), 7.26-7.22 (m, 1H), 7.14-7.08 (m, 1H), 7.05-6.99 (m, 1H), 6.84-6.76 (m, 2H), 6.73-6.68 (m, 1H), 5.28 (s, 2H), 3.74-3.67 (m, 2H), 3.57-3.48 (m, 2H), 1.82-1.73 (m, 2H), 1.33 (s, 18H); MS (ESI): m/z: 489 [M+H]⁺.

Step 2: 3-(3-Chlorodibenzo[b,e][1,4]oxazepin-5(11H)-yl)propan-1-amine 0.115 g (92%) of 3-(3-chlorodibenzo[b,e][1,4]oxazepin-5(11H)-yl)propan-1-amine were prepared according to the procedure described for Intermediate 3, Step 2, starting from 0.21 g (0.43 mmol) of di-tert-butyl [3-(3-chlorodibenzo[b,e][1,4]oxazepin-5(11H)-yl)propyl]imidodicarbonate. ¹H NMR (DMSO-d₆), δ (ppm): 7.40 (d, J=7.8 Hz, 1H), 7.27 (d, J=2.0 Hz, 1H), 7.13-7.05 (m, 2H), 6.86-6.76 (m, 2H), 6.71 (dd, J=2.0, 7.8 Hz, 1H), 5.23 (s, 2H), 3.76 (t, J=6.8 Hz, 2H), 2.56 (t, J=6.8 Hz, 2H), 2.09 (bs, 2H), 1.60 (quint, J=6.8 Hz, 2H); MS (ESI): m/z: 289 [M+H]⁺.

Intermediate 31: 4-(3-Chlorodibenzo[b,e][1,4]oxazepin-5(11H-yl)butan-1-amine

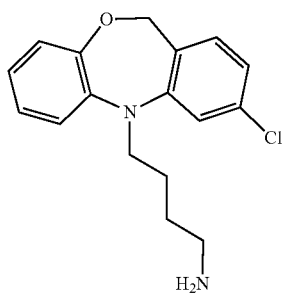 [SMILES: NCCCCN1c2cc(Cl)ccc2COc2ccccc21]

Step 1: di-tert-Butyl [4-(3-chlorodibenzo[b,e][1,4]oxazepin-5(11H)-yl)butyl]imidodicarbonate 0.093 g (55%) of di-tert-butyl [4-(3-chlorodibenzo[b,e][1,4]oxazepin-5(11H)-yl)butyl]imidodicarbonate were prepared according to the procedure described for Intermediate 3, Step 1, starting from 0.078 g (0.337 mmol) of 3-chloro-5,11-dihydro-dibenzo[b,e][1,4]oxazepine (Intermediate 4) and 0.187 g (0.505 mmol) of di-tert-butyl (4-bromobutyl)imidodicarbonate (Intermediate 15, Step 1). ¹H NMR (DMSO-d₆), δ (ppm): 7.42-7.37 (m, 1H), 7.28-7.24 (m, 1H), 7.13-7.08 (m, 1H), 7.06-7.01 (m, 1H), 6.85-6.76 (m, 2H), 6.73-6.68 (m, 1H), 5.23 (s, 2H), 3.76-3.68 (m, 2H), 3.44-3.38 (m, 2H), 1.56-1.44 (m, 4H), 1.37 (s, 18H); MS (ESI): m/z: 525 [M+Na]⁺.

Step 2: 4-(3-Chlorodibenzo[b,e][1,4]oxazepin-5(11H)-yl)butan-1-amine 0.046 g (83%) of 4-(3-chlorodibenzo[b,e][1,4]oxazepin-5(11H)-yl)butan-1-amine were prepared according to the procedure described for Intermediate 3, Step 2, starting from 0.092 g (0.183 mmol) of di-tert-butyl [4-(3-chlorodibenzo[b,e][1,4]oxazepin-5(11H)-yl)butyl]imidodicarbonate. ¹H NMR (DMSO-d₆), δ (ppm): 7.43-7.38 (m, 1H), 7.30-7.25 (m, 1H), 7.14-7.08 (m, 1H), 7.08-7.03 (m, 1H), 6.87-6.76 (m, 2H), 6.74-6.68 (m, 1H), 5.25 (s, 2H), 3.72 (t, J=6.6 Hz, 2H), 2.55 (t, J=7.1 Hz, 2H), 1.60-1.47 (m, 2H), 1.46-1.36 (m, 2H); MS (ESI): m/z: 303 [M+H]⁺.

Intermediate 32: 4-(7-Chlorodibenzo[b,e][1,4]oxazepin-5(11H)-yl)butan-1-amine

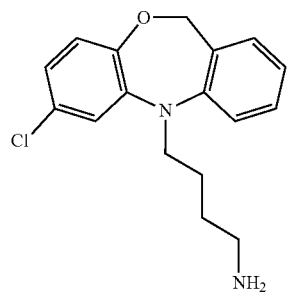 [SMILES: NCCCCN1c2ccccc2COc2ccc(Cl)cc21]

Step 1: di-tert-Butyl [4-(7-chlorodibenzo[b,e][1,4]oxazepin-5(11H)-yl)butyl]imidodicarbonate 0.193 g (59%) of di-tert-butyl [4-(7-chlorodibenzo[b,e][1,4]oxazepin-5(11H)-yl)butyl]imidodicarbonate were prepared according to the procedure described for Intermediate 3, Step 1, starting from 0.150 g (0.647 mmol) of 7-chloro-5,11-dihydro-dibenzo[b,e][1,4]oxazepine (Intermediate 4) and 0.360 g (0.971 mmol) of di-tert-butyl (4-bromobutyl)imidodicarbonate (Intermediate 15, Step 1). ¹H NMR (DMSO-d₆), δ (ppm): 7.42-7.34 (m, 2H), 7.23-7.18 (m, 1H), 7.11-7.05 (m, 1H), 7.04-7.01 (m, 1H), 6.81-6.76 (m, 1H), 6.71-6.67 (m, 1H), 5.25 (s, 2H), 3.75-3.67 (m, 2H), 3.45-3.37 (m, 2H), 1.55-1.44 (m, 4H), 1.37 (s, 18H); MS (ESI): m/z: 503 [M+Na]⁺.

Step 2: 4-(7-Chlorodibenzo[b,e][1,4]oxazepin-5(11H)-yl)butan-1-amine 0.089 g (77%) of 4-(7-chlorodibenzo[b,e][1,4]oxazepin-5(11H)-yl)butan-1-amine were prepared according to the procedure described for Intermediate 3, Step 2, starting from 0.191 g (0.380 mmol) of di-tert-butyl [4-(7-chlorodibenzo[b,e][1,4]oxazepin-5(11H)-yl)butyl]imidodicarbonate. ¹H NMR (DMSO-d₆), δ (ppm): 7.42-7.34 (m, 2H), 7.21 (d, J=8.3 Hz, 1H), 7.11-7.06 (m, 1H), 7.04 (d, J=2.4 Hz, 1H), 6.78 (dd, J=2.4, 8.3 Hz, 1H), 6.70 (d, J=8.8 Hz, 1H), 5.26 (s, 2H), 3.70 (t, J=6.8 Hz, 2H), 2.46 (t, J=6.8 Hz, 2H), 2.10 (bs, 2H), 1.53 (quint, J=7.2 Hz, 2H), 1.34 (quint, J=7.3 Hz, 2H); MS (ESI): m/z: 303 [M+H]⁺.

Intermediate 33: 4-Amino-1-(3-chloro-10,11-dihydro-5H-dibenzo[b,f]azepin-5-yl)butan-1-one

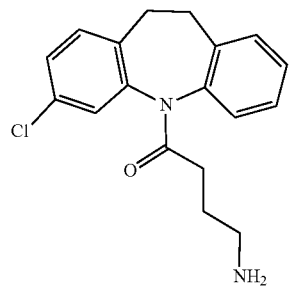 [SMILES: NCCCC(=O)N1c2ccccc2CCc2ccc(Cl)cc21]

Step 1: 4-chloro-1-(3-chloro-10,11-dihydro-5H-dibenzo[b,f]azepin-5-yl)butan-1-one 0.72 g (99%) of 4-chloro-1-(3-chloro-10,11-dihydro-5H-dibenzo[b,f]azepin-5-yl)butan-1-one were prepared according to the procedure described for Intermediate 3, Step 1, starting from 0.5 g (2.18 mmol) of 3-chloro-10,11-dihydro-5H-dibenzo[b,f]azepine and 0.256 ml (2.29 mmol) of 3-chlorobutanoyl chloride. $^1$H NMR (CDCl$_3$), mixture of rotamers, δ (ppm): 7.45-7.00 (m, 7H), 3.74-3.55 (m, 2H), 3.47-3.20 (m, 2H), 2.90-2.74 (m, 2H), 2.64-2.48 (m, 1H), 2.35-2.07 (m, 3H); MS (ESI): m/z: 334 [M+H]$^+$.

Step 2: 4-Azido-1-(3-chloro-10,11-dihydro-5H-dibenzo[b,f]azepin-5-yl)butan-1-one 0.309 g (86%) of 4-azido-1-(3-chloro-10,11-dihydro-5H-dibenzo[b,f]azepin-5-yl)butan-1-one were prepared according to the procedure described for Intermediate 3, Step 2, starting from 0.353 g (1.06 mmol) of 3-chloro-1-(3-chloro-10,11-dihydro-5H-dibenzo[b,f]azepin-5-yl)butan-1-one. $^1$H NMR (CDCl$_3$), mixture of rotamers, δ (ppm): 7.53-6.93 (m, 7H), 3.45-3.13 (m, 4H), 2.92-2.70 (m, 2H), 2.59-2.38 (m, 1H), 2.22-2.05 (m, 1H), 1.99-1.82 (m, 2H); MS (ESI): m/z: 341 [M+H]$^+$.

Step 3: 4-Amino-1-(3-chloro-10,11-dihydro-5H-dibenzo[b,f]azepin-5-yl)butan-1-one A solution of 0.309 g (0.906 mmol) of 4-azido-1-(3-chloro-10,11-dihydro-5H-dibenzo[b,f]azepin-5-yl)butan-1-one in water/THF (0.7 ml/4 ml) was treated with 0.393 g (1.5 mmol) of triphenylphosphine at 0° C., then the mixture was slowly warmed at 50° C. and it was stirred for 1.5 h till complete conversion into the product.

The solvent was evaporated and the residue was diluted with brine and extracted with EtOAc, the organic phases were dried (Na$_2$SO$_4$), filtered and concentrated. The crude was purified by flash chromatography (eluent: DCM/MeOH/7NH$_3$·MeOH (98:1/1) to afford 4-amino-1-(3-chloro-10,11-dihydro-5H-dibenzo[b,f]azepin-5-yl)butan-1-one (0.256 g, 90%) as a colorless sticky oil. $^1$H NMR (DMSO-d$_6$), δ (ppm): 7.69-7.02 (m, 7H), 3.30-3.12 (m, 2H), 2.90-2.70 (m, 2H), 2.50-2.20 (m, 3H), 2.13-1.89 (m, 1H), 1.65-1.45 (m, 2H); MS (ESI): m/z: 315 [M+H]$^+$.

Intermediate 34: 5-(4-Aminobutyl)-7-chloro-10,11-dihydro-5H-dibenzo[b,f]azepin-2-ol

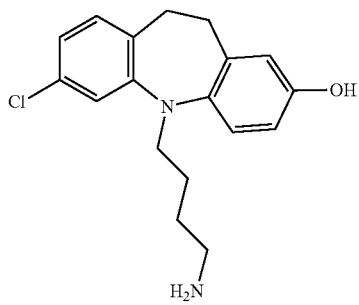 [SMILES: NCCCCN1c2ccc(O)cc2CCc2ccc(Cl)cc21]

Step 1: 7-Chloro-5-[4-(1,3-dioxo-1,3-dihydro-isoindol-2-yl)-butyl]-10,11-dihydro-5H-dibenzo[b,f]azepine-2-carbaldehyde and 3-Chloro-5-[4-(1,3-dioxo-1,3-dihydro-isoindol-2-yl)-butyl]-10,11-dihydro-5H-dibenzo[b,f]azepine-2-carbaldehyde Phosphorus oxychloride (3.558 g, 23.2 mmol) was added dropwise to DMF (3.392 g, 46.4 mmol) at 0° C., and the mixture was stirred for 1 h at this temperature. 2-[4-(3-chloro-10,11-dihydro-5H-dibenzo[b,f]azepin-5-yl)butyl]-1H-isoindole-1,3(2H)-dione (Intermediate 9, Step 1; 0.500 g, 1.16 mmol) in DCE (10 ml) was added and the reaction mixture was stirred at 100° C. for 6 h. Then, the mixture was cooled to room temperature, poured into ice water and carefully neutralized with sodium hydroxide. The solution was extracted with DCM, then, the organic phase was washed with water and dried over anhydrous Na$_2$SO$_4$. After filtration, the solvent was removed under reduced pressure. The crude was purified by silica gel column (eluent hexane/EtOAc from 98:2 to 90:10). 7-Chloro-5-[4-(1,3-dioxo-1,3-dihydro-isoindol-2-yl)-butyl]-10,11-dihydro-5H-dibenzo[b,f]azepine-2-carbaldehyde was obtained as white solid (0.21 g, 39%); $^1$H NMR (DMSO-d$_6$), δ (ppm): 9.72 (s, 1H), 7.83-7.69 (m, 4H), 7.61-7.53 (m, 1H), 7.52-7.45 (m, 1H), 7.26-7.20 (m, 1H), 7.19-7.15 (m, 1H), 7.11-7.04 (m, 1H), 6.92-6.86 (m, 1H), 3.80 (t, J=6.4 Hz, 2H), 3.48 (t, J=6.4 Hz, 2H), 3.14-2.96 (m, 4H), 1.66-1.54 (m, 2H), 1.53-1.41 (m, 2H); MS (ESI): m/z: 459 [M+H]$^+$.

3-Chloro-5-[4-(1,3-dioxo-1,3-dihydro-isoindol-2-yl)-butyl]-10,11-dihydro-5H-dibenzo[b,f]azepine-2-carbaldehyde was obtained as pale yellow solid (0.12 g, 22%). $^1$H NMR (DMSO-d$_6$), δ (ppm): 10.00 (s, 1H), 7.83-7.68 (m, 4H), 7.40 (s, 1H), 7.20-7.05 (m, 4H), 6.98-6.87 (m, 1H), 3.82 (t, J=6.1 Hz, 2H), 3.48 (t, J=6.4 Hz, 2H), 3.08-2.91 (m, 4H), 1.65-1.54 (m, 2H), 1.53-1.41 (m, 2H); MS (ESI): m/z: 459 [M+H]$^+$.

Step 2: 7-Chloro-5-[4-(1,3-dioxo-1,3-dihydro-isoindol-2-yl)-butyl]-10,11-dihydro-5H-dibenzo[b,f]azepin-2-yl formate To a solution of 7-chloro-5-[4-(1,3-dioxo-1,3-dihydro-isoindol-2-yl)-butyl]-10,11-dihydro-5H-dibenzo[b,f]azepine-2-carbaldehyde (0.2 g, 0.436 mmol) in dry DCM (30 ml), 3-chlorobenzenecarboperoxoic acid (0.075 g, 0.436 mmol) was added and the mixture was stirred r.t. for 20 h. The reaction was diluted with DCM (20 ml) and a saturated solution of NaHCO$_3$ (30 ml) was added. The product was extracted with DCM (3×15 ml) and the organic phase was dried over Na$_2$SO$_4$, filtered and evaporated. The crude was purified by silica gel column (eluent hexane/EtOAc from 98:2 to 90:10) to give 7-chloro-5-[4-(1,3-dioxo-1,3-dihydro-isoindol-2-yl)-butyl]-10,11-dihydro-5H-dibenzo[b,f]azepin-2-yl formate as white solid. (0.165 g, 80%). $^1$H NMR (DMSO-d$_6$), δ (ppm): 8.45 (s, 1H), 7.87-7.71 (m, 4H), 7.18-7.11 (m, 1H), 7.09-7.04 (m, 1H), 7.03-6.97 (m, 1H), 6.96-6.89 (m, 2H), 6.85-6.76 (m, 1H), 3.72-3.65 (m, 2H), 3.54-3.45 (m, 2H), 3.09-2.93 (m, 4H), 1.67-1.56 (m, 2H), 1.52-1.41 (m, 2H); MS (ESI): m/z: 475 [M+H]$^+$.

Step 3: 5-(4-Aminobutyl)-7-chloro-10,11-dihydro-5H-dibenzo[b,f]azepin-2-ol

To a solution of 7-chloro-5-[4-(1,3-dioxo-1,3-dihydro-isoindol-2-yl)-butyl]-10,11-dihydro-5H-dibenzo[b,f]azepin-2-yl formate (0.15 g, 0.316 mmol) in EtOH (5 ml), a 60% solution of hydrazine hydrate (0.0264 g, 0.316 mmol) was added and the mixture was stirred at reflux for 1 h. Solvents were evaporated and the crude was purified by silica gel column (DCM/MeOH/NH$_3$ 90:10:0.05) to give 5-(4-aminobutyl)-7-chloro-10,11-dihydro-5H-dibenzo[b,f]azepin-2-ol as colorless glassy solid (0.065 g, 65%). $^1$H NMR (DMSO-d$_6$), δ (ppm): 9.09 (bs, 1H), 7.06-6.97 (m, 2H), 6.94 (d, J=8.3 Hz, 1H), 6.88-6.81 (m, J=2.2, 8.1 Hz, 1H), 6.61-6.50 (m, 2H), 3.58 (t, J=6.6 Hz, 2H), 3.03-2.92 (m, 4H), 1.50-1.29 (m, 4H); MS (ESI): m/z: 317 [M+H]$^+$.

Intermediate 35: 5-(4-Amino-butyl)-3-chloro-10,11-dihydro-5H-dibenzo[b,f]azepin-2-ol

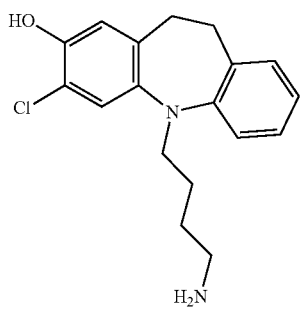 [SMILES: NCCCCN1c2ccccc2CCc2cc(O)c(Cl)cc21]

Step 1: 3-Chloro-5-[4-(1,3-dioxo-1,3-dihydro-isoindol-2-yl)-butyl]-10,11-dihydro-5H-dibenzo[b,f]azepin-2-yl formate To a solution of 3-chloro-5-[4-(1,3-dioxo-1,3-dihydro-isoindol-2-yl)-butyl]-10,11-dihydro-5H-dibenzo[b,f]azepine-2-carbaldehyde (Intermediate 34, Step 1) (0.27 g, 0.588 mmol) in dry DCM (30 ml), 3-chlorobenzenecarboperoxoic acid (0.102 g, 0.588 mmol) was added and the mixture was stirred r.t. for 20 h. The reaction was diluted with DCM (20 ml) and a saturated solution of NaHCO$_3$ (30 ml) was added. The product was extracted with DCM (3×15 ml) and the organic phase was dried over Na$_2$SO$_4$, filtered and evaporated. The crude was purified by silica gel column (eluent hexane/EtOAc from 98:2 to 90:10) to give 3-chloro-5-[4-(1,3-dioxo-1,3-dihydro-isoindol-2-yl)-butyl]-10,11-dihydro-5H-dibenzo[b,f]azepin-2-yl formate as pale yellow solid (0.07 g, 25%). $^1$H NMR (DMSO-d$_6$), δ (ppm): 8.52 (s, 1H), 7.91-7.73 (m, 4H), 7.21 (s, 1H), 7.13-6.94 (m, 4H), 6.88-6.80 (m, 1H), 3.73-3.63 (m, 2H), 3.54-3.42 (m, 2H), 3.09-2.91 (m, 4H), 1.66-1.54 (m, 2H), 1.52-1.39 (m, 2H); MS (ESI): m/z: 475 [M+H]$^+$.

Step 2: 5-(4-Amino-butyl)-3-chloro-10,11-dihydro-5H-dibenzo[b,f]azepin-2-ol

To a solution of 3-chloro-5-[4-(1,3-dioxo-1,3-dihydro-isoindol-2-yl)-butyl]-10,11-dihydro-5H-dibenzo[b,f]azepin-2-yl formate (0.06 g, 0.126 mmol) in EtOH (3 ml), a 60% solution of hydrazine hydrate (0.0105 g, 0.126 mmol) was added and the mixture was stirred at reflux for 1 h. Solvents were evaporated and the crude was purified by silica gel column (DCM/MeOH/NH$_3$ 90:10:0.05) to give 5-(4-amino-butyl)-3-chloro-10,11-dihydro-5H-dibenzo[b,f]azepin-2-ol as pale yellow glassy solid (0.039 g, 97%). $^1$H NMR (DMSO-d$_6$), δ (ppm): 7.14-6.99 (m, 4H), 6.87 (dt, J=1.5, 7.1 Hz, 1H), 6.71 (s, 1H), 3.58 (t, J=6.6 Hz, 2H), 3.06-2.92 (m, 4H), 2.46 (t, J=7.1 Hz, 2H), 1.49-1.29 (m, 4H); MS (ESI): m/z: 317 [M+H]$^+$.

Intermediate 36: 5-(4-Aminobutyl)-7-chloro-5,10-dihydro-11H-dibenzo[b,e][1,4]diazepin-11-one

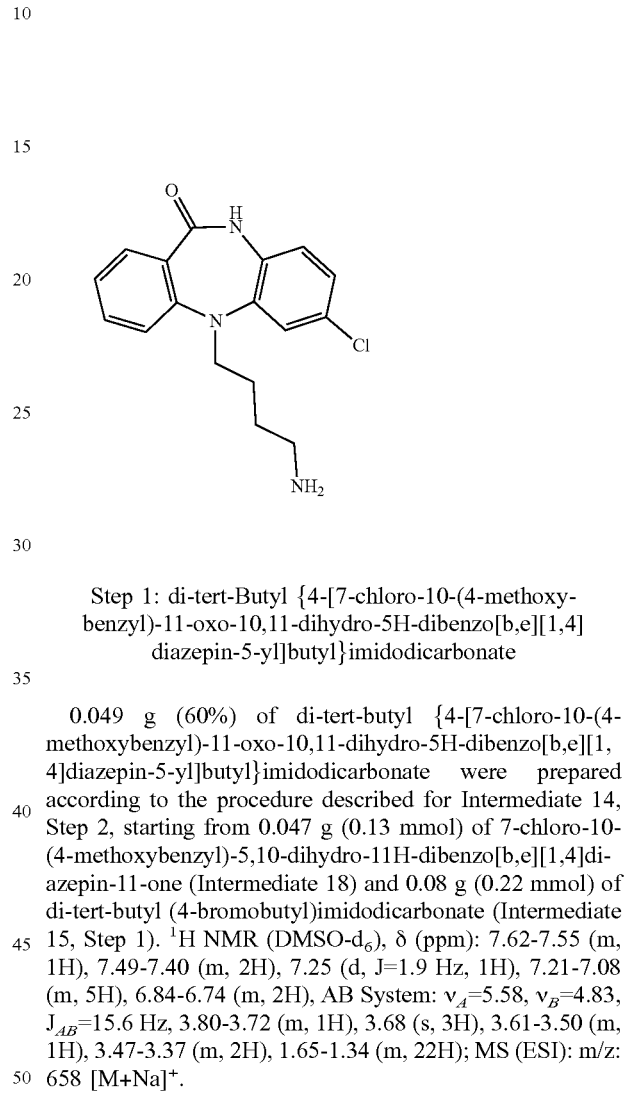

Step 1: di-tert-Butyl {4-[7-chloro-10-(4-methoxybenzyl)-11-oxo-10,11-dihydro-5H-dibenzo[b,e][1,4]diazepin-5-yl]butyl}imidodicarbonate 0.049 g (60%) of di-tert-butyl {4-[7-chloro-10-(4-methoxybenzyl)-11-oxo-10,11-dihydro-5H-dibenzo[b,e][1,4]diazepin-5-yl]butyl}imidodicarbonate were prepared according to the procedure described for Intermediate 14, Step 2, starting from 0.047 g (0.13 mmol) of 7-chloro-10-(4-methoxybenzyl)-5,10-dihydro-11H-dibenzo[b,e][1,4]diazepin-11-one (Intermediate 18) and 0.08 g (0.22 mmol) of di-tert-butyl (4-bromobutyl)imidodicarbonate (Intermediate 15, Step 1). $^1$H NMR (DMSO-d$_6$), δ (ppm): 7.62-7.55 (m, 1H), 7.49-7.40 (m, 2H), 7.25 (d, J=1.9 Hz, 1H), 7.21-7.08 (m, 5H), 6.84-6.74 (m, 2H), AB System: ν$_A$=5.58, ν$_B$=4.83, J$_{AB}$=15.6 Hz, 3.80-3.72 (m, 1H), 3.68 (s, 3H), 3.61-3.50 (m, 1H), 3.47-3.37 (m, 2H), 1.65-1.34 (m, 22H); MS (ESI): m/z: 658 [M+Na]$^+$.

Step 2: 5-(4-Aminobutyl)-7-chloro-5,10-dihydro-11H-dibenzo[b,e][1,4]diazepin-11-one 0.023 g (92%) of 5-(4-aminobutyl)-7-chloro-5,10-dihydro-11H-dibenzo[b,e][1,4]diazepin-11-one were prepared according to the procedure described for Intermediate 14, Step 3, starting from 0.049 g (0.078 mmol) of di-tert-butyl {4-[7-chloro-10-(4-methoxybenzyl)-11-oxo-10,11-dihydro-5H-dibenzo[b,e][1,4]diazepin-5-yl]butyl}imidodicarbonate. $^1$H NMR (DMSO-d$_6$) δ (ppm): 10.25 (bs, 1H), 7.58 (dd, J=1.5, 7.8 Hz, 1H), 7.53-7.45 (m, 1H), 7.24 (d, J=2.0 Hz, 1H), 7.20 (d, J=8.3 Hz, 1H), 7.13-7.07 (m, 2H), 7.06-7.00 (m, 1H), 3.82-3.60 (m, 2H), 2.46 (t, J=6.8 Hz, 2H), 1.55-1.45 (m, 2H), 1.42-1.32 (m, 2H); MS (ESI): m/z: 316 [M+H]$^+$.

Intermediate 37: 5-(4-Aminobutyl)-3-choro-10-methyl-5,10-dihydro-11H-dibenzo[b,e][1,4]diazepin-11-one

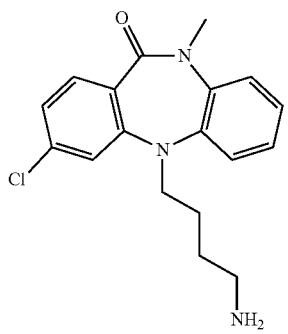 [SMILES: CN1C(=O)c2ccc(Cl)cc2N(CCCCN)c2ccccc21]

Step 1: di-tert-Butyl [4-(3-chloro-10-methyl-11-oxo-10,11-dihydro-5H-dibenzo[b,e][1,4]diazepin-5-yl]butyl]imidodicarbonate 0.217 g (73%) of di-tert-butyl [4-(3-chloro-10-methyl-11-oxo-10,11-dihydro-5H-dibenzo[b,e][1,4]diazepin-5-yl)butyl]imidodicarbonate were prepared according to the procedure described for Intermediate 14, Step 2, starting from 0.144 g (0.56 mmol) of 3-chloro-10-methyl-5,10-dihydro-11H-dibenzo[b,e][1,4]diazepin-11-one (Intermediate 20, Step 1) and 0.347 g (0.95 mmol) of di-tert-butyl(4-bromobutyl)imidodicarbonate (Intermediate 15, Step 1). $^1$H NMR (DMSO-$d_6$), δ (ppm): 7.57 (d, J=8.3 Hz, 1H), 7.36 (dd, J=2.2, 7.6 Hz, 1H), 7.26 (dd, J=1.9, 7.8 Hz, 1H), 7.22 (d, J=2.0 Hz, 1H), 7.21-7.14 (m, 2H), 7.13 (dd, J=2.0, 8.3 Hz, 1H), 3.83-3.59 (m, 2H), 3.46-3.38 (m, 5H), 1.61-1.43 (m, 4H), 1.36 (s, 18H); MS (ESI): m/z: 474 [M−56+H]$^+$.

Step 2: 5-(4-Aminobutyl)-3-chloro-10-methyl-5,10-dihydro-11H-dibenzo[b,e][1,4]diazepin-11-one 0.135 g (93%) of 5-(4-aminobutyl)-3-chloro-10-methyl-5,10-dihydro-11H-dibenzo[b,e][1,4]diazepin-11-one were prepared according to the procedure described for Intermediate 20, Step 3, starting from 0.232 g (0.44 mmol) of di-tert-butyl [4-(3-chloro-10-methyl-11-oxo-10,11-dihydro-5H-dibenzo[b,e][1,4]diazepin-5-yl)butyl]imidodicarbonate and 0.67 mL (8.8 mmol) of TFA. $^1$H NMR (DMSO-$d_6$) δ (ppm): 7.56 (d, J=8.3 Hz, 1H), 7.36 (dd, J=2.0, 7.3 Hz, 1H), 7.28-7.23 (m, 2H), 7.22-7.14 (m, 2H), 7.12 (dd, J=2.0, 8.3 Hz, 1H), 3.78-3.63 (m, 2H), 3.42 (s, 3H), 2.47 (t, J=7.1 Hz, 2H), 1.56-1.46 (m, 2H), 1.40-1.31 (m, 2H); MS (ESI): m/z: 330 [M+H]$^+$.

Intermediate 38: 4-(8-Chloro-1-methyl-4,5-dihydropyrazolo[3,4-b][1]benzazepin-10(1H)-yl)butan-1-amine

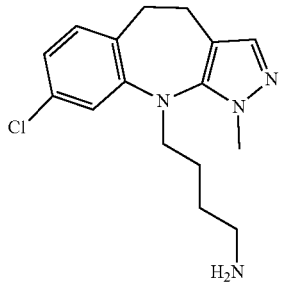 [SMILES: Cn1ncc2c1N(CCCCN)c1cc(Cl)ccc1CC2]

0.027 g (33%) of 4-(8-chloro-1-methyl-4,5-dihydropyrazolo[3,4-b][1]benzazepin-10(1H)-yl)butan-1-amine were prepared according to the procedure described for Intermediate 9, starting from 0.063 g (0.27 mmol) of 8-chloro-1-methyl-1,4,5,10-tetrahydropyrazolo[3,4-b][1]benzazepine (Intermediate 23) and 0.116 g (0.40 mmol) of N-(4-bromobutyl)phthalimide. $^1$H NMR (DMSO-$d_6$), δ (ppm): 7.37 (d, J=2.4 Hz, 1H), 7.27 (d, J=7.8 Hz, 1H), 7.20 (dd, J=2.2, 8.1 Hz, 1H), 7.08 (s, 1H), 3.73 (s, 3H), 3.45-3.38 (m, 2H), 2.94 (t, J=6.1 Hz, 2H), 2.62 (bs, 2H), 2.47 (t, J=6.8 Hz, 2H), 1.51-1.41 (m, 2H), 1.35-1.26 (m, 2H); MS (ESI): m/z: 305 [M+H]$^+$.

Intermediate 39: 5-(4-Aminobutyl)-7-chloro-10-(2-phenylethyl)-5,10-dihydro-11H-dibenzo[b,e][1,4]diazepin-11-one

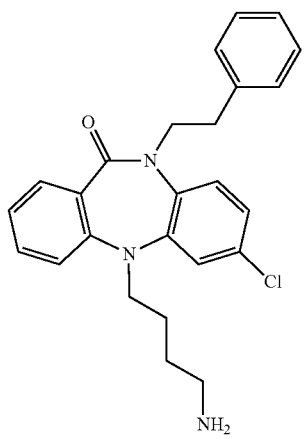 [SMILES: NCCCCN1c2ccccc2C(=O)N(CCc2ccccc2)c2ccc(Cl)cc21]

Step 1: 7-Chloro-10-(2-phenylethyl)-5,10-dihydro-11H-dibenzo[b,e][1,4]diazepin-11-one 0.026 g (34%) of 7-chloro-10-(2-phenylethyl)-5,10-dihydro-11H-dibenzo[b,e][1,4]diazepin-11-one were prepared according to the procedure described for Intermediate 14, Step 1, starting from 0.053 g (0.217 mmol) of 7-chloro-5,10-dihydro-11H-dibenzo[b,e][1,4]diazepin-11-one (Intermediate 18) and 0.031 ml (0.227 mmol) of 2-bromoethylbenzene. $^1$H NMR (DMSO-$d_6$), δ (ppm): 7.95 (s, 1H), 7.61 (dd, J=1.5, 7.8 Hz, 1H), 7.44 (d, J=8.8 Hz, 1H), 7.38-7.31

(m, 1H), 7.28-7.23 (m, 2H), 7.22-7.15 (m, 4H), 7.12 (dd, J=2.4, 8.8 Hz, 1H), 7.02 (d, J=8.3 Hz, 1H), 7.00-6.96 (m, 1H), 4.17 (t, J=7.6 Hz, 2H), 2.82 (t, J=7.6 Hz, 2H); MS (ESI): m/z: 349 [M+H]⁺.

Step 2: di-tert-Butyl {4-[7-chloro-10-(2-phenylethyl)-11-oxo-10,11-dihydro-5H-dibenzo[b,e][1,4]diazepin-5-yl]butyl}imidodicarbonate 0.033 g (74%) of di-tert-butyl {4-[7-chloro-10-(2-phenylethyl)-11-oxo-10,11-dihydro-5H-dibenzo[b,e][1,4]diazepin-5-yl)butyl]}imidodicarbonate were prepared according to the procedure described for Intermediate 14, Step 2, starting from 0.025 g (0.07 mmol) of 7-chloro-10-(2-phenylethyl)-5,10-dihydro-11H-dibenzo[b,e][1,4]diazepin-11-one and 0.045 g (0.12 mmol) of di-tert-butyl (4-bromobutyl) imidodicarbonate. ¹H NMR (DMSO-d₆), δ (ppm): 7.54 (dd, J=1.5, 7.8 Hz, 1H), 7.49 (d, J=8.3 Hz, 1H), 7.45-7.40 (m, 1H), 7.28 (d, J=2.4 Hz, 1H), 7.27-7.22 (m, 2H), 7.21-7.12 (m, 5H), 7.11-7.06 (m, 1H), 4.64-4.52 (m, 1H), 3.92-3.83 (m, 1H), 3.78-3.68 (m, 1H), 3.57-3.47 (m, 1H), 3.43 (t, J=6.8 Hz, 2H), 2.88-2.77 (m, 2H), 1.63-1.50 (m, 2H), 1.45-1.30 (m, 20H); MS (ESI): m/z: 564 [M−56+H]⁺.

Step 3: 5-(4-Aminobutyl)-7-chloro-10-(2-phenylethyl)-5,10-dihydro-11H-dibenzo[b,e][1,4]diazepin-11-one 0.021 g (97%) of 5-(4-aminobutyl)-7-chloro-10-(2-phenylethyl)-5,10-dihydro-11H-dibenzo[b,e][1,4]diazepin-11-one were prepared according to the procedure described for Intermediate 20, Step 3, starting from 0.032 g (0.05 mmol) of di-tert-butyl {4-[7-chloro-10-(2-phenylethyl)-11-oxo-10,11-dihydro-5H-dibenzo[b,e][1,4]diazepin-5-yl)butyl]}imidodicarbonate and 0.08 ml (1.03 mmol) of TFA. ¹H NMR (DMSO-d₆) δ (ppm): 7.53 (dd, J=1.5, 7.8 Hz, 1H), 7.48 (d, J=8.8 Hz, 1H), 7.45-7.40 (m, 1H), 7.30 (d, J=2.4 Hz, 1H), 7.28-7.23 (m, 2H), 7.21-7.13 (m, 5H), 7.11-7.05 (m, 1H), 4.67-4.56 (m, 1H), 3.93-3.81 (m, 1H), 3.76-3.67 (m, 1H), 3.57-3.44 (m, 1H), 2.88-2.73 (m, 2H), 1.52-1.34 (m, 4H); MS (ESI): m/z: 420 [M+H]⁺.

Intermediate 40: 5-(4-Aminobutyl)-10-benzyl-7-chloro-5,10-dihydro-11H-dibenzo[b,e][1,4]diazepin-11-one

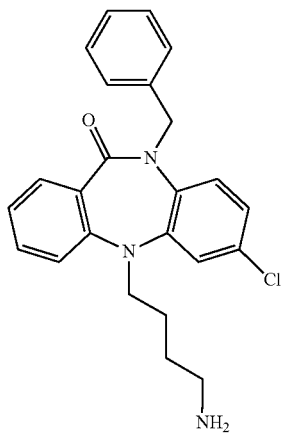 [SMILES: NCCCCN1c2ccccc2C(=O)N(Cc2ccccc2)c2ccc(Cl)cc21]

Step 1: 10-Benzyl-7-chloro-5,10-dihydro-11H-dibenzo[b,e][1,4]diazepin-11-one 0.048 g (80%) of 10-benzyl-7-chloro-5,10-dihydro-11H-dibenzo[b,e][1,4]diazepin-11-one were prepared according to the procedure described for Intermediate 14, Step 1, starting from 0.043 g (0.178 mmol) of 7-chloro-5,10-dihydro-11H-dibenzo[b,e][1,4]diazepin-11-one (Intermediate 18) and 0.023 ml (0.187 mmol) of benzyl bromide. ¹H NMR (DMSO-d₆), δ (ppm): 8.02 (s, 1H), 7.66 (dd, J=1.7, 7.6 Hz, 1H), 7.41-7.36 (m, 1H), 7.33 (d, J=8.3 Hz, 1H), 7.31-7.25 (m, 4H), 7.22-7.15 (m, 2H), 7.09-7.05 (m, 1H), 7.04-7.00 (m, 2H), 5.23 (s, 2H); MS (ESI): m/z: 335 [M+H]⁺.

Step 2: di-tert-Butyl {4-[10-benzyl-7-chloro-11-oxo-10,11-dihydro-5H-dibenzo[b,e][1,4]diazepin-5-yl]butyl}imidodicarbonate 0.064 g (79%) of di-tert-butyl {4-[10-benzyl-7-chloro-11-oxo-10,11-dihydro-5H-dibenzo[b,e][1,4]diazepin-5-yl)butyl]}imidodicarbonate were prepared according to the procedure described for Intermediate 14, Step 2, starting from 0.045 g (0.13 mmol) of 10-benzyl-7-chloro-5,10-dihydro-11H-dibenzo[b,e][1,4]diazepin-11-one and 0.084 g (0.228 mmol) of di-tert-butyl (4-bromobutyl)imidodicarbonate. ¹H NMR (DMSO-d₆), δ (ppm): 7.58 (dd, J=1.5, 7.8 Hz, 1H), 7.49-7.43 (m, 2H), 7.28-7.15 (m, 7H), 7.15-7.09 (m, 2H), AB System: $v_A$=5.64, $v_B$=4.93, $J_{AB}$=15.9 Hz, 3.85-3.76 (m, 1H), 3.61-3.51 (m, 1H), 3.50-3.38 (m, 2H), 1.69-1.30 (m, 22H); MS (ESI): m/z: 550 [M−56+H]⁺.

Step 3: 5-(4-Aminobutyl)-10-benzyl-7-chloro-5,10-dihydro-11H-dibenzo[b,e][1,4]diazepin-11-one 0.041 g (97%) of 5-(4-aminobutyl)-10-benzyl-7-chloro-5,10-dihydro-11H-dibenzo[b,e][1,4]diazepin-11-one were prepared according to the procedure described for Intermediate 20, Step 3, starting from 0.063 g (0.104 mmol) of di-tert-butyl {4-[10-benzyl-7-chloro-11-oxo-10,11-dihydro-5H-dibenzo[b,e][1,4]diazepin-5-yl)butyl]}imidodicarbonate and 0.16 ml (2.08 mmol) of TFA. ¹H NMR (DMSO-de, D₂O) δ (ppm): 7.55 (dd, J=1.5, 7.8 Hz, 1H), 7.48-7.41 (m, 2H), 7.27-7.22 (m, 5H), 7.21-7.15 (m, 2H), 7.14-7.06 (m, 2H), AB System: $v_A$=5.67, $v_B$=4.88, $J_{AB}$=15.7 Hz, 3.71-3.65 (m, 1H), 3.58-3.49 (m, 1H), 2.46 (t, J=6.8 Hz, 2H), 1.48-1.33 (m, 4H); MS (ESI): m/z: 406 [M+H]⁺.

Intermediate 41: 5-(4-Aminobutyl)-3-chloro-10-(2-hydroxyethyl)-5,10-dihydro-11H-dibenzo[b,e][1,4]diazepin-11-one

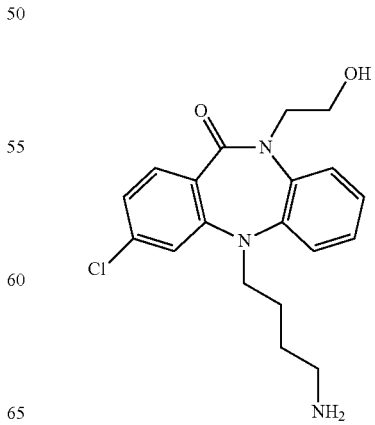

Step 1: 3-Chloro-10-[2-(tetrahydro-2H-pyran-2-yloxy)ethyl]-5,10-dihydro-11H-dibenzo[b,e][1,4]diazepin-11-one 0.313 g (76%) of 3-chloro-10-[2-(tetrahydro-2H-pyran-2-yloxy)ethyl]-5,10-dihydro-11H-dibenzo[b,e][1,4]diazepin-11-one were prepared according to the procedure described for Intermediate 14, Step 1, starting from 0.27 g (1.103 mmol) of 3-chloro-5,10-dihydro-11H-dibenzo[b,e][1,4]diazepin-11-one (prepared according to literature procedure, Synthesis 1985, 1, 550-552) and 0.182 ml (1.159 mmol) of 2-(2-bromoethoxy)tetrahydropyran. $^1$H NMR (DMSO-$d_6$), δ (ppm): 8.04 (s, 1H), 7.60 (d, J=8.3 Hz, 1H), 7.54-7.45 (m, 1H), 7.16-7.06 (m, 4H), 7.00 (dd, J=2.0, 8.3 Hz, 1H), 4.53-4.48 (m, 1H), 4.17-4.07 (m, 2H), 3.83-3.74 (m, 1H), 3.65-3.58 (m, 1H), 3.55-3.47 (m, 1H), 1.66-1.56 (m, 1H), 1.55-1.31 (m, 5H); MS (ESI): m/z: 395 [M+Na]$^+$.

Step 2: di-tert-Butyl {4-[3-chloro-10-[2-(tetrahydro-2H-pyran-2-yloxy)ethyl]-11-oxo-10,11-dihydro-5H-dibenzo[b,e][1,4]diazepin-5-yl]butyl}imidodicarbonate 0.179 g (69%) of di-tert-butyl {4-[3-chloro-10-[2-(tetrahydro-2H-pyran-2-yloxy)ethyl]-11-oxo-10,11-dihydro-5H-dibenzo[b,e][1,4]diazepin-5-yl]butyl} imidodicarbonate were prepared according to the procedure described for Intermediate 14, Step 2, starting from 0.149 g (0.4 mmol) of 3-chloro-10-[2-(tetrahydro-2H-pyran-2-yloxy)ethyl]-5,10-dihydro-11H-dibenzo[b,e][1.4]diazepin-11-one and 0.249 g (0.68 mmol) of di-tert-butyl (4-bromobutyl)imidodicarbonate. $^1$H NMR (DMSO-$d_6$), mixture of conformers, δ (ppm): 7.62-7.45 (m, 2H), 7.28-7.22 (m, 2H), 7.21-7.09 (m, 3H), 4.57-4.51 and 4.49-4.45 (2 m, 1H), 4.42-4.30 (m, 1H), 4.01-3.47 (m, 6H), 3.44 (t, J=6.6 Hz, 2H), 3.39-3.34 (m, 1H), 1.65-1.20 (m, 28H); MS (ESI): m/z: 666 [M+Na]$^+$.

Step 3: 5-(4-Aminobutyl)-3-chloro-10-(2-hydroxyethyl)-5,10-dihydro-11H-dibenzo[b,e][1,4]diazepin-11-one 0.086 g (78%) of 5-(4-aminobutyl)-3-chloro-10-(2-hydroxyethyl)-5,10-dihydro-11H-dibenzo[b,e][1,4]diazepin-11-one were prepared according to the procedure described for Intermediate 20, Step 3, starting from 0.196 g (0.304 mmol) of di-tert-butyl {4-[3-chloro-10-[2-(tetrahydro-2H-pyran-2-yloxy)ethyl]-11-oxo-10,11-dihydro-5H-dibenzo[b,e][1,4]diazepin-5-yl]butyl} imidodicarbonate and 0.47 ml (6.08 mmol) of TFA. $^1$H NMR (DMSO-$d_6$) δ (ppm): 7.55 (dd, J=1.5, 7.8 Hz, 1H), 7.52 (d, J=8.3 Hz, 1H), 7.26 (dd, J=2.0, 8.3 Hz, 1H), 7.22 (d, J=2 Hz, 1H), 7.21-7.13 (m, 2H), 7.11 (dd, J=2.0, 8.3 Hz, 1H), 4.32-4.19 (m, 1H), 3.85-3.70 (m, 2H), 3.68-3.57 (m, 2H), 3.53-3.45 (m, 1H), 2.49-2.41 (m, 2H), 1.58-1.31 (m, 4H); MS (ESI): m/z: 360 [M+H]$^+$.

Intermediate 42: 5-(3-Aminopropyl)-3-chloro-10-(2-hydroxyethyl)-5,10-dihydro-11H-dibenzo[b,e][1,4]diazepin-11-one

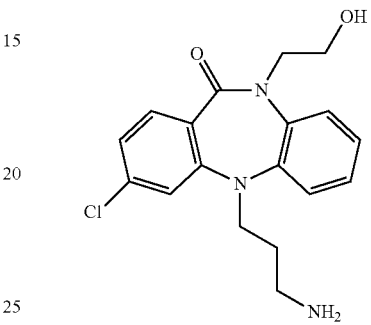

Step 1: di-tert-Butyl {3-[3-chloro-10-[2-(tetrahydro-2H-pyran-2-yloxy)ethyl]-11-oxo-10,11-dihydro-5H-dibenzo[b,e][1,4]diazepin-5-yl]propyl}imidodicarbonate 0.149 g (55%) of di-tert-butyl {3-[3-chloro-10-[2-(tetrahydro-2H-pyran-2-yloxy)ethyl]-11-oxo-10,11-dihydro-5H-dibenzo[b,e][1,4]diazepin-5-yl]propyl} imidodicarbonate were prepared according to the procedure described for Intermediate 14, Step 2, starting from 0.159 g (0.426 mmol) of 3-chloro-10-[2-(tetrahydro-2H-pyran-2-yloxy)ethyl]-5,10-dihydro-11H-dibenzo[b,e][1,4]diazepin-11-one (Intermediate 41, Step 1) and 0.250 g (0.725 mmol) of di-tert-butyl (3-bromopropyl)imidodicarbonate. $^1$H NMR (DMSO-$d_6$), mixture of conformers, δ (ppm): 7.59-7.49 (m, 2H), 7.27-7.09 (m, 5H), 4.56-4.50 and 4.48-4.38 (2 m, 2H), 4.01-3.60 (m, 5H), 3.59-3.50 (m, 3H), 3.38-3.34 (m, 1H), 1.83-1.66 (m, 2H), 1.61-1.26 (m, 24H); MS (ESI): m/z: 652 [M+Na]$^+$.

Step 2: 5-(3-Aminopropyl)-3-chloro-10-(2-hydroxyethyl)-5,10-dihydro-11H-dibenzo[b,e][1,4]diazepin-11-one 0.066 g (72%) of 5-(3-aminopropyl)-3-chloro-10-(2-hydroxyethyl)-5,10-dihydro-11H-dibenzo[b,e][1,4]diazepin-11-one were prepared according to the procedure described for Intermediate 20, Step 3, starting from 0.167 g (0.265 mmol) of di-tert-butyl {3-[3-chloro-10-[2-(tetrahydro-2H-pyran-2-yloxy)ethyl]-11-oxo-10,11-dihydro-5H-dibenzo[b,e][1,4]diazepin-5-yl]propyl} imidodicarbonate and 0.41 ml (5.3 mmol) of TFA. $^1$H NMR (DMSO-$d_6$) δ (ppm): 7.55 (dd, J=1.7, 8.1 Hz, 1H), 7.52 (d, J=8.3 Hz, 1H), 7.27 (dd, J=1.5, 7.8 Hz, 1H), 7.23 (d, J=2.0 Hz, 1H), 7.22-7.13 (m, 2H), 7.11 (dd, J=2.0, 8.3 Hz, 1H), 4.30-4.22 (m, 1H), 3.84-3.68 (m, 3H), 3.66-3.59 (m, 1H), 3.51-3.43 (m, 1H), 2.57 (t, J=6.6 Hz, 2H), 1.65-1.46 (m, 2H); MS (ESI): m/z: 346 [M+H]$^+$.

Intermediate 43: 5-(4-Aminobutyl)-3-chloro-10-(3-hydroxypropyl)-5,10-dihydro-11H-dibenzo[b,e][1,4]diazepin-11-one

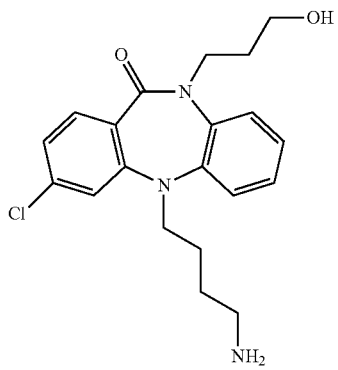 [SMILES: NCCCCN1c2cc(Cl)ccc2C(=O)N(CCCO)c2ccccc21]

Step 1: 3-Chloro-10-[3-(tetrahydro-2H-pyran-2-yloxy)propyl]-5,10-dihydro-11H-dibenzo[b,e][1,4]diazepin-11-one 0.162 g (68%) of 3-chloro-10-[3-(tetrahydro-2H-pyran-2-yloxy)propyl]-5,10-dihydro-11H-dibenzo[b,e][1,4]diazepin-11-one were prepared according to the procedure described for Intermediate 14, Step 1, starting from 0.15 g (0.613 mmol) of 3-chloro-5,10-dihydro-11H-dibenzo[b,e][1,4]diazepin-11-one (prepared according to literature procedure, Synthesis 1985, 1, 550-552) and 0.111 ml (0.644 mmol) of 2-(3-bromopropoxy)tetrahydropyran. $^1$H NMR (DMSO-d$_6$), δ (ppm): 8.04 (s, 1H), 7.69-7.55 (m, 1H), 7.42-7.30 (m, 1H), 7.15-7.07 (m, 4H), 7.00 (dd, J=2.0, 8.3 Hz, 1H), 4.29 (t, J=3.2 Hz, 1H), 4.10-3.96 (m, 2H), 3.63-3.53 (m, 2H), 3.33-3.24 (m, 2H), 1.78-1.66 (m, 2H), 1.64-1.53 (m, 1H), 1.47-1.25 (m, 5H); MS (ESI): m/z: 409 [M+Na]$^+$.

Step 2: di-tert-Butyl {4-[3-chloro-10-[3-(tetrahydro-2H-pyran-2-yloxy)propyl]-11-oxo-10,11-dihydro-5H-dibenzo[b,e][1,4]diazepin-5-yl]butyl}imidodicarbonate 0.210 g (77%) of di-tert-butyl {4-[3-chloro-10-[3-(tetrahydro-2H-pyran-2-yloxy)propyl]-11-oxo-10,11-dihydro-5H-dibenzo[b,e][1,4]diazepin-5-yl]butyl} imidodicarbonate were prepared according to the procedure described for Intermediate 14, Step 2, starting from 0.161 g (0.416 mmol) of 3-chloro-10-[3-(tetrahydro-2H-pyran-2-yloxy)propyl]-5,10-dihydro-11H-dibenzo[b,e][1,4]diazepin-11-one and 0.259 g (0.707 mmol) of di-tert-butyl (4-bromobutyl)imidodicarbonate. $^1$H NMR (DMSO-d$_6$), mixture of conformers, δ (ppm): 7.54 (d, J=8.3 Hz, 1H), 7.46-7.41 (m, 1H), 7.30-7.25 (m, 1H), 7.24-7.10 (m, 4H), 4.57-4.42 and 4.12-4.07 (2 m, 2H), 3.82-3.51 and 3.48-3.39 (2 m, 7H), 3.30-3.18 (m, 2H), 1.85-1.21 (m, 30H); MS (ESI): m/z: 680 [M+Na]$^+$.

Step 3: 5-(4-Aminobutyl)-3-chloro-10-(3-hydroxypropyl)-5,10-dihydro-11H-dibenzo[b,e][1,4]diazepin-11-one 0.063 g (53%) of 5-(4-aminobutyl)-3-chloro-10-(3-hydroxypropyl)-5,10-dihydro-11H-dibenzo[b,e][1,4]diazepin-11-one were prepared according to the procedure described for Intermediate 20, Step 3, starting from 0.208 g (0.316 mmol) of di-tert-butyl {4-[3-chloro-10-[3-(tetrahydro-2H-pyran-2-yloxy)propyl]-11-oxo-10,11-dihydro-5H-dibenzo[b,e][1,4]diazepin-5-yl]butyl} imidodicarbonate and 0.49 ml (6.32 mmol) of TFA. $^1$H NMR (DMSO-d$_6$) δ (ppm): 7.53 (d, J=8.3 Hz, 1H), 7.43 (dd, J=1.5, 7.8 Hz, 1H), 7.28 (dd, J=1.5, 7.8 Hz, 1H), 7.23 (d, J=2.0 Hz, 1H), 7.21-7.13 (m, 2H), 7.11 (dd, J=2.0, 8.3 Hz, 1H), 4.55-4.43 (m, 1H), 3.78-3.62 (m, 3H), 3.43-3.35 (m, 2H), 2.48-2.45 (m, 2H), 1.69-1.32 (m, 6H); MS (ESI): m/z: 374 [M+H]$^+$.

Intermediate 44: 5-(3-Aminopropyl)-3-chloro-10-(3-hydroxypropyl)-5,10-dihydro-11H-dibenzo[b,e][1,4]diazepin-11-one

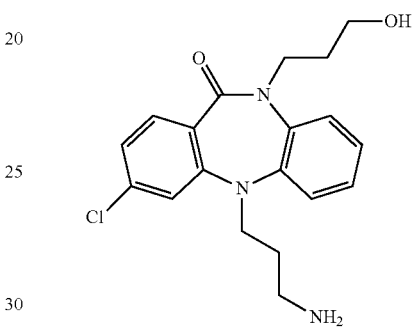

Step 1: di-tert-Butyl {3-[3-chloro-10-[3-(tetrahydro-2H-pyran-2-yloxy)propyl]-11-oxo-10,11-dihydro-5H-dibenzo[b,e][1,4]diazepin-5-yl]propyl}imidodicarbonate 0.121 g (63%) of di-tert-butyl {3-[3-chloro-10-[3-(tetrahydro-2H-pyran-2-yloxy)propyl]-11-oxo-10,11-dihydro-5H-dibenzo[b,e][1,4]diazepin-5-yl]propyl} imidodicarbonate were prepared according to the procedure described for Intermediate 14, Step 2, starting from 0.115 g (0.3 mmol) of 3-chloro-10-[3-(tetrahydro-2H-pyran-2-yloxy)propyl]-5,10-dihydro-11H-dibenzo[b,e][1,4]diazepin-11-one (Intermediate 43, Step 1) and 0.174 g (0.505 mmol) of di-tert-butyl (3-bromopropyl)imidodicarbonate. $^1$H NMR (DMSO-d$_6$), mixture of conformers, δ (ppm): 7.57-7.53 (m, 1H), 7.47-7.43 (m, 1H), 7.28-7.24 (m, 1H), 7.23-7.16 (m, 3H), 7.15-7.11 (m, 1H), 4.57-4.47 (m, 1H), 4.47-4.44 and 4.10-4.05 (2 m, 1H), 3.79-3.48 (m, 7H), 3.48-3.18 (2 m, 2H), 1.88-1.23 (m, 28H); MS (ESI): m/z: 666 [M+Na]$^+$.

Step 2: 5-(3-Aminopropyl)-3-chloro-10-(3-hydroxypropyl)-5,10-dihydro-11H-dibenzo[b,e][1,4]diazepin-11-one 0.040 g (60%) of 5-(3-aminopropyl)-3-chloro-10-(3-hydroxypropyl)-5,10-dihydro-11H-dibenzo[b,e][1,4]diazepin-11-one were prepared according to the procedure described for Intermediate 20, Step 3, starting from 0.118 g (0.183 mmol) of di-tert-butyl {3-[3-chloro-10-[3-(tetrahydro-2H-pyran-2-yloxy)propyl]-11-oxo-10,11-dihydro-5H-dibenzo[b,e][1,4]diazepin-5-yl]propyl} imidodicarbonate and 0.282 ml (3.66 mmol) of TFA. $^1$H NMR (DMSO-d$_6$) δ (ppm): 7.53 (d, J=8.3 Hz, 1H), 7.43 (dd, J=1.7, 8.1 Hz, 1H), 7.28 (dd, J=1.5, 7.8 Hz, 1H), 7.23 (d, J=2.0 Hz, 1H), 7.22-7.13 (m, 2H), 7.11 (dd, J=1.5, 8.3 Hz, 1H), 4.55-4.43 (m, 1H), 3.82-3.60 (m, 3H), 3.42-3.34 (m, 2H), 2.59 (t, J=6.6 Hz, 2H), 1.68-1.47 (m, 4H); MS (ESI): m/z: 360 [M+H]$^+$.

Intermediate 45: 5-(4-Aminobutyl)-7-chloro-10-(2-hydroxyethyl)-5,10-dihydro-11H-dibenzo[b,e][1,4]diazepin-11-one

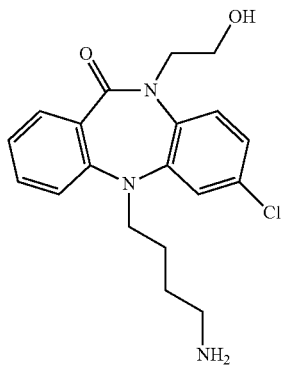 [SMILES: NCCCCN1c2ccccc2C(=O)N(CCO)c2ccc(Cl)cc21]

Step 1: 7-Chloro-10-[2-(tetrahydro-2H-pyran-2-yloxy)ethyl]-5,10-dihydro-11H-dibenzo[b,e][1,4]diazepin-11-one 0.177 g (52%) of 7-chloro-10-[2-(tetrahydro-2H-pyran-2-yloxy)ethyl]-5,10-dihydro-11H-dibenzo[b,e][1,4]diazepin-11-one were prepared according to the procedure described for Intermediate 14, Step 1, starting from 0.224 g (0.915 mmol) of 7-chloro-5,10-dihydro-11H-dibenzo[b,e][1,4]diazepin-11-one (Intermediate 18) and 0.151 ml (0.961 mmol) of 2-(2-bromoethoxy)tetrahydropyran. $^1$H NMR (DMSO-d$_6$), δ (ppm): 7.98 (s, 1H), 7.59 (dd, J=1.0, 7.8 Hz, 1H), 7.52 (d, J=8.8 Hz, 1H), 7.37-7.31 (m, 1H), 7.20 (d, J=2.4 Hz, 1H), 7.12 (dd, J=2.4, 8.3 Hz, 1H), 7.03 (d, J=8.3 Hz, 1H), 7.01-6.96 (m, 1H), 4.55-4.48 (m, 1H), 4.15-4.04 (m, 2H), 3.84-3.75 (m, 1H), 3.66-3.58 (m, 1H), 3.57-3.49 (m, 1H), 3.37-3.34 (m, 1H), 1.65-1.33 (m, 6H); MS (ESI): m/z: 395 [M+Na]$^+$.

Step 2: di-tert-Butyl {4-[7-chloro-10-[2-(tetrahydro-2H-pyran-2-yloxy)ethyl]-11-oxo-10,11-dihydro-5H-dibenzo[b,e][1,4]diazepin-5-yl]butyl}imidodicarbonate 0.140 g (74%) of di-tert-butyl {4-[7-chloro-10-[2-(tetrahydro-2H-pyran-2-yloxy)ethyl]-11-oxo-10,11-dihydro-5H-dibenzo[b,e][1,4]diazepin-5-yl]butyl} imidodicarbonate were prepared according to the procedure described for Intermediate 14, Step 2, starting from 0.110 g (0.295 mmol) of 7-chloro-10-[2-(tetrahydro-2H-pyran-2-yloxy)ethyl]-5,10-dihydro-11H-dibenzo[b,e][1,4]diazepin-11-one and 0.184 g (0.5 mmol) of di-tert-butyl (4-bromobutyl)imidodicarbonate. $^1$H NMR (DMSO-d$_6$), mixture of conformers, δ (ppm): 7.61-7.54 (m, 1H), 7.53-7.49 (m, 1H), 7.45-7.40 (m, 1H), 7.32-7.29 (m, 1H), 7.21-7.15 (m, 2H), 7.11-7.06 (m, 1H), 4.58-4.53 and 4.50-4.45 (2 m, 1H), 4.38-4.25 (m, 1H), 3.99-3.47 (m, 6H), 3.44 (t, J=6.8 Hz, 2H), 3.41-3.34 (m, 1H), 1.64-1.27 (m, 28H); MS (ESI): m/z: 666 [M+Na]$^+$.

Step 3: 5-(4-Aminobutyl)-7-chloro-10-(2-hydroxyethyl)-5,10-dihydro-11H-dibenzo[b,e][1,4]diazepin-11-one 0.060 g (72%) of 5-(4-aminobutyl)-7-chloro-10-(2-hydroxyethyl)-5,10-dihydro-11H-dibenzo[b,e][1,4]diazepin-11-one were prepared according to the procedure described for Intermediate 20, Step 3, starting from 0.149 g (0.23 mmol) of di-tert-butyl {4-[7-chloro-10-[2-(tetrahydro-2H-pyran-2-yloxy)ethyl]-11-oxo-10,11-dihydro-5H-dibenzo[b,e][1,4]diazepin-5-yl]butyl} imidodicarbonate and 0.356 ml (4.62 mmol) of TFA. $^1$H NMR (DMSO-d$_6$) δ (ppm): 7.59 (d, J=8.8 Hz, 1H), 7.51 (dd, J=1.5, 7.3 Hz, 1H), 7.45-7.39 (m, 1H), 7.31 (d, J=2.4 Hz, 1H), 7.20-7.14 (m, 2H), 7.10-7.05 (m, 1H), 4.25-4.16 (m, 1H), 3.85-3.76 (m, 1H), 3.75-3.61 (m, 3H), 3.54-3.46 (m, 1H), 2.48-2.42 (m, 2H), 1.57-1.32 (m, 4H); MS (ESI): m/z: 360 [M+H]$^+$.

Intermediate 46: 5-(4-Aminobutyl)-7-chloro-10-(3-hydroxypropyl)-5,10-dihydro-11H-dibenzo[b,e][1,4]diazepin-11-one

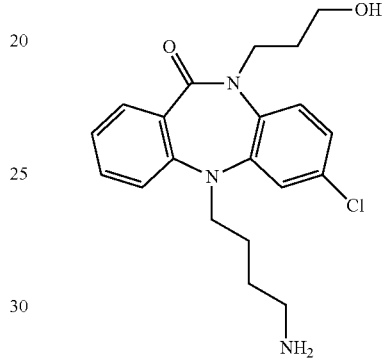

Step 1: 7-Chloro-10-[3-(tetrahydro-2H-pyran-2-yloxy)propyl]-5,10-dihydro-11H-dibenzo[b,e][1,4]diazepin-11-one 0.239 g (66%) of 7-chloro-10-[3-(tetrahydro-2H-pyran-2-yloxy)propyl]-5,10-dihydro-11H-dibenzo[b,e][1,4]diazepin-11-one were prepared according to the procedure described for Intermediate 14, Step 1, starting from 0.23 g (0.94 mmol) of 7-chloro-5,10-dihydro-11H-dibenzo[b,e][1,4]diazepin-11-one (Intermediate 18) and 0.171 ml (0.987 mmol) of 2-(3-bromopropoxy)tetrahydropyran. $^1$H NMR (DMSO-d$_6$), δ (ppm): 8.00 (s, 1H), 7.61 (dd, J=1.5, 7.8 Hz, 1H), 7.40 (d, J=8.8 Hz, 1H), 7.37-7.32 (m, 1H), 7.21 (d, J=2.4 Hz, 1H), 7.12 (dd, J=2.4, 8.8 Hz, 1H), 7.03 (d, J=7.8 Hz, 1H), 7.01-6.96 (m, 1H), 4.31 (bs, 1H), 4.05 (bs, 2H), 3.67-3.53 (m, 2H), 3.31-3.23 (m, 2H), 1.78-1.68 (m, 2H), 1.67-1.58 (m, 1H), 1.50-1.29 (m, 5H); MS (ESI): m/z: 409 [M+Na]$^+$.

Step 2: di-tert-Butyl {4-[7-chloro-10-[3-(tetrahydro-2H-pyran-2-yloxy)propyl]-11-oxo-10,11-dihydro-5H-dibenzo[b,e][1,4]diazepin-5-yl]butyl}imidodicarbonate 0.144 g (74%) of di-tert-butyl {4-[7-chloro-10-[3-(tetrahydro-2H-pyran-2-yloxy)propyl]-11-oxo-10,11-dihydro-5H-dibenzo[b,e][1,4]diazepin-5-yl]butyl} imidodicarbonate were prepared according to the procedure described for Intermediate 14, Step 2, starting from 0.111 g (0.287 mmol) of 7-chloro-10-[3-(tetrahydro-2H-pyran-2-yloxy)propyl]-5,10-dihydro-11H-dibenzo[b,e][1,4]diazepin-11-one and 0.179 g (0.488 mmol) of di-tert-butyl (4-bromobutyl)imidodicarbonate. $^1$H NMR (DMSO-d$_6$), mixture of conformers, δ (ppm): 7.53 (dd, J=1.0, 7.8 Hz, 1H), 7.48-7.40 (m, 2H), 7.33 (dd, J=2.4, 5.4 Hz, 1H), 7.21-7.14 (m, 2H), 7.11-7.06 (m, 1H), 4.56-4.49 (m, 1H), 4.48-4.46 and 4.13-4.07 (2 m, 1H), 3.82-3.60 (m, 4H), 3.59-3.52 and 3.25-3.18 (2 m, 1H), 3.48-3.38 (m, 2H), 3.32-3.26 (m, 2H), 1.86-1.27 (m, 30H); MS (ESI): m/z: 680 [M+Na]⁺.

Step 3: 5-(4-Aminobutyl)-7-chloro-10-(3-hydroxypropyl)-5,10-dihydro-11H-dibenzo[b,e][1,4]diazepin-11-one 0.066 g (74%) of 5-(4-aminobutyl)-7-chloro-10-(3-hydroxypropyl)-5,10-dihydro-11H-dibenzo[b,e][1,4]diazepin-11-one were prepared according to the procedure described for Intermediate 20, Step 3, starting from 0.157 g (0.238 mmol) of di-tert-butyl {4-[7-chloro-10-[3-(tetrahydro-2H-pyran-2-yloxy)propyl]-11-oxo-10,11-dihydro-5H-dibenzo[b,e][1,4]diazepin-5-yl]butyl} imidodicarbonate and 0.367 ml (4.76 mmol) of TFA. ¹H NMR (DMSO-d₆) δ (ppm): 7.50 (dd, J=1.5, 7.8 Hz, 1H), 7.44-7.38 (m, 2H), 7.30 (d, J=2.4 Hz, 1H), 7.19-7.13 (m, 2H), 7.10-7.04 (m, 1H), 4.52-4.42 (m, 1H), 3.69-3.57 (m, 3H), 3.40-3.30 (m, 2H), 2.47-2.41 (m, 2H), 1.69-1.35 (m, 6H); MS (ESI): m/z: 374 [M+H]⁺.

Intermediate 47: 5-(3-Aminopropyl)-7-chloro-10-(3-hydroxypropyl)-5,10-dihydro-11H-dibenzo[b,e][1,4]diazepin-11-one

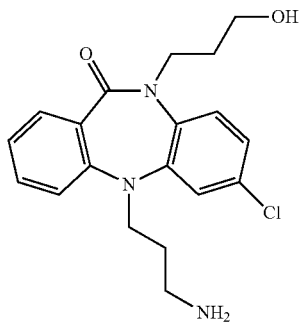 [SMILES: NCCCN1c2ccccc2C(=O)N(CCCO)c2ccc(Cl)cc21]

Step 1: di-tert-Butyl {3-[7-chloro-10-[3-(tetrahydro-2H-pyran-2-yloxy)propyl]-11-oxo-10,11-dihydro-5H-dibenzo[b,e][1,4]diazepin-5-yl]propyl}imidodicarbonate 0.153 g (75%) of di-tert-butyl {3-[7-chloro-10-[3-(tetrahydro-2H-pyran-2-yloxy)propyl]-11-oxo-10,11-dihydro-5H-dibenzo[b,e][1,4]diazepin-5-yl]propyl} imidodicarbonate were prepared according to the procedure described for Intermediate 14, Step 2, starting from 0.123 g (0.318 mmol) of 7-chloro-10-[3-(tetrahydro-2H-pyran-2-yloxy)propyl]-5,10-dihydro-11H-dibenzo[b,e][1,4]diazepin-11-one (Intermediate 46, Step 1) and 0.186 g (0.54 mmol) of di-tert-butyl (3-bromopropyl)imidodicarbonate. ¹H NMR (DMSO-d₆), mixture of conformers, δ (ppm): 7.54 (d, J=7.3 Hz, 1H), 7.49-7.41 (m, 2H), 7.30 (dd, J=2.2, 5.1 Hz, 1H), 7.23-7.13 (m, 2H), 7.13-7.05 (m, 1H), 4.57-4.47 (m, 1H), 4.47-4.44 and 4.10-4.06 (2 m, 1H), 3.80-3.38 (m, 7H), 3.32-3.17 (m, 2H), 1.88-1.23 (m, 28H); MS (ESI): m/z: 666 [M+Na]⁺.

Step 2: 5-(3-Aminopropyl)-7-chloro-10-(3-hydroxypropyl)-5,10-dihydro-11H-dibenzo[b,e][1,4]diazepin-11-one 0.065 g (69%) of 5-(3-aminopropyl)-7-chloro-10-(3-hydroxypropyl)-5,10-dihydro-11H-dibenzo[b,e][1,4]diazepin-11-one were prepared according to the procedure described for Intermediate 20, Step 3, starting from 0.168 g (0.26 mmol) of di-tert-butyl {3-[7-chloro-10-[3-(tetrahydro-2H-pyran-2-yloxy)propyl]-11-oxo-10,11-dihydro-5H-dibenzo[b,e][1,4]diazepin-5-yl]propyl} imidodicarbonate and 0.4 ml (5.2 mmol) of TFA. ¹H NMR (DMSO-d₆) δ (ppm): 7.52 (dd, J=1.5, 7.8 Hz, 1H), 7.48-7.40 (m, 2H), 7.33 (d, J=2.4 Hz, 1H), 7.21-7.15 (m, 2H), 7.11-7.05 (m, 1H), 4.55-4.45 (m, 1H), 3.79-3.68 (m, 2H), 3.68-3.58 (m, 1H), 3.43-3.34 (m, 2H), 2.59 (t, J=6.8 Hz, 2H), 1.69-1.47 (m, 4H); MS (ESI): m/z: 360 [M+H]⁺.

Intermediate 48: 5-(3-Aminopropyl)-7-chloro-10-(2-hydroxyethyl)-5,10-dihydro-11H-dibenzo[b,e][1,4]diazepin-11-one

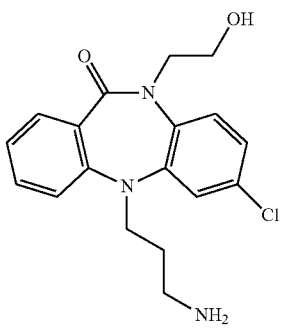 [SMILES: NCCCN1c2ccccc2C(=O)N(CCO)c2ccc(Cl)cc21]

Step 1: di-tert-Butyl {3-[7-chloro-10-[2-(tetrahydro-2H-pyran-2-yloxy)ethyl]-11-oxo-10,11-dihydro-5H-dibenzo[b,e][1,4]diazepin-5-yl]propyl}imidodicarbonate 0.132 g (79%) of di-tert-butyl {3-[7-chloro-10-[2-(tetrahydro-2H-pyran-2-yloxy)ethyl]-11-oxo-10,11-dihydro-5H-dibenzo[b,e][1,4]diazepin-5-yl]propyl} imidodicarbonate were prepared according to the procedure described for Intermediate 14, Step 2, starting from 0.098 g (0.263 mmol) of 7-chloro-10-[2-(tetrahydro-2H-pyran-2-yloxy)ethyl]-5,10-dihydro-11H-dibenzo[b,e][1,4]diazepin-11-one (Intermediate 45, Step 1) and 0.154 g (0.447 mmol) of di-tert-butyl (3-bromopropyl)imidodicarbonate. ¹H NMR (DMSO-d₆), mixture of conformers, δ (ppm): 7.62-7.49 (m, 2H), 7.46-7.41 (m, 1H), 7.31-7.27 (m, 1H), 7.22-7.14 (m, 2H), 7.13-7.06 (m, 1H), 4.59-4.34 (m, 2H), 4.01-3.69 (m, 3H), 3.68-3.59 (m, 2H), 3.58-3.49 (m, 3H), 3.40-3.34 (m, 1H), 1.82-1.66 (m, 2H), 1.60-1.19 (m, 24H); MS (ESI): m/z: 652 [M+Na]⁺.

Step 2: 5-(3-Aminopropyl)-7-chloro-10-(2-hydroxyethyl)-5,10-dihydro-11H-dibenzo[b,e][1,4]diazepin-11-one 0.058 g (72%) of 5-(3-aminobutyl)-7-chloro-10-(2-hydroxyethyl)-5,10-dihydro-11H-dibenzo[b,e][1,4]diazepin-11-one were prepared according to the procedure described for Intermediate 20, Step 3, starting from 0.132 g (0.209 mmol) of di-tert-butyl {3-[7-chloro-10-[2-(tetrahydro-2H-pyran-2-yloxy)ethyl]-11-oxo-10,11-dihydro-5H-dibenzo[b,e][1,4]diazepin-5-yl]propyl} imidodicarbonate and 0.323 ml (4.19 mmol) of TFA. ¹H NMR (DMSO-d₆) δ (ppm): 7.59 (d, J=8.3 Hz, 1H), 7.51 (dd, J=1.7, 7.6 Hz, 1H), 7.45-7.39 (m, 1H), 7.32 (d, J=2.4 Hz, 1H), 7.21-7.14 (m, 2H), 7.12-7.04 (m, 1H), 5.05 (bs, 1H), 4.25-4.13 (m, 1H), 3.83-3.70 (m, 3H), 3.69-3.62 (m, 1H), 3.52-3.44 (m, 1H), 2.57 (t, J=6.6 Hz, 2H), 1.63-1.48 (m, 2H); MS (ESI): m/z: 346 [M+H]$^+$.

Intermediate 49: 5-(4-Aminobutyl)-10-benzyl-3-chloro-5,10-dihydro-11H-dibenzo[b,e][1,4]diazepin-11-one

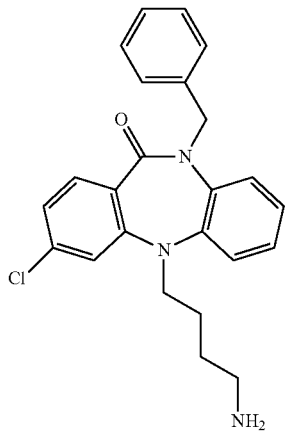 [SMILES: NCCCCN1c2cc(Cl)ccc2C(=O)N(Cc2ccccc2)c2ccccc21]

Step 1: 10-Benzyl-3-chloro-5,10-dihydro-11H-dibenzo[b,e][1,4]diazepin-11-one 0.143 g (85%) of 10-benzyl-3-chloro-5,10-dihydro-11H-dibenzo[b,e][1,4]diazepin-11-one were prepared according to the procedure described for Intermediate 14, Step 1, starting from 0.123 g (0.503 mmol) of 3-chloro-5,10-dihydro-11H-dibenzo[b,e][1,4]diazepin-11-one (prepared according to literature procedure, Synthesis 1985, 1, 550-552) and 0.064 ml (0.528 mmol) of benzyl bromide instead of p-methoxybenzyl chloride. $^1$H NMR (DMSO-d$_6$), δ (ppm): 8.10 (s, 1H), 7.66 (d, J=8.3 Hz, 1H), 7.32 (dd, J=1.5, 7.8 Hz, 1H), 7.30-7.24 (m, 4H), 7.21-7.15 (m, 2H), 7.10 (dd, J=1.5, 7.8 Hz, 1H), 7.07-6.97 (m, 3H), 5.23 (s, 2H); MS (ESI): m/z: 335 [M+H]$^+$.

Step 2: di-tert-Butyl {4-[10-benzyl-3-chloro-11-oxo-10,11-dihydro-5H-dibenzo[b,e][1,4]diazepin-5-yl]butyl}imidodicarbonate 0.103 g (77%) of di-tert-butyl {4-[10-benzyl-3-chloro-11-oxo-10,11-dihydro-5H-dibenzo[b,e][1,4]diazepin-5-yl)butyl}imidodicarbonate were prepared according to the procedure described for Intermediate 14, Step 2, starting from 0.074 g (0.22 mmol) of 10-benzyl-3-chloro-5,10-dihydro-11H-dibenzo[b,e][1,4]diazepin-11-one and 0.138 g (0.376 mmol) of di-tert-butyl (4-bromobutyl)imidodicarbonate (product of Step 1 of Intermediate 15). $^1$H NMR (DMSO-d$_6$), mixture of conformers, δ (ppm): 7.59 (d, J=8.3 Hz, 1H), 7.45 (dd, J=1.5, 7.8 Hz, 1H), 7.28-7.20 (m, 6H), 7.18-7.05 (m, 4H), AB System: ν$_A$=5.62, ν$_B$=4.96, J$_{AB}$=15.9 Hz, 3.85-3.75 (m, 1H), 3.64-3.54 (m, 1H), 3.49-3.41 (m, 2H), 1.63-1.31 (m, 22H); MS (ESI): m/z: 550 [M−56+H]$^+$.

Step 3: 5-(4-Aminobutyl)-10-benzyl-3-chloro-5,10-dihydro-11H-dibenzo[b,e][1,4]diazepin-11-one 0.067 g (98%) of 5-(4-aminobutyl)-10-benzyl-3-chloro-5,10-dihydro-11H-dibenzo[b,e][1,4]diazepin-11-one were prepared according to the procedure described for Intermediate 20, Step 3, starting from 0.102 g (0.168 mmol) of di-tert-butyl {4-[10-benzyl-3-chloro-11-oxo-10,11-dihydro-5H-dibenzo[b,e][1,4]diazepin-5-yl)butyl]}imidodicarbonate and 0.259 ml (3.37 mmol) of TFA. $^1$H NMR (DMSO-d$_6$) δ (ppm): 7.59 (d, J=8.3 Hz, 1H), 7.44 (dd, J=1.5, 7.8 Hz, 1H), 7.30-7.21 (m, 6H), 7.21-7.10 (m, 3H), 7.10-7.03 (m, 1H), AB System: ν$_A$=5.64, ν$_B$=4.98, J$_{AB}$=15.9 Hz, 3.78-3.69 (m, 1H), 3.67-3.55 (m, 1H), 2.55 (t, J=6.8 Hz, 2H), 1.53-1.38 (m, 4H); MS (ESI): m/z: 406 [M+H]$^+$.

Intermediate 50: 3-Chloro-10-methyl-5-[4-(methylamino)butyl]-5,10-dihydro-11H-dibenzo[b,e][1,4]diazepin-11-one

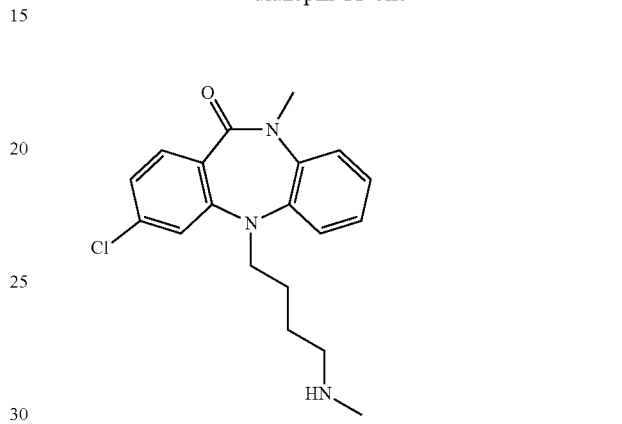

Step 1: tert-Butyl [4-(3-chloro-10-methyl-11-oxo-10,11-dihydro-5H-dibenzo[b,e][1,4]diazepin-5-yl)butyl]methylcarbamate 0.301 g (90%) of tert-butyl [4-(3-chloro-10-methyl-11-oxo-10,11-dihydro-5H-dibenzo[b,e][1,4]diazepin-5-yl)butyl]methylcarbamate were prepared according to the procedure described for Intermediate 2, Step 1, starting from 0.195 g (0.754 mmol) of 3-chloro-10-methyl-5,10-dihydro-11H-dibenzo[b,e][1,4]diazepin-11-one (Intermediate 20, Step 1) and 0.318 g (1.13 mmol) of 4-[tert-butoxycarbonyl(methyl)amino]butyl methanesulfonate (prepared according to literature procedure, J. Med. Chem. 2013, 56, 5819-5828). $^1$H NMR (CDCl$_3$), δ (ppm): 7.70 (d, J=8.3 Hz, 1H), 7.22-7.18 (m, 1H), 7.18-7.09 (m, 3H), 7.03 (dd, J=2.0, 8.3 Hz, 1H), 7.00 (d, J=2.0 Hz, 1H), 3.80-3.70 (m, 1H), 3.70-3.60 (m, 1H), 3.55 (s, 3H), 3.26-3.09 (m, 2H), 2.76 (s, 3H), 1.68-1.52 (m, 4H), 1.44 (bs, 9H); MS (ESI): m/z: 444 [M+H]$^+$.

Step 2: 3-Chloro-10-methyl-5-[4-(methylamino)butyl]-5,10-dihydro-11H-dibenzo[b,e][1,4]diazepin-11-one 0.230 g (99%) of 3-chloro-10-methyl-5-[4-(methylamino)butyl]-5,10-dihydro-11H-dibenzo[b,e][1,4]diazepin-11-one were prepared according to the procedure described for Intermediate 1, Step 2, starting from 0.300 g (0.676 mmol) of tert-butyl [4-(3-chloro-10-methyl-11-oxo-10,11-dihydro-5H-dibenzo[b,e][1,4]diazepin-5-yl)butyl]methylcarbamate and 1.04 ml (13.5 mmol) of TFA. $^1$H NMR (DMSO-d$_6$) δ (ppm): 7.58 (d, J=8.3 Hz, 1H), 7.39 (dd, J=2.0, 7.8 Hz, 1H), 7.30-7.25 (m, 2H), 7.23-7.16 (m, 2H), 7.14 (dd, J=1.7, 8.3 Hz, 1H), 3.79-3.71 (m, 2H), 3.44 (s, 3H), 2.83-2.76 (m, 2H), 2.44 (s, 3H), 1.56 (bs, 4H); MS (ESI): m/z: 344 [M+H]$^+$.

Intermediate 51: 10-Benzyl-3-chloro-5-[4-(methylamino)butyl]-5,10-dihydro-11H-dibenzo[b,e][1,4]diazepin-11-one hydrochloride

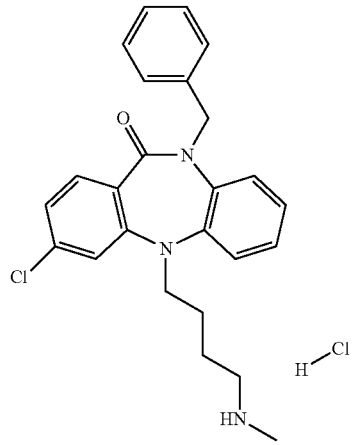 [SMILES: CNCCCCN1c2cc(Cl)ccc2C(=O)N(Cc2ccccc2)c2ccccc21 ; Cl]

Step 1: tert-Butyl [4-(10-benzyl-3-chloro-11-oxo-10,11-dihydro-5H-dibenzo[b,e][1,4]diazepin-5-yl)butyl]methylcarbamate 0.410 g (87%) of tert-butyl [4-(10-benzyl-3-chloro-11-oxo-10,11-dihydro-5H-dibenzo[b,e][1,4]diazepin-5-yl)butyl]methyl-carbamate were prepared according to the procedure described for Intermediate 2, Step 1, starting from 0.303 g (0.95 mmol) of 10-benzyl-3-chloro-5,10-dihydro-11H-dibenzo[b,e][1,4]diazepin-11-one (Intermediate 49, Step 1) and 0.382 g (1.36 mmol) of 4-[tert-butoxycarbonyl(methyl)amino]butyl methanesulfonate (prepared according to literature procedure, J. Med. Chem. 2013, 56, 5819-5828). $^1$H NMR (CDCl$_3$) δ (ppm): 7.71 (d, J=8.3 Hz, 1H), 7.33-7.19 (m, 6H), 7.15-7.02 (m, 4H), 7.00 (d, J=2.0 Hz, 1H), AB System: $v_A$=5.5, $v_B$=5.07, $J_{AB}$=15.2 Hz, 3.69-3.55 (m, 2H), 3.23-3.07 (m, 2H), 2.78 (bs, 3H), 1.55-1.35 (m, 13H); MS (ESI): m/z: 520 [M+H]$^+$.

Step 2: 10-Benzyl-3-chloro-5-[4-(methylamino)butyl]-5,10-dihydro-11H-dibenzo[b,e][1,4]diazepin-11-one hydrochloride A solution of 0.408 g (0.785 mmol) of tert-butyl [4-(10-benzyl-3-chloro-11-oxo-10,11-dihydro-5H-dibenzo[b,e][1,4]diazepin-5-yl)butyl]methyl-carbamate in dry 1,4-dioxane (3 ml) was cooled to 0° C. and treated with 1.96 ml of HCl (4M in 1,4-dioxane, 7.85 mmol). The mixture was warmed to r.t. and stirred for 4 h. The reaction was concentrated in vacuo. The residue was treated with Et$_2$O and concentrated, then the solid was taken up in Et$_2$O and the suspension was stirred for about 30 min and filtered. The filtrate was washed with ether and dried to afford 10-benzyl-3-chloro-5-[4-(methylamino)butyl]-5,10-dihydro-11H-dibenzo[b,e][1,4]diazepin-11-one hydrochloride as a white solid (351 mg, 98%). $^1$H NMR (CD$_3$OD) δ (ppm): 7.64 (d, J=8.3 Hz, 1H), 7.41 (dd, J=1.2, 8.1 Hz, 1H), 7.32-7.09 (m, 10H), AB System: $v_A$=5.59, $v_B$=5.08, $J_{AB}$=15.4 Hz, 3.89-3.81 (m, 1H), 3.66-3.60 (m, 1H), 2.96-2.85 (m, 2H), 2.63 (s, 3H), 1.72-1.54 (m, 4H); MS (ESI): m/z: 420 [M+H]$^+$.

Intermediate 52: 4-(3-Chlorodibenzo[b,e][1,4]oxazepin-5(11H)-yl)-N-methyl-butan-1-amine hydrochloride

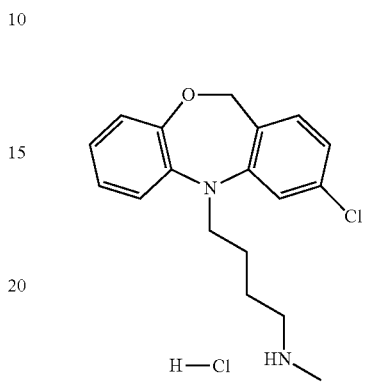

Step 1: tert-Butyl N-[4-(3-chlorodibenzo[b,e][1,4]oxazepin-5(11H)-yl)butyl]-N-methyl-carbamate 0.346 g (89%) of tert-butyl N-[4-(3-chlorodibenzo[b,e][1,4]oxazepin-5(11H)-yl)butyl]-N-methyl-carbamate were prepared according to the procedure described for Intermediate 2, Step 1, starting from 0.227 g (0.931 mmol) of 3-chloro-5,11-dihydro-dibenzo[b,e][1,4]oxazepine (Intermediate 29) and 0.393 mg (1.40 mmol) of 4-[tert-butoxycarbonyl(methyl)amino]butyl methanesulfonate (prepared according to literature procedure, J. Med. Chem. 2013, 56, 5819-5828). $^1$H NMR (CDCl$_3$), δ (ppm): 7.20 (d, J=8.3 Hz, 1H), 7.08 (d, J=1.5 Hz, 1H), 7.05-6.95 (m, 2H), 6.89-6.76 (m, 3H), 5.26 (s, 2H), 3.74 (t, J=6.6 Hz, 2H), 3.17 (bs., 2H), 2.77 (bs., 3H), 1.68-1.51 (m, 4H), 1.49-1.31 (m, 9H); MS (ESI): m/z: 417 [M+H]$^+$.

Step 2: 4-(3-Chlorodibenzo[b,e][1,4]oxazepin-5(11H)-yl)-N-methyl-butan-1-amine hydrochloride A solution of 0.344 g (0.825 mmol) of tert-butyl N-[4-(3-chlorodibenzo[b,e][1,4]oxazepin-5(11H)-yl)butyl]-N-methyl-carbamate in dry 1,4-dioxane (3 ml) was cooled to 0° C. and treated with HCl 4M in 1,4-dioxane (2.01 ml). The mixture was warmed to r.t. and stirred for 5 h. The solution was evaporated, the residue was treated with Et$_2$O and concentrated (×2), then the solid was taken up in Et$_2$O, the mixture stirred for about 15 min and filtered. The solid product was washed with ether and dried to afford 4-(3-chlorodibenzo[b,e][1,4]oxazepin-5(11H)-yl)-N-methyl-butan-1-amine hydrochloride as a. white solid (255 mg, 87.5%). $^1$H NMR (DMSO-d$_6$), δ (ppm): 8.43 (bs., 2H), 7.42 (d, J=8.3 Hz, 1H), 7.29 (d, J=2.0 Hz, 1H), 7.13 (dd, J=2.0, 7.8 Hz, 1H), 7.07 (dd, J=1.5, 7.8 Hz, 1H), 6.87-6.79 (m, 2H), 6.72 (dd, J=2.0, 7.8 Hz, 1H), 5.27 (s, 2H), 3.74 (t, J=5.9 Hz, 2H), 2.80 (t, J=7.1 Hz, 2H), 2.47 (s, 3H), 1.64-1.52 (m, 4H); MS (ESI): m/z: 317 [M+H]$^+$.

Intermediate 53: [5-(4-Amino-butyl)-7-chloro-10,11-dihydro-5H-dibenzo[b,f]azepin-2-yl]-methanol

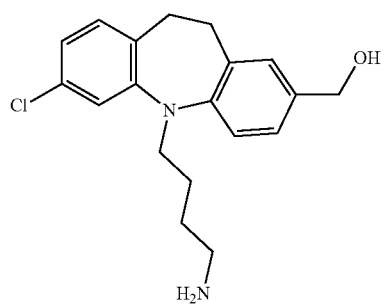 [SMILES: NCCCCN1c2ccc(CO)cc2CCc2ccc(Cl)cc21]

Step 1: 2-[4-(7-Chloro-2-hydroxymethyl-10,11-dihydro-dibenzo[b,f]azepin-5-yl)-butyl]-isoindole-1,3-dione To a solution of 7-Chloro-5-[4-(1,3-dioxo-1,3-dihydro-isoindol-2-yl)-butyl]-10,11-dihydro-5H-dibenzo[b,f]azepine-2-carbaldehyde (Intermediate 34, Step 1, 195 mg, 0.425 mmol) in EtOH (12 ml), NaBH$_4$, 16.1 mg, 0.425 mmol) was added and the mixture was stirred 1 h at r.t. Solvent was evaporated and the crude was purified by silica gel column (hexane/EtOAc 7:3) to give 2-[4-(7-chloro-2-hydroxymethyl-10,11-dihydro-dibenzo[b,f]azepin-5-yl)-butyl]-isoindole-1,3-dione as white solid. (0.151 g, 77%). $^1$H NMR (DMSO-d$_6$), δ (ppm): 7.72-7.87 (m, 4H), 6.91-7.09 (m, 5H), 6.74-6.82 (m, 1H), 5.00 (t, J=5.62 Hz, 1H), 4.31 (d, J=5.60 Hz, 2H), 3.61-3.72 (m, 2H), 3.43-3.52 (m, 2H), 2.90-3.07 (m, 4H), 1.54-1.66 (m, 2H), 1.40-1.50 (m, 2H); MS (ESI): m/z: 461 [M+H]$^+$.

Step 2: [5-(4-Amino-butyl)-7-chloro-10,11-dihydro-5H-dibenzo[b,f]azepin-2-yl]-methanol To a solution of 2-[4-(7-chloro-2-hydroxymethyl-10,11-dihydro-dibenzo[b,f]azepin-5-yl)-butyl]-isoindole-1,3-dione (150 mg, 0.325 mmol) in EtOH (5 ml), hydrazine hydrate 60% (54.4 mg, 0.650 mmol) was added and the mixture was stirred at reflux for 1 h. Solvents were evaporated and the crude was purified by silica gel column (DCM/MeOH/NH$_3$ 9:1:0.05) to give [5-(4-amino-butyl)-7-chloro-10,11-dihydro-5H-dibenzo[b,f]azepin-2-yl]-methanol as colorless glassy solid (70 mg, 65%). $^1$H NMR (DMSO-d$_6$), δ (ppm): 7.03-7.14 (m, 5H), 6.86-6.94 (m, 1H), 5.04 (br. s, 1H), 4.39 (s, 2H), 3.66 (t, J=6.60 Hz, 2H), 2.98-3.11 (m, 4H), 2.48 (s, 2H), 1.28-1.51 (m, 4H); MS (ESI): m/z: 331 [M+H]$^+$.

Intermediate 54: 4-(7-Chloro-2-methoxymethyl-10,11-dihydro-dibenzo[b,f]azepin-5-yl)-butylamine

Step 1: 2-[4-(7-Chloro-2-methoxymethyl-10,11-dihydro-dibenzo[b,f]azepin-5-yl)-butyl]-isoindole-1,3-dione To a solution of 2-[4-(7-chloro-2-hydroxymethyl-10,11-dihydro-dibenzo[b,f]azepin-5-yl)-butyl]-isoindole-1,3-dione (Intermediate 53, Step 1, 60 mg, 0.13 mmol) in MeOH (5 ml), one drop of conc. hydrochloric acid was added and the mixture was stirred at reflux for 20 h. Solvent was evaporated and 2-[4-(7-chloro-2-methoxymethyl-10,11-dihydro-dibenzo[b,f]azepin-5-yl)-butyl]-isoindole-1,3-dione was recovered as pale yellow solid (60 mg, 97%). $^1$H NMR (DMSO-d$_6$), δ (ppm): 7.71-7.89 (m, 4H), 6.90-7.11 (m, 5H), 6.74-6.83 (m, 1H), 4.20 (s, 2H), 3.63-3.75 (m, 2H), 3.42-3.53 (m, 2H), 3.21 (s, 3H), 3.00 (br. s., 4H), 1.55-1.68 (m, 2H), 1.38-1.53 (m, 2H); MS (ESI): m/z: 475 [M+H]$^+$.

Step 2: 4-(7-Chloro-2-methoxymethyl-10,11-dihydro-dibenzo[b,f]azepin-5-yl)-butylamine To a solution of 2-[4-(7-chloro-2-methoxymethyl-10,11-dihydro-dibenzo[b,f]azepin-5-yl)-butyl]-isoindole-1,3-dione (57 mg, 0.12 mmol) in EtOH (5 ml), hydrazine hydrate 60% (12 mg, 0.24 mmol) was added and the mixture was stirred at reflux for 1 h. Solvents were evaporated and the crude was purified by silica gel column (DCM/MeOH/NH$_3$ 9:1:0.05) to give 4-(7-chloro-2-methoxymethyl-10,11-dihydro-dibenzo[b,f]azepin-5-yl)-butylamine as colorless glassy solid (33 mg, 80%). $^1$H NMR (DMSO-d$_6$), δ (ppm): 7.02-7.16 (m, 5H), 6.88-6.97 (m, 1H), 4.29 (s, 2H), 3.66 (t, J=6.85 Hz, 2H), 3.24 (s, 3H), 2.97-3.12 (m, 4H), 2.43 (t, J=6.85 Hz, 2H), 1.41-1.49 (m, 2H), 1.28-1.35 (m, 2H); MS (ESI): m/z: 345 [M+H]$^+$.

Intermediate 55: 4-(7-Chloro-2-methoxyethoxymethyl-10,11-dihydro-dibenzo[b,f]azepin-5-yl)-butylamine

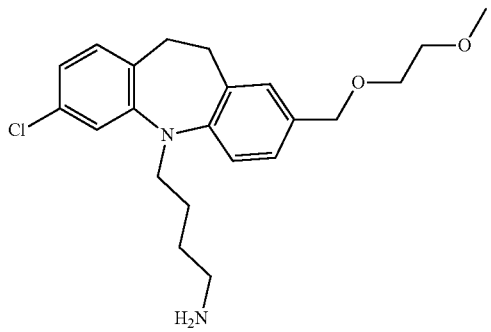 [SMILES: COCCOCc1ccc2c(c1)CCc1ccc(Cl)cc1N2CCCCN]

Step 1: 2-[4-(7-Chloro-2-methoxyethoxymethyl-10,11-dihydro-dibenzo[b,f]azepin-5-yl)-butyl]-isoindole-1,3-dione To a solution of 2-[4-(7-chloro-2-hydroxymethyl-10,11-dihydro-dibenzo[b,f]azepin-5-yl)-butyl]-isoindole-1,3-dione (Intermediate 53, Step 1, 200 mg, 0.434 mmol) in methoxymethyl alcohol (5 ml), one drop of conc. hydrochloric acid was added and the mixture was stirred at reflux for 20 h. Solvent was evaporated and 2-[4-(7-chloro-2-methoxyethoxymethyl-10,11-dihydro-dibenzo[b,f]azepin-5-yl)-butyl]-isoindole-1,3-dione was recovered as pale yellow solid (215 mg, 95%). $^1$H NMR (DMSO-$d_6$), δ (ppm): 7.74-7.87 (m, 4H), 6.93-7.09 (m, 5H), 6.79 (dd, J=2.20, 8.07 Hz, 1H), 4.28 (s, 2H), 3.63-3.72 (m, J=6.40, 6.40 Hz, 2H), 3.39-3.52 (m, 6H), 3.23 (s, 3H), 3.00 (s, 4H), 1.55-1.67 (m, 2H), 1.39-1.51 (m, 2H); MS (ESI): m/z: 520 [M+H]$^+$.

Step 2: 4-(7-Chloro-2-methoxyethoxymethyl-10,11-dihydro-dibenzo[b,f]azepin-5-yl)-butylamine To a solution of 2-[4-(7-chloro-2-methoxyethoxymethyl-10,11-dihydro-dibenzo[b,f]azepin-5-yl)-butyl]-isoindole-1,3-dione (210 mg, 0.405 mmol) in EtOH (10 ml), hydrazine hydrate 60% (67.5 mg, 0.809 mmol) was added and the mixture was stirred at reflux for 1 h. Solvents were evaporated and the crude was purified by silica gel column (DCM/MeOH/NH$_3$ 9:1:0.05) to give 4-(7-chloro-2-methoxyethoxymethyl-10,11-dihydro-dibenzo[b,f]azepin-5-yl)-butylamine as colorless glassy solid (135 mg, 86%). $^1$H NMR (DMSO-$d_6$), δ (ppm): 7.02-7.16 (m, 5H), 6.92 (dd, J=1.96, 8.31 Hz, 1H), 4.37 (s, 2H), 3.67 (t, J=6.60 Hz, 2H), 3.41-3.55 (m, 4H), 3.24 (s, 3H), 2.98-3.11 (m, 4H), 2.41-2.49 (m, 2H), 1.27-1.52 (m, 4H); MS (ESI): m/z: 389 [M+H]$^+$.

Intermediate 56: N-(prop-2-yn-1-yloxy)methanamine hydrochloride

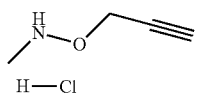

Step 1: tert-Butyl methyl(prop-2-yn-1-yloxy)carbamate 90 mg of NaH (60% oil suspension, 2.24 mmol) was gradually added at 0° C. to a solution of 0.3 g (2.04 mmol) of tert-butyl N-hydroxy-N-methyl-carbamate (prepared according to literature procedure, Org. Lett. 2017, 19(6), 1314-1317) in anhydrous DMF (10 ml) under nitrogen atmosphere. After being stirred at the same temperature for 30 min, 0.25 ml (2.24 mmol) of 3-bromoprop-1-yne were added and the reaction mixture was stirred 1 h at 0° C. followed by 1 h 30' at r.t. The reaction mixture was diluted with ice-water (50 ml) and then extracted with EtOAc (30 ml). The organic phase was dried over Na$_2$SO$_4$ and concentrated under reduced pressure. The residue was taken up with toluene and evaporated. The crude was purified by flash chromatography (eluent: Hexane/EtOAc 85:15) to afford tert-butyl methyl(prop-2-yn-1-yloxy)carbamate a colorless oil (275 mg, 73%). $^1$H NMR (CDCl$_3$) δ (ppm): 4.48 (d, J=2.4 Hz, 2H), 3.18 (s, 3H), 2.49 (t, J=2.2 Hz, 1H), 1.51 (s, 9H).

Step 2: N-(prop-2-yn-1-yloxy)methanamine hydrochloride

A solution of 0.22 g (1.19 mmol) of tert-butyl methyl (prop-2-yn-1-yloxy)carbamate in dry 1,4-dioxane (4.5 ml) was cooled to 0° C. and treated with 3 ml (11.9 mmol) of HCl 4M in 1,4-dioxane. The mixture was warmed to r.t. and stirred overnight. The solution was evaporated, the residue was treated with Et$_2$O and concentrated (×2), then the residue was taken up in Et$_2$O and the mixture stirred for about 1 h. The liquid was decanted off and the residue was dried under vacuum to afford N-(prop-2-yn-1-yloxy)methanamine hydrochloride as a yellow semi-solid (112 mg, 78%) $^1$H NMR (DMSO-$d_6$, D$_2$O) δ (ppm): 4.67 (d, J=2.4 Hz, 2H), 3.75 (t, J=2.4 Hz, 1H), 2.80 (s, 3H).

Intermediate 57: tert-Butyl 4-aminooxypiperidine-1-carboxylate

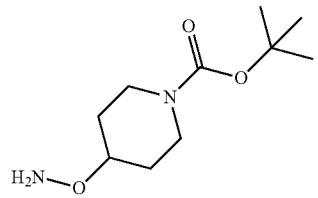

Step 1: tert-Butyl 4-(1,3-dioxoisoindolin-2-yl)oxypiperidine-1-carboxylate

To a stirred solution of 0.5 g (2.43 mmol) of tert-butyl 4-hydroxypiperidine-1-carboxylate, 0.491 g (2.92 mmol) of N-hydroxyphthalimide and 0.839 g (3.17 mmol) of TPP in dried THF (15 ml) was added di-isopropyl azodicarboxylate (0.636 ml, 3.17 mmol) dropwise under nitrogen at 0° C. The solution was stirred for 3 h 30' then allowed to warm up to r.t. The solution was concentrated in vacuo and the crude was purified by flash chromatography (eluent: Hexane-AcOEt from 90:10 to 60:40) to afford tert-butyl 4-(1,3-dioxoisoindolin-2-yl)oxypiperidine-1-carboxylate as a colorless oil that solidified on-standing (704 mg, 83.5%). $^1$H NMR (DMSO-d$_6$) δ (ppm): 7.93-7.79 (m, 4H), 4.45-4.29 (m, 1H), 3.77-3.63 (m, 2H), 3.18-3.02 (m, 2H), 1.95-1.84 (m, 2H), 1.66-1.52 (m, 2H), 1.40 (s, 9H); MS (ESI): m/z: 291 [M+H-56]$^+$.

Step 2: tert-Butyl 4-aminooxypiperidine-1-carboxylate

To a suspension of 0.56 g (1.62 mmol) of tert-butyl 4-(1,3-dioxoisoindolin-2-yl)oxypiperidine-1-carboxylate in MeOH (5.6 ml), hydrazine hydrate (0.118 ml, 2.43 mmol) was added and the mixture was stirred at r.t. for 1 h. The mixture filtered and the filter cake was washed with DCM. The filtrate was concentrated under vacuum and the crude was purified flash chromatography (eluent: DCM-MeOH from 100:1 to 97:3) to afford tert-butyl 4-aminooxypiperidine-1-carboxylate as a colorless oil that solidified on standing (276 mg, 79%). $^1$H NMR (DMSO-d$_6$) δ (ppm): 5.86 (s, 2H), 3.65-3.43 (m, 3H), 3.08-2.91 (m, 2H), 1.81-1.69 (m, 2H), 1.44-1.26 (m, 11H).

Intermediate 58: 5-(4-Aminobutyl)-3-chloro-10-[2-(2-methoxyethoxy)ethyl]-5,10-dihydro-11H-dibenzo[b,e][1,4]diazepin-11-one

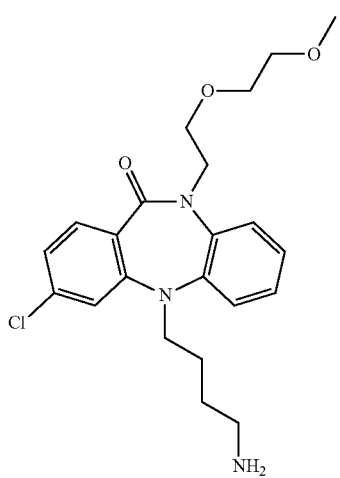 [SMILES: COCCOCCN1C(=O)c2ccc(Cl)cc2N(CCCCN)c2ccccc21]

Step 1: 3-Chloro-10-[2-(2-methoxyethoxy)ethyl]-5,10-dihydro-11H-dibenzo[b,e][1,4]diazepin-11-one 0.111 g (76%) of 3-chloro-10-[2-(2-methoxyethoxy)ethyl]-5,10-dihydro-11H-dibenzo[b,e][1,4]diazepin-11-one were prepared according to the procedure described for Intermediate 14, Step 1, starting from 0.103 g (0.42 mmol) of 3-chloro-5,10-dihydro-11H-dibenzo[b,e][1,4]diazepin-11-one (prepared according to literature procedure, Synthesis 1985, 1, 550-552) and 0.063 ml (0.442 mmol) of 1-bromo-2-(2-methoxyethoxy)ethane. $^1$H NMR (DMSO-d$_6$), δ (ppm): 8.03 (s, 1H), 7.60 (d, J=8.3 Hz, 1H), 7.53-7.45 (m, 1H), 7.13 (d, J=2.0 Hz, 1H), 7.12-7.06 (m, 3H), 7.00 (dd, J=2.0, 8.3 Hz, 1H), 4.05 (t, J=5.9 Hz, 2H), 3.60 (t, J=5.9 Hz, 2H), 3.49-3.44 (m, 2H), 3.39-3.35 (m, 2H), 3.19 (s, 3H); MS (ESI): m/z: 347 [M+H]$^+$.

Step 2: di-tert-Butyl {4-[3-chloro-10-[2-(2-methoxyethoxy)ethyl]-11-oxo-10,11-dihydro-5H-dibenzo[b,e][1,4]diazepin-5-yl]butyl}imidodicarbonate 0.154 g (79%) of di-tert-butyl {4-[3-chloro-10-[2-(2-methoxyethoxy)ethyl]-11-oxo-10,11-dihydro-5H-dibenzo[b,e][1,4]diazepin-5-yl]butyl} imidodicarbonate were prepared according to the procedure described for Intermediate 14, Step 2, starting from 0.109 g (0.314 mmol) of 3-chloro-10-[2-(2-methoxyethoxy)ethyl]-5,10-dihydro-11H-dibenzo[b,e][1,4]diazepin-11-one and 0.196 g (0.534 mmol) of di-tert-butyl (4-bromobutyl)imidodicarbonate. $^1$H NMR (DMSO-d$_6$), mixture of conformers, δ (ppm): 7.57-7.47 (m, 2H), 7.26 (dd, J=1.5, 7.8 Hz, 1H), 7.22 (d, J=2.0 Hz, 1H), 7.21-7.09 (m, 3H), 4.37-4.25 (m, 1H), 3.94-3.85 (m, 1H), 3.76-3.61 (m, 3H), 3.55-3.41 (m, 5H), 3.37-3.33 (m, 2H), 3.18 (s, 3H), 1.61-1.42 (m, 4H), 1.37 (s, 18H); MS (ESI): m/z: 562 [M−56+H]$^+$.

Step 3: 5-(4-Aminobutyl)-3-chloro-10-[2-(2-methoxyethoxy)ethyl]-5,10-dihydro-11H-dibenzo[b,e][1,4]diazepin-11-one 0.102 g (99%) of 5-(4-aminobutyl)-3-chloro-10-[2-(2-methoxyethoxy)ethyl]-5,10-dihydro-11H-dibenzo[b,e][1,4]diazepin-11-one were prepared according to the procedure described for Intermediate 20, Step 3, starting from 0.152 g (0.246 mmol) of di-tert-butyl {4-[3-chloro-10-[2-(2-methoxyethoxy)ethyl]-11-oxo-10,11-dihydro-5H-dibenzo[b,e][1,4]diazepin-5-yl]butyl} imidodicarbonate and 0.379 ml (4.92 mmol) of TFA. $^1$H NMR (DMSO-de, D$_2$O) δ (ppm): 7.58-7.45 (m, 2H), 7.28-7.24 (m, 2H), 7.23-7.10 (m, 4H), 4.40-4.27 (m, 1H), 3.95-3.85 (m, 1H), 3.68 (bs, 2H), 3.57-3.49 (m, 1H), 3.49-3.38 (m, 2H), 3.32 (t, J=4.7 Hz, 2H), 3.16 (s, 3H), 2.67-2.58 (m, 2H), 1.59-1.46 (m, 4H); MS (ESI): m/z: 418 [M+H]$^+$.

Intermediate 59: 5-(4-Aminobutyl)-3-chloro-10-[2-[2-(2-methoxyethoxy)ethoxy]ethyl]-5,10-dihydro-11H-dibenzo[b,e][1,4]diazepin-11-one

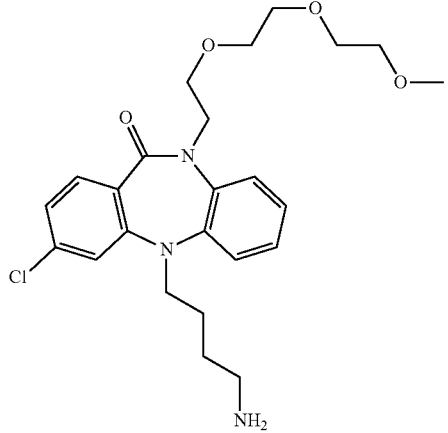 [SMILES: COCCOCCOCCN1C(=O)c2ccc(Cl)cc2N(CCCCN)c2ccccc21]

Step 1: 3-Chloro-10-[2-[2-(2-methoxyethoxy)ethoxy]ethyl]-5,10-dihydro-11H-dibenzo[b,e][1,4]diazepin-11-one 0.122 g (74%) of 3-chloro-10-[2-[2-(2-methoxyethoxy)ethoxy]ethyl]-5,10-dihydro-11H-dibenzo[b,e][1,4]diazepin-11-one were prepared according to the procedure described for Intermediate 14, Step 1, starting from 0.103 g (0.42 mmol) of 3-chloro-5,10-dihydro-11H-dibenzo[b,e][1,4]diazepin-11-one (prepared according to literature procedure, Synthesis 1985, 1, 550-552) and 0.103 mg (0.442 mmol) of 1-bromo-2-[2-(2-methoxyethoxy)ethoxy]ethane. $^1$H NMR (DMSO-d$_6$), δ (ppm): 8.01 (s, 1H), 7.60 (d, J=8.3 Hz, 1H), 7.53-7.46 (m, 1H), 7.13 (d, J=2.0 Hz, 1H), 7.12-7.06 (m, 3H), 7.00 (dd, J=2.0, 8.3 Hz, 1H), 4.05 (t, J=5.9 Hz, 2H), 3.61 (t, J=5.9 Hz, 2H), 3.50-3.41 (m, 6H), 3.39-3.35 (m, 2H), 3.19 (s, 3H); MS (ESI): m/z: 391 [M+H]$^+$.

Step 2: di-tert-Butyl {4-[3-chloro-10-[2-[2-(2-methoxyethoxy)ethoxy]ethyl]-11-oxo-10,11-dihydro-5H-dibenzo[b,e][1,4]diazepin-5-yl]butyl}imidodicarbonate 0.175 g (85%) of di-tert-butyl {4-[3-chloro-10-[2-[2-(2-methoxyethoxy)ethoxy]ethyl]-11-oxo-10,11-dihydro-5H-dibenzo[b,e][1,4]diazepin-5-yl]butyl} imidodicarbonate were prepared according to the procedure described for Intermediate 14, Step 2, starting from 0.121 g (0.31 mmol) of 3-chloro-10-[2-[2-(2-methoxyethoxy)ethoxy]ethyl]-5,10-dihydro-11H-dibenzo[b,e][1,4]diazepin-11-one and 0.193 g (0.526 mmol) of di-tert-butyl (4-bromobutyl)imidodicarbonate. $^1$H NMR (DMSO-d$_6$), mixture of conformers, δ (ppm): 7.56-7.50 (m, 2H), 7.25 (dd, J=1.5, 7.8 Hz, 1H), 7.22 (d, J=2.0 Hz, 1H), 7.21-7.10 (m, 3H), 4.35-4.22 (m, 1H), 3.95-3.86 (m, 1H), 3.74-3.62 (m, 3H), 3.56-3.49 (m, 1H), 3.48-3.40 (m, 8H), 3.39-3.35 (m, 2H), 3.19 (s, 3H), 1.60-1.42 (m, 4H), 1.37 (s, 18H); MS (ESI): m/z: 684 [M+Na]$^+$.

Step 3: 5-(4-Aminobutyl)-3-chloro-10-[2-[2-(2-methoxyethoxy)ethoxy]ethyl]-5,10-dihydro-11H-dibenzo[b,e][1,4]diazepin-11-one 0.100 g (84%) of 5-(4-aminobutyl)-3-chloro-10-[2-[2-(2-methoxyethoxy)ethoxy]ethyl]-5,10-dihydro-11H-dibenzo[b,e][1,4]diazepin-11-one were prepared according to the procedure described for Intermediate 20, Step 3, starting from 0.170 g (0.257 mmol) of di-tert-butyl {4-[3-chloro-10-[2-[2-(2-methoxyethoxy)ethoxy]ethyl]-11-oxo-10,11-dihydro-5H-dibenzo[b,e][1,4]diazepin-5-yl]butyl} imidodicarbonate and 0.396 ml (5.13 mmol) of TFA. $^1$H NMR (DMSO-d$_6$) δ (ppm): 7.58-7.47 (m, 2H), 7.29-7.24 (m, 1H), 7.23 (d, J=2.0 Hz, 1H), 7.21-7.09 (m, 3H), 4.39-4.29 (m, 1H), 3.96-3.87 (m, 1H), 3.73-3.60 (m, 3H), 3.56-3.49 (m, 1H), 3.49-3.41 (m, 6H), 3.39-3.35 (m, 2H), 3.20 (s, 3H), 2.49-2.46 (m, 2H), 1.61-1.34 (m, 4H); MS (ESI): m/z: 462 [M+H]$^+$.

Intermediate 60: 2-prop-2-ynoxyethyl 4-methylbenzenesulfonate

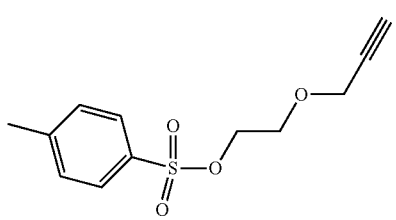 [SMILES: C#CCOCCOS(=O)(=O)c1ccc(C)cc1]

A solution of 1.16 ml (10.83 mmol) of propynol ethoxylate in dry pyridine (2.2 ml) was added dropwise to a solution of 4.13 g (21.66 mmol) of tosyl chloride in dry pyridine (4.4 ml) cooled to 0° C. After stirring at this temperature for 2 h a precipitate was noticed. The reaction was left at 0° C. for further 1 h, then it was quenched with water and extracted with DCM. The organic layer was washed first with 2N HCl then with sat NaHCO$_3$ and finally with brine, then dried over Na$_2$SO$_4$, filtered and evaporated. The crude was purified by flash chromatography (eluent: hexane/EtOAc, from 100:0 to 50:50) to afford 2-prop-2-ynoxyethyl 4-methylbenzenesulfonate as a colorless oil (1.731 g, 62%). $^1$H NMR (CDCl$_3$), δ (ppm): 7.84-7.79 (m, 2H), 7.38-7.33 (m, 2H), 4.23-4.18 (m, 2H), 4.13 (d, J=2.4 Hz, 2H), 3.77-3.71 (m, 2H), 2.46 (s, 3H), 2.43 (t, J=2.4 Hz, 1H); MS (ESI): m/z: 277 [M+Na]$^+$.

Intermediate 61: 5-(4-Aminobutyl)-3-chloro-10-[2-(prop-2-yn-1-yloxy)ethyl]-5,10-dihydro-11H-dibenzo[b,e][1,4]diazepin-11-one

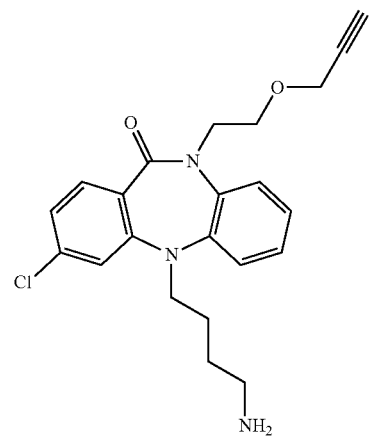 [SMILES: C#CCOCCN1C(=O)c2ccc(Cl)cc2N(CCCCN)c2ccccc21]

Step 1: 3-Chloro-10-[2-(prop-2-yn-1-yloxy)ethyl]-5,10-dihydro-11H-dibenzo[b,e][1,4]diazepin-11-one 0.126 g (76%) of 3-chloro-10-[2-(prop-2-yn-1-yloxy)ethyl]-5,10-dihydro-11H-dibenzo[b,e][1,4]diazepin-11-one were prepared according to the procedure described for Intermediate 14, Step 1, starting from 0.123 g (0.503 mmol) of 3-chloro-5,10-dihydro-11H-dibenzo[b,e][1,4]diazepin-11-one (prepared according to literature procedure, *Synthesis* 1985, 1, 550-552) and 0.134 mg (0.528 mmol) of 2-prop-2-ynoxyethyl 4-methylbenzenesulfonate (Intermediate 60). $^1$H NMR (DMSO-d$_6$), δ (ppm): 8.02 (s, 1H), 7.61 (d, J=8.3 Hz, 1H), 7.47-7.42 (m, 1H), 7.16-7.07 (m, 4H), 7.00 (dd, J=2.0, 8.3 Hz, 1H), 4.11 (d, J=2.4 Hz, 2H), 4.08 (t, J=5.9 Hz, 2H), 3.64 (t, J=5.9 Hz, 2H), 3.39 (t, J=2.4 Hz, 1H); MS (ESI): m/z: 327 [M+H]$^+$.

Step 2: di-tert-Butyl {4-[3-chloro-10-[2-(prop-2-yn-1-yloxy)ethyl]-11-oxo-10,11-dihydro-5H-dibenzo[b,e][1,4]diazepin-5-yl]butyl}imidodicarbonate 0.171 g (75%) of di-tert-butyl {4-[3-chloro-10-[2-(prop-2-yn-1-yloxy)ethyl]-11-oxo-10,11-dihydro-5H-dibenzo[b,e][1,4]diazepin-5-yl]butyl}imidodicarbonate were prepared according to the procedure described for Intermediate 14, Step 2, starting from 0.124 g (0.379 mmol) of 3-chloro-10-[2-(prop-2-yn-1-yloxy)ethyl]-5,10-dihydro-11H-dibenzo[b,e][1,4]diazepin-11-one and 0.237 g (0.645 mmol) of di-tert-butyl (4-bromobutyl)imidodicarbonate. $^1$H NMR (DMSO-d$_6$), mixture of conformers, δ (ppm): 7.53 (d, J=8.3 Hz, 1H), 7.49 (dd, J=1.5, 7.8 Hz, 1H), 7.28-7.24 (m, 1H), 7.23-7.09 (m, 4H), 4.42-4.32 (m, 1H), 4.07 (d, J=2.4 Hz, 2H), 3.94-

3.87 (m, 1H), 3.74-3.54 (m, 4H), 3.47-3.41 (m, 2H), 3.36 (t, J=2.4 Hz, 1H), 1.60-1.44 (m, 4H), 1.37 (s, 18H); MS (ESI): m/z: 542 [M−56+H]⁺.

Step 3: 5-(4-Aminobutyl)-3-chloro-10-[2-(prop-2-yn-1-yloxy)ethyl]-5,10-dihydro-11H-dibenzo[b,e][1,4]diazepin-11-one 0.097 g (87%) of 5-(4-aminobutyl)-3-chloro-10-[2-(prop-2-yn-1-yloxy)ethyl]-5,10-dihydro-11H-dibenzo[b,e][1,4]diazepin-11-one were prepared according to the procedure described for Intermediate 20, Step 3, starting from 0.167 g (0.279 mmol) of di-tert-butyl {4-[3-chloro-10-[2-(prop-2-yn-1-yloxy)ethyl]-11-oxo-10,11-dihydro-5H-dibenzo[b,e][1,4]diazepin-5-yl]butyl}imidodicarbonate and 0.430 ml (5.58 mmol) of TFA. ¹H NMR (DMSO-d₆, D₂O) δ (ppm): 7.50 (d, J=8.3 Hz, 1H), 7.45 (d, J=7.8 Hz, 1H), 7.27-7.23 (m, 1H), 7.21-7.12 (m, 3H), 7.10 (dd, J=1.5, 8.3 Hz, 1H), 4.48-4.37 (m, 1H), 4.05 (d, J=2.4 Hz, 2H), 3.90-3.83 (m, 1H), 3.71-3.51 (m, 4H), 3.28 (t, J=2.4 Hz, 1H), 2.45 (t, J=6.8 Hz, 2H), 1.55-1.32 (m, 4H); MS (ESI): m/z: 398 [M+H]⁺.

Intermediate 62: 4-[7-Chloro-2-(2-prop-2-ynoxyethoxy)-10,11-dihydro-5H-dibenzo[b,f]azepin-5-yl]-N-methyl-butan-1-amine hydrochloride

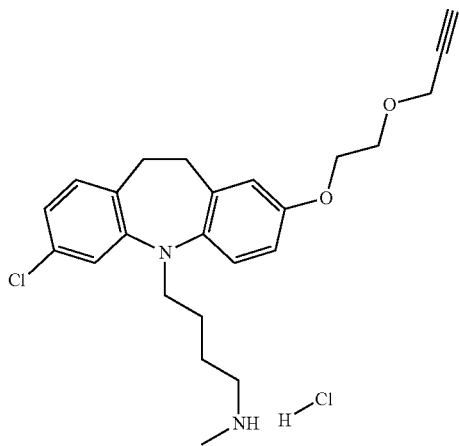

Step 1: 2-{4-(7-Chloro-2-[2-(prop-2-yn-1-yloxy)ethoxy]-10,11-dihydro-5H-dibenzo[b,f]azepin-5-yl)butyl}-1H-isoindole-1,3(2H)-dione To a solution of 0.305 g (0.682 mmol) of 2-[4-(7-chloro-2-hydroxy-10,11-dihydro-dibenzo[b,f]azepin-5-yl)-butyl]-isoindole-1,3-dione (Example 67, Step 1) in dry DMF (3 ml), potassium carbonate (0.189 g, 1.364 mmol) was added. The mixture was stirred 30 min at r.t. becoming blue. Afterwards 0.226 g (0.887 mmol) of 2-prop-2-ynoxyethyl 4-methylbenzenesulfonate (Intermediate 60) dissolved in dry DMF (1 mL) were added. The reaction was then heated to 75° C. and stirred overnight. The reaction was quenched with water and extracted with EtOAc. The organic phases were treated with Na₂SO₄, filtered and then evaporated to dryness. The crude was purified by flash chromatography (eluent: hexane/EtOAc 85:15) affording 2-{4-(7-chloro-2-[2-(prop-2-yn-1-yloxy)ethoxy]-10,11-dihydro-5H-dibenzo[b,f]azepin-5-yl)butyl}-1H-isoindole-1,3(2H)-dione as yellow solid (0.293 g, 81%). ¹H NMR (DMSO-d₆) δ (ppm): 7.86-7.75 (m, 4H), 7.00-6.96 (m, 2H), 6.94 (d, J=7.8 Hz, 1H), 6.76 (dd, J=2.0, 8.3 Hz, 1H), 6.64-6.59 (m, 2H), 4.19 (d, J=2.4 Hz, 2H), 3.98-3.93 (m, 2H), 3.74-3.68 (m, 2H), 3.62 (t, J=6.1 Hz, 2H), 3.52-3.43 (m, 3H), 2.97 (bs, 4H), 1.64-1.55 (m, 2H), 1.48-1.38 (m, 2H); MS (ESI): m/z: 529 [M+H]⁺.

Step 2: 4-{7-Chloro-2-[2-(prop-2-ynyloxy)ethoxy]-10,11-dihydro-5H-dibenzo[b,f]azepin-5-yl}butan-1-amine A mixture of 0.292 g (0.552 mmol) of 2-{4-(7-chloro-2-[2-(prop-2-yn-1-yloxy)ethoxy]-10,11-dihydro-5H-dibenzo[b,f]azepin-5-yl)butyl}-1H-isoindole-1,3(2H)-dione and 1.374 ml (11.04 mmol) of methylamine (33% in EtOH) in absolute EtOH (0.5 ml) was heated to 65° C. and stirred for 2 h. The reaction was concentrated to dryness and the crude was purified by flash chromatography (eluent: DCM/MeOH/NH₃aq 90:10:1) affording 4-{7-chloro-2-[2-(prop-2-ynyloxy)ethoxy]-10,11-dihydro-5H-dibenzo[b,f]azepin-5-yl}butan-1-amine as yellow oil (0.173 g, 78%). ¹H NMR (DMSO-d₆) δ (ppm): 7.08-7.01 (m, 3H), 6.86 (dd, J=2.0, 8.3 Hz, 1H), 6.77 (d, J=2.9 Hz, 1H), 6.72 (dd, J=2.9, 8.8 Hz, 1H), 4.19 (d, J=2.4 Hz, 2H), 4.07-4.02 (m, 2H), 3.76-3.70 (m, 2H), 3.61 (t, J=6.8 Hz, 2H), 3.45 (t, J=2.4 Hz, 1H), 3.06-2.96 (m, 4H), 2.44 (t, J=7.1 Hz, 2H), 1.49-1.38 (m, 2H), 1.36-1.26 (m, 2H); MS (ESI): m/z: 399 [M+H]⁺.

Step 3: tert-Butyl N-{4-[7-chloro-2-(2-prop-2-ynoxyethoxy)-10,11-dihydro-5H-dibenzo[b,f]azepin-5-yl]butyl}carbamate To a stirred solution of 0.171 g (0.429 mmol) of 4-{7-chloro-2-[2-(prop-2-ynyloxy)ethoxy]-10,11-dihydro-5H-dibenzo[b,f]azepin-5-yl}butan-1-amine in dry THF (1 ml) were added 0.12 ml (0.857 mmol) of TEA and the solution was cooled to 0° C. 0.112 g (0.514 mmol) of di-tert-butyl dicarbonate were added in one portion and the suspension warmed to r.t. and stirred overnight. THF was removed by evaporation and the slurry was taken up into EtOAc, the solution was washed with water, brine, dried over Na₂SO₄ and then concentrated. The crude was purified by flash chromatography (eluent: hexane/EtOAc 85:15) to afford tert-butyl N-{4-[7-chloro-2-(2-prop-2-ynoxyethoxy)-10,11-dihydro-5H-dibenzo[b,f]azepin-5-yl]butyl}carbamate as colorless oil (0.188 g, 88%). ¹H NMR (DMSO-d₆) δ (ppm): 7.08-7.01 (m, 3H), 6.86 (dd, J=2.0, 7.8 Hz, 1H), 6.76 (d, J=2.9 Hz, 1H), 6.75-6.69 (m, 2H), 4.19 (d, J=2.4 Hz, 2H), 4.06-4.03 (m, 2H), 3.75-3.71 (m, 2H), 3.60 (t, J=6.4 Hz, 2H), 3.45 (t, J=2.4 Hz, 1H), 3.01 (bs, 4H), 2.85-2.78 (m, 2H), 1.43-1.26 (m, 13H); MS (ESI): m/z: 499 [M+H]⁺.

Step 4: tert-Butyl N-{4-[7-chloro-2-[2-(prop-2-ynyloxy)ethoxy]-10,11-dihydro-5H-dibenzo[b,f]azepin-5-yl]butyl}-N-methyl-carbamate 0.187 g (0.375 mmol) of tert-butyl N-{4-[7-chloro-2-(2-prop-2-ynoxyethoxy)-10,11-dihydro-5H-dibenzo[b,f]azepin-5-yl]butyl}carbamate were dissolved in dry DMA (1.5 ml). The solution was cooled to 0° C. and treated with 0.037 g of NaH (60% oil suspension, 0.937 mmol). The mixture was warmed to r.t., stirred for 1 h, then cooled to 0° C. and treated with 0.466 ml (7.49 mmol) of methyl iodide. The mixture was warmed to r.t. and stirred for 1 h. The reaction was quenched with brine, extracted with EtOAc. The organic phase was dried (Na₂SO₄) and the solvent evaporated. The crude product was purified by flash chromatography (eluent: hexane/EtOAc 83:17) to afford tert-butyl N-{4-[7-chloro-2-[2-(prop-2-ynyloxy)ethoxy]-10,11-dihydro-5H-dibenzo[b,f]azepin-5-yl]butyl}-N-methyl-carbamate as colorless oil (0.154 g, 80%). $^1$H NMR (DMSO-d$_6$) δ (ppm): 7.08-7.01 (m, 3H), 6.87 (dd, J=2.2, 8.1 Hz, 1H), 6.77 (d, J=2.9 Hz, 1H), 6.72 (dd, J=2.9, 8.8 Hz, 1H), 4.19 (d, J=2.4 Hz, 2H), 4.06-4.03 (m, 2H), 3.76-3.71 (m, 2H), 3.63 (t, J=6.6 Hz, 2H), 3.46 (t, J=2.4 Hz, 1H), 3.07 (t, J=6.8 Hz, 2H), 3.01 (bs, 4H), 2.64 (s, 3H), 1.48-1.19 (m, 13H); MS (ESI): m/z: 513 [M+H]$^+$.

Step 5: 4-[7-chloro-2-(2-prop-2-ynoxyethoxy)-10,11-dihydro-5H-dibenzo[b,f]azepin-5-yl]-N-methyl-butan-1-amine hydrochloride A solution of 0.152 g (0.296 mmol) of tert-butyl N-{4-[7-chloro-2-[2-(prop-2-ynyloxy)ethoxy]-10,11-dihydro-5H-dibenzo[b,f]azepin-5-yl]butyl}-N-methyl-carbamate in dry 1,4-dioxane (1.1 ml) was cooled to 0° C. and treated with 0.74 ml of HCl (4M in 1,4-dioxane, 2.962 mmol).

The mixture was warmed to r.t. and stirred for 2.5 h. The reaction was concentrated in vacuo. The residue was treated with Et$_2$O and concentrated, then the solid was taken up in Et$_2$O and the suspension was stirred for about 30 min and filtered. The filtrate was washed with ether and dried to afford 4-[7-chloro-2-(2-prop-2-ynoxyethoxy)-10,11-dihydro-5H-dibenzo[b,f]azepin-5-yl]-N-methyl-butan-1-amine hydrochloride as off-white solid (123 mg, 92%). $^1$H NMR (DMSO-d$_6$) δ (ppm): 8.53 (bs, 2H), 7.11-7.02 (m, 3H), 6.89 (dd, J=2.2, 8.1 Hz, 1H), 6.78 (d, J=2.9 Hz, 1H), 6.74 (dd, J=2.9, 8.8 Hz, 1H), 4.19 (d, J=2.4 Hz, 2H), 4.08-4.02 (m, 2H), 3.77-3.70 (m, 2H), 3.65 (t, J=6.6 Hz, 2H), 3.46 (t, J=2.4 Hz, 1H), 3.10-2.97 (m, 4H), 2.78 (bs, 2H), 2.46 (bs, 3H), 1.62-1.53 (m, 2H), 1.51-1.43 (m, 2H); MS (ESI): m/z: 413 [M+H]$^+$.

Intermediate 63: 2-[2-(2-{2-[5-((3aS,4S,6aR)-2-Oxo-hexahydro-thieno[3,4-d]imidazol-4-yl)pentanoylamino]-ethoxy}-ethoxy)-ethoxy]-ethyl methanesulfonate

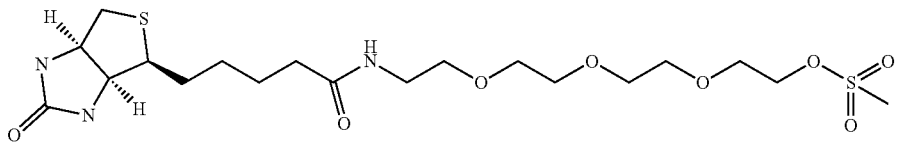 [SMILES: CS(=O)(=O)OCCOCCOCCOCCNC(=O)CCCC[C@@H]1SC[C@@H]2NC(=O)N[C@@H]21]

0.301 g (0.717 mmol) of biotin-PEG4-alcohol (BROADPHARM, Cat. No. BP-20650) were dissolved in dry pyridine and mesyl chloride (0.067 ml, 0.861 mmol) was added at 0° C. The reaction mixture was slowly warmed to r.t. in a 1 h period. Volatiles were removed under vacuum and the crude was purified by flash chromatography (silica gel-NH$_2$, eluent: DCM/MeOH, 98:2) to afford 2-[2-(2-{2-[5-((3aS,4S,6aR)-2-Oxo-hexahydro-thieno[3,4-d]imidazol-4-yl)pentanoylamino]-ethoxy}-ethoxy)-ethoxy]-ethyl methanesulfonate as white amorphous solid (0.265 g, 74%). $^1$H NMR (CDCl$_3$) δ (ppm): 6.46 (br. s., 1H), 5.96-5.81 (bs, 1H), 5.22-4.84 (bs, 1H), 4.56-4.51 (m, 1H), 4.45-4.38 (m, 2H), 4.37-4.33 (m, 1H), 3.82-3.54 (m, 12H), 3.49-3.42 (m, 2H), 3.21-3.14 (m, 1H), 3.10 (s, 3H), 2.94 (dd, J=4.9, 13.2 Hz, 1H), 2.75 (d, J=13.2 Hz, 1H), 2.30-2.20 (m, 2H), 1.81-1.61 (m, 4H), 1.53-1.41 (m, 2H); MS (ESI): m/z: 498 [M+H]$^+$.

Intermediate 64: 2-[2-[2-[2-[2-[2-[5-[(3aS,4S,6aR)-2-Oxo-hexahydrothieno[3,4-d]imidazol-4-yl]pentanoylamino]ethoxy]ethoxy]ethoxy]ethoxy]ethoxy]ethyl methanesulfonate

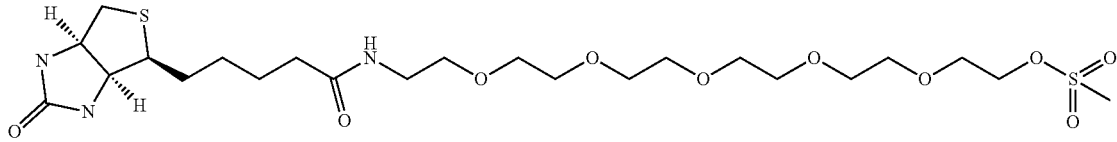 [SMILES: CS(=O)(=O)OCCOCCOCCOCCOCCOCCNC(=O)CCCC[C@@H]1SC[C@@H]2NC(=O)N[C@@H]21]

0.078 g (68%) of 2-[2-[2-[2-[2-[2-[5-[(3aS,4S,6aR)-2-Oxo-hexahydrothieno[3,4-d]imidazol-4-yl]pentanoylamino]ethoxy]ethoxy]ethoxy]ethoxy]ethoxy]ethyl methanesulfonate were prepared according to the procedure described for Intermediate 63, starting from 0.100 g (0.197 mmol) of biotin-PEG6-alcohol (BROADPHARM, Cat. No. BP-22609) and 0.018 ml (0.236 mmol) of mesyl chloride. $^1$H NMR (CDCl$_3$) δ (ppm): 6.69 (br. s., 1H) 5.71-6.06 br s, 1H) 4.73-5.37 (br s, 1H) 4.57-4.51 (m, 1H) 4.30-4.45 (m, 3H) 3.52-3.82 (m, 20H) 3.45 (br. s., 2H) 3.22-3.14 (m, 1H) 3.12 (s, 3H) 2.97-2.90 (m, 1H) 2.80-2.72 (m, 1H) 2.31-2.20 (m, 2H) 1.61-1.83 (m, 4H) 1.38-1.53 (m, 2H); MS (ESI): m/z: 586 [M+H]$^+$.

Intermediate 65: 2-[2-[2-[2-[2-[2-[2-[2-[5-[(3aS,4S,6aR)-2-oxo-hexahydrothieno[3,4-d]imidazol-4-yl]pentanoylamino]ethoxy]ethoxy]ethoxy]ethoxy]ethoxy]ethoxy]ethoxy]ethyl methanesulfonate

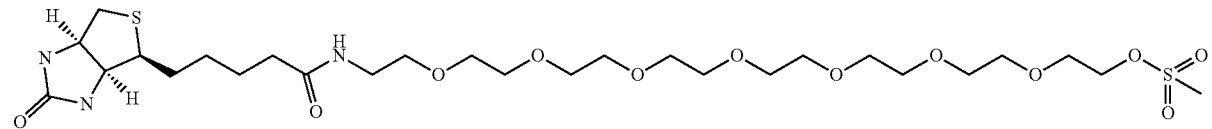 [SMILES: CS(=O)(=O)OCCOCCOCCOCCOCCOCCOCCOCCNC(=O)CCCC[C@@H]1SC[C@@H]2NC(=O)N[C@@H]21]

0.104 g (87%) of 2-[2-[2-[2-[2-[2-[2-[2-[5-[(3aS,4S,6aR)-2-oxo-hexahydrothieno[3,4-d]imidazol-4-yl]pentanoylamino]ethoxy]ethoxy]ethoxy]ethoxy]ethoxy]ethoxy]ethoxy]ethyl methanesulfonate were prepared according to the procedure described for Intermediate 63, starting from 0.105 g (0.186 mmol) of biotin-PEG8-alcohol (BROADPHARM, Cat. No. BP-23759) and 0.026 ml (0.229 mmol) of mesyl chloride. $^1$H NMR (CDCl$_3$) δ (ppm): 6.69 (br. s., 1H) 5.71-6.06 br s, 1H) 4.73-5.37 (br s, 1H) 4.57-4.51 (m, 1H) 4.30-4.45 (m, 3H) 3.52-3.82 (m, 20H) 3.45 (br. s., 2H) 3.22-3.14 (m, 1H) 3.12 (s, 3H) 2.97-2.90 (m, 1H) 2.80-2.72 (m, 1H) 2.31-2.20 (m, 2H) 1.61-1.83 (m, 4H) 1.38-1.53 (m, 2H); MS (ESI): m/z: 674 [M+H]$^+$.

Example 1: Methyl (E)-4-[3-(3-chloro-10,11-dihydro-5H-dibenzo[b,f]azepin-5-yl)propyl-methyl-amino]but-2-enoate hydrochloride

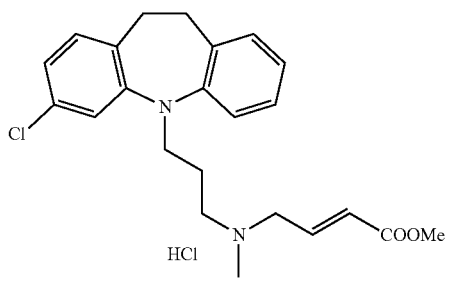 [SMILES: COC(=O)/C=C/CN(C)CCCN1c2ccccc2CCc2ccc(Cl)cc21 ; Cl]

Step 1: Methyl (E)-4-[3-(3-chloro-10,11-dihydro-5H-dibenzo[b,f]azepin-5-yl)propyl-methyl-amino]but-2-enoate 0.091 ml (0.688 mmol) of methyl 4-bromo-2-butenoate (Sigma-Aldrich, Cat. No. 16505) were added to a mixture of 0.197 g (0.655 mmol) of 3-(3-chloro-10,11-dihydro-5H-dibenzo[b,f]azepin-5-yl)-N-methyl-propan-1-amine (Intermediate 1) and 0.136 g (0.982 mmol) of K$_2$CO$_3$ in ACN (2.5 ml). The reaction mixture was warmed to 45° C. for 24 h, then filtered and concentrated. The crude product was purified by flash chromatography (eluent: DCM/MeOH from 100:1 to 94:6) to afford methyl (E)-4-[3-(3-chloro-10,11-dihydro-5H-dibenzo[b,f]azepin-5-yl)propyl-methyl-amino]but-2-enoate as a yellow oil (0.220 g, 84%). $^1$H NMR (CDCl$_3$) δ (ppm): 7.19-7.03 (m, 4H), 7.02-6.83 (m, 4H), 5.93 (d, J=15.7 Hz, 1H), 3.80-3.71 (m, 5H), 3.17-3.03 (m, 6H), 2.40 (t, J=7.1 Hz, 2H), 2.16 (s, 3H), 1.77-1.66 (m, 2H); MS (ESI): m/z: 399 [M+H]$^+$.

Step 2: Methyl (E)-4-[3-(3-chloro-10,11-dihydro-5H-dibenzo[b,f]azepin-5-yl)propyl-methyl-amino]but-2-enoate hydrochloride 0.057 g (0.143 mmol) of methyl (E)-4-[3-(3-chloro-10,11-dihydro-5H-dibenzo[b,f]azepin-5-yl)propyl-methyl-amino]but-2-enoate were solubilized in Et$_2$O (4 ml), the solution was cooled with ice and 0.143 ml of HCl (2 N in Et$_2$O, 0.286 mmol) were added. The obtained suspension was then allowed to reach r.t. and concentrated. The residue was taken up with Et$_2$O and evaporated (twice). The residue was then triturated with Et$_2$O, filtered and heated at 40° C. under vacuo to afford methyl (E)-4-[3-(3-chloro-10,11-dihydro-5H-dibenzo[b,f]azepin-5-yl)propyl-methyl-amino]but-2-enoate hydrochloride as a beige solid, (0.045 g, 72%). $^1$H NMR (DMSO-d$_6$) δ (ppm): 10.56 (bs, 1H), 7.19-6.93 (m, 7H), 6.84-6.76 (m, 1H), 6.21 (d, J=15.7 Hz, 1H), 3.93-3.73 (m, 4H), 3.70 (s, 3H), 3.16-2.92 (m, 6H), 2.63 (bs, 3H), 1.92-1.77 (m, 2H); MS (ESI): m/z: 399 [M+H]$^+$.

Example 2: Ethyl (E)-4-[3-(7-chlorodibenzo[b,e][1,4]oxazepin-5(11H)-yl)propylamino]but-2-enoate maleate

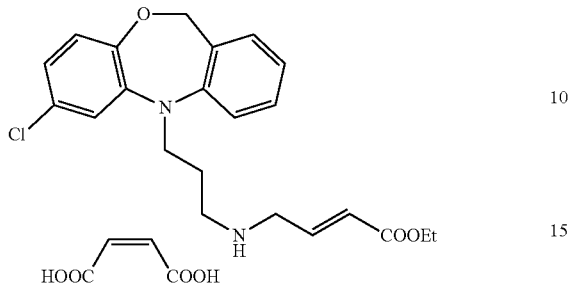

Step 1: Ethyl (E)-4-[3-(7-chlorodibenzo[b,e][1,4]oxazepin-5(11H)-yl)propylamino]but-2-enoate 0.020 ml (0.156 mmol) of fumaraldehydic acid ethyl ester (FLROCHEM, Cat. No. 235591) were added to a solution of 0.050 g (0.173 mmol) of 3-(7-chlorodibenzo[b,e][1,4]oxazepin-5(11H)-yl)propan-1-amine (Intermediate 6) in dry MeOH (2 ml), under nitrogen, and the reaction mixture was stirred at r.t. for 3 h. The reaction mixture was then ice-cooled, 0.017 g (0.433 mmol) of NaBH$_4$ were added portionwise, and the mixture was stirred at r.t. for 1 h. The reaction mixture was poured into ice-cooled water (5 ml), and then extracted with EtOAc (10 ml). The organic phase was dried (Na$_2$SO$_4$) and the solvent evaporated. The crude was purified by flash chromatography (eluent: DCM/MeOH/NH$_4$OH from 100:1:0.1 to 98:2:0.2) to afford ethyl (E)-4-[3-(7-chlorodibenzo[b,e][1,4]oxazepin-5(11H)-yl)propylamino]but-2-enoate as a colorless oil (0.025 g, 40%). $^1$H NMR (CDCl$_3$) δ (ppm): 7.38-7.32 (m, 1H), 7.32-7.28 (m, 1H), 7.14-7.04 (m, 2H), 6.99-6.88 (m, 2H), 6.78-6.73 (m, 1H), 6.72-6.68 (m, 1H), 5.94 (d, J=15.7 Hz, 1H), 5.26 (s, 2H), 4.20 (q, J=6.8 Hz, 2H), 3.80 (t, J=6.6 Hz, 2H), 3.38 (dd, J=1.5, 5.9 Hz, 2H), 2.70 (t, J=7.1 Hz, 2H), 1.86 (quint, J=6.8 Hz, 2H), 1.33-1.27 (m, 3H); MS (ESI): m/z: 401 [M+H]$^+$.

Step 2: Ethyl (E)-4-[3-(7-chlorodibenzo[b,e][1,4]oxazepin-5(11H)-yl)propylamino]but-2-enoate maleate 0.023 g (0.057 mmol) of ethyl (E)-4-[3-(7-chlorodibenzo[b,e][1,4]oxazepin-5(11H)-yl)propylamino]but-2-enoate were dissolved in dry EtOH (0.130 ml). A solution of 0.007 g of maleic acid (0.057 mmol) in dry EtOH (0.870 ml) was added in one portion to the amine solution and the reaction was stirred at r.t. for 48 h. The solvent was evaporated to ⅓ ca. of the initial volume and the salt was precipitated with Et$_2$O (8 ml). The mixture was stirred at r.t. then the solid was filtered. The filtered white solid, ethyl (E)-4-[3-(7-chlorodibenzo[b,e][1,4]oxazepin-5(11H)-yl)propylamino]but-2-enoate maleate was heated at 40° C. under vacuo (0.025 g, 84%). $^1$H NMR (DMSO-d$_6$) δ (ppm): 8.51 (bs, 2H), 7.45-7.38 (m, 2H), 7.26-7.21 (m, 1H), 7.15-7.10 (m, 1H), 7.07 (d, J=2.4 Hz, 1H), 6.83 (dd, J=2.2, 8.6 Hz, 1H), 6.79-6.69 (m, 2H), 6.17 (d, J=15.7 Hz, 1H), 6.01 (s, 2H), 5.29 (s, 2H), 4.15 (q, J=6.8 Hz, 2H), 3.81 (t, J=6.6 Hz, 2H), 3.75 (d, J=5.9 Hz, 2H), 2.94 (t, J=7.6 Hz, 2H), 1.84 (quint, J=7.1 Hz, 2H), 1.21 (t, J=7.1 Hz, 3H); MS (ESI): m/z: 401 [M+H]$^+$.

Example 3: Ethyl (E)-4-{3-[7-(trifluoromethyl)dibenzo[b,e][1,4]oxazepin-5(11H)-yl]propylamino}but-2-enoate maleate

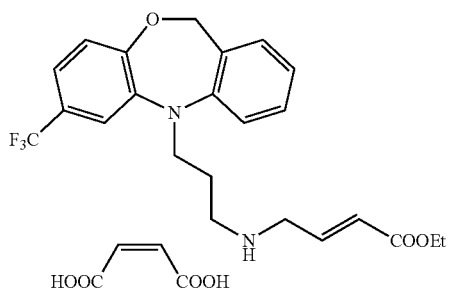

Step 1: Ethyl (E)-4-{3-[7-(trifluoromethyl)dibenzo[b,e][1,4]oxazepin-5(11H)-yl]propylamino}but-2-enoate 0.030 g (30%) of ethyl (E)-4-{3-[7-(trifluoromethyl)dibenzo[b,e][1,4]oxazepin-5(11H)-yl]propylamino}but-2-enoate were prepared according to the procedure described for Example 2, Step 1, starting from 0.074 g (0.23 mmol) of 3-[7-(trifluoromethyl)dibenzo[b,e][1,4]oxazepin-5(11H)-yl]propan-1-amine (Intermediate 7). $^1$H NMR (DMSO-d$_6$) δ (ppm): 7.48-7.34 (m, 2H), 7.31-7.19 (m, 2H), 7.16-7.01 (m, 2H), 6.91-6.69 (m, 2H), 5.90 (d, J=15.7 Hz, 1H), 5.33 (s, 2H), 4.09 (q, J=7.3 Hz, 2H), 3.81 (t, J=6.8 Hz, 2H), 3.25 (d, J=3.9 Hz, 2H), 2.55-2.49 (m, 2H), 1.70-1.60 (m, 2H), 1.19 (t, J=7.3 Hz, 3H); MS (ESI): m/z: 435 [M+H]$^+$.

Step 2: Ethyl (E)-4-{3-[7-(trifluoromethyl)dibenzo[b,e][1,4]oxazepin-5(11H)-yl]propylamino}but-2-enoate maleate 0.020 g (73%) of ethyl (E)-4-{3-[7-(trifluoromethyl)dibenzo[b,e][1,4]oxazepin-5(11H)-yl]propylamino}but-2-enoate maleate were prepared according to the procedure described for Example 2, Step 2, starting from 0.022 g (0.05 mmol) of ethyl (E)-4-{3-[7-(trifluoromethyl)dibenzo[b,e][1,4]oxazepin-5(11H)-yl]propylamino}but-2-enoate. $^1$H NMR (DMSO-d$_6$) δ (ppm): 8.49 (bs, 3H), 7.50-7.40 (m, 2H), 7.32-7.24 (m, 2H), 7.20-7.10 (m, 2H), 6.88 (d, J=8.5 Hz, 1H), 6.75 (dt, J=6.1 Hz, 1H), 6.17 (d, J=15.9 Hz, 1H), 6.01 (s, 2H), 5.39 (s, 2H), 4.15 (q, J=7.0 Hz, 2H), 3.85 (t, J=6.1 Hz, 2H), 3.74 (d, J=5.5 Hz, 2H), 2.98-2.89 (m, 2H), 1.88-1.76 (m, 2H), 1.21 (t, J=7.0 Hz, 3H); MS (ESI): m/z: 435 [M+H]$^+$.

Example 4: Ethyl (E)-4-[3-(3-chloro-10,11-dihydro-5H-dibenzo[b,f]azepin-5-yl)propylamino]but-2-enoate fumarate

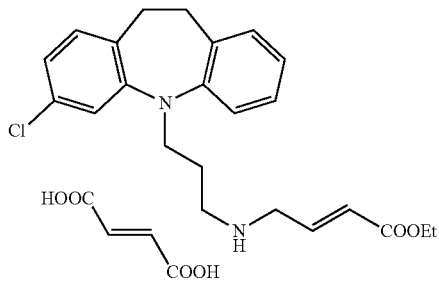

Step 1: Ethyl (E)-4-[3-(3-chloro-10,11-dihydro-5H-dibenzo[b,f]azepin-5-yl)propylamino]but-2-enoate 0.054 g (43%) of ethyl (E)-4-[3-(3-chloro-10,11-dihydro-5H-dibenzo[b,f]azepin-5-yl)propylamino]but-2-enoate were prepared according to the procedure described for Example 2, Step 1, starting from 0.100 g (0.35 mmol) of 3-(3-chloro-10,11-dihydro-5H-dibenzo[b,f]azepin-5-yl)-propan-1-amine (Intermediate 3). $^1$H NMR (CDCl$_3$) δ (ppm): 7.19-7.10 (m, 2H), 7.10-7.06 (m, 1H), 7.06-7.04 (m, 1H), 7.02-6.90 (m, 3H), 6.89-6.86 (m, 1H), 5.94 (d, J=15.7 Hz, 1H), 4.20 (q, J=7.3 Hz, 2H), 3.79 (t, J=6.6 Hz, 2H), 3.42-3.34 (m, 2H), 3.17-3.06 (m, 4H), 2.71 (t, J=7.1 Hz, 2H), 1.87-1.77 (m, 2H), 1.34-1.25 (m, 3H); MS (ESI): m/z: 399 [M+H]$^+$.

Step 2: Ethyl (E)-4-[3-(3-chloro-10,11-dihydro-5H-dibenzo[b,f]azepin-5-yl)propylamino]but-2-enoate fumarate 0.022 g (60%) of ethyl (E)-4-[3-(3-chloro-10,11-dihydro-5H-dibenzo[b,f]azepin-5-yl)propylamino]but-2-enoate fumarate were prepared according to the procedure described for Example 2, Step 2, starting from 0.029 g (0.07 mmol) of ethyl (E)-4-[3-(3-chloro-10,11-dihydro-5H-dibenzo[b,f]azepin-5-yl)propylamino]but-2-enoate and 0.008 g (0.07 mmol) of fumaric acid. $^1$H NMR (DMSO-d$_6$) δ (ppm): 7.18-7.05 (m, 5H), 7.00-6.89 (m, 2H), 6.75 (dt, J=6.1, 15.8 Hz, 1H), 6.48 (s, 2H), 6.06 (d, J=15.8 Hz, 1H), 4.12 (q, J=7.0 Hz, 2H), 3.74 (t, J=6.6 Hz, 2H), 3.57-3.53 (m, 2H), 3.03 (bs, 4H), 2.77 (t, J=7.5 Hz, 2H), 1.76-1.66 (m, 2H), 1.19 (t, J=7.2 Hz, 3H); MS (ESI): m/z: 399 [M+H]$^+$.

Example 5: Ethyl (E)-5-[3-(3-chloro-10,11-dihydro-5H-dibenzo[b,f]azepin-5-yl)propylamino]pent-2-enoate maleate

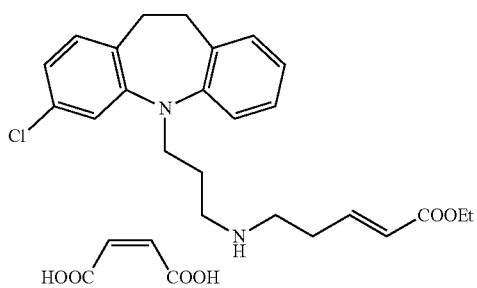

Step 1: N-[3-(3-Chloro-10,11-dihydro-5H-dibenzo[b,f]azepin-5-yl)propyl]-2,2,2-trifluoro-acetamide To a stirred solution of 1.0 g (3.49 mmol) of 3-(3-chloro-10,11-dihydro-5H-dibenzo[b,f]azepin-5-yl)-propan-1-amine (Intermediate 3) in DCM (40 ml) were added 1.10 ml (7.67 mmol) of TEA, followed by 0.73 ml (5.23 mmol) of TFAA at 0° C. and the reaction mixture was stirred at r.t. for 1 h. The reaction was diluted with DCM (50 ml), washed with water (3×50 ml), then with 10% aqueous solution of K$_2$CO$_3$ (50 ml) and brine (50 ml). The organic layer was dried (Na$_2$SO$_4$) and concentrated under vacuo. The crude was purified by flash chromatography (eluent: hexane/EtOAc 80:20) to afford N-[3-(3-chloro-10,11-dihydro-5H-dibenzo[b,f]azepin-5-yl)propyl]-2,2,2-trifluoro-acetamide as a white solid (1.13 g, 84%). $^1$H NMR (CDCl$_3$) δ (ppm): 7.21-7.12 (m, 2H), 7.10-6.98 (m, 4H), 6.94-6.89 (m, 1H), 6.26 (bs, 1H), 3.79 (t, J=6.6 Hz, 2H), 3.42 (q, J=6.8 Hz, 2H), 3.20-3.08 (m, 4H), 1.89 (quint, J=6.8 Hz, 2H); MS (ESI): m/z: 383 [M+H]$^+$.

Step 2: N-[3-(3-Chloro-10,11-dihydro-5H-dibenzo[b,f]azepin-5-yl)propyl]-N-[2-(1,3-dioxolan-2-yl)ethyl]-2,2,2-trifluoro-acetamide 0.41 ml (3.35 mmol) of 2-(2-bromoethyl)-1,3-dioxolane were added to a suspension of 0.145 g of NaH (60% oil suspension, 3.63 mmol) and 1.07 g (2.80 mmol) of N-[3-(3-chloro-10,11-dihydro-5H-dibenzo[b,f]azepin-5-yl)propyl]-2,2,2-trifluoro-acetamide in dry toluene-DMF (5:1, 3.9 ml) under an argon atmosphere with stirring at 60° C. The mixture was stirred at 80° C. for 23 h. The reaction mixture was cooled, cautiously poured into ice-water (50 ml) and extracted with EtOAc (2×50 ml). The combined extracts were washed with brine, dried (Na$_2$SO$_4$), and concentrated. The crude was purified by flash chromatography (eluent: hexane/EtOAc 80:20) to afford N-[3-(3-chloro-10,11-dihydro-5H-dibenzo[b,f]azepin-5-yl)propyl]-N-[2-(1,3-dioxolan-2-yl)ethyl]-2,2,2-trifluoro-acetamide as a colorless oil (0.381 g, 28%). $^1$H NMR (CDCl$_3$) δ (ppm): 7.22-7.11 (m, 2H), 7.11-6.96 (m, 4H), 6.94-6.85 (m, 1H), 4.87-4.78 (m, 1H), 3.98-3.69 (m, 6H), 3.48-3.30 (m, 4H), 3.21-3.08 (m, 4H), 1.97-1.80 (m, 4H); MS (ESI): m/z: 483 [M+H]$^+$.

Step 3: N-[3-(3-Chloro-10,11-dihydro-5H-dibenzo[b,f]azepin-5-yl)propyl]-2,2,2-trifluoro-N-(3-oxopropyl)acetamide 9.8 ml of 20% aqueous oxalic acid were added to a solution of 0.527 g (1.09 mmol) of N-[3-(3-chloro-10,11-dihydro-5H-dibenzo[b,f]azepin-5-yl)propyl]-N-[2-(1,3-dioxolan-2-yl)ethyl]-2,2,2-trifluoro-acetamide in THF (44 ml), the pressure tube was closed and the reaction was heated at 90° C. for 46 h 30 min. The reaction mixture was concentrated, diluted with water (35 ml) and then extracted with EtOAc (2×50 ml). The combined organic phases were washed with brine, dried (Na$_2$SO$_4$), filtered and concentrated under vacuo.

The crude was purified by flash chromatography (eluent: hexane/acetone from 95:5 to 80:20) to afford N-[3-(3-chloro-10,11-dihydro-5H-dibenzo[b,f]azepin-5-yl)propyl]-2,2,2-trifluoro-N-(3-oxopropyl)acetamide as a colorless oil (0.285 g, 60%). $^1$H NMR (CDCl$_3$), mixture of rotamers, δ (ppm): 9.72, 9.67 (2s, 1H), 7.23-7.11 (m, 2H), 7.11-6.97 (m, 4H), 6.94-6.88 (m, 1H), 3.80-3.70 (m, 2H), 3.59-3.34 (m, 4H), 3.21-3.07 (m, 4H), 2.75, 2.58 (2t, J=6.6 Hz, J=7.3 Hz, 2H), 1.97-1.85 (m, 2H); MS (ESI): m/z: 439 [M+H]+ and 457 [M+H2O+H]+.

Step 4: Ethyl (E)-5-[3-(3-chloro-10,11-dihydro-5H-dibenzo[b,f]azepin-5-yl)propyl-(2,2,2-trifluoro-acetyl)amino]pent-2-enoate 0.073 g (0.20 mmol) of ethyl (triphenylphosphoranylidene)acetate were added to a solution of 0.090 g (0.20 mmol) of N-[3-(3-chloro-10,11-dihydro-5H-dibenzo[b,f]azepin-5-yl)propyl]-2,2,2-trifluoro-N-(3-oxopropyl)acetamide in dry DCM (1 ml) in one portion with stirring at 0° C. After being stirred for 2 h at r.t., the reaction mixture was concentrated. The crude was purified by flash chromatography (eluent: hexane/EtOAc from 95:5 to 80:20) to afford ethyl (E)-5-[3-(3-chloro-10,11-dihydro-5H-dibenzo[b,f]azepin-5-yl)propyl-(2,2,2-trifluoroacetyl)amino]pent-2-enoate as a colorless oil (0.076 g, 73%). 1H NMR (CDCl3), mixture of rotamers, δ (ppm): 7.22-7.13 (m, 2H), 7.10-6.98 (m, 4H), 6.94-6.88 (m, 1H), 6.80-6.67 (m, 1H), 5.82-5.74 (m, 1H), 4.25-4.18 (m, 2H), 3.76 (t, J=6.1 Hz, 2H), 3.43-3.36 (m, 2H), 3.29-3.08 (m, 6H), 2.41-2.25 (m, 2H), 1.95-1.85 (m, 2H), 1.34-1.28 (m, 3H); MS (ESI): m/z: 509 [M+H]+.

Step 5: Ethyl (E)-5-[3-(3-chloro-10,11-dihydro-5H-dibenzo[b,f]azepin-5-yl)propylamino]pent-2-enoate 0.345 ml of 5% aqueous K2CO3 (0.125 mmol) were added to a solution of 0.040 g (0.079 mmol) of ethyl (E)-5-[3-(3-chloro-10,11-dihydro-5H-dibenzo[b,f]azepin-5-yl)propyl-(2,2,2-trifluoroacetyl)amino]pent-2-enoate in EtOH (1 ml), and the reaction mixture was stirred for 48 h at r.t., then concentrated below r.t. and extracted with DCM. The organic solution was washed with 1:2 mixture of brine and water. The aqueous layer was back-extracted twice with DCM, and the combined organic layers were washed with brine, dried (Na2SO4) and concentrated. The crude was purified by flash chromatography (eluent: DCM/MeOH/NH4OH 97:3:0.3) to afford ethyl (E)-5-[3-(3-chloro-10,11-dihydro-5H-dibenzo[b,f]azepin-5-yl)propylamino]pent-2-enoate as a light-yellow oil (0.015 g, 48%). 1H NMR (DMSO-d6) δ (ppm): 7.17-7.05 (m, 5H), 6.98-6.90 (m, 2H), 6.89-6.81 (m, 1H), 5.85-5.78 (m, 1H), 4.12-4.01 (m, 2H), 3.74-3.67 (m, 2H), 3.09-2.98 (m, 4H), 2.57-2.44 (m, 4H), 2.29-2.20 (m, 2H), 1.60-1.50 (m, 2H), 1.19 (t, J=7.1 Hz, 3H); MS (ESI): m/z: 413 [M+H]+.

Step 6: Ethyl (E)-5-[3-(3-chloro-10,11-dihydro-5H-dibenzo[b,f]azepin-5-yl)propylamino]pent-2-enoate maleate 0.016 g (94%) of ethyl (E)-5-[3-(3-chloro-10,11-dihydro-5H-dibenzo[b,f]azepin-5-yl)propylamino]pent-2-enoate maleate were prepared according to the procedure described for Example 2, Step 2, starting from 0.013 g (0.031 mmol) of ethyl (E)-5-[3-(3-chloro-10,11-dihydro-5H-dibenzo[b,f]azepin-5-yl)propylamino]pent-2-enoate. 1H NMR (DMSO-d6) δ (ppm): 8.26 (bs, 2H), 7.21-7.08 (m, 5H), 7.02-6.93 (m, 2H), 6.86-6.77 (m, 1H), 6.01 (s, 2H), 5.95 (d, J=15.7 Hz, 1H), 4.11 (q, J=7.2 Hz, 2H), 3.78 (t, J=6.6 Hz, 2H), 3.12-2.98 (m, 6H), 2.92 (t, J=7.3 Hz, 2H), 2.48-2.42 (m, 2H), 1.83-1.71 (m, 2H), 1.20 (t, J=7.1 Hz, 3H); MS (ESI): m/z: 413 [M+H]+.

Example 6: (E)-4-[3-(3-Chloro-10,11-dihydro-5H-dibenzo[b,f]azepin-5-yl)propyl-methyl-amino]-N-methoxy-N-methyl-but-2-enamide

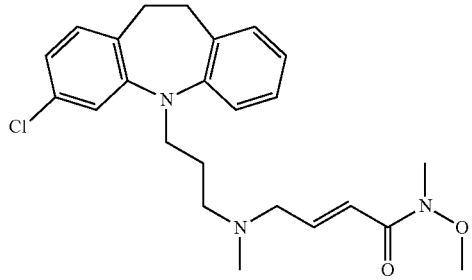 [SMILES: CON(C)C(=O)/C=C/CN(C)CCCN1c2ccccc2CCc2ccc(Cl)cc21]

A slurry of 0.163 g (1.64 mmol) of N,O-dimethylhydroxylamine hydrochloride and 0.218 g (0.546 mmol) of methyl (E)-4-[3-(3-chloro-10,11-dihydro-5H-dibenzo[b,f]azepin-5-yl)propyl-methyl-amino]but-2-enoate (Example 1, Step 1) in dry THF (8 ml), under nitrogen, was cooled to T<−10° C. with a NaCl-ice bath. To the reaction mixture were then added dropwise 1.64 ml of i-PrMgCl (2 M in THF, 3.28 mmol) and the reaction was stirred for 1 h 30 min prior to be quenched with a saturated aqueous solution of NH4Cl (6 ml) at T<0° C. Then, the mixture was diluted with water (5 ml) and extracted with EtOAc (2×10 ml). The combined organic layers were washed with brine, dried (Na2SO4) and evaporated. The crude was purified by flash chromatography (eluent: DCM/MeOH from 100:1 to 95:5) to afford (E)-4-[3-(3-chloro-10,11-dihydro-5H-dibenzo[b,f]azepin-5-yl)propyl-methyl-amino]-N-methoxy-N-methyl-but-2-enamide as a light-yellow oil (0.158 g, 68%). 1H NMR (CDCl3) δ (ppm): 7.19-7.03 (m, 4H), 7.02-6.90 (m, 3H), 6.89-6.84 (m, 1H), 6.53 (d, J=15.7 Hz, 1H), 3.75 (t, J=6.8 Hz, 2H), 3.68 (s, 3H), 3.25 (s, 3H), 3.18-3.06 (m, 6H), 2.42 (t, J=6.8 Hz, 2H), 2.18 (s, 3H), 1.80-1.67 (m, 2H); MS (ESI): m/z: 428 [M+H]+.

Example 7: (E)-5-[3-(3-chloro-10,11-dihydro-5H-dibenzo[b,f]azepin-5-yl)propyl-methyl-amino]pent-3-en-2-one maleate

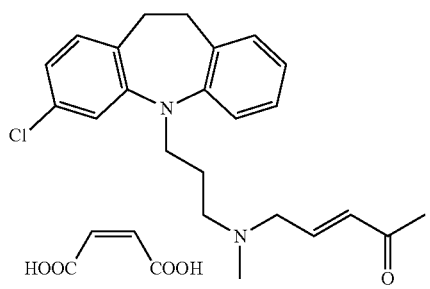 [SMILES: CC(=O)/C=C/CN(C)CCCN1c2ccccc2CCc2ccc(Cl)cc21 ; O=C(O)/C=C\C(=O)O]

Step 1: (E)-5-[3-(3-Chloro-10,11-dihydro-5H-dibenzo[b,f]azepin-5-yl)propyl-methyl-amino]pent-3-en-2-one To a solution of 0.051 g (0.119 mmol) of (E)-4-[3-(3-chloro-10,11-dihydro-5H-dibenzo[b,f]azepin-5-yl)propyl-methyl-amino]-N-methoxy-N-methyl-but-2-enamide (Example 6) in dry THF (1.5 ml) were added 0.119 ml of MeMgCl (3 M in THF, 0.357 mmol) at 0-5° C. The reaction mixture was stirred at 0° C. for 1 h 20 min. The reaction was then quenched with a saturated aqueous solution of NH₄Cl (1.5 ml) at 0-5° C., diluted with water (1 ml) and then extracted with EtOAc (2×3 ml). The combined organic phases were washed with brine, dried (Na₂SO₄) and the solvent removed under vacuo. The crude was purified by flash chromatography (eluent: DCM/MeOH 97:3) to afford (E)-5-[3-(3-chloro-10,11-dihydro-5H-dibenzo[b,f]azepin-5-yl)propyl-methyl-amino]pent-3-en-2-one as a yellow oil (0.028 g, 62%). $^1$H NMR (CDCl₃) δ (ppm): 7.19-7.03 (m, 4H), 7.02-6.94 (m, 2H), 6.90-6.83 (m, 1H), 6.71 (dt, J=6.4, 16.1 Hz, 1H), 6.13 (d, J=16.1 Hz, 1H), 3.76 (t, J=6.6 Hz, 2H), 3.16-3.05 (m, 6H), 2.41 (t, J=6.6 Hz, 2H), 2.23 (s, 3H), 2.18 (s, 3H), 1.79-1.68 (m, 2H); MS (ESI): m/z: 383 [M+H]⁺.

Step 2: (E)-5-[3-(3-Chloro-10,11-dihydro-5H-dibenzo[b,f]azepin-5-yl)propyl-methyl-amino]pent-3-en-2-one maleate 0.030 g (88%) of (E)-5-[3-(3-chloro-10,11-dihydro-5H-dibenzo[b,f]azepin-5-yl)propyl-methyl-amino]pent-3-en-2-one maleate were prepared according to the procedure described for Example 2, Step 2, starting from 0.026 g (0.068 mmol) of ethyl (E)-5-[3-(3-chloro-10,11-dihydro-5H-dibenzo[b,f]azepin-5-yl)propyl-methyl-amino]pent-3-en-2-one. $^1$H NMR (D₂O) δ (ppm): 7.12-6.98 (m, 4H), 6.94-6.88 (m, 2H), 6.82-6.78 (m, 1H), 6.55-6.47 (m, 1H), 6.17 (s, 2H), 6.13-6.08 (m, 1H), 3.74-3.68 (m, 2H), 3.67-3.61 (m, 2H), 2.99-2.84 (m, 6H), 2.68 (s, 3H), 2.16 (s, 3H), 1.88-1.77 (m, 2H); MS (ESI): m/z: 383 [M+H]⁺.

Example 8: (E)-4-[3-(3-chloro-10,11-dihydro-5H-dibenzo[b,f]azepin-5-yl)propyl-methyl-amino]-1-phenyl-but-2-en-1-one

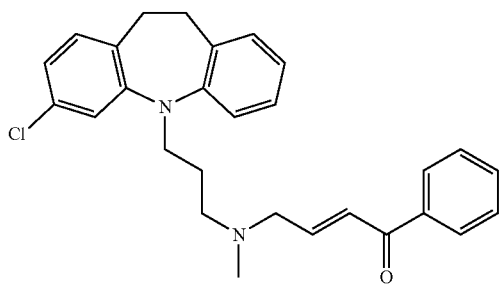 [SMILES: CN(C/C=C/C(=O)c1ccccc1)CCCN1c2ccccc2CCc2ccc(Cl)cc21]

To a solution of 0.048 g (0.112 mmol) of (E)-4-[3-(3-chloro-10,11-dihydro-5H-dibenzo[b,f]azepin-5-yl)propyl-methyl-amino]-N-methoxy-N-methyl-but-2-enamide (Example 6) in dry THF (1.5 ml) were added 0.336 ml of PhMgBr (1 M in THF, 0.336 mmol) at −10/−15° C. (NH₄Cl-ice bath). The reaction mixture was stirred at −15° C. for 3 h. The reaction mixture was quenched with a saturated aqueous solution of NH₄Cl (1.5 ml) at −10/−15° C., diluted with water (1 ml) and then extracted with EtOAc (2×3 ml). The combined organic phases were washed with brine, dried (Na₂SO₄) and the solvent removed under vacuo. The crude was purified by flash chromatography (eluent: hexane/acetone from 95:5 to 60:40) to afford ((E)-4-[3-(3-chloro-10,11-dihydro-5H-dibenzo[b,f]azepin-5-yl)propyl-methyl-amino]-1-phenyl-but-2-en-1-one as a light-yellow oil (0.018 g, 37%). $^1$H NMR (DMSO-d₆) δ (ppm): 7.94-7.89 (m, 2H), 7.68-7.62 (m, 1H), 7.56-7.51 (m, 2H), 7.16-7.10 (m, 4H), 7.10-7.06 (m, 1H), 7.04-7.01 (m, 1H), 6.95-6.90 (m, 1H), 6.90-6.86 (m, 1H), 6.84-6.77 (m, 1H), 3.76-3.69 (m, 2H), 3.20-3.13 (m, 2H), 3.04-2.94 (m, 4H), 2.39-2.31 (m, 2H), 2.11 (s, 3H), 1.65-1.57 (m, 2H); MS (ESI): m/z: 445 [M+H]⁺.

Example 9: (E)-4-[4-(3-Chloro-10,11-dihydro-5H-dibenzo[b,f]azepin-5-yl)butyl-methyl-amino]-N-methoxy-N-methyl-but-2-enamide

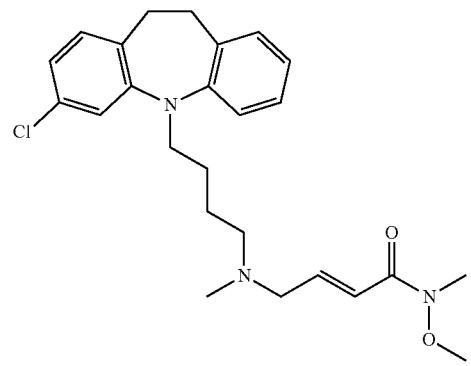 [SMILES: CON(C)C(=O)/C=C/CN(C)CCCCN1c2ccccc2CCc2ccc(Cl)cc21]

Step 1: Methyl (E)-4-[4-(3-chloro-10,11-dihydro-5H-dibenzo[b,f]azepin-5-yl)butyl-methyl-amino]but-2-enoate 0.163 g (50%) of methyl (E)-4-[4-(3-chloro-10,11-dihydro-5H-dibenzo[b,f]azepin-5-yl)butyl-methyl-amino]but-2-enoate were prepared according to the procedure described for Example 1, Step 1 starting from 0.245 g (0.778 mmol) of 4-(3-chloro-10,11-dihydro-5H-dibenzo[b,f]azepin-5-yl)-N-methyl-butan-1-amine (Intermediate 2) and 0.108 ml (0.817 mmol) of methyl 4-bromo-2-butenoate at r.t. $^1$H NMR (DMSO-d₆) δ (ppm): 7.19-7.12 (m, 4H), 7.12-7.08 (m, 1H), 7.01-6.96 (m, 1H), 6.96-6.91 (m, 1H), 6.78 (dt, J=5.9, 15.6 Hz, 1H), 5.98 (d, J=15.6 Hz, 1H), 3.70 (t, J=6.4 Hz, 2H), 3.67 (s, 3H), 3.12-3.02 (m, 6H), 2.24 (t, J=6.6 Hz, 2H), 2.07 (s, 3H), 1.52-1.39 (m, 4H); MS (ESI): m/z: 413 [M+H]⁺.

Step 2: (E)-4-[4-(3-Chloro-10,11-dihydro-5H-dibenzo[b,f]azepin-5-yl)butyl-methyl-amino]-N-methoxy-N-methyl-but-2-enamide 0.087 g (65%) of (E)-4-[4-(3-chloro-10,11-dihydro-5H-dibenzo[b,f]azepin-5-yl)butyl-methyl-amino]-N-methoxy-N-methyl-but-2-enamide were prepared according to the procedure described for Example 6, starting from 0.124 g (0.3 mmol) of methyl (E)-4-[4-(3-chloro-10,11-dihydro-5H-dibenzo[b,f]azepin-5-yl)butyl-methyl-amino]but-2-enoate and 0.09 g (0.9 mmol) of N,O-dimethylhydroxylamine hydrochloride. $^1$H NMR (DMSO-d₆) δ (ppm): 7.17-7.10 (m, 4H), 7.09-7.06 (m, 1H), 6.97-6.93 (m, 1H), 6.91 (dd, J=2.1, 8.1 Hz, 1H), 6.66 (dt J=5.9, 15.7 Hz, 1H), 6.47 (d, J=15.7 Hz, 1H), 3.68 (t, J=6.4 Hz, 2H), 3.62 (s, 3H), 3.12 (s, 3H), 3.09-3.00 (m, 6H), 2.22 (t, J=6.8 Hz, 2H), 2.05 (s, 3H), 1.51-1.35 (m, 4H); MS (ESI): m/z: 442 [M+H]⁺.

Example 10: (E)-5-[4-(3-chloro-10,11-dihydro-5H-dibenzo[b,f]azepin-5-yl)butyl-methyl-amino]pent-3-en-2-one maleate

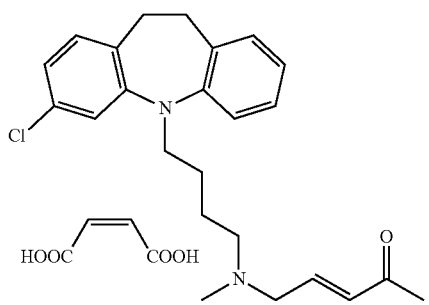 [SMILES: CC(=O)/C=C/CN(C)CCCCN1c2ccccc2CCc2ccc(Cl)cc21 ; O=C(O)/C=C\C(=O)O]

Step 1: (E)-5-[4-(3-Chloro-10,11-dihydro-5H-dibenzo[b,f]azepin-5-yl)butyl-methyl-amino]pent-3-en-2-one 0.029 g (65%) of (E)-5-[4-(3-chloro-10,11-dihydro-5H-dibenzo[b,f]azepin-5-yl)butyl-methyl-amino]pent-3-en-2-one were prepared according to the procedure described for Example 7, Step 1, starting from 0.050 g (0.113 mmol) of (E)-4-[4-(3-chloro-10,11-dihydro-5H-dibenzo[b,f]azepin-5-yl)butyl-methyl-amino]-N-methoxy-N-methyl-but-2-enamide (Example 9, Step 2) and 1.19 ml of MeMgCl (3 M in THF, 0.357 mmol). $^1$H NMR (DMSO-$d_6$) δ (ppm): 7.17-7.10 (m, 4H), 7.08 (d, J=8.3 Hz, 1H), 6.98-6.93 (m, 1H), 6.91 (dd, J=2.2, 8.1 Hz, 1H), 6.70 (dt, J=5.9, 16.1 Hz, 1H), 6.05 (dt, J=1.5, 16.1 Hz, 1H), 3.69 (t, J=6.4 Hz, 2H), 3.09-2.97 (m, 6H), 2.23 (t, J=6.6 Hz, 2H), 2.17 (s, 3H), 2.05 (s, 3H), 1.51-1.37 (m, 4H); MS (ESI): m/z: 397 [M+H]$^+$.

Step 2: (E)-5-[4-(3-Chloro-10,11-dihydro-5H-dibenzo[b,f]azepin-5-yl)butyl-methyl-amino]pent-3-en-2-one maleate 0.029 g (80%) of (E)-5-[4-(3-chloro-10,11-dihydro-5H-dibenzo[b,f]azepin-5-yl)butyl-methyl-amino]pent-3-en-2-one maleate were prepared according to the procedure described for Example 2, Step 2, starting from 0.028 g (0.07 mmol) of (E)-5-[4-(3-chloro-10,11-dihydro-5H-dibenzo[b,f]azepin-5-yl)butyl-methyl-amino]pent-3-en-2-one and 0.008 g (0.07 mmol) of maleic acid. $^1$H NMR (DMSO-$d_6$, DCl 1N) δ (ppm): 7.19-7.01 (m, 5H), 6.98-6.92 (m, 1H), 6.90 (dd, J=2.0, 8.3 Hz, 1H), 6.73 (dt, J=6.8, 16.1 Hz, 1H), 6.32 (d, J=16.1 Hz, 1H), 6.26 (s, 2H), Part AB of ABX System: $v_A$=3.88, $v_B$=3.8, $J_{AB}$=14.1 Hz, $J_{AX}$=6.6 Hz, $J_{BX}$=6.9 Hz, 3.65 (t, J=6.6 Hz, 2H), 3.10-2.87 (m, 6H), 2.66 (s, 3H), 2.22 (s, 3H), 1.73-1.59 (m, 2H), 1.50-1.42 (m, 2H); MS (ESI): m/z: 397 [M+H]$^+$.

Example 11: Ethyl (E)-4-[3-(10,11-dihydro-5H-dibenzo[b,f]azepin-5-yl)propylamino]but-2-enoate fumarate

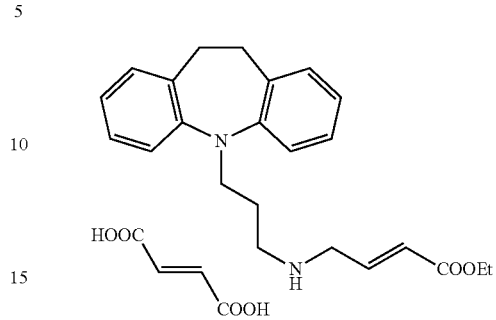

Step 1: Ethyl (E)-4-[3-(10,11-dihydro-5H-dibenzo[b,f]azepin-5-yl)propylamino]but-2-enoate 0.036 g (33%) of ethyl (E)-4-[3-(10,11-dihydro-5H-dibenzo[b,f]azepin-5-yl)propylamino]but-2-enoate were prepared according to the procedure described for Example 2, Step 1, starting from 0.09 g (0.36 mmol) of 3-(10,11-dihydro-5H-dibenzo[b,f]azepin-5-yl)-propan-1-amine (Intermediate 8). $^1$H NMR (CDCl$_3$) δ (ppm): 7.17-7.07 (m, 6H), 6.97-6.89 (m, 3H), 5.96-5.87 (m, 1H), 4.20 (q, J=6.8 Hz, 2H), 3.82 (t, J=6.8 Hz, 2H), 3.39-3.32 (m, 2H), 3.16 (s, 4H), 2.68 (t, J=7.1 Hz, 2H), 1.83-1.73 (m, 2H), 1.30 (t, J=6.8 Hz, 3H); MS (ESI): m/z: 365 [M+H]$^+$.

Step 2: Ethyl (E)-4-[3-(10,11-dihydro-5H-dibenzo[b,f]azepin-5-yl)propylamino]but-2-enoate fumarate 0.021 g (66%) of ethyl (E)-4-[3-(10,11-dihydro-5H-dibenzo[b,f]azepin-5-yl)propylamino]but-2-enoate fumarate were prepared according to the procedure described for Example 2, Step 2, starting from 0.024 g (0.07 mmol) of ethyl (E)-4-[3-(10,11-dihydro-5H-dibenzo[b,f]azepin-5-yl)propylamino]but-2-enoate and 0.008 g (0.07 mmol) of fumaric acid. $^1$H NMR (DMSO-$d_6$) δ (ppm): 7.18-7.06 (m, 6H), 6.96-6.87 (m, 2H), 6.78 (dt, J=6.0, 16.1 Hz, 1H), 6.59 (s, 2H), 6.12 (d, J=16.1 Hz, 1H), 4.14 (q, J=7.1 Hz, 2H), 3.77 (t, J=6.6 Hz, 2H), 3.63 (d, J=5.9 Hz, 2H), 3.07 (s, 4H), 2.88-2.79 (m, 2H), 1.84-1.72 (m, 2H), 1.21 (t, J=7.1 Hz, 3H); MS (ESI): m/z: 365 [M+H]$^+$.

Example 12: Ethyl (E)-4-[4-(3-chloro-10,11-dihydro-5H-dibenzo[b,f]azepin-5-yl)butylamino]but-2-enoate maleate

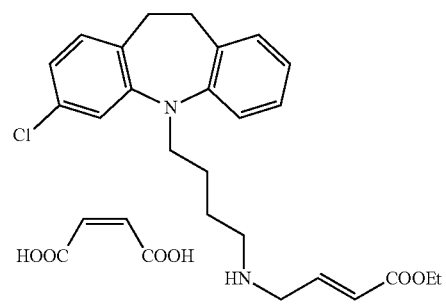 [SMILES: CCOC(=O)/C=C/CNCCCCN1c2ccccc2CCc2ccc(Cl)cc21 ; O=C(O)/C=C\C(=O)O]

Step 1: Ethyl (E)-4-[4-(3-chloro-10,11-dihydro-5H-dibenzo[b,f]azepin-5-yl)butylamino]but-2-enoate 0.067 g (41%) of ethyl (E)-4-[4-(3-chloro-10,11-dihydro-5H-dibenzo[b,f]azepin-5-yl)butylamino]but-2-enoate were prepared according to the procedure described for Example 2, Step 1, starting from 0.120 g (0.4 mmol) of 4-(3-chloro-10,11-dihydro-5H-dibenzo[b,f]azepin-5-yl)butan-1-amine (Intermediate 9). $^1$H NMR (CDCl$_3$, D$_2$O) δ (ppm): 7.19-6.91 (m, 7H), 6.87 (dd, J=2.2, 7.8 Hz, 1H), 5.93 (d, J=15.6 Hz, 1H), 4.20 (q, J=7.3 Hz, 2H), 3.72 (t, J=6.8 Hz, 2H), 3.39-3.31 (m, 2H), 3.19-3.06 (m, 4H), 2.57 (t, J=6.8 Hz, 2H), 1.66-1.48 (m, 4H), 1.29 (t, J=7.3 Hz, 3H); MS (ESI): m/z: 413 [M+H]$^+$.

Step 2: Ethyl (E)-4-[4-(3-chloro-10,11-dihydro-5H-dibenzo[b,f]azepin-5-yl)butylamino]but-2-enoate maleate 0.073 g (89%) of ethyl (E)-4-[4-(3-chloro-10,11-dihydro-5H-dibenzo[b,f]azepin-5-yl)butylamino]but-2-enoate maleate were prepared according to the procedure described for Example 2, Step 2, starting from 0.064 g (0.155 mmol) of (E)-4-[4-(3-chloro-10,11-dihydro-5H-dibenzo[b,f]azepin-5-yl)butylamino]but-2-enoate and 0.018 g (0.155 mmol) of maleic acid. $^1$H NMR (DMSO-d$_6$) δ (ppm): 8.45 (bs, 3H), 7.19-7.13 (m, 4H), 7.12-7.08 (m, 1H), 7.00-6.93 (m, 2H), 6.76 (dt, J=5.8, 15.7 Hz, 1H), 6.17 (d, J=15.7 Hz, 1H), 6.01 (s, 2H), 4.15 (q, J=7.1 Hz, 2H), 3.76-3.65 (m, 4H), 3.13-3.01 (m, 4H), 2.84 (t, J=7.3 Hz, 2H), 1.64-1.44 (m, 4H), 1.21 (t, J=7.1 Hz, 3H); MS (ESI): m/z: 413 [M+H]$^+$.

Example 13: Ethyl (E)-4-[5-(3-chloro-10,11-dihydro-5H-dibenzo[b,f]azepin-5-yl)pentylamino]but-2-enoate maleate

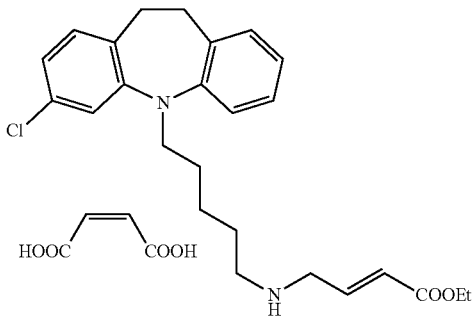 [SMILES: CCOC(=O)/C=C/CNCCCCCN1c2ccccc2CCc2ccc(Cl)cc21 ; O=C(O)/C=C\C(=O)O]

Step 1: Ethyl (E)-4-[5-(3-chloro-10,11-dihydro-5H-dibenzo[b,f]azepin-5-yl)pentylamino]but-2-enoate 0.072 g (57%) of ethyl (E)-4-[5-(3-chloro-10,11-dihydro-5H-dibenzo[b,f]azepin-5-yl)pentylamino]but-2-enoate were prepared according to the procedure described for Example 2, Step 1, starting from 0.114 g (0.36 mmol) of 5-(3-chloro-10,11-dihydro-5H-dibenzo[b,f]azepin-5-yl)pentan-1-amine (Intermediate 10). $^1$H NMR (CDCl$_3$, D$_2$O) δ (ppm): 7.18-7.10 (m, 2H), 7.09-7.05 (m, 1H), 7.04-7.01 (m, 1H), 7.01-6.93 (m, 3H), 6.86 (dd, J=2.0, 8.3 Hz, 1H), 5.96 (dt, J=1.9, 15.6 Hz, 1H), 4.20 (q, J=7.2 Hz, 2H), 3.70 (t, J=7.1 Hz, 2H), 3.37 (dd, J=1.5, 5.4 Hz, 2H), 3.18-3.07 (m, 4H), 2.56 (t, J=7.1 Hz, 2H), 1.65-1.53 (m, 2H), 1.52-1.42 (m, 2H), 1.40-1.33 (m, 2H), 1.30 (t, J=7.2 Hz, 3H); MS (ESI): m/z: 427 [M+H]$^+$.

Step 2: Ethyl (E)-4-[5-(3-chloro-10,11-dihydro-5H-dibenzo[b,f]azepin-5-yl)pentylamino]but-2-enoate maleate 0.075 g (89%) of ethyl (E)-4-[5-(3-chloro-10,11-dihydro-5H-dibenzo[b,f]azepin-5-yl)pentylamino]but-2-enoate maleate were prepared according to the procedure described for Example 2, Step 2, starting from 0.066 g (0.155 mmol) of (E)-4-[5-(3-chloro-10,11-dihydro-5H-dibenzo[b,f]azepin-5-yl)pentylamino]but-2-enoate and 0.018 g (0.155 mmol) of maleic acid. $^1$H NMR (DMSO-d$_6$) δ (ppm): 8.52 (bs, 3H), 7.19-7.07 (m, 5H), 7.00-6.90 (m, 2H), 6.77 (dt, J=6.3, 16.0 Hz, 1H), 6.19 (d, J=16.1 Hz, 1H), 6.01 (s, 2H), 4.15 (q, J=7.0 Hz, 2H), 3.75 (d, J=5.5 Hz, 2H), 3.69 (t, J=6.6 Hz, 2H), 3.11-3.00 (m, 4H), 2.87-2.81 (m, 2H), 1.55-1.42 (m, 4H), 1.35-1.26 (m, 2H), 1.21 (t, J=7.0 Hz, 3H); MS (ESI): m/z: 427 [M+H]$^+$.

Example 14: Ethyl (E)-4-[3-(3-nitro-10,11-dihydro-5H-dibenzo[b,f]azepin-5-yl)propylamino]but-2-enoate maleate

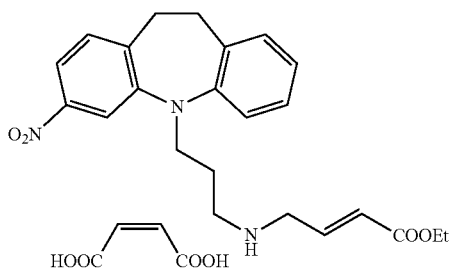

Step 1: Ethyl (E)-4-[3-(3-nitro-10,11-dihydro-5H-dibenzo[b,f]azepin-5-yl)propylamino]but-2-enoate 0.037 g (38%) of ethyl (E)-4-[3-(3-nitro-10,11-dihydro-5H-dibenzo[b,f]azepin-5-yl)propylamino]but-2-enoate were prepared according to the procedure described for Example 2, Step 1, starting from 0.078 g (0.26 mmol) of 3-(3-nitro-10,11-dihydro-5H-dibenzo[b,f]azepin-5-yl)-propan-1-amine (Intermediate 12). $^1$H NMR (CDCl$_3$) δ (ppm): 7.94-7.92 (m, 1H), 7.73 (dd, J=2.4, 8.3 Hz, 1H), 7.23-7.11 (m, 4H), 7.06-7.01 (m, 1H), 6.93 (dt, J=5.4, 15.7 Hz, 1H), 5.93 (dt, J=1.7, 15.7 Hz, 1H), 4.20 (q, J=7.3 Hz, 2H), 3.88 (t, J=6.6 Hz, 2H), 3.38 (dd, J=1.5, 5.4 Hz, 2H), 3.26-3.14 (m, 4H), 2.69 (t, J=6.8 Hz, 2H), 1.84-1.76 (m, 2H), 1.29 (t, J=7.3 Hz, 3H); MS (ESI): m/z: 410 [M+H]$^+$.

Step 2: Ethyl (E)-4-[3-(3-nitro-10,11-dihydro-5H-dibenzo[b,f]azepin-5-yl)propylamino]but-2-enoate maleate 0.039 g (87%) of ethyl (E)-4-[3-(3-nitro-10,11-dihydro-5H-dibenzo[b,f]azepin-5-yl)propylamino]but-2-enoate maleate were prepared according to the procedure described for Example 2, Step 2, starting from 0.035 g (0.09 mmol) of ethyl (E)-4-[3-(3-nitro-10,11-dihydro-5H-dibenzo[b,f]azepin-5-yl)propylamino]but-2-enoate and 0.010 g (0.09 mmol) of maleic acid. $^1$H NMR (DMSO-d$_6$) δ (ppm): 8.52 (bs, 3H), 7.94-7.87 (m, 1H), 7.77 (dd, J=2.0, 8.3 Hz, 1H), 7.41-7.35 (m, 1H), 7.27-7.17 (m, 3H), 7.07-7.00 (m, 1H), 6.74 (dt, J=6.0, 15.7 Hz, 1H), 6.17 (d, J=15.7 Hz, 1H), 6.01 (s, 2H), 4.15 (q, J=7.1 Hz, 2H), 3.90 (t, J=6.6 Hz, 2H), 3.75 (d, J=5.9 Hz, 2H), 3.23-3.07 (m, 4H), 2.94 (t, J=7.3 Hz, 2H), 1.86-1.75 (m, 2H), 1.22 (t, J=7.1 Hz, 3H); MS (ESI): m/z: 410 [M+H]⁺.

Example 15: Ethyl (E)-4-[3-(3-bromo-10,11-dihydro-5H-dibenzo[b,f]azepin-5-yl)propylamino]but-2-enoate maleate

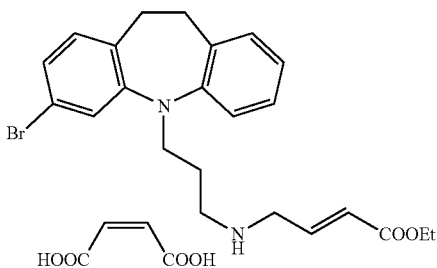

Step 1: Ethyl (E)-4-[3-(3-bromo-10,11-dihydro-5H-dibenzo[b,f]azepin-5-yl)propylamino]but-2-enoate 0.044 g (41%) of ethyl (E)-4-[3-(3-bromo-10,11-dihydro-5H-dibenzo[b,f]azepin-5-yl)propylamino]but-2-enoate were prepared according to the procedure described for Example 2, Step 1, starting from 0.089 g (0.27 mmol) of 3-(3-bromo-10,11-dihydro-5H-dibenzo[b,f]azepin-5-yl)-propan-1-amine (Intermediate 13). ¹H NMR (CDCl₃) δ (ppm): 7.21-7.18 (m, 1H), 7.18-7.07 (m, 3H), 7.02 (dd, J=2.0, 8.3 Hz, 1H), 7.00-6.91 (m, 3H), 5.93 (dt, J=1.7, 15.7 Hz, 1H), 4.20 (q, J=7.1 Hz, 2H), 3.78 (t, J=6.8 Hz, 2H), 3.37 (dd, J=1.7, 5.6 Hz, 2H), 3.16-3.06 (m, 4H), 2.68 (t, J=7.1 Hz, 2H), 1.82-1.74 (m, 2H), 1.30 (t, J=7.1 Hz, 3H); MS (ESI): m/z: 443 [M+H]⁺.

Step 2: Ethyl (E)-4-[3-(3-bromo-10,11-dihydro-5H-dibenzo[b,f]azepin-5-yl)propylamino]but-2-enoate maleate 0.046 g (85%) of ethyl (E)-4-[3-(3-bromo-10,11-dihydro-5H-dibenzo[b,f]azepin-5-yl)propylamino]but-2-enoate maleate were prepared according to the procedure described for Example 2, Step 2, starting from 0.043 g (0.1 mmol) of ethyl (E)-4-[3-(3-bromo-10,11-dihydro-5H-dibenzo[b,f]azepin-5-yl)propylamino]but-2-enoate and 0.011 g (0.1 mmol) of maleic acid. ¹H NMR (DMSO-d₆) δ (ppm): 8.52 (bs, 3H), 7.30-7.24 (m, 1H), 7.21-7.13 (m, 3H), 7.12-7.04 (m, 2H), 7.02-6.96 (m, 1H), 6.74 (dt, J=6.3, 15.8 Hz, 1H), 6.17 (d, J=15.7 Hz, 1H), 6.01 (s, 2H), 4.15 (q, J=7.1 Hz, 2H), 3.83-3.71 (m, 4H), 3.11-2.99 (m, 4H), 2.93 (t, J=7.6 Hz, 2H), 1.84-1.71 (m, 2H), 1.22 (t, J=7.1 Hz, 3H); MS (ESI): m/z: 443 [M+H]⁺.

Example 16: (E)-4-[3-(3-chloro-10,11-dihydro-5H-dibenzo[b,f]azepin-5-yl)propylamino]but-2-enoic acid 2,2,2-trifluoroacetate

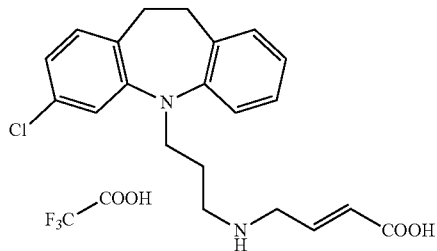 [SMILES: O=C(O)/C=C/CNCCCN1c2ccccc2CCc2ccc(Cl)cc21 ; O=C(O)C(F)(F)F]

Step 1: Ethyl (E)-4-{tert-butoxycarbonyl-[3-(3-chloro-10,11-dihydro-5H-dibenzo[b,f]azepin-5-yl)propylamino]}but-2-enoate 0.036 ml (0.26 mmol) of TEA were added to a solution of 0.091 g (0.228 mmol) of ethyl (E)-4-[3-(3-chloro-10,11-dihydro-5H-dibenzo[b,f]azepin-5-yl)propylamino]but-2-enoate (Example 4, Step 1) in dry DCM (3 ml) followed by the addition of 0.059 g (0.251 mmol) of di-tert-butyl-dicarbonate at 0° C. and the reaction mixture was stirred at r.t. for 1.5 h. Then the mixture was diluted with DCM (20 ml) and washed with brine (40 ml). The organic layer was dried (Na₂SO₄) and concentrated under vacuo. The crude was purified by flash chromatography (eluent: hexane/EtOAc from 99:1 to 90:10) to afford ethyl (E)-4-{tert-butoxycarbonyl-[3-(3-chloro-10,11-dihydro-5H-dibenzo[b,f]azepin-5-yl)propylamino]}but-2-enoate as a colorless oil (0.068 g, 61%). ¹H NMR (CDCl₃), mixture of rotamers, δ (ppm): 7.20-7.10 (m, 2H), 7.10-6.95 (m, 4H), 6.90-6.85 (m, 1H), 6.84-6.69 (bm, 1H), 5.72 (d, J=15.8 Hz, 1H), 4.20 (q, J=7.1 Hz, 2H), 3.90-3.65 (m, 4H), 3.31-3.02 (m, 6H), 1.84-1.69 (m, 2H), 1.59-1.47 (m, 9H), 1.30 (t, J=7.1 Hz, 3H); MS (ESI): m/z: 499 [M+H]⁺.

Step 2: (E)-4-{tert-butoxycarbonyl-[3-(3-chloro-10,11-dihydro-5H-dibenzo[b,f]azepin-5-yl)propylamino]}but-2-enoic acid 0.068 g, (0.136 mmol) of ethyl (E)-4-{tert-butoxycarbonyl-[3-(3-chloro-10,11-dihydro-5H-dibenzo[b,f]azepin-5-yl)propylamino]}but-2-enoate were suspended in 1:1 EtOH/water (0.4 ml) and 0.006 g (0.136 mmol) of LiOH were added. The mixture was stirred at 55-60° C. for 3 h. EtOH was removed, the residue was taken up in water (25 ml) and 2 N HCl was added at 0° C. till pH 2. The aqueous phase was extracted with EtOAc (3×40 ml), and the combined organic layers were washed with brine (50 ml), dried (Na₂SO₄) and the solvent removed under vacuo to give (E)-4-{tert-butoxycarbonyl-[3-(3-chloro-10,11-dihydro-5H-dibenzo[b,f]azepin-5-yl)propylamino]}but-2-enoic acid as a white foam (0.063 g, 98%). ¹H NMR (DMSO-d₆) δ (ppm): 12.72-11.83 (bs, 1H), 7.20-7.05 (m, 5H), 7.00-6.90 (m, 2H) 6.60 (dt, J=6.4, 15.9 Hz, 1H), 5.64 (d, J=15.9 Hz, 1H), 3.85-3.75 (bm, 2H), 3.70-3.60 (bm, 2H), 3.22-3.10 (bm, 2H), 3.10-2.98 (bm, 2H), 1.72-1.56 (bm, 2H), 1.40-1.20 (bs, 9H). MS (ESI): m/z: 471 [M+H]⁺.

Step 3: (E)-4-[3-(3-chloro-10,11-dihydro-5H-dibenzo[b,f]azepin-5-yl)propylamino]but-2-enoic acid 2,2,2-trifluoroacetate 0.071 ml (0.93 mmol) of TFA were added at 0° C. to a solution of 0.022 g (0.047 mmol) of (E)-4-{tert-butoxycarbonyl-[3-(3-chloro-10,11-dihydro-5H-dibenzo[b,f]azepin-5-yl)propylamino]}but-2-enoic acid in dry DCM (0.6 ml). The mixture was stirred at r.t. for 4 days. Volatiles were removed under vacuo and the residue was triturated and washed with ether (5×1 ml). The white sticky solid was dried under vacuo to afford (E)-4-[3-(3-chloro-10,11-dihydro-5H-dibenzo[b,f]azepin-5-yl)propylamino]but-2-enoic acid trifluoroacetate as an off-white foam (0.012 g, 54%). $^1$H NMR (DMSO-$d_6$) δ (ppm): 7.21-7.06 (m, 5H), 7.02-6.89 (m, 2H), 6.65 (dt, J=6.4 Hz, 15.7, 1H), 6.04 (d, J=15.7 Hz, 1H), 3.75 (t, J=7.3 Hz, 2H), 3.68-3.61 (d, J=6.8 Hz, 1H), 3.10-3.00 (bm, 4H), 2.87 (t, J=8.3 Hz, 2H), 1.81-1.68 (m, 2H); MS (ESI): m/z: 371 [M+H]$^+$.

Example 17: (E)-4-[4-(3-chloro-10,11-dihydro-5H-dibenzo[b,f]azepin-5-yl)butylamino]but-2-enoic acid 2,2,2-trifluoroacetate

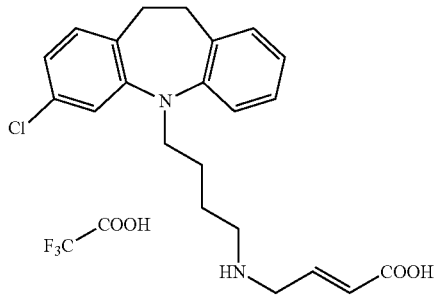 [SMILES: O=C(O)/C=C/CNCCCCN1c2ccccc2CCc2ccc(Cl)cc21 ; O=C(O)C(F)(F)F]

Step 1: Ethyl (E)-4-{tert-butoxycarbonyl-[4-(3-chloro-10,11-dihydro-5H-dibenzo[b,f]azepin-5-yl)butyl]amino}but-2-enoate 0.079 g (95%) of ethyl (E)-4-{tert-butoxycarbonyl-[4-(3-chloro-10,11-dihydro-5H-dibenzo[b,f]azepin-5-yl)butyl]amino}but-2-enoate were prepared according to the procedure described for Example 16, Step 1, starting from 0.067 g (0.162 mmol) of ethyl (E)-4-[4-(3-chloro-10,11-dihydro-5H-dibenzo[b,f]azepin-5-yl)butylamino]but-2-enoate (Example 12, Step 1) and 0.039 g (0.178 mmol) of di-tert-butyl dicarbonate. $^1$H NMR (CDCl$_3$), mixture of rotamers, δ (ppm): 7.19-6.94 (m, 6H), 6.90-6.76 (m, 2H), 5.80 (d, J=15.7 Hz, 1H), 4.20 (q, J=6.8 Hz, 2H), 3.92 and 3.82 (2 bs, 2H), 3.70 (bs, 2H), 3.20-3.03 (m, 6H), 1.54 (bs, 4H), 1.41 and 1.38 (2 bs, 9H), 1.26 (t, J=6.8 Hz, 3H); MS (ESI): m/z: 513 [M+H]$^+$.

Step 2: (E)-4-{tert-butoxycarbonyl-[4-(3-chloro-10,11-dihydro-5H-dibenzo[b,f]azepin-5-yl)butyl]amino}but-2-enoic acid 0.069 g (95%) of (E)-4-{tert-butoxycarbonyl-[4-(3-chloro-10,11-dihydro-5H-dibenzo[b,f]azepin-5-yl)butyl]amino}but-2-enoic acid were prepared according to the procedure described for Example 16, Step 2, starting from 0.079 g (0.15 mmol) of ethyl (E)-4-{tert-butoxycarbonyl-[4-(3-chloro-10,11-dihydro-5H-dibenzo[b,f]azepin-5-yl)butyl]amino}but-2-enoate and 0.004 g (0.165 mmol) of LiOH. $^1$H NMR (DMSO-$d_6$), mixture of rotamers, δ (ppm): 12.36 (bs, 1H), 7.17-7.05 (m, 5H), 6.98-6.89 (m, 2H), 6.67-6.56 (m, 1H), 5.68 (d, J=15.6 Hz, 1H), 3.81 (bs, 2H), 3.68 (t, J=6.3 Hz, 2H), 3.12-2.97 (m, 6H), 1.51-1.35 (m, 4H), 1.31 and 1.26 (2 bs, 9H); MS (ESI): m/z: 485 [M+H]$^+$.

Step 3: (E)-4-[4-(3-chloro-10,11-dihydro-5H-dibenzo[b,f]azepin-5-yl)butylamino]but-2-enoic acid 2,2,2 trifluoroacetate 0.034 g (87%) of (E)-4-[4-(3-chloro-10,11-dihydro-5H-dibenzo[b,f]azepin-5-yl)butylamino]but-2-enoic acid 2,2,2-trifluoroacetate were prepared according to the procedure described for Example 16, Step 3, starting from 0.034 g (0.07 mmol) of E)-4-{tert-butoxycarbonyl-[4-(3-chloro-10,11-dihydro-5H-dibenzo[b,f]azepin-5-yl)butyl]amino}but-2-enoic acid and 0.108 ml (1.4 mmol) of TFA. $^1$H NMR (DMSO-$d_6$), δ (ppm): 12.71 (bs, 1H), 8.69 (bs, 2H), 7.19-7.12 (m, 4H), 7.10 (d, J=8.3 Hz, 1H), 7.00-6.95 (m, 1H), 6.94 (dd, J=2.0, 8.3 Hz, 1H), 6.70 (dt, J=6.4, 15.7 Hz, 1H), 6.08 (d, J=15.7 Hz, 1H), 3.77-3.66 (m, 4H), 3.11-3.01 (m, 4H), 2.85 (bs, 2H), 1.63-1.45 (m, 4H); MS (ESI): m/z: 385 [M+H]$^+$.

Example 18: (E)-4-{[3-(3-chloro-10,11-dihydro-5H-dibenzo[b,f]azepin-5-yl)propyl]amino}but-2-enamide hydrochloride

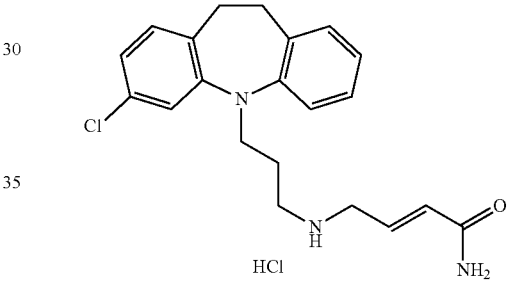

Step 1: (E)-4-{tert-butoxycarbonyl-[3-(3-chloro-10,11-dihydro-5H-dibenzo[b,f]azepin-5-yl)propylamino]}but-2-enamide 0.009 ml (0.064 mmol) of TEA were added to a solution of 0.015 g (0.032 mmol) of (E)-4-{tert-butoxycarbonyl-[3-(3-chloro-10,11-dihydro-5H-dibenzo[b,f]azepin-5-yl)propylamino]}but-2-enoic acid (Example 16, Step 2) in dry DCM (0.2 ml) followed by the addition of 0.006 g (0.048 mmol) of HOBt and 0.009 g (0.048 mmol) of EDC at 0° C. The resulting mixture was stirred at 0° C. for 30 min; then 0.027 ml of ammonia (7N in MeOH, 0.191 mmol) was added at 0° C. and the mixture was stirred at r.t. overnight. The mixture was diluted with DCM (20 ml) and washed with saturated aqueous NH$_4$Cl (30 ml) and then with saturated aqueous NaHCO$_3$ (30 ml). The organic layer was dried (Na$_2$SO$_4$) and the solvent was removed under vacuo. The crude was purified by flash chromatography (eluent: hexane/EtOAc from 80:20 to 0:100) to afford (E)-4-{tert-butoxycarbonyl-[3-(3-chloro-10,11-dihydro-5H-dibenzo[b,f]azepin-5-yl)propylamino]}but-2-enamide as a colorless sticky oil (0.022 g, 61%). $^1$H NMR (DMSO-$d_6$), δ (ppm): 7.45 (bs, 1H), 7.19-7.05 (m, 5H), 7.02-6.88 (m, 3H), 6.42 (dt, J=4.9, 15.7 Hz, 1H), 5.80 (d, J=15.7 Hz, 1H), 3.80-3.61 (bm, 4H), 3.21-2.97 (bm, 6H), 1.64 (bm, 2H), 1.28 (bs, 9H); MS (ESI): m/z: 470 [M+H]$^+$.

Step 2: (E)-4-{[3-(3-chloro-10,11-dihydro-5H-dibenzo[b,f]azepin-5-yl)propyl]amino}but-2-enamide 0.022 g (0.046 mmol) of (E)-4-{tert-butoxycarbonyl-[3-(3-chloro-10,11-dihydro-5H-dibenzo[b,f]azepin-5-yl)propylamino]}but-2-enamide were dissolved in 2:1 1,4-dioxane/MeOH (0.06 ml) and 0.114 ml of HCl (4N in 1,4-dioxane, 0.457 mmol) were added at 0° C. The mixture was stirred overnight at r.t. Volatiles were removed under vacuo and the residue was treated with 0.5 ml of ammonia (7 N in MeOH). Solvent was evaporated and the crude was purified by flash chromatography (eluent: DCM/MeOH/7 N NH$_3$-MeOH 96:2:2) to afford (E)-4-{[3-(3-chloro-10,11-dihydro-5H-dibenzo[b,f]azepin-5-yl)propyl]amino}but-2-enamide as a colourless sticky solid (0.010 g, 59%). $^1$H NMR (DMSO-d6), δ (ppm): 7.34 (bs, 1H), 7.18-7.04 (m, 5H), 7.00-6.83 (m, 3H), 6.54 (dt, J=6.4 Hz, 15.7, 1H), 5.92 (d, J=15.7 Hz, 1H), 3.72 (t, J=6.8 Hz, 2H), 3.16 (d, J=4.4 Hz, 2H), 3.08-2.98 (m, 4H), 2.49-2.44 (m, 2H), 1.57 (t, J=6.6 Hz, 2H); MS (ESI): m/z: 370 [M+H]$^+$.

Step 3: (E)-4-{[3-(3-chloro-10,11-dihydro-5H-dibenzo[b,f]azepin-5-yl)propyl]amino}but-2-enamide hydrochloride 0.006 g (0.017 mmol) of (E)-4-{[3-(3-chloro-10,11-dihydro-5H-dibenzo[b,f]azepin-5-yl)propyl]amino}but-2-enamide were suspended in Et$_2$O (0.15 ml) and 0.043 ml of HCl (2M in Et$_2$O, 0.085 mmol) were added at 0° C.; after stirring at this temperature for 15 min. further Et$_2$O (0.5 ml) was added and the white solid was triturated with Et$_2$O. Solvent was decanted off and then the residue was dried at 40° C. under vacuo to afford (E)-4-{[3-(3-chloro-10,11-dihydro-5H-dibenzo[b,f]azepin-5-yl)propyl]amino}but-2-enamide hydrochloride as a white powder (0.006 g, 84%). $^1$H NMR (DMSO-d$_6$), δ (ppm): 9.03-7.97 (bs, 2H), 7.62-7.49 (bs, 1H), 7.21-7.06 (m, 6H), 7.02-6.92 (m, 2H), 6.54 (dt, J=6.4 Hz, 15.7, 1H), 6.10 (d, J=15.7 Hz, 1H), 3.77 (t, J=6.8 Hz, 2H), 3.65-3.51 (bm, 2H), 3.10-3.00 (bm, 4H), 2.89-2.76 (bm, 2H), 1.82-1.68 (bm, 2H); MS (ESI): m/z: 370 [M+H]$^+$.

Example 19: (E)-4-{[3-(3-chloro-10,11-dihydro-5H-dibenzo[b,f]azepin-5-yl)propyl]amino}-N-methyl-but-2-enamide hydrochloride

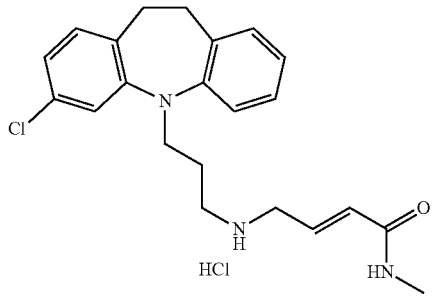 [SMILES: CNC(=O)/C=C/CNCCCN1c2ccccc2CCc2ccc(Cl)cc21 ; Cl]

Step 1: (E)-4-{tert-butoxycarbonyl-[3-(3-chloro-10,11-dihydro-5H-dibenzo[b,f]azepin-5-yl)propyl]amino}-N-methyl-but-2-enamide 0.012 ml (0.089 mmol) of TEA were added to a solution of 0.021 g (0.045 mmol) of (E)-4-{tert-butoxycarbonyl-[3-(3-chloro-10,11-dihydro-5H-dibenzo[b,f]azepin-5-yl)propylamino]}but-2-enoic acid (Example 16, Step 2) in dry DCM (0.2 ml) followed by the addition of 0.013 g (0.067 mmol) of EDC at 0° C. The resulting mixture was stirred at 0° C. for 1 h; then 0.027 ml of methylamine (2M in THF, 0.054 mmol) were added at and the mixture was stirred at r.t. for 24 h. The mixture was diluted with DCM (20 ml) and washed first with a 5% solution of citric acid (30 ml) and then with brine (40 ml). The organic layer was dried (Na$_2$SO$_4$) and the solvent was removed under vacuo. The crude was purified by flash chromatography (eluent: hexane/acetone from 93:7 to 40:60) to afford (E)-4-{tert-butoxycarbonyl-[3-(3-chloro-10,11-dihydro-5H-dibenzo[b,f]azepin-5-yl)propyl]amino}-N-methyl-but-2-enamide as a colorless sticky oil (0.007 g, 31%). $^1$H NMR (DMSO-d$_6$), δ (ppm): 8.00-7.85 (bs, 1H), 7.19-7.06 (m, 5H), 7.00-6.89 (m, 2H), 6.41 (dt, J=5.4, 15.7 Hz, 1H), 5.80 (d, J=15.7 Hz, 1H), 3.86-3.57 (bm, 4H), 3.20-2.98 (bm, 6H), 2.61 (d, J=4.4 Hz, 3H), 1.71-1.54 (bm, 2H), 1.28 (bs, 9H); MS (ESI): m/z: 484 [M+H]$^+$.

Step 2: (E)-4-{[3-(3-chloro-10,11-dihydro-5H-dibenzo[b,f]azepin-5-yl)propyl]amino}-N-methyl-but-2-enamide hydrochloride 0.006 g (0.012 mmol) of (E)-4-{tert-butoxycarbonyl-[3-(3-chloro-10,11-dihydro-5H-dibenzo[b,f]azepin-5-yl)propyl]amino}-N-methyl-but-2-enamide were dissolved in 5:1 1,4-dioxane/MeOH (0.06 ml) and 0.031 ml of HCl (4N in 1,4-dioxane, 0.124 mmol) were added at 0° C. The mixture was then stirred at r.t. overnight. Volatiles were removed under vacuo and the residue was triturated and washed with Et$_2$O (4×0.7 ml) to afford (E)-4-{[3-(3-chloro-10,11-dihydro-5H-dibenzo[b,f]azepin-5-yl)propyl]amino}-N-methyl-but-2-enamide hydrochloride as a white powder (0.005 g, 99%). $^1$H NMR (DMSO-d$_6$), δ (ppm): 8.96-8.66 (bs, 2H), 8.22-8.07 (q, J=4.9 Hz, 1H), 7.22-7.06 (m, 5H), 7.04-6.93 (m, 2H), 6.51 (dt, J=6.8, 15.7 Hz, 1H), 6.14 (d, J=15.7 Hz, 1H), 3.78 (t, J=6.6 Hz, 2H), 3.66 (d, J=6.4 Hz, 2H) 3.11-3.00 (bm, 4H), 2.96-2.83 (bm, 2H), 2.65 (d, J=4.9 Hz, 3H), 1.85-1.72 (bm, 2H); MS (ESI): m/z: 384 [M+H]$^+$.

Example 20: (E)-4-{[3-(3-chloro-10,11-dihydro-5H-dibenzo[b,f]azepin-5-yl)propyl]amino}-N,N-dimethyl-but-2-enamide hydrochloride

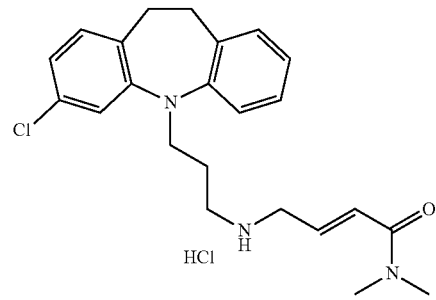 [SMILES: CN(C)C(=O)/C=C/CNCCCN1c2ccccc2CCc2ccc(Cl)cc21 ; Cl]

Step 1: (E)-4-{tert-butoxycarbonyl-[3-(3-chloro-10,11-dihydro-5H-dibenzo[b,f]azepin-5-yl)propyl]amino}-N,N-dimethyl-but-2-enamide 0.013 g (60%) of (E)-4-{tert-butoxycarbonyl-[3-(3-chloro-10,11-dihydro-5H-dibenzo[b,f]azepin-5-yl)propyl]

amino}-N,N-dimethyl-but-2-enamide were prepared according to the procedure described for Example 18, Step 1, starting from 0.021 g (0.044 mmol) of (E)-4-{tert-butoxycarbonyl-[3-(3-chloro-10,11-dihydro-5H-dibenzo[b,f]azepin-5-yl)propylamino]}but-2-enoic acid (Example 16, Step 2) and 0.026 ml of dimethylamine (2M in THF, 0.052 mmol). $^1$H NMR (DMSO-d$_6$) δ (ppm): 7.19-7.05 (m, 5H), 7.00-6.86 (m, 2H), 6.49-6.38 (bm, 1H), 6.36-6.23 (bm, 1H), 3.87-3.73 (bm, 2H), 3.71-3.62 (bm, 2H), 3.19-3.11 (bm, 2H), 3.09-2.88 (bm, 4H), 2.94 (s, 3H), 2.84 (s, 3H), 1.71-1.57 (bm, 2H), 1.29 (bs, 9H); MS (ESI): m/z: 498 [M+H]$^+$.

Step 2: (E)-4-{[3-(3-chloro-10,11-dihydro-5H-dibenzo[b,f]azepin-5-yl)propyl]amino}-N,N-dimethyl-but-2-enamide hydrochloride 0.009 g (86%) of (E)-4-{[3-(3-chloro-10,11-dihydro-5H-dibenzo[b,f]azepin-5-yl)propyl]amino}-N,N-dimethyl-but-2-enamide hydrochloride were prepared according to the procedure described for Example 19, Step 2, starting from 0.012 g (0.024 mmol) of (E)-4-{tert-butoxycarbonyl-[2-(3-chloro-10,11-dihydro-5H-dibenzo[b,f]azepin-5-yl)propyl]amino}-N,N-dimethyl-but-2-enamide and 0.060 ml of HCl (4N in 1,4-dioxane, 0.241 mmol). $^1$H NMR (DMSO-d$_6$) δ (ppm): 8.91 (bs, 2H), 7.22-7.05 (m, 5H), 7.22-6.90 (m, 2H), 6.78 (d, J=15.2 Hz, 1H), 6.52 (dt, J=5.9, 15.2 Hz, 1H), 3.79 (t, J=6.6 Hz, 2H), 3.68 (d, J=6.4 Hz, 2H), 3.11-2.97 (m, 7H), 2.94-2.83 (m, 5H), 1.86-1.75 (m, 2H); MS (ESI): m/z: 398 [M+H]$^+$.

Example 21: (E)-4-{[3-(3-chloro-10,11-dihydro-5H-dibenzo[b,f]azepin-5-yl)propyl]amino}-N-phenyl-but-2-enamide hydrochloride

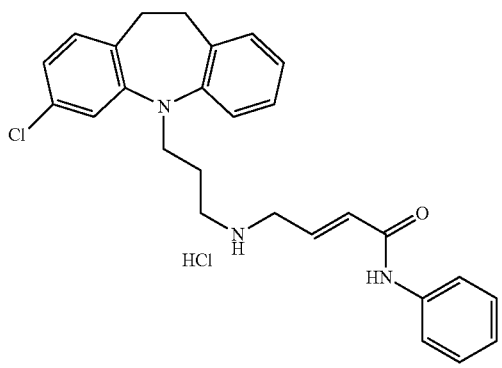 [SMILES: O=C(/C=C/CNCCCN1c2ccccc2CCc2ccc(Cl)cc21)Nc1ccccc1 ; Cl]

Step 1: (E)-4-{tert-butoxycarbonyl-[3-(3-chloro-10,11-dihydro-5H-dibenzo[b,f]azepin-5-yl)propyl]amino}-N-phenyl-but-2-enamide 0.045 g (35%) of (E)-4-{tert-butoxycarbonyl-[3-(3-chloro-10,11-dihydro-5H-dibenzo[b,f]azepin-5-yl)propyl]amino}-N-phenyl-but-2-enamide were prepared according to the procedure described for Example 19, Step 1, starting from 0.110 g (0.233 mmol) of (E)-4-{tert-butoxycarbonyl-[3-(3-chloro-10,11-dihydro-5H-dibenzo[b,f]azepin-5-yl)propylamino]}but-2-enoic acid (Example 16, Step 2) and 0.025 ml (0.279 mmol) of aniline. $^1$H NMR (DMSO-d$_6$) δ (ppm): 10.11-9.95 (bs, 1H), 7.66-7.57 (m, 2H), 7.34-7.26 (m, 2H), 7.19-7.00 (m, 6H), 6.99-7.00 (m, 2H), 6.65 (dt, J=4.9, 15.7 Hz, 1H), 6.04 (d, J=15.7 Hz, 1H), 3.90-3.80 (m, 2H), 3.74-3.63 (bm, 2H), 3.25-3.13 (bm, 2H), 3.12-2.96 (m, 4H), 1.76-1.59 (bm, 2H), 1.39-1.24 (bs, 9H); MS (ESI): m/z: 546 [M+H]$^+$.

Step 2: (E)-4-{[3-(3-chloro-10,11-dihydro-5H-dibenzo[b,f]azepin-5-yl)propyl]amino}-N-phenyl-but-2-enamide 0.021 g (84%) of (E)-4-{[3-(3-chloro-10,11-dihydro-5H-dibenzo[b,f]azepin-5-yl)propyl]amino}-N-phenyl-but-2-enamide were prepared according to the procedure described for Example 18, Step 2, starting from 0.045 g (0.082 mmol) of (E)-4-{tert-butoxycarbonyl-[3-(3-chloro-10,11-dihydro-5H-dibenzo[b,f]azepin-5-yl)propyl]amino}-N-phenyl-but-2-enamide and 0.206 ml of HCl (4 N in 1,4-dioxane, 0.824 mmol). $^1$H NMR (DMSO-d$_6$) δ (ppm): 9.96 (s, 1H), 7.66-7.58 (m, 2H), 7.33-7.25 (m, 2H), 77.19-7.00 (m, 6H), 6.99-6.88 (m, 2H), 6.74 (dt, J=5.4, 15.7 Hz, 1H), 6.19 (d, J=15.7 Hz, 1H), 3.74 (t, J=6.8 Hz, 2H), 3.24 (d, J=4.9 Hz, 2H), 3.10-2.97 (m, 4H), 2.55-2.48 (m, 2H), 1.65-1.53 (m, 2H); MS (ESI): m/z: 446 [M+H]$^+$.

Step 3: (E)-4-{[3-(3-chloro-10,11-dihydro-5H-dibenzo[b,f]azepin-5-yl)propyl]amino}-N-phenyl-but-2-enamide hydrochloride 0.009 g (95%) of (E)-4-{[3-(3-chloro-10,11-dihydro-5H-dibenzo[b,f]azepin-5-yl)propyl]amino}-N-phenyl-but-2-enamide hydrochloride were prepared according to the procedure described for Example 18, Step 3, starting from 0.009 g (0.020 mmol) of (E)-4-{[3-(3-chloro-10,11-dihydro-5H-dibenzo[b,f]azepin-5-yl)propyl]amino}-N-phenyl-but-2-enamide and 0.051 ml of HCl (2 N in Et$_2$O, 0.102 mmol). $^1$H NMR (DMSO-d$_6$) δ (ppm): 10.37 (s, 1H), 8.97 (bs, 2H), 7.70-7.62 (m, 2H), 7.35-7.28 (m, 2H), 7.22-7.03 (m, 6H), 7.01-6.90 (m, 2H), 6.70 (dt, J=6.8, 15.7 Hz, 1H), 6.40 (d, J=15.7 Hz, 1H), 3.84-3.68 (m, 4H), 3.11-2.99 (m, 4H), 2.94 (bm, 2H), 1.89-1.75 (m, 2H); MS (ESI): m/z: 446 [M+H]$^+$.

Example 22: (E)-4-{[3-(3-chloro-10,11-dihydro-5H-dibenzo[b,f]azepin-5-yl)propyl]amino}but-2-enenitrile hydrochloride

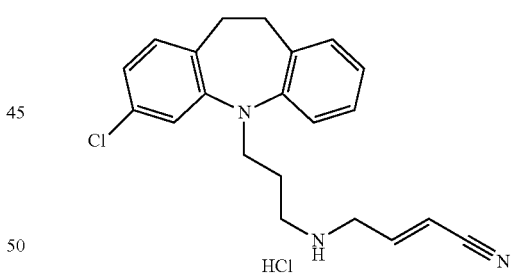

Step 1: (E)-4-{tert-butoxycarbonyl-[3-(3-chloro-10,11-dihydro-5H-dibenzo[b,f]azepin-5-yl)propylamino]}but-2-enenitrile 0.020 ml (0.170 mmol) of ethyl dichlorophosphate were added to a solution of 0.033 g (0.071 mmol) of (E)-4-{tert-butoxycarbonyl-[3-(3-chloro-10,11-dihydro-5H-dibenzo[b,f]azepin-5-yl)propylamino]}but-2-enamide (Example 18, Step 1) in dry DCM (0.4 ml) followed by 0.032 ml (0.223 mmol) of DBU at 0° C. The resulting mixture was stirred at r.t. for 6 h. The reaction was diluted with water (10 ml) and acidified with 2 N HCl till pH 3. The aqueous phase was extracted with DCM (3×25 ml) and the combined organic layers were dried (Na$_2$SO$_4$) and concentrated under vacuo.

The crude was purified by flash chromatography (eluent: hexane/EtOAc from 97:3 to 70:30) to afford (E)-4-{tert-butoxycarbonyl-[3-(3-chloro-10,11-dihydro-5H-dibenzo[b,f]azepin-5-yl)propylamino]}but-2-enenitrile as a colorless sticky oil (0.037 g, 74%). $^1$H NMR (DMSO-$d_6$) 7.19-7.04 (m, 5H), 7.02-6.86 (m, 2H), 6.75 (dt, J=4.9, 16.1 Hz, 1H), 5.58 (d, J=16.1 Hz, 1H), 3.90-3.75 (bm, 2H), 3.72-3.61 (bm, 2H), 3.21-3.10 (bm, 2H), 3.10-2.99 (m, 4H), 1.70-1.55 (bm, 2H), 1.28 (bs, 9H); MS (ESI): m/z: 452 [M+H]$^+$.

Step 2: (E)-4-{[3-(3-chloro-10,11-dihydro-5H-dibenzo[b,f]azepin-5-yl)propyl]amino}but-2-enenitrile 0.017 g (60%) of (E)-4-{[3-(3-chloro-10,11-dihydro-5H-dibenzo[b,f]azepin-5-yl)propyl]amino}but-2-enenitrile were prepared according to the procedure described for Example 18, Step 2, starting from 0.036 g (0.080 mmol) of (E)-4-{tert-butoxycarbonyl-[3-(3-chloro-10,11-dihydro-5H-dibenzo[b,f]azepin-5-yl)propylamino]}but-2-enenitrile and 0.199 ml of HCl (4 N in 1,4-dioxane, 0.796 mmol). $^1$H NMR (DMSO-$d_6$) δ (ppm): 7.19-7.04 (m, 5H), 7.00-6.88 (m, 2H), 6.81 (dt, J=4.7, 16.5 Hz, 1H), 5.67 (d, J=16.1 Hz, 1H), 3.73 (t, J=6.6 Hz, 2H), 3.24-3.19 (m, 2H), 3.10-2.99 (m, 4H), 2.45 (t, J=6.8 Hz, 2H), 1.60-1.51 (m, 2H); MS (ESI): m/z: 352 [M+H]$^+$.

Step 3: (E)-4-{[3-(3-chloro-10,11-dihydro-5H-dibenzo[b,f]azepin-5-yl)propyl]amino}but-2-enenitrile hydrochloride 0.015 g (84%) of (E)-4-{[3-(3-chloro-10,11-dihydro-5H-dibenzo[b,f]azepin-5-yl)propyl]amino}but-2-enenitrile hydrochloride were prepared according to the procedure described for Example 18, Step 3, starting from 0.016 g (0.045 mmol) of (E)-4-{[3-(3-chloro-10,11-dihydro-5H-dibenzo[b,f]azepin-5-yl)propyl]amino}but-2-enenitrile and 0.114 ml of HCl (2 N in Et$_2$O, 0.227 mmol). $^1$H NMR (DMSO-$d_6$) δ (ppm): 8.91 (bs, 2H), 7.21-7.06 (m, 5H), 7.02-6.93 (m, 2H), 6.78 (dt, J=6.5, 16.6 Hz, 1H), 6.07 (d, J=16.6 Hz, 1H), 3.83-3.68 (m, 4H), 3.12-2.99 (m, 4H), 2.97-2.86 (bm, 2H), 1.84-1.71 (m, 2H); MS (ESI): m/z: 352 [M+H]$^+$.

Example 23: Ethyl (E)-4-{[3-(3-chloro-11-oxo-10,11-dihydro-5H-dibenzo[b,e][1,4]diazepin-5-yl)propyl]amino}but-2-enoate maleate

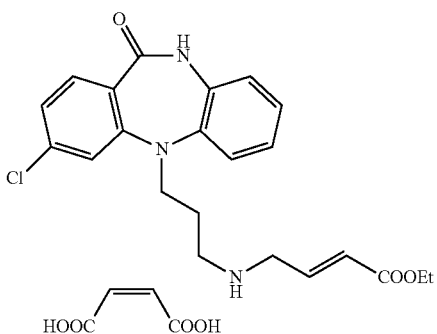

Step 1: Ethyl (E)-4-{[3-(3-chloro-11-oxo-10,11-dihydro-5H-dibenzo[b,e][1,4]diazepin-5-yl)propyl]amino}but-2-enoate 0.023 g (20%) of ethyl (E)-4-{[3-(3-chloro-11-oxo-10,11-dihydro-5H-dibenzo[b,e][1,4]diazepin-5-yl)propyl]amino}but-2-enoate were prepared according to the procedure described for Example 2, Step 1, starting from 0.087 g (0.29 mmol) of 5-(3-aminopropyl)-3-chloro-5,10-dihydro-11H-dibenzo[b,e][1,4]diazepin-11-one (Intermediate 14). $^1$H NMR (DMSO-$d_6$) δ (ppm): 10.29 (s, 1H), 7.65-7.53 (m, 1H), 7.29-7.25 (m, 1H), 7.22-7.18 (m, 1H), 7.16-7.09 (m, 2H), 7.07-7.02 (m, 2H), 6.83 (dt, J=5.1, 15.7 Hz, 1H), 5.91 (d, J=15.7 Hz, 1H), 4.09 (q, J=7.1 Hz, 2H), 3.77 (bs, 2H), 3.23 (dd, J=1.4, 5.4 Hz, 2H), 2.53 (t, J=6.3 Hz, 2H), 1.65-1.55 (m, 2H), 1.19 (t, J=7.1 Hz, 3H); MS (ESI): m/z: 414 [M+H]$^+$.

Step 2: Ethyl (E)-4-{[3-(3-chloro-11-oxo-10,11-dihydro-5H-dibenzo[b,e][1,4]diazepin-5-yl)propyl]amino}but-2-enoate maleate 0.023 g (88%) of ethyl (E)-4-{[3-(3-chloro-11-oxo-10,11-dihydro-5H-dibenzo[b,e][1,4]diazepin-5-yl)propyl]amino}but-2-enoate maleate were prepared according to the procedure described for Example 2, Step 2, starting from 0.020 g (0.05 mmol) of ethyl (E)-4-{[3-(3-chloro-11-oxo-10,11-dihydro-5H-dibenzo[b,e][1,4]diazepin-5-yl)propyl]amino}but-2-enoate and 0.006 g (0.05 mmol) of maleic acid. $^1$H NMR (DMSO-$d_6$) δ (ppm): 10.33 (s, 1H), 8.59 (bs, 3H), 7.67-7.58 (m, 1H), 7.33-7.28 (m, 1H), 7.24-7.21 (m, 1H), 7.19 (dd, J=1.7, 8.6 Hz, 1H), 7.16-7.12 (m, 1H), 7.11-7.06 (m, 2H), 6.75 (dt, J=6.0, 15.7 Hz, 1H), 6.18 (d, J=15.7 Hz, 1H), 6.02 (s, 2H), 4.15 (q, J=7.3 Hz, 2H), 3.91-3.71 (m, 4H), 2.97 (t, J=7.3 Hz, 2H), 1.87-1.77 (m, 2H), 1.21 (t, J=7.3 Hz, 3H); MS (ESI): m/z: 414 [M+H]$^+$.

Example 24: Ethyl (E)-4-{[4-(3-chloro-11-oxo-10,11-dihydro-5H-dibenzo[b,e][1,4]diazepin-5-yl)butyl]amino}but-2-enoate maleate

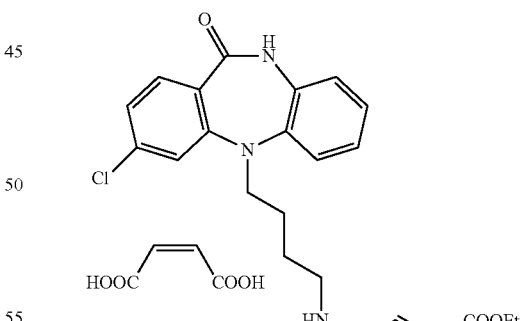

Step 1: Ethyl (E)-4-{[4-(3-chloro-11-oxo-10,11-dihydro-5H-dibenzo[b,e][1,4]diazepin-5-yl)butyl]amino}but-2-enoate 0.043 g (50%) of ethyl (E)-4-{[4-(3-chloro-11-oxo-10,11-dihydro-5H-dibenzo[b,e][1,4]diazepin-5-yl)butyl]amino}but-2-enoate were prepared according to the procedure described for Example 2, Step 1, starting from 0.069 g (0.22 mmol) of 5-(4-aminobutyl)-3-chloro-5,10-dihydro- 11H-dibenzo[b,e][1,4]diazepin-11-one (Intermediate 15). ¹H NMR (CDCl₃) δ (ppm): 7.86 (bs, 1H), 7.78-7.73 (m, 1H), 7.19-7.03 (m, 5H), 7.01-6.90 (m, 2H), 5.94 (d, J=15.7 Hz, 1H), 4.20 (q, J=7.3 Hz, 2H), 3.74 (bs, 2H), 3.37 (d, J=4.9 Hz, 2H), 2.60 (bs, 2H), 1.72-1.52 (m, 5H), 1.29 (t, J=7.3 Hz, 3H); MS (ESI): m/z: 428 [M+H]⁺.

Step 2: Ethyl (E)-4-{[4-(3-chloro-11-oxo-10,11-dihydro-5H-dibenzo[b,e][1,4]diazepin-5-yl)butyl]amino}but-2-enoate maleate 0.045 g (88%) of ethyl (E)-4-{[4-(3-chloro-11-oxo-10,11-dihydro-5H-dibenzo[b,e][1,4]diazepin-5-yl)butyl]amino}but-2-enoate maleate were prepared according to the procedure described for Example 2, Step 2, starting from 0.040 g (0.09 mmol) of ethyl (E)-4-{[4-(3-chloro-11-oxo-10,11-dihydro-5H-dibenzo[b,e][1,4]diazepin-5-yl)butyl]amino}but-2-enoate and 0.011 g (0.09 mmol) of maleic acid. ¹H NMR (DMSO-d₆) δ (ppm): 10.32 (s, 1H), 8.58 (bs, 3H), 7.66-7.53 (m, 1H), 7.30-7.28 (m, 1H), 7.23-7.19 (m, 1H), 7.17 (dd, J=2.0, 8.3 Hz, 1H), 7.15-7.11 (m, 1H), 7.09-7.05 (m, 2H), 6.76 (dt, J=6.4, 15.7 Hz, 1H), 6.18 (d, J=15.7 Hz, 1H), 6.02 (s, 2H), 4.14 (q, J=7.3 Hz, 2H), 3.84-3.69 (m, 4H), 2.89 (t, J=7.1 Hz, 2H), 1.69-1.50 (m, 4H), 1.21 (t, J=7.3 Hz, 3H); MS (ESI): m/z: 428 [M+H]⁺.

Example 25: Ethyl (E)-4-{[3-(11-oxo-3-(trifluoromethyl)-10,11-dihydro-5H-dibenzo[b,e][1,4]diazepin-5-yl)propyl]amino}but-2-enoate maleate

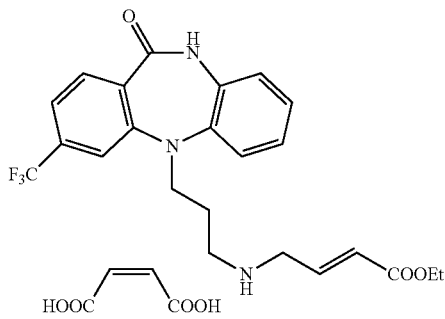

Step 1: Ethyl (E)-4-{[3-(11-oxo-3-(trifluoromethyl)-10,11-dihydro-5H-dibenzo[b,e][1,4]diazepin-5-yl)propyl]amino}but-2-enoate 0.052 g (42%) of ethyl (E)-4-{[3-(11-oxo-3-(trifluoromethyl)-10,11-dihydro-5H-dibenzo[b,e][1,4]diazepin-5-yl)propyl]amino}but-2-enoate were prepared according to the procedure described for Example 2, Step 1, starting from 0.103 g (0.31 mmol) of 5-(3-aminopropyl)-3-(trifluoromethyl)-5,10-dihydro-11H-dibenzo[b,e][1,4]diazepin-11-one (Intermediate 17). ¹H NMR (DMSO-d₆) δ (ppm): 10.45 (s, 1H), 7.82-7.75 (m, 1H), 7.51-7.47 (m, 1H), 7.45-7.40 (m, 1H), 7.27-7.22 (m, 1H), 7.16-7.09 (m, 1H), 7.09-7.05 (m, 2H), 6.83 (dt, J=5.4, 16.1 Hz, 1H), 5.90 (d, J=16.1 Hz, 1H), 4.09 (q, J=7.3 Hz, 2H), 3.84 (t, J=6.8 Hz, 2H), 3.22 (dd, J=1.5, 5.4 Hz, 2H), 2.52 (t, J=6.6 Hz, 2H), 1.65-1.55 (m, 2H), 1.19 (t, J=7.1 Hz, 3H); MS (ESI): m/z: 448 [M+H]⁺.

Step 2: Ethyl (E)-4-{[3-(11-oxo-3-(trifluoromethyl)-10,11-dihydro-5H-dibenzo[b,e][1,4]diazepin-5-yl)propyl]amino}but-2-enoate maleate 0.059 g (97%) of ethyl (E)-4-{[3-(11-oxo-3-(trifluoromethyl)-10,11-dihydro-5H-dibenzo[b,e][1,4]diazepin-5-yl)propyl]amino}but-2-enoate maleate were prepared according to the procedure described for Example 2, Step 2, starting from 0.048 g (0.107 mmol) of ethyl (E)-4-{[3-(11-oxo-3-(trifluoromethyl)-10,11-dihydro-5H-dibenzo[b,e][1,4]diazepin-5-yl)propyl]amino}but-2-enoate and 0.013 g (0.107 mmol) of maleic acid. ¹H NMR (DMSO-d₆) δ (ppm): 10.49 (s, 1H), 8.55 (bs, 3H), 7.87-7.75 (m, 1H), 7.54-7.50 (m, 1H), 7.49-7.42 (m, 1H), 7.30-7.24 (m, 1H), 7.19-7.06 (m, 3H), 6.75 (dt, J=6.2, 15.9 Hz, 1H), 6.17 (d, J=15.8 Hz, 1H), 6.02 (s, 2H), 4.14 (q, J=7.2 Hz, 2H), 3.91 (t, J=6.6 Hz, 2H), 3.75 (d, J=5.9 Hz, 2H), 2.97 (t, J=7.3 Hz, 2H), 1.89-1.76 (m, 2H), 1.21 (t, J=7.2 Hz, 3H); MS (ESI): m/z: 448 [M+H]⁺.

Example 26: Ethyl (E)-4-{[3-(7-chloro-11-oxo-10,11-dihydro-5H-dibenzo[b,e][1,4]diazepin-5-yl)propyl]amino}but-2-enoate maleate

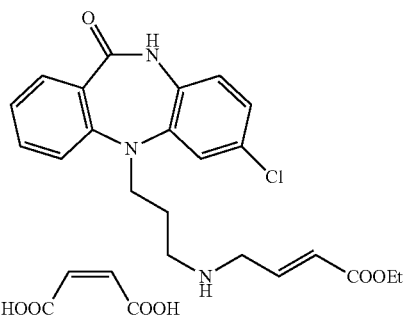

Step 1: Ethyl (E)-4-{[3-(7-chloro-11-oxo-10,11-dihydro-5H-dibenzo[b,e][1,4]diazepin-5-yl)propyl]amino}but-2-enoate 0.035 g (36%) of ethyl (E)-4-{[3-(7-chloro-11-oxo-3-10,11-dihydro-5H-dibenzo[b,e][1,4]diazepin-5-yl)propyl]amino}but-2-enoate were prepared according to the procedure described for Example 2, Step 1, starting from 0.071 g (0.23 mmol) of 5-(3-aminopropyl)-7-chloro-5,10-dihydro-11H-dibenzo[b,e][1,4]diazepin-11-one (Intermediate 19). ¹H NMR (DMSO-d₆) δ (ppm): 10.28 (s, 1H), 7.58 (dd, J=1.5, 7.8 Hz, 1H), 7.53-7.46 (m, 1H), 7.26-7.24 (m, 1H), 7.22-7.18 (m, 1H), 7.13-7.07 (m, 2H), 7.05-7.01 (m, 1H), 6.84 (dt, J=4.9, 15.7 Hz, 1H), 5.91 (d, J=15.7 Hz, 1H), 4.09 (q, J=7.2 Hz, 2H), 3.86-3.67 (m, 2H), 3.23 (dd, J=1.5, 4.9 Hz, 2H), 2.53 (t, J=6.8 Hz, 2H), 1.64-1.57 (m, 2H), 1.19 (t, J=7.1 Hz, 3H); MS (ESI): m/z: 414 [M+H]⁺.

Step 2: Ethyl (E)-4-{[3-(7-chloro-11-oxo-10,11-dihydro-5H-dibenzo[b,e][1,4]diazepin-5-yl)propyl]amino}but-2-enoate maleate 0.035 g (85%) of ethyl (E)-4-{[3-(7-chloro-11-oxo-10,11-dihydro-5H-dibenzo[b,e][1,4]diazepin-5-yl)propyl]amino}but-2-enoate maleate were prepared according to the procedure described for Example 2, Step 2, starting from 0.032 g (0.077 mmol) of ethyl (E)-4-{[3-(7-chloro-11-oxo-10,11-dihydro-5H-dibenzo[b,e][1,4]diazepin-5-yl)propyl]amino}but-2-enoate and 0.009 g (0.077 mmol) of maleic acid. ¹H NMR (DMSO-d₆) δ (ppm): 10.33 (s, 1H), 8.58 (bs, 3H), 7.62 (dd, J=1.7, 7.9 Hz, 1H), 7.56-7.49 (m, 1H), 7.28 (d, J=2.2 Hz, 1H), 7.25-7.21 (m, 1H), 7.17-7.11 (m, 2H), 7.08 (d, J=8.4 Hz, 1H), 6.75 (dt, J=6.2, 16.1 Hz, 1H), 6.18

(dt, J=1.5, 16.1 Hz, 1H), 6.02 (s, 2H), 4.15 (q, J=7.2 Hz, 2H), 3.90-3.77 (m, 2H), 3.76-3.73 (m, 2H), 3.01-2.93 (m, 2H), 1.86-1.78 (m, 2H), 1.21 (t, J=7.2 Hz, 3H); MS (ESI): m/z: 414 [M+H]$^+$.

Example 27: Ethyl (E)-4-{[3-(3-chloro-10-methyl-11-oxo-10,11-dihydro-5H-dibenzo[b,e][1,4]diazepin-5-yl)propyl]amino}but-2-enoate maleate

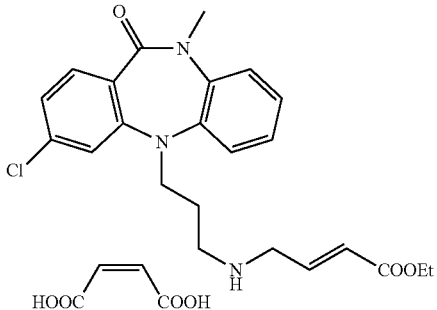

Step 1: Ethyl (E)-4-{[3-(3-chloro-10-methyl-11-oxo-10,11-dihydro-5H-dibenzo[b,e][1,4]diazepin-5-yl)propyl]amino}but-2-enoate 0.061 g (55%) of ethyl (E)-4-{[3-(3-chloro-10-methyl-11-oxo-10,11-dihydro-5H-dibenzo[b,e][1,4]diazepin-5-yl)propyl]amino}but-2-enoate were prepared according to the procedure described for Example 2, Step 1, starting from 0.081 g (0.256 mmol) of 5-(3-aminopropyl)-3-chloro-10-methyl-5,10-dihydro-11H-dibenzo[b,e][1,4]diazepin-11-one (Intermediate 20). $^1$H NMR (DMSO-d$_6$) δ (ppm): 7.59-7.53 (m, 1H), 7.39-7.34 (m, J=2.4 Hz, 1H), 7.29-7.23 (m, 2H), 7.22-7.15 (m, 2H), 7.12 (dd, J=2.0, 8.3 Hz, 1H), 6.82 (dt, J=4.9, 15.7 Hz, 1H), 5.90 (d, J=15.7 Hz, 1H), 4.09 (q, J=7.1 Hz, 2H), 3.84-3.68 (m, 2H), 3.41 (s, 3H), 3.22 (d, J=4.9 Hz, 2H), 2.05 (bs, 1H), 1.69-1.57 (m, 2H), 1.19 (t, J=7.1 Hz, 3H); MS (ESI): m/z: 428 [M+H]$^+$.

Step 2: Ethyl (E)-4-{[3-(3-chloro-10-methyl-11-oxo-10,11-dihydro-5H-dibenzo[b,e][1,4]diazepin-5-yl)propyl]amino}but-2-enoate maleate 0.061 g (81%) of ethyl (E)-4-{[3-(3-chloro-10-methyl-11-oxo-10,11-dihydro-5H-dibenzo[b,e][1,4]diazepin-5-yl)propyl]amino}but-2-enoate maleate were prepared according to the procedure described for Example 2, Step 2, starting from 0.059 g (0.14 mmol) of ethyl (E)-4-{[3-(3-chloro-10-methyl-11-oxo-10,11-dihydro-5H-dibenzo[b,e][1,4]diazepin-5-yl)propyl]amino}but-2-enoate and 0.016 g (0.14 mmol) of maleic acid. $^1$H NMR (DMSO-d$_6$) δ (ppm): 8.57 (bs, 3H), 7.62-7.56 (m, 1H), 7.43-7.37 (m, 1H), 7.32-7.26 (m, 2H), 7.25-7.18 (m, 2H), 7.16 (dd, J=2.0, 8.3 Hz, 1H), 6.73 (dt, J=6.3, 15.8 Hz, 1H), 6.18 (d, J=15.8 Hz, 1H), 6.02 (s, 2H), 4.15 (q, J=7.3 Hz, 2H), 3.90-3.77 (m, 2H), 3.75 (d, J=5.9 Hz, 2H), 3.43 (s, 3H), 2.99-2.85 (m, 2H), 1.89-1.78 (m, 2H), 1.22 (t, J=7.3 Hz, 3H); MS (ESI): m/z: 428 [M+H]$^+$.

Example 28: Ethyl (E)-4-{[3-(7-chloro-10-methyl-11-oxo-10,11-dihydro-5H-dibenzo[b,e][1,4]diazepin-5-yl)propyl]amino}but-2-enoate maleate

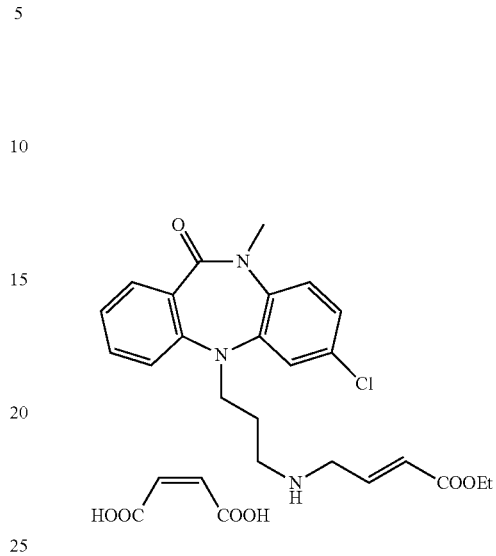

Step 1: Ethyl (E)-4-{[3-(7-chloro-10-methyl-11-oxo-10,11-dihydro-5H-dibenzo[b,e][1,4]diazepin-5-yl)propyl]amino}but-2-enoate 0.054 g (35%) of ethyl (E)-4-{[3-(7-chloro-10-methyl-11-oxo-10,11-dihydro-5H-dibenzo[b,e][1,4]diazepin-5-yl)propyl]amino}but-2-enoate were prepared according to the procedure described for Example 2, Step 1, starting from 0.112 g (0.35 mmol) of 5-(3-aminopropyl)-7-chloro-10-methyl-5,10-dihydro-11H-dibenzo[b,e][1,4]diazepin-11-one (Intermediate 21). $^1$H NMR (DMSO-d$_6$) δ (ppm): 7.59-7.53 (m, 1H), 7.48-7.42 (m, 1H), 7.40-7.35 (m, 1H), 7.34-7.31 (m, 1H), 7.23-7.16 (m, 2H), 7.12-7.06 (m, 1H), 6.82 (dt, J=4.9, 15.6 Hz, 1H), 5.91 (d, J=15.6 Hz, 1H), 4.09 (q, J=7.1 Hz, 2H), 3.76 (t, J=6.8 Hz, 2H), 3.40 (s, 3H), 3.22 (d, J=4.9 Hz, 2H), 2.51 (t, J=6.8 Hz, 2H), 1.69-1.59 (m, 2H), 1.19 (t, J=7.1 Hz, 3H); MS (ESI): m/z: 428 [M+H]$^+$.

Step 2: Ethyl (E)-4-{[3-(7-chloro-10-methyl-11-oxo-10,11-dihydro-5H-dibenzo[b,e][1,4]diazepin-5-yl)propyl]amino}but-2-enoate maleate 0.064 g (90%) of ethyl (E)-4-{[3-(7-chloro-10-methyl-11-oxo-10,11-dihydro-5H-dibenzo[b,e][1,4]diazepin-5-yl)propyl]amino}but-2-enoate maleate were prepared according to the procedure described for Example 2, Step 2, starting from 0.050 g (0.117 mmol) of ethyl (E)-4-{[3-(7-chloro-10-methyl-11-oxo-10,11-dihydro-5H-dibenzo[b,e][1,4]diazepin-5-yl)propyl]amino}but-2-enoate and 0.014 g (0.117 mmol) of maleic acid. $^1$H NMR (DMSO-d$_6$) δ (ppm): 8.60 (bs, 3H), 7.58 (dd, J=1.7, 7.9 Hz, 1H), 7.51-7.46 (m, 1H), 7.41 (d, J=8.6 Hz, 1H), 7.36 (d, J=2.4 Hz, 1H), 7.24 (dd, J=2.4, 8.6 Hz, 1H), 7.22-7.19 (m, 1H), 7.16-7.09 (m, 1H), 6.74 (dt, J=6.1, 16.1 Hz, 1H), 6.19 (dt, J=1.4, 16.1 Hz, 1H), 6.03 (s, 2H), 4.15 (q, J=7.2 Hz, 2H), 3.90-3.78 (m, 2H), 3.77-3.70 (m, 2H), 3.42 (s, 3H), 3.00-2.85 (m, 2H), 1.90-1.79 (m, 2H), 1.22 (t, J=7.2 Hz, 3H); MS (ESI): m/z: 428 [M+H]$^+$.

Example 29: Ethyl (E)-4-{[4-(7-chloro-10-methyl-11-oxo-10,11-dihydro-5H-dibenzo[b,e][1,4]diazepin-5-yl)butyl]amino}but-2-enoate maleate

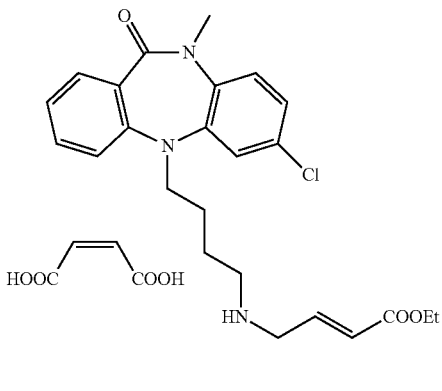 [SMILES: CCOC(=O)/C=C/CNCCCCN1c2ccccc2C(=O)N(C)c2ccc(Cl)cc21 ; O=C(O)/C=C\C(=O)O]

Step 1: Ethyl (E)-4-{[4-(7-chloro-10-methyl-11-oxo-10,11-dihydro-5H-dibenzo[b,e][1,4]diazepin-5-yl)butyl]amino}but-2-enoate 0.055 g (49%) of ethyl (E)-4-{[4-(7-chloro-10-methyl-11-oxo-10,11-dihydro-5H-dibenzo[b,e][1,4]diazepin-5-yl)butyl]amino}but-2-enoate were prepared according to the procedure described for Example 2, Step 1, starting from 0.084 g (0.256 mmol) of 5-(4-aminobutyl)-7-chloro-10-methyl-5,10-dihydro-11H-dibenzo[b,e][1,4]diazepin-11-one (Intermediate 22). $^1$H NMR (DMSO-$d_6$) δ (ppm): 7.58-7.53 (m, 1H), 7.48-7.41 (m, 1H), 7.40-7.35 (m, 1H), 7.32 (d, J=2.4 Hz, 1H), 7.22-7.15 (m, 2H), 7.12-7.05 (m, 1H), 6.83 (dt, J=5.4, 15.6 Hz, 1H), 5.90 (d, J=15.7 Hz, 1H), 4.09 (q, J=7.3 Hz, 2H), 3.74-3.66 (m, 2H), 3.41 (s, 3H), 3.22 (dd, J=1.5, 4.9 Hz, 2H), 2.43 (t, J=6.8 Hz, 2H), 1.59-1.49 (m, 2H), 1.47-1.37 (m, 2H), 1.19 (t, J=73.0 Hz, 3H); MS (ESI): m/z: 442 [M+H]$^+$.

Step 2: Ethyl (E)-4-{[4-(7-chloro-10-methyl-11-oxo-10,11-dihydro-5H-dibenzo[b,e][1,4]diazepin-5-yl)butyl]amino}but-2-enoate maleate 0.062 g (93%) of ethyl (E)-4-{[4-(7-chloro-10-methyl-11-oxo-10,11-dihydro-5H-dibenzo[b,e][1,4]diazepin-5-yl)butyl]amino}but-2-enoate maleate were prepared according to the procedure described for Example 2, Step 2, starting from 0.053 g (0.12 mmol) of ethyl (E)-4-{[4-(7-chloro-10-methyl-11-oxo-10,11-dihydro-5H-dibenzo[b,e][1,4]diazepin-5-yl)butyl]amino}but-2-enoate and 0.014 g (0.12 mmol) of maleic acid. $^1$H NMR (DMSO-$d_6$) δ (ppm): 8.60 (bs, 3H), 7.58 (dd, J=1.7, 7.6 Hz, 1H), 7.50-7.45 (m, 1H), 7.40 (d, J=8.3 Hz, 1H), 7.34 (d, J=2.0 Hz, 1H), 7.24-7.18 (m, 2H), 7.13-7.09 (m, 1H), 6.77 (dt, J=6.4, 15.7 Hz, 1H), 6.19 (dt, J=1.5, 15.7 Hz, 1H), 6.05 (s, 2H), 4.15 (q, J=7.1 Hz, 2H), 3.82-3.67 (m, 4H), 3.43 (s, 3H), 2.95-2.85 (m, 2H), 1.69-1.52 (m, 4H), 1.21 (t, J=7.1 Hz, 3H); MS (ESI): m/z: 428 [M+H]$^+$.

Example 30: Ethyl (E)-4-{[3-(8-chloro-1-methyl-4,5-dihydropyrazolo-[3,4-b][1]-benzazepin-10(1H)-yl)propyl]amino}but-2-enoate maleate

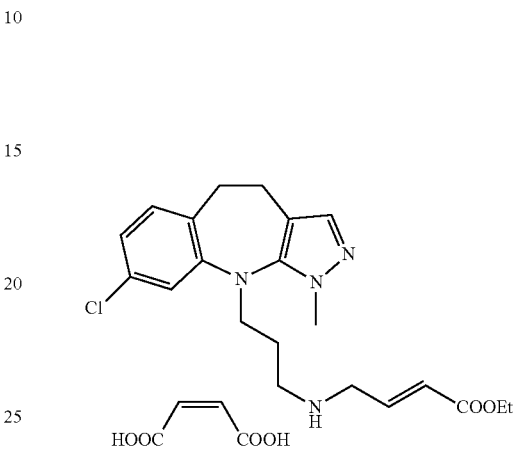

Step 1: Ethyl (E)-4-{[3-(8-chloro-1-methyl-4,5-dihydropyrazolo[3,4-b][1]benzazepin-10(1H)-yl)propyl]amino}but-2-enoate 0.020 g (56%) of ethyl (E)-4-{[3-(8-chloro-1-methyl-4,5-dihydropyrazolo[3,4-b][1]benzazepin-10(1H)-yl)propyl]amino}but-2-enoate were prepared according to the procedure described for Example 2, Step 1, starting from 0.026 g (0.089 mmol) of 3-(8-chloro-1-methyl-4,5-dihydropyrazolo[3,4-b][1]benzazepin-10(1H)-yl)propan-1-amine (Intermediate 25). $^1$H NMR (CDCl$_3$) δ (ppm): 7.21-7.11 (m, 4H), 6.95 (dt, J=5.4, 15.7 Hz, 1H), 5.99-5.91 (m, 1H), 4.20 (q, J=7.3 Hz, 2H), 3.82 (s, 3H), 3.50-3.42 (m, 2H), 3.37 (dd, J=1.7, 5.6 Hz, 2H), 2.98 (bs, 2H), 2.72 (bs, 2H), 2.64 (t, J=6.8 Hz, 2H), 1.85-1.73 (m, 2H), 1.30 (t, J=7.3 Hz, 3H); MS (ESI): m/z: 403 [M+H]$^+$.

Step 2: Ethyl (E)-4-{[3-(8-chloro-1-methyl-4,5-dihydropyrazolo[3,4-b][1]benzazepin-10(1H)-yl)propyl]amino}but-2-enoate maleate 0.021 g (92%) of ethyl (E)-4-{[3-(8-chloro-1-methyl-4,5-dihydropyrazolo[3,4-b][1]benzazepin-10(1H)-yl)propyl]amino}but-2-enoate maleate were prepared according to the procedure described for Example 2, Step 2, starting from 0.018 g (0.045 mmol) of ethyl (E)-4-{[3-(8-chloro-1-methyl-4,5-dihydropyrazolo[3,4-b][1]benzazepin-10(1H)-yl)propyl]amino}but-2-enoate maleate and 0.005 g (0.045 mmol) of maleic acid. $^1$H NMR (DMSO-$d_6$) δ (ppm): 8.56 (bs, 3H), 7.45-7.39 (m, 1H), 7.33-7.29 (m, 1H), 7.24 (dd, J=2.2, 8.1 Hz, 1H), 7.11 (s, 1H), 6.76 (dt, J=6.3, 16.1 Hz, 1H), 6.22-6.16 (m, 1H), 6.05 (s, 2H), 4.15 (q, J=7.3 Hz, 2H), 3.80-3.73 (m, 5H), 3.54-3.46 (m, 2H), 2.98-2.90 (m, 4H), 2.63 (bs, 2H), 1.84-1.75 (m, 2H), 1.21 (t, J=7.3 Hz, 3H); MS (ESI): m/z: 403 [M+H]$^+$.

Example 31: Ethyl (E)-4-{[3-(8-chloro-2-methyl-4,5-dihydropyrazolo-[3,4-b][1]-benzazepin-10(2H-yl)propyl]amino}but-2-enoate

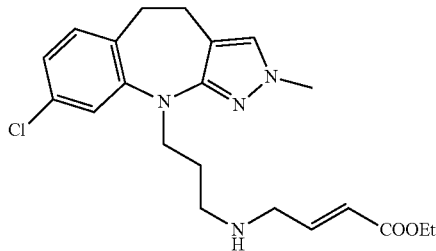 [SMILES: CCOC(=O)/C=C/CNCCCN1c2cc(Cl)ccc2CCc2cn(C)nc21]

0.008 g (25%) of ethyl (E)-4-{[3-(8-chloro-2-methyl-4,5-dihydropyrazolo[3,4-b][1]benzazepin-10(2H)-yl)propyl]amino}but-2-enoate were prepared according to the procedure described for Example 2, Step 1, starting from 0.022 g (0.076 mmol) of 3-(8-chloro-2-methyl-4,5-dihydropyrazolo[3,4-b][1]benzazepin-10(2H)-yl)propan-1-amine (Intermediate 26). $^1$H NMR (CDCl$_3$) δ (ppm): 7.11-7.08 (m, 1H), 7.07-7.03 (m, 1H), 6.98-6.90 (m, 3H), 5.93 (d, J=15.7 Hz, 1H), 4.20 (q, J=7.3 Hz, 2H), 3.96 (t, J=6.6 Hz, 2H), 3.71 (s, 3H), 3.37 (dd, J=1.5, 5.9 Hz, 2H), 2.99-2.90 (m, 2H), 2.77-2.72 (m, 2H), 2.68 (t, J=6.8 Hz, 2H), 1.95-1.86 (m, 2H), 1.29 (t, J=7.3 Hz, 3H); MS (ESI): m/z: 403 [M+H]$^+$.

Example 32: Ethyl (E)-4-{[3-(9-chloro-5,6-dihydro-11H-pyrimido[4,5-b][1]-benzazepin-11-yl)propyl]amino}but-2-enoate fumarate

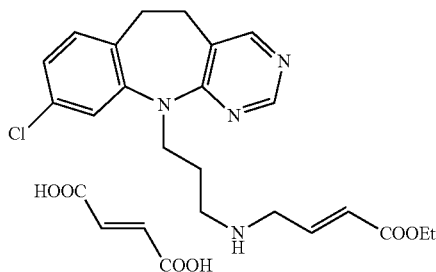

Step 1: Ethyl (E)-4-{[3-(9-chloro-5,6-dihydro-11H-pyrimido[4,5-b][1]benzazepin-11-yl)propyl]amino}but-2-enoate 0.026 g (42%) of ethyl (E)-4-{[3-(9-chloro-5,6-dihydro-11H-pyrimido[4,5-b][1]benzazepin-11-yl)propyl]amino}but-2-enoate were prepared according to the procedure described for Example 2, Step 1, starting from 0.055 g (0.19 mmol) of 3-(9-chloro-5,6-dihydro-11H-pyrimido[4,5-b][1]benzazepin-11-yl)propan-1-amine (Intermediate 27). $^1$H NMR (CDCl$_3$) δ (ppm): 8.62 (s, 1H), 8.13 (s, 1H), 7.25-7.23 (m, 1H), 7.12-7.05 (m, 2H), 6.94 (dt, J=5.6, 15.8 Hz, 1H), 5.94 (dt, J=1.7, 15.8 Hz, 1H), 4.27-4.17 (m, 4H), 3.38 (dd, J=1.7, 5.6 Hz, 2H), 3.07-3.01 (m, 2H), 2.99-2.93 (m, 2H), 2.67 (t, J=7.1 Hz, 2H), 1.93-1.84 (m, 2H), 1.30 (t, J=7.3 Hz, 3H); MS (ESI): m/z: 401 [M+H]$^+$.

Step 2: Ethyl (E)-4-{[3-(9-chloro-5,6-dihydro-11H-pyrimido[4,5-b][1]benzazepin-11-yl)propyl]amino}but-2-enoate fumarate 0.025 g (90%) of ethyl (E)-4-{[3-(9-chloro-5,6-dihydro-11H-pyrimido[4,5-b][1]benzazepin-11-yl)propyl]amino}but-2-enoate fumarate were prepared according to the procedure described for Example 2, Step 2, starting from 0.022 g (0.05 mmol) of ethyl (E)-4-{[3-(9-chloro-5,6-dihydro-11H-pyrimido[4,5-b][1]benzazepin-11-yl)propyl]amino}but-2-enoate and 0.006 g (0.05 mmol) of fumaric acid. $^1$H NMR (DMSO-d$_6$) δ (ppm): 8.59 (s, 1H), 8.19 (s, 1H), 7.43-7.35 (m, 1H), 7.28-7.24 (m, 1H), 7.21-7.16 (m, 1H), 6.78 (dt, J=5.8, 15.8 Hz, 1H), 6.55 (s, 2H), 5.99 (d, J=15.7 Hz, 1H), 4.19 (t, J=6.6 Hz, 2H), 4.12 (q, J=7.3 Hz, 2H), 3.43 (d, J=4.9 Hz, 2H), 3.04-2.96 (m, 2H), 2.94-2.85 (m, 2H), 2.62 (t, J=7.1 Hz, 2H), 1.83-1.72 (m, 2H), 1.21 (t, J=7.3 Hz, 3H); MS (ESI): m/z: 401 [M+H]$^+$.

Example 33: Ethyl (E)-4-{[3-(3-chloro-10,11-dihydro-5H-dibenzo[b,f]azepin-5-yl)-3-oxo-propyl]amino}but-2-enoate maleate

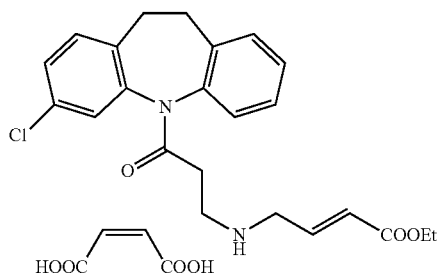

Step 1: Ethyl (E)-4-{[3-(3-chloro-10,11-dihydro-5H-dibenzo[b,f]azepin-5-yl)-3-oxo-propyl]amino}but-2-enoate 0.056 g (57%) of ethyl (E)-4-{[3-(3-chloro-10,11-dihydro-5H-dibenzo[b,f]azepin-5-yl)3-oxo-propyl]amino}but-2-enoate were prepared according to the procedure described for Example 2, Step 1, starting from 0.079 g (0.26 mmol) of 3-amino-1-(3-chloro-10,11-dihydro-5H-dibenzo[b,f]azepin-5-yl)propan-1-one (Intermediate 28). $^1$H NMR (CDCl$_3$) δ (ppm): 7.44-7.04 (m, 7H), 6.96 (dt, J=5.6, 15.7 Hz, 1H), 5.98 (d, J=15.7 Hz, 1H), 4.19 (q, J=7.3 Hz, 2H), 3.46-3.23 (m, 4H), 3.00-2.75 (m, 4H), 2.72-2.56 (m, 1H), 2.37-2.23 (m, 1H), 1.29 (t, J=7.3 Hz, 3H); MS (ESI): m/z: 413 [M+H]$^+$.

Step 2: Ethyl (E)-4-{[3-(3-chloro-10,11-dihydro-5H-dibenzo[b,f]azepin-5-yl)3-oxo-propyl]amino}but-2-enoate maleate 0.040 g (92%) of ethyl (E)-4-{[3-(3-chloro-10,11-dihydro-5H-dibenzo[b,f]azepin-5-yl)-3-oxo-propyl]amino}but-2-enoate maleate were prepared according to the procedure described for Example 2, Step 2, starting from 0.034 g (0.082 mmol) of ethyl (E)-4-{[3-(3-chloro-10,11-dihydro-5H-dibenzo[b,f]azepin-5-yl)3-oxo-propyl]amino}but-2-enoate and 0.010 g (0.082 mmol) of maleic acid. $^1$H NMR (DMSO-d$_6$) δ (ppm): 8.62 (bs, 3H), 7.80-7.15 (m, 7H), 6.79 (dt, J=6.0, 15.7 Hz, 1H), 6.21 (d, J=15.7 Hz, 1H), 6.06 (s, 2H), 4.15 (q, J=7.1 Hz, 2H), 3.80 (d, J=5.9 Hz, 2H), 3.31-3.08 (m, 4H), 2.95-2.73 (m, 3H), 2.40-2.21 (m, 1H), 1.21 (t, J=7.1 Hz, 3H); MS (ESI): m/z: 413 [M+H]⁺.

Example 34: Ethyl (E)-4-{[2-hydroxy-3-(3-chloro-10,11-dihydro-5H-dibenzo[b,f]azepin-5-yl)]propylamino}but-2-enoate

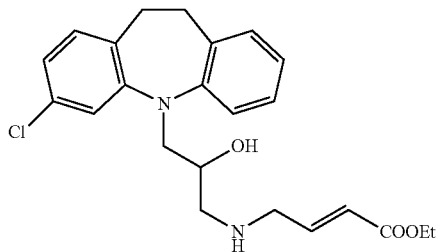 [SMILES: CCOC(=O)/C=C/CNCC(O)CN1c2ccccc2CCc2ccc(Cl)cc21]

Step 1: 2-(3-Chloro-10,11-dihydro-5H-dibenzo[b,f]azepin-5-yl)methyloxirane 0.798 ml of n-BuLi (2.5 M in hexane; 1.99 mmol) were added to a solution of 0.229 g (0.997 mmol) of 3-chloro-10,11-dihydro-5H-dibenzo[b,f]azepine (FLOROCHEM Cat. No. 211409) in dry THF (1.2 ml), under argon, at −78° C.; the resulting solution was stirred for about 20 min at −78° C., then 0.391 ml (4.98 mmol) of epichlorhydrin were added. The reaction was stirred for about 23 h, allowing it to reach r.t.

Water (5 ml) and EtOAc (10 ml) were added, the two phases separated; the aqueous phase was extracted with EtOAc (2×5 ml), the combined organic layers were washed with brine, dried (Na$_2$SO$_4$) and concentrated under vacuo. The crude was purified by flash chromatography (eluent: hexane/EtOAc from 99:1 to 90:10) to afford 2-(3-chloro-10,11-dihydro-5H-dibenzo[b,f]azepin-5-yl)methyloxirane as a light-yellow oil (0.250 g, 88%). ¹H NMR (DMSO-d$_6$) δ (ppm): 7.22-7.07 (m, 5H), 7.03-6.91 (m, 2H), 4.08-4.00 (m, 1H), 3.70 (dd, J=5.9, 14.2 Hz, 1H), 3.19-2.99 (m, 4H), 2.99-2.92 (m, 1H), 2.69-2.54 (m, 2H); MS (ESI): m/z: 286 [M+H]⁺.

Step 2: 1-Azido-3-(3-chloro-10,11-dihydro-5H-dibenzo[b,f]azepin-5-yl)propan-2-ol A suspension of 0.186 g (0.651 mmol) of 2-(3-chloro-10,11-dihydro-5H-dibenzo[b,f]azepin-5-yl)methyloxirane in a 4:1 mixture of EtOH:H$_2$O (9 ml) was treated with 0.055 g (0.846 mmol) of NaN$_3$ and 0.0453 g (0.846 mmol) of NH$_4$Cl and stirred at 80° C. for about 21 h. EtOH was removed under vacuo, the residue was diluted with EtOAc (10 ml), washed with brine (5 ml), dried (Na$_2$SO$_4$) and concentrated. The crude was purified by flash chromatography (eluent: hexane/EtOAc from 97:3 to 70:30) to afford 1-azido-3-(3-chloro-10,11-dihydro-5H-dibenzo[b,f]azepin-5-yl)propan-2-ol as a yellow oil (0.210 g, 98%). ¹H NMR (DMSO-d$_6$) δ (ppm): 7.23-7.06 (m, 5H), 7.01-6.88 (m, 2H), 5.37-5.27 (m, 1H), 3.82-3.59 (m, 3H), 3.31-3.16 (m, 2H), 3.11-2.97 (m, 4H); MS (ESI): m/z: 329 [M+H]⁺.

Step 3: 1-Amino-3-(3-chloro-10,11-dihydro-5H-dibenzo[b,f]azepin-5-yl)propan-2-ol A solution of 0.210 g (0.639 mmol) of 1-azido-3-(3-chloro-10,11-dihydro-5H-dibenzo[b,f]azepin-5-yl)propan-2-ol in dry THF (3 ml) was treated with 0.184 g (0.703 mmol) of TPP at 0° C., followed by 5 drops of water. The mixture was stirred at r.t. for about 24 h, then solvents were removed under vacuo. The crude was purified by flash chromatography (eluent: i. hexane/EtOAc from 100:0 to 60:40; ii. DCM/MeOH/NH$_4$OH from 92:8:0.8 to 90:10:1) to afford 1-amino-3-(3-chloro-10,11-dihydro-5H-dibenzo[b,f]azepin-5-yl)propan-2-ol as a colorless solid (0.150 g, 77%). ¹H NMR (DMSO-d$_6$) δ (ppm): 7.19-7.03 (m, 5H), 6.99-6.87 (m, 2H), 4.66 (bs, 1H), 3.74-3.56 (m, 2H), 3.43 (bs, 1H), 3.16-3.00 (m, 4H), 2.65-2.56 (m, 1H), 2.46-2.36 (m, 1H), 1.76 (bs, 2H); MS (ESI): m/z: 303 [M+H]⁺.

Step 4: Ethyl (E)-4-{[2-hydroxy-3-(3-chloro-10,11-dihydro-5H-dibenzo[b,f]azepin-5-yl]propylamino}but-2-enoate 0.010 g (15%) of ethyl (E)-4-{[2-hydroxy-3-(3-chloro-10,11-dihydro-5H-dibenzo[b,f]azepin-5-yl)]propylamino}but-2-enoate were prepared according to the procedure described for Example 2, Step 1, starting from 0.050 g (0.165 mmol) of 1-amino-3-(3-chloro-10,11-dihydro-5H-dibenzo[b,f]azepin-5-yl)propan-2-ol. ¹H NMR (DMSO-d$_6$) δ (ppm): 7.15 (d, J=1.5 Hz, 5H), 7.00-6.87 (m, 2H), 6.86-6.78 (m, 1H), 5.93-5.84 (m, 1H), 4.79-4.71 (m, 1H), 4.11 (d, J=7.3 Hz, 2H), 3.76-3.55 (m, 3H), 3.29-3.21 (m, 1H), 3.03 (s, 4H), 2.61-2.52 (m, 1H), 2.45-2.36 (m, 1H), 1.38-1.12 (m, 5H); MS (ESI): m/z: 415 [M+H]⁺.

Example 35: Ethyl (E)-4-{3-[3-chlorodibenzo[b,e][1,4]oxazepin-5(11H)-yl]propylamino}but-2-enoate maleate

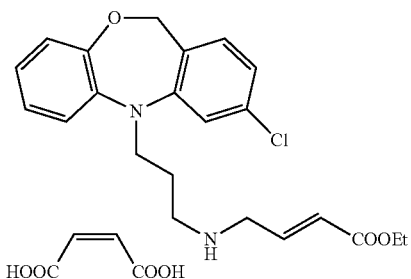

Step 1: Ethyl (E)-4-{3-[3-chlorodibenzo[b,e][1,4]oxazepin-5(11H)-yl]propylamino}but-2-enoate 0.031 g (40%) of ethyl (E)-4-{3-[3-chlorodibenzo[b,e][1,4]oxazepin-5(11H)-yl]propylamino}but-2-enoate were prepared according to the procedure described for Example 2, Step 1, starting from 0.069 g (0.214 mmol) of 3-[3-chlorodibenzo[b,e][1,4]oxazepin-5(11H)-yl]propan-1-amine (Intermediate 30). ¹H NMR (CDCl$_3$) δ (ppm): 7.20 (d, J=8.3 Hz, 1H), 7.10 (d, J=2.0 Hz, 1H), 7.04-6.98 (m, 2H), 6.97-6.90 (m, 1H), 6.89-6.78 (m, 3H), 5.93 (td, J=1.7, 15.7 Hz, 1H), 5.24 (s, 2H), 4.20 (q, J=7.3 Hz, 2H), 3.81 (t, J=6.6 Hz, 2H), 3.37 (dd, J=1.7, 5.6 Hz, 2H), 2.69 (t, J=6.8 Hz, 2H), 1.85 (quint, J=6.8 Hz, 2H), 1.34-1.24 (m, 3H); MS (ESI): m/z: 401 [M+H]⁺.

Step 2: Ethyl (E)-4-{3-[3-chlorodibenzo[b,e][1,4]oxazepin-5(11H)-yl]propylamino}but-2-enoate maleate 0.033 g (88%) of ethyl (E)-4-{3-[3-chlorodibenzo[b,e][1,4]oxazepin-5(11H)-yl]propylamino}but-2-enoate maleate were prepared according to the procedure described for Example 2, Step 2, starting from 0.029 g (0.072 mmol) of ethyl (E)-4-{3-[3-chlorodibenzo[b,e][1,4]oxazepin-5(11H)-yl]propylamino}but-2-enoate. $^1$H NMR (DMSO-d$_6$) δ (ppm): 8.52 (bs, 2H), 7.44 (d, J=8.3 Hz, 1H), 7.30 (d, J=2.0 Hz, 1H), 7.15 (dd, J=2.0, 8.3 Hz, 1H), 7.07 (dd, J=2.2, 7.6 Hz, 1H), 6.89-6.80 (m, 2H), 6.79-6.70 (m, 2H), 6.17 (d, J=15.7 Hz, 1H), 6.01 (s, 2H), 5.27 (s, 2H), 4.15 (q, J=6.8 Hz, 2H), 3.81 (t, J=6.4 Hz, 2H), 3.75 (d, J=5.9 Hz, 2H), 3.01-2.88 (m, 2H), 1.90-1.80 (m, 2H), 1.21 (t, J=7.1 Hz, 3H); MS (ESI): m/z: 401 [M+H]$^+$.

Example 36: Ethyl (E)-4-{4-[3-chlorodibenzo[b,e][1,4]oxazepin-5(11H)-yl]butylamino}but-2-enoate maleate

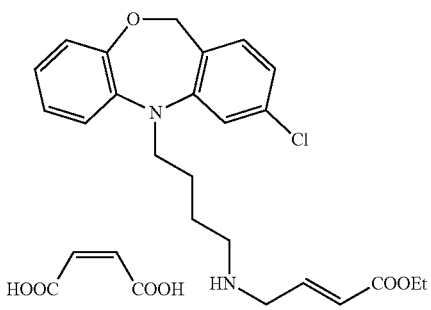 [SMILES: CCOC(=O)/C=C/CNCCCCN1c2cc(Cl)ccc2COc2ccccc21 ; O=C(O)/C=C\C(=O)O]

Step 1: Ethyl (E)-4-{4-[3-chlorodibenzo[b,e][1,4]oxazepin-5(11H)-yl]butylamino}but-2-enoate 0.010 g (17%) of ethyl (E)-4-{4-[3-chlorodibenzo[b,e][1,4]oxazepin-5(11H)-yl]butylamino}but-2-enoate were prepared according to the procedure described for Example 2, Step 1, starting from 0.044 g (0.147 mmol) of 4-[3-chlorodibenzo[b,e][1,4]oxazepin-5(11H)-yl]butan-1-amine (Intermediate 31) and 0.022 g (0.161 mmol) of fumaraldehydic acid ethyl ester (FLROCHEM, Cat. No. 235591). $^1$H NMR (CDCl$_3$) δ (ppm): 7.20 (d, J=8.3 Hz, 1H), 7.08 (d, J=2.0 Hz, 1H), 7.04-6.91 (m, 3H), 6.89-6.76 (m, 3H), 5.97-5.89 (m, 1H), 5.26 (s, 2H), 4.20 (q, J=7.2 Hz, 2H), 3.73 (t, J=6.8 Hz, 2H), 3.35 (dd, J=1.7, 5.6 Hz, 2H), 2.58 (t, J=7.1 Hz, 2H), 1.75-1.64 (m, 2H), 1.60-1.49 (m, 2H), 1.34-1.23 (m, 3H); MS (ESI): m/z: 415 [M+H]$^+$.

Step 2: Ethyl (E)-4-{4-[3-chlorodibenzo[b,e][1,4]oxazepin-5(11H)-yl]butylamino}but-2-enoate maleate 0.009 g (78%) of ethyl (E)-4-{4-[3-chlorodibenzo[b,e][1,4]oxazepin-5(11H)-yl]butylamino}but-2-enoate maleate were prepared according to the procedure described for Example 2, Step 2, starting from 0.009 g (0.022 mmol) of ethyl (E)-4-{4-[3-chlorodibenzo[b,e][1,4]oxazepin-5(11H)-yl]butylamino}but-2-enoate. $^1$H NMR (DMSO-d$_6$) δ (ppm): 8.50 (bs, 2H), 7.42 (d, J=8.3 Hz, 1H), 7.29 (d, J=2.0 Hz, 1H), 7.13 (dd, J=2.2, 8.1 Hz, 1H), 7.07 (dd, J=2.0, 7.8 Hz, 1H), 6.87-6.70 (m, 4H), 6.18 (d, J=15.7 Hz, 1H), 6.01 (s, 2H), 5.27 (s, 2H), 4.15 (q, J=7.3 Hz, 2H), 3.79-3.69 (m, 4H), 2.86 (t, J=6.6 Hz, 2H), 1.65-1.51 (m, 4H), 1.21 (t, J=7.1 Hz, 3H); MS (ESI): m/z: 415 [M+H]$^+$.

Example 37: Ethyl (E)-4-{4-[7-chlorodibenzo[b,e][1,4]oxazepin-5(11H)-yl]butylamino}but-2-enoate maleate

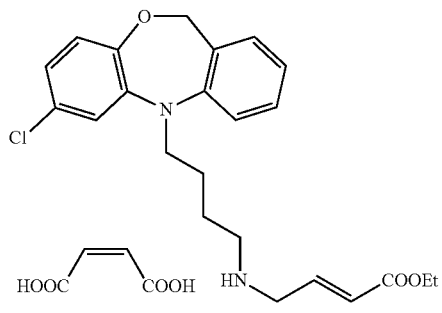 [SMILES: CCOC(=O)/C=C/CNCCCCN1c2ccccc2COc2ccc(Cl)cc21 ; O=C(O)/C=C\C(=O)O]

Step 1: Ethyl (E)-4-{4-[7-chlorodibenzo[b,e][1,4]oxazepin-5(11H)-yl]butylamino}but-2-enoate 0.021 g (20%) of ethyl (E)-4-{4-[7-chlorodibenzo[b,e][1,4]oxazepin-5(11H)-yl]butylamino}but-2-enoate were prepared according to the procedure described for Example 2, Step 1, starting from 0.086 g (0.256 mmol) of 4-[7-chlorodibenzo[b,e][1,4]oxazepin-5(11H)-yl]butan-1-amine (Intermediate 32) and 0.034 g (0.256 mmol) of fumaraldehydic acid ethyl ester (FLROCHEM, Cat. No. 235591). $^1$H NMR (CDCl$_3$) δ (ppm): 7.37-7.32 (m, 1H), 7.32-7.28 (m, 1H), 7.12-7.05 (m, 2H), 6.98-6.91 (m, 2H), 6.76-6.72 (m, 1H), 6.72-6.68 (m, 1H), 5.93 (td, J=1.7, 15.7 Hz, 1H), 5.27 (s, 2H), 4.20 (q, J=6.8 Hz, 2H), 3.72 (t, J=6.8 Hz, 2H), 3.35 (dd, J=1.7, 5.6 Hz, 2H), 2.58 (t, J=7.1 Hz, 2H), 1.73-1.65 (m, 2H), 1.59-1.49 (m, 2H), 1.33-1.25 (m, 3H); MS (ESI): m/z: 415 [M+H]$^+$.

Step 2: Ethyl (E)-4-{4-[7-chlorodibenzo[b,e][1,4]oxazepin-5(11H)-yl]butylamino}but-2-enoate maleate 0.020 g (84%) of ethyl (E)-4-{4-[7-chlorodibenzo[b,e][1,4]oxazepin-5(11H)-yl]butylamino}but-2-enoate maleate were prepared according to the procedure described for Example 2, Step 2, starting from 0.019 g (0.046 mmol) of ethyl (E)-4-{4-[7-chlorodibenzo[b,e][1,4]oxazepin-5(11H)-yl]butylamino}but-2-enoate. $^1$H NMR (DMSO-d$_6$) δ (ppm): 8.50 (bs, 2H), 7.44-7.36 (m, 2H), 7.25-7.20 (m, 1H), 7.13-7.08 (m, 1H), 7.06 (d, J=2.4 Hz, 1H), 6.84-6.68 (m, 3H), 6.18 (d, J=15.7 Hz, 1H), 6.01 (s, 2H), 5.29 (s, 2H), 4.15 (q, J=6.8 Hz, 2H), 3.78-3.70 (m, 4H), 2.90-2.80 (m, 2H), 1.64-1.51 (m, 4H), 1.21 (t, J=7.1 Hz, 3H); MS (ESI): m/z: 415 [M+H]$^+$.

Example 38: Ethyl (E)-4-{[4-(3-chloro-10,11-dihydro-5H-dibenzo[b,f]azepin-5-yl)-4-oxo-butyl]amino}but-2-enoate maleate

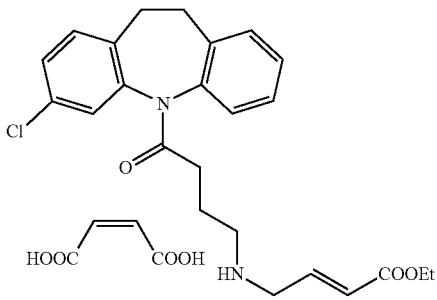

Step 1: Ethyl (E)-4-{[4-(3-chloro-10,11-dihydro-5H-dibenzo[b,f]azepin-5-yl)-4-oxo-butyl]amino}but-2-enoate 0.055 g (33%) of ethyl (E)-4-{[4-(3-chloro-10,11-dihydro-5H-dibenzo[b,f]azepin-5-yl)4-oxo-butyl]amino}but-2-enoate were prepared according to the procedure described for Example 2, Step 1, starting from 0.123 g (0.389 mmol) of 4-amino-1-(3-chloro-10,11-dihydro-5H-dibenzo[b,f]azepin-5-yl)butan-1-one (Intermediate 33). $^1$H NMR (DMSO-$d_6$) δ (ppm): 7.71-7.09 (m, 8H), 6.89-6.76 (m, 1H), 5.95-5.82 (m, 1H), 4.11 (q, J=7.3 Hz, 2H), 3.29-3.15 (m, 4H), 2.85-2.68 (m, 2H), 2.46-2.30 (bs, 3H), 2.15-2.00 (m, 1H), 1.67-1.53 (m, 2H), 1.20 (t, J=7.1 Hz, 3H)); MS (ESI): m/z: 427 [M+H]$^+$.

Step 2: Ethyl (E)-4-{[4-(3-chloro-10,11-dihydro-5H-dibenzo[b,f]azepin-5-yl)4-oxo-butyl]amino}but-2-enoate maleate 0.019 g (76%) of ethyl (E)-4-{[4-(3-chloro-10,11-dihydro-5H-dibenzo[b,f]azepin-5-yl)-4-oxo-propyl]amino}but-2-enoate maleate were prepared according to the procedure described for Example 2, Step 2, starting from 0.019 g (0.046 mmol) of ethyl (E)-4-{[4-(3-chloro-10,11-dihydro-5H-dibenzo[b,f]azepin-5-yl)4-oxo-butyl]amino}but-2-enoate. $^1$H NMR (DMSO-$d_6$) δ (ppm): 8.66 (bs, 2H), 7.72-7.10 (m, 7H), 6.78 (td, J=6.2, 16.0 Hz, 1H), 6.21 (d, J=15.7 Hz, 1H), 6.05 (s, 2H), 4.15 (q, J=7.3 Hz, 2H), 3.77 (d, J=5.4 Hz, 2H), 3.29-3.13 (m, 2H), 2.97-2.71 (m, 4H), 2.60-2.49 (m, 1H), 2.15-1.96 (m, 1H), 1.88-1.73 (m, 2H), 1.21 (t, J=7.1 Hz, 3H); MS (ESI): m/z: 427 [M+H]$^+$.

Example 39: Ethyl (E)-4-[4-(7-Chloro-2-hydroxy-10,11-dihydro-dibenzo[b,f]azepin-5-yl)-butylamino]-but-2-enoate maleate

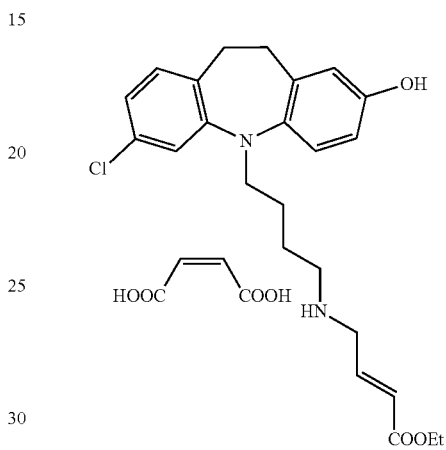

Step 1: Ethyl (E)-4-[4-(7-Chloro-2-hydroxy-10,11-dihydro-dibenzo[b,f]azepin-5-yl)-butylamino]-but-2-enoate 0.020 g (25%) of ethyl (E)-4-[4-(7-chloro-2-hydroxy-10,11-dihydro-dibenzo[b,f]azepin-5-yl)-butylamino]-but-2-enoate were prepared according to the procedure described for Example 2, Step 1, starting from 0.060 g (0.189 mmol) 5-(4-amino-butyl)-7-chloro-10,11-dihydro-5H-dibenzo[b,f]azepin-2-ol (Intermediate 34). $^1$H NMR (DMSO-$d_6$) δ (ppm): 9.08 (s, 1H), 7.05-6.98 (m, 2H), 6.96-6.90 (m, 1H), 6.87-6.78 (m, 2H), 6.58-6.49 (m, 2H), 5.95-5.86 (m, 1H), 4.09 (q, J=6.8 Hz, 2H), 3.61-3.54 (m, 2H), 3.25-3.18 (m, 2H), 3.04-2.88 (m, 4H), 2.41-2.35 (m, 2H), 1.50-1.32 (m, 4H), 1.19 (t, J=6.3 Hz, 3H); MS (ESI): m/z: 429 [M+H]$^+$.

Step 2: Ethyl (E)-4-[4-(7-Chloro-2-hydroxy-10,11-dihydro-dibenzo[b,f]azepin-5-yl)-butylamino]-but-2-enoate maleate 0.018 g (79%) of ethyl (E)-4-[4-(7-chloro-2-hydroxy-10,11-dihydro-dibenzo[b,f]azepin-5-yl)-butylamino]-but-2-enoate maleate were prepared according to the procedure described for Example 2, Step 2, starting from 0.018 g (0.042 mmol) of ethyl (E)-4-[4-(7-chloro-2-hydroxy-10,11-dihydro-dibenzo[b,f]azepin-5-yl)-butylamino]-but-2-enoate. $^1$H NMR (DMSO-$d_6$) δ (ppm): 9.11 (s, 1H), 8.50 (bs, 2H), 7.07-6.99 (m, 2H), 6.95 (d, J=8.5 Hz, 1H), 6.87 (dd, J=2.1, 8.1 Hz, 1H), 6.76 (td, J=6.3, 15.9 Hz, 1H), 6.61-6.50 (m, 2H), 6.18 (d, J=15.9 Hz, 1H), 6.01 (s, 2H), 4.15 (q, J=7.0 Hz, 2H), 3.73 (d, J=6.3 Hz, 2H), 3.62 (t, J=6.6 Hz, 2H), 2.99 (bs, 4H), 2.84 (t, J=7.7 Hz, 2H), 1.62-1.52 (m, 2H), 1.51-1.41 (m, 2H), 1.21 (t, J=7.0 Hz, 3H); MS (ESI): m/z: 429 [M+H]$^+$.

Example 40: Ethyl (E)-4-[4-(3-Chloro-2-hydroxy-10,11-dihydro-dibenzo[b,f]azepin-5-yl)-butylamino]-but-2-enoate maleate

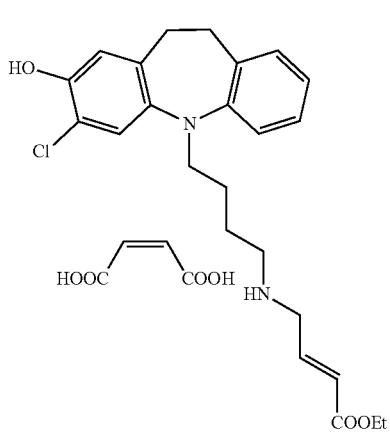 [SMILES: CCOC(=O)/C=C/CNCCCCN1c2ccccc2CCc2cc(O)c(Cl)cc21 ; O=C(O)/C=C\C(=O)O]

Step 1: Ethyl (E)-4-[4-(3-Chloro-2-hydroxy-10,11-dihydro-dibenzo[b,f]azepin-5-yl)-butylamino]-but-2-enoate 0.015 g (32%) of ethyl (E)-4-[4-(3-chloro-2-hydroxy-10,11-dihydro-dibenzo[b,f]azepin-5-yl)-butylamino]-but-2-enoate were prepared according to the procedure described for Example 2, Step 1, starting from 0.035 g (0.11 mmol) of 5-(4-amino-butyl)-3-chloro-10,11-dihydro-5H-dibenzo[b,f]azepin-2-ol (Intermediate 35). $^1$H NMR (DMSO-$d_6$) δ (ppm): 9.69 (bs, 1H), 7.17-6.96 (m, 4H), 6.91-6.76 (m, 2H), 6.71 (s, 1H), 5.94-5.85 (m, 1H), 4.09 (d, J=6.8 Hz, 2H), 3.62-3.52 (m, 2H), 3.26-3.18 (m, 2H), 3.08-2.92 (m, 4H), 2.42-2.33 (m, 2H), 1.51-1.33 (m, 4H), 1.19 (t, J=6.8 Hz, 3H); MS (ESI): m/z: 429 [M+H]$^+$.

Step 2: Ethyl (E)-4-[4-(3-Chloro-2-hydroxy-10,11-dihydro-dibenzo[b,f]azepin-5-yl)-butylamino]-but-2-enoate maleate 0.013 g (85%) of ethyl (E)-4-[4-(3-chloro-2-hydroxy-10,11-dihydro-dibenzo[b,f]azepin-5-yl)-butylamino]-but-2-enoate maleate were prepared according to the procedure described for Example 2, Step 2, starting from 0.012 g (0.028 mmol) of ethyl (E)-4-[4-(3-chloro-2-hydroxy-10,11-dihydro-dibenzo[b,f]azepin-5-yl)-butylamino]-but-2-enoate. $^1$H NMR (DMSO-$d_6$) δ (ppm): 9.69 (s, 1H), 8.50 (bs, 2H), 7.17-7.00 (m, 4H), 6.93-6.84 (m, 1H), 6.82-6.67 (m, 2H), 6.18 (d, J=15.7 Hz, 1H), 6.01 (s, 2H), 4.15 (q, J=7.3 Hz, 2H), 3.78-3.69 (m, 2H), 3.67-3.56 (m, 2H), 3.10-2.92 (m, 4H), 2.89-2.79 (m, 2H), 1.64-1.42 (m, 4H), 1.21 (t, J=7.3 Hz, 3H) MS (ESI): m/z: 429 [M+H]$^+$.

Example 41: Ethyl (E)-4-{[4-(7-chloro-11-oxo-10,11-dihydro-5H-dibenzo[b,e][1,4]diazepin-5-yl)butyl]amino}but-2-enoate maleate

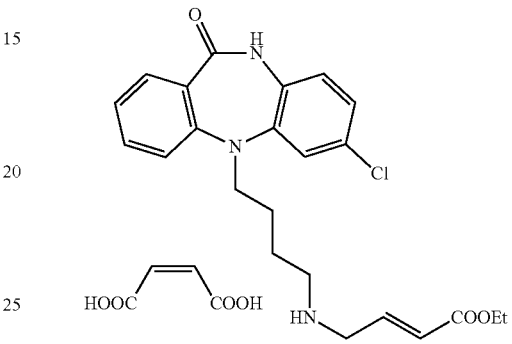

Step 1: Ethyl (E)-4-{[4-(7-chloro-11-oxo-10,11-dihydro-5H-dibenzo[b,e][1,4]diazepin-5-yl)butyl]amino}but-2-enoate 0.010 g (33%) of ethyl (E)-4-{[4-(7-chloro-11-oxo-3-10,11-dihydro-5H-dibenzo[b,e][1,4]diazepin-5-yl)butyl]amino}but-2-enoate were prepared according to the procedure described for Example 2, Step 1, starting from 0.022 g (0.07 mmol) of 5-(4-aminobutyl)-7-chloro-5,10-dihydro-11H-dibenzo[b,e][1,4]diazepin-11-one (Intermediate 36). $^1$H NMR (DMSO-$d_6$) δ (ppm): 10.30 (s, 1H), 7.58 (dd, J=1.5, 7.6 Hz, 1H), 7.52-7.46 (m, 1H), 7.24 (d, J=1.9 Hz, 1H), 7.19 (d, J=8.3 Hz, 1H), 7.14-7.06 (m, 2H), 7.03 (d, J=8.8 Hz, 1H), 6.83 (dt, J=5.4, 15.7 Hz, 1H), 5.89 (dt, J=1.5, 15.7 Hz, 1H), 4.09 (q, J=7.3 Hz, 2H), 3.80-3.61 (m, 2H), 3.21 (dd, J=1.5, 5.4 Hz, 2H), 2.42 (t, J=6.8 Hz, 2H), 1.56-1.39 (m, 4H), 1.19 (t, J=7.3 Hz, 3H); MS (ESI): m/z: 428 [M+H]$^+$.

Step 2: Ethyl (E)-4-{[4-(7-chloro-11-oxo-10,11-dihydro-5H-dibenzo[b,e][1,4]diazepin-5-yl)butyl]amino}but-2-enoate maleate 0.011 g (96%) of ethyl (E)-4-{[4-(7-chloro-11-oxo-10,11-dihydro-5H-dibenzo[b,e][1,4]diazepin-5-yl)butyl]amino}but-2-enoate maleate were prepared according to the procedure described for Example 2, Step 2, starting from 0.009 g (0.02 mmol) of ethyl (E)-4-{[4-(7-chloro-11-oxo-10,11-dihydro-5H-dibenzo[b,e][1,4]diazepin-5-yl)butyl]amino}but-2-enoate. $^1$H NMR (DMSO-$d_6$) δ (ppm): 10.30 (s, 1H), 8.57 (bs, 3H), 7.61 (dd, J=1.5, 7.8 Hz, 1H), 7.55-7.48 (m, 1H), 7.27 (d, J=2.0 Hz, 1H), 7.22 (d, J=8.3 Hz, 1H), 7.16-7.09 (m, 2H), 7.09-7.03 (m, 1H), 6.76 (dt, J=6.4, 15.7 Hz, 1H), 6.18 (d, J=15.7 Hz, 1H), 6.02 (s, 2H), 4.15 (q, J=7.3 Hz, 2H), 3.87-3.64 (m, 4H), 2.89 (t, J=7.1 Hz, 2H), 1.69-1.50 (m, 4H), 1.21 (t, J=73.0 Hz, 3H); MS (ESI): m/z: 428 [M+H]$^+$.

Example 42: Ethyl (E)-4-{[4-(3-chloro-10-methyl-11-oxo-10,11-dihydro-5H-dibenzo[b,e][1,4]diazepin-5-yl)butyl]amino}but-2-enoate maleate

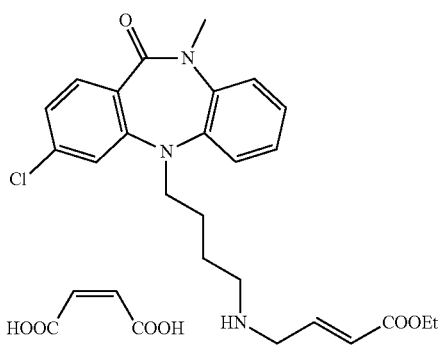 [SMILES: CCOC(=O)/C=C/CNCCCCN1c2cc(Cl)ccc2C(=O)N(C)c2ccccc21 ; O=C(O)/C=C\C(=O)O]

Step 1: Ethyl (E)-4-{[4-(3-chloro-10-methyl-11-oxo-10,11-dihydro-5H-dibenzo[b,e][1,4]diazepin-5-yl)butyl]amino}but-2-enoate 0.027 g (46%) of ethyl (E)-4-{[4-(3-chloro-10-methyl-11-oxo-10,11-dihydro-5H-dibenzo[b,e][1,4]diazepin-5-yl)butyl]amino}but-2-enoate were prepared according to the procedure described for Example 2, Step 1, starting from 0.044 g (0.133 mmol) of 5-(4-aminobutyl)-3-chloro-10-methyl-5,10-dihydro-11H-dibenzo[b,e][1,4]diazepin-11-one (Intermediate 37). $^1$H NMR (DMSO-$d_6$) δ (ppm): 7.56 (d, J=8.3 Hz, 1H), 7.36 (dd, J=1.5, 7.3 Hz, 1H), 7.28-7.23 (m, 2H), 7.21-7.14 (m, 2H), 7.11 (dd, J=1.9, 8.3 Hz, 1H), 6.83 (dt, J=5.4, 15.7 Hz, 1H), 5.90 (dt, J=1.5, 15.7 Hz, 1H), 4.10 (q, J=7.3 Hz, 2H), 3.77-3.64 (m, 2H), 3.42 (s, 3H), 3.21 (dd, J=1.5, 5.4 Hz, 2H), 2.41 (t, J=6.8 Hz, 2H), 1.59-1.38 (m, 4H), 1.19 (t, J=7.1 Hz, 3H); MS (ESI): m/z: 442 [M+H]$^+$.

Step 2: Ethyl (E)-4-{[4-(3-chloro-10-methyl-11-oxo-10,11-dihydro-5H-dibenzo[b,e][1,4]diazepin-5-yl)butyl]amino}but-2-enoate maleate 0.027 g (82%) of ethyl (E)-4-{[4-(3-chloro-10-methyl-11-oxo-10,11-dihydro-5H-dibenzo[b,e][1,4]diazepin-5-yl)butyl]amino}but-2-enoate maleate were prepared according to the procedure described for Example 2, Step 2, starting from 0.026 g (0.059 mmol) of ethyl (E)-4-{[4-(3-chloro-10-methyl-11-oxo-10,11-dihydro-5H-dibenzo[b,e][1,4]diazepin-5-yl)butyl]amino}but-2-enoate. $^1$H NMR (DMSO-$d_6$) δ (ppm): 8.55 (bs, 3H), 7.58 (d, J=8.3 Hz, 1H), 7.39 (dd, J=2.2, 7.6 Hz, 1H), 7.30-7.26 (m, 2H), 7.23-7.17 (m, 2H), 7.15 (dd, J=1.7, 8.6 Hz, 1H), 6.76 (dt, J=6.4, 15.7 Hz, 1H), 6.18 (d, J=15.7 Hz, 1H), 6.04 (s, 2 H), 4.15 (q, J=7.3 Hz, 2H), 3.81-3.68 (m, 4H), 3.44 (s, 3H), 2.89 (bs, 2H), 1.66-1.48 (m, 4H), 1.21 (t, J=7.3 Hz, 3H); MS (ESI): m/z: 442 [M+H]$^+$.

Example 43: Ethyl (E)-4-{[4-(8-chloro-1-methyl-4,5-dihydropyrazolo-[3,4-b][1]-benzazepin-10(1H)-yl)butyl]amino}but-2-enoate maleate

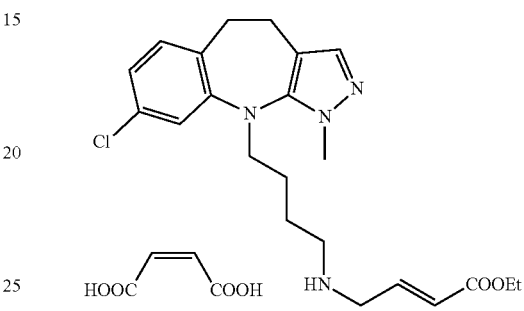

Step 1: Ethyl (E)-4-{[4-(8-chloro-1-methyl-4,5-dihydropyrazolo[3,4-b][1]benzazepin-10(1H)-yl)butyl]amino}but-2-enoate 0.016 g (47%) of ethyl (E)-4-{[4-(8-chloro-1-methyl-4,5-dihydropyrazolo[3,4-b][1]benzazepin-10(1H)-yl)butyl]amino}but-2-enoate were prepared according to the procedure described for Example 2, Step 1, starting from 0.025 g (0.082 mmol) of 4-(8-chloro-1-methyl-4,5-dihydropyrazolo[3,4-b][1]benzazepin-10(1H)-yl)butan-1-amine (Intermediate 38). $^1$H NMR (DMSO-$d_6$) δ (ppm): 7.36 (d, J=1.9 Hz, 1H), 7.27 (d, J=7.8 Hz, 1H), 7.20 (dd, J=1.9, 8.3 Hz, 1H), 7.08 (s, 1H), 6.84 (dt, J=5.4, 15.7 Hz, 1H), 5.92 (dt, J=1.5, 15.7 Hz, 1H), 4.10 (q, J=7.3 Hz, 2H), 3.73 (s, 3H), 3.46-3.38 (m, 2H), 3.24 (dd, J=1.5, 5.4 Hz, 2H), 2.97-2.87 (m, 2H), 2.62 (bs, 2H), 2.41 (t, J=6.8 Hz, 2H), 1.53-1.34 (m, 4H), 1.20 (t, J=7.3 Hz, 3H); MS (ESI): m/z: 417 [M+H]$^+$.

Step 2: Ethyl (E)-4-{[4-(8-chloro-1-methyl-4,5-dihydropyrazolo[3,4-b][1]benzazepin-10(1H)-yl)butyl]amino}but-2-enoate maleate 0.014 g (73%) of ethyl (E)-4-{[4-(8-chloro-1-methyl-4,5-dihydropyrazolo[3,4-b][1]benzazepin-10(1H)-yl)butyl]amino}but-2-enoate maleate were prepared according to the procedure described for Example 2, Step 2, starting from 0.015 g (0.036 mmol) of ethyl (E)-4-{[4-(8-chloro-1-methyl-4,5-dihydropyrazolo[3,4-b][1]benzazepin-10(1H)-yl)butyl]amino}but-2-enoate maleate. $^1$H NMR (DMSO-$d_6$) δ (ppm): 8.57 (bs, 3H), 7.39 (d, J=2.0 Hz, 1H), 7.29 (d, J=8.3 Hz, 1H), 7.22 (dd, J=1.9, 8.1 Hz, 1H), 7.10 (s, 1H), 6.78 (dt, J=6.4, 16.1 Hz, 1H), 6.20 (d, J=16.1 Hz, 1H), 6.05 (s, 2H), 4.15 (q, J=7.1 Hz, 2H), 3.75 (s, 3H), 3.50-3.42 (m, 2H), 3.00-2.84 (m, 4H), 2.63 (bs, 2H), 1.62-1.45 (m, 4H), 1.21 (t, J=7.1 Hz, 3H); MS (ESI): m/z: 417 [M+H]$^+$.

Example 44: Ethyl (E)-4-{[4-(7-chloro-10-(2-phenylethyl)-11-oxo-10,11-dihydro-5H-dibenzo[b,e][1,4]diazepin-5-yl)butyl]amino}but-2-enoate maleate

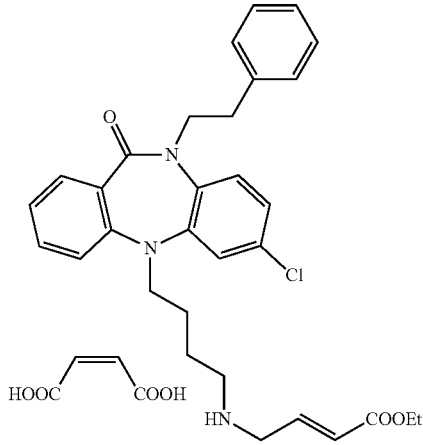 [SMILES: CCOC(=O)/C=C/CNCCCCN1c2ccccc2C(=O)N(CCc2ccccc2)c2ccc(Cl)cc21 ; O=C(O)/C=C\C(=O)O]

Step 1: Ethyl (E)-4-{[4-(7-chloro-10-(2-phenylethyl)-11-oxo-10,11-dihydro-5H-dibenzo[b,e][1,4]diazepin-5-yl)butyl]amino}but-2-enoate 0.012 g (45%) of ethyl (E)-4-{[4-(7-chloro-10-(2-phenylethyl)-11-oxo-10,11-dihydro-5H-dibenzo[b,e][1,4]diazepin-5-yl)butyl]amino}but-2-enoate were prepared according to the procedure described for Example 2, Step 1, starting from 0.021 g (0.05 mmol) of 5-(4-aminobutyl)-7-chloro-10-(2-phenylethyl)-5,10-dihydro-11H-dibenzo[b,e][1,4]diazepin-11-one (Intermediate 39). $^1$H NMR (DMSO-$d_6$) δ (ppm): 7.54 (dd, J=1.5, 7.8 Hz, 1H), 7.49 (d, J=8.3 Hz, 1H), 7.45-7.40 (m, 1H), 7.30 (d, J=2.4 Hz, 1H), 7.27-7.21 (m, 2H), 7.21-7.13 (m, 5H), 7.11-7.06 (m, 1H), 6.82 (dt, J=4.9, 15.7 Hz, 1H), 5.90 (dt, J=1.5, 15.7 Hz, 1H), 4.68-4.57 (m, 1H), 4.08 (q, J=7.3 Hz, 2H), 3.92-3.83 (m, 1H), 3.76-3.67 (m, 1H), 3.56-3.48 (m, 1H), 3.22 (dd, J=1.5, 4.9 Hz, 2H), 2.87-2.74 (m, 2H), 2.46-2.40 (m, 2H), 1.46 (bs, 4H), 1.18 (t, J=7.3 Hz, 3H); MS (ESI): m/z: 532 [M+H]$^+$.

Step 2: Ethyl (E)-4-{[4-(7-chloro-10-(2-phenylethyl)-11-oxo-10,11-dihydro-5H-dibenzo[b,e][1,4]diazepin-5-yl)butyl]amino}but-2-enoate maleate 0.009 g (70%) of ethyl (E)-4-{[4-(7-chloro-10-(2-phenylethyl)-11-oxo-10,11-dihydro-5H-dibenzo[b,e][1,4]diazepin-5-yl)butyl]amino}but-2-enoate maleate were prepared according to the procedure described for Example 2, Step 2, starting from 0.011 g (0.021 mmol) of ethyl (E)-4-{[4-(7-chloro-10-(2-phenylethyl)-11-oxo-10,11-dihydro-5H-dibenzo[b,e][1,4]diazepin-5-yl)butyl]amino}but-2-enoate. $^1$H NMR (DMSO-$d_6$) δ (ppm): 8.58 (bs, 3H), 7.55 (dd, J=1.7, 7.6 Hz, 1H), 7.51 (d, J=8.8 Hz, 1H), 7.47-7.42 (m, 1H), 7.32 (d, J=2.0 Hz, 1H), 7.29-7.24 (m, 2H), 7.23-7.15 (m, 5H), 7.13-7.08 (m, 1H), 6.77 (dt, J=6.4, 15.7 Hz, 1H), 6.17 (d, J=15.7 Hz, 1H), 6.01 (s, 2H), 4.64-4.54 (m, 1H), 4.14 (q, J=7.1 Hz, 2H), 3.95-3.86 (m, 1H), 3.82-3.71 (m, 3H), 3.59-3.46 (m, 1H), 2.97-2.77 (m, 4H), 1.70-1.57 (m, 2H), 1.56-1.41 (m, 2H), 1.21 (t, J=7.1 Hz, 3H); MS (ESI): m/z: 532 [M+H]$^+$.

Example 45: Ethyl (E)-4-{[4-(10-benzyl-7-chloro-11-oxo-10,11-dihydro-5H-dibenzo[b,e][1,4]diazepin-5-yl)butyl]amino}but-2-enoate maleate

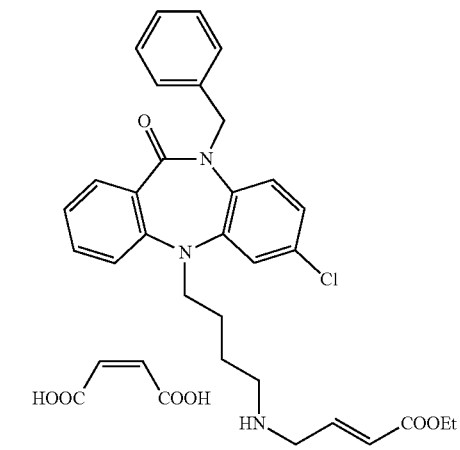 [SMILES: CCOC(=O)/C=C/CNCCCCN1c2ccccc2C(=O)N(Cc2ccccc2)c2ccc(Cl)cc21 ; O=C(O)/C=C\C(=O)O]

Step 1: Ethyl (E)-4-{[4-(10-benzyl-7-chloro-11-oxo-10,11-dihydro-5H-dibenzo[b,e][1,4]diazepin-5-yl)butyl]amino}but-2-enoate 0.019 g (37%) of ethyl (E)-4-{[4-(10-benzyl-7-chloro-11-oxo-10,11-dihydro-5H-dibenzo[b,e][1,4]diazepin-5-yl)butyl]amino}but-2-enoate were prepared according to the procedure described for Example 2, Step 1, starting from 0.04 g (0.1 mmol) of 5-(4-aminobutyl)-10-benzyl-7-chloro-5,10-dihydro-11H-dibenzo[b,e][1,4]diazepin-11-one (Intermediate 40). $^1$H NMR (DMSO-$d_6$) δ (ppm): 7.58 (dd, J=1.5, 7.8 Hz, 1H), 7.49-7.43 (m, 2H), 7.30-7.23 (m, 5H), 7.23-7.15 (m, 2H), 7.15-7.08 (m, 2H), 6.87 (dt, J=5.4, 15.7 Hz, 1H), 5.94 (d, J=15.7 Hz, 1H), AB System: $v_A$=5.66, $v_B$=4.94, $J_{AB}$=15.9 Hz, 4.10 (q, J=7.3 Hz, 2H), 3.78-3.70 (m, 1H), 3.64-3.53 (m, 1H), 3.27 (dd, J=1.5, 5.4 Hz, 2H), 2.48-2.43 (m, 2H), 1.58-1.38 (m, 4H), 1.19 (t, J=7.3 Hz, 3H); MS (ESI): m/z: 518 [M+H]$^+$.

Step 2: Ethyl (E)-4-{[4-(10-benzyl-7-chloro-11-oxo-10,11-dihydro-5H-dibenzo[b,e][1,4]diazepin-5-yl)butyl]amino}but-2-enoate maleate 0.019 g (91%) of ethyl (E)-4-{[4-(10-benzyl-7-chloro-11-oxo-10,11-dihydro-5H-dibenzo[b,e][1,4]diazepin-5-yl)butyl]amino}but-2-enoate maleate were prepared according to the procedure described for Example 2, Step 2, starting from 0.017 g (0.033 mmol) of ethyl (E)-4-{[4-(10-benzyl-7-chloro-11-oxo-10,11-dihydro-5H-dibenzo[b,e][1,4]diazepin-5-yl)butyl]amino}but-2-enoate. $^1$H NMR (DMSO-$d_6$) δ (ppm): 8.62 (bs, 3H), 7.60 (dd, J=1.5, 7.8 Hz, 1H), 7.51-7.46 (m, 1H), 7.44 (d, J=8.8 Hz, 1H), 7.32-7.25 (m, 5H), 7.25-7.18 (m, 2H), 7.17-7.09 (m, 2H), 6.80 (dt, J=6.4, 15.7 Hz, 1H), 6.21 (d, J=15.7 Hz, 1H), 6.03 (s, 2H), AB System: $v_A$=5.66, $v_B$=4.94, $J_{AB}$=15.9 Hz, 4.16 (q, J=7.3 Hz, 2H), 3.86-3.73 (m, 3H), 3.66-3.58 (m, 1H), 2.92 (t, J=7.3 Hz, 2H), 1.73-1.57 (m, 2H), 1.57-1.47 (m, 2H), 1.22 (t, J=7.3 Hz, 3H); MS (ESI): m/z: 518 [M+H]$^+$.

Example 46: Ethyl (E)-4-({4-[3-chloro-10-(2-hydroxyethyl)-11-oxo-10,11-dihydro-5H-dibenzo[b,e][1,4]diazepin-5-yl]butyl}amino)but-2-enoate maleate

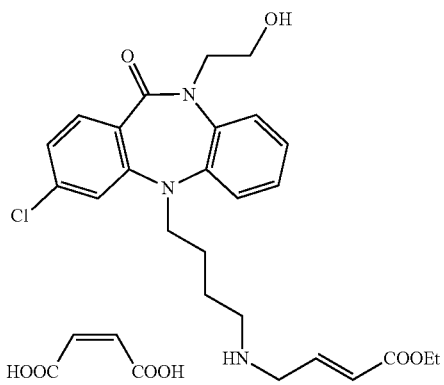 [SMILES: CCOC(=O)/C=C/CNCCCCN1c2cc(Cl)ccc2C(=O)N(CCO)c2ccccc21 ; O=C(O)/C=C\C(=O)O]

Step 1: Ethyl (E)-4-({4-[3-chloro-10-(2-hydroxyethyl)-11-oxo-10,11-dihydro-5H-dibenzo[b,e][1,4]diazepin-5-yl]butyl}amino)but-2-enoate 0.059 g (54%) of ethyl (E)-4-({4-[3-chloro-10-(2-hydroxyethyl)-11-oxo-10,11-dihydro-5H-dibenzo[b,e][1,4]diazepin-5-yl]butyl}amino)but-2-enoate were prepared according to the procedure described for Example 2, Step 1, starting from 0.084 g (0.233 mmol) of 5-(4-aminobutyl)-3-chloro-10-(2-hydroxyethyl)-5,10-dihydro-11H-dibenzo[b,e][1,4]diazepin-11-one (Intermediate 41). $^1$H NMR (DMSO-$d_6$) δ (ppm): 7.57 (dd, J=1.5, 7.8 Hz, 1H), 7.51 (d, J=8.3 Hz, 1H), 7.26 (dd, J=1.5, 7.8 Hz, 1H), 7.22 (d, J=2.0 Hz, 1H), 7.21-7.13 (m, 2H), 7.11 (dd, J=2.0, 8.3 Hz, 1H), 6.83 (dt, J=5.1, 15.6 Hz, 1H), 5.91 (dt, J=1.4, 15.6 Hz, 1H), 4.91 (bs, 1H), 4.26-4.18 (m, 1H), 4.09 (q, J=7.3 Hz, 2H), 3.85-3.78 (m, 1H), 3.77-3.70 (m, 1H), 3.69-3.61 (m, 2H), 3.52-3.43 (m, 1H), 3.22 (dd, J=1.7, 5.1 Hz, 2H), 2.42 (t, J=6.8 Hz, 2H), 1.60-1.38 (m, 4H), 1.19 (t, J=7.3 Hz, 3H); MS (ESI): m/z: 472 [M+H]$^+$.

Step 2: Ethyl (E)-4-({4-[3-chloro-10-(2-hydroxyethyl)-11-oxo-10,11-dihydro-5H-dibenzo[b,e][1,4]diazepin-5-yl]butyl}amino)but-2-enoate maleate 0.058 g (88%) of ethyl (E)-4-({4-[3-chloro-10-(2-hydroxyethyl)-11-oxo-10,11-dihydro-5H-dibenzo[b,e][1,4]diazepin-5-yl]butyl}amino)but-2-enoate maleate were prepared according to the procedure described for Example 2, Step 2, starting from 0.053 g (0.11 mmol) of ethyl (E)-4-({4-[3-chloro-10-(2-hydroxyethyl)-11-oxo-10,11-dihydro-5H-dibenzo[b,e][1,4]diazepin-5-yl]butyl}amino)but-2-enoate. $^1$H NMR (DMSO-$d_6$) δ (ppm): 8.56 (bs, 3H), 7.58 (dd, J=1.5, 7.8 Hz, 1H), 7.53 (d, J=8.3 Hz, 1H), 7.30-7.24 (m, 2H), 7.23-7.15 (m, 2H), 7.13 (dd, J=2.0, 8.3 Hz, 1H), 6.77 (dt, J=6.2, 16.0 Hz, 1H), 6.18 (d, J=16.1 Hz, 1H), 6.01 (s, 2H), 4.86 (bs, 1H), 4.26-4.18 (m, 1H), 4.15 (q, J=7.1 Hz, 2H), 3.89-3.82 (m, 1H), 3.78-3.64 (m, 5H), 3.57-3.48 (m, 1H), 2.95-2.84 (m, 2H), 1.70-1.48 (m, 4H), 1.21 (t, J=7.1 Hz, 3H); MS (ESI): m/z: 472 [M+H]$^+$.

Example 47: Ethyl (E)-4-({3-[3-chloro-10-(2-hydroxyethyl)-11-oxo-10,11-dihydro-5H-dibenzo[b,e][1,4]diazepin-5-yl]propyl}amino)but-2-enoate maleate

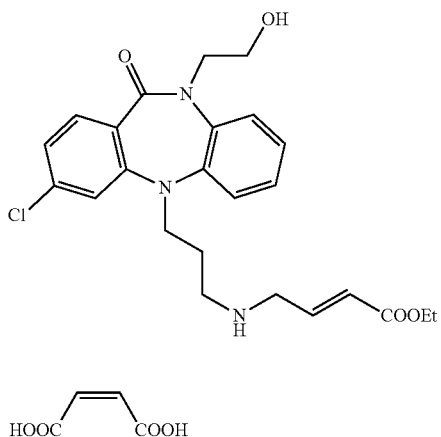 [SMILES: CCOC(=O)/C=C/CNCCCN1c2cc(Cl)ccc2C(=O)N(CCO)c2ccccc21 ; O=C(O)/C=C\C(=O)O]

Step 1: Ethyl (E)-4-({3-[3-chloro-10-(2-hydroxyethyl)-11-oxo-10,11-dihydro-5H-dibenzo[b,e][1,4]diazepin-5-yl]propyl}amino)but-2-enoate 0.043 g (50%) of ethyl (E)-4-({3-[3-chloro-10-(2-hydroxyethyl)-11-oxo-10,11-dihydro-5H-dibenzo[b,e][1,4]diazepin-5-yl]propyl}amino)but-2-enoate were prepared according to the procedure described for Example 2, Step 1, starting from 0.065 g (0.233 mmol) of 5-(3-aminopropyl)-3-chloro-10-(2-hydroxyethyl)-5,10-dihydro-11H-dibenzo[b,e][1,4]diazepin-11-one (Intermediate 42). $^1$H NMR (DMSO-$d_6$) δ (ppm): 7.56 (dd, J=2.0, 7.8 Hz, 1H), 7.51 (d, J=8.3 Hz, 1H), 7.26 (dd, J=2.0, 7.8 Hz, 1H), 7.23 (d, J=1.9 Hz, 1H), 7.21-7.13 (m, 2H), 7.11 (dd, J=1.9, 8.3 Hz, 1H), 6.84 (dt, J=5.4, 15.7 Hz, 1H), 5.91 (dt, J=1.9, 15.7 Hz, 1H), 4.86 (bs, 1H), 4.26-4.17 (m, 1H), 4.09 (q, J=7.1 Hz, 2H), 3.85-3.75 (m, 2H), 3.74-3.60 (m, 2H), 3.47 (bs, 1H), 3.23 (dd, J=1.7, 5.1 Hz, 2H), 2.53 (t, J=6.8 Hz, 2H), 2.06 (bs, 1H), 1.69-1.55 (m, 2H), 1.19 (t, J=7.1 Hz, 3H); MS (ESI): m/z: 480 [M+Na]$^+$.

Step 2: Ethyl (E)-4-({3-[3-chloro-10-(2-hydroxyethyl)-11-oxo-10,11-dihydro-5H-dibenzo[b,e][1,4]diazepin-5-yl]propyl}amino)but-2-enoate maleate 0.036 g (76%) of ethyl (E)-4-({3-[3-chloro-10-(2-hydroxyethyl)-11-oxo-10,11-dihydro-5H-dibenzo[b,e][1,4]diazepin-5-yl]propyl}amino)but-2-enoate maleate were prepared according to the procedure described for Example 2, Step 2, starting from 0.038 g (0.083 mmol) of ethyl (E)-4-({3-[3-chloro-10-(2-hydroxyethyl)-11-oxo-10,11-dihydro-5H-dibenzo[b,e][1,4]diazepin-5-yl]propyl}amino)but-2-enoate. $^1$H NMR (DMSO-$d_6$) δ (ppm): 8.54 (bs, 3H), 7.60-7.49 (m, 2H), 7.31-7.27 (m, 1H), 7.26 (d, J=1.5 Hz, 1H), 7.24-7.13 (m, 3H), 6.74 (dt, J=5.9, 15.7 Hz, 1H), 6.18 (d, J=15.7 Hz, 1H), 6.03 (s, 2H), 4.83 (t, J=5.4 Hz, 1H), 4.38-4.29 (m, 1H), 4.15 (q, J=7.2 Hz, 2H), 3.92-3.77 (m, 3H), 3.73 (bs, 2H), 3.67-3.52 (m, 2H), 3.00 (bs, 2H), 1.88-1.79 (m, 2H), 1.21 (t, J=7.1 Hz, 3H); MS (ESI): m/z: 458 [M+H]$^+$.

Example 48: Ethyl (E)-4-({4-[3-chloro-10-(3-hydroxypropyl)-11-oxo-10,11-dihydro-5H-dibenzo[b,e][1,4]diazepin-5-yl]butyl}amino)but-2-enoate maleate

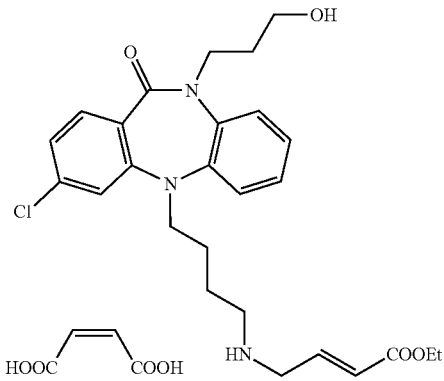 [SMILES: CCOC(=O)/C=C/CNCCCCN1c2cc(Cl)ccc2C(=O)N(CCCO)c2ccccc21 ; O=C(O)/C=C\C(=O)O]

Step 1: Ethyl (E)-4-({4-[3-chloro-10-(3-hydroxypropyl)-11-oxo-10,11-dihydro-5H-dibenzo[b,e][1,4]diazepin-5-yl]butyl}amino)but-2-enoate 0.043 g (54%) of ethyl (E)-4-({4-[3-chloro-10-(3-hydroxypropyl)-11-oxo-10,11-dihydro-5H-dibenzo[b,e][1,4]diazepin-5-yl]butyl}amino)but-2-enoate were prepared according to the procedure described for Example 2, Step 1, starting from 0.061 g (0.163 mmol) of 5-(4-aminobutyl)-3-chloro-10-(3-hydroxypropyl)-5,10-dihydro-11H-dibenzo[b,e][1,4]diazepin-11-one (Intermediate 43). $^1$H NMR (DMSO-$d_6$) δ (ppm): 7.53 (d, J=8.3 Hz, 1H), 7.42 (dd, J=1.5, 8.1 Hz, 1H), 7.28 (dd, J=1.9, 8.1 Hz, 1H), 7.23 (d, J=2.0 Hz, 1H), 7.21-7.13 (m, 2H), 7.11 (dd, J=2.0, 8.3 Hz, 1H), 6.84 (dt, J=5.4, 15.6 Hz, 1H), 5.91 (dt, J=1.9, 15.6 Hz, 1H), 4.57-4.44 (m, 2H), 4.09 (q, J=7.3 Hz, 2H), 3.76-3.61 (m, 3H), 3.43-3.35 (m, 2H), 3.24 (dd, J=1.9, 5.4 Hz, 2H), 2.44 (t, J=6.8 Hz, 2H), 1.68-1.42 (m, 6H), 1.19 (t, J=7.3 Hz, 3H); MS (ESI): m/z: 486 [M+H]$^+$.

Step 2: Ethyl (E)-4-({4-[3-chloro-10-(3-hydroxypropyl)-11-oxo-10,11-dihydro-5H-dibenzo[b,e][1,4]diazepin-5-yl]butyl}amino)but-2-enoate maleate 0.049 g (90%) of ethyl (E)-4-({4-[3-chloro-10-(3-hydroxypropyl)-11-oxo-10,11-dihydro-5H-dibenzo[b,e][1,4]diazepin-5-yl]butyl}amino)but-2-enoate maleate were prepared according to the procedure described for Example 2, Step 2, starting from 0.043 g (0.09 mmol) of ethyl (E)-4-({4-[3-chloro-10-(3-hydroxypropyl)-11-oxo-10,11-dihydro-5H-dibenzo[b,e][1,4]diazepin-5-yl]butyl}amino)but-2-enoate. $^1$H NMR (DMSO-$d_6$) δ (ppm): 8.61 (bs, 3H), 7.54 (d, J=8.3 Hz, 1H), 7.44 (dd, J=2.0, 7.8 Hz, 1H), 7.29 (dd, J=1.5, 8.3 Hz, 1H), 7.25 (d, J=1.9 Hz, 1H), 7.24-7.15 (m, 2H), 7.13 (dd, J=1.9, 8.3 Hz, 1H), 6.78 (dt, J=6.2, 15.7 Hz, 1H), 6.19 (d, J=15.7 Hz, 1H), 6.02 (s, 2H), 4.57-4.37 (m, 2H), 4.15 (q, J=7.3 Hz, 2H), 3.82-3.65 (m, 5H), 3.47-3.36 (m, 2H), 2.97-2.86 (m, 2H), 1.74-1.48 (m, 6H), 1.21 (t, J=7.3 Hz, 3H); MS (ESI): m/z: 486 [M+H]$^+$.

Example 49: Ethyl (E)-4-({3-[3-chloro-10-(3-hydroxypropyl)-11-oxo-10,11-dihydro-5H-dibenzo[b,e][1,4]diazepin-5-yl]propyl}amino)but-2-enoate maleate

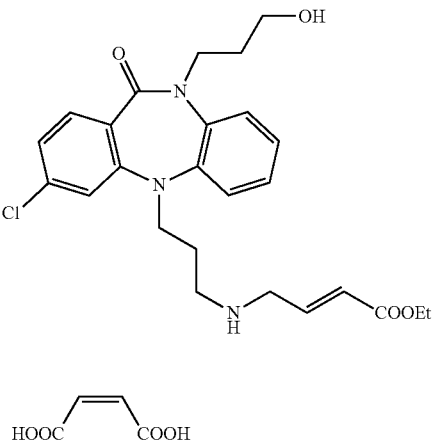 [SMILES: CCOC(=O)/C=C/CNCCCN1c2cc(Cl)ccc2C(=O)N(CCCO)c2ccccc21 ; O=C(O)/C=C\C(=O)O]

Step 1: Ethyl (E)-4-({3-[3-chloro-10-(3-hydroxypropyl)-11-oxo-10,11-dihydro-5H-dibenzo[b,e][1,4]diazepin-5-yl]propyl}amino)but-2-enoate 0.035 g (51%) of ethyl (E)-4-({3-[3-chloro-10-(3-hydroxypropyl)-11-oxo-10,11-dihydro-5H-dibenzo[b,e][1,4]diazepin-5-yl]propyl}amino)but-2-enoate were prepared according to the procedure described for Example 2, Step 1, starting from 0.053 g (0.147 mmol) of 5-(3-aminopropyl)-3-chloro-10-(3-hydroxypropyl)-5,10-dihydro-11H-dibenzo[b,e][1,4]diazepin-11-one (Intermediate 44). $^1$H NMR (DMSO-$d_6$) δ (ppm): 7.53 (d, J=8.3 Hz, 1H), 7.42 (dd, J=1.5, 7.8 Hz, 1H), 7.27 (dd, J=1.4, 7.8 Hz, 1H), 7.23 (d, J=2.0 Hz, 1H), 7.22-7.13 (m, 2H), 7.11 (dd, J=2.0, 8.3 Hz, 1H), 6.83 (dt, J=5.4, 15.7 Hz, 1H), 5.92 (d, J=15.7 Hz, 1H), 4.54-4.39 (m, 2H), 4.09 (q, J=7.3 Hz, 2H), 3.82-3.61 (m, 3H), 3.44-3.35 (m, 2H), 3.24 (dd, J=1.7, 5.1 Hz, 2H), 2.54 (t, J=6.6 Hz, 2H), 1.71-1.55 (m, 4H), 1.19 (t, J=7.3 Hz, 3H); MS (ESI): m/z: 472 [M+H]$^+$.

Step 2: Ethyl (E)-4-({3-[3-chloro-10-(3-hydroxypropyl)-11-oxo-10,11-dihydro-5H-dibenzo[b,e][1,4]diazepin-5-yl]propyl}amino)but-2-enoate maleate 0.035 g (84%) of ethyl (E)-4-({3-[3-chloro-10-(3-hydroxypropyl)-11-oxo-10,11-dihydro-5H-dibenzo[b,e][1,4]diazepin-5-yl]propyl}amino)but-2-enoate maleate were prepared according to the procedure described for Example 2, Step 2, starting from 0.033 g (0.07 mmol) of ethyl (E)-4-({3-[3-chloro-10-(3-hydroxypropyl)-11-oxo-10,11-dihydro-5H-dibenzo[b,e][1,4]diazepin-5-yl]propyl}amino)but-2-enoate. $^1$H NMR (DMSO-$d_6$) δ (ppm): 8.66 (bs, 3H), 7.56 (d, J=8.3 Hz, 1H), 7.46 (dd, J=1.0, 7.8 Hz, 1H), 7.33-7.28 (m, 1H), 7.26 (d, J=1.5 Hz, 1H), 7.25-7.12 (m, 3H), 6.76 (dt, J=6.3, 15.7 Hz, 1H), 6.20 (d, J=15.7 Hz, 1H), 6.06 (s, 2H), 4.57-4.40 (m, 2H), 4.15 (q, J=6.8 Hz, 2H), 3.91-3.64 (m, 5H), 3.46-3.37 (m, 2H), 2.98 (bs, 2H), 1.94-1.76 (m, 2H), 1.75-1.57 (m, 2H), 1.21 (t, J=6.8 Hz, 3H); MS (ESI): m/z: 472 [M+H]$^+$.

Example 50: Ethyl (E)-4-({4-[7-chloro-10-(2-hydroxyethyl)-11-oxo-10,11-dihydro-5H-dibenzo[b,e][1,4]diazepin-5-yl]butyl}amino)but-2-enoate maleate

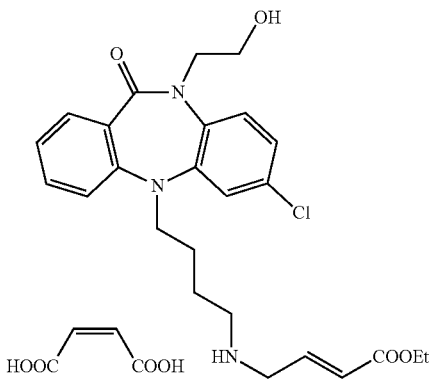 [SMILES: CCOC(=O)/C=C/CNCCCCN1c2ccccc2C(=O)N(CCO)c2ccc(Cl)cc21 ; O=C(O)/C=C\C(=O)O]

Step 1: Ethyl (E)-4-({4-[7-chloro-10-(2-hydroxyethyl)-11-oxo-10,11-dihydro-5H-dibenzo[b,e][1,4]diazepin-5-yl]butyl}amino)but-2-enoate 0.033 g (43%) of ethyl (E)-4-({4-[7-chloro-10-(2-hydroxyethyl)-11-oxo-10,11-dihydro-5H-dibenzo[b,e][1,4]diazepin-5-yl]butyl}amino)but-2-enoate were prepared according to the procedure described for Example 2, Step 1, starting from 0.059 g (0.164 mmol) of 5-(4-aminobutyl)-7-chloro-10-(2-hydroxyethyl)-5,10-dihydro-11H-dibenzo[b,e][1,4]diazepin-11-one (Intermediate 45). $^1$H NMR (DMSO-$d_6$) δ (ppm): 7.60 (d, J=8.8 Hz, 1H), 7.51 (dd, J=1.7, 7.6 Hz, 1H), 7.45-7.39 (m, 1H), 7.31 (d, J=2.0 Hz, 1H), 7.20-7.14 (m, 2H), 7.11-7.05 (m, 1H), 6.84 (dt, J=5.4, 15.7 Hz, 1H), 5.90 (dt, J=2.0, 15.7 Hz, 1H), 4.96 (bs, 1H), 4.19-4.12 (m, 1H), 4.09 (q, J=7.1 Hz, 2H), 3.86-3.79 (m, 1H), 3.73-3.64 (m, 3H), 3.53-3.46 (m, 1H), 3.23 (dd, J=2.0, 5.4 Hz, 2H), 2.42 (t, J=6.8 Hz, 2H), 1.59-1.40 (m, 4H), 1.19 (t, J=7.1 Hz, 3H); MS (ESI): m/z: 472 [M+H]$^+$.

Step 2: Ethyl (E)-4-({4-[7-chloro-10-(2-hydroxyethyl)-11-oxo-10,11-dihydro-5H-dibenzo[b,e][1,4]diazepin-5-yl]butyl}amino)but-2-enoate maleate 0.034 g (94%) of ethyl (E)-4-({4-[7-chloro-10-(2-hydroxyethyl)-11-oxo-10,11-dihydro-5H-dibenzo[b,e][1,4]diazepin-5-yl]butyl}amino)but-2-enoate maleate were prepared according to the procedure described for Example 2, Step 2, starting from 0.029 g (0.06 mmol) of ethyl (E)-4-({4-[7-chloro-10-(2-hydroxyethyl)-11-oxo-10,11-dihydro-5H-dibenzo[b,e][1,4]diazepin-5-yl]butyl}amino)but-2-enoate. $^1$H NMR (DMSO-$d_6$) δ (ppm): 8.57 (bs, 3H), 7.63 (d, J=8.8 Hz, 1H), 7.53 (dd, J=1.7, 7.6 Hz, 1H), 7.48-7.41 (m, 1H), 7.33 (d, J=2.4 Hz, 1H), 7.23-7.15 (m, 2H), 7.13-7.07 (m, 1H), 6.77 (dt, J=6.4, 15.7 Hz, 1H), 6.19 (d, J=15.7 Hz, 1H), 6.02 (s, 2H), 4.89 (bs, 1H), 4.19-4.10 (m, 3H), 3.91-3.83 (m, 1H), 3.77-3.67 (m, 5H), 3.58-3.49 (m, 1H), 2.93-2.85 (m, 2H), 1.71-1.49 (m, 4H), 1.21 (t, J=7.1 Hz, 3H); MS (ESI): m/z: 472 [M+H]$^+$.

Example 51: Ethyl (E)-4-({4-[7-chloro-10-(3-hydroxypropyl)-11-oxo-10,11-dihydro-5H-dibenzo[b,e][1,4]diazepin-5-yl]butyl}amino)but-2-enoate maleate

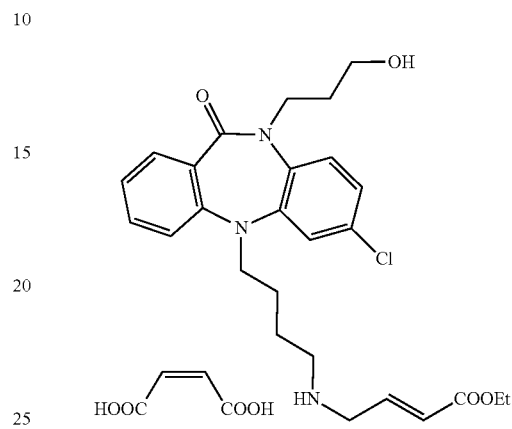

Step 1: Ethyl (E)-4-({4-[7-chloro-10-(3-hydroxypropyl)-11-oxo-10,11-dihydro-5H-dibenzo[b,e][1,4]diazepin-5-yl]butyl}amino)but-2-enoate 0.049 g (59%) of ethyl (E)-4-({4-[7-chloro-10-(3-hydroxypropyl)-11-oxo-10,11-dihydro-5H-dibenzo[b,e][1,4]diazepin-5-yl]butyl}amino)but-2-enoate were prepared according to the procedure described for Example 2, Step 1, starting from 0.064 g (0.171 mmol) of 5-(4-aminobutyl)-7-chloro-10-(3-hydroxypropyl)-5,10-dihydro-11H-dibenzo[b,e][1,4]diazepin-11-one (Intermediate 46). $^1$H NMR (DMSO-$d_6$) δ (ppm): 7.52 (dd, J=1.5, 7.3 Hz, 1H), 7.47-7.39 (m, 2H), 7.33 (d, J=2.4 Hz, 1H), 7.22-7.14 (m, 2H), 7.11-7.04 (m, 1H), 6.84 (dt, J=5.4, 15.7 Hz, 1H), 5.91 (d, J=15.7 Hz, 1H), 4.59-4.42 (m, 2H), 4.09 (q, J=7.1 Hz, 2H), 3.76-3.59 (m, 3H), 3.44-3.33 (m, 2H), 3.23 (dd, J=1.5, 4.9 Hz, 2H), 2.47-2.40 (m, 2H), 1.70-1.42 (m, 6H), 1.19 (t, J=7.1 Hz, 3H); MS (ESI): m/z: 486 [M+H]$^+$.

Step 2: Ethyl (E)-4-({4-[7-chloro-10-(3-hydroxypropyl)-11-oxo-10,11-dihydro-5H-dibenzo[b,e][1,4]diazepin-5-yl]butyl}amino)but-2-enoate maleate 0.046 g (81%) of ethyl (E)-4-({4-[7-chloro-10-(3-hydroxypropyl)-11-oxo-10,11-dihydro-5H-dibenzo[b,e][1,4]diazepin-5-yl]butyl}amino)but-2-enoate maleate were prepared according to the procedure described for Example 2, Step 2, starting from 0.046 g (0.094 mmol) of ethyl (E)-4-({4-[7-chloro-10-(3-hydroxypropyl)-11-oxo-10,11-dihydro-5H-dibenzo[b,e][1,4]diazepin-5-yl]butyl}amino)but-2-enoate. $^1$H NMR (DMSO-$d_6$) δ (ppm): 8.61 (bs, 3H), 7.54 (dd, J=1.5, 7.8 Hz, 1H), 7.48-7.41 (m, 2H), 7.35 (d, J=2.4 Hz, 1H), 7.23-7.15 (m, 2H), 7.13-7.06 (m, 1H), 6.78 (dt, J=6.4, 15.7 Hz, 1H), 6.19 (d, J=15.7 Hz, 1H), 6.02 (s, 2H), 4.57-4.39 (m, 2H), 4.15 (q, J=7.1 Hz, 2H), 3.81-3.64 (m, 5H), 3.45-3.36 (m, 2H), 2.97-2.84 (m, 2H), 1.73-1.49 (m, 6H), 1.21 (t, J=7.1 Hz, 3H); MS (ESI): m/z: 486 [M+H]$^+$.

149

Example 52: Ethyl (E)-4-({3-[7-chloro-10-(3-hydroxypropyl)-11-oxo-10,11-dihydro-5H-dibenzo[b,e][1,4]diazepin-5-yl]propyl}amino)but-2-enoate maleate

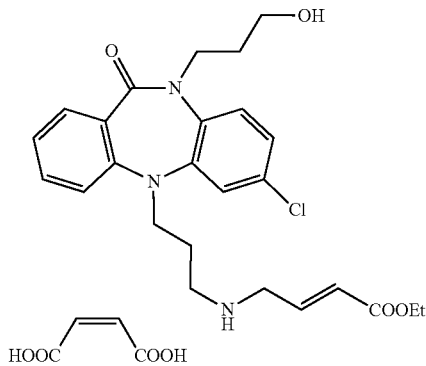 [SMILES: CCOC(=O)/C=C/CNCCCN1c2ccccc2C(=O)N(CCCO)c2ccc(Cl)cc21 ; O=C(O)/C=C\C(=O)O]

Step 1: Ethyl (E)-4-({3-[7-chloro-10-(3-hydroxypropyl)-11-oxo-10,11-dihydro-5H-dibenzo[b,e][1,4]diazepin-5-yl]propyl}amino)but-2-enoate 0.046 g (54%) of ethyl (E)-4-({3-[7-chloro-10-(3-hydroxypropyl)-11-oxo-10,11-dihydro-5H-dibenzo[b,e][1,4]diazepin-5-yl]propyl}amino)but-2-enoate were prepared according to the procedure described for Example 2, Step 1, starting from 0.065 g (0.18 mmol) of 5-(3-aminopropyl)-7-chloro-10-(3-hydroxypropyl)-5,10-dihydro-11H-dibenzo[b,e][1,4]diazepin-11-one (Intermediate 47). $^1$H NMR (DMSO-$d_6$) δ (ppm): 7.52 (dd, J=1.5, 7.8 Hz, 1H), 7.46-7.39 (m, 2H), 7.34 (d, J=2.4 Hz, 1H), 7.21-7.14 (m, 2H), 7.12-7.05 (m, 1H), 6.84 (dt, J=5.4, 15.7 Hz, 1H), 5.92 (dt, J=1.5, 15.7 Hz, 1H), 4.53-4.39 (m, 2H), 4.09 (q, J=7.1 Hz, 2H), 3.75 (t, J=6.9 Hz, 2H), 3.68-3.58 (m, 1H), 3.45-3.35 (m, 2H), 3.24 (dd, J=1.5, 5.4 Hz, 2H), 2.52 (t, J=6.8 Hz, 2H), 1.70-1.57 (m, 4H), 1.19 (t, J=7.1 Hz, 3H); MS (ESI): m/z: 472 [M+H]$^+$.

Step 2: Ethyl (E)-4-({3-[7-chloro-10-(3-hydroxypropyl)-11-oxo-10,11-dihydro-5H-dibenzo[b,e][1,4]diazepin-5-yl]propyl}amino)but-2-enoate maleate 0.052 g (95%) of ethyl (E)-4-({3-[7-chloro-10-(3-hydroxypropyl)-11-oxo-10,11-dihydro-5H-dibenzo[b,e][1,4]diazepin-5-yl]propyl}amino)but-2-enoate maleate were prepared according to the procedure described for Example 2, Step 2, starting from 0.044 g (0.093 mmol) of ethyl (E)-4-({3-[7-chloro-10-(3-hydroxypropyl)-11-oxo-10,11-dihydro-5H-dibenzo[b,e][1,4]diazepin-5-yl]propyl}amino)but-2-enoate. $^1$H NMR (DMSO-$d_6$) δ (ppm): 8.62 (bs, 3H), 7.55 (dd, J=1.5, 7.8 Hz, 1H), 7.50-7.43 (m, 2H), 7.36 (d, J=2.0 Hz, 1H), 7.25-7.16 (m, 2H), 7.15-7.07 (m, 1H), 6.76 (dt, J=6.0, 15.9 Hz, 1H), 6.19 (d, J=15.7 Hz, 1H), 6.02 (s, 2H), 4.54-4.42 (m, 2H), 4.15 (q, J=7.1 Hz, 2H), 3.88-3.73 (m, 4H), 3.71-3.63 (m, 1H), 3.46-3.37 (m, 2H), 3.03-2.91 (m, 2H), 1.91-1.79 (m, 2H), 1.74-1.59 (m, 2H), 1.21 (t, J=7.1 Hz, 3H); MS (ESI): m/z: 472 [M+H]$^+$.

150

Example 53: (E)-6-[4-(3-chloro-10,11-dihydro-5H-dibenzo[b,f]azepin-5-yl)butyl-methyl-amino]-1-phenyl-hex-4-en-3-one maleate

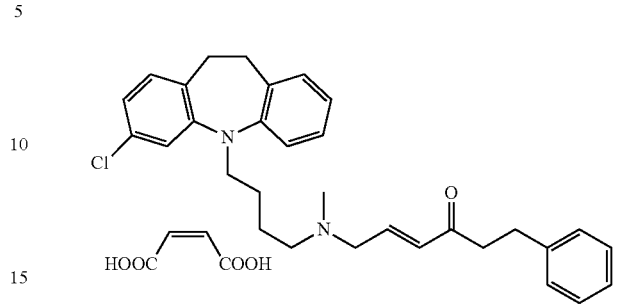

Step 1: (E)-6-(4-(3-chloro-10,11-dihydro-5H-dibenzo[b,f]azepin-5-yl)butyl-methyl-amino]-1-phenyl-hex-4-en-3-one 0.008 g (14.5%) of (E)-6-[4-(3-chloro-10,11-dihydro-5H-dibenzo[b,f]azepin-5-yl)butyl-methyl-amino]-1-phenyl-hex-4-en-3-one were prepared according to the procedure described for Example 7, Step 1, starting from 0.050 g (0.113 mmol) of (E)-4-[4-(3-chloro-10,11-dihydro-5H-dibenzo[b,f]azepin-5-yl)butyl-methyl-amino]-N-methoxy-N-methyl-but-2-enamide (Example 9, Step 2) and 0.566 ml of PhenethylMgCl (1 M in THF, 0.566 mmol); MS (ESI): m/z: 488 [M+H]$^+$.

Step 2: (E)-6-[4-(3-chloro-10,11-dihydro-5H-dibenzo[b,f]azepin-5-yl)butyl-methyl-amino]-1-phenyl-hex-4-en-3-one maleate 0.008 g (80%) of (E)-6-[4-(3-chloro-10,11-dihydro-5H-dibenzo[b,f]azepin-5-yl)butyl-methyl-amino]-1-phenyl-hex-4-en-3-one maleate were prepared according to the procedure described for Example 2, Step 2, starting from 0.008 g (0.017 mmol) of (E)-6-[4-(3-chloro-10,11-dihydro-5H-dibenzo[b,f]azepin-5-yl)butyl-methyl-amino]-1-phenyl-hex-4-en-3-one. $^1$H NMR (DMSO-$d_6$) δ (ppm): 9.47 (bs, 1H), 7.33-6.84 (m, 12H), 6.78-6.63 (m, 1H), 6.39 (d, J=15.7 Hz, 1H), 6.03 (s, 2H), 3.93-3.61 (m, 4H), 3.13-2.53 (m, 13H), 1.72-1.37 (bs, 4H); MS (ESI): m/z: 488 [M+H]$^+$.

Example 54: (E)-6-[4-(3-chloro-10,11-dihydro-5H-dibenzo[b,f]azepin-5-yl)butyl-methyl-amino]hex-4-en-3-one maleate

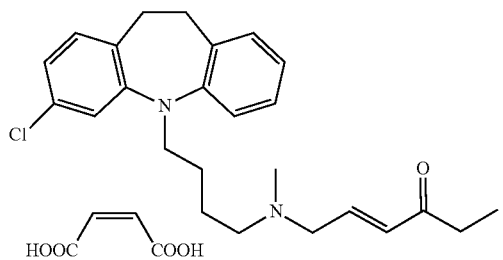

Step 1: (E)-6-[4-(3-chloro-10,11-dihydro-5H-dibenzo[b,f]azepin-5-yl)butyl-methyl-amino]hex-4-en-3-one 0.013 g (28%) of (E)-6-[4-(3-chloro-10,11-dihydro-5H-dibenzo[b,f]azepin-5-yl)butyl-methyl-amino]hex-4-en-3-one were prepared according to the procedure described for Example 7, Step 1, starting from 0.050 g (0.113 mmol) of (E)-4-[4-(3-chloro-10,11-dihydro-5H-dibenzo[b,f]azepin-5-yl)butyl-methyl-amino]-N-methoxy-N-methyl-but-2-enamide (Example 9, Step 2) and 0.113 ml of EthylMgCl (3 M in THF, 0.339 mmol); $^1$H NMR (DMSO-$d_6$) δ (ppm): 7.13 (s, 5H), 7.00-6.87 (m, 2H), 6.67 (td, J=5.9, 16.1 Hz, 1H), 6.11 (d, J=16.1 Hz, 1H), 3.71-3.65 (m, 2H), 3.11-2.97 (m, 6H), 2.58-2.51 (m, 2H), 2.25-2.18 (m, 2H), 2.05 (s, 3H), 1.50-1.37 (m, 4H), 0.93 (t, J=7.1 Hz, 3H); MS (ESI): m/z: 411 [M+H]$^+$.

Step 2: (E)-6-[4-(3-chloro-10,11-dihydro-5H-dibenzo[b,f]azepin-5-yl)butyl-methyl-amino]hex-4-en-3-one maleate 0.011 g (78%) of (E)-6-[4-(3-chloro-10,11-dihydro-5H-dibenzo[b,f]azepin-5-yl)butyl-methyl-amino]hex-4-en-3-one maleate were prepared according to the procedure described for Example 2, Step 2, starting from 0.011 g (0.027 mmol) of (E)-6-[4-(3-chloro-10,11-dihydro-5H-dibenzo[b,f]azepin-5-yl)butyl-methyl-amino]hex-4-en-3-one. $^1$H NMR (DMSO-$d_6$) δ (ppm): 9.53 (bs, 1H), 7.22-6.86 (m, 7H), 6.69 (td, J=6.8, 15.7 Hz, 1H), 6.37 (d, J=16.1 Hz, 1H), 6.02 (s, 2H), 3.94-3.61 (m, 4H), 3.14-2.84 (m, 6H), 2.72-2.53 (m, 5H), 1.69-1.39 (m, 4H), 0.96 (t, J=7.1 Hz, 3H); MS (ESI): m/z: 411 [M+H]$^+$.

Example 55: Ethyl (E)-4-({3-[7-chloro-10-(2-hydroxyethyl)-11-oxo-10,11-dihydro-5H-dibenzo[b,e][1,4]diazepin-5-yl]propyl}amino)but-2-enoate maleate

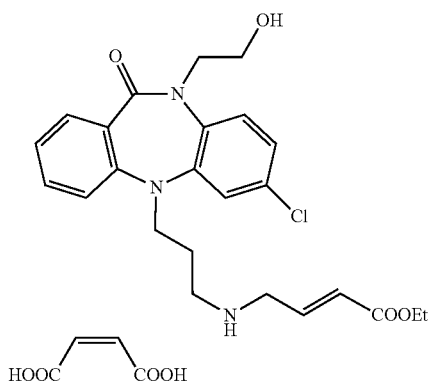 [SMILES: CCOC(=O)/C=C/CNCCCN1c2ccccc2C(=O)N(CCO)c2ccc(Cl)cc21 ; O=C(O)/C=C\C(=O)O]

Step 1: Ethyl (E)-4-({3-[7-chloro-10-(2-hydroxyethyl)-11-oxo-10,11-dihydro-5H-dibenzo[b,e][1,4]diazepin-5-yl]propyl}amino)but-2-enoate 0.031 g (41%) of ethyl (E)-4-({3-[7-chloro-10-(2-hydroxyethyl)-11-oxo-10,11-dihydro-5H-dibenzo[b,e][1,4]diazepin-5-yl]propyl}amino)but-2-enoate were prepared according to the procedure described for Example 2, Step 1, starting from 0.056 g (0.165 mmol) of 5-(3-aminopropyl)-7-chloro-10-(2-hydroxyethyl)-5,10-dihydro-11H-dibenzo[b,e][1,4]diazepin-11-one (Intermediate 48). $^1$H NMR (DMSO-$d_6$) δ (ppm): 7.61 (d, J=8.8 Hz, 1H), 7.50 (dd, J=1.7, 7.6 Hz, 1H), 7.45-7.40 (m, 1H), 7.32 (d, J=2.0 Hz, 1H), 7.21-7.14 (m, 2H), 7.10-7.05 (m, 1H), 6.84 (dt, J=5.1, 15.7 Hz, 1H), 5.91 (dt, J=1.7, 15.7 Hz, 1H), 4.90 (br. s, 1H), 4.18-4.06 (m, 3H), 3.85-3.65 (m, 4H), 3.53-3.45 (m, 1H), 3.23 (dd, J=1.7, 5.1 Hz, 2H), 2.53 (t, J=6.3 Hz, 2H), 1.68-1.56 (m, 2H), 1.19 (t, J=7.1 Hz, 3H); MS (ESI): m/z: 458 [M+H]$^+$.

Step 2: Ethyl (E)-4-({3-[7-chloro-10-(2-hydroxyethyl)-11-oxo-10,11-dihydro-5H-dibenzo[b,e][1,4]diazepin-5-yl]propyl}amino)but-2-enoate maleate 0.022 g (60%) of ethyl (E)-4-({3-[7-chloro-10-(2-hydroxyethyl)-11-oxo-10,11-dihydro-5H-dibenzo[b,e][1,4]diazepin-5-yl]propyl}amino)but-2-enoate maleate were prepared according to the procedure described for Example 2, Step 2, starting from 0.029 g (0.06 mmol) of ethyl (E)-4-({3-[7-chloro-10-(2-hydroxyethyl)-11-oxo-10,11-dihydro-5H-dibenzo[b,e][1,4]diazepin-5-yl]propyl}amino)but-2-enoate. $^1$H NMR (DMSO-$d_6$) δ (ppm): 8.49 (bs, 3H), 7.60 (d, J=8.8 Hz, 1H), 7.54 (dd, J=1.5, 7.3 Hz, 1H), 7.49-7.43 (m, 1H), 7.36 (d, J=2.0 Hz, 1H), 7.23 (dd, J=2.4, 8.8 Hz, 1H), 7.19 (d, J=8.3 Hz, 1H), 7.14-7.09 (m, 1H), 6.75 (dt, J=6.3, 15.7 Hz, 1H), 6.17 (d, J=15.7 Hz, 1H), 6.00 (s, 2H), 4.86 (bs, 1H), 4.33-4.24 (m, 1H), 4.14 (q, J=7.1 Hz, 2H), 3.90-3.74 (m, 3H), 3.73-3.62 (m, 3H), 3.59-3.51 (m, 1H), 3.04-2.92 (m, 2H), 1.88-1.79 (m, 2H), 1.21 (t, J=7.1 Hz, 3H); MS (ESI): m/z: 458 [M+H]$^+$.

Example 56: Ethyl (E)-4-((4-(10-benzyl-3-chloro-11-oxo-10,11-dihydro-5H-dibenzo[b,e][1,4]diazepin-5-yl)butyl)amino)but-2-enoate maleate

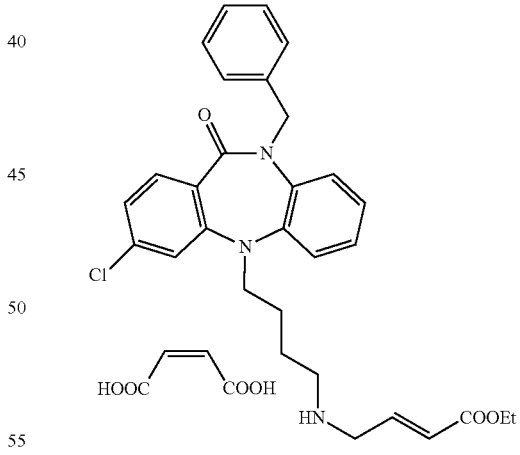

Step 1: Ethyl (E)-4-((4-(10-benzyl-3-chloro-11-oxo-10,11-dihydro-5H-dibenzo[b,e][1,4]diazepin-5-yl)butyl)amino)but-2-enoate 0.028 g (33%) of ethyl (E)-4-{[4-(10-benzyl-3-chloro-11-oxo-10,11-dihydro-5H-dibenzo[b,e][1,4]diazepin-5-yl)butyl]amino}but-2-enoate were prepared according to the procedure described for Example 2, Step 1, starting from 0.067 g (0.165 mmol) of 5-(4-aminobutyl)-10-benzyl-3-chloro-5,10-dihydro-11H-dibenzo[b,e][1,4]diazepin-11-one (Intermediate 49). $^1$H NMR (DMSO-d$_6$) δ (ppm): 7.58 (d, J=8.3 Hz, 1H), 7.44 (dd, J=1.5, 7.8 Hz, 1H), 7.29-7.21 (m, 6H), 7.19-7.10 (m, 3H), 7.10-7.04 (m, 1H), 6.87 (dt, J=5.4, 15.7 Hz, 1H), 5.96 (dt, J=1.5, 15.7 Hz, 1H), AB System: ν$_A$=5.65, ν$_B$=4.97, J$_{AB}$=15.6 Hz, 4.10 (q, J=7.3 Hz, 2H), 3.76-3.58 (m, 2H), 3.26 (dd, J=1.5, 5.4 Hz, 2H), 2.45 (t, J=6.3 Hz, 2H), 1.55-1.39 (m, 4H), 1.19 (t, J=7.3 Hz, 3H); MS (ESI): m/z: 518 [M+H]$^+$.

Step 2: Ethyl (E)-4-((4-(10-benzyl-3-chloro-11-oxo-10,11-dihydro-5H-dibenzo[b,e][1,4]diazepin-5-yl)butyl)amino)but-2-enoate maleate 0.028 g (88%) of Ethyl (E)-4-((4-(10-benzyl-3-chloro-11-oxo-10,11-dihydro-5H-dibenzo[b,e][1,4]diazepin-5-yl)butyl)amino)but-2-enoate maleate were prepared according to the procedure described for Example 2, Step 2, starting from 0.026 g (0.05 mmol) of Ethyl (E)-4-((4-(10-benzyl-3-chloro-11-oxo-10,11-dihydro-5H-dibenzo[b,e][1,4]diazepin-5-yl)butyl)amino)but-2-enoate. $^1$H NMR (DMSO-d$_6$) δ (ppm): 8.64 (bs, 3H), 7.60 (d, J=8.3 Hz, 1H), 7.44 (dd, J=1.5, 8.3 Hz, 1H), 7.30 (d, J=2.0 Hz, 1H), 7.29-7.26 (m, 4H), 7.24 (dd, J=1.5, 8.3 Hz, 1H), 7.22-7.17 (m, 2H), 7.16-7.12 (m, 1H), 7.11-7.06 (m, 1H), 6.80 (dt, J=6.4, 15.7 Hz, 1H), 6.21 (dt, J=1.5, 15.7 Hz, 1H), 6.02 (s, 2H), AB System: ν$_A$=5.61, ν$_B$=5.02, J$_{AB}$=15.9 Hz, 4.16 (q, J=7.1 Hz, 2H), 3.84-3.74 (m, 3H), 3.69-3.60 (m, 1H), 2.92 (t, J=7.6 Hz, 2H), 1.71-1.58 (m, 2H), 1.56-1.47 (m, 2H), 1.22 (t, J=7.1 Hz, 3H); MS (ESI): m/z: 518 [M+H]$^+$.

Example 57: 3-Chloro-10-methyl-5-(4-{methyl[(E)-4-oxopent-2-en-1-yl]amino}butyl)-5,10-dihydro-11H-dibenzo[b,e][1,4]diazepin-11-one maleate

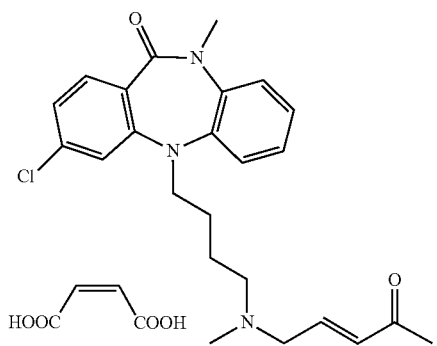 [SMILES: CC(=O)/C=C/CN(C)CCCCN1c2cc(Cl)ccc2C(=O)N(C)c2ccccc21 ; O=C(O)/C=C\C(=O)O]

Step 1: Methyl (E)-4-{[4-(3-chloro-10-methyl-11-oxo-10,11-dihydro-5H-dibenzo[b,e][1,4]diazepin-5-yl)butyl](methyl)amino}but-2-enoate 0.069 g (23%) of methyl (E)-4-{[4-(3-chloro-10-methyl-11-oxo-10,11-dihydro-5H-dibenzo[b,e][1,4]diazepin-5-yl)butyl](methyl)amino}but-2-enoate were prepared according to the procedure described for Example 1, Step 1 starting from 0.230 g (0.67 mmol) of 3-chloro-10-methyl-5-[4-(methylamino)butyl]-5,10-dihydro-11H-dibenzo[b,e][1,4]diazepin-11-one (Intermediate 50) and 0.093 ml (0.702 mmol) of methyl 4-bromo-2-butenoate at r.t. $^1$H NMR (DMSO-d$_6$) δ (ppm): 7.56 (d, J=8.3 Hz, 1H), 7.36 (dd, J=1.9, 7.6 Hz, 1H), 7.28-7.23 (m, 2H), 7.22-7.14 (m, 2H), 7.12 (dd, J=2.0, 8.3 Hz, 1H), 6.74 (dt, J=5.9, 15.6 Hz, 1H), 5.93 (d, J=15.6 Hz, 1H), 3.79-3.66 (m, 2H), 3.64 (s, 3H), 3.42 (s, 3H), 3.02 (d, J=4.9 Hz, 2H), 2.25 (t, J=6.8 Hz, 2H), 2.03 (s, 3H), 1.57-1.40 (m, 4H); MS (ESI): m/z: 442 [M+H]$^+$.

Step 2: (E)-4-{[4-(3-chloro-10-methyl-11-oxo-10,11-dihydro-5H-dibenzo[b,e][1,4]diazepin-5-yl)butyl](methyl)amino}-N-methoxy-N-methyl-but-2-enamide 0.045 g (63%) of (E)-4-{[4-(3-chloro-10-methyl-11-oxo-10,11-dihydro-5H-dibenzo[b,e][1,4]diazepin-5-yl)butyl](methyl)amino}-N-methoxy-N-methyl-but-2-enamide were prepared according to the procedure described for Example 6, starting from 0.067 g (0.151 mmol) of methyl (E)-4-{[4-(3-chloro-10-methyl-11-oxo-10,11-dihydro-5H-dibenzo[b,e][1,4]diazepin-5-yl)butyl](methyl)amino}but-2-enoate and 0.045 g (0.453 mmol) of N,O-dimethylhydroxylamine hydrochloride. $^1$H NMR (DMSO-d$_6$) δ (ppm): 7.56 (d, J=8.3 Hz, 1H), 7.36 (dd, J=2.2, 7.6 Hz, 1H), 7.29-7.23 (m, 2H), 7.22-7.14 (m, 2H), 7.12 (dd, J=2.0, 8.3 Hz, 1H), 6.65 (dt, J=5.9, 15.2 Hz, 1H), 6.47 (d, J=15.2 Hz, 1H), 3.81-3.65 (m, 2H), 3.61 (s, 3H), 3.42 (s, 3H), 3.12 (s, 3H), 3.05 (d, J=5.9 Hz, 2H), 2.25 (t, J=6.8 Hz, 2H), 2.05 (s, 3H), 1.58-1.39 (m, 4H); MS (ESI): m/z: 471 [M+H]$^+$.

Step 3: 3-Chloro-10-methyl-5-(4-{methyl[(E)-4-oxopent-2-en-1-yl]amino}butyl)-5,10-dihydro-11H-dibenzo[b,e][1,4]diazepin-11-one 0.023 g (60%) of 3-chloro-10-methyl-5-(4-{methyl[(E)-4-oxopent-2-en-1-yl]amino}butyl)-5,10-dihydro-11H-dibenzo[b,e][1,4]diazepin-11-one were prepared according to the procedure described for Example 7, Step 1, starting from 0.042 g (0.089 mmol) of (E)-4-{[4-(3-chloro-1 O-methyl-11-oxo-10,11-dihydro-5H-dibenzo[b,e][1,4]diazepin-5-yl)butyl](methyl)amino}-N-methoxy-N-methyl-but-2-enamide and 0.089 ml of MeMgCl (3 M in THF, 0.268 mmol). $^1$H NMR (DMSO-d$_6$) δ (ppm): 7.56 (d, J=8.3 Hz, 1H), 7.36 (dd, J=2.0, 7.3 Hz, 1H), 7.28-7.23 (m, 2H), 7.22-7.14 (m, 2H), 7.12 (dd, J=1.7, 8.3 Hz, 1H), 6.69 (dt, J=5.4, 15.7 Hz, 1H), 6.05 (d, J=15.7 Hz, 1H), 3.81-3.62 (m, 2H), 3.42 (s, 3H), 3.03 (d, J=5.4 Hz, 2H), 2.26 (t, J=6.8 Hz, 2H), 2.17 (s, 3H), 2.04 (s, 3H), 1.58-1.38 (m, 4H); MS (ESI): m/z: 426 [M+H]$^+$.

Step 4: 3-Chloro-10-methyl-5-(4-{methyl[(E)-4-oxopent-2-en-1-yl]amino}butyl)-5,10-dihydro-11H-dibenzo[b,e][1,4]diazepin-11-one maleate 0.025 g (91%) of 3-chloro-10-methyl-5-(4-{methyl[(E)-4-oxopent-2-en-1-yl]amino}butyl)-5,10-dihydro-11H-dibenzo[b,e][1,4]diazepin-11-one maleate were prepared according to the procedure described for Example 2, Step 2, starting from 0.021 g (0.050 mmol) of 3-chloro-10-methyl-5-(4-{methyl[(E)-4-oxopent-2-en-1-yl]amino}butyl)-5,10-dihydro-11H-dibenzo[b,e][1,4]diazepin-11-one. $^1$H NMR (CD$_3$OD) δ (ppm): 7.63 (d, J=8.3 Hz, 1H), 7.39-7.36 (m, 1H), 7.31-7.27 (m, 1H), 7.26-7.19 (m, 3H), 7.13 (dd, J=2.0, 8.3 Hz, 1H), 6.73 (dt, J=6.9, 15.9 Hz, 1H), 6.45 (dt, J=1.1, 15.9 Hz, 1H), 6.26 (s, 2H), 3.91 (d, J=6.9 Hz, 2H), 3.89-3.78 (m, 2H), 3.55 (s, 3H), 3.14 (t, J=7.8 Hz, 2H), 2.81 (s, 3H), 2.31 (s, 3H), 1.88-1.78 (m, 2H), 1.77-1.70 (m, 2H); MS (ESI): m/z: 426 [M+H]$^+$.

Example 58: Methyl (E)-4-{[4-(10-benzyl-3-chloro-11-oxo-10,11-dihydro-5H-dibenzo[b,e][1,4]diazepin-5-yl)butyl](methyl)amino}but-2-enoate maleate

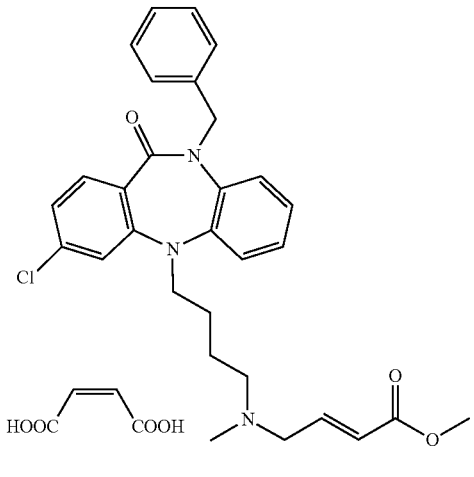 [SMILES: COC(=O)/C=C/CN(C)CCCCN1c2cc(Cl)ccc2C(=O)N(Cc2ccccc2)c2ccccc21 ; O=C(O)/C=C\C(=O)O]

Step 1: Methyl (E)-4-{[4-(10-benzyl-3-chloro-11-oxo-10,11-dihydro-5H-dibenzo[b,e][1,4]diazepin-5-yl)butyl](methyl)amino}but-2-enoate 0.341 g (85%) of methyl (E)-4-{[4-(10-benzyl-3-chloro-11-oxo-10,11-dihydro-5H-dibenzo[b,e][1,4]diazepin-5-yl)butyl](methyl)amino}but-2-enoate were prepared according to the procedure described for Example 1, Step 1 starting from 0.351 g (0.77 mmol) 10-benzyl-3-chloro-5-[4-(methylamino)butyl]-5,10-dihydro-11H-dibenzo[b,e][1,4]diazepin-11-one hydrochloride (Intermediate 51) and 0.107 ml (0.808 mmol) of methyl 4-bromo-2-butenoate at r.t. $^1$H NMR (DMSO-$d_6$) δ (ppm): 7.58 (d, J=8.3 Hz, 1H), 7.44 (dd, J=1.5, 7.8 Hz, 1H), 7.29-7.21 (m, 6H), 7.20-7.10 (m, 3H), 7.10-7.04 (m, 1H), 6.80 (dt, J=5.9, 15.7 Hz, 1H), 5.97 (dt, J=1.5, 15.7 Hz, 1H), AB System: $v_A$=5.63, $v_B$=4.98, $J_{AB}$=15.7 Hz, 3.79-3.60 (m, 5H), 3.10-3.02 (m, 2H), 2.33-2.23 (m, 2H), 2.08 (s, 3H), 1.54-1.41 (m, 4H); MS (ESI): m/z: 518 [M+H]$^+$.

Step 2: Methyl (E)-4-{[4-(10-benzyl-3-chloro-11-oxo-10,11-dihydro-5H-dibenzo[b,e][1,4]diazepin-5-yl)butyl](methyl)amino}but-2-enoate maleate 0.027 g (87%) of methyl (E)-4-{[4-(10-benzyl-3-chloro-11-oxo-10,11-dihydro-5H-dibenzo[b,e][1,4]diazepin-5-yl)butyl](methyl)amino}but-2-enoate maleate were prepared according to the procedure described for Example 2, Step 2, starting from 0.025 g (0.049 mmol) of methyl (E)-4-{[4-(10-benzyl-3-chloro-11-oxo-10,11-dihydro-5H-dibenzo[b,e][1,4]diazepin-5-yl)butyl](methyl)amino}but-2-enoate. $^1$H NMR (CD$_3$OD) δ (ppm): 7.63 (d, J=8.3 Hz, 1H), 7.41 (dd, J=1.2, 8.1 Hz, 1H), 7.31-7.18 (m, 8H), 7.17-7.11 (m, 2H), 6.85 (dt, J=7.1, 15.7 Hz, 1H), 6.30 (dt, J=1.5, 15.7 Hz, 1H), 6.27 (s, 2H), AB System: $v_A$=5.57, $v_B$=5.1, $J_{AB}$=15.2 Hz, 3.90-3.83 (m, 3H), 3.78 (s, 3H), 3.71-3.62 (m, 1H), 3.12-3.02 (m, 2H), 2.76 (s, 3H), 1.81-1.52 (m, 4H); MS (ESI): m/z: 518 [M+H]$^+$.

Example 59: (E)-4-{[4-(10-Benzyl-3-chloro-11-oxo-10,11-dihydro-5H-dibenzo[b,e][1,4]diazepin-5-yl)butyl](methyl)amino}-N-methoxy-N-methyl-but-2-enamide maleate

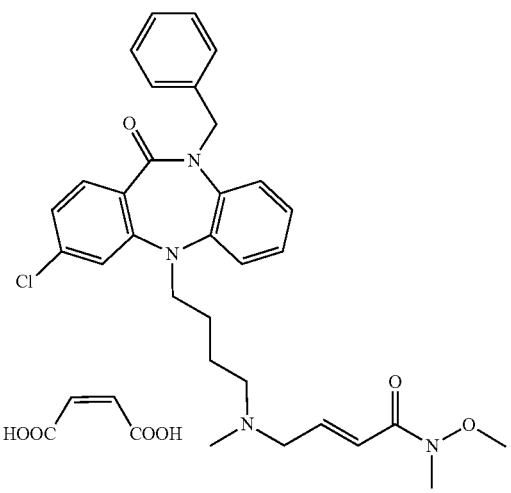 [SMILES: CON(C)C(=O)/C=C/CN(C)CCCCN1c2cc(Cl)ccc2C(=O)N(Cc2ccccc2)c2ccccc21 ; O=C(O)/C=C\C(=O)O]

Step 1: (E)-4-{[4-(10-Benzyl-3-chloro-11-oxo-10,11-dihydro-5H-dibenzo[b,e][1,4]diazepin-5-yl)butyl](methyl)amino}-N-methoxy-N-methyl-but-2-enamide 0.077 g (59%) of (E)-4-{[4-(10-benzyl-3-chloro-11-oxo-10,11-dihydro-5H-dibenzo[b,e][1,4]diazepin-5-yl)butyl](methyl)amino}-N-methoxy-N-methyl-but-2-enamide were prepared according to the procedure described for Example 6, starting from 0.124 g (0.239 mmol) of methyl (E)-4-{[4-(10-benzyl-3-chloro-11-oxo-10,11-dihydro-5H-dibenzo[b,e][1,4]diazepin-5-yl)butyl](methyl)amino}but-2-enoate (Example 58, Step 1) and 0.071 g (0.718 mmol) of N,O-dimethylhydroxylamine hydrochloride. $^1$H NMR (DMSO-$d_6$) δ (ppm): 7.59 (d, J=8.3 Hz, 1H), 7.44 (dd, J=1.5, 8.3 Hz, 1H), 7.29-7.22 (m, 6H), 7.20-7.10 (m, 3H), 7.09-7.05 (m, 1H), 6.71 (dt, J=6.4, 15.7 Hz, 1H), 6.51 (dt, J=1.5, 15.7 Hz, 1H), AB System: $v_A$=5.64, $v_B$=4.98, $J_{AB}$=15.6 Hz, 3.77-3.61 (m, 2H), 3.59 (s, 3H), 3.12 (s, 3H), 3.10 (dd, J=1.5, 6.4 Hz, 2H), 2.28 (bs, 2H), 2.10 (s, 3H), 1.49 (bs, 4H); MS (ESI): m/z: 547 [M+H]$^+$.

Step 2: (E)-4-{[4-(10-Benzyl-3-chloro-11-oxo-10,11-dihydro-5H-dibenzo[b,e][1,4]diazepin-5-yl)butyl](methyl)amino}-N-methoxy-N-methyl-but-2-enamide maleate 0.016 g (86%) of (E)-4-{[4-(10-benzyl-3-chloro-11-oxo-10,11-dihydro-5H-dibenzo[b,e][1,4]diazepin-5-yl)butyl](methyl)amino}-N-methoxy-N-methyl-but-2-enamide maleate were prepared according to the procedure described for Example 2, Step 2, starting from 0.015 g (0.028 mmol) of (E)-4-{[4-(10-benzyl-3-chloro-11-oxo-10,11-dihydro-5H-dibenzo[b,e][1,4]diazepin-5-yl)butyl](methyl)amino}-N-methoxy-N-methyl-but-2-enamide. $^1$H NMR (CD$_3$OD) δ (ppm): 7.63 (d, J=8.3 Hz, 1H), 7.41 (dd, J=1.5, 8.3 Hz, 1H), 7.31-7.18 (m, 8H), 7.17-7.09 (m, 2H), v6.76 (dt, J=7.3, 15.1 Hz, 1H), 6.26 (s, 2H), AB System: $v_A$=5.57, $v_B$=5.1, $J_{AB}$=15.4 Hz, 3.95-3.81 (m, 3H), 3.76 (s, 3H), 3.72-3.60 (m, 1H), 3.28 (s, 3H), 3.12-3.02 (m, 2H), 2.77 (s, 3H), 1.81-1.56 (m, 4H); MS (ESI): m/z: 547 [M+H]+.

Example 60: 10-Benzyl-3-chloro-5-(4-{methyl[(E)-4-oxo-pent-2-en-1-yl]amino}butyl)-5,10-dihydro-11H-dibenzo[b,e][1,4]diazepin-11-one maleate

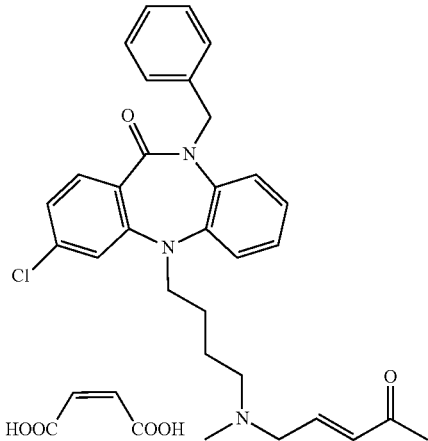 [SMILES: CC(=O)/C=C/CN(C)CCCCN1c2cc(Cl)ccc2C(=O)N(Cc2ccccc2)c2ccccc21 ; O=C(O)/C=C\C(=O)O]

Step 1: 10-Benzyl-3-chloro-5-(4-{methyl[(E)-4-oxo-pent-2-en-1-yl]amino}butyl)-5,10-dihydro-11H-dibenzo[b,e][1,4]diazepin-11-one 0.035 g (69%) of 10-benzyl-3-chloro-5-(4-{methyl[(E)-4-oxo-pent-2-en-1-yl]amino}butyl)-5,10-dihydro-11H-dibenzo[b,e][1,4]diazepin-11-one were prepared according to the procedure described for Example 7, Step 1, starting from 0.055 g (0.101 mmol) of (E)-4-{[4-(10-benzyl-3-chloro-10-11-oxo-10,11-dihydro-5H-dibenzo[b,e][1,4]diazepin-5-yl)butyl](methyl)amino}-N-methoxy-N-methyl-but-2-enamide (Example 59, Step 1) and 0.101 ml of MeMgCl (3 M in THF, 0.302 mmol). $^1$H NMR (DMSO-$d_6$) δ (ppm): 7.58 (d, J=8.3 Hz, 1H), 7.44 (dd, J=1.5, 8.3 Hz, 1H), 7.29-7.21 (m, 6H), 7.20-7.11 (m, 3H), 7.10-7.04 (m, 1H), 6.73 (dt, J=6.1, 16.1 Hz, 1H), 6.08 (d, J=16.1 Hz, 1H), AB System: $v_A$=5.63, $v_B$=4.98, $J_{AB}$=16.2 Hz, 3.79-3.71 (m, 1H), 3.69-3.59 (m, 1H), 3.07 (d, J=6.1 Hz, 2H), 2.33-2.26 (m, 2H), 2.16 (s, 3H), 2.09 (s, 3H), 1.53-1.42 (m, 4H); MS (ESI): m/z: 502 [M+H]+.

Step 2: 10-Benzyl-3-chloro-5-(4-{methyl[(E)-4-oxo-pent-2-en-1-yl]amino}butyl)-5,10-dihydro-11H-dibenzo[b,e][1,4]diazepin-11-one maleate 0.035 g (83%) of 10-benzyl-3-chloro-5-(4-{methyl[(E)-4-oxo-pent-2-en-1-yl]amino}butyl)-5,10-dihydro-11H-dibenzo[b,e][1,4]diazepin-11-one maleate were prepared according to the procedure described for Example 2, Step 2, starting from 0.034 g (0.068 mmol) of 10-benzyl-3-chloro-5-(4-{methyl[(E)-4-oxo-pent-2-en-1-yl]amino}butyl)-5,10-dihydro-11H-dibenzo[b,e][1,4]diazepin-11-one. $^1$H NMR (CD$_3$OD) δ (ppm): 7.63 (d, J=8.8 Hz, 1H), 7.41 (dd, J=1.2, 8.1 Hz, 1H), 7.31-7.18 (m, 8H), 7.17-7.10 (m, 2H), 6.72 (dt, J=7.0, 15.9 Hz, 1H), 6.45 (dt, J=2.4, 15.7 Hz, 1H), 6.26 (s, 2H), AB System: $v_A$=5.56, $v_B$=5.1, $J_{AB}$=15.2 Hz, 3.92-3.82 (m, 3H), 3.72-3.62 (m, 1H), 3.13-3.01 (m, 2H), 2.77 (s, 3H), 2.32 (s, 3H), 1.81-1.55 (m, 4H); MS (ESI): m/z: 502 [M+H]+.

Example 61: (E)-4-{[4-(10-benzyl-3-chloro-11-oxo-10,11-dihydro-5H-dibenzo[b,e][1,4]diazepin-5-yl)butyl](methyl)amino}but-2-enenitrile maleate

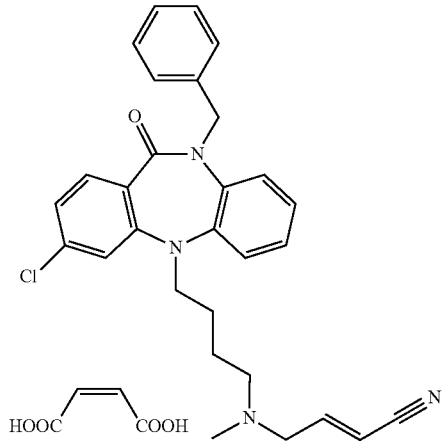 [SMILES: CN(C/C=C/C#N)CCCCN1c2cc(Cl)ccc2C(=O)N(Cc2ccccc2)c2ccccc21 ; O=C(O)/C=C\C(=O)O]

Step 1: Lithium (E)-4-{[4-(10-benzyl-3-chloro-11-oxo-10,11-dihydro-5H-dibenzo[b,e][1,4]diazepin-5-yl)butyl](methyl)amino}but-2-enoate 0.182 g, (0.351 mmol) of methyl (E)-4-{[4-(10-benzyl-3-chloro-11-oxo-10,11-dihydro-5H-dibenzo[b,e][1,4]diazepin-5-yl)butyl](methyl)amino}but-2-enoate (Example 58, Step 1) were suspended in 3:1 THF/water (2.4 ml) and 0.013 g (0.527 mmol) of LiOH were added. The mixture was stirred at r.t. for 7 h. The solvent was removed, the residue was taken up in toluene, concentrated and then triturated with Et$_2$O. The solid was filtered and dried at 40° C. under vacuum to afford lithium (E)-4-{[4-(10-benzyl-3-chloro-11-oxo-10,11-dihydro-5H-dibenzo[b,e][1,4]diazepin-5-yl)butyl](methyl)amino}but-2-enoate as an off-white solid (0.167 g, 93%). $^1$H NMR (DMSO-$d_6$) δ (ppm): 7.56 (d, J=8.3 Hz, 1H), 7.41 (d, J=7.8 Hz, 1H), 7.26-7.18 (m, 7H), 7.17-7.11 (m, 2H), 7.08-7.03 (m, 1H), 6.22 (dt, J=6.6, 15.7 Hz, 1H), 5.70 (d, J=15.7 Hz, 1H), AB System: $v_A$=5.62, $v_B$=4.94, $J_{AB}$=15.9 Hz, 3.66-3.57 (m, 2H), 2.89 (d, J=6.4 Hz, 2H), 2.24-2.17 (m, 2H), 2.02 (s, 3H), 1.43 (bs, 4H); MS (ESI): m/z: 504 [M+H]+.

Step 2: (E)-4-{[4-(10-Benzyl-3-chloro-11-oxo-10,11-dihydro-5H-dibenzo[b,e][1,4]diazepin-5-yl)butyl](methyl)amino}but-2-enamide 0.058 g (35%) of ((E)-4-{[4-(10-benzyl-3-chloro-11-oxo-10,11-dihydro-5H-dibenzo[b,e][1,4]diazepin-5-yl)butyl](methyl)amino}but-2-enamide were prepared according to the procedure described for Example 18, Step 1, starting from 0.167 g (0.327 mmol) of lithium (E)-4-{[4-(10-benzyl-3-chloro-11-oxo-10,11-dihydro-5H-dibenzo[b,e][1,4]diazepin-5-yl)butyl](methyl)amino}but-2-enoate, 0.114 ml (0.655 mmol) of TEA, 0.066 g (0.426 mmol) of HOBt, 0.126 mg (0.655 mmol) of EDC and 0.281 ml of ammonia (7N in MeOH, 1.96 mmol). $^1$H NMR (DMSO-$d_6$) δ (ppm): 7.59 (d, J=8.3 Hz, 1H), 7.44 (dd, J=1.5, 8.3 Hz, 1H), 7.38 (bs, 1H), 7.29-7.22 (m, 6H), 7.21-7.17 (m, 1H), 7.17-7.11 (m, 2H), 7.09-7.05 (m, 1H), 6.93 (bs, 1H), 6.54 (dt, J=5.9, 15.7 Hz, 1H), 5.96 (dt, J=1.5, 15.7 Hz, 1H), AB System: $v_A$=5.64, ν$_B$=4.98, J$_{AB}$=15.9 Hz, 3.78-3.59 (m, 2H), 3.01 (d, J=5.9 Hz, 2H), 2.26 (bs, 2H), 2.08 (s, 3H), 1.48 (bs, 4H); MS (ESI): m/z: 503 [M+H]$^+$.

Step 3: (E)-4-{[4-(10-Benzyl-3-chloro-11-oxo-10,11-dihydro-5H-dibenzo[b,e][1,4]diazepin-5-yl)butyl](methyl)amino}but-2-enenitrile 0.045 g (85%) of (E)-4-{[4-(10-benzyl-3-chloro-11-oxo-10,11-dihydro-5H-dibenzo[b,e][1,4]diazepin-5-yl)butyl](methyl)amino}but-2-enenitrile were prepared according to the procedure described for Example 22, Step 1, starting from 0.055 mg (0.109 mmol) of (E)-4-{[4-(10-benzyl-3-chloro-11-oxo-10,11-dihydro-5H-dibenzo[b,e][1,4]diazepin-5-yl)butyl](methyl)amino}but-2-enamide, 0.027 ml (0.219 mmol) of ethyl dichlorophosphate and 0.049 ml (0.328 mmol) of DBU. $^1$H NMR (DMSO-d$_6$, D$_2$O, DCl 1N) δ (ppm): 7.57 (d, J=8.3 Hz, 1H), 7.42 (d, J=8.3 Hz, 1H), 7.30-7.22 (m, 6H), 7.21-7.11 (m, 3H), 7.11-7.05 (m, 1H), 6.88 (dt, J=7.0, 16.1 Hz, 1H), 6.11 (d, J=16.1 Hz, 1H), AB System: ν$_A$=5.6, ν$_B$=4.96, J$_{AB}$=16.1 Hz, 3.97-3.88 (m, 2H), 3.76-3.60 (m, 2H), 3.12-2.93 (m, 2H), 2.69 (s, 3H), 1.74-1.61 (m, 2H), 1.52-1.39 (m, 2H); MS (ESI): m/z: 485 [M+H]$^+$.

Step 4: (E)-4-{[4-(10-Benzyl-3-chloro-11-oxo-10,11-dihydro-5H-dibenzo[b,e][1,4]diazepin-5-yl)butyl](methyl)amino}but-2-enenitrile maleate 0.047 g (90%) of (E)-4-{[4-(10-benzyl-3-chloro-11-oxo-10,11-dihydro-5H-dibenzo[b,e][1,4]diazepin-5-yl)butyl](methyl)amino}but-2-enenitrile maleate were prepared according to the procedure described for Example 2, Step 2, starting from 0.042 g (0.087 mmol) of (E)-4-{[4-(10-benzyl-3-chloro-11-oxo-10,11-dihydro-5H-dibenzo[b,e][1,4]diazepin-5-yl)butyl](methyl)amino}but-2-enenitrile. $^1$H NMR (CD$_3$OD) δ (ppm): 7.64 (d, J=8.3 Hz, 1H), 7.41 (d, J=7.8 Hz, 1H), 7.32-7.18 (m, 8H), 7.17-7.10 (m, 2H), 6.80 (bs, 1H), 6.28 (s, 2H), 6.05 (d, J=16.1 Hz, 1H), AB System: ν$_A$=5.56, ν$_B$=5.1, J$_{AB}$=15.7 Hz, 3.94-3.79 (m, 3H), 3.71-3.60 (m, 1H), 3.06 (bs, 2H), 2.77 (bs, 3H), 1.81-1.54 (m, 4H); MS (ESI): m/z: 485 [M+H]$^+$.

Example 62: Methyl (E)-4-[4-(3-chloro-10,11-dihydro-5H-dibenzo[b,f]azepin-5-yl)butylamino]but-2-enoate maleate

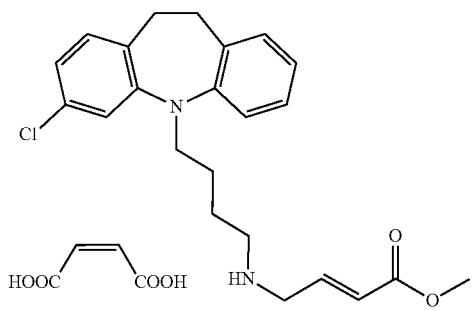 [SMILES: COC(=O)/C=C/CNCCCCN1c2ccccc2CCc2ccc(Cl)cc21 ; O=C(O)/C=C\C(=O)O]

Step 1: Methyl (E)-4-[4-(3-chloro-10,11-dihydro-5H-dibenzo[b,f]azepin-5-yl)butylamino]but-2-enoate 0.013 ml (0.101 mmol) of methyl 4-bromo-2-butenoate were added to a solution of 0.061 g (0.202 mmol) of 4-(3-chloro-10,11-dihydro-5H-dibenzo[b,f]azepin-5-yl)butan-1-amine (Intermediate 9) in dry THF (0.3 ml) at −20° C. and the mixture was stirred at −5° for 5 h. The mixture was filtered and washed with THF, the filtrate was concentrated to dryness and purified by flash chromatography (eluent DCM/MeOH/NH$_3$ aq from 100:0:0 to 98:2:0.2) to afford methyl (E)-4-[4-(3-chloro-10,11-dihydro-5H-dibenzo[b,f]azepin-5-yl)butylamino]but-2-enoate as a pale yellow oil (0.018 g, 40%). $^1$H NMR (CDCl$_3$, D$_2$O) δ (ppm): 7.19-7.10 (m, 2H), 7.09-7.05 (m, 1H), 7.05-7.02 (m, 1H), 7.02-6.92 (m, 3H), 6.87 (dd, J=2.2, 8.1 Hz, 1H), 5.94 (dt, J=1.7, 15.9 Hz, 1H), 3.80-3.66 (m, 5H), 3.35 (dd, J=1.7, 5.6 Hz, 2H), 3.19-3.06 (m, 4H), 2.56 (t, J=7.1 Hz, 2H), 1.67-1.44 (m, 4H); MS (ESI): m/z: 399 [M+H]$^+$.

Step 2: Methyl (E)-4-[4-(3-chloro-10,11-dihydro-5H-dibenzo[b,f]azepin-5-yl)butylamino]but-2-enoate maleate 0.018 g (80%) of methyl (E)-4-[4-(3-chloro-10,11-dihydro-5H-dibenzo[b,f]azepin-5-yl)butylamino]but-2-enoate maleate were prepared according to the procedure described for Example 2, Step 2, starting from 0.017 g (0.043 mmol) of methyl (E)-4-[4-(3-chloro-10,11-dihydro-5H-dibenzo[b,f]azepin-5-yl)butylamino]but-2-enoate. $^1$H NMR (DMSO-d$_6$) δ (ppm): 8.55 (bs, 3H), 7.19-7.12 (m, 4H), 7.12-7.08 (m, 1H), 7.00-6.91 (m, 2H), 6.77 (dt, J=6.3, 15.7 Hz, 1H), 6.19 (d, J=15.7 Hz, 1H), 6.01 (s, 2H), 3.78-3.64 (m, 7H), 3.12-2.99 (m, 4H), 2.85 (t, J=7.6 Hz, 2H), 1.63-1.44 (m, 4H); MS (ESI): m/z: 399 [M+H]$^+$.

Example 63: Ethyl (E)-4-{[4-(3-chloro-10,11-dihydro-5H-dibenzo[b,f]azepin-5-yl)butyl]-methyl-amino}but-2-enoate maleate

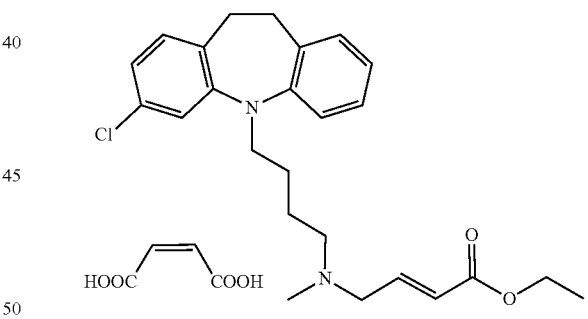

Step 1: Ethyl (E)-4-{[4-(3-chloro-10,11-dihydro-5H-dibenzo[b,f]azepin-5-yl)butyl]-methyl-amino}but-2-enoate 0.020 g (60%) of ethyl (E)-4-{[4-(3-chloro-10,11-dihydro-5H-dibenzo[b,f]azepin-5-yl)butyl]-methyl-amino}-but-2-enoate were prepared according to the procedure described for Example 1, Step 1 starting from 0.024 g (0.077 mmol) of 4-(3-chloro-10,11-dihydro-5H-dibenzo[b,f]azepin-5-yl)-N-methyl-butan-1-amine (Intermediate 2) and 0.013 ml (0.081 mmol) of ethyl 4-bromo-2-butenoate at r.t. $^1$H NMR (DMSO-d$_6$) δ (ppm): 7.13 (d, J=2.9 Hz, 3H), 7.17-7.10 (m, 4H), 7.08 (d, J=8.3 Hz, 1H), 6.98-6.93 (m, 1H), 6.91 (dd, J=2.0, 8.3 Hz, 1H), 6.75 (dt, J=6.0, 15.7 Hz, 1H), 5.92 (dt, J=1.5, 15.7 Hz, 1H), 4.10 (q, J=7.1 Hz, 2H), 3.68 (t, J=6.4 Hz, 2H), 3.11-2.98 (m, 6H), 2.22 (t, J=6.6 Hz, 2H), 1.50-1.36 (m, 4H), 1.20 (t, J=7.1 Hz, 3H); MS (ESI): m/z: 427 [M+H]$^+$.

Step 2: Ethyl (E)-4-{[4-(3-chloro-10,11-dihydro-5H-dibenzo[b,f]azepin-5-yl)butyl]-methyl-amino}but-2-enoate maleate 0.021 g (91%) of ethyl (E)-4-{[4-(3-chloro-10,11-dihydro-5H-dibenzo[b,f]azepin-5-yl)butyl]-methyl-amino]but-2-enoate maleate were prepared according to the procedure described for Example 2, Step 2, starting from 0.018 g (0.042 mmol) of ethyl (E)-4-{[4-(3-chloro-10,11-dihydro-5H-dibenzo[b,f]azepin-5-yl)butyl]-methyl-amino]but-2-enoate. $^1$H NMR (CD$_3$OD) δ (ppm): 7.19-7.13 (m, 3H), 7.11 (d, J=2.0 Hz, 1H), 7.05 (d, J=8.3 Hz, 1H), 7.01-6.96 (m, 1H), 6.90-6.80 (m, 2H), 6.28-6.23 (m, 3H), 4.23 (q, J=7.3 Hz, 2H), 3.87 (dd, J=1.5, 7.3 Hz, 2H), 3.80 (t, J=7.1 Hz, 2H), 3.19-3.09 (m, 4H), 3.09-3.02 (m, 2H), 2.77 (s, 3H), 1.83-1.73 (m, 2H), 1.68-1.59 (m, 2H), 1.30 (t, J=7.1 Hz, 3H); MS (ESI): m/z: 427 [M+H]$^+$.

Example 64: Ethyl (E)-4-{[4-(3-chloro-10,11-dihydro-dibenzo[b,f]azepin-5-yl)butyl]-ethyl-amino}but-2-enoate maleate

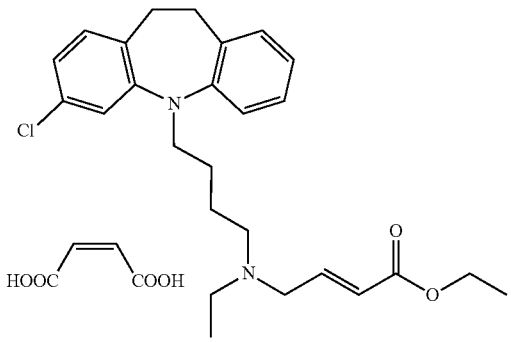 [SMILES: CCOC(=O)/C=C/CN(CC)CCCCN1c2ccccc2CCc2ccc(Cl)cc21 ; O=C(O)/C=C\C(=O)O]

Step 1: Ethyl (E)-4-{[4-(3-chloro-10,11-dihydro-dibenzo[b,f]azepin-5-yl)butyl]-ethyl-amino}but-2-enoate 0.009 ml (0.118 mmol) of ethyl bromide were added to a solution of 0.047 g (0.113 mmol) of ethyl (E)-4-[4-(3-chloro-10,11-dihydro-5H-dibenzo[b,f]azepin-5-yl)butylamino]but-2-enoate (Example 12, Step 1) and 0.023 g (0.169 mmol) of K$_2$CO$_3$ in dry ACN (2.4 ml) and the reaction was stirred at r.t. After 1 h 0.009 ml (0.118 mmol) of ethyl bromide were added and the mixture was stirred at 60° C. overnight. The reaction mixture was filtered and concentrated. The crude product was purified by flash chromatography (eluent: hexane/acetone 93:7) to afford ethyl (E)-4-{[4-(3-chloro-10,11-dihydro-dibenzo[b,f]azepin-5-yl)butyl]-ethyl-amino}but-2-enoate as a pale yellow oil (0.015 g, 30%). $^1$H NMR (DMSO-d$_6$) δ (ppm): 7.16-7.11 (m, 3H), 7.11 (d, J=2.2 Hz, 1H), 7.08 (d, J=7.8 Hz, 1H), 6.97-6.93 (m, 1H), 6.91 (dd, J=2.2, 8.1 Hz, 1H), 6.76 (dt, J=5.9, 15.7 Hz, 1H), 5.93 (dt, J=1.5, 15.7 Hz, 1H), 4.10 (q, J=7.3 Hz, 2H), 3.68 (t, J=6.6 Hz, 2H), 3.09 (dd, J=1.5, 5.9 Hz, 2H), 3.08-3.01 (m, 4H), 2.35 (q, J=7.1 Hz, 2H), 2.28 (t, J=6.8 Hz, 2H), 1.49-1.35 (m, 4H), 1.19 (t, J=7.3 Hz, 3H), 0.85 (t, J=7.1 Hz, 3H); MS (ESI): m/z: 441 [M+H]$^+$.

Step 2: Ethyl (E)-4-{[4-(3-chloro-10,11-dihydro-dibenzo[b,f]azepin-5-yl)butyl]-ethyl-amino}but-2-enoate maleate 0.016 g (99%) of ethyl (E)-4-{[4-(3-chloro-10,11-dihydro-dibenzo[b,f]azepin-5-yl)butyl]-ethyl-amino}but-2-enoate maleate were prepared according to the procedure described for Example 2, Step 2, starting from 0.013 g (0.029 mmol) of ethyl (E)-4-{[4-(3-chloro-10,11-dihydro-dibenzo[b,f]azepin-5-yl)butyl]-ethyl-amino}but-2-enoate. $^1$H NMR (CD$_3$OD) δ (ppm): 7.19-7.14 (m, 3H), 7.12 (d, J=2.2 Hz, 1H), 7.06 (d, J=8.3 Hz, 1H), 7.01-6.97 (m, 1H), 6.89 (dd, J=2.2, 8.3 Hz, 1H), 6.87-6.79 (m, 1H), 6.31-6.26 (m, 3H), 4.23 (q, J=7.0 Hz, 2H), 3.94 (dd, J=1.0, 7.3 Hz, 2H), 3.81 (t, J=6.4 Hz, 2H), 3.23-3.03 (m, 8H), 1.82-1.72 (m, 2H), 1.70-1.61 (m, 2H), 1.33-1.25 (m, 6H); MS (ESI): m/z: 441 [M+H]$^+$.

Example 65: Ethyl (E)-4-{[4-(3-chloro-10,11-dihydro-dibenzo[b,f]azepin-5-yl)butyl]-isopropyl-amino}but-2-enoate maleate

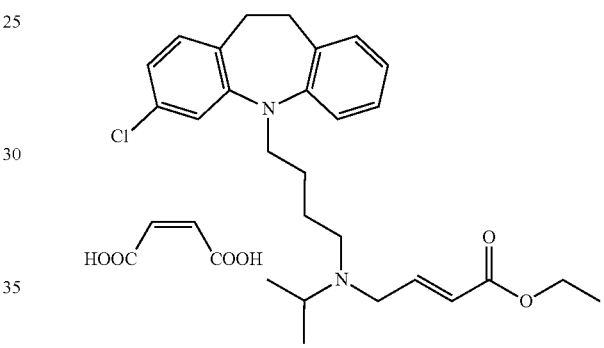

Step 1: Ethyl (E)-4-{[4-(3-chloro-10,11-dihydro-dibenzo[b,f]azepin-5-yl)butyl]-isopropyl-amino}but-2-enoate 0.018 g (26%) of ethyl (E)-4-{[4-(3-chloro-10,11-dihydro-5H-dibenzo[b,f]azepin-5-yl)butyl]-isopropyl-amino}but-2-enoate were prepared according to the procedure described for Example 64, Step 1 starting from 0.063 g (0.153 mmol) of ethyl (E)-4-[4-(3-chloro-10,11-dihydro-5H-dibenzo[b,f]azepin-5-yl)butylamino]but-2-enoate (Example 12, Step 1) and 0.617 ml (6.12 mmol) of 2-iodopropane at 75° C. $^1$H NMR (DMSO-d$_6$) δ (ppm): 7.16-7.11 (m, 3H), 7.10 (d, J=2.0 Hz, 1H), 7.07 (d, J=8.3 Hz, 1H), 6.97-6.92 (m, 1H), 6.91 (dd, J=2.2, 8.1 Hz, 1H), 6.75 (dt, J=5.4, 15.7 Hz, 1H), 5.94 (dt, J=1.7, 15.7 Hz, 1H), 4.09 (q, J=7.2 Hz, 2H), 3.67 (t, J=6.6 Hz, 2H), 3.10-2.99 (m, 6H), 2.77-2.69 (m, 1H), 2.25 (t, J=6.8 Hz, 2H), 1.50-1.41 (m, 2H), 1.39-1.30 (m, 2H), 1.20 (t, J=7.1 Hz, 3H), 0.84 (d, J=6.8 Hz, 6H); MS (ESI): m/z: 455 [M+H]$^+$.

Step 2: Ethyl (E)-4-{[4-(3-chloro-10,11-dihydro-dibenzo[b,f]azepin-5-yl)butyl]-isopropyl-amino}but-2-enoate maleate 0.020 g (96%) of ethyl (E)-4-{[4-(3-chloro-10,11-dihydro-dibenzo[b,f]azepin-5-yl)butyl]-isopropyl-amino}but-2-enoate maleate were prepared according to the procedure described for Example 2, Step 2, starting from 0.017 g (0.036 mmol) of ethyl (E)-4-{[4-(3-chloro-10,11-dihydro-dibenzo[b,f]azepin-5-yl)butyl]-isopropyl-amino}but-2-enoate. ¹H NMR (CD₃OD) δ (ppm): 7.19-7.13 (m, 3H), 7.12 (d, J=2.0 Hz, 1H), 7.06 (d, J=8.3 Hz, 1H), 7.01-6.97 (m, 1H), 6.91-6.82 (m, 2H), 6.32-6.24 (m, 3H), 4.23 (q, J=7.3 Hz, 2H), 3.92 (bs, 2H), 3.81 (t, J=6.4 Hz, 2H), 3.60 (dt, J=6.8, 13.3 Hz, 1H), 3.19-2.98 (m, 6H), 1.82-1.72 (m, 2H), 1.69-1.59 (m, 2H), 1.32-1.26 (m, 9H); MS (ESI): m/z: 455 [M+H]⁺.

Example 66: (E)-4-{[4-(3-chloro-10,11-dihydro-5H-dibenzo[b,f]azepin-5-yl)butyl]amino}-N-methyl-but-2-enamide hydrochloride

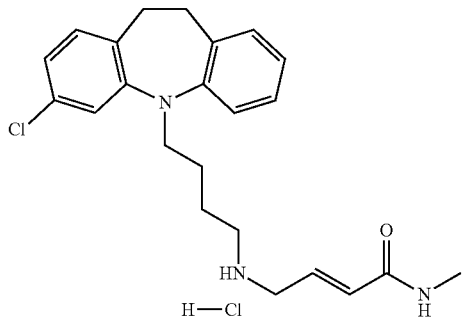

Step 1: (E)-4-{tert-butoxycarbonyl-[4-(3-chloro-10,11-dihydro-5H-dibenzo[b,f]azepin-5-yl)butyl]amino}-N-methyl-but-2-enamide 0.056 ml (0.408 mmol) of TEA were added to a solution of 0.098 g (0.204 mmol) of (E)-4-{tert-butoxycarbonyl-[4-(3-chloro-10,11-dihydro-5H-dibenzo[b,f]azepin-5-yl)butyl]amino}but-2-enoic acid (Example 17, Step 2) in dry DMF (0.4 ml) followed by the addition of 0.116 g (0.306 mmol) of HATU at 0° C. The resulting mixture was stirred at 0° C. for 15 h; then 0.132 ml of methylamine (2M in THF, 0.265 mmol) were added and the mixture was stirred at r.t. for 1 h. The mixture was quenched with water and extracted with EtOAc (2×25 ml). The combined organic layers were dried (Na₂SO₄) and the solvent was removed under vacuo. The crude was purified by flash chromatography (eluent: hexane/acetone from 93:7 to 40:60) to afford (E)-4-{tert-butoxycarbonyl-[4-(3-chloro-10,11-dihydro-5H-dibenzo[b,f]azepin-5-yl)butyl]amino}-N-methyl-but-2-enamide as a white foam (0.019 g, 13%). ¹H NMR (DMSO-d₆), δ (ppm): 8.02-7.87 (bm, 1H), 7.17-7.04 (m, 5H), 6.99-6.86 (m, 2H), 6.50-6.35 (bm, 1H), 5.87-5.73 (m, 1H), 3.85-3.60 (m, 4H), 3.18-2.94 (m, 6H), 2.61 (d, J=4.9 Hz, 3H), 1.50-1.18 (m, 13H); MS (ESI): m/z: 498 [M+H]⁺.

Step 2: (E)-4-{[4-(3-chloro-10,11-dihydro-5H-dibenzo[b,f]azepin-5-yl)butyl]amino}-N-methyl-but-2-enamide hydrochloride 0.013 g (83%) of (E)-4-{[4-(3-chloro-10,11-dihydro-5H-dibenzo[b,f]azepin-5-yl)butyl]amino}-N-methyl-but-2-enamide hydrochloride were prepared according to the procedure described for Example 19, Step 2, starting from 0.018 g (0.036 mmol) of (E)-4-{tert-butoxycarbonyl-[4-(3-chloro-10,11-dihydro-5H-dibenzo[b,f]azepin-5-yl)butyl]amino}-N-methyl-but-2-enamide and 0.090 ml of HCl (4N in 1,4-dioxane, 0.361 mmol). ¹H NMR (DMSO-d₆), δ (ppm): 8.90 (bs, 2H), 8.16 (d, J=4.9 z, 1H), 7.19-7.06 (m, 5H), 7.01-6.86 (m, 2H), 6.54 (td, J=6.8, 15.2 Hz, 1H), 6.14 (d, J=15.2 Hz, 1H), 3.71 (t, J=6.6 Hz, 2H), 3.67-3.60 (m, 2H), 3.12-3.01 (m, 4H), 2.81 (bm, 2H), 2.64 (d, J=4.9 Hz, 3H), 1.66-1.56 (m, 2H), 1.54-1.44 (m, 2H); MS (ESI): m/z: 398 [M+H]⁺.

Example 67: Ethyl (E)-4-[4-(7-Chloro-2-methoxy-10,11-dihydro-dibenzo[b,f]azepin-5-yl)-butylamino]-but-2-enoate maleate

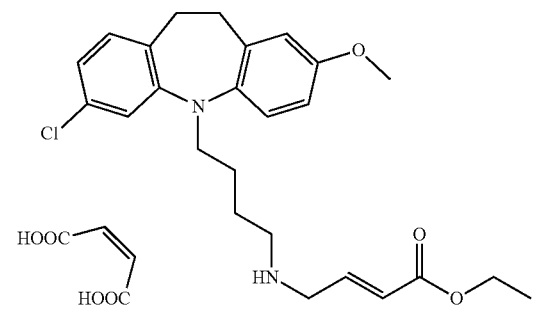 [SMILES: CCOC(=O)/C=C/CNCCCCN1c2ccc(OC)cc2CCc2ccc(Cl)cc21 ; O=C(O)/C=C\C(=O)O]

Step 1: 2-[4-(7-Chloro-2-hydroxy-10,11-dihydro-dibenzo[b,f]azepin-5-yl)-butyl]-isoindole-1,3-dione 1.300 g (2.74 mmol) of 7-Chloro-5-[4-(1,3-dioxo-1,3-dihydro-isoindol-2-yl)-butyl]-10,11-dihydro-5H-dibenzo[b,f]azepin-2-yl formate (Intermediate 34, Step 2) were dissolved in THF (50.0 ml), water (1.30 ml) and MeOH (6.50 ml). Then hydrochloric acid (3 M solution in methanol) was added drop-wise keeping the mixture at 0° C. The off yellow mixture was stirred 40 min at r.t. Solvents were evaporated under vacuum. The resulting crude was treated with MeOH obtaining a suspension that after filtration afforded 2-[4-(7-Chloro-2-hydroxy-10,11-dihydro-dibenzo[b,f]azepin-5-yl)-butyl]-isoindole-1,3-dione as an off white powder (1.050, 82%). ¹H NMR (DMSO-d₆) δ (ppm): 9.03 (s, 1H), 7.80 (s, 4H), 6.99-6.84 (m, 3H), 6.73 (dd, J=2.0, 8.3 Hz, 1H), 6.51-6.42 (m, 2H), 3.59 (t, J=6.1 Hz, 2H), 3.48 (t, J=6.6 Hz, 2H), 2.93 (s, 4H), 1.64-1.54 (m, 2H), 1.48-1.38 (m, 2H); MS (ESI): m/z: 447 [M+H]⁺.

Step 2: 2-[4-(7-Chloro-2-methoxy-10,11-dihydro-dibenzo[b,f]azepin-5-yl)-butyl]-isoindole-1,3-dione To a solution of 0.100 g (0.224 mmol) of 2-[4-(7-Chloro-2-hydroxy-10,11-dihydro-dibenzo[b,f]azepin-5-yl)-butyl]-isoindole-1,3-dione in dry DMF (1.20 ml), potassium carbonate (0.062 g, 0.448 mmol) was added. The mixture was stirred 30 min at r. t. becoming blue. Afterwards methyl iodide (0.062 g, 0.448 mmol) was added at 0° C. The reaction was then warmed to room temperature and stirred 5 h obtaining the completion.

The reaction was quenched with citric acid (5% water solution) and extracted with DCM (15 ml×3). The organic phases were treated with Na$_2$SO$_4$, filtered and then evaporated to dryness affording 2-[4-(7-Chloro-2-methoxy-10,11-dihydro-dibenzo[b,f]azepin-5-yl)-butyl]-isoindole-1,3-dione as yellow solid (0.102 g, 99%). $^1$H NMR (CDCl$_3$) δ (ppm): 7.83-7.78 (m, 2H), 7.73-7.67 (m, 2H), 6.98-6.93 (m, 2H), 6.90 (d, J=8.3 Hz, 1H), 6.75 (dd, J=2.0, 8.3 Hz, 1H), 6.64-6.59 (m, 2H), 3.72 (s, 3H), 3.70-3.60 (m, 4H), 3.13-3.02 (m, 4H), 1.78-1.68 (m, 2H), 1.66-1.52 (m, 2H); MS (ESI): m/z: 461 [M+H]$^+$.

Step 3: 4-(7-Chloro-2-methoxy-10,11-dihydro-dibenzo[b,f]azepin-5-yl)-butylamine 0.061 g (85%) of 4-(7-Chloro-2-methoxy-10,11-dihydro-dibenzo[b,f]azepin-5-yl)-butylamine were prepared according to the procedure described for Intermediate 9, Step 2, starting from 0.100 g (0.217 mmol) of 2-[4-(7-Chloro-2-methoxy-10,11-dihydro-dibenzo[b,f]azepin-5-yl)-butyl]-isoindole-1,3-dione and 0.022 g (0.434 mmol) of hydrazine hydrate. $^1$H NMR (CDCl$_3$) δ (ppm): 7.02-6.93 (m, 3H), 6.82 (dd, J=2.0, 8.3 Hz, 1H), 6.73-6.67 (m, 2H), 3.77 (s, 3H), 3.66 (t, J=6.8 Hz, 2H), 3.16-3.04 (m, 4H), 2.65 (t, J=7.1 Hz, 2H), 1.64-1.54 (m, 2H), 1.52-1.43 (m, 1H); MS (ESI): m/z: 331 [M+H]$^+$.

Step 4: Ethyl (E)-4-[4-(7-Chloro-2-methoxy-10,11-dihydro-dibenzo[b,f]azepin-5-yl)-butylamino]-but-2-enoate 0.017 g (23%) of ethyl (E)-4-[4-(7-Chloro-2-methoxy-10,11-dihydro-dibenzo[b,f]azepin-5-yl)-butylamino]-but-2-enoate were prepared according to the procedure described for Example 2, Step 1, starting from 0.055 g (0.166 mmol) of 4-(7-Chloro-2-methoxy-10,11-dihydro-dibenzo[b,f]azepin-5-yl)-butylamine and 0.021 g (0.166 mmol) of ethyl (E)-4-oxobut-2-enoate. $^1$H NMR (DMSO-d$_6$) δ (ppm): 7.08-7.00 (m, 3H), 6.89-6.65 (m, 4H), 5.94 (d, J=15.7 Hz, 1H), 4.10 (q, J=7.1 Hz, 2H), 3.69 (s, 3H), 3.65-3.59 (m, 2H), 3.30 (d, J=3.9 Hz, 2H), 3.02 (d, J=3.9 Hz, 4H), 2.48-2.41 (m, 2H), 1.50-1.34 (m, 4H), 1.20 (t, J=7.1 Hz, 3H); MS (ESI): m/z: 443 [M+H]$^+$.

Step 5: Ethyl (E)-4-[4-(7-Chloro-2-methoxy-10,11-dihydro-dibenzo[b,f]azepin-5-yl)-butylamino]-but-2-enoate maleate 0.007 g (46%) of ethyl (E)-4-[4-(7-Chloro-2-methoxy-10,11-dihydro-dibenzo[b,f]azepin-5-yl)-butylamino]-but-2-enoate maleate were prepared according to the procedure described for Example 2, Step 2, starting from 0.012 g (0.027 mmol) of ethyl (E)-4-[4-(7-Chloro-2-methoxy-10,11-dihydro-dibenzo[b,f]azepin-5-yl)-butylamino]-but-2-enoate and 0.003 g (0.027 mmol) of maleic acid. $^1$H NMR (DMSO-d$_6$) δ (ppm): 8.48 (br. s., 2H), 7.10-7.03 (m, 3H), 6.89 (dd, J=2.0, 8.3 Hz, 1H), 6.81-6.69 (m, 3H), 6.17 (d, J=15.7 Hz, 1H), 6.01 (s, 2H), 4.15 (q, J=7.1 Hz, 2H), 3.75-3.62 (m, 7H), 3.08-2.99 (m, 4H), 2.88-2.79 (m, 2H), 1.63-1.41 (m, 4H), 1.21 (t, J=7.1 Hz, 3H); MS (ESI): m/z: 443 [M+H]$^+$.

Example 68: Methyl (E)-4-[4-(3-chlorodibenzo[b,e][1,4]oxazepin-5(11H)-yl)butyl-methyl-amino]but-2-enoate

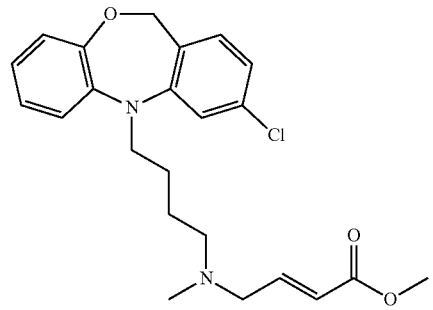 [SMILES: COC(=O)/C=C/CN(C)CCCCN1c2cc(Cl)ccc2COc2ccccc21]

0.217 g (73%) of methyl (E)-4-[4-(3-chlorodibenzo[b,e][1,4]oxazepin-5(11H)-yl))butyl-methyl-amino]but-2-enoate were prepared according to the procedure described for Example 1, Step 1 starting from 0.254 g (0.719 mmol) of 4-(3-chlorodibenzo[b,e][1,4]oxazepin-5(11H)-yl)-N-methyl-butan-1-amine hydrochloride (Intermediate 52), 0.1 ml (0.755 mmol) of methyl 4-bromo-2-butenoate and 0.298 g (2.16 mmol) of K$_2$CO$_3$ at r.t. $^1$H NMR (DMSO-d$_6$) δ (ppm): 7.39 (d, J=8.3 Hz, 1H), 7.27 (d, J=2.0 Hz, 1H), 7.12-7.03 (m, 2H), 6.86-6.68 (m, 4H), 5.97-5.91 (m, 1H), 5.23 (s, 2H), 3.75-3.69 (m, 2H), 3.64 (s, 3H), 3.03 (dd, J=1.5, 5.9 Hz, 2H), 2.27-2.20 (m, 2H), 2.04 (s, 3H), 1.58-1.49 (m, 2H), 1.46-1.38 (m, 2H); MS (ESI): m/z: 415 [M+H]$^+$.

Example 69: (E)-4-[4-(3-Chlorodibenzo[b,e][1,4]oxazepin-5(11H)-yl)butyl-methyl-amino]-N-methoxy-N-methyl-but-2-enamide

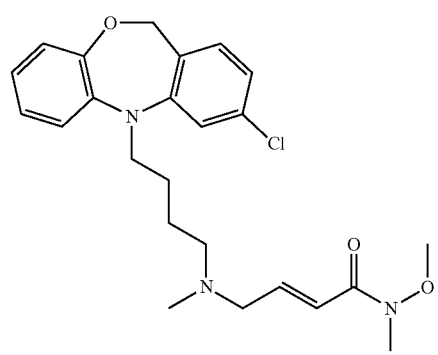 [SMILES: CON(C)C(=O)/C=C/CN(C)CCCCN1c2cc(Cl)ccc2COc2ccccc21]

0.147 g (64%) of (E)-4-[4-(3-chlorodibenzo[b,e][1,4]oxazepin-5(11H)-yl)butyl-methyl-amino]-N-methoxy-N-methyl-but-2-enamide were prepared according to the procedure described for Example 6, starting from 0.214 g (0.516 mmol) of methyl (E)-4-[4-(3-chlorodibenzo[b,e][1,4]oxazepin-5(11H)-yl))butyl-methyl-amino]but-2-enoate (Example 68) and 0.154 g (1.55 mmol) of N,O-dimethyl-hydroxylamine hydrochloride. $^1$H NMR (DMSO-d$_6$) δ (ppm): 7.41-7.36 (m, 1H), 7.28-7.25 (m, 1H), 7.12-7.03 (m, 2H), 6.86-6.76 (m, 2H), 6.74-6.62 (m, 2H), 6.51-6.45 (m, 1H), 5.23 (s, 2H), 3.75-3.69 (m, 2H), 3.62 (s, 3H), 3.12 (s, 3H), 3.08-3.03 (m, 2H), 2.27-2.21 (m, 2H), 2.06 (s, 3H), 1.59-1.51 (m, 2H), 1.48-1.39 (m, 2H); MS (ESI): m/z: 444 [M+H]+.

Example 70: (E)-5-[4-(3-Chlorodibenzo[b,e][1,4]oxazepin-5(11H)-yl)butyl-methyl-amino]pent-3-en-2-one maleate

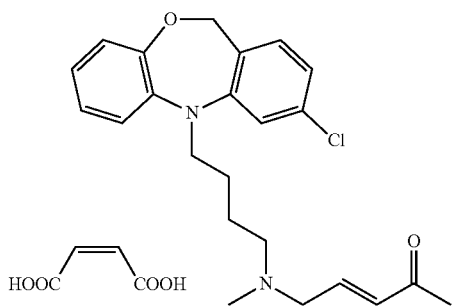 [SMILES: O=C(O)/C=C\C(=O)O ; CC(=O)/C=C/CN(C)CCCCN1c2cc(Cl)ccc2COc2ccccc21]

Step 1: (E)-5-[4-(3-Chlorodibenzo[b,e][1,4]oxazepin-5(11H)-yl)butyl-methyl-amino]pent-3-en-2-one 0.022 g (49%) of ((E)-5-[4-(3-chlorodibenzo[b,e][1,4] oxazepin-5(11H)-yl)butyl-methyl-amino]pent-3-en-2-one were prepared according to the procedure described for Example 7, Step 1, starting from 0.050 g (0.113 mmol) of (E)-4-[4-(3-chlorodibenzo[b,e][1,4]oxazepin-5(11H)-yl) butyl-methyl-amino]-N-methoxy-N-methyl-but-2-enamide (Example 69) and 0.173 ml of MeMgCl (3 M in THF, 0.518 mmol). $^1$H NMR (DMSO-$d_6$) δ (ppm): 7.41-7.37 (m, 1H), 7.28-7.26 (m, 1H), 7.12-7.04 (m, 2H), 6.86-6.76 (m, 2H), 6.74-6.67 (m, 2H), 6.09-6.03 (m, 1H), 5.24 (s, 2H), 3.75-3.69 (m, 2H), 3.06-3.01 (m, 2H), 2.28-2.22 (m, 2H), 2.17 (s, 3H), 2.05 (s, 3H), 1.59-1.51 (m, 2H), 1.47-1.39 (m, 2H); MS (ESI): m/z: 399 [M+H]+.

Step 2: (E)-5-[4-(3-Chlorodibenzo[b,e][1,4]oxazepin-5(11H)-yl)butyl-methyl-amino]pent-3-en-2-one maleate 0.025 g (97%) of (E)-5-[4-(3-chlorodibenzo[b,e][1,4] oxazepin-5(11H)-yl)butyl-methyl-amino]pent-3-en-2-one maleate were prepared according to the procedure described for Example 2, Step 2, starting from 0.020 g (0.050 mmol) of (E)-5-[4-(3-chlorodibenzo[b,e][1,4]oxazepin-5(11H)-yl) butyl-methyl-amino]pent-3-en-2-one and 0.006 g (0.050 mmol) of maleic acid. $^1$H NMR (MeOH-$d_4$) δ (ppm): 7.28 (d, J=8.0 Hz, 1H), 7.22 (d, J=1.9 Hz, 1H), 7.10 (dd, J=1.9, 7.7 Hz, 1H), 7.05 (dd, J=2.1, 8.1 Hz, 1H), 6.90-6.83 (m, 2H), 6.80-6.77 (m, 1H), 6.77-6.69 (m, 1H), 6.44 (d, J=15.9 Hz, 1H), 6.26 (s, 2H), 5.28 (s, 2H), 3.91 (d, J=6.9 Hz, 2H), 3.85 (t, J=6.3 Hz, 2H), 3.15-3.07 (m, 2H), 2.81 (s, 3H), 2.30 (s, 3H), 1.85-1.69 (m, 4H); MS (ESI): m/z: 399 [M+H]+.

Example 71: (E)-4-[4-(3-chloro-10,11-dihydro-5H-dibenzo[b,f]azepin-5-yl)butylamino]but-2-enenitrile maleate

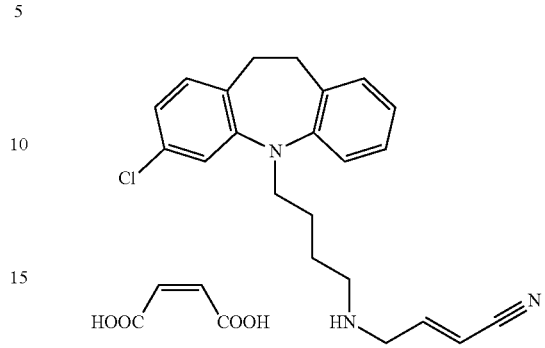

Step 1: (E)-4-{tert-butoxycarbonyl-[4-(3-chloro-10,11-dihydro-5H-dibenzo[b,f]azepin-5-yl)butylamino]}but-2-enamide 0.048 g (32.5%) of (E)-4-{tert-butoxycarbonyl-[4-(3-chloro-10,11-dihydro-5H-dibenzo[b,f]azepin-5-yl)butylamino]}but-2-enamide were prepared according to the procedure described for Example 18, Step 1, starting from 0.148 g (0.306 mmol) of (E)-4-{tert-butoxycarbonyl-[4-(3-chloro-10,11-dihydro-5H-dibenzo[b,f]azepin-5-yl)butyl] amino}but-2-enoic acid (Example 17, Step 2), 0.085 ml (0.611 mmol) of TEA, 0.061 mg (0.397 mmol) of HOBt, 0.117 g (0.611 mmol) EDC and 0.262 ml of ammonia (7N in MeOH, 1.83 mmol). $^1$H NMR (DMSO-$d_6$) δ (ppm): 7.43 (bs, 1H), 7.17-7.05 (m, 5H), 7.00-6.88 (m, 3H), 6.49-6.37 (m, 1H), 5.83 (d, J=15.7 Hz, 1H), 3.83-3.72 (m, 2H), 3.68 (t, J=6.4 Hz, 2H), 3.10-2.99 (m, 6H), 1.51-1.36 (m, 4H), 1.35-1.22 (m, 9H); MS (ESI): m/z: 384 [M+H]+.

Step 2: (E)-4-{tert-Butoxycarbonyl-[4-(3-chloro-10,11-dihydro-5H-dibenzo[b,f]azepin-5-yl)butylamino]}but-2-enenitrile 0.033 g (73%) of (E)-4-{tert-butoxycarbonyl-[4-(3-chloro-10,11-dihydro-5H-dibenzo[b,f]azepin-5-yl)butylamino]}but-2-enenitrile were prepared according to the procedure described for Example 22, Step 1, starting from 0.047 g (0.097 mmol) of (E)-4-{tert-butoxycarbonyl-[4-(3-chloro-10,11-dihydro-5H-dibenzo[b,f]azepin-5-yl)butylamino]}but-2-enamide, 0.024 ml (0.194 mmol) of ethyl dichlorophosphate and 0.044 ml (0.291 mmol) of DBU. $^1$H NMR (DMSO-$d_6$) δ (ppm): 7.17-7.06 (m, 5H), 6.98-6.89 (m, 2H), 6.78-6.70 (m, 1H), 5.64-5.57 (m, 1H), 3.88-3.77 (m, 2H), 3.71-3.65 (m, 2H), 3.10-3.00 (m, 6H), 1.48-1.36 (m, 4H), 1.35-1.20 (m, 9H); MS (ESI): m/z: 466 [M+H]+.

Step 3: (E)-4-[4-(3-Chloro-10,11-dihydro-5H-dibenzo[b,f]azepin-5-yl)butylamino]but-2-enenitrile 0.016 g (66%) of (E)-4-[4-(3-chloro-10,11-dihydro-5H-dibenzo[b,f]azepin-5-yl)butylamino]but-2-enenitrile were prepared according to the procedure described for Intermediate 1, Step 2, starting from 0.031 g (0.066 mmol) of (E)-4-{tert-butoxycarbonyl-[4-(3-chloro-10,11-dihydro-5H-dibenzo[b,f]azepin-5-yl)butylamino]}but-2-enenitrile and 0.102 ml (1.33 mmol) of TFA. $^1$H NMR (DMSO-$d_6$) δ (ppm): 7.18-7.05 (m, 5H), 6.99-6.89 (m, 2H), 6.86-6.78 (m, 1H), 5.73-5.66 (m, 1H), 3.71-3.63 (m, 2H), 3.24-3.17 (m, 2H), 3.10-2.99 (m, 4H), 2.41-2.33 (m, 2H), 1.91 (br. s, 1H), 1.53-1.32 (m, 4H); MS (ESI): m/z: 366 [M+H]$^+$.

Step 4: (E)-4-[4-(3-Chloro-10,11-dihydro-5H-dibenzo[b,f]azepin-5-yl)butylamino]but-2-enenitrile maleate 0.017 g (87%) of (E)-4-[4-(3-chloro-10,11-dihydro-5H-dibenzo[b,f]azepin-5-yl)butylamino]but-2-enenitrile maleate were prepared according to the procedure described for Example 2, Step 2, starting from 0.015 g (0.040 mmol) of (E)-4-[4-(3-chloro-10,11-dihydro-5H-dibenzo[b,f]azepin-5-yl)butylamino]but-2-enenitrile and 0.005 g (0.040 mmol) of maleic acid. $^1$H NMR (DMSO-d$_6$) δ (ppm): 8.47 (bs, 2H), 7.19-7.14 (m, 3H), 7.14 (d, J=2.0 Hz, 1H), 7.11 (d, J=8.3 Hz, 1H), 7.00-6.96 (m, 1H), 6.94 (dd, J=2.0, 8.3 Hz, 1H), 6.78 (td, J=6.4, 16.5 Hz, 1H), 6.05 (d, J=16.1 Hz, 1H), 6.02 (s, 2H), 3.76-3.66 (m, 4H), 3.12-3.01 (m, 4H), 2.84 (t, J=7.6 Hz, 2H), 1.62-1.44 (m, 4H); MS (ESI): m/z: 366 [M+H]$^+$.

Example 72: (E)-4-[4-(3-Chloro-10,11-dihydro-5H-dibenzo[b,f]azepin-5-yl)butyl-methyl-amino]but-2-enamide

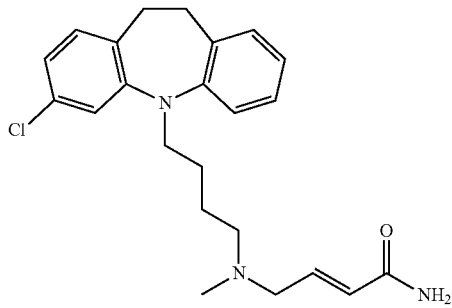 [SMILES: CN(C/C=C/C(N)=O)CCCCN1c2ccccc2CCc2ccc(Cl)cc21]

Step 1: (E)-4-[4-(3Chloro-10,11-dihydro-5H-dibenzo[b,f]azepin-5-yl)butyl-methyl-amino]but-2-enoic acid lithium salt 1.51 g (3.66 mmol) of methyl (E)-4-[4-(3-chloro-10,11-dihydro-5H-dibenzo[b,f]azepin-5-yl)butyl-methyl-amino]but-2-enoate (Example 9, Step 1) were dissolved in THF (18 ml) to which was added LiOH (0.134 g, 5.48 mmol) dissolved in water (6 ml). The resulting mixture was stirred at r.t for 6 h then the solvent was evaporated. The residue was taken up with toluene and evaporated (×3) to remove water by azeotropic distillation. The residue was triturated with diethyl ether, the solid was filtered and heated at 40° C. under vacuum to afford (E)-4-[4-(3-chloro-10,11-dihydro-5H-dibenzo[b,f]azepin-5-yl)butyl-methyl-amino]but-2-enoic acid lithium salt as a white solid (1.357 g, 92%). $^1$H NMR (DMSO-d$_6$) δ (ppm): 7.20-7.03 (m, 5H), 7.00-6.86 (m, 2H), 6.12-5.99 (m, 1H), 5.62 (d, J=15.7 Hz, 1H), 3.68 (t, J=5.9 Hz, 2H), 3.13-2.97 (m, 4H), 2.83 (d, J=6.4 Hz, 2H), 2.16 (t, J=6.4 Hz, 2H), 1.98 (s, 3H), 1.42 (bs, 4H); MS (ESI): m/z: 399 [M+H]$^+$.

Step 2: (E)-4-[4-(3-Chloro-10,11-dihydro-5H-dibenzo[b,f]azepin-5-yl)butyl-methyl-amino]but-2-enamide 0.231 g (67%) of (E)-4-[4-(3-chloro-10,11-dihydro-5H-dibenzo[b,f]azepin-5-yl)butyl-methyl-amino]but-2-enamide were prepared according to the procedure described for Example 18, Step 1, starting from 0.350 g (0.864 mmol) of (E)-4-[4-(3-chloro-10,11-dihydro-5H-dibenzo[b,f]azepin-5-yl)butyl-methyl-amino]but-2-enoic acid lithium salt, 0.301 ml (1.73 mmol) of DIPEA, 0.176 mg (1.12 mmol) of HOBt, 0.497 g (2.59 mmol) of EDC and 1.111 ml of ammonia (7N in MeOH, 7.78 mmol). $^1$H NMR (DMSO-d$_6$) δ (ppm): 7.37 (bs, 1H), 7.18-7.04 (m, 5H), 6.99-6.88 (m, 3H), 6.49 (td, J=6.2, 15.4 Hz, 1H), 5.93 (d, J=15.7 Hz, 1H), 3.68 (t. J=6.4 Hz, 2H), 3.10-3.00 (m, 4H), 2.96 (d. J=5.4 Hz, 2H), 2.20 (t. J=6.6 Hz, 2H), 2.02 (s, 3H), 1.50-1.35 (m, 4H); MS (ESI): m/z: 398 [M+H]$^+$.

Example 73: (E)-4-[4-(3-Chloro-10,11-dihydro-5H-dibenzo[b,f]azepin-5-yl)butyl-methyl-amino]but-2-enenitrile maleate

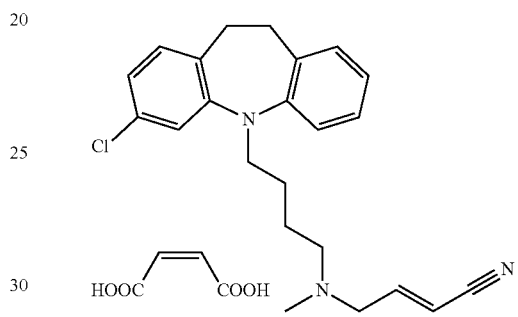

Step 1: (E)-4-[4-(3-Chloro-10,11-dihydro-5H-dibenzo[b,f]azepin-5-yl)butyl-methyl-amino]but-2-enenitrile 0.049 g (64%) of (E)-4-[4-(3-chloro-10,11-dihydro-5H-dibenzo[b,f]azepin-5-yl)butyl-methyl-amino]but-2-enenitrile were prepared according to the procedure described for Example 22, Step 1, starting from 0.080 g (0.201 mmol) of (E)-4-[4-(3-chloro-10,11-dihydro-5H-dibenzo[b,f]azepin-5-yl)butyl-methyl-amino]but-2-enamide (Example 72), 0.050 ml (0.402 mmol) of ethyl dichlorophosphate and 0.090 ml (0.603 mmol) of DBU. $^1$H NMR (DMSO-d$_6$) δ (ppm): 7.20-7.04 (m, 5H), 7.01-6.87 (m, 2H), 6.81-6.70 (m, 1H), 5.78-5.70 (m, 1H), 3.72-3.63 (m, 2H), 3.10-2.97 (m, 6H), 2.26-2.17 (m, 2H), 2.03 (s, 3H), 1.50-1.33 (m, 4H); MS (ESI): m/z: 380 [M+H]$^+$.

Step 2: (E)-4-[4-(3-Chloro-10,11-dihydro-5H-dibenzo[b,f]azepin-5-yl)butyl-methyl-amino]but-2-enenitrile maleate 0.053 g (87%) of (E)-4-[4-(3-chloro-10,11-dihydro-5H-dibenzo[b,f]azepin-5-yl)butyl-methyl-amino]but-2-enenitrile maleate were prepared according to the procedure described for Example 2, Step 2, starting from 0.047 g (0.122 mmol) of (E)-4-[4-(3-chloro-10,11-dihydro-5H-dibenzo[b,f]azepin-5-yl)butyl-methyl-amino]but-2-enenitrile and 0.014 g (0.122 mmol) of maleic acid. $^1$H NMR (MeOH-d$_4$) δ (ppm): 7.19-7.13 (m, 3H), 7.12 (d, J=2.0 Hz, 1H), 7.06 (d, J=7.8 Hz, 1H), 7.01-6.97 (m, 1H), 6.89 (dd, J=2.0, 8.3 Hz, 1H), 6.79 (td, J=7.1, 16.1 Hz, 1H), 6.26 (s, 2H), 6.01 (d, J=16.1 Hz, 1H), 3.87 (d, J=6.8 Hz, 2H), 3.80 (t, J=6.6 Hz, 2H), 3.18-3.14 (m, 2H), 3.14-3.09 (m, 2H), 3.08-3.02 (m, 2H), 2.76 (s, 3H), 1.81-1.71 (m, 2H), 1.69-1.60 (m, 2H); MS (ESI): m/z: 380 [M+H]$^+$.

Example 74: Ethyl (E)-4-[4-(7-Chloro-2-hydroxymethyl-10,11-dihydro-dibenzo[b,f]azepin-5-yl)-butylamino]-but-2-enoate maleate

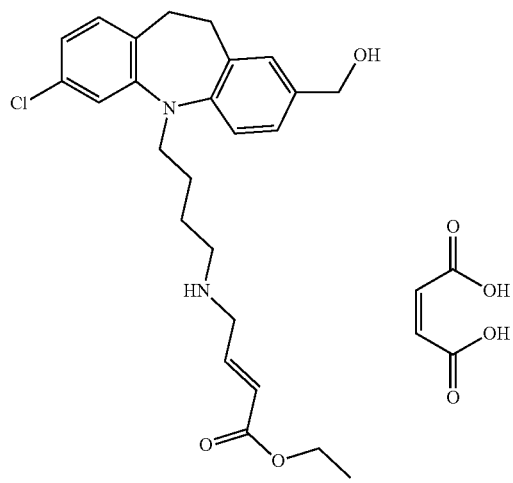 [SMILES: CCOC(=O)/C=C/CNCCCCN1c2ccc(CO)cc2CCc2ccc(Cl)cc21 ; O=C(O)/C=C\C(=O)O]

Step 1: Ethyl (E)-4-[4-(7-chloro-2-hydroxymethyl-10,11-dihydro-dibenzo[b,f]azepin-5-yl)-butylamino]-but-2-enoate 0.020 g (23%) of ethyl (E)-4-[4-(7-chloro-2-hydroxymethyl-10,11-dihydro-dibenzo[b,f]azepin-5-yl)-butylamino]-but-2-enoate were prepared according to the procedure described for Example 2, Step 1, starting from 0.065 g (0.196 mmol) of [5-(4-amino-butyl)-7-chloro-10,11-dihydro-5H-dibenzo[b,f]azepin-2-yl]-methanol (Intermediate 53). $^1$H NMR (DMSO-d$_6$) δ (ppm): 7.03-7.13 (m, 5H), 6.87-6.93 (m, 1H), 6.79-6.86 (m, 1H), 5.90 (d, J=15.65 Hz, 1H), 5.01-5.07 (m, 1H), 4.38 (d, J=5.87 Hz, 2H), 4.09 (d, J=7.34 Hz, 2H), 3.62-3.69 (m, 2H), 3.18-3.24 (m, 2H), 2.98-3.09 (m, 4H), 2.33-2.42 (m, 2H), 1.34-1.50 (m, 4H), 1.19 (t, J=7.30 Hz, 3H); MS (ESI): m/z: 443 [M+H]$^+$.

Step 2: Ethyl (E)-4-[4-(7-chloro-2-hydroxymethyl-10,11-dihydro-dibenzo[b,f]azepin-5-yl)-butylamino]-but-2-enoate maleate 0.017 g (75%) of Ethyl (E)-4-[4-(7-Chloro-2-hydroxymethyl-10,11-dihydro-dibenzo[b,f]azepin-5-yl)-butylamino]-but-2-enoate maleate were prepared according to the procedure described for Example 2, Step 2, starting from 0.018 g (0.040 mmol) of ethyl (E)-4-[4-(7-Chloro-2-hydroxymethyl-10,11-dihydro-dibenzo[b,f]azepin-5-yl)-butylamino]-but-2-enoate. $^1$H NMR (DMSO-d$_6$) δ (ppm): 8.47 (br. s, 1H), 7.00-7.19 (m, 5H), 6.87-6.97 (m, 1H), 6.70-6.82 (m, 1H), 6.17 (d, J=16.14 Hz, 1H), 6.01 (s, 2H), 5.05 (t, J=5.38 Hz, 1H), 4.39 (d, J=5.40 Hz, 2H), 4.15 (q, J=7.34 Hz, 2H), 3.61-3.77 (m, 4H), 2.97-3.14 (m, 4H), 2.77-2.89 (m, 2H), 1.42-1.66 (m, 4H), 1.21 (t, J=7.30 Hz, 3H); MS (ESI): m/z: 443 [M+H]$^+$.

Example 75: Ethyl (E)-4-[4-(7-chloro-2-methoxymethyl-10,11-dihydro-dibenzo[b,f]azepin-5-yl)-butylamino]-but-2-enoate maleate

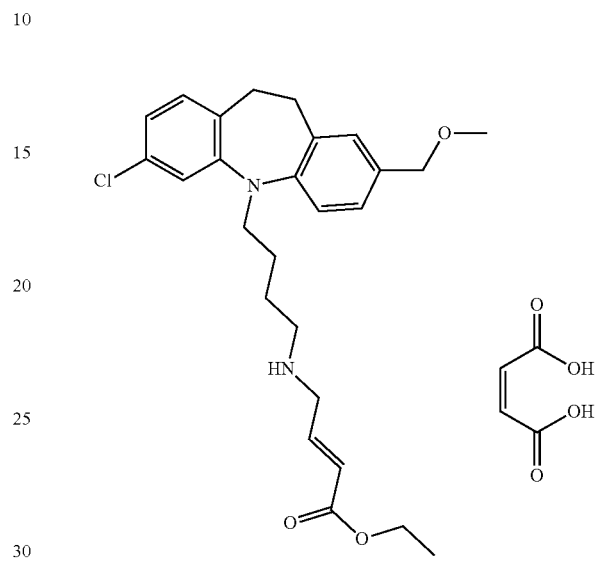

Step 1: Ethyl (E)-4-[4-(7-chloro-2-methoxymethyl-10,11-dihydro-dibenzo[b,f]azepin-5-yl)-butylamino]-but-2-enoate 0.020 g (50%) of Ethyl (E)-4-[4-(7-chloro-2-methoxymethyl-10,11-dihydro-dibenzo[b,f]azepin-5-yl)-butylamino]-but-2-enoate were prepared according to the procedure described for Example 2, Step 1, starting from 0.030 g (0.087 mmol) of 4-[7-chloro-2-methoxymethyl-10,11-dihydro-dibenzo[b,f]azepin-5-yl]-butylamine (Intermediate 54). $^1$H NMR (DMSO-d$_6$) δ (ppm): 7.03-7.16 (m, 5H), 6.88-6.94 (m, 1H), 6.77-6.86 (m, 1H), 5.89 (d, J=15.65 Hz, 1H), 4.29 (s, 2H), 4.09 (q, J=7.34 Hz, 2H), 3.67 (t, J=6.60 Hz, 2H), 3.17-3.27 (m, 5H), 3.05 (br. s., 4H), 2.39 (t, J=6.85 Hz, 2H), 1.34-1.53 (m, 4H), 1.19 (t, J=7.30 Hz, 3H); MS (ESI): m/z: 457 [M+H]$^+$.

Step 2: Ethyl (E)-4-[4-(7-chloro-2-methoxymethyl-10,11-dihydro-dibenzo[b,f]azepin-5-yl)-butylamino]-but-2-enoate maleate 0.020 g (94%) of ethyl (E)-4-[4-(7-chloro-2-methoxymethyl-10,11-dihydro-dibenzo[b,f]azepin-5-yl)-butylamino]-but-2-enoate maleate were prepared according to the procedure described for Example 2, Step 2, starting from 0.017 g (0.037 mmol) of ethyl (E)-4-[4-(7-chloro-2-methoxymethyl-10,11-dihydro-dibenzo[b,f]azepin-5-yl)-butylamino]-but-2-enoate. $^1$H NMR (DMSO-d$_6$) δ (ppm): 8.35 (br. s., 2H), 7.02-7.19 (m, 5H), 6.91-6.97 (m, 1H), 6.71-6.82 (m, 1H), 6.15 (d, J=15.65 Hz, 1H), 6.00 (s, 2H), 4.30 (s, 2H), 4.14 (q, J=6.85 Hz, 2H), 3.60-3.77 (m, 4H), 3.25 (s, 3H), 2.97-3.12 (m, 4H), 2.74-2.84 (m, 2H), 1.41-1.63 (m, 4H), 1.21 (t, J=6.80 Hz, 3H); MS (ESI): m/z: 457 [M+H]$^+$.

Example 76: Ethyl (E)-4-[4-(7-chloro-2-methoxy-ethoxymethyl-10,11-dihydro-dibenzo[b,f]azepin-5-yl)-butylamino]-but-2-enoate maleate

Example 77: (E)-4-[4-(3-Chloro-10,11-dihydro-5H-dibenzo[b,f]azepin-5-yl)butyl-methyl-amino]-N-methyl-N-prop-2-ynoxy-but-2-enamide maleate

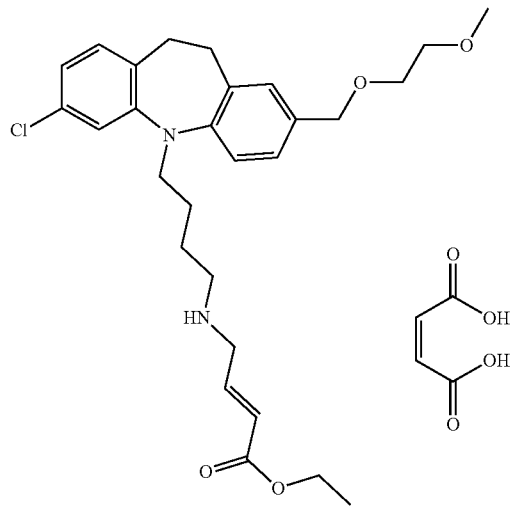 [SMILES: CCOC(=O)/C=C/CNCCCCN1c2ccc(COCCOC)cc2CCc2ccc(Cl)cc21 ; O=C(O)/C=C\C(=O)O]

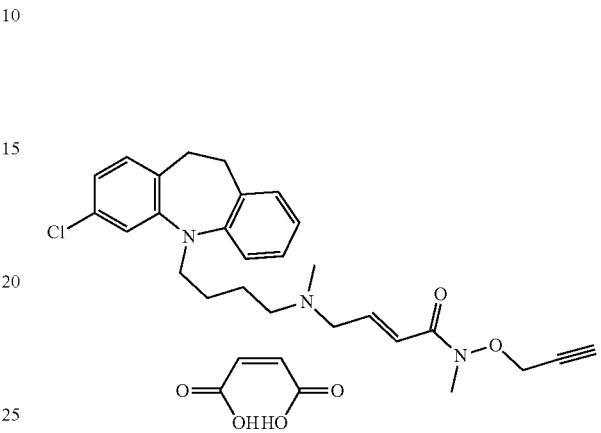

Step 1: Ethyl (E)-4-[4-(7-chloro-2-methoxy-ethoxymethyl-10,11-dihydro-dibenzo[b,f]azepin-5-yl)-butylamino]-but-2-enoate 0.040 g (24%) of ethyl (E)-4-[4-(7-chloro-2-methoxy-ethoxymethyl-10,11-dihydro-dibenzo[b,f]azepin-5-yl)-butylamino]-but-2-enoate were prepared according to the procedure described for Example 2, Step 1, starting from 0.130 g (0.334 mmol) of 4-[7-chloro-2-methoxyethoxymethyl-10,11-dihydro-dibenzo[b,f]azepin-5-yl]-butylamine (Intermediate 55). $^1$H NMR (DMSO-$d_6$) δ (ppm): 7.03-7.15 (m, 5H), 6.92 (dd, J=1.96, 7.83 Hz, 1H), 6.78-6.86 (m, 1H), 5.90 (d, J=15.65 Hz, 1H), 4.36 (s, 2H), 4.09 (q, J=6.85 Hz, 2H), 3.63-3.71 (m, 2H), 3.42-3.53 (m, 4H), 3.23 (s, 3H), 3.05 (br. s., 6H), 2.36-2.44 (m, 2H), 1.34-1.51 (m, 4H), 1.19 (t, J=6.80 Hz, 3H); MS (ESI): m/z: 502 [M+H]$^+$.

Step 2: Ethyl (E)-4-[4-(7-chloro-2-methoxy-ethoxymethyl-10,11-dihydro-dibenzo[b,f]azepin-5-yl)-butylamino]-but-2-enoate maleate 0.020 g (46%) of ethyl (E)-4-[4-(7-chloro-2-methoxy-ethoxymethyl-10,11-dihydro-dibenzo[b,f]azepin-5-yl)-butylamino]-but-2-enoate maleate were prepared according to the procedure described for Example 2, Step 2, starting from 0.035 g (0.070 mmol) of ethyl (E)-4-[4-(7-chloro-2-methoxyethoxymethyl-10,11-dihydro-dibenzo[b,f]azepin-5-yl)-butylamino]-but-2-enoate. $^1$H NMR (DMSO-$d_6$) δ (ppm): 8.55 (br. s., 2H), 7.04-7.23 (m, 5H), 6.94 (dd, J=2.20, 8.07 Hz, 1H), 6.69-6.81 (m, 1H), 6.18 (d, J=15.65 Hz, 1H), 6.06 (s, 2H), 4.37 (s, 2H), 4.15 (q, J=7.34 Hz, 2H), 3.65-3.78 (m, 4H), 3.42-3.55 (m, 4H), 3.24 (s, 3H), 2.99-3.12 (m, 4H), 2.78-2.89 (m, 2H), 1.41-1.64 (m, 4H), 1.21 (t, J=7.30 Hz, 3H); MS (ESI): m/z: 502 [M+H]$^+$.

Step 1: (E)-4-[4-(3-Chloro-10,11-dihydro-5H-dibenzo[b,f]azepin-5-yl)butyl-methyl-amino]-N-methyl-N-prop-2-ynoxy-but-2-enamide 0.012 g (26%) of (E)-4-[4-(3-chloro-10,11-dihydro-5H-dibenzo[b,f]azepin-5-yl)butyl-methyl-amino]-N-methyl-N-prop-2-ynoxy-but-2-enamide were prepared according to the procedure described for Example 6, starting from 0.041 g (0.099 mmol) of methyl (E)-4-[4-(3-chloro-10,11-dihydro-5H-dibenzo[b,f]azepin-5-yl)butyl-methyl-amino]but-2-enoate (Example 9, Step 1) and 0.036 g (0.298 mmol) of N-(prop-2-yn-1-yloxy)methanamine hydrochloride (Intermediate 56). $^1$H NMR (DMSO-$d_6$) δ (ppm): 7.17-7.10 (m, 4H), 7.10-7.06 (m, 1H), 6.98-6.89 (m, 2H), 6.68-6.60 (m, 1H), 6.58-6.51 (m, 1H), 4.62-4.58 (m, 2H), 3.71-3.66 (m, 2H), 3.65-3.62 (m, 1H), 3.16 (s, 3H), 3.10-2.99 (m, 6H), 2.25-2.19 (m, 2H), 2.04 (s, 3H), 1.52-1.35 (m, 4H); MS (ESI): m/z: 466 [M+H]$^+$.

Step 2: (E)-4-[4-(3-Chloro-10,11-dihydro-5H-dibenzo[b,f]azepin-5-yl)butyl-methyl-amino]-N-methyl-N-prop-2-ynoxy-but-2-enamide maleate 0.010 g (88%) of (E)-4-[4-(3-chloro-10,11-dihydro-5H-dibenzo[b,f]azepin-5-yl)butyl-methyl-amino]-N-methyl-N-prop-2-ynoxy-but-2-enamide maleate were prepared according to the procedure described for Example 2, Step 2, starting from 0.009 g (0.020 mmol) of (E)-4-[4-(3-chloro-10,11-dihydro-5H-dibenzo[b,f]azepin-5-yl)butyl-methyl-amino]-N-methyl-N-prop-2-ynoxy-but-2-enamide and 0.002 g (0.020 mmol) of maleic acid. $^1$H NMR (MeOH-$d_4$) δ (ppm): 7.20-7.13 (m, 3H), 7.12 (d, J=2.0 Hz, 1H), 7.06 (d, J=8.3 Hz, 1H), 7.02-6.95 (m, 2H), 6.89 (dd, J=2.0, 7.8 Hz, 1H), 6.78-6.69 (m, 1H), 6.26 (s, 2H), 4.65 (d, J=2.4 Hz, 2H), 3.92 (d, J=7.3 Hz, 2H), 3.81 (t, J=6.6 Hz, 2H), 3.19-3.04 (m, 7H), 2.78 (s, 3H), 1.84-1.74 (m, 2H), 1.69-1.60 (m, 2H); MS (ESI): m/z: 466 [M+H]$^+$.

Example 78: (E)-4-[4-(3-Chloro-10,11-dihydro-5H-dibenzo[b,f]azepin-5-yl)butylamino]-N-methoxy-but-2-enamide maleate

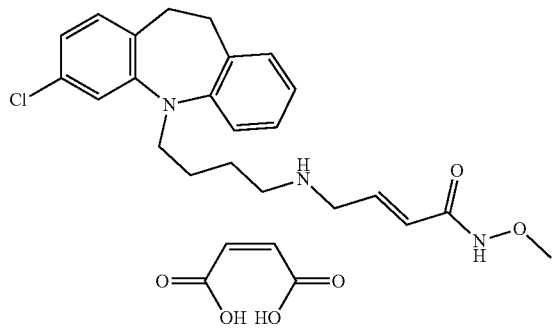

Step 1: (E)-4-{tert-butoxycarbonyl-[4-(3-chloro-10,11-dihydro-5H-dibenzo[b,f]azepin-5-yl)butylamino]}-N-methoxy-but-2-enamide 0.042 g (0.487 mmol) of O-methylhydroxylamine hydrochloride were slowly added to a stirred solution of 1 M LiHMDS in dry THF (0.975 ml, 0.975 mmol) at −70° C. ca. After 40 min, 0.1 g (0.195 mmol) of ethyl (E)-4-{tert-butoxycarbonyl-[4-(3-chloro-10,11-dihydro-5H-dibenzo[b,f]azepin-5-yl)butyl]amino}but-2-enoate (Example 17, Step 1) in dry THF (0.7 ml) were added slowly and the mixture was stirred at −70° C. ca. for 2 h. The mixture was treated with sat. aq. NH$_4$Cl (1 ml), allowed to warm to r.t., diluted with water (2 ml) and extracted with EtOAc (2×5 ml). The combined organic layers were dried (Na$_2$SO$_4$), filtered and concentrated in vacuo. The crude was purified by flash chromatography (eluent: DCM/MeOH 98:2) to afford (E)-4-{tert-butoxycarbonyl-[4-(3-chloro-10,11-dihydro-5H-dibenzo[b,f]azepin-5-yl)butylamino]}-N-methoxy-but-2-enamide as a colorless oil that solidified (49 mg, 49%). $^1$H NMR (DMSO-d$_6$) δ (ppm): 11.19 (s, 1H), 7.18-7.05 (m, 5H), 6.99-6.88 (m, 2H), 6.59-6.46 (m, 1H), 5.70-5.62 (m, 1H), 3.85-3.74 (m, 2H), 3.71-3.64 (m, 2H), 3.59 (s, 3H), 3.10-2.99 (m, 6H), 1.50-1.36 (m, 4H), 1.35-1.21 (m, 9H); MS (ESI): m/z: 514 [M+H]$^+$.

Step 2: (E)-4-[4-(3-Chloro-10,11-dihydro-5H-dibenzo[b,f]azepin-5-yl)butylamino]-N-methoxy-but-2-enamide A solution of 0.040 g (0.078 mmol) of (E)-4-{tert-butoxycarbonyl-[4-(3-chloro-10,11-dihydro-5H-dibenzo[b,f]azepin-5-yl)butylamino]}-N-methoxy-but-2-enamide in dry DCM (1 ml) was cooled to 0° C. and treated with TFA (0.119 ml, 1.56 mmol). The mixture was warmed to r.t. and stirred for 2 h. The reaction was concentrated under a nitrogen stream. The residue was treated with EtOAc (8 ml), water (4 ml ca.) was added and the aqueous phase was basified with NaHCO$_3$ (pH 8, ice-cooling). The organic phase was separated, washed with brine, dried and evaporated. The crude was purified by flash chromatography (eluent: DCM/MeOH/NH$_4$OH 95:5:0.5) to afford (E)-4-[4-(3-chloro-10,11-dihydro-5H-dibenzo[b,f]azepin-5-yl)butylamino]-N-methoxy-but-2-enamide as a colorless oil that solidified (27 mg, 84%). $^1$H NMR (DMSO-d$_6$) δ (ppm): 11.20-10.99 (m, 1H), 7.20-7.03 (m, 5H), 7.00-6.87 (m, 2H), 6.69-6.57 (m, 1H), 5.84-5.71 (m, 1H), 3.67 (t, J=6.6 Hz, 2H), 3.58 (s, 3H), 3.16 (d, J=4.4 Hz, 2H), 3.11-2.99 (m, 4H), 2.43-2.33 (m, 2H), 1.54-1.32 (m, 4H); MS (ESI): m/z: 414 [M+H]$^+$.

Step 3: (E)-4-[4-(3-Chloro-10,11-dihydro-5H-dibenzo[b,f]azepin-5-yl)butylamino]-N-methoxy-but-2-enamide maleate 0.029 g (89%) of ((E)-4-[4-(3-chloro-10,11-dihydro-5H-dibenzo[b,f]azepin-5-yl)butylamino]-N-methoxy-but-2-enamide maleate were prepared according to the procedure described for Example 2, Step 2, starting from 0.026 g (0.062 mmol) of (E)-4-[4-(3-chloro-10,11-dihydro-5H-dibenzo[b,f]azepin-5-yl)butylamino]-N-methoxy-but-2-enamide and 0.007 g (0.062 mmol) of maleic acid. $^1$H NMR (DMSO-d$_6$) δ (ppm): 11.41 (bs, 1H), 8.49 (bs, 2H), 7.19-7.14 (m, 3H), 7.14 (d, J=2.0 Hz, 1H), 7.11 (d, J=8.3 Hz, 1H), 7.00-6.96 (m, 1H), 6.94 (dd, J=2.0, 8.3 Hz, 1H), 6.66-6.56 (m, 1H), 6.01 (s, 2H), 5.98 (d, J=16.1 Hz, 1H), 3.75-3.65 (m, 4H), 3.62 (s, 3H), 3.12-3.02 (m, 4H), 2.83 (t, J=7.3 Hz, 2H), 1.62-1.54 (m, 2H), 1.53-1.45 (m, 2H); MS (ESI): m/z: 414 [M+H]$^+$.

Example 79: (E)-4-[4-(3-chloro-10,11-dihydro-5H-dibenzo[b,f]azepin-5-yl)butylamino]-N-benzyloxy-but-2-enamide maleate

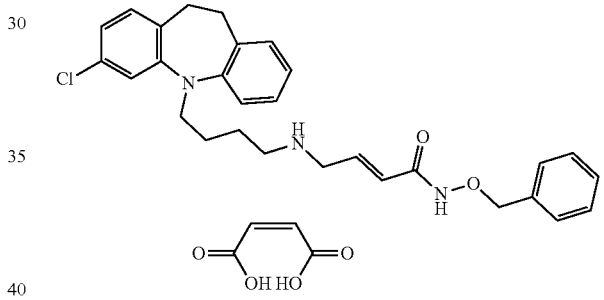

Step 1: (E)-4-{tert-butoxycarbonyl-[4-(3-chloro-10,11-dihydro-5H-dibenzo[b,f]azepin-5-yl)butylamino]}-N-benzyloxy-but-2-enamide 0.081 g (62%) of (E)-4-{tert-butoxycarbonyl-[4-(3-chloro-10,11-dihydro-5H-dibenzo[b,f]azepin-5-yl)butylamino]}-N-benzyloxy-but-2-enamide were prepared according to the procedure described for Example 78, Step 1, starting from 0.113 g (0.22 mmol) of ethyl (E)-4-{tert-butoxycarbonyl-[4-(3-chloro-10,11-dihydro-5H-dibenzo[b,f]azepin-5-yl)butyl]amino}but-2-enoate (Example 17, Step 1) and 0.089 g (0.551 mmol) of O-benzylhydroxylamine hydrochloride. $^1$H NMR (DMSO-d$_6$) δ (ppm): 11.18 (bs, 1H), 7.40-7.30 (m, 5H), 7.17-7.05 (m, 5H), 6.98-6.89 (m, 2H), 6.60-6.47 (m, 1H), 5.73-5.63 (m, 1H), 4.80 (s, 2H), 3.85-3.72 (m, 2H), 3.71-3.64 (m, 2H), 3.09-2.98 (m, 6H), 1.49-1.35 (m, 4H), 1.34-1.20 (m, 9H); MS (ESI): m/z: 590 [M+H]$^+$.

Step 2: (E)-4-[4-(3-chloro-10,11-dihydro-5H-dibenzo[b,f]azepin-5-yl)butylamino]-N-benzyloxy-but-2-enamide 0.070 g (quant.) of (E)-4-[4-(3-chloro-10,11-dihydro-5H-dibenzo[b,f]azepin-5-yl)butylamino]-N-benzyloxy-but-2- enamide were prepared according to the procedure described for Example 78, Step 2, starting from 0.080 g (0.136 mmol) of (E)-4-{tert-butoxycarbonyl-[4-(3-chloro-10,11-dihydro-5H-dibenzo[b,f]azepin-5-yl)butylamino]}-N-benzyloxy-but-2-enamide and 0.208 ml (2.71 mmol) of TFA. $^1$H NMR (MeOH-d$_4$, D$_2$O) δ (ppm): 7.46-7.32 (m, 5H), 7.20-7.11 (m, 3H), 7.10-7.03 (m, 2H), 7.01-6.95 (m, 1H), 6.90-6.85 (m, 1H), 6.76-6.68 (m, 1H), 5.95 (d, J=15.7 Hz, 1H), 4.89 (s, 2H), 3.78-3.70 (m, 2H), 3.46 (d, J=6.4 Hz, 2H), 3.16-3.05 (m, 4H), 2.67 (br. s., 2H), 1.66-1.55 (m, 4H); MS (ESI): m/z: 490 [M+H]$^+$.

Step 3: (E)-4-[4-(3-chloro-10,11-dihydro-5H-dibenzo[b,f]azepin-5-yl)butylamino]-N-benzyloxy-but-2-enamide maleate 0.064 g (77%) of (E)-4-[4-(3-chloro-10,11-dihydro-5H-dibenzo[b,f]azepin-5-yl)butylamino]-N-benzyloxy-but-2-enamide maleate were prepared according to the procedure described for Example 2, Step 2, starting from 0.067 g (0.137 mmol) of (E)-4-[4-(3-chloro-10,11-dihydro-5H-dibenzo[b,f]azepin-5-yl)butylamino]-N-benzyloxy-but-2-enamide and 0.016 g (0.137 mmol) of maleic acid. $^1$H NMR (DMSO-d$_6$) δ (ppm): 11.40 (s, 1H), 8.55 (bs, 2H), 7.42-7.31 (m, 5H), 7.19-7.12 (m, 4H), 7.10 (d, J=8.3 Hz, 1H), 7.00-6.91 (m, 2H), 6.68-6.56 (m, 1H), 6.05-5.94 (m, 3H), 4.83 (s, 2H), 3.77-3.61 (m, 4H), 3.12-3.00 (m, 4H), 2.83 (t, J=7.3 Hz, 2H), 1.64-1.54 (m, 2H), 1.54-1.44 (m, 2H); MS (ESI): m/z: 490 [M+H]$^+$.

Example 80: (E)-4-[4-(3-chloro-10,11-dihydro-5H-dibenzo[b,f]azepin-5-yl)butylamino]-N-ethoxy-but-2-enamide maleate

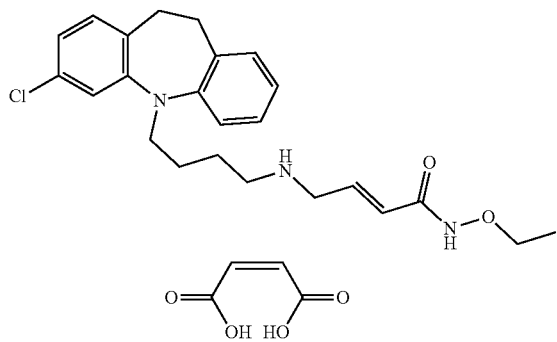 [SMILES: CCONC(=O)/C=C/CNCCCCN1c2ccccc2CCc2ccc(Cl)cc21 ; O=C(O)/C=C\C(=O)O]

Step 1: (E)-4-{tert-butoxycarbonyl-[4-(3-chloro-10,11-dihydro-5H-dibenzo[b,f]azepin-5-yl)butylamino]}-N-ethoxy-but-2-enamide 0.047 g (45%) of (E)-4-{tert-butoxycarbonyl-[4-(3-chloro-10,11-dihydro-5H-dibenzo[b,f]azepin-5-yl)butylamino]}-N-ethoxy-but-2-enamide were prepared according to the procedure described for Example 78, Step 1, starting from 0.102 g (0.199 mmol) of ethyl (E)-4-{tert-butoxycarbonyl-[4-(3-chloro-10,11-dihydro-5H-dibenzo[b,f]azepin-5-yl)butyl]amino}but-2-enoate (Example 17, Step 1) and 0.050 g (0.497 mmol) of O-ethyl-hydroxylamine hydrochloride. $^1$H NMR (DMSO-d$_6$) δ (ppm): 11.07 (s, 1H), 7.18-7.04 (m, 5H), 6.98-6.88 (m, 2H), 6.58-6.44 (m, 1H), 5.73-5.63 (m, 1H), 3.88-3.72 (m, 4H), 3.71-3.64 (m, 2H), 3.04 (br. s., 6H), 1.50-1.36 (m, 4H), 1.35-1.19 (m, 9H), 1.12 (t, J=6.8 Hz, 3H); MS (ESI): m/z: 528 [M+H]$^+$.

Step 2: (E)-4-[4-(3-chloro-10,11-dihydro-5H-dibenzo[b,f]azepin-5-yl)butylamino]-N-ethoxy-but-2-enamide 0.028 g (75%) of (E)-4-[4-(3-chloro-10,11-dihydro-5H-dibenzo[b,f]azepin-5-yl)butylamino]-N-ethoxy-but-2-enamide were prepared according to the procedure described for Example 78, Step 2, starting from 0.046 g (0.087 mmol) of (E)-4-{tert-butoxycarbonyl-[4-(3-chloro-10,11-dihydro-5H-dibenzo[b,f]azepin-5-yl)butylamino]}-N-ethoxy-but-2-enamide and 0.133 ml (1.74 mmol) of TFA. $^1$H NMR (DMSO-d$_6$) δ (ppm): 10.98 (bs, 1H), 7.18-7.05 (m, 5H), 6.98-6.89 (m, 2H), 6.67-6.57 (m, 1H), 5.80 (d, J=15.2 Hz, 1H), 3.79 (q, J=6.8 Hz, 2H), 3.67 (t, J=6.6 Hz, 2H), 3.16 (d, J=4.4 Hz, 2H), 3.09-3.00 (m, 4H), 2.38 (t, J=6.6 Hz, 2H), 1.51-1.34 (m, 4H), 1.12 (t, J=7.1 Hz, 3H); MS (ESI): m/z: 428 [M+H]$^+$.

Step 3: (E)-4-[4-(3-chloro-10,11-dihydro-5H-dibenzo[b,f]azepin-5-yl)butylamino]-N-ethoxy-but-2-enamide maleate 0.031 g (90%) of (E)-4-[4-(3-chloro-10,11-dihydro-5H-dibenzo[b,f]azepin-5-yl)butylamino]-N-ethoxy-but-2-enamide maleate were prepared according to the procedure described for Example 2, Step 2, starting from 0.027 g (0.063 mmol) of (E)-4-[4-(3-chloro-10,11-dihydro-5H-dibenzo[b,f]azepin-5-yl)butylamino]-N-ethoxy-but-2-enamide and 0.007 g (0.063 mmol) of maleic acid. $^1$H NMR (DMSO-d$_6$) δ (ppm): 11.29 (s, 1H), 8.49 (bs, 2H), 7.18-7.12 (m, 4H), 7.10 (d, J=8.3 Hz, 1H), 7.00-6.91 (m, 2H), 6.65-6.54 (m, 1H), 6.04-5.95 (m, 3H), 3.82 (q, J=6.8 Hz, 2H), 3.75-3.63 (m, 4H), 3.11-3.00 (m, 4H), 2.83 (t, J=7.3 Hz, 2H), 1.62-1.54 (m, 2H), 1.53-1.44 (m, 2H), 1.14 (t, J=6.8 Hz, 3H); MS (ESI): m/z: 428 [M+H]$^+$.

Example 81: (E)-4-[4-(3-chloro-10,11-dihydro-5H-dibenzo[b,f]azepin-5-yl)butylamino]-N-isopropoxy-but-2-enamide maleate

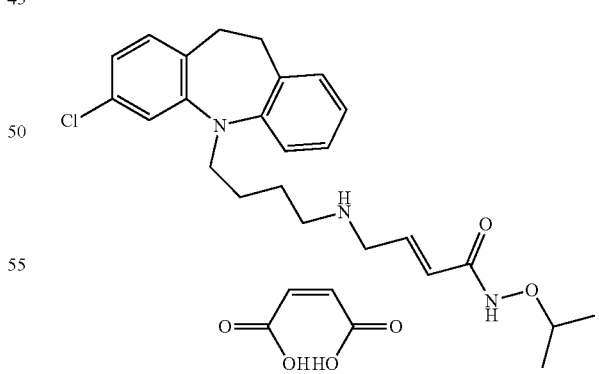

Step 1: (E)-4-{tert-butoxycarbonyl-[4-(3-chloro-10,11-dihydro-5H-dibenzo[b,f]azepin-5-yl)butylamino]}-N-isopropoxy-but-2-enamide 0.035 g (29%) of (E)-4-{tert-butoxycarbonyl-[4-(3-chloro-10,11-dihydro-5H-dibenzo[b,f]azepin-5-yl)butylamino]}-N-isopropoxy-but-2-enamide were prepared according to the procedure described for Example 78, Step 1, starting from 0.116 g (0.226 mmol) of ethyl (E)-4-{tert-butoxycarbonyl-[4-(3-chloro-10,11-dihydro-5H-dibenzo[b,f]azepin-5-yl)butyl]amino}but-2-enoate (Example 17, Step 1) and 0.066 g (0.565 mmol) of O-isopropylhydroxylamine hydrochloride. $^1$H NMR (DMSO-$d_6$) δ (ppm): 10.90 (bs, 1H), 7.18-7.05 (m, 5H), 6.99-6.88 (m, 2H), 6.57-6.45 (m, 1H), 5.75-5.68 (m, 1H), 4.02-3.92 (m, 1H), 3.85-3.72 (m, 2H), 3.68 (t, J=6.4 Hz, 2H), 3.04 (br. s., 6H), 1.50-1.36 (m, 4H), 1.35-1.20 (m, 9H), 1.11 (d, J=6.4 Hz, 6H); MS (ESI): m/z: 542 [M+H]$^+$.

Step 2: (E)-4-[4-(3-chloro-10,11-dihydro-5H-dibenzo[b,f]azepin-5-yl)butylamino]-N-isopropoxy-but-2-enamide 0.027 g (97%) of (E)-4-[4-(3-chloro-10,11-dihydro-5H-dibenzo[b,f]azepin-5-yl)butylamino]-N-isopropoxy-but-2-enamide were prepared according to the procedure described for Example 78, Step 2, starting from 0.034 g (0.063 mmol) of (E)-4-{tert-butoxycarbonyl-[4-(3-chloro-10,11-dihydro-5H-dibenzo[b,f]azepin-5-yl)butylamino]}-N-isopropoxy-but-2-enamide and 0.096 ml (1.25 mmol) of TFA. $^1$H NMR (DMSO-$d_6$) δ (ppm): 10.84 (bs, 1H), 7.18-7.05 (m, 5H), 6.98-6.89 (m, 2H), 6.67-6.56 (m, 1H), 5.85 (d, J=15.2 Hz, 1H), 3.99-3.93 (m, 1H), 3.67 (t, J=6.6 Hz, 2H), 3.20 (d, J=3.4 Hz, 2H), 3.10-2.99 (m, 4H), 2.41 (t, J=6.4 Hz, 2H), 1.52-1.35 (m, 4H), 1.12 (d, J=6.4 Hz, 6H); MS (ESI): m/z: 442 [M+H]$^+$.

Step 3: (E)-4-[4-(3-chloro-10,11-dihydro-5H-dibenzo[b,f]azepin-5-yl)butylamino]-N-isopropoxy-but-2-enamide maleate 0.028 g (87%) of (E)-4-[4-(3-chloro-10,11-dihydro-5H-dibenzo[b,f]azepin-5-yl)butylamino]-N-isopropoxy-but-2-enamide maleate were prepared according to the procedure described for Example 2, Step 2, starting from 0.026 g (0.058 mmol) of (E)-4-[4-(3-chloro-10,11-dihydro-5H-dibenzo[b,f]azepin-5-yl)butylamino]-N-isopropoxy-but-2-enamide and 0.007 g (0.058 mmol) of maleic acid. $^1$H NMR (DMSO-$d_6$) δ (ppm): 11.13 (s, 1H), 8.48 (bs, 2H), 7.18-7.12 (m, 4H), 7.10 (d, J=8.3 Hz, 1H), 7.00-6.91 (m, 2H), 6.64-6.55 (m, 1H), 6.06-5.97 (m, 3H), 4.05-3.95 (m, 1H), 3.75-3.62 (m, 4H), 3.12-3.00 (m, 4H), 2.83 (t, J=7.3 Hz, 2H), 1.63-1.54 (m, 2H), 1.53-1.44 (m, 2H), 1.19-1.08 (m, 6H); MS (ESI): m/z: 442 [M+H]$^+$.

Example 82: (E)-4-[4-(3-chloro-10,11-dihydro-5H-dibenzo[b,f]azepin-5-yl)butylamino]-N-phenoxy-but-2-enamide maleate

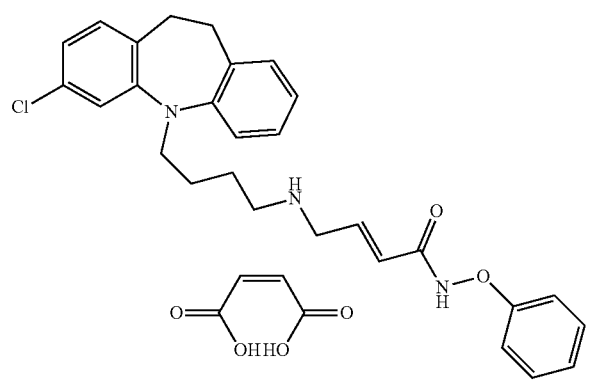

Step 1: (E)-4-{tert-butoxycarbonyl-[4-(3-chloro-10,11-dihydro-5H-dibenzo[b,f]azepin-5-yl)butylamino]}-N-phenoxy-but-2-enamide 0.061 g (45%) of (E)-4-{tert-butoxycarbonyl-[4-(3-chloro-10,11-dihydro-5H-dibenzo[b,f]azepin-5-yl)butylamino]}-N-phenoxy-but-2-enamide were prepared according to the procedure described for Example 78, Step 1, starting from 0.120 g (0.234 mmol) of ethyl (E)-4-{tert-butoxycarbonyl-[4-(3-chloro-10,11-dihydro-5H-dibenzo[b,f]azepin-5-yl)butyl]amino}but-2-enoate (Example 17, Step 1) and 0.088 g (0.585 mmol) of O-phenylhydroxylamine hydrochloride. $^1$H NMR (DMSO-$d_6$) δ (ppm): 11.93 (bs, 1H), 7.37-7.25 (m, 2H), 7.19-7.06 (m, 5H), 7.05-6.88 (m, 5H), 6.73-6.53 (m, 1H), 5.95-5.80 (m, 1H), 3.94-3.77 (m, 2H), 3.75-3.61 (m, 2H), 3.19-2.89 (m, 6H), 1.58-1.07 (m, 13H); MS (ESI): m/z: 576 [M+H]$^+$.

Step 2: (E)-4-[4-(3-chloro-10,11-dihydro-5H-dibenzo[b,f]azepin-5-yl)butylamino]-N-phenoxy-but-2-enamide 0.035 g (71%) of (E)-4-[4-(3-chloro-10,11-dihydro-5H-dibenzo[b,f]azepin-5-yl)butylamino]-N-phenoxy-but-2-enamide were prepared according to the procedure described for Example 78, Step 2, starting from 0.060 g (0.104 mmol) of (E)-4-{tert-butoxycarbonyl-[4-(3-chloro-10,11-dihydro-5H-dibenzo[b,f]azepin-5-yl)butylamino]}-N-phenoxy-but-2-enamide and 0.160 ml (2.08 mmol) of TFA. $^1$H NMR (DMSO-$d_6$) δ (ppm): 7.34-7.26 (m, 2H), 7.18-7.05 (m, 5H), 7.04-6.88 (m, 5H), 6.78-6.67 (m, 1H), 6.05-5.94 (m, 1H), 3.68 (t, J=6.1 Hz, 2H), 3.22 (d, J=4.4 Hz, 2H), 3.10-2.99 (m, 4H), 2.46-2.37 (m, 2H), 1.56-1.32 (m, 4H); MS (ESI): m/z: 476 [M+H]$^+$.

Step 3: (E)-4-[4-(3-chloro-10,11-dihydro-5H-dibenzo[b,f]azepin-5-yl)butylamino]-N-phenoxy-but-2-enamide maleate 0.038 g (91%) of (E)-4-[4-(3-chloro-10,11-dihydro-5H-dibenzo[b,f]azepin-5-yl)butylamino]-N-phenoxy-but-2-enamide maleate were prepared according to the procedure described for Example 2, Step 2, starting from 0.034 g (0.071 mmol) of (E)-4-[4-(3-chloro-10,11-dihydro-5H-dibenzo[b,f]azepin-5-yl)butylamino]-N-phenoxy-but-2-enamide and 0.008 g (0.071 mmol) of maleic acid. $^1$H NMR (DMSO-$d_6$) δ (ppm): 12.17 (bs, 1H), 8.57 (bs, 2H), 7.39-7.27 (m, 2H), 7.20-7.08 (m, 5H), 7.08-6.91 (m, 5H), 6.70 (bs, 1H), 6.20 (d, J=15.7 Hz, 1H), 6.01 (s, 2H), 3.80-3.64 (m, 4H), 3.14-2.99 (m, 4H), 2.93-2.81 (m, 2H), 1.66-1.43 (m, 4H); MS (ESI): m/z: 476 [M+H]$^+$.

Example 83: (E)-4-[4-(3-Chloro-10,11-dihydro-5H-dibenzo[b,f]azepin-5-yl)butylamino]-N-(4-piperidyloxy)-but-2-enamide dimaleate

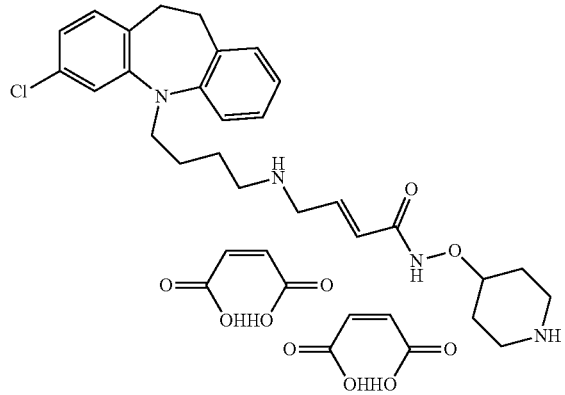

Step 1: (E)-4-{tert-butoxycarbonyl-[4-(3-chloro-10,11-dihydro-5H-dibenzo[b,f]azepin-5-yl)butylamino]}-N-(1-tert-butoxycarbonyl-4-piperidyloxy)-but-2-enamide 0.042 g (26%) of (E)-4-{tert-butoxycarbonyl-[4-(3-chloro-10,11-dihydro-5H-dibenzo[b,f]azepin-5-yl)butylamino]}-N-(1-tert-butoxycarbonyl-4-piperidyloxy)-but-2-enamide were prepared according to the procedure described for Example 78, Step 1, starting from 0.123 g (0.24 mmol) of ethyl (E)-4-{tert-butoxycarbonyl-[4-(3-chloro-10,11-dihydro-5H-dibenzo[b,f]azepin-5-yl)butyl]amino}but-2-enoate (Example 17, Step 1), 0.719 ml (0.719 mmol) of 1 M LiHMDS in dry THF and 0.130 g (0.599 mmol) of tert-butyl 4-aminooxypiperidine-1-carboxylate (Intermediate 57). $^1$H NMR (DMSO-d$_6$) δ (ppm): 11.04 (bs, 1H), 7.18-7.05 (m, 5H), 6.98-6.89 (m, 2H), 6.59-6.47 (m, 1H), 5.74-5.67 (m, 1H), 3.97-3.87 (m, 1H), 3.85-3.73 (m, 2H), 3.68 (t, J=6.4 Hz, 2H), 3.63-3.54 (m, 2H), 3.14-2.97 (m, 8H), 1.80-1.70 (m, 2H), 1.52-1.35 (m, 15H), 1.34-1.20 (m, 9H); MS (ESI): m/z: 683 [M+H]$^+$.

Step 2: (E)-4-[4-(3-Chloro-10,11-dihydro-5H-dibenzo[b,f]azepin-5-yl)butylamino]-N-(4-piperidyloxy)-but-2-enamide 0.011 g (38%) of (E)-4-[4-(3-chloro-10,11-dihydro-5H-dibenzo[b,f]azepin-5-yl)butylamino]-N-(4-piperidyloxy)-but-2-enamide were prepared according to the procedure described for Example 78, Step 2, starting from 0.041 g (0.060 mmol) of (E)-4-{tert-butoxycarbonyl-[4-(3-chloro-10,11-dihydro-5H-dibenzo[b,f]azepin-5-yl)butylamino]}-N-(1-tert-butoxycarbonyl-4-piperidyloxy)-but-2-enamide and 0.184 ml (2.40 mmol) of TFA. $^1$H NMR (DMSO-d$_6$) δ (ppm): 10.87 (bs, 1H), 7.19-7.05 (m, 5H), 6.99-6.88 (m, 2H), 6.67-6.56 (m, 1H), 5.87-5.78 (m, 1H), 3.82-3.72 (m, 1H), 3.67 (t, J=6.6 Hz, 2H), 3.16 (d, J=4.4 Hz, 2H), 3.10-2.99 (m, 4H), 2.97-2.85 (m, 2H), 2.47-2.32 (m, 4H), 1.84-1.75 (m, 2H), 1.53-1.28 (m, 6H); MS (ESI): m/z: 483 [M+H]$^+$.

Step 3: (E)-4-[4-(3-Chloro-10,11-dihydro-5H-dibenzo[b,f]azepin-5-yl)butylamino]-N-(4-piperidyloxy)-but-2-enamide dimaleate 0.014 g (91%) of (E)-4-[4-(3-chloro-10,11-dihydro-5H-dibenzo[b,f]azepin-5-yl)butylamino]-N-(4-piperidyloxy)-but-2-enamide dimaleate were prepared according to the procedure described for Example 2, Step 2, starting from 0.010 g (0.021 mmol) of (E)-4-[4-(3-chloro-10,11-dihydro-5H-dibenzo[b,f]azepin-5-yl)butylamino]-N-(4-piperidyloxy)-but-2-enamide and 0.005 g (0.041 mmol) of maleic acid. $^1$H NMR (MeOH-d$_4$) δ (ppm): 7.19-7.12 (m, 3H), 7.11 (d, J=2.0 Hz, 1H), 7.05 (d, J=7.8 Hz, 1H), 7.00-6.96 (m, 1H), 6.88 (dd, J=2.0, 7.8 Hz, 1H), 6.83-6.71 (m, 1H), 6.26 (s, 4H), 6.17 (d, J=15.7 Hz, 1H), 4.19-4.12 (m, 1H), 3.82-3.74 (m, 4H), 3.47-3.39 (m, 2H), 3.21-3.06 (m, 6H), 3.01-2.94 (m, 2H), 2.14-1.95 (m, 4H), 1.80-1.71 (m, 2H), 1.70-1.62 (m, 2H); MS (ESI): m/z: 483 [M+H]$^+$.

Example 84: (E)-4-[4-(3-Chloro-10,11-dihydro-5H-dibenzo[b,f]azepin-5-yl)butylamino]-N-(2-phenylethyloxy)-but-2-enamide maleate

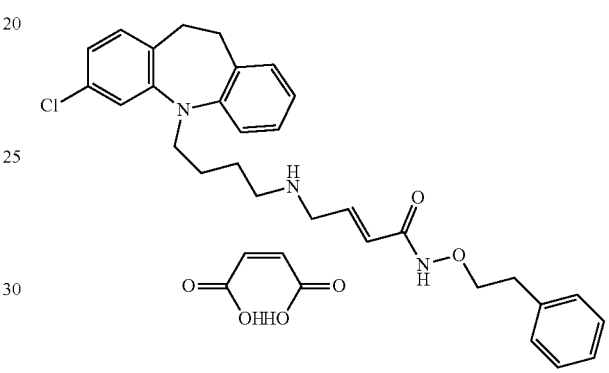

Step 1: (E)-4-{tert-butoxycarbonyl-[4-(3-chloro-10,11-dihydro-5H-dibenzo[b,f]azepin-5-yl)butylamino]}-N-(2-phenylethyloxy)-but-2-enamide 0.051 g (43%) of (E)-4-{tert-butoxycarbonyl-[4-(3-chloro-10,11-dihydro-5H-dibenzo[b,f]azepin-5-yl)butylamino]}-N-(2-phenylethyloxy)-but-2-enamide were prepared according to the procedure described for Example 78, Step 1, starting from 0.100 g (0.195 mmol) of ethyl (E)-4-{tert-butoxycarbonyl-[4-(3-chloro-10,11-dihydro-5H-dibenzo[b,f]azepin-5-yl)butyl]amino}but-2-enoate (Example 17, Step 1) and 0.085 g (0.487 mmol) of O-(2-phenylethyl)hydroxylamine hydrochloride (prepared according to literature procedure, Eur. J. Med. Chem. 2016, 108, 564-576). $^1$H NMR (DMSO-d$_6$) δ (ppm): 11.17 (bs, 1H), 7.32-7.03 (m, 10H), 6.98-6.87 (m, 2H), 6.61-6.45 (m, 1H), 5.74-5.64 (m, 1H), 4.03-3.93 (m, 2H), 3.85-3.72 (m, 2H), 3.68 (t, J=6.4 Hz, 2H), 3.04 (bs, 6H), 2.86 (t, J=6.6 Hz, 2H), 1.50-1.36 (m, 4H), 1.35-1.19 (m, 9H); MS (ESI): m/z: 604 [M+H]$^+$.

Step 2: (E)-4-[4-(3-Chloro-10,11-dihydro-5H-dibenzo[b,f]azepin-5-yl)butylamino]-N-(2-phenylethyloxy)-but-2-enamide 0.042 g (quant.) of (E)-4-[4-(3-chloro-10,11-dihydro-5H-dibenzo[b,f]azepin-5-yl)butylamino]-N-(2-phenylethyloxy)-but-2-enamide were prepared according to the procedure described for Example 78, Step 2, starting from 0.050 g (0.083 mmol) of (E)-4-{tert-butoxycarbonyl-[4-(3-chloro-10,11-dihydro-5H-dibenzo[b,f]azepin-5-yl)butylamino]}-N-(2-phenylethyloxy)-but-2-enamide and 0.127 ml (1.66 mmol) of TFA. ¹H NMR (MeOH-d₄) δ (ppm): 7.31-7.11 (m, 8H), 7.09 (d, J=2.0 Hz, 1H), 7.03 (d, J=7.8 Hz, 1H), 6.99-6.93 (m, 1H), 6.86 (dd, J=2.0, 8.3 Hz, 1H), 6.83-6.76 (m, 1H), 5.96-5.88 (m, 1H), 4.06 (t, J=7.1 Hz, 2H), 3.75 (t, J=5.9 Hz, 2H), 3.37 (d, J=5.4 Hz, 2H), 3.19-3.06 (m, 4H), 2.97 (t, J=7.1 Hz, 2H), 2.64-2.54 (m, 2H), 1.66-1.52 (m, 4H); MS (ESI): m/z: 504 [M+H]⁺.

Step 3: (E)-4-[4-(3-Chloro-10,11-dihydro-5H-dibenzo[b,f]azepin-5-yl)butylamino]-N-(2-phenyl-ethyloxy)-but-2-enamide maleate 0.037 g (75%) of (E)-4-[4-(3-chloro-10,11-dihydro-5H-dibenzo[b,f]azepin-5-yl)butylamino]-N-(2-phenylethyl-oxy)-but-2-enamide maleate were prepared according to the procedure described for Example 2, Step 2, starting from 0.040 g (0.079 mmol) of (E)-4-[4-(3-chloro-10,11-dihydro-5H-dibenzo[b,f]azepin-5-yl)butylamino]-N-(2-phenylethyl-oxy)-but-2-enamide and 0.009 g (0.079 mmol) of maleic acid. ¹H NMR (DMSO-d₆) δ (ppm): 11.40 (s, 1H), 8.57 (bs, 2H), 7.35-7.05 (m, 10H), 7.01-6.89 (m, 2H), 6.68-6.55 (m, 1H), 6.06-5.95 (m, 3H), 4.01 (t, J=6.6 Hz, 2H), 3.77-3.58 (m, 4H), 3.13-3.00 (m, 4H), 2.94-2.75 (m, 4H), 1.64-1.43 (m, 4H); MS (ESI): m/z: 504 [M+H]⁺.

Example 85: (E)-4-[4-(3-Chloro-10,11-dihydro-5H-dibenzo[b,f]azepin-5-yl)butyl-methyl-amino]-N-methoxy-but-2-enamide maleate

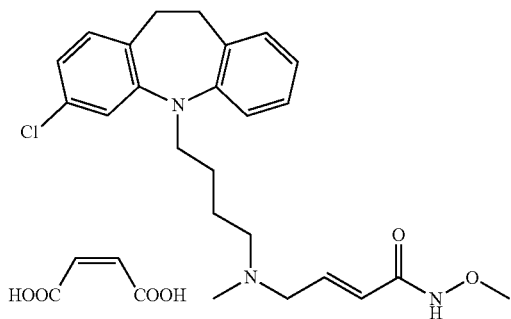 [SMILES: CONC(=O)/C=C/CN(C)CCCCN1c2ccccc2CCc2ccc(Cl)cc21 ; O=C(O)/C=C\C(=O)O]

Step 1: (E)-4-[4-(3-Chloro-10,11-dihydro-5H-dibenzo[b,f]azepin-5-yl)butyl-methyl-amino]-N-methoxy-but-2-enamide 0.031 g (73%) of ((E)-4-[4-(3-chloro-10,11-dihydro-5H-dibenzo[b,f]azepin-5-yl)butyl-methyl-amino]-N-methoxy-but-2-enamide were prepared according to the procedure described for Example 18, Step 1, starting from 0.040 g (0.099 mmol) of (E)-4-[4-(3-chloro-10,11-dihydro-5H-dibenzo[b,f]azepin-5-yl)butyl-methyl-amino]but-2-enoic acid lithium salt (Example 72, Step 1), 0.069 ml (0.395 mmol) of DIPEA, 0.020 mg (0.128 mmol) of HOBt, 0.038 g (0.198 mmol) of EDC and 0.017 mg (0.198 mmol) of O-methylhydroxylamine hydrochloride. ¹H NMR (DMSO-d₆) δ (ppm): 11.13 (bs, 1H), 7.18-7.04 (m, 5H), 6.99-6.88 (m, 2H), 6.62-6.52 (m, 1H), 5.83-5.76 (m, 1H), 3.68 (t, J=6.1 Hz, 2H), 3.60 (s, 3H), 3.10-3.01 (m, 4H), 2.97 (d, J=5.4 Hz, 2H), 2.20 (t, J=6.1 Hz, 2H), 2.02 (s, 3H), 1.43 (br. s., 4H); MS (ESI): m/z: 428 [M+H]⁺.

Step 2: (E)-4-[4-(3-Chloro-10,11-dihydro-5H-dibenzo[b,f]azepin-5-yl)butyl-methyl-amino]-N-methoxy-but-2-enamide maleate 0.025 g (63%) of (E)-4-[4-(3-chloro-10,11-dihydro-5H-dibenzo[b,f]azepin-5-yl)butyl-methyl-amino]-N-methoxy-but-2-enamide maleate were prepared according to the procedure described for Example 2, Step 2, starting from 0.031 g (0.072 mmol) of ((E)-4-[4-(3-chloro-10,11-dihydro-5H-dibenzo[b,f]azepin-5-yl)butyl-methyl-amino]-N-methoxy-but-2-enamide and 0.008 g (0.072 mmol) of maleic acid. ¹H NMR (MeOH-d₄) δ (ppm): 7.20-7.13 (m, 3H), 7.11 (d, J=2.4 Hz, 1H), 7.05 (d, J=7.8 Hz, 1H), 7.01-6.96 (m, 1H), 6.89 (dd, J=2.2, 8.1 Hz, 1H), 6.81-6.70 (m, 1H), 6.26 (s, 2H), 6.18 (d, J=15.2 Hz, 1H), 3.89 (d, J=7.3 Hz, 2H), 3.81 (t, J=6.6 Hz, 2H), 3.75 (s, 3H), 3.18-3.13 (m, 2H), 3.13-3.05 (m, 4H), 2.79 (s, 3H), 1.83-1.74 (m, 2H), 1.69-1.60 (m, 2H); MS (ESI): m/z: 428 [M+H]⁺.

Example 86: Ethyl (E)-4-{[4-(3-chloro-10-[2-(2-methoxyethoxy)ethyl]-11-oxo-10,11-dihydro-5H-dibenzo[b,e][1,4]diazepin-5-yl)butyl]amino}but-2-enoate maleate

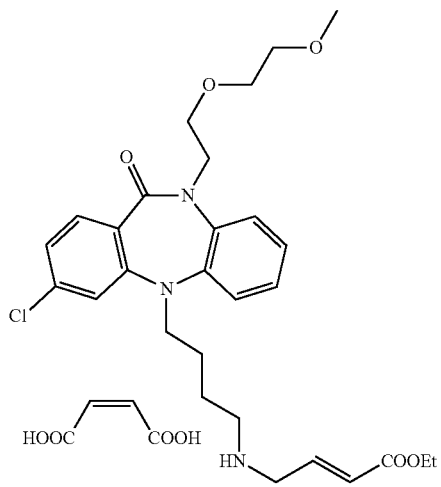 [SMILES: CCOC(=O)/C=C/CNCCCCN1c2cc(Cl)ccc2C(=O)N(CCOCCOC)c2ccccc21 ; O=C(O)/C=C\C(=O)O]

Step 1: Ethyl (E)-4-{[4-(3-chloro-10-[2-(2-methoxyethoxy)ethyl]-11-oxo-10,11-dihydro-5H-dibenzo[b,e][1,4]diazepin-5-yl)butyl]amino}but-2-enoate 0.012 g (30%) of ethyl (E)-4-{[4-(3-chloro-10-[2-(2-methoxyethoxy)ethyl]-11-oxo-10,11-dihydro-5H-dibenzo[b,e][1,4]diazepin-5-yl)butyl]amino}but-2-enoate were prepared according to the procedure described for Example 2, Step 1, starting from 0.032 g (0.076 mmol) of 5-(4-aminobutyl)-3-chloro-10-[2-(2-methoxyethoxy)ethyl]-5,10-dihydro-11H-dibenzo[b,e][1,4]diazepin-11-one (Intermediate 58). ¹H NMR (DMSO-d₆) δ (ppm): 7.60-7.48 (m, 2H), 7.27 (dd, J=1.5, 7.8 Hz, 1H), 7.23 (d, J=2.0 Hz, 1H), 7.21-7.08 (m, 3H), 6.83 (dt, J=5.4, 15.7 Hz, 1H), 5.91 (dt, J=1.5, 15.6 Hz, 1H), 4.41-4.32 (m, 1H), 4.09 (q, J=7.1 Hz, 2H), 3.94-3.85 (m, 1H), 3.72-3.67 (m, 2H), 3.67-3.60 (m, 1H), 3.54-3.40 (m, 3H), 3.37-3.32 (m, 2H), 3.23 (dd, J=1.5, 5.4 Hz, 2H), 3.17 (s, 3H), 2.44 (t, J=6.8 Hz, 2H), 1.58-1.42 (m, 4H), 1.19 (t, J=7.1 Hz, 3H); MS (ESI): m/z: 530 [M+H]⁺.

Step 2: Ethyl (E)-4-{[4-(3-chloro-10-[2-(2-methoxyethoxy)ethyl]-11-oxo-10,11-dihydro-5H-dibenzo[b,e][1,4]diazepin-5-yl)butyl]amino}but-2-enoate maleate 0.012 g (89%) of ethyl (E)-4-{[4-(3-chloro-10-[2-(2-methoxyethoxy)ethyl]-11-oxo-10,11-dihydro-5H-dibenzo

[b,e][1,4]diazepin-5-yl)butyl]amino}but-2-enoate maleate were prepared according to the procedure described for Example 2, Step 2, starting from 0.011 g (0.021 mmol) of ethyl (E)-4-{[4-(3-chloro-10-[2-(2-methoxyethoxy)ethyl]-11-oxo-10,11-dihydro-5H-dibenzo[b,e][1,4]diazepin-5-yl)butyl]amino}but-2-enoate and 0.002 g (0.021 mmol) of maleic acid. $^1$H NMR (CD$_3$OD) δ (ppm): 7.62-7.53 (m, 2H), 7.30 (dd, J=1.5, 7.8 Hz, 1H), 7.26-7.17 (m, 3H), 7.12 (dd, J=1.7, 8.6 Hz, 1H), 6.84 (dt, J=6.5, 15.9 Hz, 1H), 6.26 (s, 2H), 6.21 (dt, J=1.5, 15.7 Hz, 1H), 4.59-4.50 (m, 1H), 4.22 (q, J=7.1 Hz, 2H), 4.10-4.01 (m, 1H), 3.90-3.72 (m, 6H), 3.66-3.59 (m, 1H), 3.55-3.49 (m, 1H), 3.48-3.42 (m, 1H), 3.39-3.34 (m, 1H), 3.30 (s, 3H), 3.06-2.97 (m, 2H), 1.90-1.67 (m, 4H), 1.29 (t, J=7.1 Hz, 3H); MS (ESI): m/z: 530 [M+H]$^+$.

Example 87: Ethyl (E)-4-{[4-(3-chloro-10-[2-[2-(2-methoxyethoxy)ethoxy]ethyl]-11-oxo-10,11-dihydro-5H-dibenzo[b,e][1,4]diazepin-5-yl)butyl]amino}but-2-enoate maleate

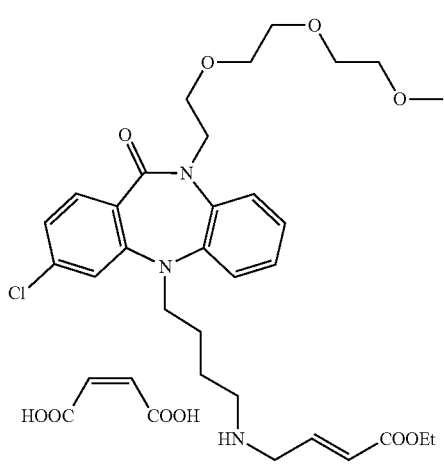 [SMILES: CCOC(=O)/C=C/CNCCCCN1c2cc(Cl)ccc2C(=O)N(CCOCCOCCOC)c2ccccc21 ; O=C(O)/C=C\C(=O)O]

Step 1: Ethyl (E)-4-{[4-(3-chloro-10-[2-[2-(2-methoxyethoxy)ethoxy]ethyl]-11-oxo-10,11-dihydro-5H-dibenzo[b,e][1,4]diazepin-5-yl)butyl]amino}but-2-enoate 0.046 g (37%) of ethyl (E)-4-{[4-(3-chloro-10-[2-[2-(2-methoxyethoxy)ethoxy]ethyl]-11-oxo-10,11-dihydro-5H-dibenzo[b,e][1,4]diazepin-5-yl)butyl]amino}but-2-enoate were prepared according to the procedure described for Example 2, Step 1, starting from 0.100 g (0.216 mmol) of 5-(4-aminobutyl)-3-chloro-10-[2-[2-(2-methoxyethoxy)ethoxy]ethyl]-5,10-dihydro-11H-dibenzo[b,e][1,4]diazepin-11-one (Intermediate 59). $^1$H NMR (DMSO-d$_6$) δ (ppm): 7.56-7.49 (m, 2H), 7.26 (dd, J=1.5, 8.3 Hz, 1H), 7.23 (d, J=2.0 Hz, 1H), 7.21-7.09 (m, 3H), 6.84 (dt, J=5.4, 15.7 Hz, 1H), 5.90 (dt, J=2.0, 15.7 Hz, 1H), 4.42-4.28 (m, 1H), 4.09 (q, J=7.3 Hz, 2H), 3.95-3.86 (m, 1H), 3.72-3.60 (m, 3H), 3.56-3.49 (m, 1H), 3.48-3.39 (m, 6H), 3.38-3.34 (m, 2H), 3.23 (dd, J=2.0, 5.4 Hz, 2H), 3.19 (s, 3H), 2.43 (t, J=6.8 Hz, 2H), 1.57-1.40 (m, 4H), 1.19 (t, J=7.3 Hz, 3H); MS (ESI): m/z: 574 [M+H]$^+$.

Step 2: Ethyl (E)-4-{[4-(3-chloro-10-[2-[2-(2-methoxyethoxy)ethoxy]ethyl]-11-oxo-10,11-dihydro-5H-dibenzo[b,e][1,4]diazepin-5-yl)butyl]amino}but-2-enoate maleate 0.041 g (76%) of ethyl (E)-4-{[4-(3-chloro-10-[2-[2-(2-methoxyethoxy)ethoxy]ethyl]-11-oxo-10,11-dihydro-5H-dibenzo[b,e][1,4]diazepin-5-yl)butyl]amino}but-2-enoate maleate were prepared according to the procedure described for Example 2, Step 2, starting from 0.045 g (0.078 mmol) of ethyl (E)-4-{[4-(3-chloro-10-[2-[2-(2-methoxyethoxy)ethoxy]ethyl]-11-oxo-10,11-dihydro-5H-dibenzo[b,e][1,4]diazepin-5-yl)butyl]amino}but-2-enoate and 0.009 g (0.078 mmol) of maleic acid. $^1$H NMR (DMSO-d$_6$) δ (ppm): 8.57 (bs, 3H), 7.57 (dd, J=1.5, 7.8 Hz, 1H), 7.53 (d, J=8.8 Hz, 1H), 7.30-7.24 (m, 2H), 7.23-7.19 (m, 1H), 7.18-7.12 (m, 2H), 6.78 (dt, J=6.4, 15.7 Hz, 1H), 6.18 (dt, J=1.5, 15.7 Hz, 1H), 6.02 (s, 2H), 4.34-4.24 (m, 1H), 4.15 (q, J=7.1 Hz, 2H), 4.02-3.93 (m, 1H), 3.80-3.64 (m, 5H), 3.62-3.54 (m, 1H), 3.51-3.40 (m, 6H), 3.39-3.35 (m, 2H), 3.20 (s, 3H), 2.90 (t, J=7.1 Hz, 2H), 1.68-1.50 (m, 4H), 1.21 (t, J=7.1 Hz, 3H); MS (ESI): m/z: 574 [M+H]$^+$.

Example 88: Ethyl (E)-4-{[4-[3-chloro-10-[2-(prop-2-yn-1-yloxy)ethyl]-11-oxo-10,11-dihydro-5H-dibenzo[b,e][1,4]diazepin-5-yl)butyl]amino}but-2-enoate maleate

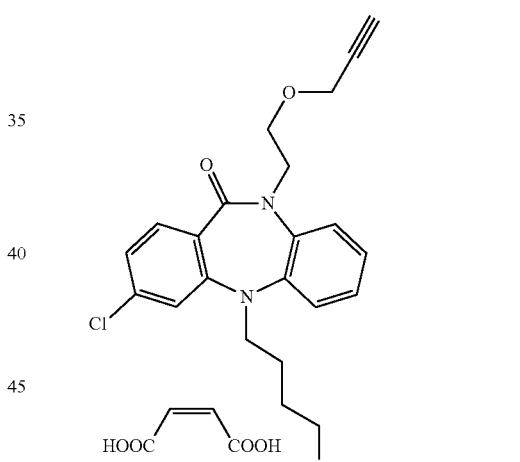

Step 1: Ethyl (E)-4-{[4-[3-chloro-10-[2-(prop-2-yn-1-yloxy)ethyl]-11-oxo-10,11-dihydro-5H-dibenzo[b,e][1,4]diazepin-5-yl)butyl]amino}but-2-enoate 0.049 g (40%) of ethyl (E)-4-{[4-[3-chloro-10-[2-(prop-2-yn-1-yloxy)ethyl]-11-oxo-10,11-dihydro-5H-dibenzo[b,e][1,4]diazepin-5-yl)butyl]amino}but-2-enoate were prepared according to the procedure described for Example 2, Step 1, starting from 0.096 g (0.241 mmol) of 5-(4-aminobutyl)-3-chloro-10-[2-(prop-2-yn-1-yloxy)ethyl]-5,10-dihydro-11H-dibenzo[b,e][1,4]diazepin-11-one (Intermediate 61). $^1$H NMR (DMSO-d$_6$) δ (ppm): 7.54-7.47 (m, 2H), 7.26 (d, J=7.8 Hz, 1H), 7.23 (d, J=1.5 Hz, 1H), 7.21-7.13 (m, 2H), 7.11 (dd, J=1.5, 8.3 Hz, 1H), 6.83 (dt, J=5.4, 15.7 Hz, 1H), 5.91 (d, J=15.7 Hz, 1H), 4.48-4.36 (m, 1H), 4.15-4.05 (m, 4H), 3.95-3.85 (m, 1H), 3.75-3.50 (m, 4H), 3.36 (t, J=2.4

Hz, 1H), 3.23 (d, J=5.4 Hz, 2H), 2.45 (t, J=6.8 Hz, 2H), 1.59-1.41 (m, 4H), 1.19 (t, J=7.1 Hz, 3H); MS (ESI): m/z: 510 [M+H]⁺.

Step 2: Ethyl (E)-4-{[4-[3-chloro-10-[2-(prop-2-yn-1-yloxy)ethyl]-11-oxo-10,11-dihydro-5H-dibenzo[b,e][1,4]diazepin-5-yl)butyl]amino}but-2-enoate maleate 0.053 g (96%) of ethyl (E)-4-{[4-[3-chloro-10-[2-(prop-2-yn-1-yloxy)ethyl]-11-oxo-10,11-dihydro-5H-dibenzo[b,e][1,4]diazepin-5-yl)butyl]amino}but-2-enoate maleate were prepared according to the procedure described for Example 2, Step 2, starting from 0.045 g (0.088 mmol) of ethyl (E)-4-{[4-[3-chloro-10-[2-(prop-2-yn-1-yloxy)ethyl]-11-oxo-10,11-dihydro-5H-dibenzo[b,e][1,4]diazepin-5-yl)butyl]amino}but-2-enoate and 0.010 g (0.088 mmol) of maleic acid. ¹H NMR (DMSO-d₆) δ (ppm): 8.59 (bs, 3H), 7.56-7.49 (m, 2H), 7.30-7.27 (m, 1H), 7.26 (d, J=2.0 Hz, 1H), 7.23-7.19 (m, 1H), 7.19-7.15 (m, 1H), 7.14 (dd, J=2.0, 8.3 Hz, 1H), 6.78 (dt, J=6.4, 16.1 Hz, 1H), 6.19 (d, J=16.1 Hz, 1H), 6.02 (s, 2H), 4.43-4.33 (m, 1H), 4.15 (q, J=7.1 Hz, 2H), 4.10 (d, J=2.4 Hz, 2H), 3.99-3.92 (m, 1H), 3.80-3.59 (m, 6H), 3.39 (t, J=2.4 Hz, 1H), 2.95-2.87 (m, 2H), 1.70-1.48 (m, 4H), 1.21 (t, J=7.1 Hz, 3H); MS (ESI): m/z: 510 [M+H]⁺.

Example 89: Methyl (E)-4-{4-[7-chloro-2-(2-prop-2-ynoxyethoxy)-10,11-dihydro-5H-dibenzo[b,f]azepin-5-yl]-butyl-methyl-amino}-but-2-enoate maleate

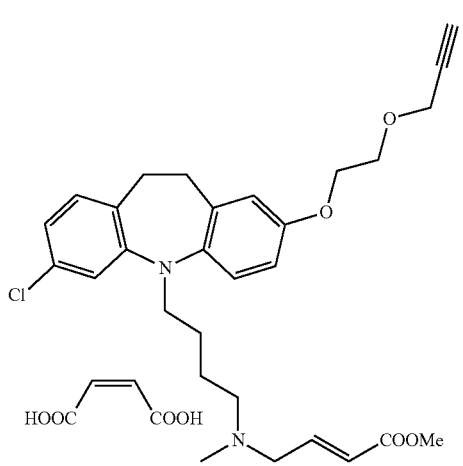 [SMILES: C#CCOCCOc1ccc2c(c1)CCc1ccc(Cl)cc1N2CCCCN(C)C/C=C/C(=O)OC ; O=C(O)/C=C\C(=O)O]

Step 1: Methyl (E)-4-{4-[7-chloro-2-(2-prop-2-ynoxyethoxy)-10,11-dihydro-5H-dibenzo[b,f]azepin-5-yl]-butyl-methyl-amino]-but-2-enoate 0.021 g (52%) of methyl (E)-4-{4-[7-chloro-2-(2-prop-2-ynoxyethoxy)-10,11-dihydro-5H-dibenzo[b,f]azepin-5-yl]-butyl-methyl-amino}-but-2-enoate were prepared according to the procedure described for Example 1, Step 1 starting from 0.037 g (0.082 mmol) of 4-[7-chloro-2-(2-prop-2-ynoxyethoxy)-10,11-dihydro-5H-dibenzo[b,f]azepin-5-yl]-N-methyl-butan-1-amine hydrochloride (Intermediate 62), 0.011 ml (0.086 mmol) of methyl 4-bromo-2-butenoate and 0.034 g (0.247 mmol) of K₂CO₃ at r.t. ¹H NMR (DMSO-d₆) δ (ppm): 7.07-7.01 (m, 3H), 6.86 (dd, J=2.0, 7.8 Hz, 1H), 6.79-6.70 (m, 3H), 5.94 (dt, J=1.7, 15.8 Hz, 1H), 4.19 (d, J=2.4 Hz, 2H), 4.06-4.01 (m, 2H), 3.75-3.70 (m, 2H), 3.66-3.59 (m, 5H), 3.46 (t, J=2.4 Hz, 1H), 3.07-2.96 (m, 6H), 2.21 (t, J=6.8 Hz, 2H), 2.04 (s, 3H), 1.50-1.34 (m, 4H); MS (ESI): m/z: 511 [M+H]⁺.

Step 2: Methyl (E)-4-{4-[7-chloro-2-(2-prop-2-ynoxyethoxy)-10,11-dihydro-5H-dibenzo[b,f]azepin-5-yl]-butyl-methyl-amino}-but-2-enoate maleate 0.019 g (81%) of methyl (E)-4-{4-[7-chloro-2-(2-prop-2-ynoxyethoxy)-10,11-dihydro-5H-dibenzo[b,f]azepin-5-yl]-butyl-methyl-amino}-but-2-enoate maleate were prepared according to the procedure described for Example 2, Step 2, starting from 0.019 g (0.037 mmol) of methyl (E)-4-{4-[7-chloro-2-(2-prop-2-ynoxyethoxy)-10,11-dihydro-5H-dibenzo[b,f]azepin-5-yl]-butyl-methyl-amino}-but-2-enoate and 0.004 g (0.037 mmol) of maleic acid. ¹H NMR (CD₃OD) δ (ppm): 7.10-7.06 (m, 2H), 7.02 (d, J=8.3 Hz, 1H), 6.88-6.80 (m, 2H), 6.79-6.74 (m, 2H), 6.30-6.25 (m, 3H), 4.24 (d, J=2.4 Hz, 2H), 4.12-4.04 (m, 2H), 3.89 (d, J=6.8 Hz, 2H), 3.87-3.84 (m, 2H), 3.78 (s, 3H), 3.75 (t, J=6.6 Hz, 2H), 3.15-3.05 (m, 6H), 2.87 (t, J=2.4 Hz, 1H), 2.80 (s, 3H), 1.81-1.72 (m, 2H), 1.68-1.59 (m, 2H); MS (ESI): m/z: 511 [M+H]⁺.

Example 90: (E)-4-{4-[7-chloro-2-(2-prop-2-ynoxyethoxy)-10,11-dihydro-5H-dibenzo[b,f]azepin-5-yl]butyl-methyl-amino}but-2-enenitrile maleate

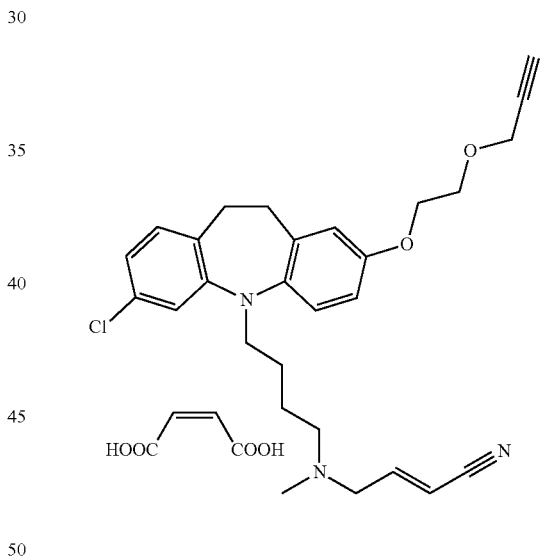

Step 1: (E)-4-{4-[7-chloro-2-(2-prop-2-ynoxyethoxy)-10,11-dihydro-5H-dibenzo[b,f]azepin-5-yl]butyl-methyl-amino}but-2-enenitrile 0.067 g (75%) of (E)-4-{4-[7-chloro-2-(2-prop-2-ynoxyethoxy)-10,11-dihydro-5H-dibenzo[b,f]azepin-5-yl]butyl-methyl-amino}but-2-enenitrile were prepared according to the procedure described for Example 1, Step 1 starting from 0.084 g (0.187 mmol) of 4-[7-chloro-2-(2-prop-2-ynoxyethoxy)-10,11-dihydro-5H-dibenzo[b,f]azepin-5-yl]-N-methyl-butan-1-amine hydrochloride (Intermediate 62), 0.030 mg (0.196 mmol) of (2E)-4-bromobut-2-enenitrile and 0.077 g (0.561 mmol) of K₂CO₃ at r.t. ¹H NMR (DMSO-d₆) δ (ppm): 7.08-7.02 (m, 3H), 6.87 (dd, J=2.0, 8.3 Hz, 1H), 6.81-6.69 (m, 3H), 5.75 (dt, J=1.6, 16.4 Hz, 1H), 4.19 (d, J=2.4 Hz, 2H), 4.08-4.00 (m, 2H), 3.76-3.70 (m, 2H), 3.62 (t, J=6.4 Hz, 2H), 3.45 (t, J=2.4 Hz, 1H), 3.07-2.95

(m, 6H), 2.21 (t, J=6.6 Hz, 2H), 2.04 (s, 3H), 1.49-1.33 (m, 4H); MS (ESI): m/z: 478 [M+H]⁺.

Step 2: (E)-4-{4-[7-chloro-2-(2-prop-2-ynoxy-ethoxy)-10,11-dihydro-5H-dibenzo[b,f]azepin-5-yl]butyl-methyl-amino}but-2-enenitrile maleate 0.032 g (95%) of (E)-4-{4-[7-chloro-2-(2-prop-2-ynoxyethoxy)-10,11-dihydro-5H-dibenzo[b,f]azepin-5-yl]butyl-methyl-amino}but-2-enenitrile maleate were prepared according to the procedure described for Example 2, Step 2, starting from 0.027 g (0.056 mmol) of (E)-4-{4-[7-chloro-2-(2-prop-2-ynoxyethoxy)-10,11-dihydro-5H-dibenzo[b,f]azepin-5-yl]butyl-methyl-amino}but-2-enenitrile and 0.007 g (0.056 mmol) of maleic acid. ¹H NMR (CD₃OD) δ (ppm): 7.10-7.06 (m, 2H), 7.02 (d, J=7.8 Hz, 1H), 6.85 (dd, J=2.2, 8.1 Hz, 1H), 6.82-6.74 (m, 3H), 6.27 (s, 2H), 6.03 (dt, J=1.5, 16.1 Hz, 1H), 4.24 (d, J=2.4 Hz, 2H), 4.12-4.07 (m, 2H), 3.89 (dd, J=1.5, 7.1 Hz, 2H), 3.87-3.83 (m, 2H), 3.75 (t, J=6.6 Hz, 2H), 3.16-3.05 (m, 6H), 2.87 (t, J=2.4 Hz, 1H), 2.79 (s, 3H), 1.80-1.71 (m, 2H), 1.67-1.58 (m, 2H); MS (ESI): m/z: 478 [M+H]⁺.

Example 91: Prop-2-yn-1-yl (E)-4-[4-(3-chloro-10,11-dihydro-5H-dibenzo[b,f]azepin-5-yl)butylamino]but-2-enoate maleate

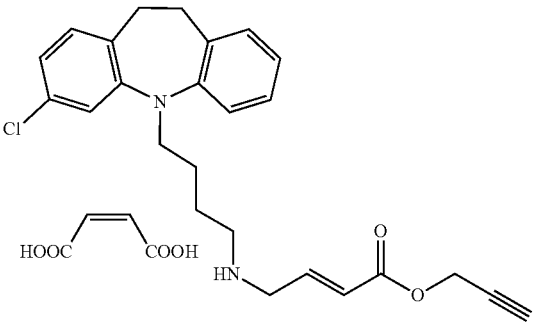 [SMILES: C#CCOC(=O)/C=C/CNCCCCN1c2ccccc2CCc2ccc(Cl)cc21 ; O=C(O)/C=C\C(=O)O]

Step 1: (E)-4-{tert-butoxycarbonyl-[4-(3-chloro-10,11-dihydro-5H-dibenzo[b,f]azepin-5-yl)butyl]amino}but-2-enoic acid lithium salt 1.22 g (97%) of (E)-4-{tert-butoxycarbonyl-[4-(3-chloro-10,11-dihydro-5H-dibenzo[b,f]azepin-5-yl)butyl]amino}but-2-enoic acid lithium salt were prepared according to the procedure described for Example 72, Step 1, starting from 1.27 g (2.48 mmol) of ethyl (E)-4-{tert-butoxycarbonyl-[4-(3-chloro-10,11-dihydro-5H-dibenzo[b,f]azepin-5-yl)butyl]amino}but-2-enoate (Example 17, Step 1) and 0.066 g (2.72 mmol) of LiOH. ¹H NMR (DMSO-d₆) δ (ppm): 12.36 (bs, 1H), 7.17-7.05 (m, 5H), 6.98-6.89 (m, 2H), 6.67-6.56 (m, 1H), 5.68 (d, J=15.6 Hz, 1H), 3.81 (br. s, 2H), 3.68 (t, J=6.3 Hz, 2H), 3.12-2.97 (m, 6H), 1.51-1.35 (m, 4H), 1.31 and 1.26 (2 br. s, 9H); MS (ESI): m/z: 485 [M+H]⁺.

Step 2: Prop-2-yn-1-yl (E)-4-{tert-butoxycarbonyl-[4-(3-chloro-10,11-dihydro-dibenzo[b,f]azepin-5-yl)-butyl]-amino}but-2-enoate 0.110 g (0.22 mmol) of (E)-4-{tert-butoxycarbonyl-[4-(3-chloro-10,11-dihydro-5H-dibenzo[b,f]azepin-5-yl)butyl]amino}but-2-enoic acid lithium salt were dissolved in dry DMF (0.8 ml) to which were added 0.036 ml of propargyl bromide (80% in toluene, 0.323 mmol). The resulting mixture was stirred at 60° C. for 2 h then the reaction was quenched with water and extracted with EtOAc. The organic layer was dried (Na₂SO₄) and concentrated under vacuo. The crude was purified by flash chromatography (eluent: hexane/EtOAc from 97:3 to 70:30) to afford prop-2-yn-1-yl (E)-4-{tert-butoxycarbonyl-[4-(3-chloro-10,11-dihydro-dibenzo[b,f]azepin-5-yl)-butyl]-amino}but-2-enoate as pale yellow oil (0.082 g, 72%). ¹H NMR (DMSO-d₆) δ (ppm): 7.17-7.04 (m, 5H), 7.00-6.87 (m, 2H), 6.84-6.71 (bm, 1H), 5.79 (d, J=15.7 Hz, 1H), 4.75 (br. s., 2H), 3.93-3.76 (m, 2H), 3.68 (t, J=6.4 Hz, 2H), 3.56 (t, J=2.4 Hz, 1H), 3.16-2.97 (m, 6H), 1.50-1.20 (m, 13H); MS (ESI): m/z: 523 [M+H]⁺.

Step 3: Prop-2-yn-1-yl (E)-4-[4-(3-chloro-10,11-dihydro-di benzo[b,f]azepin-5-yl)-butylamino]but-2-enoate 0.119 ml (1.55 mmol) of TFA were added at 0° C. to a solution of 0.081 g (0.155 mmol) of prop-2-yn-1-yl (E)-4-{tert-butoxycarbonyl-[4-(3-chloro-10,11-dihydro-dibenzo[b,f]azepin-5-yl)-butyl]-amino}but-2-enoate in dry DCM (0.6 ml). The mixture was stirred at r.t. for 24 h. Then it was cooled to 0° C., treated with saturated aqueous NaHCO₃ and extracted with DCM; the organic layer was dried (Na₂SO₄) and concentrated under vacuo. The crude was purified by flash chromatography (eluent: hexane/EtOAc from 88:12 to 0:100) to afford prop-2-yn-1-yl (E)-4-[4-(3-chloro-10,11-dihydro-di benzo[b,f]azepin-5-yl)-butylamino]but-2-enoate as pale yellow oil (0.061 g, 93%). ¹H NMR (DMSO-d₆) δ (ppm): 7.17-7.05 (m, 5H), 6.98-6.85 (m, 3H), 5.93 (dt, J=15.6, 1.0 Hz, 1H), 4.73 (d, J=2.4 Hz, 2H), 3.67 (t, J=6.6 Hz, 2H), 3.55 (t, J=2.4 Hz, 1H), 3.23 (dd, J=1.7, 5.1 Hz, 2H), 3.12-2.98 (m, 4H), 2.39 (t, J=7.1 Hz, 2H), 1.54-1.30 (m, 4H); MS (ESI): m/z: 423 [M+H]⁺.

Step 4: Prop-2-yn-1-yl (E)-4-[4-(3-chloro-10,11-dihydro-5H-dibenzo[b,f]azepin-5-yl)butylamino]but-2-enoate maleate 0.065 g (84%) of prop-2-yn-1-yl (E)-4-[4-(3-chloro-10,11-dihydro-5H-dibenzo[b,f]azepin-5-yl)butylamino]but-2-enoate maleate were prepared according to the procedure described for Example 2, Step 2, starting from 0.060 g (0.143 mmol) of prop-2-yn-1-yl (E)-4-[4-(3-Chloro-10,11-dihydro-di benzo[b,f]azepin-5-yl)-butylamino]but-2-enoate and 0.017 g (0.143 mmol) of maleic acid. ¹H NMR (DMSO-d₆) δ (ppm): 8.52 (br. s., 3H), 7.18-7.06 (m, 5H), 7.01-6.90 (m, 2H), 6.83 (dt, J=6.3, 15.8 Hz, 1H), 6.22 (d, J=15.7 Hz, 1H), 6.01 (s, 2H), 4.80 (d, J=2.4 Hz, 2H), 3.79-3.66 (m, 4H), 3.59 (t, J=2.4 Hz, 1H), 3.13-2.99 (m, 4H), 2.86 (t, J=7.6 Hz, 2H), 1.65-1.44 (m, 4H); MS (ESI): m/z: 423 [M+H]⁺.

Example 92: 2-Prop-2-ynyloxy-ethyl (E)-4-[4-(3-chloro-10,11-dihydro-5H-dibenzo[b,f]azepin-5-yl)butylamino]but-2-enoate maleate

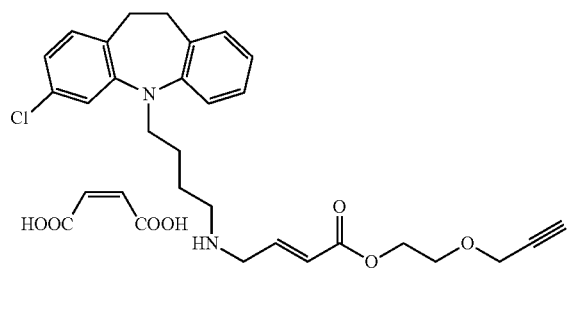 [SMILES: C#CCOCCOC(=O)/C=C/CNCCCCN1c2ccccc2CCc2ccc(Cl)cc21 ; O=C(O)/C=C\C(=O)O]

Step 1: 2-Prop-2-ynyloxy-ethyl (E)-4-[tert-butoxycarbonyl-[4-(3-chloro-10,11-dihydro-5H-dibenzo[b,f]azepin-5-yl)butylamino]but-2-enoate 0.075 g (67%) of 2-prop-2-ynyloxy-ethyl (E)-4-[tert-butoxycarbonyl-[4-(3-chloro-10,11-dihydro-5H-dibenzo[b,f]azepin-5-yl)butylamino]but-2-enoate were prepared according to the procedure described for Example 91, Step 2, starting from 0.10 g (0.197 mmol) of (E)-4-{tert-butoxycarbonyl-[4-(3-chloro-10,11-dihydro-5H-dibenzo[b,f]azepin-5-yl)butyl]amino}but-2-enoic acid lithium salt (Example 91, Step 1) and 0.083 g (0.263 mmol) of 2-(prop-2-yn-1-yloxy)ethyl 4-methylbenzenesulfonate (Intermediate 60). $^1$H NMR (DMSO-$d_6$) δ (ppm): 7.18-7.03 (m, 5H), 7.00-6.85 (m, 2H), 6.82-6.69 (m, 1H), 5.79 (d, J=15.7 Hz, 1H), 4.24-4.17 (bm, 2H), 4.15 (d, J=2.4 Hz, 2H), 3.92-3.75 (bm, 2H), 3.71-3.58 (m, 4H), 3.44 (t, J=2.4 Hz, 1H), 3.14-2.95 (m, 6H), 1.50-1.21 (m, 13H); MS (ESI): m/z: 567 [M+H]$^+$.

Step 2: 2-Prop-2-ynyloxy-ethyl (E)-4-[4-(3-chloro-10,11-dihydro-5H-dibenzo[b,f]azepin-5-yl)butylamino]but-2-enoate 0.052 g (86%) of 2-prop-2-ynyloxy-ethyl (E)-4-[4-(3-chloro-10,11-dihydro-5H-dibenzo[b,f]azepin-5-yl)butylamino]but-2-enoate were prepared according to the procedure described for Example 91, Step 3, starting from 0.073 g (0.129 mmol) of 2-prop-2-ynyloxy-ethyl (E)-4-[tert-butoxycarbonyl-[4-(3-chloro-10,11-dihydro-5H-dibenzo[b,f]azepin-5-yl)butylamino]but-2-enoate and 0.098 ml (1.29 mmol) of TFA. $^1$H NMR (DMSO-$d_6$) δ (ppm): 7.18-7.03 (m, 5H), 7.00-6.89 (m, 2H), 6.85 (dt, J=15.7 Hz, 5.4 Hz, 1H), 5.93 (d, J=15.7 Hz, 1H), 4.23-4.17 (m, 2H), 4.16 (d, J=2.0 Hz, 2H), 3.71-3.58 (m, 4H), 3.45 (t, J=2.2 Hz, 1H), 3.22 (d, J=3.4 Hz, 2H), 3.10-2.97 (m, 4H), 2.39 (t, J=6.8 Hz, 2H), 1.53-1.34 (m, 4H); MS (ESI): m/z: 467 [M+H]$^+$.

Step 3: 2-prop-2-ynyloxy-ethyl (E)-4-[4-(3-chloro-10,11-dihydro-5H-dibenzo[b,f]azepin-5-yl)butylamino] but-2-enoate maleate 0.055 g (86%) of 2-prop-2-ynyloxy-ethyl (E)-4-[4-(3-chloro-10,11-dihydro-5H-dibenzo[b,f]azepin-5-yl)butylamino] but-2-enoate maleate were prepared according to the procedure described for Example 2, Step 2, starting from 0.051 (0.110 mmol) of 2-prop-2-ynyloxy-ethyl (E)-4-[4-(3-chloro-10,11-dihydro-5H-dibenzo[b,f]azepin-5-yl)butylamino] but-2-enoate and 0.013 g (0.110 mmol) of maleic acid. $^1$H NMR (DMSO-$d_6$) δ (ppm): 8.85-8.19 (bm, 3H), 7.19-7.06 (m, 5H), 7.02-6.90 (m, 2H), 6.78 (dt, J=6.3, 15.8 Hz, 1H), 6.21 (d, J=15.7 Hz, 1H), 6.01 (s, 2H), 4.28-4.21 (m, 2H), 4.16 (d, J=2.4 Hz, 2H), 3.78-3.61 (m, 6H), 3.46 (t, J=2.2 Hz, 1H), 3.14-2.99 (m, 4H), 2.85 (t, J=7.6 Hz, 2H), 1.64-1.44 (m, 4H); MS (ESI): m/z: 467 [M+H]$^+$.

Example 93: 2-(2-Methoxy-ethoxy)-ethyl (E)-4-[4-(3-chloro-10,11-dihydro-dibenzo[b,f]azepin-5-yl)-butylamino]but-2-enoate maleate

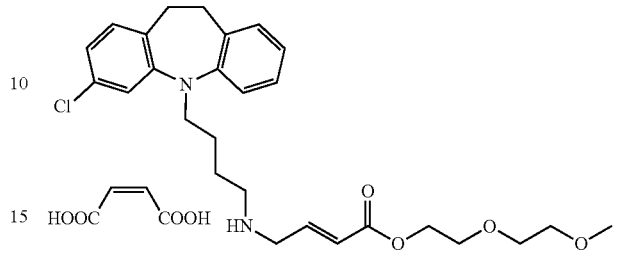

Step 1: 2-(2-Methoxy-ethoxy)-ethyl (E)-4-{tert-butoxycarbonyl-[4-(3-chloro-10,11-dihydro-dibenzo[b,f]azepin-5-yl)-butyl]-amino}but-2-enoate 0.042 g (61%) of 2-(2-methoxy-ethoxy)-ethyl (E)-4-{tert-butoxycarbonyl-[4-(3-chloro-10,11-dihydro-dibenzo[b,f]azepin-5-yl)-butyl]-amino}but-2-enoate were prepared according to the procedure described for Example 91, Step 2, starting from 0.60 g (0.122 mmol) of (E)-4-{tert-butoxycarbonyl-[4-(3-chloro-10,11-dihydro-5H-dibenzo[b,f]azepin-5-yl)butyl]amino}but-2-enoic acid lithium salt (Example 91, Step 1) and 0.038 g (0.196 mmol) of 1-(2-bromoethoxy)-2-methoxy-ethane. $^1$H NMR (DMSO-$d_6$) δ (ppm): 7.18-7.03 (m, 5H), 6.99-6.87 (m, 2H), 6.74 (d, J=15.7 Hz, 1H), 5.79 (d, J=15.7 Hz, 1H), 4.22-4.13 (m, 2H), 3.92-3.78 (bm, 2H), 3.68 (t, J=6.4 Hz, 2H), 3.63-3.57 (m, 2H), 3.54-3.49 (m, 2H), 3.43-3.38 (m, 2H), 3.22 (s, 3H), 3.16-2.99 (m, 6H), 1.51-1.36 (m, 4H), 1.35-1.21 (m, 9H); MS (ESI): m/z: 587 [M+H]$^+$.

Step 2: 2-(2-Methoxy-ethoxy)-ethyl (E)-4-[4-(3-chloro-10,11-dihydro-dibenzo[b,f]azepin-5-yl)-butylamino]but-2-enoate 0.024 g (71%) of 2-(2-methoxy-ethoxy)-ethyl (E)-4-[4-(3-chloro-10,11-dihydro-dibenzo[b,f]azepin-5-yl)butylamino]but-2-enoate were prepared according to the procedure described for Example 91, Step 3, starting from 0.040 g (0.068 mmol) of 2-(2-methoxy-ethoxy)-ethyl (E)-4-[tert-butoxycarbonyl-[4-(3-chloro-10,11-dihydro-dibenzo[b,f]azepin-5-yl)butylamino]but-2-enoate and 0.052 ml (0.68 mmol) of TFA. $^1$H NMR (DMSO-$d_6$) δ (ppm): 7.20-7.03 (m, 5H), 6.99-6.80 (m, 3H), 5.93 (dt, J=15.7, 1.0 Hz, 1H), 4.20-4.11 (m, 2H), 3.67 (t, J=6.6 Hz, 2H), 3.63-3.58 (m, 2H), 3.52 (dd, J=3.7, 5.6 Hz, 2H), 3.42 (dd, J=3.7, 5.6 Hz, 2H), 3.26-3.17 (m, 5H), 3.09-2.98 (m, 4H), 2.39 (t, J=6.8 Hz, 2H), 1.53-1.34 (m, 4H); MS (ESI): m/z: 487 [M+H]$^+$.

Step 3: 2-(2-Methoxy-ethoxy)-ethyl (E)-4-[4-(3-chloro-10,11-dihydro-dibenzo[b,f]azepin-5-yl)-butylamino]but-2-enoate maleate 0.020 g (75%) of 2-(2-methoxy-ethoxy)-ethyl (E)-4-[4-(3-chloro-10,11-dihydro-dibenzo[b,f]azepin-5-yl)butylamino]but-2-enoate maleate were prepared according to the procedure described for Example 2, Step 2, starting from 0.022 g (0.045 mmol) of 2-(2-methoxy-ethoxy)-ethyl (E)-4-[4-(3-chloro-10,11-dihydro-di benzo[b,f]azepin-5-yl)-butylamino]but-2-enoate and 0.005 g (0.045 mmol) of maleic acid. $^1$H NMR (DMSO-$d_6$) δ (ppm): 8.64-8.27 (m, 3H), 7.20-7.06 (m, 5H), 7.02-6.89 (m, 2H), 6.78 (td, J=6.2, 16.0 Hz, 1H), 6.21 (d, J=16.0 Hz, 1H), 6.01 (s, 2H), 4.25-4.19 (m, 2H), 3.77-3.68 (m, 4H), 3.65-3.56 (m, 2H), 3.54-3.50 (m, 2H), 3.45-3.38 (m, 2H), 3.23 (s, 3H), 3.13-3.00 (m, 4H), 2.85 (t, J=7.3 Hz, 2H), 1.63-1.44 (m, 4H); MS (ESI): m/z: 487 [M+H]$^+$.

Example 94: 2-[2-(2-{2-[5-((3aS,4S,6aR)-2-Oxo-hexahydro-thieno[3,4-d]imidazol-4-yl)-pentanoylamino]-ethoxy}-ethoxy)-ethoxy]-ethyl (E)-4-{[4-(3-chloro-10,11-dihydro-dibenzo[b,f]azepin-5-yl)-butyl]-methyl-amino}but-2-enoate

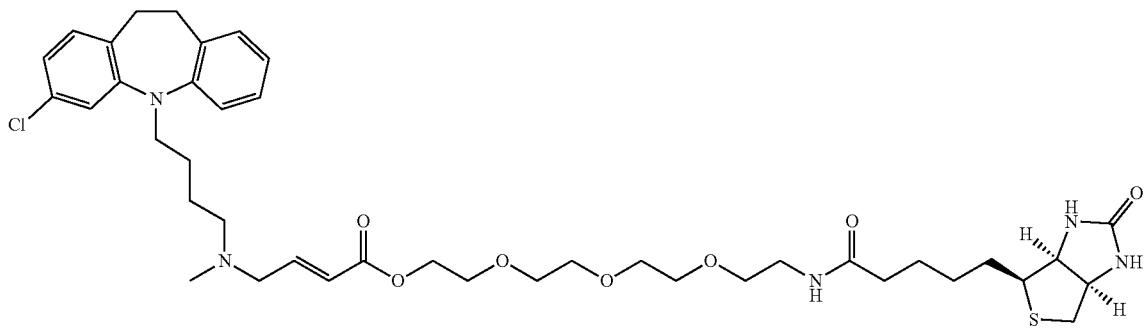 [SMILES: CN(C/C=C/C(=O)OCCOCCOCCOCCNC(=O)CCCC[C@@H]1SC[C@@H]2NC(=O)N[C@@H]21)CCCCN1c2ccccc2CCc2ccc(Cl)cc21]

0.164 g (51%) of 2-[2-(2-{2-[5-((3aS,4S,6aR)-2-oxo-hexahydro-thieno[3,4-d]imidazol-4-yl)-pentanoylamino]-ethoxy}-ethoxy)-ethoxy]-ethyl (E)-4-{[4-(3-chloro-10,11-dihydro-dibenzo[b,f]azepin-5-yl)-butyl]-methyl-amino}but-2-enoate were prepared according to the procedure described for Example 91, Step 2, starting from 0.164 g (0.405 mmol) of (E)-4-[4-(3-chloro-10,11-dihydro-5H-dibenzo[b,f]azepin-5-yl)butyl-methyl-amino]but-2-enoic acid lithium salt (Example 72, Step 1), and 0.262 g (0.527 mmol) of 2-[2-(2-{2-[5-((3aS,4S,6aR)-2-oxo-hexahydro-thieno[3,4-d]imidazol-4-yl)pentanoylamino]-ethoxy}-ethoxy)-ethoxy]-ethyl methanesulfonate (Intermediate 63). $^1$H NMR (DMSO-d$_6$) δ (ppm): 7.87-7.73 (m, 1H), 7.20-7.03 (m, 5H), 7.00-6.88 (m, 2H), 6.76 (dt, J=5.9 Hz, J=15.7 Hz, 1H), 6.40 (s, 1H), 6.34 (s, 1H), 5.95 (d, J=15.7 Hz, 1H), 4.33-4.24 (m, 1H), 4.21-4.15 (m, 2H), 4.13-4.07 (m, 1H), 3.73-3.65 (m, 2H), 3.64-3.59 (m, 2H), 3.56-3.43 (m, 8H), 3.38 (t, J=5.9 Hz, 2H), 3.17 (q, J=5.9 Hz, 2H), 3.11-2.97 (m, 7H), 2.85-2.75 (m, 1H), 2.57 (d, J=12.5 Hz, 1H), 2.29-2.17 (m, 2H), 2.10-2.00 (m, 5H), 1.67-1.19 (m, 10H); MS (ESI): m/z: 800 [M+H]$^+$.

Example 95: 2-(2-{2-[2-(2-{2-[5-((3aS,4S,6aR)-2-Oxo-hexahydro-thieno[3,4-d]imidazol-4-yl)-pentanoylamino]-ethoxy}-ethoxy)-ethoxy]-ethoxy}-ethoxy)-ethyl (E)-4-{[4-(3-chloro-10,11-dihydro-dibenzo[b,f]azepin-5-yl)-butyl]-methyl-amino}but-2-enoate

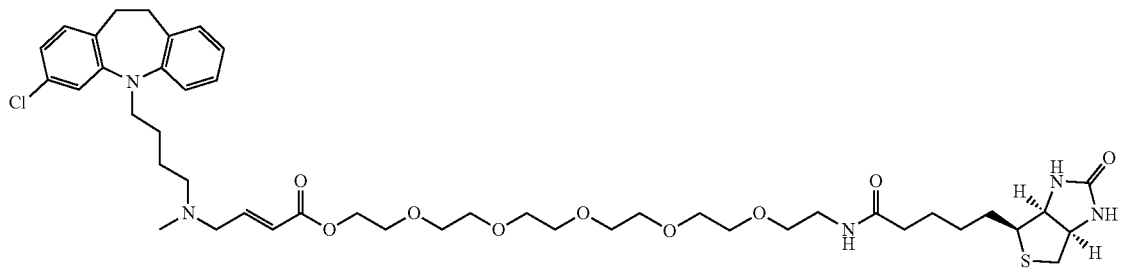 [SMILES: CN(C/C=C/C(=O)OCCOCCOCCOCCOCCOCCNC(=O)CCCC[C@@H]1SC[C@@H]2NC(=O)N[C@@H]21)CCCCN1c2ccccc2CCc2ccc(Cl)cc21]

0.053 g (38%) of 2-(2-{2-[2-(2-{2-[5-((3aS,4S,6aR)-2-oxo-hexahydro-thieno[3,4-d]imidazol-4-yl)-pentanoylamino]-ethoxy}-ethoxy)-ethoxy]-ethoxy}-ethoxy)-ethyl (E)-4-{[4-(3-chloro-10,11-dihydro-dibenzo[b,f]azepin-5-yl)-butyl]-methyl-amino}but-2-enoate were prepared according to the procedure described for Example 91, Step 2, starting from 0.024 g (0.059 mmol) of (E)-4-[4-(3-chloro-10,11-dihydro-5H-dibenzo[b,f]azepin-5-yl)butyl-methyl-amino]but-2-enoic acid lithium salt (Example 72, Step 1), and 0.045 g (0.077 mmol) of 2-[2-[2-[2-[2-[2-[5-[(3aS,4S,6aR)-2-oxo-hexahydrothieno[3,4-d]imidazol-4-yl]pentanoylamino]ethoxy]ethoxy]ethoxy]ethoxy]ethoxy]ethyl methanesulfonate (Intermediate 64). $^1$H NMR (DMSO-$d_6$) δ (ppm): 7.81 (s, 1H) 7.10-7.17 (m, 4H) 7.08 (d, J=8.31 Hz, 1H) 6.98-6.93 (m, 1H) 6.91 (dd, J=8.07, 2.20 Hz, 1H) 6.77 (dt, J=5.9 Hz, J=15.7 Hz, 1H) 6.40 (s, 1H) 6.34 (s, 1H) 5.95 (d, J=15.7 Hz, 1H), 4.35-4.25 (m, 1H) 4.22-4.14 (m, 2H) 4.11 (m, 1H) 3.68 (t, J=6.11 Hz, 2H) 3.59-3.64 (m, 2H) 3.43-3.56 (m, 16H) 3.35-3.41 (m, 2H) 3.17 (q, J=5.87 Hz, 2H) 2.94-3.12 (m, 7H) 2.81 (dd, J=12.23, 4.89 Hz, 1H) 2.57 (d, J=12.72 Hz, 1H) 2.14-2.34 (m, 2H) 2.11-2.02 (m, 5H) 1.18-1.67 (m, 10H); MS (ESI): m/z: 889 [M+H]$^+$.

Example 96: 2-(2-{2-[2-(2-{2-[2-(2-[5-((3aS,4S,6aR)-2-Oxo-hexahydro-thieno[3,4-d]imidazol-4-yl)-pentanoylamino]-ethoxy)-ethoxy]-ethoxy}-ethoxy)-ethoxy]-ethoxy}-ethoxy)-ethyl (E)-4-{[4-(3-chloro-10,11-dihydro-dibenzo[b,f]azepin-5-yl)-butyl]-methyl-amino} but-2-enoate

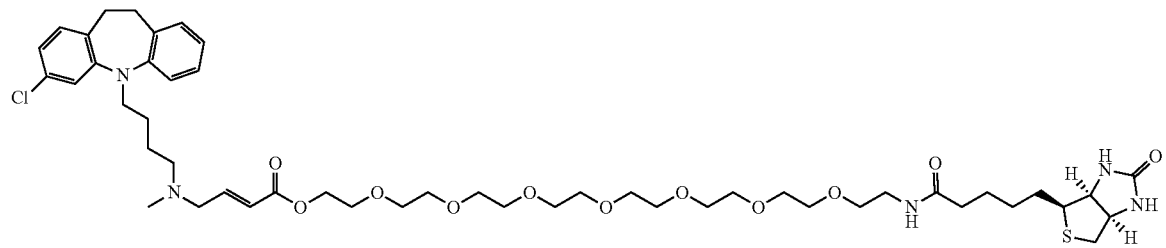 [SMILES: CN(C/C=C/C(=O)OCCOCCOCCOCCOCCOCCOCCOCCNC(=O)CCCC[C@@H]1SC[C@@H]2NC(=O)N[C@@H]21)CCCCN1c2ccccc2CCc2ccc(Cl)cc21]

0.022 g (35%) of 2-(2-{2-[2-(2-{2-[2-(2-[5-((3aS,4S,6aR)-2-oxo-hexahydro-thieno[3,4-d]imidazol-4-yl)-pentanoylamino]-ethoxy)-ethoxy]-ethoxy}-ethoxy)-ethoxy]-ethoxy}-ethoxy)-ethyl (E)-4-{[4-(3-chloro-10,11-dihydro-dibenzo[b,f]azepin-5-yl)-butyl]-methyl-amino} but-2-enoate were prepared according to the procedure described for Example 91, Step 2, starting from 0.024 g (0.059 mmol) of (E)-4-[4-(3-chloro-10,11-dihydro-5H-dibenzo[b,f]azepin-5-yl)butyl-methyl-amino]but-2-enoic acid lithium salt (Example 72, Step 1), and 0.026 g (0.064 mmol) of 2-[2-[2-[2-[2-[2-[2-[5-[(3aS,4S,6aR)-2-oxo-hexahydrothieno[3,4-d]imidazol-4-yl]pentanoylamino]ethoxy]ethoxy]ethoxy]ethoxy]ethoxy]ethoxy]ethyl methanesulfonate (Intermediate 65). $^1$H NMR (DMSO-$d_6$) δ (ppm): 7.82 (t, J=5.9 Hz, 1H) 7.04-7.19 (m, 5H) 6.86-7.00 (m, 2H) 6.70-6.83 (m, 1H) 6.40 (s, 1H) 6.34 (s, 1H) 5.83-6.12 (m, 1H) 4.34-4.24 (m, 1H) 4.15-4.22 (m, 2H) 4.06-4.14 (m, 1H) 3.58-3.76 (m, 4H) 3.43-3.57 (m, 24H) 3.34-3.41 (m, 2H) 3.14-3.21 (m, 2H) 2.97-3.11 (m, 7H) 2.76-2.85 (m, 1H) 2.57 (d, J=12.72 Hz, 1H) 2.45-2.00 (m, 7H) 1.16-1.68 (m, 10H)); MS (ESI): m/z: 977 [M+H]$^+$.

Example 97: Ethyl (E)-4-{4-[7-Chloro-2-(2-methoxy-ethoxy)-10,11-dihydro-5H-dibenzo[b,f]azepin-5-yl]-butylamino}-but-2-enoate maleate

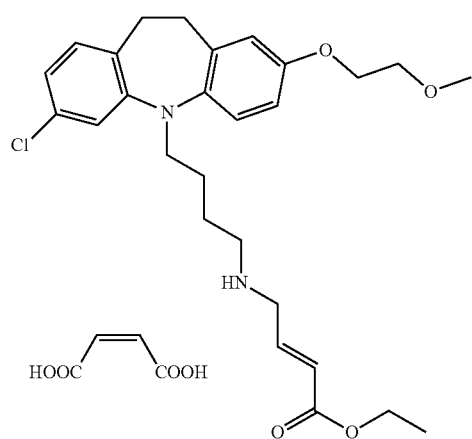 [SMILES: CCOC(=O)/C=C/CNCCCCN1c2ccc(OCCOC)cc2CCc2ccc(Cl)cc21 ; O=C(O)/C=C\C(=O)O]

Step 1: 2-{4-[7-Chloro-2-(2-methoxy-ethoxy)-10,11-dihydro-5H-dibenzo[b,f]azepin-5-yl]-butyl}-isoindole-1,3-dione To a solution of 0.120 g (0.269 mmol) of 2-[4-(7-chloro-2-hydroxy-10,11-dihydro-dibenzo[b,f]azepin-5-yl)-butyl]-isoindole-1,3-dione (Example 67, Step 1) in dry DMF (1.3 ml), potassium carbonate (0.074 g, 0.537 mmol) was added. The mixture was stirred 30 min at r. t. becoming blue. Afterwards 1-bromo-2-methoxy-ethane (0.045 g, 0.322 mmol) was added at 0° C.; then the reaction mixture was stirred overnight at 65° C. It was quenched with water and extracted with EtOAc; the organic layer was dried (Na$_2$SO$_4$) and concentrated under vacuo. The crude was purified by flash chromatography (eluent: hexane/EtOAc from 93:7 to 40:60) to afford 2-{4-[7-chloro-2-(2-methoxy-ethoxy)-10,11-dihydro-5H-dibenzo[b,f]azepin-5-yl]-butyl}-isoindole-1,3-dione as pale yellow foam (0.125 g, 92%). $^1$H NMR (DMSO-d$_6$) δ (ppm): 7.80 (s, 4H), 7.02-6.89 (m, 3H), 6.76 (dd, J=2.2, 8.1 Hz, 1H), 6.65-6.58 (m, 2H), 3.97-3.90 (m, 2H), 3.66-3.55 (m, 4H), 3.48 (t, J=6.6 Hz, 2H), 3.28 (s, 3H), 3.03-2.91 (m, 4H), 1.64-1.54 (m, 2H), 1.48-1.38 (m, 2H); MS (ESI): m/z: 505 [M+H]$^+$.

Step 2: 4-[7-Chloro-2-(2-methoxy-ethoxy)-10,11-dihydro-5H-dibenzo[b,f]azepin-5-yl]-butylamine 0.049 g (75%) of 4-[7-chloro-2-(2-methoxy-ethoxy)-10,11-dihydro-5H-dibenzo[b,f]azepin-5-yl]-butylamine were prepared according to the procedure described for Intermediate 9, Step 2, starting from 0.115 g (0.227 mmol) of 2-{4-[7-chloro-2-(2-methoxy-ethoxy)-10,11-dihydro-5H-dibenzo[b,f]azepin-5-yl]-butyl}-isoindole-1,3-dione and 0.023 g (0.454 mmol) of hydrazine hydrate. $^1$H NMR (DMSO-d$_6$) δ (ppm): 7.08-6.96 (m, 3H), 6.86 (dd, J=2.2, 8.1 Hz, 1H), 6.79-6.65 (m, 2H), 4.05-3.93 (m, 2H), 3.65-3.52 (m, 4H), 3.28 (s, 3H), 3.01 (br. s., 4H), 2.43 (t, J=6.8 Hz, 2H), 1.57-1.22 (m, 6H); MS (ESI): m/z: 375 [M+H]$^+$.

Step 3: Ethyl (E)-4-{4-[7-Chloro-2-(2-methoxy-ethoxy)-10,11-dihydro-5H-dibenzo[b,f]azepin-5-yl]-butylamino}-but-2-enoate 0.017 g (27%) of ethyl (E)-4-{4-[7-Chloro-2-(2-methoxy-ethoxy)-10,11-dihydro-5H-dibenzo[b,f]azepin-5-yl]-butylamino}-but-2-enoate were prepared according to the procedure described for Example 2, Step 1, starting from 0.048 g (0.128 mmol) of 4-[7-chloro-2-(2-methoxy-ethoxy)-10,11-dihydro-5H-dibenzo[b,f]azepin-5-yl]-butylamine and 0.004 g (0.032 mmol) of ethyl (E)-4-oxobut-2-enoate. $^1$H NMR (DMSO-d$_6$) δ (ppm): 7.09-6.99 (m, 3H), 6.90-6.66 (m, 4H), 5.90 (dt, J=15.7, 1.7 Hz, 1H), 4.09 (q, J=7.3 Hz, 2H), 4.01 (dd, J=3.9, 5.4 Hz, 2H), 3.65-3.55 (m, 4H), 3.28 (s, 3H), 3.21 (dd, J=1.7, 5.1 Hz, 2H), 3.02 (br. s., 4H), 2.38 (t, J=6.8 Hz, 2H), 1.50-1.32 (m, 4H), 1.22-1.15 (t, J=6.8 Hz, 3H); MS (ESI): m/z: 487 [M+H]$^+$.

Step 4: Ethyl (E)-4-{4-[7-chloro-2-(2-methoxy-ethoxy)-10,11-dihydro-5H-dibenzo[b,f]azepin-5-yl]-butylamino}-but-2-enoate maleate 0.017 g (79%) of ethyl (E)-4-{4-[7-Chloro-2-(2-methoxy-ethoxy)-10,11-dihydro-5H-dibenzo[b,f]azepin-5-yl]-butylamino}-but-2-enoate maleate were prepared according to the procedure described for Example 2, Step 2, starting from 0.017 g (0.035 mmol) of ethyl (E)-4-{4-[7-chloro-2-(2-methoxy-ethoxy)-10,11-dihydro-5H-dibenzo[b,f]azepin-5-yl]-butylamino}-but-2-enoate and 0.004 g (0.035 mmol) of maleic acid. $^1$H NMR (DMSO-d$_6$) δ (ppm): 8.50 (br. s., 3H), 7.11-7.00 (m, 3H), 6.89 (dd, J=2.0, 8.3 Hz, 1H), 6.81-6.69 (m, 3H), 6.17 (d, J=15.7 Hz, 1H), 6.01 (s, 2H), 4.15 (q, J=6.8 Hz, 2H), 4.05-3.99 (m, 2H), 3.72 (d, J=5.9 Hz, 2H), 3.67-3.58 (m, 4H), 3.28 (s, 3H), 3.08-2.98 (m., 4H), 2.84 (t, J=7.6 Hz, 2H), 1.63-1.40 (m, 4H), 1.21 (t, J=7.1 Hz, 3H); MS (ESI): m/z: 487 [M+H]$^+$.

Example 98: Ethyl (E)-4-(4-{7-chloro-2-[2-(2-methoxy-ethoxy)-ethoxy]-10,11-dihydro-5H-dibenzo[b,f]azepin-5-yl}-butylamino)-but-2-enoate maleate

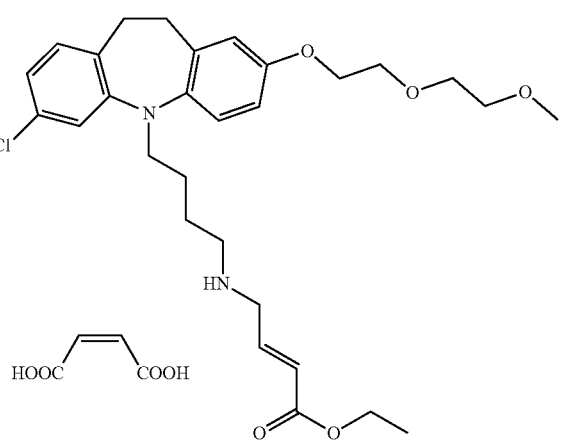

Step 1: 2-(4-{7-Chloro-2-[2-(2-methoxy-ethoxy)-ethoxy]-10,11-dihydro-5H-dibenzo[b,f]azepin-5-yl}-butyl)-isoindole1,3-dione 0.141 g (96%) of 2-(4-{7-chloro-2-[2-(2-methoxy-ethoxy)-ethoxy]-10,11-dihydro-5H-dibenzo[b,f]azepin-5-yl}-butyl)-isoindole1,3-dione were prepared according to the procedure described for Example 97, Step 1, starting from 0.120 g (0.269 mmol) of 2-[4-(7-chloro-2-hydroxy-10,11-dihydro-dibenzo[b,f]azepin-5-yl)-butyl]-isoindole-1,3-dione (Example 67, Step 1) and 0.059 g (0.322 mmol) of 1-(2-bromoethoxy)-2-methoxy-ethane. $^1$H NMR (DMSO-d$_6$) δ (ppm): 7.84-7.75 (m, 4H), 7.01-6.91 (m, 3H), 6.78-6.72 (m, 1H), 6.66-6.54 (m, 2H), 3.97-3.88 (m, 2H), 3.69-3.66 (m, 2H), 3.62 (t, J=6.4 Hz, 2H), 3.58-3.53 (m, 2H), 3.51-3.40 (m, 4H), 3.23 (s, 3H), 3.03-3.91 (m, 4H), 1.66-1.53 (m, 2H), 1.49-1.37 (m, 2H)); MS (ESI): m/z: 549 [M+H]$^+$.

Step 2: 4-{7-Chloro-2-[2-(2-methoxy-ethoxy)-ethoxy]-10,11-dihydro-5H-dibenzo[b,f]azepin-5-yl}-butylamine 0.065 g (68%) of 4-{7-chloro-2-[2-(2-methoxy-ethoxy)-ethoxy]-10,11-dihydro-5H-dibenzo[b,f]azepin-5-yl}-butylamine were prepared according to the procedure described for Intermediate 9, Step 2, starting from 0.126 g (0.229 mmol) of 2-(4-{7-chloro-2-[2-(2-methoxy-ethoxy)-ethoxy]-10,11-dihydro-5H-dibenzo[b,f]azepin-5-yl}-butyl)-isoindole1,3-dione and 0.023 g (0.459 mmol) of hydrazine hydrate. $^1$H NMR (DMSO-d$_6$) δ (ppm): 7.10-6.98 (m, 3H), 6.86 (dd, J=2.0, 8.3 Hz, 1H), 6.80-6.66 (m, 2H), 4.06-3.97 (m, 2H), 3.72-3.66 (m, 2H), 3.64-3.52 (m, 4H), 3.48-3.39

(m, 2H), 3.23 (s, 3H), 3.02 (br s., 4H), 2.43 (t, J=7.1 Hz, 2H), 1.52-1.38 (m, 4H), 1.36-1.24 (m, 2H); MS (ESI): m/z: 419 [M+H]$^+$.

Step 3: Ethyl (E)-4-(4-{7-Chloro-2-[2-(2-methoxy-ethoxy)-ethoxy]-10,11-dihydro-5H-dibenzo[b,f]azepin-5-yl}-butylamino)-but-2-enoate 0.025 g (27%) of ethyl (E)-4-(4-{7-Chloro-2-[2-(2-methoxy-ethoxy)-ethoxy]-10,11-dihydro-5H-dibenzo[b,f]azepin-5-yl}-butylamino)-but-2-enoate were prepared according to the procedure described for Example 2, Step 1, starting from 0.064 g (0.153 mmol) of 4-{7-chloro-2-[2-(2-methoxy-ethoxy)-ethoxy]-10,11-dihydro-5H-dibenzo[b,f]azepin-5-yl}-butylamine and 0.023 g (0.168 mmol) of ethyl (E)-4-oxobut-2-enoate. $^1$H NMR (DMSO-d$_6$) δ (ppm): 7.07-6.97 (m, 3H), 6.90-6.68 (m, 4H), 5.90 (dt, J=1.7, 15.7 Hz, 1H), 4.09 (q, J=6.8 Hz, 2H), 4.04-3.98 (m, 2H), 3.72-3.66 (m, 2H), 3.61 (t, J=6.6 Hz, 2H), 3.56 (dd, J=3.7, 5.6 Hz, 2H), 3.44 (dd, J=3.7, 5.6 Hz, 2H), 3.25-3.18 (m, 5H), 3.02 (br. s., 4H), 2.38 (t, J=6.8 Hz, 2H), 1.50-1.30 (m, 4H), 1.19 (t, J=7.1 Hz, 3H); MS (ESI): m/z: 531 [M+H]$^+$.

Step 4: Ethyl (E)-4-(4-{7-Chloro-2-[2-(2-methoxy-ethoxy)-ethoxy]-10,11-dihydro-5H-dibenzo[b,f]azepin-5-yl}-butylamino)-but-2-enoate maleate 0.024 g (83%) of ethyl (E)-4-(4-{7-Chloro-2-[2-(2-methoxy-ethoxy)-ethoxy]-10,11-dihydro-5H-dibenzo[b,f]azepin-5-yl}-butylamino)-but-2-enoate maleate were prepared according to the procedure described for Example 2, Step 2, starting from 0.024 g (0.043 mmol) of ethyl (E)-4-(4-{7-Chloro-2-[2-(2-methoxy-ethoxy)-ethoxy]-10,11-dihydro-5H-dibenzo[b,f]azepin-5-yl}-butylamino)-but-2-enoate and 0.005 g (0.043 mmol) of maleic acid. $^1$H NMR (DMSO-d$_6$) δ (ppm): 8.52 (bs, 2H), 7.13-7.00 (m, 3H), 6.89 (dd, J=2.2, 8.1 Hz, 1H), 6.82-6.66 (m, 3H), 6.18 (d, J=15.7 Hz, 1H), 6.01 (s, 2H), 4.15 (q, J=7.3 Hz, 2H), 4.05-3.98 (m, 2H), 3.78-3.60 (m, 6H), 3.58-3.54 (m, 2H), 3.46-3.41 (m, 2H), 3.23 (s, 3H), 3.08-2.98 (m, 4H), 2.84 (t, J=7.6 Hz, 2H), 1.62-1.41 (m, 4H), 1.21 (t, J=7.1 Hz, 3H); MS (ESI): m/z: 531 [M+H]$^+$.

Example 99: 5-((3aS,4S,6aR)-2-Oxo-hexahydro-thieno[3,4-d]imidazol-4-yl)-(2-{2-[2-(2-{4-[2-(7-chloro-5-{4-[((E)-3-cyano-allyl)-methyl-amino]-butyl}-10,11-dihydro-5H-dibenzo[b,f]azepin-2-yloxy)-ethoxymethyl]-[1,2,3] triazol-1-yl}-ethoxy]-ethoxy}-ethyl)pentanamide

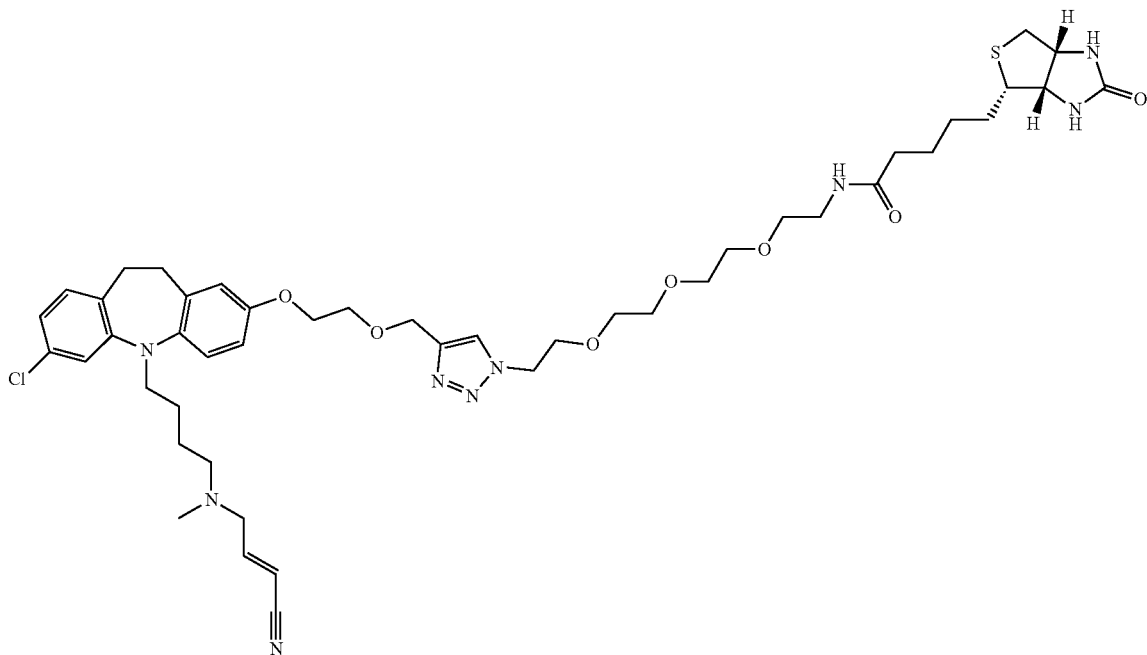 [SMILES: CN(C/C=C/C#N)CCCCN1c2ccc(OCCOCc3cn(CCOCCOCCOCCNC(=O)CCCC[C@@H]4SC[C@@H]5NC(=O)N[C@@H]54)nn3)cc2CCc2ccc(Cl)cc21]

0.020 g (0.042 mmol) of (E)-4-{4-[7-chloro-2-(2-prop-2-ynoxyethoxy)-10,11-dihydro-5H-dibenzo[b,f]zazepin-5-yl]butyl-methyl-amino}but-2-enenitrile (Example 90, step 1) and 0.019 g (0.044 mmol) of Biotin-PEG4-azide (BROAD-PHARM, Cat. No. BP-22119) were dissolved in THF/t-BuOH/H$_2$O (0.2:0.1:0.1 ml) followed by the addition of 0.829 g (0.004 mmol) of sodium ascorbate and 0.001 g (0.004 mmol) of copper sulphate pentahydrate and the reaction mixture was stirred at r.t. overnight. Then the mixture was diluted with water and extracted with EtOAc and the organic layer was dried (Na$_2$SO$_4$) and concentrated under vacuo. The crude was purified by flash chromatography (silica gel-NH$_2$, eluent: DCM/MeOH, 98:2) to afford 5-((3aS,4S,6aR)-2-Oxo-hexahydro-thieno[3,4-d]imidazol-4-yl)-(2-{2-[2-(2-{4-[2-(7-chloro-5-{4-[((E)-3-cyano-allyl)-methyl-amino]-butyl}-10,11-dihydro-5H-dibenzo[b,f]azepin-2-yloxy)-ethoxymethyl]-[1,2,3] triazol-1-yl}-ethoxy)-ethoxy]-ethoxy}-ethyl)pentanamide as white powder (0.020 g, 52%). $^1$H NMR (DMSO-d$_6$) δ (ppm): 8.06 (s, 1H) 7.80 (t, J=5.50 Hz, 1H) 6.99-7.09 (m, 3H) 6.83-6.90 (m, 1H) 6.81-6.69 (m, 3H) 6.40 (s, 1H) 6.34 (s, 1H) 5.76 (q, J=16.9 Hz, 1H) 4.57 (s, 2H) 4.50 (t, J=5.32 Hz, 2H) 4.23-4.33 (m, 1H) 4.08-4.16 (m, 1H) 4.06-4.01 (m, 2H) 3.80 (t, J=5.32 Hz, 2H) 3.76-3.72 (m, 2H) 3.62 (t, J=6.62 Hz, 2H) 3.42-3.53 (m, 8H) 3.36 (t, J=5.87 Hz, 2H) 3.16 (d, J=5.87 Hz, 2H) 3.11-2.94 (m, 7H) 2.77-2.83 (m, 1H) 2.60-2.53 (m, 1H) 2.15-2.33 (m, 2H) 2.14-2.00 (m, 5H) 1.65-1.15 (m, 10H)); MS (ESI): m/z: 922 [M+H]$^+$.

Example 100: Ethyl (E)-4-[4-(7-Chloro-2-prop-2-ynyloxy-10,11-dihydro-dibenzo[b,f]azepin-5-yl)-butylamino]-but-2-enoate maleate

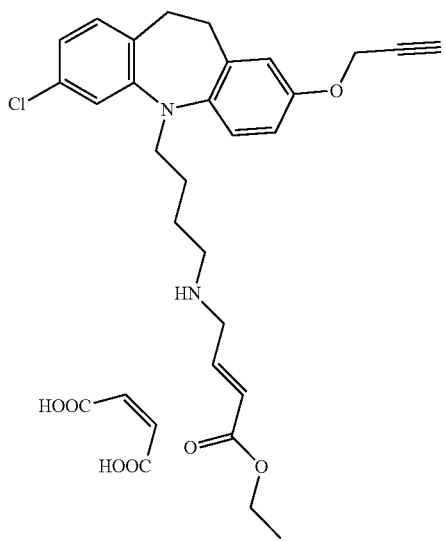

Step 1: 2-[4-(7-Chloro-2-prop-2-ynyloxy-10,11-dihydro-dibenzo[b,f]azepin-5-yl-butyl]-isoindole-1,3-dione 0.121 g (93%) of 2-[4-(7-chloro-2-prop-2-ynyloxy-10,11-dihydro-dibenzo[b,f]azepin-5-yl)-butyl]-isoindole-1,3-dione were prepared according to the procedure described for Example 97, Step 1, starting from 0.120 g (0.269 mmol) of 2-[4-(7-chloro-2-hydroxy-10,11-dihydro-dibenzo[b,f]azepin-5-yl)-butyl]-isoindole-1,3-dione (Example 67, Step 1) and 0.038 g (0.322 mmol) of propargyl bromide. $^1$H NMR (CDCl$_3$) δ (ppm): 7.84-7.78 (m, 2H), 7.74-7.68 (m, 2H), 6.98-6.88 (m, 3H), 6.76 (dd, J=2.0, 7.8 Hz, 1H), 6.72-6.66 (m, 2H), 4.59 (d, J=2.2 Hz, 2H), 3.72-3.59 (m, 4H), 3.13-3.03 (m, 4H), 2.51 (t, J=2.2 Hz, 1H), 1.78-1.68 (m, 2H), 1.66-1.54 (m, 2H); MS (ESI): m/z: 485 [M+H]$^+$.

Step 2: 4-[7-chloro-2-(prop-2-yn-1-yloxy)-10,11-dihydro-5H-dibenzo[b,f]azepin-5-yl]butan-1-amine 0.024 g (29%) of 4-[7-chloro-2-(prop-2-yn-1-yloxy)-10,11-dihydro-5H-dibenzo[b,f]azepin-5-yl]butan-1-amine were prepared according to the procedure described for Intermediate 9, Step 2, starting from 0.115 g (0.237 mmol) of 2-[4-(7-Chloro-2-prop-2-ynyloxy-10,11-dihydro-dibenzo[b,f]azepin-5-yl)-butyl]-isoindole-1,3-dione and 0.024 g (0.474 mmol) of hydrazine hydrate. $^1$H NMR (DMSO-d$_6$) δ (ppm): 7.10-7.02 (m, 3H), 6.88 (dd, J=2.0, 7.8 Hz, 1H), 6.81-6.74 (m, 2H), 4.72 (d, J=2.2 Hz, 2H), 3.61 (t, J=6.8 Hz, 2H), 3.53 (t, J=2.2 Hz, 1H), 3.02 (br. s., 4H), 2.45 (t, J=6.8 Hz, 2H), 1.50-1.26 (m, 4H); MS (ESI): m/z: 355 [M+H]$^+$.

Step 3: Ethyl (E)-4-[4-(7-chloro-2-prop-2-ynyloxy-10,11-dihydro-dibenzo[b,f]azepin-5-yl)-butylamino]-but-2-enoate 0.006 g (22%) of ethyl (E)-4-[4-(7-chloro-2-prop-2-ynyloxy-10,11-dihydro-dibenzo[b,f]azepin-5-yl)-butylamino]-but-2-enoate were prepared according to the procedure described for Example 2, Step 1, starting from 0.021 g (0.059 mmol) of 4-[7-chloro-2-(prop-2-yn-1-yloxy)-10,11-dihydro-5H-dibenzo[b,f]azepin-5-yl]butan-1-amine and 0.009 g (0.071 mmol) of ethyl (E)-4-oxobut-2-enoate. $^1$H NMR (DCM-d$_2$) δ (ppm): 7.06-6.98 (m, 3H), 6.94 (td, J=5.5, 15.9 Hz, 1H), 6.86 (dd, J=2.2, 8.1 Hz, 1H), 6.81-6.76 (m, 2H), 6.02-5.96 (m, 1H), 4.67 (d, J=2.4 Hz, 1H), 4.18 (q, J=7.2 Hz, 2H), 3.67 (t, J=6.1 Hz, 2H), 3.43 (dd, J=1.5, 5.9 Hz, 2H), 3.17-3.07 (m, 4H), 2.65 (t, J=6.6 Hz, 2H), 2.58 (t, J=2.4 Hz, 2H), 1.66-1.55 (m, 4H), 1.28 (t, J=7.2 Hz, 3H); MS (ESI): m/z: 467 [M+H]$^+$.

Step 4: Ethyl (E)-4-[4-(7-Chloro-2-prop-2-ynyloxy-10,11-dihydro-dibenzo[b,f]azepin-5-yl)-butylamino]-but-2-enoate maleate 0.005 g (73%) of methyl (E)-4-[4-(7-Chloro-2-prop-2-ynyloxy-10,11-dihydro-dibenzo[b,f]azepin-5-yl)-butylamino]-but-2-enoate maleate were prepared according to the procedure described for Example 2, Step 2, starting from 0.005 g (0.012 mmol) of Ethyl (E)-4-[4-(7-chloro-2-prop-2-ynyloxy-10,11-dihydro-dibenzo[b,f]azepin-5-yl)-butylamino]-but-2-enoate and 0.001 g (0.012 mmol) of maleic acid. $^1$H NMR (Methanol-d$_4$) δ (ppm): 7.12-7.06 (m, 2H), 7.02 (d, J=8.3 Hz, 1H), 6.88-6.78 (m, 4H), 6.26 (s, 2H), 6.22-6.17 (m, 1H), 4.67 (d, J=2.4 Hz, 2H), 4.22 (q, J=7.1 Hz, 2H), 3.79-3.72 (m, 4H), 3.34-3.30 (m, 1H), 3.17-3.06 (m, 4H), 3.00-2.95 (m, 2H), 2.92 (t, J=2.4 Hz, 1H), 1.78-1.61 (m, 4H), 1.29 (t, J=7.1 Hz, 3H) MS (ESI): m/z: 467 [M+H]$^+$.

Example 101: Ethyl (E)-4-[4-(2-benzyloxy-7-chloro-10,11-dihydro-dibenzo[b,f]azepin-5-yl)-butylamino]-but-2-enoate maleate

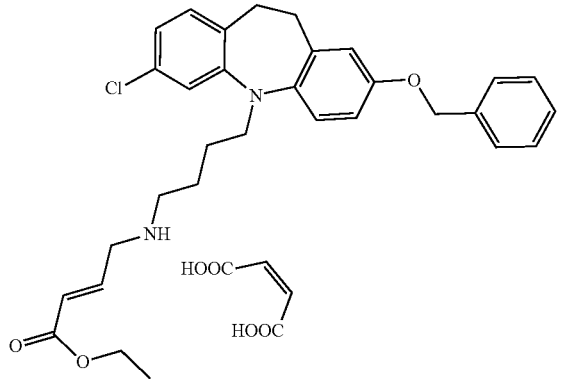 [SMILES: CCOC(=O)/C=C/CNCCCCN1c2ccc(OCc3ccccc3)cc2CCc2ccc(Cl)cc21 ; O=C(O)/C=C\C(=O)O]

Step 1: 2-[4-(2-Benzyloxy-7-chloro-10,11-dihydro-dibenzo[b,f]azepin-5-yl)-butyl]-isoindole-1,3-dione 0.120 g (83%) of 2-[4-(2-benzyloxy-7-chloro-10,11-dihydro-dibenzo[b,f]azepin-5-yl)-butyl]-isoindole-1,3-dione were prepared according to the procedure described for Example 97, Step 1, starting from 0.120 g (0.269 mmol) of 2-[4-(7-chloro-2-hydroxy-10,11-dihydro-dibenzo[b,f]azepin-5-yl)-butyl]-isoindole-1,3-dione (Example 67, Step 1) and 0.048 g (0.282 mmol) of benzyl bromide. $^1$H NMR (CDCl$_3$) δ (ppm): 7.84-7.77 (m, 2H), 7.72-7.66 (m, 2H), 7.44-7.36 (m, 4H), 7.35-7.30 (m, 1H), 6.98-6.93 (m, 2H), 6.91 (d, J=8.3 Hz, 1H), 6.75 (dd, J=2.2, 8.1 Hz, 1H), 6.72-6.67 (m, 2H), 4.96 (s, 2H), 3.72-3.60 (m, 4H), 3.12-3.02 (m, 4H), 1.78-1.69 (m, 2H), 1.65-1.57 (m, 2H) MS (ESI): m/z: 537 [M+H]$^+$.

Step 2: 4-(2-Benzyloxy-7-chloro-10,11-dihydro-dibenzo[b,f]azepin-5-yl)-butylamine 0.073 g (85%) of 4-(2-benzyloxy-7-chloro-10,11-dihydro-dibenzo[b,f]azepin-5-yl)-butylamine were prepared according to the procedure described for Intermediate 9, Step 2, starting from 0.113 g (0.210 mmol) of 2-[4-(2-benzyloxy-7-chloro-10,11-dihydro-dibenzo[b,f]azepin-5-yl)-butyl]-isoindole-1,3-dione and 0.021 g (0.421 mmol) of hydrazine hydrate. $^1$H NMR (CDCl$_3$) δ (ppm): 7.45-7.36 (m, 2H), 7.35-7.30 (m, 1H), 7.03-6.94 (m, 1H), 6.83 (dd, J=2.2, 8.1 Hz, 1H), 6.80-6.74 (m, 1H), 5.02 (s, 2H), 3.69-3.63 (m, 2H), 3.14-3.06 (m, 4H), 2.66 (t, J=6.8 Hz, 2H), 1.64-1.53 (m, 2H), 1.52-1.40 (m, 2H) MS (ESI): m/z: 407 [M+H]$^+$.

Step 3: Ethyl (E)-4-[4-(2-benzyloxy-7-chloro-10,11-dihydro-dibenzo[b,f]azepin-5-yl)-butylamino]-but-2-enoate 0.022 g (25%) of ethyl (E)-4-[4-(2-benzyloxy-7-chloro-10,11-dihydro-dibenzo[b,f]azepin-5-yl)-butylamino]-but-2-enoate were prepared according to the procedure described for Example 2, Step 1, starting from 0.070 g (0.172 mmol) of 4-(2-benzyloxy-7-chloro-10,11-dihydro-dibenzo[b,f]azepin-5-yl)-butylamine and 0.022 g (0.172 mmol) of ethyl (E)-4-oxobut-2-enoate. $^1$H NMR (DMSO-d$_6$) δ (ppm): 7.45-7.35 (m, 4H), 7.33-7.29 (m, 1H), 7.08-7.01 (m, 3H), 6.89-6.77 (m, 4H), 5.91 (d, J=15.7 Hz, 1H), 5.03 (s, 2H), 4.09 (q, J=7.3 Hz, 2H), 3.61 (t, J=6.6 Hz, 2H), 3.22 (d, J=3.9 Hz, 2H), 3.07-2.97 (m, 4H), 2.39 (t, J=6.8 Hz, 2H), 1.49-1.31 (m, 4H), 1.19 (t, J=7.1 Hz, 3H) MS (ESI): m/z: 520 [M+H]$^+$.

Step 4: Ethyl (E)-4-[4-(2-benzyloxy-7-chloro-10,11-dihydro-dibenzo[b,f]azepin-5-yl)-butylamino]-but-2-enoate maleate 0.013 g (71%) of ethyl (E)-4-[4-(2-benzyloxy-7-chloro-10,11-dihydro-dibenzo[b,f]azepin-5-yl)-butylamino]-but-2-enoate maleate were prepared according to the procedure described for Example 2, Step 2, starting from 0.015 g (0.029 mmol) of ethyl (E)-4-[4-(2-benzyloxy-7-chloro-10,11-dihydro-dibenzo[b,f]azepin-5-yl)-butylamino]-but-2-enoate and 0.003 g (0.029 mmol) of maleic acid. $^1$H NMR (DMSO-d$_6$) δ (ppm): 8.51 (br. s., 2H), 7.44-7.40 (m, 2H), 7.40-7.36 (m, 2H), 7.34-7.29 (m, 1H), 7.09-7.05 (m, 3H), 6.89 (dd, J=2.0, 8.3 Hz, 1H), 6.87 (d, J=3.4 Hz, 1H), 6.81 (dd, J=3.2, 8.6 Hz, 1H), 6.79-6.73 (m, 1H), 6.18 (d, J=15.7 Hz, 1H), 6.01 (s, 2H), 5.03 (s, 2H), 4.15 (q, J=7.2 Hz, 2H), 3.73 (d, J=5.9 Hz, 2H), 3.65 (t, J=6.6 Hz, 2H), 3.08-2.97 (m, 4H), 2.88-2.81 (m, 2H), 1.62-1.42 (m, 4H), 1.21 (t, J=7.1 Hz, 3H); MS (ESI): m/z: 520 [M+H]$^+$.

Example 102: 2-methoxy-ethyl (E)-4-[4-(3-chloro-10,11-dihydro-dibenzo[b,f]azepin-5-yl)-butylamino]-but-2-enoate maleate

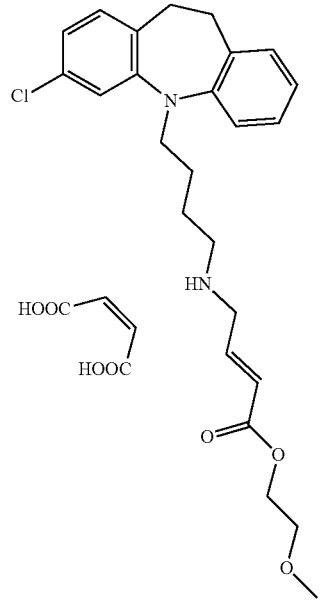 [SMILES: COCCOC(=O)/C=C/CNCCCCN1c2ccccc2CCc2ccc(Cl)cc21 ; O=C(O)/C=C\C(=O)O]

Step 1: 2-Methoxy-ethyl (E)-4-{tert-butoxycarbonyl-[4-(3-chloro-10,11-dihydro-dibenzo[b,f]azepin-5-yl)-butyl]-amino}-but-2-enoate 0.070 g (0.144 mmol) of (E)-4-{tert-butoxycarbonyl-[4-(3-chloro-10,11-dihydro-5H-dibenzo[b,f]azepin-5-yl)butyl]amino}but-2-enoic acid (Example 17, step 2) was dissolved in DCM (2.5 mL) followed by the addition of 0.056 g (0.433 mmol) of DIEA and 0.042 g (0.159 mmol) of tetramethyl-fluoroformamidinium hexafluorophosphate and the reaction mixture was stirred 1.5 h at r.t. 0.033 g (0.433 mmol) of 2-methoxyethanol were then added and the mixture was refluxed 2 h. The mixture was evaporated to dryness and the crude was purified by flash chromatography (silica gel, eluent: n-hex/AcOEt), to afford 2-methoxy-ethyl (E)-4-{tert-butoxycarbonyl-[4-(3-chloro-10,11-dihydro-dibenzo[b,f]azepin-5-yl)-butyl]-amino}-but-2-enoate as colorless oil (0.014 g, 18%). $^1$H NMR (CDCl$_3$) δ (ppm): 7.20-6.75 (m, 8H), 5.93-5.79 (m, 1H), 4.34-4.25 (m, 2H), 3.99-3.78 (m, 2H), 3.75-3.58 (m, 4H), 3.46-3.33 (m, 3H), 3.21-2.99 (m, 6H), 1.65-1.47 (m, 4H), 1.38 (br. s., 9H); MS (ESI): m/z: 544 [M+H]$^+$.

Step 2: 2-methoxy-ethyl (E)-4-[4-(3-chloro-10,11-dihydro-dibenzo[b,f]azepin-5-yl)-butylamino]-but-2-enoate 0.010 g (59%) of 2-methoxy-ethyl (E)-4-[4-(3-chloro-10,11-dihydro-dibenzo[b,f]azepin-5-yl)-butylamino]-but-2-enoate were prepared according to the procedure described for Example 91, Step 3, starting from 0.021 g (0.039 mmol) of 2-methoxy-ethyl (E)-4-{tert-butoxycarbonyl-[4-(3-chloro-10,11-dihydro-dibenzo[b,f]azepin-5-yl)-butyl]-amino}-but-2-enoate and 0.015 ml (0.193 mmol) of TFA. $^1$H NMR (DCM-d2) δ (ppm): 7.23-6.83 (m, 8H), 5.98 (d, J=16.1 Hz, 1H), 4.28-4.23 (m, 2H), 3.72 (t, J=6.6 Hz, 2H), 3.63-3.58 (m, 2H), 3.40-3.33 (m, 5H), 3.20-3.08 (m, 4H), 2.58 (t, J=7.1 Hz, 2H), 1.67-1.48 (m, 4H); MS (ESI): m/z: 443 [M+H]$^+$.

Step 3: 2-methoxy-ethyl (E)-4-[4-(3-chloro-10,11-dihydro-dibenzo[b,f]azepin-5-yl)-butylamino]-but-2-enoate maleate 0.010 g (79%) of 2-methoxy-ethyl (E)-4-[4-(3-chloro-10,11-dihydro-dibenzo[b,f]azepin-5-yl)-butylamino]-but-2-enoate maleate were prepared according to the procedure described for Example 2, Step 2, starting from 0.010 (0.023 mmol) of 2-methoxy-ethyl (E)-4-[4-(3-chloro-10,11-dihydro-dibenzo[b,f]azepin-5-yl)-butylamino]-but-2-enoate and 0.003 g (0.023 mmol) of maleic acid. $^1$H NMR (DMSO-d$_6$) δ (ppm): 8.60 (br. s., 2H), 7.19-7.08 (m, 5H), 7.00-6.92 (m, 2H), 6.79 (td, J=6.4, 15.7 Hz, 1H), 6.21 (d, J=15.7 Hz, 1H), 6.02 (s, 2H), 4.25-4.21 (m, 2H), 3.77-3.68 (m, 4H), 3.56-3.52 (m, 2H), 3.25 (s, 3H), 3.11-3.02 (m, 4H), 2.85 (t, J=7.3 Hz, 2H), 1.67-1.43 (m, 4H)); MS (ESI): m/z: 443 [M+H]$^+$.

2. BIOLOGICAL AND STRUCTURAL CHARACTERIZATION OF THE COMPOUNDS

The following is a description of biological and structural characterization of the compounds herein below, which provides experimental data supporting the invention and means of performing the invention, as non-limiting examples.

2.1. NEDD4 Inhibition

The NEDD4 inhibitors according to the invention are capable of inhibiting or decreasing the functional activity of the ligase. In the present study, two different in vitro ubiquitination assays have been conducted, one to quantitatively determine the potency of the different exemplary compounds (TR-FRET assay) and another one to determine their selectivity (western blot assay).

In Vitro Ubiquitination Assay TR-FRET Based

In order to quantitatively measure the self-ubiquitination process of the E3 HECT ligase NEDD4 the inventors employed a TR-FRET based assay. TR-FRET technology exploits the long-lasting emission of lanthanide fluorescence to interpose a short time-delay between FRET donor excitation and emission. This phenomenon enables to isolate real fluorescent signals from short-lived background emissions, thus reducing possible interference from compounds.

In the present study, elongation of the ubiquitin chain by NEDD4 is measured by adding bacterially expressed E1, His-tagged UBE2D3 (E2) and untagged HECT of NEDD4 wild-type (WT) (E3 ligase) (named in FIG. 1 as WT) enzymes to a mixture of Eu-cryptate ubiquitin, Cy5-ubiquitin and wild-type ubiquitin, combined in a ratio optimized for TR-FRET based conjugation (100×TRF-Ubiquitin Mix, SBB-TR0051). As a negative control, a catalytically inactive (Cys867/Ala) HECT NEDD4 mutant named in FIG. 1 as C/A is used. Bacterially expressed E1, His-tagged UBE2D3 (E2), untagged HECT NEDD4 (E3 ligase) WT and NEDD4 C/A enzymes were produced and purified as reported in E. Maspero et al. Methods Mol Biol. 1449:153-60 (2016).

Enzymatic incorporation of the labeled TRF-Ubiquitin mix into chains leads to an increase in fluorescence emission at 665 nm (emission of the acceptor Cy5-Ubiquitin, Emacceptor) and decrease at emission wavelength 620 nm (emission of the donor Eu-cryptate Ubiquitin, Emdonor).

The assay was performed in a 384-well plate format (Optiplate, Perkin Elmer, #6007290) on an automated liquid-handler (Hamilton STAR, Hamilton Robotics, Switzerland).

All compounds were dissolved in 100% DMSO and serially diluted in 96-well plates (from 100 μM to 0.005 μM).

Briefly, all reagents were thawed and kept on ice. A master mix containing E1, E2, E3 and TRF-Ubiquitin Mix (SBB-TR0051) diluted in the assay buffer (Tris-HCl pH 7.6 25 mM, NaCl 100 mM, MgCl$_2$ 5 mM and Tween 0.01%) is prepared and 50 μl/well is dispensed in a 384 well plate. 3 μl of compounds dissolved in DMSO in the above-indicated concentration range were added and pre-incubated for 1 hour. Final E1, E2 and E3 concentrations in the assay buffer (Tris-HCl pH 7.6 25 mM, NaCl 100 mM, MgCl$_2$ 5 mM and Tween 0.01%) were 30, 350 and 50 nanomolars, respectively. The reaction was initiated with the addition of ATP (22 μl of 2 mM ATP, JenaBioscience, NU-1010) and was allowed to proceed for 120 minutes, measuring fluorescence emission at 665 nm and 620 nm in real-time on an EnSpire microplate reader (Perkin Elmer).

Kinetic raw data were analyzed by Area Under the Curve (AUC) method using Prism GraphPad software.

% signal/background corresponds to the following equation:

(Experimental signal−Background signal)/Background signal×100%

Experimental signal corresponds to the signal obtained by the enzymatic reaction in presence of the vehicle (DMSO) and/or the different compound concentrations. Background signal corresponds to the signal obtained by the enzymatic reaction in absence of ATP.

The relative potency of the compounds was evaluated by dose-response curves following the enzymatic reaction of HECT NEDD4 WT in real time for 120 minutes.

Percentage of inhibition is then determined by the equation:

% inhibition=100×[1−(X)/(MAX)], where MAX correspond to AUC of the vehicle (DMSO) treated enzyme, and X corresponds to the AUC of the compound treated enzyme.

Example of the performed assay with compound 12 is reported in FIG. 1. As reported in FIG. 1, a dose dependent inhibition of enzymatic activity is determined by compound 12. The concentrations of compound 12 used are indicated in the figure. The catalytic inactive mutant (C/A) validates the assay showing almost no TR-FRET signal (considered as background level).

Compounds 16-21, 25, 31, 33, 55 and 101 exhibit percentages of inhibition lower than 30% at 11 µM, compounds 1, 3, 11, 23, 52 and 66 exhibit percentages of inhibition between 30% and 50% at 11 µM, and compounds 2, 4-6, 7-10, 12-15, 22, 24, 26-30, 32, 34-51, 53-54, 56-65, 67-83, 85-100 and 102 exhibit percentages of inhibition higher than 50% at 11 µM.

2.2 Determination of the Structure of NEDD4 HECT in Complex with Compound 12

The inventors obtained by X-Ray the crystal structure of the HECT domain of NEDD4 in complex with compound 12.

For crystallization studies, the cleaved HECT of NEDD4, produced as previously described (E. Maspero et al. EMBO Rep. 12(4):342-9 (2011)), was concentrated in Vivaspin concentrators (MW cut-off 30 kDa, Sartorius Stedim Biotech) and loaded onto a Superdex 200 size exclusion chromatography column (GE Healthcare) equilibrated with size exclusion buffer (20 mM Tris-HCl, pH 8.0, 200 mM NaCl, 1 mM EDTA, 1 mM DTT, 5% glycerol). The protein was eluted within the above indicated buffer in a clear, well isolated, peak according to its size and shape. Purity of the peak can be assayed by SDS-PAGE gel. The desired fractions were collected, pooled, and concentrated as needed using Vivaspin tubes.

Crystals of NEDD4 HECT were grown in hanging drops in 24 wells with the vapour diffusion technique. Drops were set up mixing 1 µl of protein solution in size exclusion buffer at ca. 10 mg/ml with 1 µl of reservoir solution containing 100 mM MES pH 6.0, 6-10% PEG 400, 90 mM $MgCl_2$, 5 mM TCEP. Nicely diffracting crystals were obtained by microseeding the drops after an overnight equilibration. Crystals of the complexes were obtained soaking the HECT crystals with the compounds, adding to the crystal drops 1-2 µl of a cryoprotectant solution containing 100 mM MES pH 6.0, 8-10% PEG 400, 20% glycerol, 1-4 mM compound 12 (0.25-1% DMSO). Crystals were harvested and cryo-cooled in liquid nitrogen after few hours or overnight soak and used to determine the three dimensional structure of the inhibitor-bound NEDD4 HECT domain as described in E. Maspero et al. EMBO Rep. 12(4):342-9 (2011). HECT NEDD4 N-lobe and C-lobe models, from pdb entry 2xbf (version 1.2, 13 Jul. 2011), independently, were used as search models for molecular replacement. As shown in FIG. 2, compound 12 binds to the N-lobe of the NEDD4 HECT domain by burying its dibenzazepine and the Cl moiety into a hydrophobic pocket shaped by Leu553, Tyr557, Met600, Tyr605, Leu607, Tyr634, Phe637 and Ile638 and flanked by polar residues Glu554 and Asn628. Furthermore, the α,β-unsaturated ester of compound 12 is attacked by the thiol group of Cys627 generating a covalent link to the protein.

The overall conformation of NEDD4 HECT in complex with compound 12 is virtually identical to the previously reported apo structure of NEDD4 (pdb entry 2xbf, version 1.2, 13 Jul. 2011, E. Maspero et al. EMBO Rep. 12:342-9 (2011)) with few exceptions in the pocket region. As shown in FIG. 3, major rearrangements occur at the level of the side chains of Tyr634 and Glu554, which move in order to accommodate the dibenzazepine moiety, and of the main and side chain of Cys627, to which the compound is covalently bound. Moreover, Asn628 side chain is tilted: rather than pointing towards Tyr634, which is displaced, it forms a hydrogen bond with the amino group present in the side chain of compound 12.

2.3. Compounds Selectivity

In Vitro Ubiquitination Assay Detected by Western Blot

An in vitro ubiquitination assay followed by western blot detection was used to determine the selectivity of the different compounds. The full protocol is described in (E. Maspero et al. Methods Mol Biol. 1449:153-60 (2016)). Briefly, the assay was performed with bacterially purified enzymes (20 nM E1, 250 nM of purified His6-tagged UBE2D3 and 250 nM untagged HECT of NEDD4 WT or NEDD4 L553F or NEDD4L WT) and 1 µM of untagged ubiquitin in ubiquitination buffer (25 mM Tris-HCl, pH 7.6, 5 mM $MgCl_2$, 100 mM NaCl, 0.2 µM DTT). Compounds dissolved in DMSO were added at the final concentration of 10 µM (final DMSO concentration 2%) and pre-incubated for 1 hour at room temperature. Reactions were started by addition of ATP (2 mM final concentration), incubated at 25° C. for 30 or 60 minutes and stopped by addition of 2× Laemmli sample buffer (4% SDS, 125 mM Tris pH 6.8, 20% glycerol, 0.002% saturated bromophenol blue, 200 mM DTT). Bacterially expressed E1, His-tagged UBE2D3 (E2), untagged HECT of NEDD4 (E3 ligase) WT or L553F or NEDD4LWT enzymes and untagged Ub WT were produced and purified as reported in E. Maspero et al. Methods Mol Biol. 1449:153-60 (2016). Detection was performed by immunoblotting using anti-Ub antibody (P4D1, Santa Cruz, sc8017). NEDD4 inhibitors described in the invention are capable of inhibiting NEDD4 but not NEDD4L as visible in FIG. 4a where the indicated compounds at 10 µM concentration were tested on the HECT domain of NEDD4 WT and NEDD4L WT. Anti-ubiquitin immunoblot clearly indicates the ability of the reported compounds to almost completely abolish the activity of HECT NEDD4 WT respect the vehicle-treated sample (indicated as –). Differently and importantly, the compounds were unable to inhibit the HECT of NEDD4L WT. This selective inhibition depends on the exquisite binding specificity of the compounds. The binding pocket determined by X-ray is highly conserved among the various members of the NEDD4 family with few important exceptions. In particular, Leu553 of NEDD4 corresponds to a sterically bulkier phenylalanine residue, Phe608 in NEDD4L that is predicted to impede the binding of NEDD4 inhibitors (FIG. 4b).

To demonstrate the importance of this residue for compound specificity, the inventors generated the NEDD4 mutant L553F, introducing the phenylalanine residue in the context of NEDD4 protein and tested its activity with compound 12. As shown in FIG. 4c, this single point mutation is sufficient to fully abrogate the activity of compound 12.

In Vitro Ubiquitination Assay TR-FRET Based

To determine the selectivity of identified NEDD4 inhibitors, it was quantitatively measured the self-ubiquitination process of the E3 HECT ligase belonging to NEDD4 family such as NEDD4L, HECW2 and ITCH in presence or not of some compounds such as 5, 9, 12, 29, 42, 45, 56, 58, 61, 77, 78, 85 and 94 employing TR-FRET based assays.

NEDD4L

The assay was performed as described above in the paragraph titled "In vitro ubiquitination assay TR-FRET based" under the heading "2.1. NEDD4 UBIQUITINATION ASSAYS" using untagged HECT of NEDD4L (E3 ligase) instead of untagged HECT of NEDD4 wild-type (WT) (E3 ligase). In this case, final E1, E2 and E3 concentrations in the assay buffer (Tris-HCl pH 7.6 25 mM, NaCl 100 mM, MgCl$_2$ 5 mM and Tween 0.01%) were 30, 350 and 31.3 nanomolars, respectively. Untagged HECT NEDD4L (E3 ligase) enzyme was produced and purified as reported in E. Maspero et al. Methods Mol Biol. 1449:153-60 (2016) and in E. Maspero et al. EMBO Reports 12:342-349(2011).

HECW2

The assay was performed as described above in the paragraph titled "In vitro ubiquitination assay TR-FRET based" under the heading "2.1. NEDD4 UBIQUITINATION ASSAYS" using His-MPB tagged HECT of HECW2 (E3 ligase) instead of untagged HECT of NEDD4 wild-type (WT) (E3 ligase). In this case, final E1, E2 and E3 concentrations in the assay buffer (Tris-HCl pH 7.6 25 mM, NaCl 100 mM, MgCl$_2$ 5 mM and Tween 0.01%) were 30, 350 and 62.5 nanomolars, respectively. His-MPB tagged HECT of HECW2 (E3 ligase) enzyme was produced and purified as reported in E. Maspero et al. Methods Mol Biol. 1449:153-60 (2016) and in E. Maspero et al. EMBO Reports 12:342-349(2011).

ITCH

The assay was performed as described above in the paragraph titled "In vitro ubiquitination assay TR-FRET based" under the heading "2.1. NEDD4 UBIQUITINATION ASSAYS" using untagged HECT of ITCH (E3 ligase) instead of untagged HECT of NEDD4 wild-type (WT) (E3 ligase). In this case, final E1, E2 and E3 concentrations in the assay buffer (Tris-HCl pH 7.6 25 mM, NaCl 100 mM, MgCl$_2$ 5 mM and Tween 0.01%) were 30, 350 and 60 nanomolars, respectively. Untagged HECT of ITCH (E3 ligase) enzyme was produced and purified as reported in E. Maspero et al. Methods Mol Biol. 1449:153-60 (2016) and in E. Maspero et al. EMBO Reports 12:342-349(2011).

Regarding NEDD4L, compounds 9, 58, 61, 78 and 85, exhibit a percentage of inhibition lower than 5% at 11 µM, compounds 5, 42, 94, 77 and 12 exhibit a percentage of inhibition lower than 15% at 11 µM, compounds 29, 56 and 45 exhibit a percentage of inhibition lower or equal to 20% at 11 µM.

Regarding HECW2, compounds 9, 58, 85, 61, 78 and 12 exhibit a percentage of inhibition lower than 5% at 11 µM, compounds 5, 29, 42, 56, 94 and 77 exhibit a percentage of inhibition lower than 15% at 11 µM, compound 45 exhibits a percentage of inhibition lower to 20% at 11 µM.

Regarding ITCH, compounds 12, 29, 61, 77 and 45 exhibit a percentage of inhibition lower than 5% at 11 µM, compounds 5, 42, 56, 58 and 94 exhibit a percentage of inhibition lower than 15% at 11 µM, compounds 78 and 9 exhibit a percentage of inhibition lower to 20% at 11 µM, compound 85 exhibits a percentage of inhibition lower than 25% at 11 µM.

Overall the data obtained on the enzymes belonging to NEDD4 family such as NEDD4L, ITCH and HECW2, revealed that the compounds have a good selectivity profile and particularly the compounds showed a clear and strong preferential inhibitory activity versus NEDD4 respect ITCH, NEDD4L and HECW2.

2.4. Cell Growth

CellTiter-Glo® Luminescent Cell Viability Assay (Promega, Catalog number: G7571) is a homogeneous method of determining the number of viable cells in culture based on quantitation of the present ATP, which indicates the presence of metabolically active cells. The homogeneous assay procedure involves addition of a single reagent (CellTiter-Glo® Reagent) directly to the cells, which leads to cell lysis and generation of a luminescent signal proportional to the amount of the ATP and the number of cells present in culture. The assay relies on the properties of a proprietary thermostable luciferase (Ultra-Glo® recombinant luciferase), which generates a luminescent signal.

DU145 cells (obtained from CLS Cell Lines Service GmbH item 300168) were grown in DMEM (Sigma Aldrich catalog number D6171-500 ml) supplemented with 10% Fetal Bovine Serum (Euroclone, catalog number. ECS0180L), 2 mM L-Glutamine (Euroclone catalog number LOBE17605F) and 100 U/ml penicillin-0.1 µg/ml streptomycin (EuroClone, ECB3001L). LNCaP cells (obtained from CLS Cell Lines Service GmbH item 300265) were grown in RPMI1640 (Lonza catalog number BE12-167F) supplemented with 10% Fetal Bovine Serum (Euroclone, catalog number. ECS0180L), 2 mM L-Glutamine (Euroclone catalog number LOBE17605F) and 100 U/ml penicillin-0.1 µg/ml streptomycin (EuroClone, ECB3001 L).

To determine the antiproliferative activity of the compounds, 3000 DU145 cells and 5000 LNCap cells were seeded in 96 multiwell plate (Sigma catalog number CLS9102) per well. 24 hours after seeding, the cells were incubated for 48 hours with different concentrations of the inhibitors (from 50 to 0 µM with a 3-fold dilution) dissolved in DMSO. After 48 hours, a volume of CellTiter-Glo® Reagent equal to the volume of cell culture medium was added. The content was mixed for 2 min to induce cell lysis. The luminescence was measured and recorded with Tecan Infinite 200 multimode plate reader after further 10 min at room temperature in order to obtain a stable luminescent signal.

The IC$_{50}$ was calculated using GraphPad Software from the recorded luminescent signal. The obtained results are reported in Table 1:

TABLE 1

Antiproliferative activity of compounds 5,12,42,45 and 85 on human cancer cells DU145 and LNCaP

| Example Cpds | DU145[a] IC$_{50}$ µM | LNCaP[a] IC$_{50}$ µM |
|---|---|---|
| 5 | 7.68 | 10.91 |
| 12 | 6.81 | 6.67 |
| 42 | 9.18 | 6.49 |
| 45 | 4.97 | 5.69 |
| 85 | 11.26 | 16.27 |

[a]Data are expressed as the mean of at least two determinations.

As reported in Table 1, the compounds resulted to have an evident antiproliferative activity on cancer cells.

The invention claimed is:

1. A compound of general formula (I):

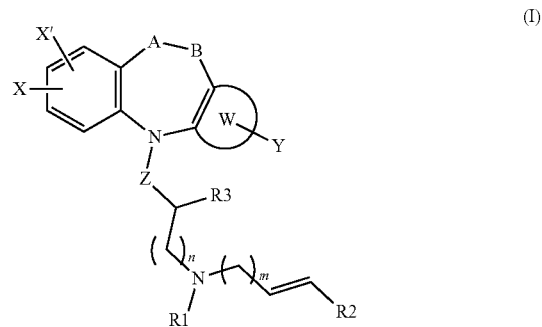

wherein:

Z is CH₂ or CO;

R1 is hydrogen or $C_1$-$C_6$ alkyl;

R2 is COOR4, CO—R5, CN or CONR6R7;

R3 is H or OH;

n is an integer from 1 to 3;

m is 1 or 2;

W is aryl or heteroaryl;

A-B is CH₂—CH₂, O—CH₂, CH₂—O, NR8-CO or CO—NR8;

X, X', Y are each independently selected from the group consisting of: hydrogen, $C_1$-$C_6$ alkyl, OH, NH₂, $C_1$-$C_6$-alkoxy, $C_1$-$C_6$-alkylamino, $C_1$-$C_6$-dialkylamino, CONR6R7, halogen, CF₃, NO₂ and CN, said $C_1$-$C_6$ alkyl or $C_1$-$C_6$ alkoxy being optionally substituted with a substituent selected from the group consisting of: R9, OH, NH₂, $C_1$-$C_6$-alkoxy, ($C_1$-$C_6$-alkoxy)$C_1$-$C_6$-alkoxy, $C_2$-$C_6$-alkynyloxy, $C_2$-$C_6$-alkynyl, $C_1$-$C_6$-alkylamino, $C_1$-$C_6$-dialkylamino, aryl and heteroaryl;

R4 is hydrogen or $C_1$-$C_6$ alkyl, said $C_1$-$C_6$ alkyl being optionally substituted with a substituent selected from the group consisting of: R9, $C_2$-$C_6$-alkynyl, $C_1$-$C_6$-alkoxy, $C_2$-$C_6$-alkynyloxy and ($C_1$-$C_6$-alkoxy)$C_1$-$C_6$-alkoxy;

R5 is $C_{3-6}$ cycloalkyl, $C_1$-$C_6$ alkyl, aryl, heteroaryl, said $C_1$-$C_6$ alkyl being optionally substituted by aryl or heteroaryl;

R6, R7 are each independently selected from the group consisting of: hydrogen, aryl, $C_1$-$C_6$ alkyl, $C_1$-$C_6$-alkoxy, O-aryl and O-heterocycloalkyl, said $C_1$-$C_6$ alkyl, $C_1$-$C_6$-alkoxy, O-aryl or O-heterocycloalkyl being optionally substituted with a substituent selected from the group consisting of: OH, NH₂, $C_1$-$C_6$-alkoxy, $C_1$-$C_6$-alkylamino, $C_1$-$C_6$-dialkylamino, aryl, heteroaryl and $C_2$-$C_6$-alkynyl;

R8 is hydrogen or $C_1$-$C_6$ alkyl, said $C_1$-$C_6$ alkyl being optionally substituted with a substituent selected from the group consisting of: OH, NH₂, $C_1$-$C_6$-alkoxy, $C_1$-$C_6$-alkylamino, $C_1$-$C_6$-dialkylamino, aryl, heteroaryl, ($C_1$-$C_6$-alkoxy)$C_1$-$C_6$-alkoxy, [($C_1$-$C_6$-alkoxy)$C_1$-$C_6$-alkoxy]$C_1$-$C_6$-alkoxy and $C_2$-$C_6$-alkynyloxy;

R9 is k or k is an integer from 1 to 10;

or a stereoisomer, solvate, tautomer or pharmaceutically acceptable salt thereof.

2. The compound or stereoisomer, solvate, tautomer or pharmaceutically acceptable salt thereof according to claim 1, wherein:

X, X', Y are each independently hydrogen, $C_1$-$C_6$ alkyl, OH, NH₂, $C_1$-$C_6$-alkoxy, $C_1$-$C_6$-alkylamino, $C_1$-$C_6$-dialkylamino, CONR6R7, halogen, CF₃, NO₂ or CN;

R4 is hydrogen or $C_1$-$C_6$ alkyl;

R5 is $C_{3-6}$ cycloalkyl, $C_1$-$C_6$ alkyl, aryl or heteroaryl, said $C_1$-$C_6$ alkyl being optionally substituted by aryl or heteroaryl;

R6, R7 are each independently hydrogen, aryl, $C_1$-$C_6$ alkyl or O—$C_1$-$C_6$ alkyl, said $C_1$-$C_6$ alkyl or O—$C_1$-$C_6$ alkyl being optionally substituted with a substituent selected from the group consisting of: OH, NH₂, $C_1$-$C_6$-alkoxy, $C_1$-$C_6$-alkylamino, $C_1$-$C_6$-dialkylamino, aryl and heteroaryl, with the proviso that when R6 is O—$C_1$-$C_6$ alkyl, R7 is $C_1$-$C_6$ alkyl; and R8 is hydrogen or $C_1$-$C_6$ alkyl, said $C_1$-$C_6$ alkyl being optionally substituted with a substituent selected from the group consisting of: OH, NH₂, $C_1$-$C_6$-alkoxy, $C_1$-$C_6$-alkylamino, $C_1$-$C_6$-dialkylamino, aryl and heteroaryl.

3. The compound or stereoisomer, solvate, tautomer or pharmaceutically acceptable salt thereof according to claim 1, wherein when R3 is OH, n is 1.

4. The compound or stereoisomer, solvate, tautomer or pharmaceutically acceptable salt thereof according to claim 1, wherein:

R1 is hydrogen or $C_1$-$C_3$ alkyl;

X, X', Y are each independently hydrogen, OH, halogen, CF₃ or NO₂;

R4 is hydrogen or $C_1$-$C_3$ alkyl;

R5 is cyclopropyl, phenyl or $C_1$-$C_3$ alkyl optionally substituted by aryl or heteroaryl;

R6, R7 are each independently hydrogen, phenyl, $C_1$-$C_3$ alkyl or O—$C_1$-$C_3$ alkyl; and R8 is hydrogen or $C_1$-$C_3$ alkyl optionally substituted with OH, NH₂ or aryl;

or wherein:

R1 is hydrogen or $C_1$-$C_3$ alkyl;

R2 is COOR4 or CONR6R7;

A-B is CH₂—CH₂ or CO—NR8;

X, X', Y are each independently halogen, hydrogen, OH, $CF_3$ or $NO_2$;
R4 is hydrogen or $C_1$-$C_3$ alkyl;
R6, R7 are each independently hydrogen, phenyl, $C_1$-$C_3$ alkyl or O—$C_1$-$C_3$ alkyl; and
R8 is hydrogen or $C_1$-$C_3$ alkyl optionally substituted with OH, $NH_2$ or aryl;
or wherein:
R2 is COOR4;
R3 is H;
m is 1; and
R4 is $C_1$-$C_6$ alkyl;
or wherein:
Z is $CH_2$;
R2 is COOR4;
R3 is OH;
n is 1;
m is 1; and
R4 is $C_1$-$C_6$ alkyl;
or wherein:
R2 is COOR4;
m is 2; and
R4 is $C_1$-$C_6$ alkyl.

5. The compound or stereoisomer, solvate, tautomer or pharmaceutically acceptable salt thereof according to claim 1, wherein W is selected from the group consisting of: benzene, pyrazole, pyrimidine, pyridine, pyrrole, thiophene and oxazole.

6. A compound according to claim 1 selected from the group consisting of:
Methyl (E)-4-[3-(3-chloro-10,11-dihydro-5H-dibenzo[b,f]azepin-5-yl)propyl-methyl-amino]but-2-enoate;
Ethyl (E)-4-[3-(7-chlorodibenzo[b,e][1,4]oxazepin-5(11H)-yl)propylamino]but-2-enoate;
Ethyl (E)-4-{3-[7-(trifluoromethyl)dibenzo[b,e][1,4]oxazepin-5(11H)-yl]propylamino}but-2-enoate;
Ethyl (E)-4-[3-(3-chloro-10,11-dihydro-5H-dibenzo[b,f]azepin-5-yl)propylamino]but-2-enoate;
Ethyl (E)-5-[3-(3-chloro-10,11-dihydro-5H-dibenzo[b,f]azepin-5-yl)propylamino]pent-2-enoate;
(E)-4-[3-(3-Chloro-10,11-dihydro-5H-dibenzo[b,f]azepin-5-yl)propyl-methyl-amino]-N-methoxy-N-methyl-but-2-enamide;
(E)-5-[3-(3-chloro-10,11-dihydro-5H-dibenzo[b,f]azepin-5-yl)propyl-methyl-amino]pent-3-en-2-one;
(E)-4-(3-(3-chloro-10,11-dihydro-5H-dibenzo[b,f]azepin-5-yl)propyl-methyl-amino]-1-phenyl-but-2-en-1-one;
(E)-4-[4-(3-Chloro-10,11-dihydro-5H-dibenzo[b,f]azepin-5-yl)butyl-methyl-amino]-N-methoxy-N-methyl-but-2-enamide;
(E)-5-[4-(3-chloro-10,11-dihydro-5H-dibenzo[b,f]azepin-5-yl)butyl-methyl-amino]pent-3-en-2-one;
Ethyl (E)-4-[3-(10,11-dihydro-5H-dibenzo[b,f]azepin-5-yl)propylamino]but-2-enoate;
Ethyl (E)-4-[4-(3-chloro-10,11-dihydro-5H-dibenzo[b,f]azepin-5-yl)butylamino]but-2-enoate;
Ethyl (E)-4-[5-(3-chloro-10,11-dihydro-5H-dibenzo[b,f]azepin-5-yl)pentylamino]but-2-enoate;
Ethyl (E)-4-[3-(3-nitro-10,11-dihydro-5H-dibenzo[b,f]azepin-5-yl)propylamino]but-2-enoate;
Ethyl (E)-4-[3-(3-bromo-10,11-dihydro-5H-dibenzo[b,f]azepin-5-yl)propylamino]but-2-enoate;
(E)-4-[3-(3-chloro-10,11-dihydro-5H-dibenzo[b,f]azepin-5-yl)propylamino]but-2-enoic acid;
(E)-4-[4-(3-chloro-10,11-dihydro-5H-dibenzo[b,f]azepin-5-yl)butylamino]but-2-enoic acid;
(E)-4-{[3-(3-chloro-10,11-dihydro-5H-dibenzo[b,f]azepin-5-yl)propyl]amino}but-2-enamide;
(E)-4-{[3-(3-chloro-10,11-dihydro-5H-dibenzo[b,f]azepin-5-yl)propyl]amino}-N-methyl-but-2-enamide;
(E)-4-{[3-(3-chloro-10,11-dihydro-5H-dibenzo[b,f]azepin-5-yl)propyl]amino}-N,N-dimethyl-but-2-enamide;
(E)-4-{[3-(3-chloro-10,11-dihydro-5H-dibenzo[b,f]azepin-5-yl)propyl]amino}-N-phenyl-but-2-enamide;
(E)-4-{[3-(3-chloro-10,11-dihydro-5H-dibenzo[b,f]azepin-5-yl)propyl]amino}but-2-enenitrile;
Ethyl (E)-4-{[3-(3-chloro-11-oxo-10,11-dihydro-5H-dibenzo[b,e][1,4]diazepin-5-yl)propyl]amino}but-2-enoate;
Ethyl (E)-4-{[4-(3-chloro-11-oxo-10,11-dihydro-5H-dibenzo[b,e][1,4]diazepin-5-yl)butyl]amino}but-2-enoate;
Ethyl (E)-4-{[3-(11-oxo-3-(trifluoromethyl)-10,11-dihydro-5H-dibenzo[b,e][1,4]diazepin-5-yl)propyl]amino}but-2-enoate;
Ethyl (E)-4-{[3-(7-chloro-11-oxo-10,11-dihydro-5H-dibenzo[b,e][1,4]diazepin-5-yl)propyl]amino}but-2-enoate;
Ethyl (E)-4-{[3-(3-chloro-10-methyl-11-oxo-10,11-dihydro-5H-dibenzo[b,e][1,4]diazepin-5-yl)propyl]amino}but-2-enoate;
Ethyl (E)-4-{[3-(7-chloro-10-methyl-11-oxo-10,11-dihydro-5H-dibenzo[b,e][1,4]diazepin-5-yl)propyl]amino}but-2-enoate;
Ethyl (E)-4-{[4-(7-chloro-10-methyl-11-oxo-10,11-dihydro-5H-dibenzo[b,e][1,4]diazepin-5-yl)butyl]amino}but-2-enoate;
Ethyl (E)-4-{[3-(8-chloro-1-methyl-4,5-dihydropyrazolo-[3,4-b][1]-benzazepin-10(1H)-yl)propyl]amino}but-2-enoate;
Ethyl (E)-4-{[3-(8-chloro-2-methyl-4,5-dihydropyrazolo-[3,4-b][1]-benzazepin-10(2H)-yl)propyl]amino}but-2-enoate;
Ethyl (E)-4-{[3-(9-chloro-5,6-dihydro-11H-pyrimido[4,5-b][1]-benzazepin-11-yl)propyl]amino}but-2-enoate;
Ethyl (E)-4-{[3-(3-chloro-10,11-dihydro-5H-dibenzo[b,f]azepin-5-yl)-3-oxo-propyl]amino}but-2-enoate;
Ethyl (E)-4-{[2-hydroxy-3-(3-chloro-10,11-dihydro-5H-dibenzo[b,f]azepin-5-yl)]propylamino}but-2-enoate;
Ethyl (E)-4-{3-[3-chlorodibenzo[b,e][1,4]oxazepin-5(11H)-yl]propylamino}but-2-enoate;
Ethyl (E)-4-{4-[3-chlorodibenzo[b,e][1,4]oxazepin-5(11H)-yl]butylamino}but-2-enoate;
Ethyl (E)-4-{4-[7-chlorodibenzo[b,e][1,4]oxazepin-5(11H)-yl]butylamino}but-2-enoate;
Ethyl (E)-4-{[4-(3-chloro-10,11-dihydro-5H-dibenzo[b,f]azepin-5-yl)-4-oxo-butyl]amino}but-2-enoate;
Ethyl (E)-4-[4-(7-Chloro-2-hydroxy-10,11-dihydro-dibenzo[b,f]azepin-5-yl)-butylamino]-but-2-enoate;
Ethyl (E)-4-[4-(3-Chloro-2-hydroxy-10,11-dihydro-dibenzo[b,f]azepin-5-yl)-butylamino]-but-2-enoate;
Ethyl (E)-4-{[4-(7-chloro-11-oxo-10,11-dihydro-5H-dibenzo[b,e][1,4]diazepin-5-yl)butyl]amino}but-2-enoate;
Ethyl (E)-4-{[4-(3-chloro-10-methyl-11-oxo-10,11-dihydro-5H-dibenzo[b,e][1,4]diazepin-5-yl)butyl]amino}but-2-enoate;
Ethyl (E)-4-{[4-(8-chloro-1-methyl-4,5-dihydropyrazolo-[3,4-b][1]-benzazepin-10(1H)-yl)butyl]amino}but-2-enoate;
Ethyl (E)-4-{[4-(7-chloro-10-(2-phenylethyl)-11-oxo-10,11-dihydro-5H-dibenzo[b,e][1,4]diazepin-5-yl)butyl]amino}but-2-enoate;

Ethyl (E)-4-{[4-(10-benzyl-7-chloro-11-oxo-10,11-dihydro-5H-dibenzo[b,e][1,4]diazepin-5-yl)butyl]amino}but-2-enoate;
Ethyl (E)-4-({4-[3-chloro-10-(2-hydroxyethyl)-11-oxo-10,11-dihydro-5H-dibenzo[b,e][1,4]diazepin-5-yl]butyl}amino)but-2-enoate;
Ethyl (E)-4-({3-[3-chloro-10-(2-hydroxyethyl)-11-oxo-10,11-dihydro-5H-dibenzo[b,e][1,4]diazepin-5-yl]propyl}amino)but-2-enoate;
Ethyl (E)-4-({4-[3-chloro-10-(3-hydroxypropyl)-11-oxo-10,11-dihydro-5H-dibenzo[b,e][1,4]diazepin-5-yl]butyl}amino)but-2-enoate;
Ethyl (E)-4-({3-[3-chloro-10-(3-hydroxypropyl)-11-oxo-10,11-dihydro-5H-dibenzo[b,e][1,4]diazepin-5-yl]propyl}amino)but-2-enoate;
Ethyl (E)-4-({4-[7-chloro-10-(2-hydroxyethyl)-11-oxo-10,11-dihydro-5H-dibenzo[b,e][1,4]diazepin-5-yl]butyl}amino)but-2-enoate;
Ethyl (E)-4-({4-[7-chloro-10-(3-hydroxypropyl)-11-oxo-10,11-dihydro-5H-dibenzo[b,e][1,4]diazepin-5-yl]butyl}amino)but-2-enoate;
Ethyl (E)-4-({3-[7-chloro-10-(3-hydroxypropyl)-11-oxo-10,11-dihydro-5H-dibenzo[b,e][1,4]diazepin-5-yl]propyl}amino)but-2-enoate;
(E)-6-[4-(3-chloro-10,11-dihydro-5H-dibenzo[b,f]azepin-5-yl)butyl-methyl-amino]-1-phenyl-hex-4-en-3-one;
(E)-6-[4-(3-chloro-10,11-dihydro-5H-dibenzo[b,f]azepin-5-yl)butyl-methyl-amino]hex-4-en-3-one;
Ethyl (E)-4-({3-[7-chloro-10-(2-hydroxyethyl)-11-oxo-10,11-dihydro-5H-dibenzo[b,e][1,4]diazepin-5-yl]propyl}amino)but-2-enoate;
Ethyl (E)-4-((4-(10-benzyl-3-chloro-11-oxo-10,11-dihydro-5H-dibenzo[b,e][1,4]diazepin-5-yl)butyl)amino)but-2-enoate;
Methyl (E)-4-{[4-(3-chloro-10-methyl-11-oxo-10,11-dihydro-5H-dibenzo[b,e][1,4]diazepin-5-yl)butyl](methyl)amino}but-2-enoate;
(E)-4-{[4-(3-chloro-10-methyl-11-oxo-10,11-dihydro-5H-dibenzo[b,e][1,4]diazepin-5-yl)butyl](methyl)amino}-N-methoxy-N-methyl-but-2-enamide;
3-Chloro-10-methyl-5-(4-{methyl[(E)-4-oxopent-2-en-1-yl]amino}butyl)-5,10-dihydro-11H-dibenzo[b,e][1,4]diazepin-11-one;
Methyl (E)-4-{[4-(10-benzyl-3-chloro-11-oxo-10,11-dihydro-5H-dibenzo[b,e][1,4]diazepin-5-yl)butyl](methyl)amino}but-2-enoate;
(E)-4-{[4-(10-Benzyl-3-chloro-11-oxo-10,11-dihydro-5H-dibenzo[b,e][1,4]diazepin-5-yl)butyl](methyl)amino}-N-methoxy-N-methyl-but-2-enamide;
10-Benzyl-3-chloro-5-(4-{methyl[(E)-4-oxo-pent-2-en-1-yl]amino}butyl)-5,10-dihydro-11H-dibenzo[b,e][1,4]diazepin-11-one;
(E)-4-{[4-(10-benzyl-3-chloro-II-oxo-10,11-dihydro-5H-dibenzo[b,e][1,4]diazepin-5-yl)butyl](methyl)amino}but-2-enenitrile;
Methyl (E)-4-[4-(3-chloro-10,11-dihydro-5H-dibenzo[b,f]azepin-5-yl)butylamino]but-2-enoate;
Ethyl (E)-4-{[4-(3-chloro-10,11-dihydro-5H-dibenzo[b,f]azepin-5-yl)butyl]-methyl-amino}but-2-enoate;
Ethyl (E)-4-{[4-(3-chloro-10,11-dihydro-dibenzo[b,f]azepin-5-yl)butyl]-ethyl-amino}but-2-enoate;
Ethyl (E)-4-{[4-(3-chloro-10,11-dihydro-dibenzo[b,f]azepin-5-yl)butyl]-isopropyl-amino}but-2-enoate;
(E)-4-{[4-(3-chloro-10,11-dihydro-5H-dibenzo[b,f]azepin-5-yl)butyl]amino}-N-methyl-but-2-enamide;
Ethyl (E)-4-[4-(7-Chloro-2-methoxy-10,11-dihydro-dibenzo[b,f]azepin-5-yl)-butylamino]-but-2-enoate;
Methyl (E)-4-[4-(3-chlorodibenzo[b,e][1,4]oxazepin-5(11H)-yl)butyl-methyl-amino]but-2-enoate;
(E)-4-[4-(3-Chlorodibenzo[b,e][1,4]oxazepin-5(11H)-yl)butyl-methyl-amino]-N-methoxy-N-methyl-but-2-enamide;
(E)-5-[4-(3-Chlorodibenzo[b,e][1,4]oxazepin-5(11H)-yl)butyl-methyl-amino]pent-3-en-2-one;
(E)-4-[4-(3-chloro-10,11-dihydro-5H-dibenzo[b,f]azepin-5-yl)butylamino]but-2-enenitrile;
(E)-4-[4-(3-Chloro-10,11-dihydro-5H-dibenzo[b,f]azepin-5-yl)butyl-methyl-amino]but-2-enamide;
(E)-4-[4-(3-Chloro-10,11-dihydro-5H-dibenzo[b,f]azepin-5-yl)butyl-methyl-amino]but-2-enenitrile;
Ethyl (E)-4-[4-(7-Chloro-2-hydroxymethyl-10,11-dihydro-dibenzo[b,f]azepin-5-yl)-butylamino]-but-2-enoate;
Ethyl (E)-4-[4-(7-chloro-2-methoxymethyl-10,11-dihydro-dibenzo[b,f]azepin-5-yl)-butylamino]-but-2-enoate;
Ethyl (E)-4-[4-(7-chloro-2-methoxyethoxymethyl-10,11-dihydro-dibenzo[b,f]azepin-5-yl)-butylamino]-but-2-enoate;
(E)-4-[4-(3-Chloro-10,11-dihydro-5H-dibenzo[b,f]azepin-5-yl)butyl-methyl-amino]-N-methyl-N-prop-2-ynoxy-but-2-enamide;
(E)-4-[4-(3-Chloro-10,11-dihydro-5H-dibenzo[b,f]azepin-5-yl)butylamino]-N-methoxy-but-2-enamide;
(E)-4-[4-(3-chloro-10,11-dihydro-5H-dibenzo[b,f]azepin-5-yl)butylamino]-N-benzyloxy-but-2-enamide;
(E)-4-[4-(3-chloro-10,11-dihydro-5H-dibenzo[b,f]azepin-5-yl)butylamino]-N-ethoxy-but-2-enamide;
(E)-4-[4-(3-chloro-10,11-dihydro-5H-dibenzo[b,f]azepin-5-yl)butylamino]-N-isopropoxy-but-2-enamide;
(E)-4-[4-(3-chloro-10,11-dihydro-5H-dibenzo[b,f]azepin-5-yl)butylamino]-N-phenoxy-but-2-enamide;
(E)-4-[4-(3-Chloro-10,11-dihydro-5H-dibenzo[b,f]azepin-5-yl)butylamino]-N-(4-piperidyloxy)-but-2-enamide;
(E)-4-[4-(3-Chloro-10,11-dihydro-5H-dibenzo[b,f]azepin-5-yl)butylamino]-N-(2-phenylethyloxy)-but-2-enamide;
(E)-4-[4-(3-Chloro-10,11-dihydro-5H-dibenzo[b,f]azepin-5-yl)butyl-methyl-amino]-N-methoxy-but-2-enamide;
Ethyl (E)-4-{[4-(3-chloro-10-[2-(2-methoxyethoxy)ethyl]-11-oxo-10,11-dihydro-5H-dibenzo[b,e][1,4]diazepin-5-yl)butyl]amino}but-2-enoate;
Ethyl (E)-4-{[4-(3-chloro-10-[2-[2-(2-methoxyethoxy)ethoxy]ethyl]-11-oxo-10,11-dihydro-5H-dibenzo[b,e][1,4]diazepin-5-yl)butyl]amino}but-2-enoate;
Ethyl (E)-4-{[4-(3-chloro-10-[2-(prop-2-yn-1-yloxy)ethyl]-11-oxo-10,11-dihydro-5H-dibenzo[b,e][1,4]diazepin-5-yl)butyl]amino}but-2-enoate;
Methyl (E)-4-{4-[7-chloro-2-(2-prop-2-ynoxyethoxy)-10,11-dihydro-5H-dibenzo[b,f]azepin-5-yl]-butyl-methyl-amino}-but-2-enoate;
(E)-4-{4-[7-chloro-2-(2-prop-2-ynoxyethoxy)-10,11-dihydro-5H-dibenzo[b,f]azepin-5-yl]butyl-methyl-amino}but-2-enenitrile;
Prop-2-yn-1-yl (E)-4-[4-(3-chloro-10,11-dihydro-5H-dibenzo[b,f]azepin-5-yl)butylamino]but-2-enoate;
2-Prop-2-ynyloxy-ethyl (E)-4-[4-(3-chloro-10,11-dihydro-5H-dibenzo[b,f]azepin-5-yl)butylamino]but-2-enoate;

2-(2-Methoxy-ethoxy)-ethyl (E)-4-[4-(3-chloro-10,11-di-hydro-dibenzo[b,f]azepin-5-yl)-butylamino]but-2-enoate;

2-[2-(2-{2-[5-((3aS,4S,6aR)-2-Oxo-hexahydro-thieno[3,4-d]imidazol-4-yl)-pentanoylamino]-ethoxy}-ethoxy)-ethoxy]-ethyl (E)-4-{[4-(3-chloro-10,11-dihydro-dibenzo[b,f]azepin-5-yl)-butyl]-methyl-amino}but-2-enoate;

2-(2-{2-[2-(2-{2-[5-((3aS,4S,6aR)-2-Oxo-hexahydro-thieno[3,4-d]imidazol-4-yl)-pentanoylamino]-ethoxy}-ethoxy)-ethoxy]-ethoxy}-ethoxy)-ethyl (E)-4-{[4-(3-chloro-10,11-dihydro-dibenzo[b,f]azepin-5-yl)-butyl]-methyl-amino}but-2-enoate;

2-(2-{2-[2-(2-{2-[2-(2-[5-((3aS,4S,6aR)-2-Oxo-hexahydro-thieno[3,4-d]imidazol-4-yl)-pentanoylamino]-ethoxy)-ethoxy]-ethoxy}-ethoxy)-ethoxy]-ethoxy}-ethoxy)-ethyl (E)-4-{[4-(3-chloro-10,11-dihydro-dibenzo[b,f]azepin-5-yl)-butyl]-methyl-amino}but-2-enoate;

Ethyl (E)-4-{4-[7-Chloro-2-(2-methoxy-ethoxy)-10,11-dihydro-5H-dibenzo[b,f]azepin-5-yl]-butylamino}-but-2-enoate;

Ethyl (E)-4-(4-{7-chloro-2-[2-(2-methoxy-ethoxy)-ethoxy]-10,11-dihydro-5H-dibenzo[b,f]azepin-5-yl}-butylamino)-but-2-enoate;

5-((3aS,4S,6aR)-2-Oxo-hexahydro-thieno[3,4-d]imidazol-4-yl)-(2-{2-[2-(2-{4-[2-(7-chloro-5-{4-[((E)-3-cyano-allyl)-methyl-amino]-butyl}-10,11-dihydro-5H-dibenzo[b,f]azepin-2-yloxy)-ethoxymethyl]-[1,2,3]triazol-1-yl}-ethoxy)-ethoxy]-ethoxy}-ethyl) pentanamide;

Ethyl (E)-4-[4-(7-Chloro-2-prop-2-ynyloxy-10,11-dihydro-dibenzo[b,f]azepin-5-yl)-butylamino]-but-2-enoate;

Ethyl (E)-4-[4-(2-benzyloxy-7-chloro-10,11-dihydro-dibenzo[b,f]azepin-5-yl)-butylamino]-but-2-enoate; and 2-methoxy-ethyl (E)-4-[4-(3-chloro-10,11-dihydro-dibenzo[b,f]azepin-5-yl)-butylamino]-but-2-enoate;

or a stereoisomer, a solvate, a tautomer or a pharmaceutically acceptable salt thereof.

7. The compound or stereoisomer, solvate, tautomer or pharmaceutically acceptable salt thereof according to claim 1, wherein said pharmaceutically acceptable salt is a hydrochloride salt, a fumarate salt or a maleate salt.

8. A method for the treatment of a condition wherein an E3 ligase comprising a HECT domain is deregulated, comprising administering a compound or stereoisomer, solvate, tautomer or pharmaceutically acceptable salt of claim 1 to a patient in need thereof.

9. A method for the treatment of a condition according to claim 8 wherein the condition is selected from the group consisting of: cancer, an infectious disease, hypertension, a cardiovascular disease, a neurological disorder, a neurodegenerative disease, inflammation, an autoimmune disorder and an autism spectrum disorder, the method comprising administering a compound or stereoisomer, solvate, tautomer or pharmaceutically acceptable salt of claim 1 to a patient in need thereof.

10. The method according to claim 9, wherein the condition is cancer and the cancer is selected from the group consisting of: leukemia, lymphoma, gastric carcinoma, breast cancer, medulloblastoma, prostate cancer, colon cancer, non-small cell lung cancer, hepatocellular carcinoma, pancreas cancer, glioblastoma, glioma, colorectal cancer, pancreatic adenocarcinoma, endometrial cancer, bladder cancer, lung cancer, a myelodysplastic syndrome, multiple myeloma, mammary tumor, pulmonary tumor, pleural mesothelioma, adenocarcinoma, small-cell lung cancer, skin tumor, Kaposi's sarcoma, osteosarcoma, fibrosarcoma, rhabdomyosarcoma, neuroblastoma, cerebral tumor, head and neck cancer, testicular tumor, ovarian tumor, cervical carcinoma, thyroid carcinoma, gastric tumor, gastrointestinal adenocarcinoma, pancreatic carcinoma, renal tumor, teratocarcinoma and embryonic carcinoma.

11. The method according to claim 9, wherein said infectious disease is caused by a virus.

12. The method according to claim 9, further comprising administering the compound or stereoisomer, solvate, tautomer or pharmaceutically acceptable salt thereof in combination with radiotherapy and/or an additional therapeutic agent.

13. A pharmaceutical composition comprising the compound or stereoisomer, solvate, tautomer or pharmaceutically acceptable salt thereof of claim 1 and a pharmaceutically acceptable excipient and/or diluent.

14. The pharmaceutical composition according to claim 13 further comprising an additional therapeutic agent.

15. A process for the preparation of a compound of formula (I) as defined in claim 1, comprising at least one of the following steps:

reacting a compound of formula A1

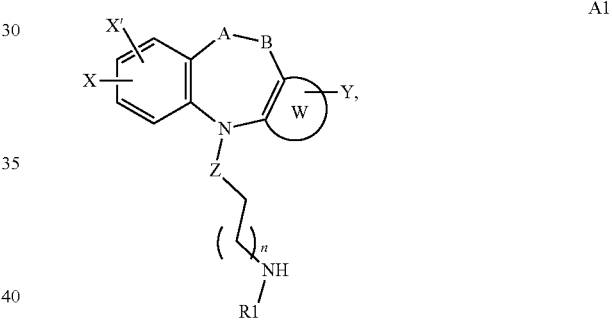

wherein A-B, X, X' Y, W, Z, R1 and n are as previously defined, with an aldehyde of formula CHOCH=CHCOOR4, in the presence of a reducing agent to obtain a compound of formula (I), wherein R2 is COOR4, R3 is H, and m is 1; or reacting a compound of formula A1

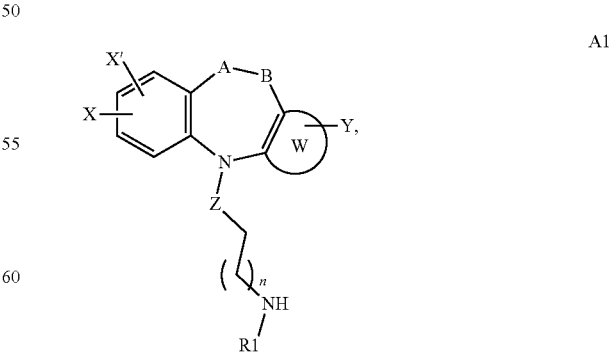

wherein A-B, X, X', Y, W, Z, R1 and n are as previously defined, with an allylic compound of formula LG-CH₂CH=CHCOOR4, and LG is a leaving group, optionally in the presence of a base to obtain a compound of formula (I), wherein R2 is COOR4, R3 is H, and m is 1; or reacting a compound of formula A1d

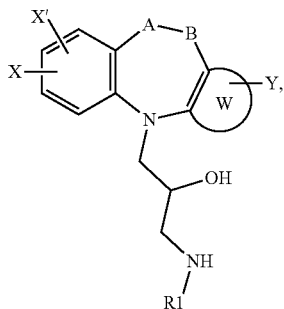

A1d wherein A-B, X, X', Y, W and R1 are as previously defined, with an aldehyde of formula CHOCH=CHCOOR4, in the presence of a reducing agent to obtain a compound of formula (I), wherein Z is CH$_2$, R2 is COOR4, R3 is OH, m is 1 and n is 1; or reacting a compound of formula A1d

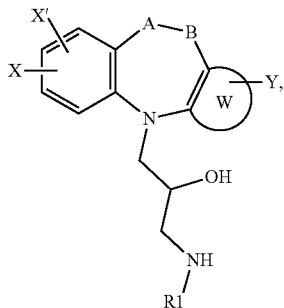

A1d wherein A-B, X, X', Y, W and R1 are as previously defined, with an allylic compound of formula LG-CH$_2$CH=CHCOOR4 and LG is a leaving group, optionally in the presence of a base to obtain a compound of formula (I), wherein Z is CH$_2$, R2 is COOR4, R3 is OH, m is 1 and n is 1; or reacting a compound of formula A10

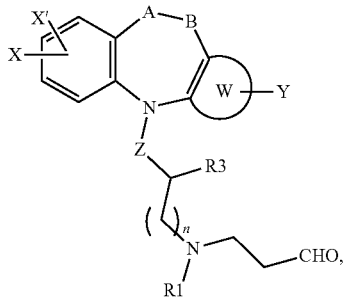

A10 wherein A-B, X, X', Y, W, Z, R1, R3 and n are as previously defined, with a phosphorane of formula Ph$_3$P=CHCOOR4, to obtain a compound of formula (I) wherein R2 is COOR4 and m is 2.

16. The process according to claim 15, wherein the compound A1 wherein Z is CH$_2$ and R1 is H, labelled as compound A1a, is prepared by a process according to scheme B1:

Scheme B1

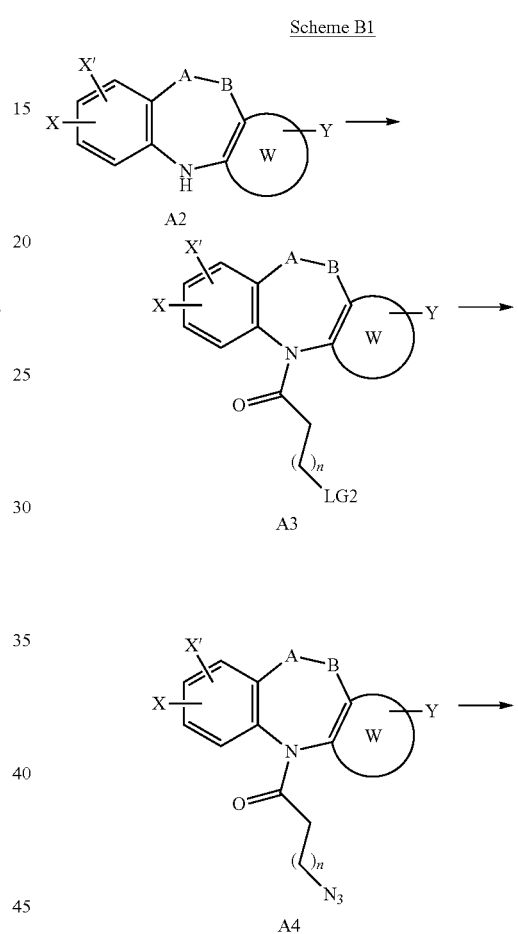

or wherein the compound A1 wherein Z is CH$_2$, labelled as compound A1b, is prepared by a process according to scheme B2:

Scheme B2
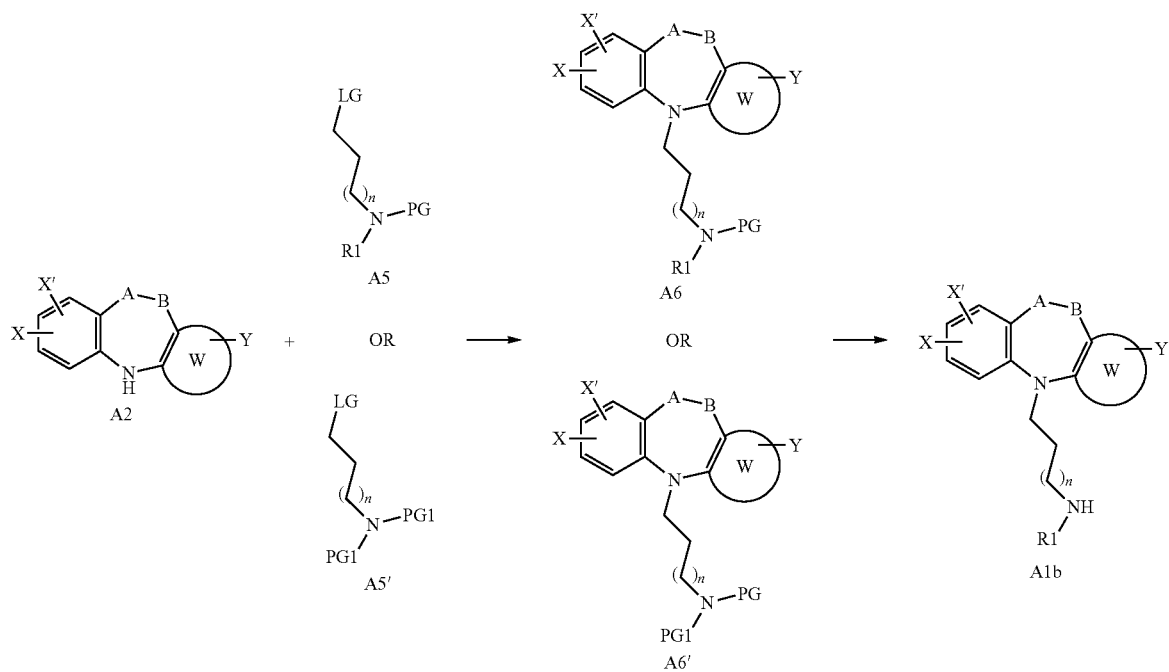
or wherein the compound of formula A1 wherein Z is CO, labelled as compound A1c, is prepared by a process according to scheme B3:
Scheme B3
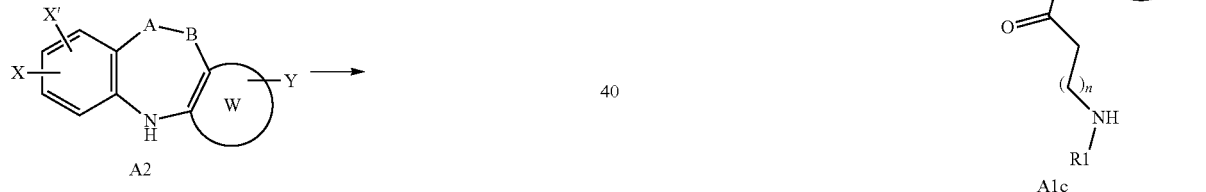
-continued
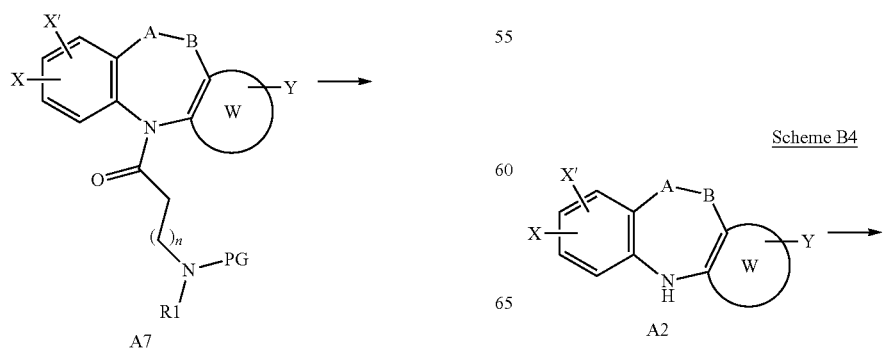
or wherein the compound of formula A1d is prepared by a process according to scheme B4:
Scheme B4

-continued

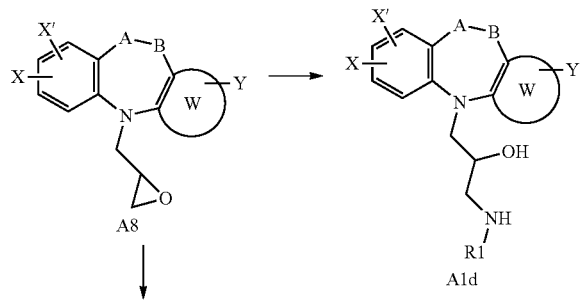

or wherein the compound of formula A10 is prepared by a process according to scheme B5:

Scheme B5.

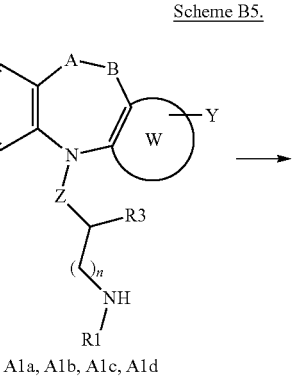

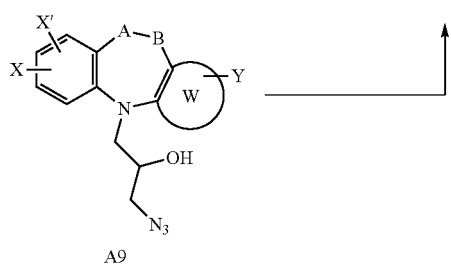

17. An in vitro method of inhibiting an E3 ligase comprising a HECT domain by using the compound or stereoisomer, solvate, tautomer or pharmaceutically acceptable salt thereof as defined in claim 1, said E3 ligase comprising a HECT domain.

18. An in vitro method according to claim 17, wherein the HECT domain is NEDD4, ITCH, SMURF1, SMURF2, WWP1, WWP2, HECW1 or HECW2.

19. An in vitro method according to claim 17, wherein the HECT domain is NEDD4.

* * * * *